(12) United States Patent
Blumenfeld et al.

(10) Patent No.: US 7,547,771 B2
(45) Date of Patent: Jun. 16, 2009

(54) POLYMORPHIC MARKERS OF PROSTATE CARCINOMA TUMOR ANTIGEN -1(PCTA-1)

(75) Inventors: Marta Blumenfeld, Paris (FR); Lydie Bougueleret, Vanves (FR); Ilya Chumakov, Vaux-le-Penil (FR)

(73) Assignee: Serono Genetics Institute S.A., Evry (FR)

( * ) Notice: Subject to any disclaimer, the term of this patent is extended or adjusted under 35 U.S.C. 154(b) by 658 days.

(21) Appl. No.: 10/856,888

(22) Filed: May 27, 2004

(65) Prior Publication Data

US 2004/0235037 A1 Nov. 25, 2004

Related U.S. Application Data

(62) Division of application No. 09/326,402, filed on Jun. 4, 1999, now Pat. No. 6,759,192.

(60) Provisional application No. 60/102,324, filed on Sep. 28, 1998, provisional application No. 60/088,187, filed on Jun. 5, 1998.

(51) Int. Cl.
C07H 21/04 (2006.01)
(52) U.S. Cl. .................... 536/23.1; 536/23.4; 536/24.3; 536/24.31
(58) Field of Classification Search .................. None
See application file for complete search history.

(56) References Cited

U.S. PATENT DOCUMENTS

| 5,110,920 | A |   | 5/1992  | Erlich         |        |
|-----------|---|---|---------|----------------|--------|
| 5,612,179 | A |   | 3/1997  | Simons         |        |
| 5,840,686 | A | * | 11/1998 | Chader et al.  | 514/12 |
| 6,027,889 | A |   | 2/2000  | Barany et al.  |        |
| 6,537,751 | B1| * | 3/2003  | Cohen et al.   | 435/6  |

FOREIGN PATENT DOCUMENTS

| WO | WO 96/21671 | 7/1996 |
|----|-------------|--------|
| WO | WO 98/07830 | 2/1998 |
| WO | WO 98/18967 | 5/1998 |
| WO | WO 98/20165 | 5/1998 |

OTHER PUBLICATIONS

GenBank Accession No. CU459202, Oct. 9, 2007.*
Entrez Gene Entry for LGALS8, alias PCTA-1, GeneID: 3964, updated Oct. 21, 2007, URL: http://www.ncbi.nlm.nih.gov/sites/entrez.*
Su, Z. Z. et al. "Surface-epitope Masking and Expression Cloning Identifies the Human Prostate Carcinoma Tumor Antigen Gene PCTA-1 a Member of the Galectin Gene Family", *Proc. Natl. Acad. Sci. USA*, Jul. 1996, pp. 7252-7257, vol. 92.
Syvanen, A. C. et al. "Identification of Individuals by Analysis of Biallelic DNA Markers, Using PCR and Solid-phase Minisequencing", *Am. J. Hum. Genet*, Jan. 1993, pp. 46-59, vol. 52, No. 1.
GenBank, Apr. 10, 1997, L78132.
Berthon, et al. "Predisposing Gene for Early-Onset Prostate Cancer, Localized on Chromosome 1q42.2-43", *Am. J. Hum Genet.*, 1998, pp. 1416-1424, vol. 62.
Hadari, Y. R. et al. "A New Rat Lectin, Related to Galectin-4", *J. Biol. Chem*., Feb. 1995, pp. 3447-3453, vol. 270, No. 7.
Shen, et al. "Identification of the Human Prostatic Carcinoma Oncogene PTI-1 by Rapid Expression Cloning and Differential RNA Display," *Proc. Natl. Acad. Sci. USA*, Jul. 1995, pp. 6778-6782, vol. 92.
Wang, et al. "Large-Scale Identification, Mapping, and Genotyping of Single-nucleotide Polymorphisms in the Human Genome", *Science*, 1998, vol. 280.

* cited by examiner

*Primary Examiner*—Juliet C Switzer
(74) *Attorney, Agent, or Firm*—Saliwanchik, Lloyd & Saliwanchik

(57) ABSTRACT

The invention concerns the geNo.mic sequence and cDNA sequences of the PCTA-1 gene. The invention also concerns biallelic markers of the PCTA-1 gene and the association established between these markers and prostate cancer. The invention provides means to determine the predisposition of individuals to prostate cancer as well as means for the diagNo.sis of prostate cancer and for the progNo.sis/detection of an eventual treatment response to agents acting against prostate cancer.

41 Claims, 11 Drawing Sheets

```
            1                                                            50
     leg2   ~~~~~~~~~~ ~~~~~~~~~~ ~~~~~~~~~~ ~~~~~~~~~~ ~~~~~~~~~~
     leg1   ~~~~~~~~~~ ~~~~~~~~~~ ~~~~~~~~~~ ~~~~~~~~~~ ~~~~~~~~~~
     PCTA   ~~~~~~~~~~ ~~~~~~~~~~ ~~~~~~~~~~ ~~~~~~~~~~ ~~~~~~~~~~
 PCTA.var   ~~~~~~~~~~ ~~~~~~~~~~ ~~~~~~~~~~ ~~~~~~~~~~ ~~~~~~~~~~
 PCTA.mus   ~~~~~~~~~~ ~~~~~~~~~~ ~~~~~~~~~~ ~~~~~~~~~~ ~~~~~~~~~~
    gal9-1  ~~~~~~~~~~ ~~~~~~~~~~ ~~~~~~~~~~ ~~~~~~~~~~ ~~~~~~~~~~
      gal   ~~~~~~~~~~ ~~~~~~~~~~ ~~~~~~~~~~ ~~~~~~~~~~ ~~~~~~~~~~
     leg7   ~~~~~~~~~~ ~~~~~~~~~~ ~~~~~~~~~~ ~~~~~~~~~~ ~~~~~~~~~~
     gal4   ~~~~~~~~~~ ~~~~~~~~~~ ~~~~~~~~~~ ~~~~~~~~~~ ~~~~~~~~~~
Consensus   ---------- ---------- ---------- ---------- ----------
            51                                                          100
     leg2   ~~~~~~~~~~ ~~~~~~~~~~ ~~~~~~~~~~ ~~~~~~~~~~ ~~~~~~~~~~
     leg1   ~~~~~~~~~~ ~~~~~~~~~~ ~~~~~~~~~~ ~~~~~~~~~~ ~~~~~~~~~~
     PCTA   ~~~~~~~~~~ ~~~~~~~~~~ ~~~~~~~~~~ ~~~~~~~~~~ ~~~~~~~~~~
 PCTA.var   ~~~~~~~~~~ ~~~~~~~~~~ ~~~~~~~~~~ ~~~~~~~~~~ ~~~~~~~~~~
 PCTA.mus   ~~~~~~~~~~ ~~~~~~~~~~ ~~~~~~~~~~ ~~~~~~~~~~ ~~~~~~~~~~
    gal9-1  ~~~~~~~~~~ ~~~~~~~~~~ ~~~~~~~~~~ ~~~~~~~~~~ ~~~~~~~~~~
      gal   ~~~~~~~~~~ ~~~~~~~~~~ ~~~~~~~~~~ ~~~~~~~~~~ ~~~~~~~~~~
     leg7   ~~~~~~~~~~ ~~~~~~~~~~ ~~~~~~~~~~ ~~~~~~~~~~ ~~~~~~~~~~
     gal4   ~~~~~~~~~~ ~~~~~~~~~~ ~~~~~~~~~~ ~~~~~~~~~~ ~~~~~~~~~M
Consensus   ---------- ---------- ---------- ---------- ----------
            101                                                         150
     leg2   ~~~~~~~~~~ ~~~~MTGELE VKNMDMKPGS TLKITGSIAD .GTDGFVINL
     leg1   ~~~~~~~~~~ ~~~~~~ACGLV ASNLNLKPGE CLRVRGEVAP .DAKSFVLNL
     PCTA   MLSLNNLQNI IYNPVIPYVG TIPDQLDPGT LIVICGHV.P SDADRFQVDL
 PCTA.var   MLSLNNLQNI IYNPVIPYVG TIPDQLDPGT LIVICGHV.P SDADRFQVDL
 PCTA.mus   MLSLNNLQNI IYNPIIPYVG TITEQLKPGS LIVIRGHV.P KDSERFQVDF
    gal9-1  ~MAFSGSQAP YLSPAVPFSG TIQGGLQDGL QITVNGTVLS SSGTRFAVNF
      gal   ~MAFSGSQAP YLSPAVPFSG TIQGGLQDGL QITVNGTVLS SSGTRFAVNF
     leg7   ~~~~~~~~~~ ~~~SNVPHKS SLPEGIRPGT VLRIRG.LVP PNASRFHVNL
     gal4   AYVPAPGYQP TYNPTLPYYQ PIPGGLNVGM SVYIQG.VAS EHMKRFFVNF
Consensus   ---------- ---P--P--- -IP-GL-PG- ---I-G-V-P --A-RF-VNL
```

FIG. 7A

```
           151                                                      200
    leg2   GQGTD.....  KLNLHFNPRF  S....ESTIV  CNSLDGSNWG  QEQREDHLCF
    leg1   GKDSN.....  NLCLHFNPRF  NAHGDANTIV  CNSKDGGAWG  TEQREAVFPF
    PCTA   QNGSSVKPRA  DVAFHFNPRF  K.RAGC.IV   CNTLINEKWG  REEITYDTPF
PCTA.var   QNGSSVKPRA  DVAFHFNPRF  K.RAGC.IV   CNTLINEKWG  REEITYDTPF
PCTA.mus   QLGNSLKPRA  DVAFHFNPRF  K.RSSC.IV   CNTLTQEKWG  WEEITYDMPF
  gal9-1   QTGFS...GN  DIAFHFNPRF  E.DGGY.VV   CNTRQNGSWG  PEERKTHMPF
     gal   QTGFS...GN  DIAFHFNPRF  E.DGGY.VV   CNTRQNGSWG  PEERRTHMPF
    leg7   LCGEE..QGS  DAALHFNPRL  D..TSE.VV   FNSKEQGSWG  REERGPGVPF
    gal4   VVGQD..PGS  DVAFHFNPRF  D.GWDK..VV  FNTLQGGKWG  SEERKRSMPF
Consensus  --G-----G-  D-AFHFNPRF  --------VV  CNT---G-WG  -EER----PF 201                                                      250
    leg2   SPGSEVKFTV  TFESDKFKVK  LPDGHELTFP  NRLG.HSHLS  YLSVRGGFNM
    leg1   QPGSVAEVCI  TFDQANLTVK  LPDGYEFKFP  NRLN.LEAIN  YMAADGDFKI
    PCTA   KREKSFEIVI  MVLKDKFQVA  VNGKHTLLYG  HRI.GPEKID  TLGIYGKVNI
PCTA.var   KREKSFEIVI  MVLKDKFQVA  VNGKHTLLYG  HRI.GPEKID  TLGIYGKVNI
PCTA.mus   RKEKSFEIVF  MVLKNKFQVA  VNGRHVLLYA  HRI.SPEQID  TVGIYGKVNI
  gal9-1   QKGMPFDLCF  LVQSSDFKVM  VNGILFVQYF  HRV.PFHRVD  TISVNGSVQL
     gal   QKGMPFDLCF  LVQSSDFKVM  VNGILFVQYF  HRV.PFHRVD  TIFVNGSVQL
    leg7   QRGQPFEVLI  IASDDGFKAV  VGDAQYHHFR  HRL.PLARVR  LVEVGGDVQL
    gal4   KKGAAFELVF  IVLAEHYKVV  VNGNPFYEYG  HRL.PLQMVT  HLQVDGDLQL
Consensus  --G--FE---  -V--D-FKV-  VNG-----Y-  HRL-PL--V-  ---V-GDVQL 251                                                      300
    leg2   SSFKLKE~~~  ~~~~~~~~~~  ~~~~~~~~~~  ~~~~~~~~~~  ~~~~~~~~~~
    leg1   KCVAFD~~~~  ~~~~~~~~~~  ~~~~~~~~~~  ~~~~~~~~~~  ~~~~~~~~~~
    PCTA   HSIGFSFSSD  LQSTQASSLE  LTEISRENVP  KSGTPQL...  ..........
PCTA.var   HSIGFSFSSD  LQSTQASSLE  LTEISRENVP  KSGTPQLPSN  RGGDISKIAP
PCTA.mus   HSIGFRFSSD  LQSMETSALG  LTQINRENIQ  KPGKLQL...  ..........
  gal9-1   SYISFQNPRT  VPVQPAFSTV  PFSQPVCFPP  RPRGRRQKPP  GVWPANPAPI
     gal   SYISFQ....  ..........  ..........  ........PP  GVWPANPAPI
    leg7   DSVRIF~~~~  ~~~~~~~~~~  ~~~~~~~~~~  ~~~~~~~~~~  ~~~~~~~~~~
    gal4   QSINFI....  ..........  ..........  ......GGQP  .LRPQGPPMM
Consensus  -SI-F-----  ----------  ----------  ----------  ----------
```

FIG. 7B

```
              301                                                          350
     leg2     ----------  ----------  ----------  ----------  ----------
     leg1     ----------  ----------  ----------  ----------  ----------
     PCTA     ..........  ..........  .........S  ..LPFAARLN  TPMGPGRTVV
 PCTA.var     RTVYTKSKDS  TVNHTLTCTK  IPPMNYVSKS  ..LPFAARLN  TPMGPGRTVV
 PCTA.mus     ..........  ..........  .........S  ..LPFEARLN  ASMGPGRTVV
    gal9-1    TQTVIHTVQS  APGQMFSTPA  IPPMMYPHPA  YPMPFITTIL  GGLYPSKSIL
       gal    TQTVIHTVQS  APGQMFSTPA  IPPMMYPHPA  YPMPFITTIL  GGLYPSKSIL
      leg7    ----------  ----------  ----------  ----------  ----------
      gal4    PPYPGPGHCH  QQLNSLPTME  GPPTFNP...  .PVPYFGRLQ  GGLTARRTII
 Consensus    ----------  ----------  ----------  ---P------  ----------

351                                                          400
     leg2     ----------  ----------  ----------  ----------  ----------
     leg1     ----------  ----------  ----------  ----------  ----------
     PCTA     VKGEVNANAK  SFNVDLLAGK  SKDIALHLNP  RLNIKAFVRN  SFLQESWGEE
 PCTA.var     VKGEVNANAK  SFNVDLLAGK  SKDIALHLNP  RLNIKAFVRN  SFLQESWGEE
 PCTA.mus     IKGEVNTNAR  SFNVDLVAGK  TRDIALHLNP  RLNVKAFVRN  SFLQDAWGEE
    gal9-1    LSGTVLPSAQ  RFHIN..LCS  GNHIAFHLNP  RFDENAVVRN  TQIDNSWGSE
       gal    LSGTVLPSAQ  RFHIN..LCS  GNHIAFHLNL  RFDENAVVRN  TQIDNSWGSE
      leg7    ----------  ----------  ----------  ----------  ----------
      gal4    IKGYVPPTGK  SFAINFKVGS  SGDIALHINP  RMGNGTVVRN  SLLNGSWGSE
 Consensus    --G-V-----  -F--------  ---IA-H-N-  R------VRN  ------WG-E 401                                                          450
     leg2     ----------  ----------  ----------  ----------  ----------
     leg1     ----------  ----------  ----------  ----------  ----------
     PCTA     ERNIT.SFPF  SPGMYFEMII  YCDVREFKVA  VNGVHSLEYK  HRFKELSSID
 PCTA.var     ERNIT.SFPF  SPGMYFEMII  YCDVREFKVA  VNGVHSLEYK  HRFKELSSID
 PCTA.mus     ERNIT.CFPF  SSGMYFEMII  YCDVREFKVA  INGVHSLEYK  HRFKDLSSID
    gal9-1    ERSLPRKMPF  VRGQSFSVWI  LCEAHCLKVA  VDGQHLFEYY  HRLRNLPTIN
       gal    ERSLPRKMPF  VRGQSFSVWI  LCGAHCLKVA  VDGQHLFEYY  HRLRNLPTIN
      leg7    ----------  ----------  ----------  ----------  ----------
      gal4    EKKITHN.PF  GPGQFFDLSI  RCGLDRFKVY  ANGQHLFDFA  HRLSAFQRVD
 Consensus    E-------PF  --G--F---I  -C-----KV-  --G-H-----  HR--------
```

FIG. 7C

```
              451       466
       leg2   ~~~~~~~~~~ ~~~~~~
       leg1   ~~~~~~~~~~ ~~~~~~
       PCTA   TLEINGDIHL LEVRSW
   PCTA.var   TLEINGDIHL LEVRSW
   PCTA.mus   TLSVDGDIRL LDVRSW
     gal9-1   RLEVGGDIQL THVQT~
        gal   RLEVGGDIQL THVQT~
       leg7   ~~~~~~~~~~ ~~~~~~
       gal4   TLEIQGDVTL SYVQI~
  Consensus   -L---GD--L --V---
```

■ Galactoside binding site

FIG. 7D

SEQUENCE LISTING

```
<160> NUMBER OF SEQ ID NOS: 22

<210> SEQ ID NO 1
<211> LENGTH: 106746
<212> TYPE: DNA
<213> ORGANISM: Homo sapiens
<220> FEATURE:
<221> NAME/KEY: misc_feature
<222> LOCATION: 1..68647
<223> OTHER INFORMATION: 5'regulation  region
<220> FEATURE:
<221> NAME/KEY: misc_feature
<222> LOCATION: 66647..68647
<223> OTHER INFORMATION: promoter
<220> FEATURE:
<221> NAME/KEY: misc_feature
<222> LOCATION: 97156..106746
<223> OTHER INFORMATION: 3'regulation  region
<220> FEATURE:
<221> NAME/KEY: exon
<222> LOCATION: 68648..68741
<223> OTHER INFORMATION: exon0
<220> FEATURE:
<221> NAME/KEY: exon
<222> LOCATION: 70647..70794
<223> OTHER INFORMATION: exon1
<220> FEATURE:
<221> NAME/KEY: exon
<222> LOCATION: 82208..82296
<223> OTHER INFORMATION: exon2
<220> FEATURE:
<221> NAME/KEY: exon
<222> LOCATION: 83613..83823
<223> OTHER INFORMATION: exon3
<220> FEATURE:
<221> NAME/KEY: exon
<222> LOCATION: 85298..85417
<223> OTHER INFORMATION: exon4
<220> FEATURE:
<221> NAME/KEY: exon
<222> LOCATION: 86389..86445
<223> OTHER INFORMATION: exon5
<220> FEATURE:
<221> NAME/KEY: exon
<222> LOCATION: 87496..87522
<223> OTHER INFORMATION: exon6
<220> FEATURE:
<221> NAME/KEY: exon
<222> LOCATION: 87650..87775
<223> OTHER INFORMATION: exon6bis
<220> FEATURE:
<221> NAME/KEY: exon
<222> LOCATION: 88295..88383
<223> OTHER INFORMATION: exon7
<220> FEATURE:
<221> NAME/KEY: exon
<222> LOCATION: 89484..89649
<223> OTHER INFORMATION: exon8
<220> FEATURE:
<221> NAME/KEY: exon
<222> LOCATION: 92749..97155
<223> OTHER INFORMATION: exon9
<220> FEATURE:
<221> NAME/KEY: exon
<222> LOCATION: 92749..92883
<223> OTHER INFORMATION: exon9bis
<220> FEATURE:
<221> NAME/KEY: exon
<222> LOCATION: 95821..97155
```

```
<223> OTHER INFORMATION: exon9ter
<220> FEATURE:
<221> NAME/KEY: misc_feature
<222> LOCATION: 70647..70794
<223> OTHER INFORMATION: homology with genset EST : A241850
<220> FEATURE:
<221> NAME/KEY: misc_feature
<222> LOCATION: 68648..68741
<223> OTHER INFORMATION: homology with genset EST : A241850
<220> FEATURE:
<221> NAME/KEY: misc_feature
<222> LOCATION: 82208..82229
<223> OTHER INFORMATION: homology with genset EST : A241850
<220> FEATURE:
<221> NAME/KEY: allele
<222> LOCATION: 278
<223> OTHER INFORMATION: 99-1601-278 : polymorphic base A or C
<220> FEATURE:
<221> NAME/KEY: allele
<222> LOCATION: 402
<223> OTHER INFORMATION: 99-1601-402 : polymorphic base A or T
<220> FEATURE:
<221> NAME/KEY: allele
<222> LOCATION: 472
<223> OTHER INFORMATION: 99-1601-472 : polymorphic base A or T
<220> FEATURE:
<221> NAME/KEY: allele
<222> LOCATION: 2955
<223> OTHER INFORMATION: 99-13801-100 : polymorphic base T or C
<220> FEATURE:
<221> NAME/KEY: allele
<222> LOCATION: 12167
<223> OTHER INFORMATION: 99-13806-166 : polymorphic base G or A
<220> FEATURE:
<221> NAME/KEY: allele
<222> LOCATION: 12536
<223> OTHER INFORMATION: 99-13799-376 : polymorphic base T or G
<220> FEATURE:
<221> NAME/KEY: allele
<222> LOCATION: 17593
<223> OTHER INFORMATION: 99-13798-297 : polymorphic base T or C
<220> FEATURE:
<221> NAME/KEY: allele
<222> LOCATION: 17606
<223> OTHER INFORMATION: 99-13798-284 : polymorphic base T or C
<220> FEATURE:
<221> NAME/KEY: allele
<222> LOCATION: 22079
<223> OTHER INFORMATION: 99-1602-200 : polymorphic base G or C
<220> FEATURE:
<221> NAME/KEY: allele
<222> LOCATION: 28964
<223> OTHER INFORMATION: 99-13794-186 : polymorphic base T or C
<220> FEATURE:
<221> NAME/KEY: allele
<222> LOCATION: 29003
<223> OTHER INFORMATION: 99-13794-147 : polymorphic base C or G
<220> FEATURE:
<221> NAME/KEY: allele
<222> LOCATION: 31077
<223> OTHER INFORMATION: 99-13812-384 : polymorphic base T or C
<220> FEATURE:
<221> NAME/KEY: allele
<222> LOCATION: 31766
<223> OTHER INFORMATION: 99-13805-313 : polymorphic base T or C
<220> FEATURE:
<221> NAME/KEY: allele
<222> LOCATION: 34791
<223> OTHER INFORMATION: 99-1587-281 : polymorphic base A or G
<220> FEATURE:
<221> NAME/KEY: allele
<222> LOCATION: 45751
<223> OTHER INFORMATION: 99-1582-430 : polymorphic base C or T
<220> FEATURE:
<221> NAME/KEY: allele
<222> LOCATION: 49847
<223> OTHER INFORMATION: 99-1585-465 : polymorphic base T or C
<220> FEATURE:
<221> NAME/KEY: allele
```

```
<222> LOCATION: 49855
<223> OTHER INFORMATION: 99-1585-457 : polymorphic base T or C
<220> FEATURE:
<221> NAME/KEY: allele
<222> LOCATION: 49886
<223> OTHER INFORMATION: 99-1585-426 : polymorphic base G or A
<220> FEATURE:
<221> NAME/KEY: allele
<222> LOCATION: 49900
<223> OTHER INFORMATION: 99-1585-412 : polymorphic base G or A
<220> FEATURE:
<221> NAME/KEY: allele
<222> LOCATION: 49906
<223> OTHER INFORMATION: 99-1585-406 : polymorphic base C or A
<220> FEATURE:
<221> NAME/KEY: allele
<222> LOCATION: 49921
<223> OTHER INFORMATION: 99-1585-391 : polymorphic base C or A
<220> FEATURE:
<221> NAME/KEY: allele
<222> LOCATION: 49939
<223> OTHER INFORMATION: 99-1585-373 : polymorphic base G or A
<220> FEATURE:
<221> NAME/KEY: allele
<222> LOCATION: 50256
<223> OTHER INFORMATION: 99-1585-55 : polymorphic base C or A
<220> FEATURE:
<221> NAME/KEY: allele
<222> LOCATION: 54955
<223> OTHER INFORMATION: 99-1607-373 : polymorphic base T or C
<220> FEATURE:
<221> NAME/KEY: allele
<222> LOCATION: 64239
<223> OTHER INFORMATION: 99-1577-105 : polymorphic base A or G
<220> FEATURE:
<221> NAME/KEY: allele
<222> LOCATION: 65436
<223> OTHER INFORMATION: 99-1591-235 : polymorphic base A or G
<220> FEATURE:
<221> NAME/KEY: allele
<222> LOCATION: 65496
<223> OTHER INFORMATION: 99-1591-295 : polymorphic base G or T
<220> FEATURE:
<221> NAME/KEY: allele
<222> LOCATION: 66967
<223> OTHER INFORMATION: 99-1572-315 : polymorphic base C or T
<220> FEATURE:
<221> NAME/KEY: allele
<222> LOCATION: 66987
<223> OTHER INFORMATION: 99-1572-335 : polymorphic base A or G
<220> FEATURE:
<221> NAME/KEY: allele
<222> LOCATION: 67092
<223> OTHER INFORMATION: 99-1572-440 : polymorphic base C or T
<220> FEATURE:
<221> NAME/KEY: allele
<222> LOCATION: 67129
<223> OTHER INFORMATION: 99-1572-477 : polymorphic base A or T
<220> FEATURE:
<221> NAME/KEY: allele
<222> LOCATION: 67229
<223> OTHER INFORMATION: 99-1572-578 : polymorphic base C or T
<220> FEATURE:
<221> NAME/KEY: allele
<222> LOCATION: 67433
<223> OTHER INFORMATION: 5-264-188 : polymorphic base A or G
<220> FEATURE:
<221> NAME/KEY: allele
<222> LOCATION: 67723
<223> OTHER INFORMATION: 5-169-97 : polymorphic base G or C
<220> FEATURE:
<221> NAME/KEY: allele
<222> LOCATION: 67834
<223> OTHER INFORMATION: 5-169-208 : polymorphic base A or G
<220> FEATURE:
<221> NAME/KEY: allele
<222> LOCATION: 67955
<223> OTHER INFORMATION: 5-169-331 : polymorphic base C or T
<220> FEATURE:
```

-continued

```
<221> NAME/KEY: allele
<222> LOCATION: 68213
<223> OTHER INFORMATION: 5-170-238 : polymorphic base A or G
<220> FEATURE:
<221> NAME/KEY: allele
<222> LOCATION: 68263
<223> OTHER INFORMATION: 5-170-288 : polymorphic base A or C
<220> FEATURE:
<221> NAME/KEY: allele
<222> LOCATION: 68375
<223> OTHER INFORMATION: 5-170-400 : polymorphic base G or C
<220> FEATURE:
<221> NAME/KEY: allele
<222> LOCATION: 68477
<223> OTHER INFORMATION: 5-171-156 : polymorphic base G or T
<220> FEATURE:
<221> NAME/KEY: allele
<222> LOCATION: 68525
<223> OTHER INFORMATION: 5-171-204 : polymorphic base C or T
<220> FEATURE:
<221> NAME/KEY: allele
<222> LOCATION: 68594
<223> OTHER INFORMATION: 5-171-273 : polymorphic base A or G
<220> FEATURE:
<221> NAME/KEY: allele
<222> LOCATION: 68610
<223> OTHER INFORMATION: 5-171-289 : polymorphic base C or T
<220> FEATURE:
<221> NAME/KEY: allele
<222> LOCATION: 70566
<223> OTHER INFORMATION: 5-1-60 : polymorphic base C or T
<220> FEATURE:
<221> NAME/KEY: allele
<222> LOCATION: 70728
<223> OTHER INFORMATION: 5-1-222 : polymorphic base A or G
<220> FEATURE:
<221> NAME/KEY: allele
<222> LOCATION: 80038
<223> OTHER INFORMATION: 99-1578-99 : polymorphic base G or T
<220> FEATURE:
<221> NAME/KEY: allele
<222> LOCATION: 80118
<223> OTHER INFORMATION: 99-1578-179 : polymorphic base A or T
<220> FEATURE:
<221> NAME/KEY: allele
<222> LOCATION: 80170
<223> OTHER INFORMATION: 99-1578-231 : insertion AC
<220> FEATURE:
<221> NAME/KEY: allele
<222> LOCATION: 80183
<223> OTHER INFORMATION: 99-1578-245 : deletion AT
<220> FEATURE:
<221> NAME/KEY: allele
<222> LOCATION: 80435
<223> OTHER INFORMATION: 99-1578-496 : polymorphic base C or T
<220> FEATURE:
<221> NAME/KEY: allele
<222> LOCATION: 82090
<223> OTHER INFORMATION: 5-2-30 : insertion CAG
<220> FEATURE:
<221> NAME/KEY: allele
<222> LOCATION: 82165
<223> OTHER INFORMATION: 5-2-109 : polymorphic base G or T
<220> FEATURE:
<221> NAME/KEY: allele
<222> LOCATION: 82169
<223> OTHER INFORMATION: 5-2-113 : deletion GTTT
<220> FEATURE:
<221> NAME/KEY: allele
<222> LOCATION: 82218
<223> OTHER INFORMATION: 5-2-162 : polymorphic base A or T
<220> FEATURE:
<221> NAME/KEY: allele
<222> LOCATION: 82234
<223> OTHER INFORMATION: 5-2-178 : polymorphic base C or T
<220> FEATURE:
<221> NAME/KEY: allele
<222> LOCATION: 82268
<223> OTHER INFORMATION: 5-2-213 : polymorphic base C or T
```

```
<220> FEATURE:
<221> NAME/KEY: allele
<222> LOCATION: 82393
<223> OTHER INFORMATION: 99-1605-112 : polymorphic base T or C
<220> FEATURE:
<221> NAME/KEY: allele
<222> LOCATION: 83587
<223> OTHER INFORMATION: 5-3-27 : polymorphic base A or G
<220> FEATURE:
<221> NAME/KEY: allele
<222> LOCATION: 83643
<223> OTHER INFORMATION: 5-3-83 : polymorphic base C or T
<220> FEATURE:
<221> NAME/KEY: allele
<222> LOCATION: 83644
<223> OTHER INFORMATION: 5-3-84 : polymorphic base A or G
<220> FEATURE:
<221> NAME/KEY: allele
<222> LOCATION: 83808
<223> OTHER INFORMATION: 5-3-248 : polymorphic base A or G
<220> FEATURE:
<221> NAME/KEY: allele
<222> LOCATION: 83881
<223> OTHER INFORMATION: 5-3-321 : polymorphic base G or T
<220> FEATURE:
<221> NAME/KEY: allele
<222> LOCATION: 83884
<223> OTHER INFORMATION: 5-3-324 : polymorphic base C or T
<220> FEATURE:
<221> NAME/KEY: allele
<222> LOCATION: 83909
<223> OTHER INFORMATION: 5-4-313 : polymorphic base A or G
<220> FEATURE:
<221> NAME/KEY: allele
<222> LOCATION: 83937
<223> OTHER INFORMATION: 5-3-377 : insertion TTTG
<220> FEATURE:
<221> NAME/KEY: allele
<222> LOCATION: 83947
<223> OTHER INFORMATION: 5-4-351 : polymorphic base C or T
<220> FEATURE:
<221> NAME/KEY: allele
<222> LOCATION: 83982
<223> OTHER INFORMATION: 5-4-386 : polymorphic base A or G
<220> FEATURE:
<221> NAME/KEY: allele
<222> LOCATION: 83988
<223> OTHER INFORMATION: 5-4-392 : polymorphic base GGG or TA
<220> FEATURE:
<221> NAME/KEY: allele
<222> LOCATION: 84047
<223> OTHER INFORMATION: 5-260-255 : polymorphic base C or T
<220> FEATURE:
<221> NAME/KEY: allele
<222> LOCATION: 84092
<223> OTHER INFORMATION: 5-260-300 : polymorphic base C or T
<220> FEATURE:
<221> NAME/KEY: allele
<222> LOCATION: 84145
<223> OTHER INFORMATION: 5-260-353 : polymorphic base C or T
<220> FEATURE:
<221> NAME/KEY: allele
<222> LOCATION: 85202
<223> OTHER INFORMATION: 5-9-50 : polymorphic base C or T
<220> FEATURE:
<221> NAME/KEY: allele
<222> LOCATION: 86259
<223> OTHER INFORMATION: 5-5-21 : polymorphic base A or G
<220> FEATURE:
<221> NAME/KEY: allele
<222> LOCATION: 86323
<223> OTHER INFORMATION: 5-5-85 : polymorphic base TATAAAATATT or
      ACAGGTTATATA
<220> FEATURE:
<221> NAME/KEY: allele
<222> LOCATION: 87713
<223> OTHER INFORMATION: 5-202-95 : polymorphic base G or T
<220> FEATURE:
<221> NAME/KEY: allele
```

```
<222> LOCATION: 87735
<223> OTHER INFORMATION: 5-202-117 : polymorphic base A or T
<220> FEATURE:
<221> NAME/KEY: allele
<222> LOCATION: 87787
<223> OTHER INFORMATION: 5-202-169 : polymorphic base A or C
<220> FEATURE:
<221> NAME/KEY: allele
<222> LOCATION: 87806
<223> OTHER INFORMATION: 5-202-188 : polymorphic base A or G
<220> FEATURE:
<221> NAME/KEY: allele
<222> LOCATION: 87860
<223> OTHER INFORMATION: 5-202-242 : polymorphic base A or G
<220> FEATURE:
<221> NAME/KEY: allele
<222> LOCATION: 87902
<223> OTHER INFORMATION: 5-202-284 : polymorphic base C or T
<220> FEATURE:
<221> NAME/KEY: allele
<222> LOCATION: 87980
<223> OTHER INFORMATION: 5-202-362 : deletion CC
<220> FEATURE:
<221> NAME/KEY: allele
<222> LOCATION: 88012
<223> OTHER INFORMATION: 5-202-394 : polymorphic base C or T
<220> FEATURE:
<221> NAME/KEY: allele
<222> LOCATION: 88215
<223> OTHER INFORMATION: 5-7-113 : polymorphic base C or T
<220> FEATURE:
<221> NAME/KEY: allele
<222> LOCATION: 88283
<223> OTHER INFORMATION: 5-7-181 : polymorphic base G or C
<220> FEATURE:
<221> NAME/KEY: allele
<222> LOCATION: 88297
<223> OTHER INFORMATION: 5-7-195 : polymorphic base G or C
<220> FEATURE:
<221> NAME/KEY: allele
<222> LOCATION: 88442
<223> OTHER INFORMATION: 5-7-340 : polymorphic base C or T
<220> FEATURE:
<221> NAME/KEY: allele
<222> LOCATION: 88471
<223> OTHER INFORMATION: 5-7-369 : polymorphic base A or T
<220> FEATURE:
<221> NAME/KEY: allele
<222> LOCATION: 88480
<223> OTHER INFORMATION: 5-7-378 : polymorphic base C or T
<220> FEATURE:
<221> NAME/KEY: allele
<222> LOCATION: 89394
<223> OTHER INFORMATION: 5-181-57 : polymorphic base A or G
<220> FEATURE:
<221> NAME/KEY: allele
<222> LOCATION: 89464
<223> OTHER INFORMATION: 5-181-127 : polymorphic base C or T
<220> FEATURE:
<221> NAME/KEY: allele
<222> LOCATION: 89471
<223> OTHER INFORMATION: 5-181-134 : polymorphic base C or T
<220> FEATURE:
<221> NAME/KEY: allele
<222> LOCATION: 89658
<223> OTHER INFORMATION: 5-181-321 : polymorphic base A or C
<220> FEATURE:
<221> NAME/KEY: allele
<222> LOCATION: 92760
<223> OTHER INFORMATION: 5-10-39 : polymorphic base C or T
<220> FEATURE:
<221> NAME/KEY: allele
<222> LOCATION: 93023
<223> OTHER INFORMATION: 5-10-302 : polymorphic base A or G
<220> FEATURE:
<221> NAME/KEY: allele
<222> LOCATION: 93055
<223> OTHER INFORMATION: 5-10-334 : polymorphic base A or C
<220> FEATURE:
```

```
<221> NAME/KEY: allele
<222> LOCATION: 93247
<223> OTHER INFORMATION: 5-11-158 : polymorphic base A or G
<220> FEATURE:
<221> NAME/KEY: allele
<222> LOCATION: 93319
<223> OTHER INFORMATION: 5-11-230 : polymorphic base G or T
<220> FEATURE:
<221> NAME/KEY: allele
<222> LOCATION: 93323
<223> OTHER INFORMATION: 5-11-234 : polymorphic base C or T
<220> FEATURE:
<221> NAME/KEY: allele
<222> LOCATION: 93388
<223> OTHER INFORMATION: 5-11-299 : polymorphic base A or T
<220> FEATURE:
<221> NAME/KEY: allele
<222> LOCATION: 93393
<223> OTHER INFORMATION: 5-11-304 : polymorphic base A or C
<220> FEATURE:
<221> NAME/KEY: allele
<222> LOCATION: 93418
<223> OTHER INFORMATION: 5-11-329 : polymorphic base C or T
<220> FEATURE:
<221> NAME/KEY: allele
<222> LOCATION: 93515
<223> OTHER INFORMATION: 5-12-56 : insertion CTTT
<220> FEATURE:
<221> NAME/KEY: allele
<222> LOCATION: 93726
<223> OTHER INFORMATION: 5-12-267 : polymorphic base A or C
<220> FEATURE:
<221> NAME/KEY: allele
<222> LOCATION: 93903
<223> OTHER INFORMATION: 5-13-145 : polymorphic base C or T
<220> FEATURE:
<221> NAME/KEY: allele
<222> LOCATION: 94170
<223> OTHER INFORMATION: 5-14-44 : polymorphic base C or T
<220> FEATURE:
<221> NAME/KEY: allele
<222> LOCATION: 94218
<223> OTHER INFORMATION: 5-14-93 : polymorphic base A or T
<220> FEATURE:
<221> NAME/KEY: allele
<222> LOCATION: 94269
<223> OTHER INFORMATION: 5-14-144 : insertion T
<220> FEATURE:
<221> NAME/KEY: allele
<222> LOCATION: 94290
<223> OTHER INFORMATION: 5-14-165 : polymorphic base C or T
<220> FEATURE:
<221> NAME/KEY: allele
<222> LOCATION: 94422
<223> OTHER INFORMATION: 5-14-297 : polymorphic base A or C
<220> FEATURE:
<221> NAME/KEY: allele
<222> LOCATION: 94432
<223> OTHER INFORMATION: 5-14-307 : polymorphic base G or T
<220> FEATURE:
<221> NAME/KEY: allele
<222> LOCATION: 94720
<223> OTHER INFORMATION: 5-15-219 : polymorphic base A or T
<220> FEATURE:
<221> NAME/KEY: allele
<222> LOCATION: 94989
<223> OTHER INFORMATION: 5-16-157 : polymorphic base A or G
<220> FEATURE:
<221> NAME/KEY: allele
<222> LOCATION: 95261
<223> OTHER INFORMATION: 5-17-140 : polymorphic base A or G
<220> FEATURE:
<221> NAME/KEY: allele
<222> LOCATION: 95340
<223> OTHER INFORMATION: 5-18-51 : polymorphic base G or T
<220> FEATURE:
<221> NAME/KEY: allele
<222> LOCATION: 95497
<223> OTHER INFORMATION: 5-18-208 : polymorphic base A or C
```

```
<220> FEATURE:
<221> NAME/KEY: allele
<222> LOCATION: 95770
<223> OTHER INFORMATION: 5-300-238 : polymorphic base C or T
<220> FEATURE:
<221> NAME/KEY: allele
<222> LOCATION: 95819
<223> OTHER INFORMATION: 5-300-287 : polymorphic base A or G
<220> FEATURE:
<221> NAME/KEY: allele
<222> LOCATION: 96145
<223> OTHER INFORMATION: 5-262-49 : insertion C
<220> FEATURE:
<221> NAME/KEY: allele
<222> LOCATION: 96181
<223> OTHER INFORMATION: 5-262-85 : polymorphic base C or T
<220> FEATURE:
<221> NAME/KEY: allele
<222> LOCATION: 96350
<223> OTHER INFORMATION: 5-262-254 : polymorphic base C or T
<220> FEATURE:
<221> NAME/KEY: allele
<222> LOCATION: 96951
<223> OTHER INFORMATION: 5-263-404 : polymorphic base C or T
<220> FEATURE:
<221> NAME/KEY: allele
<222> LOCATION: 97144
<223> OTHER INFORMATION: 5-265-244 : polymorphic base A or G
<220> FEATURE:
<221> NAME/KEY: allele
<222> LOCATION: 97276
<223> OTHER INFORMATION: 5-265-376 : polymorphic base A or G
<220> FEATURE:
<221> NAME/KEY: allele
<222> LOCATION: 102267
<223> OTHER INFORMATION: 99-7183-338 : polymorphic base C or T
<220> FEATURE:
<221> NAME/KEY: allele
<222> LOCATION: 105937
<223> OTHER INFORMATION: 99-7207-138 : polymorphic base A or G
<220> FEATURE:
<221> NAME/KEY: misc_binding
<222> LOCATION: 258..277
<223> OTHER INFORMATION: 99-1601-278.mis1
<220> FEATURE:
<221> NAME/KEY: misc_binding
<222> LOCATION: 279..298
<223> OTHER INFORMATION: 99-1601-278.mis2 complement
<220> FEATURE:
<221> NAME/KEY: misc_binding
<222> LOCATION: 382..401
<223> OTHER INFORMATION: 99-1601-402.mis1
<220> FEATURE:
<221> NAME/KEY: misc_binding
<222> LOCATION: 403..422
<223> OTHER INFORMATION: 99-1601-402.mis2 complement
<220> FEATURE:
<221> NAME/KEY: misc_binding
<222> LOCATION: 452..471
<223> OTHER INFORMATION: 99-1601-472.mis1
<220> FEATURE:
<221> NAME/KEY: misc_binding
<222> LOCATION: 473..492
<223> OTHER INFORMATION: 99-1601-472.mis2 complement
<220> FEATURE:
<221> NAME/KEY: misc_binding
<222> LOCATION: 2935..2954
<223> OTHER INFORMATION: 99-13801-100.mis2
<220> FEATURE:
<221> NAME/KEY: misc_binding
<222> LOCATION: 2956..2975
<223> OTHER INFORMATION: 99-13801-100.mis1 complement
<220> FEATURE:
<221> NAME/KEY: misc_binding
<222> LOCATION: 12147..12166
<223> OTHER INFORMATION: 99-13806-166.mis2
<220> FEATURE:
<221> NAME/KEY: misc_binding
<222> LOCATION: 12168..12187
```

```
<223> OTHER INFORMATION: 99-13806-166.mis1 complement
<220> FEATURE:
<221> NAME/KEY: misc_binding
<222> LOCATION: 12516..12535
<223> OTHER INFORMATION: 99-13799-376.mis2
<220> FEATURE:
<221> NAME/KEY: misc_binding
<222> LOCATION: 12537..12556
<223> OTHER INFORMATION: 99-13799-376.mis1 complement
<220> FEATURE:
<221> NAME/KEY: misc_binding
<222> LOCATION: 17573..17592
<223> OTHER INFORMATION: 99-13798-297.mis2
<220> FEATURE:
<221> NAME/KEY: misc_binding
<222> LOCATION: 17594..17613
<223> OTHER INFORMATION: 99-13798-297.mis1 complement
<220> FEATURE:
<221> NAME/KEY: misc_binding
<222> LOCATION: 17586..17605
<223> OTHER INFORMATION: 99-13798-284.mis2
<220> FEATURE:
<221> NAME/KEY: misc_binding
<222> LOCATION: 17607..17626
<223> OTHER INFORMATION: 99-13798-284.mis1 complement
<220> FEATURE:
<221> NAME/KEY: misc_binding
<222> LOCATION: 22059..22078
<223> OTHER INFORMATION: 99-1602-200.mis1
<220> FEATURE:
<221> NAME/KEY: misc_binding
<222> LOCATION: 22080..22099
<223> OTHER INFORMATION: 99-1602-200.mis2 complement
<220> FEATURE:
<221> NAME/KEY: misc_binding
<222> LOCATION: 28944..28963
<223> OTHER INFORMATION: 99-13794-186.mis2
<220> FEATURE:
<221> NAME/KEY: misc_binding
<222> LOCATION: 28965..28984
<223> OTHER INFORMATION: 99-13794-186.mis1 complement
<220> FEATURE:
<221> NAME/KEY: misc_binding
<222> LOCATION: 28983..29002
<223> OTHER INFORMATION: 99-13794-147.mis2
<220> FEATURE:
<221> NAME/KEY: misc_binding
<222> LOCATION: 29004..29023
<223> OTHER INFORMATION: 99-13794-147.mis1 complement
<220> FEATURE:
<221> NAME/KEY: misc_binding
<222> LOCATION: 31057..31076
<223> OTHER INFORMATION: 99-13812-384.mis2
<220> FEATURE:
<221> NAME/KEY: misc_binding
<222> LOCATION: 31078..31097
<223> OTHER INFORMATION: 99-13812-384.mis1 complement
<220> FEATURE:
<221> NAME/KEY: misc_binding
<222> LOCATION: 31746..31765
<223> OTHER INFORMATION: 99-13805-313.mis2
<220> FEATURE:
<221> NAME/KEY: misc_binding
<222> LOCATION: 31767..31786
<223> OTHER INFORMATION: 99-13805-313.mis1 complement
<220> FEATURE:
<221> NAME/KEY: misc_binding
<222> LOCATION: 34771..34790
<223> OTHER INFORMATION: 99-1587-281.mis1
<220> FEATURE:
<221> NAME/KEY: misc_binding
<222> LOCATION: 34792..34811
<223> OTHER INFORMATION: 99-1587-281.mis2 complement
<220> FEATURE:
<221> NAME/KEY: misc_binding
<222> LOCATION: 45731..45750
<223> OTHER INFORMATION: 99-1582-430.mis1
<220> FEATURE:
<221> NAME/KEY: misc_binding
```

-continued

```
<222> LOCATION: 45752..45771
<223> OTHER INFORMATION: 99-1582-430.mis2 complement
<220> FEATURE:
<221> NAME/KEY: misc_binding
<222> LOCATION: 49827..49846
<223> OTHER INFORMATION: 99-1585-465.mis2
<220> FEATURE:
<221> NAME/KEY: misc_binding
<222> LOCATION: 49848..49867
<223> OTHER INFORMATION: 99-1585-465.mis1 complement
<220> FEATURE:
<221> NAME/KEY: misc_binding
<222> LOCATION: 49835..49854
<223> OTHER INFORMATION: 99-1585-457.mis2
<220> FEATURE:
<221> NAME/KEY: misc_binding
<222> LOCATION: 49856..49875
<223> OTHER INFORMATION: 99-1585-457.mis1 complement
<220> FEATURE:
<221> NAME/KEY: misc_binding
<222> LOCATION: 49866..49885
<223> OTHER INFORMATION: 99-1585-426.mis2
<220> FEATURE:
<221> NAME/KEY: misc_binding
<222> LOCATION: 49887..49906
<223> OTHER INFORMATION: 99-1585-426.mis1 complement
<220> FEATURE:
<221> NAME/KEY: misc_binding
<222> LOCATION: 49880..49899
<223> OTHER INFORMATION: 99-1585-412.mis2
<220> FEATURE:
<221> NAME/KEY: misc_binding
<222> LOCATION: 49901..49920
<223> OTHER INFORMATION: 99-1585-412.mis1 complement
<220> FEATURE:
<221> NAME/KEY: misc_binding
<222> LOCATION: 49886..49905
<223> OTHER INFORMATION: 99-1585-406.mis2
<220> FEATURE:
<221> NAME/KEY: misc_binding
<222> LOCATION: 49907..49926
<223> OTHER INFORMATION: 99-1585-406.mis1 complement
<220> FEATURE:
<221> NAME/KEY: misc_binding
<222> LOCATION: 49901..49920
<223> OTHER INFORMATION: 99-1585-391.mis2
<220> FEATURE:
<221> NAME/KEY: misc_binding
<222> LOCATION: 49922..49941
<223> OTHER INFORMATION: 99-1585-391.mis1 complement
<220> FEATURE:
<221> NAME/KEY: misc_binding
<222> LOCATION: 49919..49938
<223> OTHER INFORMATION: 99-1585-373.mis2
<220> FEATURE:
<221> NAME/KEY: misc_binding
<222> LOCATION: 49940..49959
<223> OTHER INFORMATION: 99-1585-373.mis1 complement
<220> FEATURE:
<221> NAME/KEY: misc_binding
<222> LOCATION: 50236..50255
<223> OTHER INFORMATION: 99-1585-55.mis2
<220> FEATURE:
<221> NAME/KEY: misc_binding
<222> LOCATION: 50257..50276
<223> OTHER INFORMATION: 99-1585-55.mis1 complement
<220> FEATURE:
<221> NAME/KEY: misc_binding
<222> LOCATION: 54935..54954
<223> OTHER INFORMATION: 99-1607-373.mis2
<220> FEATURE:
<221> NAME/KEY: misc_binding
<222> LOCATION: 54956..54975
<223> OTHER INFORMATION: 99-1607-373.mis1 complement
<220> FEATURE:
<221> NAME/KEY: misc_binding
<222> LOCATION: 64219..64238
<223> OTHER INFORMATION: 99-1577-105.mis1
<220> FEATURE:
```

```
<221> NAME/KEY: misc_binding
<222> LOCATION: 64240..64259
<223> OTHER INFORMATION: 99-1577-105.mis2 complement
<220> FEATURE:
<221> NAME/KEY: misc_binding
<222> LOCATION: 65416..65435
<223> OTHER INFORMATION: 99-1591-235.mis1
<220> FEATURE:
<221> NAME/KEY: misc_binding
<222> LOCATION: 65437..65456
<223> OTHER INFORMATION: 99-1591-235.mis2 complement
<220> FEATURE:
<221> NAME/KEY: misc_binding
<222> LOCATION: 65476..65495
<223> OTHER INFORMATION: 99-1591-295.mis1
<220> FEATURE:
<221> NAME/KEY: misc_binding
<222> LOCATION: 65497..65516
<223> OTHER INFORMATION: 99-1591-295.mis2 complement
<220> FEATURE:
<221> NAME/KEY: misc_binding
<222> LOCATION: 66947..66966
<223> OTHER INFORMATION: 99-1572-315.mis1
<220> FEATURE:
<221> NAME/KEY: misc_binding
<222> LOCATION: 66968..66987
<223> OTHER INFORMATION: 99-1572-315.mis2 complement
<220> FEATURE:
<221> NAME/KEY: misc_binding
<222> LOCATION: 66967..66986
<223> OTHER INFORMATION: 99-1572-335.mis1
<220> FEATURE:
<221> NAME/KEY: misc_binding
<222> LOCATION: 66988..67007
<223> OTHER INFORMATION: 99-1572-335.mis2 complement
<220> FEATURE:
<221> NAME/KEY: misc_binding
<222> LOCATION: 67072..67091
<223> OTHER INFORMATION: 99-1572-440.mis1
<220> FEATURE:
<221> NAME/KEY: misc_binding
<222> LOCATION: 67093..67112
<223> OTHER INFORMATION: 99-1572-440.mis2 complement
<220> FEATURE:
<221> NAME/KEY: misc_binding
<222> LOCATION: 67109..67128
<223> OTHER INFORMATION: 99-1572-477.mis1
<220> FEATURE:
<221> NAME/KEY: misc_binding
<222> LOCATION: 67130..67149
<223> OTHER INFORMATION: 99-1572-477.mis2 complement
<220> FEATURE:
<221> NAME/KEY: misc_binding
<222> LOCATION: 67209..67228
<223> OTHER INFORMATION: 99-1572-578.mis1
<220> FEATURE:
<221> NAME/KEY: misc_binding
<222> LOCATION: 67230..67249
<223> OTHER INFORMATION: 99-1572-578.mis2 complement
<220> FEATURE:
<221> NAME/KEY: misc_binding
<222> LOCATION: 67413..67432
<223> OTHER INFORMATION: 5-264-188.mis1
<220> FEATURE:
<221> NAME/KEY: misc_binding
<222> LOCATION: 67434..67453
<223> OTHER INFORMATION: 5-264-188.mis2 complement
<220> FEATURE:
<221> NAME/KEY: misc_binding
<222> LOCATION: 67703..67722
<223> OTHER INFORMATION: 5-169-97.mis1
<220> FEATURE:
<221> NAME/KEY: misc_binding
<222> LOCATION: 67724..67743
<223> OTHER INFORMATION: 5-169-97.mis2 complement
<220> FEATURE:
<221> NAME/KEY: misc_binding
<222> LOCATION: 67814..67833
<223> OTHER INFORMATION: 5-169-208.mis1
```

```
<220> FEATURE:
<221> NAME/KEY: misc_binding
<222> LOCATION: 67835..67854
<223> OTHER INFORMATION: 5-169-208.mis2 complement
<220> FEATURE:
<221> NAME/KEY: misc_binding
<222> LOCATION: 67935..67954
<223> OTHER INFORMATION: 5-169-331.mis1
<220> FEATURE:
<221> NAME/KEY: misc_binding
<222> LOCATION: 67956..67975
<223> OTHER INFORMATION: 5-169-331.mis2 complement
<220> FEATURE:
<221> NAME/KEY: misc_binding
<222> LOCATION: 68193..68212
<223> OTHER INFORMATION: 5-170-238.mis1
<220> FEATURE:
<221> NAME/KEY: misc_binding
<222> LOCATION: 68214..68233
<223> OTHER INFORMATION: 5-170-238.mis2 complement
<220> FEATURE:
<221> NAME/KEY: misc_binding
<222> LOCATION: 68243..68262
<223> OTHER INFORMATION: 5-170-288.mis1
<220> FEATURE:
<221> NAME/KEY: misc_binding
<222> LOCATION: 68264..68283
<223> OTHER INFORMATION: 5-170-288.mis2 complement
<220> FEATURE:
<221> NAME/KEY: misc_binding
<222> LOCATION: 68355..68374
<223> OTHER INFORMATION: 5-170-400.mis1
<220> FEATURE:
<221> NAME/KEY: misc_binding
<222> LOCATION: 68376..68395
<223> OTHER INFORMATION: 5-170-400.mis2 complement
<220> FEATURE:
<221> NAME/KEY: misc_binding
<222> LOCATION: 68457..68476
<223> OTHER INFORMATION: 5-171-156.mis1
<220> FEATURE:
<221> NAME/KEY: misc_binding
<222> LOCATION: 68478..68497
<223> OTHER INFORMATION: 5-171-156.mis2 complement
<220> FEATURE:
<221> NAME/KEY: misc_binding
<222> LOCATION: 68505..68524
<223> OTHER INFORMATION: 5-171-204.mis1
<220> FEATURE:
<221> NAME/KEY: misc_binding
<222> LOCATION: 68526..68545
<223> OTHER INFORMATION: 5-171-204.mis2 complement
<220> FEATURE:
<221> NAME/KEY: misc_binding
<222> LOCATION: 68574..68593
<223> OTHER INFORMATION: 5-171-273.mis1
<220> FEATURE:
<221> NAME/KEY: misc_binding
<222> LOCATION: 68595..68614
<223> OTHER INFORMATION: 5-171-273.mis2 complement
<220> FEATURE:
<221> NAME/KEY: misc_binding
<222> LOCATION: 68590..68609
<223> OTHER INFORMATION: 5-171-289.mis1
<220> FEATURE:
<221> NAME/KEY: misc_binding
<222> LOCATION: 68611..68630
<223> OTHER INFORMATION: 5-171-289.mis2 complement
<220> FEATURE:
<221> NAME/KEY: misc_binding
<222> LOCATION: 70546..70565
<223> OTHER INFORMATION: 5-1-60.mis1
<220> FEATURE:
<221> NAME/KEY: misc_binding
<222> LOCATION: 70567..70586
<223> OTHER INFORMATION: 5-1-60.mis2 complement
<220> FEATURE:
<221> NAME/KEY: misc_binding
<222> LOCATION: 70708..70727
```

```
<223> OTHER INFORMATION: 5-1-222.mis1
<220> FEATURE:
<221> NAME/KEY: misc_binding
<222> LOCATION: 70729..70748
<223> OTHER INFORMATION: 5-1-222.mis2 complement
<220> FEATURE:
<221> NAME/KEY: misc_binding
<222> LOCATION: 80018..80037
<223> OTHER INFORMATION: 99-1578-99.mis1
<220> FEATURE:
<221> NAME/KEY: misc_binding
<222> LOCATION: 80039..80058
<223> OTHER INFORMATION: 99-1578-99.mis2 complement
<220> FEATURE:
<221> NAME/KEY: misc_binding
<222> LOCATION: 80098..80117
<223> OTHER INFORMATION: 99-1578-179.mis1
<220> FEATURE:
<221> NAME/KEY: misc_binding
<222> LOCATION: 80119..80138
<223> OTHER INFORMATION: 99-1578-179.mis2 complement
<220> FEATURE:
<221> NAME/KEY: misc_binding
<222> LOCATION: 80150..80169
<223> OTHER INFORMATION: 99-1578-231.mis1
<220> FEATURE:
<221> NAME/KEY: misc_binding
<222> LOCATION: 80171..80190
<223> OTHER INFORMATION: 99-1578-231.mis2 complement
<220> FEATURE:
<221> NAME/KEY: misc_binding
<222> LOCATION: 80163..80182
<223> OTHER INFORMATION: 99-1578-245.mis1
<220> FEATURE:
<221> NAME/KEY: misc_binding
<222> LOCATION: 80184..80203
<223> OTHER INFORMATION: 99-1578-245.mis2 complement
<220> FEATURE:
<221> NAME/KEY: misc_binding
<222> LOCATION: 80415..80434
<223> OTHER INFORMATION: 99-1578-496.mis1
<220> FEATURE:
<221> NAME/KEY: misc_binding
<222> LOCATION: 80436..80455
<223> OTHER INFORMATION: 99-1578-496.mis2 complement
<220> FEATURE:
<221> NAME/KEY: misc_binding
<222> LOCATION: 82070..82089
<223> OTHER INFORMATION: 5-2-30.mis1
<220> FEATURE:
<221> NAME/KEY: misc_binding
<222> LOCATION: 82091..82110
<223> OTHER INFORMATION: 5-2-30.mis2 complement
<220> FEATURE:
<221> NAME/KEY: misc_binding
<222> LOCATION: 82145..82164
<223> OTHER INFORMATION: 5-2-109.mis1
<220> FEATURE:
<221> NAME/KEY: misc_binding
<222> LOCATION: 82166..82185
<223> OTHER INFORMATION: 5-2-109.mis2 complement
<220> FEATURE:
<221> NAME/KEY: misc_binding
<222> LOCATION: 82149..82168
<223> OTHER INFORMATION: 5-2-113.mis1
<220> FEATURE:
<221> NAME/KEY: misc_binding
<222> LOCATION: 82170..82189
<223> OTHER INFORMATION: 5-2-113.mis2 complement
<220> FEATURE:
<221> NAME/KEY: misc_binding
<222> LOCATION: 82198..82217
<223> OTHER INFORMATION: 5-2-162.mis1
<220> FEATURE:
<221> NAME/KEY: misc_binding
<222> LOCATION: 82219..82238
<223> OTHER INFORMATION: 5-2-162.mis2 complement
<220> FEATURE:
<221> NAME/KEY: misc_binding
```

-continued

```
<222> LOCATION: 82214..82233
<223> OTHER INFORMATION: 5-2-178.mis1
<220> FEATURE:
<221> NAME/KEY: misc_binding
<222> LOCATION: 82235..82254
<223> OTHER INFORMATION: 5-2-178.mis2 complement
<220> FEATURE:
<221> NAME/KEY: misc_binding
<222> LOCATION: 82248..82267
<223> OTHER INFORMATION: 5-2-213.mis1
<220> FEATURE:
<221> NAME/KEY: misc_binding
<222> LOCATION: 82269..82288
<223> OTHER INFORMATION: 5-2-213.mis2 complement
<220> FEATURE:
<221> NAME/KEY: misc_binding
<222> LOCATION: 82373..82392
<223> OTHER INFORMATION: 99-1605-112.mis2
<220> FEATURE:
<221> NAME/KEY: misc_binding
<222> LOCATION: 82394..82413
<223> OTHER INFORMATION: 99-1605-112.mis1 complement
<220> FEATURE:
<221> NAME/KEY: misc_binding
<222> LOCATION: 83567..83586
<223> OTHER INFORMATION: 5-3-27.mis1
<220> FEATURE:
<221> NAME/KEY: misc_binding
<222> LOCATION: 83588..83607
<223> OTHER INFORMATION: 5-3-27.mis2 complement
<220> FEATURE:
<221> NAME/KEY: misc_binding
<222> LOCATION: 83623..83642
<223> OTHER INFORMATION: 5-3-83.mis1
<220> FEATURE:
<221> NAME/KEY: misc_binding
<222> LOCATION: 83644..83663
<223> OTHER INFORMATION: 5-3-83.mis2 complement
<220> FEATURE:
<221> NAME/KEY: misc_binding
<222> LOCATION: 83624..83643
<223> OTHER INFORMATION: 5-3-84.mis1
<220> FEATURE:
<221> NAME/KEY: misc_binding
<222> LOCATION: 83645..83664
<223> OTHER INFORMATION: 5-3-84.mis2 complement
<220> FEATURE:
<221> NAME/KEY: misc_binding
<222> LOCATION: 83788..83807
<223> OTHER INFORMATION: 5-3-248.mis1
<220> FEATURE:
<221> NAME/KEY: misc_binding
<222> LOCATION: 83809..83828
<223> OTHER INFORMATION: 5-3-248.mis2 complement
<220> FEATURE:
<221> NAME/KEY: misc_binding
<222> LOCATION: 83861..83880
<223> OTHER INFORMATION: 5-3-321.mis1
<220> FEATURE:
<221> NAME/KEY: misc_binding
<222> LOCATION: 83882..83901
<223> OTHER INFORMATION: 5-3-321.mis2 complement
<220> FEATURE:
<221> NAME/KEY: misc_binding
<222> LOCATION: 83864..83883
<223> OTHER INFORMATION: 5-3-324.mis1
<220> FEATURE:
<221> NAME/KEY: misc_binding
<222> LOCATION: 83885..83904
<223> OTHER INFORMATION: 5-3-324.mis2 complement
<220> FEATURE:
<221> NAME/KEY: misc_binding
<222> LOCATION: 83889..83908
<223> OTHER INFORMATION: 5-4-313.mis1
<220> FEATURE:
<221> NAME/KEY: misc_binding
<222> LOCATION: 83910..83929
<223> OTHER INFORMATION: 5-4-313.mis2 complement
<220> FEATURE:
```

```
<221> NAME/KEY: misc_binding
<222> LOCATION: 83917..83936
<223> OTHER INFORMATION: 5-3-377.mis1
<220> FEATURE:
<221> NAME/KEY: misc_binding
<222> LOCATION: 83938..83957
<223> OTHER INFORMATION: 5-3-377.mis2 complement
<220> FEATURE:
<221> NAME/KEY: misc_binding
<222> LOCATION: 83927..83946
<223> OTHER INFORMATION: 5-4-351.mis1
<220> FEATURE:
<221> NAME/KEY: misc_binding
<222> LOCATION: 83948..83967
<223> OTHER INFORMATION: 5-4-351.mis2 complement
<220> FEATURE:
<221> NAME/KEY: misc_binding
<222> LOCATION: 83962..83981
<223> OTHER INFORMATION: 5-4-386.mis1
<220> FEATURE:
<221> NAME/KEY: misc_binding
<222> LOCATION: 83983..84002
<223> OTHER INFORMATION: 5-4-386.mis2 complement
<220> FEATURE:
<221> NAME/KEY: misc_binding
<222> LOCATION: 83968..83987
<223> OTHER INFORMATION: 5-4-392.mis1
<220> FEATURE:
<221> NAME/KEY: misc_binding
<222> LOCATION: 83989..84008
<223> OTHER INFORMATION: 5-4-392.mis2 complement
<220> FEATURE:
<221> NAME/KEY: misc_binding
<222> LOCATION: 84027..84046
<223> OTHER INFORMATION: 5-260-255.mis1
<220> FEATURE:
<221> NAME/KEY: misc_binding
<222> LOCATION: 84048..84067
<223> OTHER INFORMATION: 5-260-255.mis2 complement
<220> FEATURE:
<221> NAME/KEY: misc_binding
<222> LOCATION: 84072..84091
<223> OTHER INFORMATION: 5-260-300.mis1
<220> FEATURE:
<221> NAME/KEY: misc_binding
<222> LOCATION: 84093..84112
<223> OTHER INFORMATION: 5-260-300.mis2 complement
<220> FEATURE:
<221> NAME/KEY: misc_binding
<222> LOCATION: 84125..84144
<223> OTHER INFORMATION: 5-260-353.mis1
<220> FEATURE:
<221> NAME/KEY: misc_binding
<222> LOCATION: 84146..84165
<223> OTHER INFORMATION: 5-260-353.mis2 complement
<220> FEATURE:
<221> NAME/KEY: misc_binding
<222> LOCATION: 85182..85201
<223> OTHER INFORMATION: 5-9-50.mis1
<220> FEATURE:
<221> NAME/KEY: misc_binding
<222> LOCATION: 85203..85222
<223> OTHER INFORMATION: 5-9-50.mis2 complement
<220> FEATURE:
<221> NAME/KEY: misc_binding
<222> LOCATION: 86239..86258
<223> OTHER INFORMATION: 5-5-21.mis1
<220> FEATURE:
<221> NAME/KEY: misc_binding
<222> LOCATION: 86260..86279
<223> OTHER INFORMATION: 5-5-21.mis2 complement
<220> FEATURE:
<221> NAME/KEY: misc_binding
<222> LOCATION: 86303..86322
<223> OTHER INFORMATION: 5-5-85.mis1
<220> FEATURE:
<221> NAME/KEY: misc_binding
<222> LOCATION: 86324..86343
<223> OTHER INFORMATION: 5-5-85.mis2 complement
```

```
-continued

<220> FEATURE:
<221> NAME/KEY: misc_binding
<222> LOCATION: 87693..87712
<223> OTHER INFORMATION: 5-202-95.mis1
<220> FEATURE:
<221> NAME/KEY: misc_binding
<222> LOCATION: 87714..87733
<223> OTHER INFORMATION: 5-202-95.mis2 complement
<220> FEATURE:
<221> NAME/KEY: misc_binding
<222> LOCATION: 87715..87734
<223> OTHER INFORMATION: 5-202-117.mis1
<220> FEATURE:
<221> NAME/KEY: misc_binding
<222> LOCATION: 87736..87755
<223> OTHER INFORMATION: 5-202-117.mis2 complement
<220> FEATURE:
<221> NAME/KEY: misc_binding
<222> LOCATION: 87767..87786
<223> OTHER INFORMATION: 5-202-169.mis1
<220> FEATURE:
<221> NAME/KEY: misc_binding
<222> LOCATION: 87788..87807
<223> OTHER INFORMATION: 5-202-169.mis2 complement
<220> FEATURE:
<221> NAME/KEY: misc_binding
<222> LOCATION: 87786..87805
<223> OTHER INFORMATION: 5-202-188.mis1
<220> FEATURE:
<221> NAME/KEY: misc_binding
<222> LOCATION: 87807..87826
<223> OTHER INFORMATION: 5-202-188.mis2 complement
<220> FEATURE:
<221> NAME/KEY: misc_binding
<222> LOCATION: 87840..87859
<223> OTHER INFORMATION: 5-202-242.mis1
<220> FEATURE:
<221> NAME/KEY: misc_binding
<222> LOCATION: 87861..87880
<223> OTHER INFORMATION: 5-202-242.mis2 complement
<220> FEATURE:
<221> NAME/KEY: misc_binding
<222> LOCATION: 87882..87901
<223> OTHER INFORMATION: 5-202-284.mis1
<220> FEATURE:
<221> NAME/KEY: misc_binding
<222> LOCATION: 87903..87922
<223> OTHER INFORMATION: 5-202-284.mis2 complement
<220> FEATURE:
<221> NAME/KEY: misc_binding
<222> LOCATION: 87960..87979
<223> OTHER INFORMATION: 5-202-362.mis1
<220> FEATURE:
<221> NAME/KEY: misc_binding
<222> LOCATION: 87981..88000
<223> OTHER INFORMATION: 5-202-362.mis2 complement
<220> FEATURE:
<221> NAME/KEY: misc_binding
<222> LOCATION: 87992..88011
<223> OTHER INFORMATION: 5-202-394.mis1
<220> FEATURE:
<221> NAME/KEY: misc_binding
<222> LOCATION: 88013..88032
<223> OTHER INFORMATION: 5-202-394.mis2 complement
<220> FEATURE:
<221> NAME/KEY: misc_binding
<222> LOCATION: 88195..88214
<223> OTHER INFORMATION: 5-7-113.mis1
<220> FEATURE:
<221> NAME/KEY: misc_binding
<222> LOCATION: 88216..88235
<223> OTHER INFORMATION: 5-7-113.mis2 complement
<220> FEATURE:
<221> NAME/KEY: misc_binding
<222> LOCATION: 88263..88282
<223> OTHER INFORMATION: 5-7-181.mis1
<220> FEATURE:
<221> NAME/KEY: misc_binding
<222> LOCATION: 88284..88303
```

```
<223> OTHER INFORMATION: 5-7-181.mis2 complement
<220> FEATURE:
<221> NAME/KEY: misc_binding
<222> LOCATION: 88277..88296
<223> OTHER INFORMATION: 5-7-195.mis1
<220> FEATURE:
<221> NAME/KEY: misc_binding
<222> LOCATION: 88298..88317
<223> OTHER INFORMATION: 5-7-195.mis2 complement
<220> FEATURE:
<221> NAME/KEY: misc_binding
<222> LOCATION: 88422..88441
<223> OTHER INFORMATION: 5-7-340.mis1
<220> FEATURE:
<221> NAME/KEY: misc_binding
<222> LOCATION: 88443..88462
<223> OTHER INFORMATION: 5-7-340.mis2 complement
<220> FEATURE:
<221> NAME/KEY: misc_binding
<222> LOCATION: 88451..88470
<223> OTHER INFORMATION: 5-7-369.mis1
<220> FEATURE:
<221> NAME/KEY: misc_binding
<222> LOCATION: 88472..88491
<223> OTHER INFORMATION: 5-7-369.mis2 complement
<220> FEATURE:
<221> NAME/KEY: misc_binding
<222> LOCATION: 88460..88479
<223> OTHER INFORMATION: 5-7-378.mis1
<220> FEATURE:
<221> NAME/KEY: misc_binding
<222> LOCATION: 88481..88500
<223> OTHER INFORMATION: 5-7-378.mis2 complement
<220> FEATURE:
<221> NAME/KEY: misc_binding
<222> LOCATION: 89374..89393
<223> OTHER INFORMATION: 5-181-57.mis1
<220> FEATURE:
<221> NAME/KEY: misc_binding
<222> LOCATION: 89395..89414
<223> OTHER INFORMATION: 5-181-57.mis2 complement
<220> FEATURE:
<221> NAME/KEY: misc_binding
<222> LOCATION: 89444..89463
<223> OTHER INFORMATION: 5-181-127.mis1
<220> FEATURE:
<221> NAME/KEY: misc_binding
<222> LOCATION: 89465..89484
<223> OTHER INFORMATION: 5-181-127.mis2 complement
<220> FEATURE:
<221> NAME/KEY: misc_binding
<222> LOCATION: 89451..89470
<223> OTHER INFORMATION: 5-181-134.mis1
<220> FEATURE:
<221> NAME/KEY: misc_binding
<222> LOCATION: 89472..89491
<223> OTHER INFORMATION: 5-181-134.mis2 complement
<220> FEATURE:
<221> NAME/KEY: misc_binding
<222> LOCATION: 89638..89657
<223> OTHER INFORMATION: 5-181-321.mis1
<220> FEATURE:
<221> NAME/KEY: misc_binding
<222> LOCATION: 89659..89678
<223> OTHER INFORMATION: 5-181-321.mis2 complement
<220> FEATURE:
<221> NAME/KEY: misc_binding
<222> LOCATION: 92740..92759
<223> OTHER INFORMATION: 5-10-39.mis1
<220> FEATURE:
<221> NAME/KEY: misc_binding
<222> LOCATION: 92761..92780
<223> OTHER INFORMATION: 5-10-39.mis2 complement
<220> FEATURE:
<221> NAME/KEY: misc_binding
<222> LOCATION: 93003..93022
<223> OTHER INFORMATION: 5-10-302.mis1
<220> FEATURE:
<221> NAME/KEY: misc_binding
```

```
<222> LOCATION: 93024..93043
<223> OTHER INFORMATION: 5-10-302.mis2 complement
<220> FEATURE:
<221> NAME/KEY: misc_binding
<222> LOCATION: 93035..93054
<223> OTHER INFORMATION: 5-10-334.mis1
<220> FEATURE:
<221> NAME/KEY: misc_binding
<222> LOCATION: 93056..93075
<223> OTHER INFORMATION: 5-10-334.mis2 complement
<220> FEATURE:
<221> NAME/KEY: misc_binding
<222> LOCATION: 93227..93246
<223> OTHER INFORMATION: 5-11-158.mis1
<220> FEATURE:
<221> NAME/KEY: misc_binding
<222> LOCATION: 93248..93267
<223> OTHER INFORMATION: 5-11-158.mis2 complement
<220> FEATURE:
<221> NAME/KEY: misc_binding
<222> LOCATION: 93299..93318
<223> OTHER INFORMATION: 5-11-230.mis1
<220> FEATURE:
<221> NAME/KEY: misc_binding
<222> LOCATION: 93320..93339
<223> OTHER INFORMATION: 5-11-230.mis2 complement
<220> FEATURE:
<221> NAME/KEY: misc_binding
<222> LOCATION: 93303..93322
<223> OTHER INFORMATION: 5-11-234.mis1
<220> FEATURE:
<221> NAME/KEY: misc_binding
<222> LOCATION: 93324..93343
<223> OTHER INFORMATION: 5-11-234.mis2 complement
<220> FEATURE:
<221> NAME/KEY: misc_binding
<222> LOCATION: 93368..93387
<223> OTHER INFORMATION: 5-11-299.mis1
<220> FEATURE:
<221> NAME/KEY: misc_binding
<222> LOCATION: 93389..93408
<223> OTHER INFORMATION: 5-11-299.mis2 complement
<220> FEATURE:
<221> NAME/KEY: misc_binding
<222> LOCATION: 93373..93392
<223> OTHER INFORMATION: 5-11-304.mis1
<220> FEATURE:
<221> NAME/KEY: misc_binding
<222> LOCATION: 93394..93413
<223> OTHER INFORMATION: 5-11-304.mis2 complement
<220> FEATURE:
<221> NAME/KEY: misc_binding
<222> LOCATION: 93398..93417
<223> OTHER INFORMATION: 5-11-329.mis1
<220> FEATURE:
<221> NAME/KEY: misc_binding
<222> LOCATION: 93419..93438
<223> OTHER INFORMATION: 5-11-329.mis2 complement
<220> FEATURE:
<221> NAME/KEY: misc_binding
<222> LOCATION: 93495..93514
<223> OTHER INFORMATION: 5-12-56.mis1
<220> FEATURE:
<221> NAME/KEY: misc_binding
<222> LOCATION: 93516..93535
<223> OTHER INFORMATION: 5-12-56.mis2 complement
<220> FEATURE:
<221> NAME/KEY: misc_binding
<222> LOCATION: 93706..93725
<223> OTHER INFORMATION: 5-12-267.mis1
<220> FEATURE:
<221> NAME/KEY: misc_binding
<222> LOCATION: 93727..93746
<223> OTHER INFORMATION: 5-12-267.mis2 complement
<220> FEATURE:
<221> NAME/KEY: misc_binding
<222> LOCATION: 93883..93902
<223> OTHER INFORMATION: 5-13-145.mis1
<220> FEATURE:
```

-continued

```
<221> NAME/KEY: misc_binding
<222> LOCATION: 93904..93923
<223> OTHER INFORMATION: 5-13-145.mis2 complement
<220> FEATURE:
<221> NAME/KEY: misc_binding
<222> LOCATION: 94150..94169
<223> OTHER INFORMATION: 5-14-44.mis1
<220> FEATURE:
<221> NAME/KEY: misc_binding
<222> LOCATION: 94171..94190
<223> OTHER INFORMATION: 5-14-44.mis2 complement
<220> FEATURE:
<221> NAME/KEY: misc_binding
<222> LOCATION: 94198..94217
<223> OTHER INFORMATION: 5-14-93.mis1
<220> FEATURE:
<221> NAME/KEY: misc_binding
<222> LOCATION: 94219..94238
<223> OTHER INFORMATION: 5-14-93.mis2 complement
<220> FEATURE:
<221> NAME/KEY: misc_binding
<222> LOCATION: 94249..94268
<223> OTHER INFORMATION: 5-14-144.mis1
<220> FEATURE:
<221> NAME/KEY: misc_binding
<222> LOCATION: 94270..94289
<223> OTHER INFORMATION: 5-14-144.mis2 complement
<220> FEATURE:
<221> NAME/KEY: misc_binding
<222> LOCATION: 94270..94289
<223> OTHER INFORMATION: 5-14-165.mis1
<220> FEATURE:
<221> NAME/KEY: misc_binding
<222> LOCATION: 94291..94310
<223> OTHER INFORMATION: 5-14-165.mis2 complement
<220> FEATURE:
<221> NAME/KEY: misc_binding
<222> LOCATION: 94402..94421
<223> OTHER INFORMATION: 5-14-297.mis1
<220> FEATURE:
<221> NAME/KEY: misc_binding
<222> LOCATION: 94423..94442
<223> OTHER INFORMATION: 5-14-297.mis2 complement
<220> FEATURE:
<221> NAME/KEY: misc_binding
<222> LOCATION: 94412..94431
<223> OTHER INFORMATION: 5-14-307.mis1
<220> FEATURE:
<221> NAME/KEY: misc_binding
<222> LOCATION: 94433..94452
<223> OTHER INFORMATION: 5-14-307.mis2 complement
<220> FEATURE:
<221> NAME/KEY: misc_binding
<222> LOCATION: 94700..94719
<223> OTHER INFORMATION: 5-15-219.mis1
<220> FEATURE:
<221> NAME/KEY: misc_binding
<222> LOCATION: 94721..94740
<223> OTHER INFORMATION: 5-15-219.mis2 complement
<220> FEATURE:
<221> NAME/KEY: misc_binding
<222> LOCATION: 94969..94988
<223> OTHER INFORMATION: 5-16-157.mis1
<220> FEATURE:
<221> NAME/KEY: misc_binding
<222> LOCATION: 94990..95009
<223> OTHER INFORMATION: 5-16-157.mis2 complement
<220> FEATURE:
<221> NAME/KEY: misc_binding
<222> LOCATION: 95241..95260
<223> OTHER INFORMATION: 5-17-140.mis1
<220> FEATURE:
<221> NAME/KEY: misc_binding
<222> LOCATION: 95262..95281
<223> OTHER INFORMATION: 5-17-140.mis2 complement
<220> FEATURE:
<221> NAME/KEY: misc_binding
<222> LOCATION: 95320..95339
<223> OTHER INFORMATION: 5-18-51.mis1
```

```
<220> FEATURE:
<221> NAME/KEY: misc_binding
<222> LOCATION: 95341..95360
<223> OTHER INFORMATION: 5-18-51.mis2 complement
<220> FEATURE:
<221> NAME/KEY: misc_binding
<222> LOCATION: 95477..95496
<223> OTHER INFORMATION: 5-18-208.mis1
<220> FEATURE:
<221> NAME/KEY: misc_binding
<222> LOCATION: 95498..95517
<223> OTHER INFORMATION: 5-18-208.mis2 complement
<220> FEATURE:
<221> NAME/KEY: misc_binding
<222> LOCATION: 95750..95769
<223> OTHER INFORMATION: 5-300-238.mis1
<220> FEATURE:
<221> NAME/KEY: misc_binding
<222> LOCATION: 95771..95790
<223> OTHER INFORMATION: 5-300-238.mis2 complement
<220> FEATURE:
<221> NAME/KEY: misc_binding
<222> LOCATION: 95799..95818
<223> OTHER INFORMATION: 5-300-287.mis1
<220> FEATURE:
<221> NAME/KEY: misc_binding
<222> LOCATION: 95820..95839
<223> OTHER INFORMATION: 5-300-287.mis2 complement
<220> FEATURE:
<221> NAME/KEY: misc_binding
<222> LOCATION: 96125..96144
<223> OTHER INFORMATION: 5-262-49.mis1
<220> FEATURE:
<221> NAME/KEY: misc_binding
<222> LOCATION: 96146..96165
<223> OTHER INFORMATION: 5-262-49.mis2 complement
<220> FEATURE:
<221> NAME/KEY: misc_binding
<222> LOCATION: 96161..96180
<223> OTHER INFORMATION: 5-262-85.mis1
<220> FEATURE:
<221> NAME/KEY: misc_binding
<222> LOCATION: 96182..96201
<223> OTHER INFORMATION: 5-262-85.mis2 complement
<220> FEATURE:
<221> NAME/KEY: misc_binding
<222> LOCATION: 96330..96349
<223> OTHER INFORMATION: 5-262-254.mis1
<220> FEATURE:
<221> NAME/KEY: misc_binding
<222> LOCATION: 96351..96370
<223> OTHER INFORMATION: 5-262-254.mis2 complement
<220> FEATURE:
<221> NAME/KEY: misc_binding
<222> LOCATION: 96931..96950
<223> OTHER INFORMATION: 5-263-404.mis1
<220> FEATURE:
<221> NAME/KEY: misc_binding
<222> LOCATION: 96952..96971
<223> OTHER INFORMATION: 5-263-404.mis2 complement
<220> FEATURE:
<221> NAME/KEY: misc_binding
<222> LOCATION: 97124..97143
<223> OTHER INFORMATION: 5-265-244.mis1
<220> FEATURE:
<221> NAME/KEY: misc_binding
<222> LOCATION: 97145..97164
<223> OTHER INFORMATION: 5-265-244.mis2 complement
<220> FEATURE:
<221> NAME/KEY: misc_binding
<222> LOCATION: 97256..97275
<223> OTHER INFORMATION: 5-265-376.mis1
<220> FEATURE:
<221> NAME/KEY: misc_binding
<222> LOCATION: 97277..97296
<223> OTHER INFORMATION: 5-265-376.mis2 complement
<220> FEATURE:
<221> NAME/KEY: misc_binding
<222> LOCATION: 102247..102266
```

```
<223> OTHER INFORMATION: 99-7183-338.mis2
<220> FEATURE:
<221> NAME/KEY: misc_binding
<222> LOCATION: 102268..102287
<223> OTHER INFORMATION: 99-7183-338.mis1 complement
<220> FEATURE:
<221> NAME/KEY: misc_binding
<222> LOCATION: 105917..105936
<223> OTHER INFORMATION: 99-7207-138.mis2
<220> FEATURE:
<221> NAME/KEY: misc_binding
<222> LOCATION: 105938..105957
<223> OTHER INFORMATION: 99-7207-138.mis1 complement
<220> FEATURE:
<221> NAME/KEY: misc_binding
<222> LOCATION: 255..301
<223> OTHER INFORMATION: 99-1601-278.probe
<220> FEATURE:
<221> NAME/KEY: misc_binding
<222> LOCATION: 379..425
<223> OTHER INFORMATION: 99-1601-402.probe
<220> FEATURE:
<221> NAME/KEY: misc_binding
<222> LOCATION: 449..495
<223> OTHER INFORMATION: 99-1601-472.probe
<220> FEATURE:
<221> NAME/KEY: misc_binding
<222> LOCATION: 2932..2978
<223> OTHER INFORMATION: 99-13801-100.probe
<220> FEATURE:
<221> NAME/KEY: misc_binding
<222> LOCATION: 12144..12190
<223> OTHER INFORMATION: 99-13806-166.probe
<220> FEATURE:
<221> NAME/KEY: misc_binding
<222> LOCATION: 12513..12559
<223> OTHER INFORMATION: 99-13799-376.probe
<220> FEATURE:
<221> NAME/KEY: misc_binding
<222> LOCATION: 17570..17616
<223> OTHER INFORMATION: 99-13798-297.probe
<220> FEATURE:
<221> NAME/KEY: misc_binding
<222> LOCATION: 17583..17629
<223> OTHER INFORMATION: 99-13798-284.probe
<220> FEATURE:
<221> NAME/KEY: misc_binding
<222> LOCATION: 22056..22102
<223> OTHER INFORMATION: 99-1602-200.probe
<220> FEATURE:
<221> NAME/KEY: misc_binding
<222> LOCATION: 28941..28987
<223> OTHER INFORMATION: 99-13794-186.probe
<220> FEATURE:
<221> NAME/KEY: misc_binding
<222> LOCATION: 28980..29026
<223> OTHER INFORMATION: 99-13794-147.probe
<220> FEATURE:
<221> NAME/KEY: misc_binding
<222> LOCATION: 31054..31100
<223> OTHER INFORMATION: 99-13812-384.probe
<220> FEATURE:
<221> NAME/KEY: misc_binding
<222> LOCATION: 31743..31789
<223> OTHER INFORMATION: 99-13805-313.probe
<220> FEATURE:
<221> NAME/KEY: misc_binding
<222> LOCATION: 34768..34814
<223> OTHER INFORMATION: 99-1587-281.probe
<220> FEATURE:
<221> NAME/KEY: misc_binding
<222> LOCATION: 45728..45774
<223> OTHER INFORMATION: 99-1582-430.probe
<220> FEATURE:
<221> NAME/KEY: misc_binding
<222> LOCATION: 49824..49870
<223> OTHER INFORMATION: 99-1585-465.probe
<220> FEATURE:
<221> NAME/KEY: misc_binding
```

-continued

```
<222> LOCATION: 49832..49878
<223> OTHER INFORMATION: 99-1585-457.probe
<220> FEATURE:
<221> NAME/KEY: misc_binding
<222> LOCATION: 49863..49909
<223> OTHER INFORMATION: 99-1585-426.probe
<220> FEATURE:
<221> NAME/KEY: misc_binding
<222> LOCATION: 49877..49923
<223> OTHER INFORMATION: 99-1585-412.probe
<220> FEATURE:
<221> NAME/KEY: misc_binding
<222> LOCATION: 49883..49929
<223> OTHER INFORMATION: 99-1585-406.probe
<220> FEATURE:
<221> NAME/KEY: misc_binding
<222> LOCATION: 49898..49944
<223> OTHER INFORMATION: 99-1585-391.probe
<220> FEATURE:
<221> NAME/KEY: misc_binding
<222> LOCATION: 49916..49962
<223> OTHER INFORMATION: 99-1585-373.probe
<220> FEATURE:
<221> NAME/KEY: misc_binding
<222> LOCATION: 50233..50279
<223> OTHER INFORMATION: 99-1585-55.probe
<220> FEATURE:
<221> NAME/KEY: misc_binding
<222> LOCATION: 54932..54978
<223> OTHER INFORMATION: 99-1607-373.probe
<220> FEATURE:
<221> NAME/KEY: misc_binding
<222> LOCATION: 64216..64262
<223> OTHER INFORMATION: 99-1577-105.probe
<220> FEATURE:
<221> NAME/KEY: misc_binding
<222> LOCATION: 65413..65459
<223> OTHER INFORMATION: 99-1591-235.probe
<220> FEATURE:
<221> NAME/KEY: misc_binding
<222> LOCATION: 65473..65519
<223> OTHER INFORMATION: 99-1591-295.probe
<220> FEATURE:
<221> NAME/KEY: misc_binding
<222> LOCATION: 66944..66990
<223> OTHER INFORMATION: 99-1572-315.probe
<220> FEATURE:
<221> NAME/KEY: misc_binding
<222> LOCATION: 66964..67010
<223> OTHER INFORMATION: 99-1572-335.probe
<220> FEATURE:
<221> NAME/KEY: misc_binding
<222> LOCATION: 67069..67115
<223> OTHER INFORMATION: 99-1572-440.probe
<220> FEATURE:
<221> NAME/KEY: misc_binding
<222> LOCATION: 67106..67152
<223> OTHER INFORMATION: 99-1572-477.probe
<220> FEATURE:
<221> NAME/KEY: misc_binding
<222> LOCATION: 67206..67252
<223> OTHER INFORMATION: 99-1572-578.probe
<220> FEATURE:
<221> NAME/KEY: misc_binding
<222> LOCATION: 67410..67456
<223> OTHER INFORMATION: 5-264-188.probe
<220> FEATURE:
<221> NAME/KEY: misc_binding
<222> LOCATION: 67700..67746
<223> OTHER INFORMATION: 5-169-97.probe
<220> FEATURE:
<221> NAME/KEY: misc_binding
<222> LOCATION: 67811..67857
<223> OTHER INFORMATION: 5-169-208.probe
<220> FEATURE:
<221> NAME/KEY: misc_binding
<222> LOCATION: 67932..67978
<223> OTHER INFORMATION: 5-169-331.probe
<220> FEATURE:
```

```
<221> NAME/KEY: misc_binding
<222> LOCATION: 68190..68236
<223> OTHER INFORMATION: 5-170-238.probe
<220> FEATURE:
<221> NAME/KEY: misc_binding
<222> LOCATION: 68240..68286
<223> OTHER INFORMATION: 5-170-288.probe
<220> FEATURE:
<221> NAME/KEY: misc_binding
<222> LOCATION: 68352..68398
<223> OTHER INFORMATION: 5-170-400.probe
<220> FEATURE:
<221> NAME/KEY: misc_binding
<222> LOCATION: 68454..68500
<223> OTHER INFORMATION: 5-171-156.probe
<220> FEATURE:
<221> NAME/KEY: misc_binding
<222> LOCATION: 68502..68548
<223> OTHER INFORMATION: 5-171-204.probe
<220> FEATURE:
<221> NAME/KEY: misc_binding
<222> LOCATION: 68571..68617
<223> OTHER INFORMATION: 5-171-273.probe
<220> FEATURE:
<221> NAME/KEY: misc_binding
<222> LOCATION: 68587..68633
<223> OTHER INFORMATION: 5-171-289.probe
<220> FEATURE:
<221> NAME/KEY: misc_binding
<222> LOCATION: 70543..70589
<223> OTHER INFORMATION: 5-1-60.probe
<220> FEATURE:
<221> NAME/KEY: misc_binding
<222> LOCATION: 70705..70751
<223> OTHER INFORMATION: 5-1-222.probe
<220> FEATURE:
<221> NAME/KEY: misc_binding
<222> LOCATION: 80015..80061
<223> OTHER INFORMATION: 99-1578-99.probe
<220> FEATURE:
<221> NAME/KEY: misc_binding
<222> LOCATION: 80095..80141
<223> OTHER INFORMATION: 99-1578-179.probe
<220> FEATURE:
<221> NAME/KEY: misc_binding
<222> LOCATION: 80147..80193
<223> OTHER INFORMATION: 99-1578-231.probe
<220> FEATURE:
<221> NAME/KEY: misc_binding
<222> LOCATION: 80160..80206
<223> OTHER INFORMATION: 99-1578-245.probe
<220> FEATURE:
<221> NAME/KEY: misc_binding
<222> LOCATION: 80412..80458
<223> OTHER INFORMATION: 99-1578-496.probe
<220> FEATURE:
<221> NAME/KEY: misc_binding
<222> LOCATION: 82067..82113
<223> OTHER INFORMATION: 5-2-30.probe
<220> FEATURE:
<221> NAME/KEY: misc_binding
<222> LOCATION: 82142..82188
<223> OTHER INFORMATION: 5-2-109.probe
<220> FEATURE:
<221> NAME/KEY: misc_binding
<222> LOCATION: 82146..82192
<223> OTHER INFORMATION: 5-2-113.probe
<220> FEATURE:
<221> NAME/KEY: misc_binding
<222> LOCATION: 82195..82241
<223> OTHER INFORMATION: 5-2-162.probe
<220> FEATURE:
<221> NAME/KEY: misc_binding
<222> LOCATION: 82211..82257
<223> OTHER INFORMATION: 5-2-178.probe
<220> FEATURE:
<221> NAME/KEY: misc_binding
<222> LOCATION: 82245..82291
<223> OTHER INFORMATION: 5-2-213.probe
```

```
<220> FEATURE:
<221> NAME/KEY: misc_binding
<222> LOCATION: 82370..82416
<223> OTHER INFORMATION: 99-1605-112.probe
<220> FEATURE:
<221> NAME/KEY: misc_binding
<222> LOCATION: 83564..83610
<223> OTHER INFORMATION: 5-3-27.probe
<220> FEATURE:
<221> NAME/KEY: misc_binding
<222> LOCATION: 83620..83666
<223> OTHER INFORMATION: 5-3-83.probe
<220> FEATURE:
<221> NAME/KEY: misc_binding
<222> LOCATION: 83621..83667
<223> OTHER INFORMATION: 5-3-84.probe
<220> FEATURE:
<221> NAME/KEY: misc_binding
<222> LOCATION: 83785..83831
<223> OTHER INFORMATION: 5-3-248.probe
<220> FEATURE:
<221> NAME/KEY: misc_binding
<222> LOCATION: 83858..83904
<223> OTHER INFORMATION: 5-3-321.probe
<220> FEATURE:
<221> NAME/KEY: misc_binding
<222> LOCATION: 83861..83907
<223> OTHER INFORMATION: 5-3-324.probe
<220> FEATURE:
<221> NAME/KEY: misc_binding
<222> LOCATION: 83886..83932
<223> OTHER INFORMATION: 5-4-313.probe
<220> FEATURE:
<221> NAME/KEY: misc_binding
<222> LOCATION: 83914..83960
<223> OTHER INFORMATION: 5-3-377.probe
<220> FEATURE:
<221> NAME/KEY: misc_binding
<222> LOCATION: 83924..83970
<223> OTHER INFORMATION: 5-4-351.probe
<220> FEATURE:
<221> NAME/KEY: misc_binding
<222> LOCATION: 83959..84005
<223> OTHER INFORMATION: 5-4-386.probe
<220> FEATURE:
<221> NAME/KEY: misc_binding
<222> LOCATION: 83965..84011
<223> OTHER INFORMATION: 5-4-392.probe
<220> FEATURE:
<221> NAME/KEY: misc_binding
<222> LOCATION: 84024..84070
<223> OTHER INFORMATION: 5-260-255.probe
<220> FEATURE:
<221> NAME/KEY: misc_binding
<222> LOCATION: 84069..84115
<223> OTHER INFORMATION: 5-260-300.probe
<220> FEATURE:
<221> NAME/KEY: misc_binding
<222> LOCATION: 84122..84168
<223> OTHER INFORMATION: 5-260-353.probe
<220> FEATURE:
<221> NAME/KEY: misc_binding
<222> LOCATION: 85179..85225
<223> OTHER INFORMATION: 5-9-50.probe
<220> FEATURE:
<221> NAME/KEY: misc_binding
<222> LOCATION: 86236..86282
<223> OTHER INFORMATION: 5-5-21.probe
<220> FEATURE:
<221> NAME/KEY: misc_binding
<222> LOCATION: 86300..86346
<223> OTHER INFORMATION: 5-5-85.probe
<220> FEATURE:
<221> NAME/KEY: misc_binding
<222> LOCATION: 87690..87736
<223> OTHER INFORMATION: 5-202-95.probe
<220> FEATURE:
<221> NAME/KEY: misc_binding
<222> LOCATION: 87712..87758
```

```
<223> OTHER INFORMATION: 5-202-117.probe
<220> FEATURE:
<221> NAME/KEY: misc_binding
<222> LOCATION: 87764..87810
<223> OTHER INFORMATION: 5-202-169.probe
<220> FEATURE:
<221> NAME/KEY: misc_binding
<222> LOCATION: 87783..87829
<223> OTHER INFORMATION: 5-202-188.probe
<220> FEATURE:
<221> NAME/KEY: misc_binding
<222> LOCATION: 87837..87883
<223> OTHER INFORMATION: 5-202-242.probe
<220> FEATURE:
<221> NAME/KEY: misc_binding
<222> LOCATION: 87879..87925
<223> OTHER INFORMATION: 5-202-284.probe
<220> FEATURE:
<221> NAME/KEY: misc_binding
<222> LOCATION: 87957..88003
<223> OTHER INFORMATION: 5-202-362.probe
<220> FEATURE:
<221> NAME/KEY: misc_binding
<222> LOCATION: 87989..88035
<223> OTHER INFORMATION: 5-202-394.probe
<220> FEATURE:
<221> NAME/KEY: misc_binding
<222> LOCATION: 88192..88238
<223> OTHER INFORMATION: 5-7-113.probe
<220> FEATURE:
<221> NAME/KEY: misc_binding
<222> LOCATION: 88260..88306
<223> OTHER INFORMATION: 5-7-181.probe
<220> FEATURE:
<221> NAME/KEY: misc_binding
<222> LOCATION: 88274..88320
<223> OTHER INFORMATION: 5-7-195.probe
<220> FEATURE:
<221> NAME/KEY: misc_binding
<222> LOCATION: 88419..88465
<223> OTHER INFORMATION: 5-7-340.probe
<220> FEATURE:
<221> NAME/KEY: misc_binding
<222> LOCATION: 88448..88494
<223> OTHER INFORMATION: 5-7-369.probe
<220> FEATURE:
<221> NAME/KEY: misc_binding
<222> LOCATION: 88457..88503
<223> OTHER INFORMATION: 5-7-378.probe
<220> FEATURE:
<221> NAME/KEY: misc_binding
<222> LOCATION: 89371..89417
<223> OTHER INFORMATION: 5-181-57.probe
<220> FEATURE:
<221> NAME/KEY: misc_binding
<222> LOCATION: 89441..89487
<223> OTHER INFORMATION: 5-181-127.probe
<220> FEATURE:
<221> NAME/KEY: misc_binding
<222> LOCATION: 89448..89494
<223> OTHER INFORMATION: 5-181-134.probe
<220> FEATURE:
<221> NAME/KEY: misc_binding
<222> LOCATION: 89635..89681
<223> OTHER INFORMATION: 5-181-321.probe
<220> FEATURE:
<221> NAME/KEY: misc_binding
<222> LOCATION: 92737..92783
<223> OTHER INFORMATION: 5-10-39.probe
<220> FEATURE:
<221> NAME/KEY: misc_binding
<222> LOCATION: 93000..93046
<223> OTHER INFORMATION: 5-10-302.probe
<220> FEATURE:
<221> NAME/KEY: misc_binding
<222> LOCATION: 93032..93078
<223> OTHER INFORMATION: 5-10-334.probe
<220> FEATURE:
<221> NAME/KEY: misc_binding
```

```
<222> LOCATION: 93224..93270
<223> OTHER INFORMATION: 5-11-158.probe
<220> FEATURE:
<221> NAME/KEY: misc_binding
<222> LOCATION: 93296..93342
<223> OTHER INFORMATION: 5-11-230.probe
<220> FEATURE:
<221> NAME/KEY: misc_binding
<222> LOCATION: 93300..93346
<223> OTHER INFORMATION: 5-11-234.probe
<220> FEATURE:
<221> NAME/KEY: misc_binding
<222> LOCATION: 93365..93411
<223> OTHER INFORMATION: 5-11-299.probe
<220> FEATURE:
<221> NAME/KEY: misc_binding
<222> LOCATION: 93370..93416
<223> OTHER INFORMATION: 5-11-304.probe
<220> FEATURE:
<221> NAME/KEY: misc_binding
<222> LOCATION: 93395..93441
<223> OTHER INFORMATION: 5-11-329.probe
<220> FEATURE:
<221> NAME/KEY: misc_binding
<222> LOCATION: 93492..93538
<223> OTHER INFORMATION: 5-12-56.probe
<220> FEATURE:
<221> NAME/KEY: misc_binding
<222> LOCATION: 93703..93749
<223> OTHER INFORMATION: 5-12-267.probe
<220> FEATURE:
<221> NAME/KEY: misc_binding
<222> LOCATION: 93880..93926
<223> OTHER INFORMATION: 5-13-145.probe
<220> FEATURE:
<221> NAME/KEY: misc_binding
<222> LOCATION: 94147..94193
<223> OTHER INFORMATION: 5-14-44.probe
<220> FEATURE:
<221> NAME/KEY: misc_binding
<222> LOCATION: 94195..94241
<223> OTHER INFORMATION: 5-14-93.probe
<220> FEATURE:
<221> NAME/KEY: misc_binding
<222> LOCATION: 94246..94292
<223> OTHER INFORMATION: 5-14-144.probe
<220> FEATURE:
<221> NAME/KEY: misc_binding
<222> LOCATION: 94267..94313
<223> OTHER INFORMATION: 5-14-165.probe
<220> FEATURE:
<221> NAME/KEY: misc_binding
<222> LOCATION: 94399..94445
<223> OTHER INFORMATION: 5-14-297.probe
<220> FEATURE:
<221> NAME/KEY: misc_binding
<222> LOCATION: 94409..94455
<223> OTHER INFORMATION: 5-14-307.probe
<220> FEATURE:
<221> NAME/KEY: misc_binding
<222> LOCATION: 94697..94743
<223> OTHER INFORMATION: 5-15-219.probe
<220> FEATURE:
<221> NAME/KEY: misc_binding
<222> LOCATION: 94966..95012
<223> OTHER INFORMATION: 5-16-157.probe
<220> FEATURE:
<221> NAME/KEY: misc_binding
<222> LOCATION: 95238..95284
<223> OTHER INFORMATION: 5-17-140.probe
<220> FEATURE:
<221> NAME/KEY: misc_binding
<222> LOCATION: 95317..95363
<223> OTHER INFORMATION: 5-18-51.probe
<220> FEATURE:
<221> NAME/KEY: misc_binding
<222> LOCATION: 95474..95520
<223> OTHER INFORMATION: 5-18-208.probe
<220> FEATURE:
```

```
<221> NAME/KEY: misc_binding
<222> LOCATION: 95747..95793
<223> OTHER INFORMATION: 5-300-238.probe
<220> FEATURE:
<221> NAME/KEY: misc_binding
<222> LOCATION: 95796..95842
<223> OTHER INFORMATION: 5-300-287.probe
<220> FEATURE:
<221> NAME/KEY: misc_binding
<222> LOCATION: 96122..96168
<223> OTHER INFORMATION: 5-262-49.probe
<220> FEATURE:
<221> NAME/KEY: misc_binding
<222> LOCATION: 96158..96204
<223> OTHER INFORMATION: 5-262-85.probe
<220> FEATURE:
<221> NAME/KEY: misc_binding
<222> LOCATION: 96327..96373
<223> OTHER INFORMATION: 5-262-254.probe
<220> FEATURE:
<221> NAME/KEY: misc_binding
<222> LOCATION: 96928..96974
<223> OTHER INFORMATION: 5-263-404.probe
<220> FEATURE:
<221> NAME/KEY: misc_binding
<222> LOCATION: 97121..97167
<223> OTHER INFORMATION: 5-265-244.probe
<220> FEATURE:
<221> NAME/KEY: misc_binding
<222> LOCATION: 97253..97299
<223> OTHER INFORMATION: 5-265-376.probe
<220> FEATURE:
<221> NAME/KEY: misc_binding
<222> LOCATION: 102244..102290
<223> OTHER INFORMATION: 99-7183-338.probe
<220> FEATURE:
<221> NAME/KEY: misc_binding
<222> LOCATION: 105914..105960
<223> OTHER INFORMATION: 99-7207-138.probe
<220> FEATURE:
<221> NAME/KEY: misc_binding
<222> LOCATION: 1..18
<223> OTHER INFORMATION: 99-1601.pu
<220> FEATURE:
<221> NAME/KEY: misc_binding
<222> LOCATION: 486..506
<223> OTHER INFORMATION: 99-1601.rp complement
<220> FEATURE:
<221> NAME/KEY: misc_binding
<222> LOCATION: 2607..2627
<223> OTHER INFORMATION: 99-13801.rp
<220> FEATURE:
<221> NAME/KEY: misc_binding
<222> LOCATION: 3035..3054
<223> OTHER INFORMATION: 99-13801.pu complement
<220> FEATURE:
<221> NAME/KEY: misc_binding
<222> LOCATION: 11883..11902
<223> OTHER INFORMATION: 99-13806.rp
<220> FEATURE:
<221> NAME/KEY: misc_binding
<222> LOCATION: 12313..12331
<223> OTHER INFORMATION: 99-13806.pu complement
<220> FEATURE:
<221> NAME/KEY: misc_binding
<222> LOCATION: 12379..12399
<223> OTHER INFORMATION: 99-13799.rp
<220> FEATURE:
<221> NAME/KEY: misc_binding
<222> LOCATION: 12889..12909
<223> OTHER INFORMATION: 99-13799.pu complement
<220> FEATURE:
<221> NAME/KEY: misc_binding
<222> LOCATION: 17442..17462
<223> OTHER INFORMATION: 99-13798.rp
<220> FEATURE:
<221> NAME/KEY: misc_binding
<222> LOCATION: 17868..17887
<223> OTHER INFORMATION: 99-13798.pu complement
```

```
-continued

<220> FEATURE:
<221> NAME/KEY: misc_binding
<222> LOCATION: 21881..21899
<223> OTHER INFORMATION: 99-1602.pu
<220> FEATURE:
<221> NAME/KEY: misc_binding
<222> LOCATION: 22487..22506
<223> OTHER INFORMATION: 99-1602.rp complement
<220> FEATURE:
<221> NAME/KEY: misc_binding
<222> LOCATION: 28669..28689
<223> OTHER INFORMATION: 99-13794.rp
<220> FEATURE:
<221> NAME/KEY: misc_binding
<222> LOCATION: 29131..29149
<223> OTHER INFORMATION: 99-13794.pu complement
<220> FEATURE:
<221> NAME/KEY: misc_binding
<222> LOCATION: 30941..30961
<223> OTHER INFORMATION: 99-13812.rp
<220> FEATURE:
<221> NAME/KEY: misc_binding
<222> LOCATION: 31437..31457
<223> OTHER INFORMATION: 99-13812.pu complement
<220> FEATURE:
<221> NAME/KEY: misc_binding
<222> LOCATION: 31560..31579
<223> OTHER INFORMATION: 99-13805.rp
<220> FEATURE:
<221> NAME/KEY: misc_binding
<222> LOCATION: 32057..32075
<223> OTHER INFORMATION: 99-13805.pu complement
<220> FEATURE:
<221> NAME/KEY: misc_binding
<222> LOCATION: 34515..34535
<223> OTHER INFORMATION: 99-1587.pu
<220> FEATURE:
<221> NAME/KEY: misc_binding
<222> LOCATION: 34890..34909
<223> OTHER INFORMATION: 99-1587.rp complement
<220> FEATURE:
<221> NAME/KEY: misc_binding
<222> LOCATION: 45325..45343
<223> OTHER INFORMATION: 99-1582.pu
<220> FEATURE:
<221> NAME/KEY: misc_binding
<222> LOCATION: 46000..46018
<223> OTHER INFORMATION: 99-1582.rp complement
<220> FEATURE:
<221> NAME/KEY: misc_binding
<222> LOCATION: 49765..49784
<223> OTHER INFORMATION: 99-1585.rp
<220> FEATURE:
<221> NAME/KEY: misc_binding
<222> LOCATION: 50291..50310
<223> OTHER INFORMATION: 99-1585.pu complement
<220> FEATURE:
<221> NAME/KEY: misc_binding
<222> LOCATION: 54726..54746
<223> OTHER INFORMATION: 99-1607.rp
<220> FEATURE:
<221> NAME/KEY: misc_binding
<222> LOCATION: 55307..55325
<223> OTHER INFORMATION: 99-1607.pu complement
<220> FEATURE:
<221> NAME/KEY: misc_binding
<222> LOCATION: 64135..64153
<223> OTHER INFORMATION: 99-1577.pu
<220> FEATURE:
<221> NAME/KEY: misc_binding
<222> LOCATION: 64518..64536
<223> OTHER INFORMATION: 99-1577.rp complement
<220> FEATURE:
<221> NAME/KEY: misc_binding
<222> LOCATION: 65202..65219
<223> OTHER INFORMATION: 99-1591.pu
<220> FEATURE:
<221> NAME/KEY: misc_binding
<222> LOCATION: 65815..65834
```

```
<223> OTHER INFORMATION: 99-1591.rp complement
<220> FEATURE:
<221> NAME/KEY: misc_binding
<222> LOCATION: 66653..66671
<223> OTHER INFORMATION: 99-1572.pu
<220> FEATURE:
<221> NAME/KEY: misc_binding
<222> LOCATION: 67275..67295
<223> OTHER INFORMATION: 99-1572.rp complement
<220> FEATURE:
<221> NAME/KEY: misc_binding
<222> LOCATION: 67627..67646
<223> OTHER INFORMATION: 5-169.pu
<220> FEATURE:
<221> NAME/KEY: misc_binding
<222> LOCATION: 68024..68043
<223> OTHER INFORMATION: 5-169.rp complement
<220> FEATURE:
<221> NAME/KEY: misc_binding
<222> LOCATION: 67246..67263
<223> OTHER INFORMATION: 5-264.pu
<220> FEATURE:
<221> NAME/KEY: misc_binding
<222> LOCATION: 67678..67696
<223> OTHER INFORMATION: 5-264.rp complement
<220> FEATURE:
<221> NAME/KEY: misc_binding
<222> LOCATION: 67977..67994
<223> OTHER INFORMATION: 5-170.pu
<220> FEATURE:
<221> NAME/KEY: misc_binding
<222> LOCATION: 68406..68424
<223> OTHER INFORMATION: 5-170.rp complement
<220> FEATURE:
<221> NAME/KEY: misc_binding
<222> LOCATION: 68322..68340
<223> OTHER INFORMATION: 5-171.pu
<220> FEATURE:
<221> NAME/KEY: misc_binding
<222> LOCATION: 68725..68742
<223> OTHER INFORMATION: 5-171.rp complement
<220> FEATURE:
<221> NAME/KEY: misc_binding
<222> LOCATION: 70507..70524
<223> OTHER INFORMATION: 5-1.pu
<220> FEATURE:
<221> NAME/KEY: misc_binding
<222> LOCATION: 70909..70928
<223> OTHER INFORMATION: 5-1.rp complement
<220> FEATURE:
<221> NAME/KEY: misc_binding
<222> LOCATION: 79940..79957
<223> OTHER INFORMATION: 99-1578.pu
<220> FEATURE:
<221> NAME/KEY: misc_binding
<222> LOCATION: 80557..80575
<223> OTHER INFORMATION: 99-1578.rp complement
<220> FEATURE:
<221> NAME/KEY: misc_binding
<222> LOCATION: 82057..82077
<223> OTHER INFORMATION: 99-1605.rp
<220> FEATURE:
<221> NAME/KEY: misc_binding
<222> LOCATION: 82484..82504
<223> OTHER INFORMATION: 99-1605.pu complement
<220> FEATURE:
<221> NAME/KEY: misc_binding
<222> LOCATION: 82058..82077
<223> OTHER INFORMATION: 5-2.pu
<220> FEATURE:
<221> NAME/KEY: misc_binding
<222> LOCATION: 82473..82492
<223> OTHER INFORMATION: 5-2.rp complement
<220> FEATURE:
<221> NAME/KEY: misc_binding
<222> LOCATION: 83561..83578
<223> OTHER INFORMATION: 5-3.pu
<220> FEATURE:
<221> NAME/KEY: misc_binding
```

```
<222> LOCATION: 83965..83982
<223> OTHER INFORMATION: 5-3.rp complement
<220> FEATURE:
<221> NAME/KEY: misc_binding
<222> LOCATION: 83597..83616
<223> OTHER INFORMATION: 5-4.pu
<220> FEATURE:
<221> NAME/KEY: misc_binding
<222> LOCATION: 83999..84017
<223> OTHER INFORMATION: 5-4.rp complement
<220> FEATURE:
<221> NAME/KEY: misc_binding
<222> LOCATION: 83793..83812
<223> OTHER INFORMATION: 5-260.pu
<220> FEATURE:
<221> NAME/KEY: misc_binding
<222> LOCATION: 84148..84167
<223> OTHER INFORMATION: 5-260.rp complement
<220> FEATURE:
<221> NAME/KEY: misc_binding
<222> LOCATION: 85153..85170
<223> OTHER INFORMATION: 5-9.pu
<220> FEATURE:
<221> NAME/KEY: misc_binding
<222> LOCATION: 85559..85576
<223> OTHER INFORMATION: 5-9.rp complement
<220> FEATURE:
<221> NAME/KEY: misc_binding
<222> LOCATION: 86239..86257
<223> OTHER INFORMATION: 5-5.pu
<220> FEATURE:
<221> NAME/KEY: misc_binding
<222> LOCATION: 86519..86539
<223> OTHER INFORMATION: 5-5.rp complement
<220> FEATURE:
<221> NAME/KEY: misc_binding
<222> LOCATION: 87619..87638
<223> OTHER INFORMATION: 5-202.pu
<220> FEATURE:
<221> NAME/KEY: misc_binding
<222> LOCATION: 88033..88050
<223> OTHER INFORMATION: 5-202.rp complement
<220> FEATURE:
<221> NAME/KEY: misc_binding
<222> LOCATION: 88104..88122
<223> OTHER INFORMATION: 5-7.pu
<220> FEATURE:
<221> NAME/KEY: misc_binding
<222> LOCATION: 88519..88536
<223> OTHER INFORMATION: 5-7.rp complement
<220> FEATURE:
<221> NAME/KEY: misc_binding
<222> LOCATION: 89338..89357
<223> OTHER INFORMATION: 5-181.pu
<220> FEATURE:
<221> NAME/KEY: misc_binding
<222> LOCATION: 89739..89758
<223> OTHER INFORMATION: 5-181.rp complement
<220> FEATURE:
<221> NAME/KEY: misc_binding
<222> LOCATION: 92722..92741
<223> OTHER INFORMATION: 5-10.pu
<220> FEATURE:
<221> NAME/KEY: misc_binding
<222> LOCATION: 93124..93142
<223> OTHER INFORMATION: 5-10.rp complement
<220> FEATURE:
<221> NAME/KEY: misc_binding
<222> LOCATION: 93090..93108
<223> OTHER INFORMATION: 5-11.pu
<220> FEATURE:
<221> NAME/KEY: misc_binding
<222> LOCATION: 93490..93509
<223> OTHER INFORMATION: 5-11.rp complement
<220> FEATURE:
<221> NAME/KEY: misc_binding
<222> LOCATION: 93460..93478
<223> OTHER INFORMATION: 5-12.pu
<220> FEATURE:
```

```
<221> NAME/KEY: misc_binding
<222> LOCATION: 93862..93881
<223> OTHER INFORMATION: 5-12.rp complement
<220> FEATURE:
<221> NAME/KEY: misc_binding
<222> LOCATION: 93759..93776
<223> OTHER INFORMATION: 5-13.pu
<220> FEATURE:
<221> NAME/KEY: misc_binding
<222> LOCATION: 94175..94192
<223> OTHER INFORMATION: 5-13.rp complement
<220> FEATURE:
<221> NAME/KEY: misc_binding
<222> LOCATION: 94127..94144
<223> OTHER INFORMATION: 5-14.pu
<220> FEATURE:
<221> NAME/KEY: misc_binding
<222> LOCATION: 94535..94554
<223> OTHER INFORMATION: 5-14.rp complement
<220> FEATURE:
<221> NAME/KEY: misc_binding
<222> LOCATION: 94504..94521
<223> OTHER INFORMATION: 5-15.pu
<220> FEATURE:
<221> NAME/KEY: misc_binding
<222> LOCATION: 94904..94921
<223> OTHER INFORMATION: 5-15.rp complement
<220> FEATURE:
<221> NAME/KEY: misc_binding
<222> LOCATION: 94833..94850
<223> OTHER INFORMATION: 5-16.pu
<220> FEATURE:
<221> NAME/KEY: misc_binding
<222> LOCATION: 95232..95251
<223> OTHER INFORMATION: 5-16.rp complement
<220> FEATURE:
<221> NAME/KEY: misc_binding
<222> LOCATION: 95124..95142
<223> OTHER INFORMATION: 5-17.pu
<220> FEATURE:
<221> NAME/KEY: misc_binding
<222> LOCATION: 95542..95561
<223> OTHER INFORMATION: 5-17.rp complement
<220> FEATURE:
<221> NAME/KEY: misc_binding
<222> LOCATION: 95290..95308
<223> OTHER INFORMATION: 5-18.pu
<220> FEATURE:
<221> NAME/KEY: misc_binding
<222> LOCATION: 95689..95708
<223> OTHER INFORMATION: 5-18.rp complement
<220> FEATURE:
<221> NAME/KEY: misc_binding
<222> LOCATION: 95533..95551
<223> OTHER INFORMATION: 5-300.pu
<220> FEATURE:
<221> NAME/KEY: misc_binding
<222> LOCATION: 95934..95952
<223> OTHER INFORMATION: 5-300.rp complement
<220> FEATURE:
<221> NAME/KEY: misc_binding
<222> LOCATION: 96097..96115
<223> OTHER INFORMATION: 5-262.pu
<220> FEATURE:
<221> NAME/KEY: misc_binding
<222> LOCATION: 96574..96591
<223> OTHER INFORMATION: 5-262.rp complement
<220> FEATURE:
<221> NAME/KEY: misc_binding
<222> LOCATION: 96548..96565
<223> OTHER INFORMATION: 5-263.pu
<220> FEATURE:
<221> NAME/KEY: misc_binding
<222> LOCATION: 96982..97001
<223> OTHER INFORMATION: 5-263.rp complement
<220> FEATURE:
<221> NAME/KEY: misc_binding
<222> LOCATION: 96901..96918
<223> OTHER INFORMATION: 5-265.pu
```

```
<220> FEATURE:
<221> NAME/KEY: misc_binding
<222> LOCATION: 97292..97309
<223> OTHER INFORMATION: 5-265.rp complement
<220> FEATURE:
<221> NAME/KEY: misc_binding
<222> LOCATION: 102156..102176
<223> OTHER INFORMATION: 99-7183.rp
<220> FEATURE:
<221> NAME/KEY: misc_binding
<222> LOCATION: 102584..102604
<223> OTHER INFORMATION: 99-7183.pu complement
<220> FEATURE:
<221> NAME/KEY: misc_binding
<222> LOCATION: 105570..105588
<223> OTHER INFORMATION: 99-7207.rp
<220> FEATURE:
<221> NAME/KEY: misc_binding
<222> LOCATION: 106056..106074
<223> OTHER INFORMATION: 99-7207.pu complement
<220> FEATURE:
<221> NAME/KEY: misc_feature
<222> LOCATION: 86434
<223> OTHER INFORMATION: diverging nucleotide G in reference genbank :
      L78132
<220> FEATURE:
<221> NAME/KEY: misc_feature
<222> LOCATION: 86435
<223> OTHER INFORMATION: diverging nucleotide T in reference genbank :
      L78132
<220> FEATURE:
<221> NAME/KEY: misc_feature
<222> LOCATION: 88355
<223> OTHER INFORMATION: diverging nucleotide C in reference genbank :
      L78132
<220> FEATURE:
<221> NAME/KEY: misc_feature
<222> LOCATION: 92976
<223> OTHER INFORMATION: insertion of G in reference genbank : L78132
<220> FEATURE:
<221> NAME/KEY: misc_feature
<222> LOCATION: 93240
<223> OTHER INFORMATION: diverging nucleotide T in reference genbank :
      L78132
<220> FEATURE:
<221> NAME/KEY: misc_feature
<222> LOCATION: 93471
<223> OTHER INFORMATION: diverging nucleotide G in reference genbank :
      L78132
<220> FEATURE:
<221> NAME/KEY: misc_feature
<222> LOCATION: 93592
<223> OTHER INFORMATION: diverging nucleotide C in reference genbank :
      L78132
<220> FEATURE:
<221> NAME/KEY: misc_feature
<222> LOCATION: 93680
<223> OTHER INFORMATION: diverging nucleotide C in reference genbank :
      L78132
<220> FEATURE:
<221> NAME/KEY: misc_feature
<222> LOCATION: 93681
<223> OTHER INFORMATION: diverging nucleotide C in reference genbank :
      L78132
<220> FEATURE:
<221> NAME/KEY: misc_feature
<222> LOCATION: 93682
<223> OTHER INFORMATION: diverging nucleotide C in reference genbank :
      L78132
<220> FEATURE:
<221> NAME/KEY: misc_feature
<222> LOCATION: 93683
<223> OTHER INFORMATION: diverging nucleotide G in reference genbank :
      L78132
<220> FEATURE:
<221> NAME/KEY: misc_feature
<222> LOCATION: 93712
<223> OTHER INFORMATION: deletion of A in reference genbank : L78132
<220> FEATURE:
```

-continued

```
<221> NAME/KEY: misc_feature
<222> LOCATION: 93728
<223> OTHER INFORMATION: diverging nucleotide C in reference genbank :
      L78132
<220> FEATURE:
<221> NAME/KEY: misc_feature
<222> LOCATION: 93747
<223> OTHER INFORMATION: diverging nucleotide T in reference genbank :
      L78132
<220> FEATURE:
<221> NAME/KEY: misc_feature
<222> LOCATION: 93761
<223> OTHER INFORMATION: diverging nucleotide C in reference genbank :
      L78132
<220> FEATURE:
<221> NAME/KEY: misc_feature
<222> LOCATION: 94151
<223> OTHER INFORMATION: deletion of TTA in reference genbank : L78132
<220> FEATURE:
<221> NAME/KEY: misc_feature
<222> LOCATION: 94154
<223> OTHER INFORMATION: diverging nucleotide C in reference genbank :
      L78132
<220> FEATURE:
<221> NAME/KEY: misc_feature
<222> LOCATION: 94241
<223> OTHER INFORMATION: insertion of G in reference genbank : L78132
<220> FEATURE:
<221> NAME/KEY: misc_feature
<222> LOCATION: 94430
<223> OTHER INFORMATION: diverging nucleotide C in reference genbank :
      L78132
<220> FEATURE:
<221> NAME/KEY: misc_feature
<222> LOCATION: 94771
<223> OTHER INFORMATION: insertion of A in reference genbank : L78132
<220> FEATURE:
<221> NAME/KEY: misc_feature
<222> LOCATION: 94805
<223> OTHER INFORMATION: insertion of T in reference genbank : L78132
<220> FEATURE:
<221> NAME/KEY: misc_feature
<222> LOCATION: 95121
<223> OTHER INFORMATION: deletion of AG in reference genbank : L78132
<220> FEATURE:
<221> NAME/KEY: misc_feature
<222> LOCATION: 95126
<223> OTHER INFORMATION: diverging nucleotide A in reference genbank :
      L78132
<220> FEATURE:
<221> NAME/KEY: misc_feature
<222> LOCATION: 95130
<223> OTHER INFORMATION: deletion of G in reference genbank : L78132
<220> FEATURE:
<221> NAME/KEY: misc_feature
<222> LOCATION: 95134
<223> OTHER INFORMATION: deletion of G in reference genbank : L78132
<220> FEATURE:
<221> NAME/KEY: misc_feature
<222> LOCATION: 95149
<223> OTHER INFORMATION: deletion of A in reference genbank : L78132
<220> FEATURE:
<221> NAME/KEY: misc_feature
<222> LOCATION: 95155
<223> OTHER INFORMATION: deletion of A in reference genbank : L78132
<220> FEATURE:
<221> NAME/KEY: misc_feature
<222> LOCATION: 95174
<223> OTHER INFORMATION: deletion of AA in reference genbank : L78132
<220> FEATURE:
<221> NAME/KEY: misc_feature
<222> LOCATION: 95368
<223> OTHER INFORMATION: deletion of A in reference genbank : L78132
<220> FEATURE:
<221> NAME/KEY: misc_feature
<222> LOCATION: 95411
<223> OTHER INFORMATION: deletion of C in reference genbank : L78132
<220> FEATURE:
<221> NAME/KEY: misc_feature
```

```
<222> LOCATION: 95419
<223> OTHER INFORMATION: deletion of C in reference genbank : L78132
<220> FEATURE:
<221> NAME/KEY: misc_feature
<222> LOCATION: 95431
<223> OTHER INFORMATION: insertion of TG in reference genbank : L78132
<220> FEATURE:
<221> NAME/KEY: misc_feature
<222> LOCATION: 95435
<223> OTHER INFORMATION: insertion of C in reference genbank : L78132
<220> FEATURE:
<221> NAME/KEY: misc_feature
<222> LOCATION: 95444
<223> OTHER INFORMATION: diverging nucleotide G in reference genbank :
      L78132
<220> FEATURE:
<221> NAME/KEY: misc_feature
<222> LOCATION: 95445
<223> OTHER INFORMATION: diverging nucleotide C in reference genbank :
      L78132
<220> FEATURE:
<221> NAME/KEY: misc_feature
<222> LOCATION: 95534
<223> OTHER INFORMATION: insertion of A in reference genbank : L78132
<220> FEATURE:
<221> NAME/KEY: misc_feature
<222> LOCATION: 95678
<223> OTHER INFORMATION: insertion of G in reference genbank : L78132
<220> FEATURE:
<221> NAME/KEY: primer_bind
<222> LOCATION: 67820..67850
<223> OTHER INFORMATION: 5-169-208_A_AS complement
<220> FEATURE:
<221> NAME/KEY: primer_bind
<222> LOCATION: 67820..67848
<223> OTHER INFORMATION: 5-169-208_A_S
<220> FEATURE:
<221> NAME/KEY: primer_bind
<222> LOCATION: 67820..67850
<223> OTHER INFORMATION: 5-169-208_G_AS complement
<220> FEATURE:
<221> NAME/KEY: primer_bind
<222> LOCATION: 67820..67848
<223> OTHER INFORMATION: 5-169-208_G_S
<220> FEATURE:
<221> NAME/KEY: primer_bind
<222> LOCATION: 67941..67969
<223> OTHER INFORMATION: 5-169-331_C_AS complement
<220> FEATURE:
<221> NAME/KEY: primer_bind
<222> LOCATION: 67940..67969
<223> OTHER INFORMATION: 5-169-331_C_S
<220> FEATURE:
<221> NAME/KEY: primer_bind
<222> LOCATION: 67941..67969
<223> OTHER INFORMATION: 5-169-331_T_AS complement
<220> FEATURE:
<221> NAME/KEY: primer_bind
<222> LOCATION: 67940..67969
<223> OTHER INFORMATION: 5-169-331_T_S
<220> FEATURE:
<221> NAME/KEY: primer_bind
<222> LOCATION: 67709..67738
<223> OTHER INFORMATION: 5-169-97_C_AS complement
<220> FEATURE:
<221> NAME/KEY: primer_bind
<222> LOCATION: 67707..67737
<223> OTHER INFORMATION: 5-169-97_C_S
<220> FEATURE:
<221> NAME/KEY: primer_bind
<222> LOCATION: 67709..67738
<223> OTHER INFORMATION: 5-169-97_G_AS complement
<220> FEATURE:
<221> NAME/KEY: primer_bind
<222> LOCATION: 67707..67737
<223> OTHER INFORMATION: 5-169-97_G_S
<220> FEATURE:
<221> NAME/KEY: primer_bind
<222> LOCATION: 68199..68228
```

-continued

```
<223> OTHER INFORMATION: 5-170-238_A_AS complement
<220> FEATURE:
<221> NAME/KEY: primer_bind
<222> LOCATION: 68198..68227
<223> OTHER INFORMATION: 5-170-238_A_S
<220> FEATURE:
<221> NAME/KEY: primer_bind
<222> LOCATION: 68199..68228
<223> OTHER INFORMATION: 5-170-238_G_AS complement
<220> FEATURE:
<221> NAME/KEY: primer_bind
<222> LOCATION: 68198..68227
<223> OTHER INFORMATION: 5-170-238_G_S
<220> FEATURE:
<221> NAME/KEY: primer_bind
<222> LOCATION: 68249..68277
<223> OTHER INFORMATION: 5-170-288_A_AS complement
<220> FEATURE:
<221> NAME/KEY: primer_bind
<222> LOCATION: 68247..68277
<223> OTHER INFORMATION: 5-170-288_A_S
<220> FEATURE:
<221> NAME/KEY: primer_bind
<222> LOCATION: 68249..68277
<223> OTHER INFORMATION: 5-170-288_C_AS complement
<220> FEATURE:
<221> NAME/KEY: primer_bind
<222> LOCATION: 68247..68277
<223> OTHER INFORMATION: 5-170-288_C_S
<220> FEATURE:
<221> NAME/KEY: primer_bind
<222> LOCATION: 68463..68492
<223> OTHER INFORMATION: 5-171-156_G_AS complement
<220> FEATURE:
<221> NAME/KEY: primer_bind
<222> LOCATION: 68463..68491
<223> OTHER INFORMATION: 5-171-156_G_S
<220> FEATURE:
<221> NAME/KEY: primer_bind
<222> LOCATION: 68463..68492
<223> OTHER INFORMATION: 5-171-156_T_AS complement
<220> FEATURE:
<221> NAME/KEY: primer_bind
<222> LOCATION: 68463..68491
<223> OTHER INFORMATION: 5-171-156_T_S
<220> FEATURE:
<221> NAME/KEY: primer_bind
<222> LOCATION: 68511..68539
<223> OTHER INFORMATION: 5-171-204_C_AS complement
<220> FEATURE:
<221> NAME/KEY: primer_bind
<222> LOCATION: 68511..68539
<223> OTHER INFORMATION: 5-171-204_C_S
<220> FEATURE:
<221> NAME/KEY: primer_bind
<222> LOCATION: 68511..68539
<223> OTHER INFORMATION: 5-171-204_T_AS complement
<220> FEATURE:
<221> NAME/KEY: primer_bind
<222> LOCATION: 68511..68539
<223> OTHER INFORMATION: 5-171-204_T_S
<220> FEATURE:
<221> NAME/KEY: primer_bind
<222> LOCATION: 68580..68608
<223> OTHER INFORMATION: 5-171-273_A_AS complement
<220> FEATURE:
<221> NAME/KEY: primer_bind
<222> LOCATION: 68580..68608
<223> OTHER INFORMATION: 5-171-273_A_S
<220> FEATURE:
<221> NAME/KEY: primer_bind
<222> LOCATION: 68580..68608
<223> OTHER INFORMATION: 5-171-273_G_AS complement
<220> FEATURE:
<221> NAME/KEY: primer_bind
<222> LOCATION: 68580..68608
<223> OTHER INFORMATION: 5-171-273_G_S
<220> FEATURE:
<221> NAME/KEY: primer_bind
```

```
<222> LOCATION: 68596..68626
<223> OTHER INFORMATION: 5-171-289_C_AS complement
<220> FEATURE:
<221> NAME/KEY: primer_bind
<222> LOCATION: 68596..68624
<223> OTHER INFORMATION: 5-171-289_C_S
<220> FEATURE:
<221> NAME/KEY: primer_bind
<222> LOCATION: 68596..68626
<223> OTHER INFORMATION: 5-171-289_T_AS complement
<220> FEATURE:
<221> NAME/KEY: primer_bind
<222> LOCATION: 68596..68624
<223> OTHER INFORMATION: 5-171-289_T_S
<220> FEATURE:
<221> NAME/KEY: primer_bind
<222> LOCATION: 68361..68389
<223> OTHER INFORMATION: 5-171-54_C_AS complement
<220> FEATURE:
<221> NAME/KEY: primer_bind
<222> LOCATION: 68360..68389
<223> OTHER INFORMATION: 5-171-54_C_S
<220> FEATURE:
<221> NAME/KEY: primer_bind
<222> LOCATION: 68361..68389
<223> OTHER INFORMATION: 5-171-54_G_AS complement
<220> FEATURE:
<221> NAME/KEY: primer_bind
<222> LOCATION: 68360..68389
<223> OTHER INFORMATION: 5-171-54_G_S
<220> FEATURE:
<221> NAME/KEY: primer_bind
<222> LOCATION: 66953..66983
<223> OTHER INFORMATION: 99-1572-315_C_AS complement
<220> FEATURE:
<221> NAME/KEY: primer_bind
<222> LOCATION: 66951..66981
<223> OTHER INFORMATION: 99-1572-315_C_S
<220> FEATURE:
<221> NAME/KEY: primer_bind
<222> LOCATION: 66953..66983
<223> OTHER INFORMATION: 99-1572-315_T_AS complement
<220> FEATURE:
<221> NAME/KEY: primer_bind
<222> LOCATION: 66951..66981
<223> OTHER INFORMATION: 99-1572-315_T_S
<220> FEATURE:
<221> NAME/KEY: primer_bind
<222> LOCATION: 66973..67002
<223> OTHER INFORMATION: 99-1572-335_A_AS complement
<220> FEATURE:
<221> NAME/KEY: primer_bind
<222> LOCATION: 66973..67001
<223> OTHER INFORMATION: 99-1572-335_A_S
<220> FEATURE:
<221> NAME/KEY: primer_bind
<222> LOCATION: 66973..67002
<223> OTHER INFORMATION: 99-1572-335_G_AS complement
<220> FEATURE:
<221> NAME/KEY: primer_bind
<222> LOCATION: 66973..67001
<223> OTHER INFORMATION: 99-1572-335_G_S
<220> FEATURE:
<221> NAME/KEY: primer_bind
<222> LOCATION: 67078..67106
<223> OTHER INFORMATION: 99-1572-440_C_AS complement
<220> FEATURE:
<221> NAME/KEY: primer_bind
<222> LOCATION: 67078..67106
<223> OTHER INFORMATION: 99-1572-440_C_S
<220> FEATURE:
<221> NAME/KEY: primer_bind
<222> LOCATION: 67078..67106
<223> OTHER INFORMATION: 99-1572-440_T_AS complement
<220> FEATURE:
<221> NAME/KEY: primer_bind
<222> LOCATION: 67078..67106
<223> OTHER INFORMATION: 99-1572-440_T_S
<220> FEATURE:
```

```
<221> NAME/KEY: primer_bind
<222> LOCATION: 67115..67144
<223> OTHER INFORMATION: 99-1572-477_A_AS complement
<220> FEATURE:
<221> NAME/KEY: primer_bind
<222> LOCATION: 67113..67143
<223> OTHER INFORMATION: 99-1572-477_A_S
<220> FEATURE:
<221> NAME/KEY: primer_bind
<222> LOCATION: 67115..67144
<223> OTHER INFORMATION: 99-1572-477_T_AS complement
<220> FEATURE:
<221> NAME/KEY: primer_bind
<222> LOCATION: 67113..67143
<223> OTHER INFORMATION: 99-1572-477_T_S
<220> FEATURE:
<221> NAME/KEY: primer_bind
<222> LOCATION: 67215..67247
<223> OTHER INFORMATION: 99-1572-578_C_AS complement
<220> FEATURE:
<221> NAME/KEY: primer_bind
<222> LOCATION: 67212..67243
<223> OTHER INFORMATION: 99-1572-578_C_S
<220> FEATURE:
<221> NAME/KEY: primer_bind
<222> LOCATION: 67215..67247
<223> OTHER INFORMATION: 99-1572-578_T_AS complement
<220> FEATURE:
<221> NAME/KEY: primer_bind
<222> LOCATION: 67212..67243
<223> OTHER INFORMATION: 99-1572-578_T_S
<220> FEATURE:
<221> NAME/KEY: misc_feature
<222> LOCATION: 8187,14867,14970,29204,29487,34266
<223> OTHER INFORMATION: n=a, g, c or t

<400> SEQUENCE: 1
ttggcttggc agggcaacca gctcaccaga ctctctgcag acccgaagtc attacataca      60
gtatgataac agggaatgga cccgaccagc atttgctgga gatgatatct ggtgtcagcc     120
cgacaggccc ctacctgctt ctcttgatat gcaggaatcc cttcaagctc aacaagatc      180
tgtttaatag actggagagt cctttagttc cttcctctaa gggaaaatca gatcgttctg     240
gtttgcttgg taactcctta cttcatccct gatgggaagt ttatagaatg aggaaccagg     300
gctattacat gaaactataa aactgcctag agcacatact tggtattttt aacattgttg     360
agagggactc acttaattca gccttgcagc tattgcattc ctgtccaaac caacggcagg     420
ttctcaaaac aagcggtgaa agggttcctg ttgcagagct gtctggacat ttaaagaagg     480
gagaggaaat ctcaagggt cggttgcact ggaatagaaa tcgcctgttc ttttttttg      540
agacggagtc tcgctctgtc acccaggctg gagagcagtt gcgcgatctt tgctcactgc     600
aacctctgcc tcccgggttc acgccattct cctgcctcag cctcctgaat agctgggact     660
acaggcgccc gccaccacgt ctggctcatt ttttgtattt ttagtagaga tggagtttca     720
ccattttagc caggatggtc tcgatctgct gaccttgtaa tccacccgcc tcggcctccc     780
aaagtacagg gattataggc gtgagccacc gcgcccaggt gcctgttcct tttttaagag     840
tctcactctg tcgcccaggc tggcgtgcag tggcgcgatc tctgcttact gcagtctccg     900
tctcctgagt tcaaatcaag cgagaaatca cttgttctct tctgtgaacg gaagcatcgc     960
agatctctct tggcctcaca ctcctccatc tccctgattc ctctgttctt catttaccta    1020
ccttcccagc agtctgcaga gctggccgct cactcacctc tagtaagggg atggagggtc    1080
ctgtgttgga ataactcact gaccgctaga aagttaaaaa taatgggta atgccaggag     1140
aacttggctg gtgccttaaa agccatagaa cttctctttc catctgtaga taactgtaga    1200
caattttgtc caaaacagat aatgatctga ttctacctcc cattggtatt tcccttcctc    1260
```

```
ggcctgtgac atctcacttt ctctagactg aactttatcc cagactgtga ccttgccatg   1320
accttcctcc tgcgtgtgcc tctgccacca caggaatggc cacgcctcag atcatgtcac   1380
cgctgggaac aaaccctcta cctgcgactc tgaagttccc tctctgaccc tcttttcttt   1440
cttcccctcc cccctcccct cactccctct gcacctgtgt ttcgctgtca cgctcccaac   1500
tcatccctgt agagctggtg aagagatgct gatgtagttc ttgaccttga acccagccc   1560
tgcagccgtc ctgtggcctc actgacccag cgtcatgccc tggtcaagca ttttggtgat   1620
gctcttggtg attttcaatg ggacctgcct tgccaagccc tgggcttagg tgaaccagga   1680
ccacctgcat tctatgtttt tgattgctgg aaaaaaatca tgaaatgtca actgttgttc   1740
tcattttcc cactgccagt tcctgctacc caacctccgc cctcatttca aggccttgag   1800
tacttttttt ctatagtgaa gtctcccaaa aatgatattt ttttaaaaaa gaaaagccat   1860
agtactctga tttgatgtgg tctgttaata cctatgggct ttgacttgtt ctgctttta   1920
gacctagaca aaataaaata tctgtggtaa acatattca agtttaccgg gcacgggggc   1980
tcacgcctgt aatcccagca ctttgggagg ctggggcagg cagatcactt gagcccagga   2040
gtttgagacc agcctgggca cagggtgaa acaacatctc tacaaaaata caaaaatac   2100
ctgggcattg tggtgcatgc ctgtagtcgc agctactcgg gagactgagg tgggaggatg   2160
gcttgagctc tggaggcgga ggtcatagtg agccaagatc gtgccactga actccagcct   2220
gggcaacaga ggcagattct ttctctctaa aaaacataaa ataaaaaaag gccaggcgca   2280
gtggctcaca cctgtaatcc cagcactttg ggaggctgag ggggcggac gaagaggtca   2340
ggagatagag accatcctgg ccaacatggt gaaaccctgc ctctactaaa aatacaaaaa   2400
ttagccgggt gtagtggtgc atgcctgtaa tctcaactac tcaggaggct gaggcaggaa   2460
aatcgcttga acccaggagg cggaggctgc agtgagccaa gatcgcacca ctgcactcca   2520
gcctgggtga cagagcaaga ctctgtcccc caccaaaaaa aataaataaa taaatcaggc   2580
caaagggcaa aaatgcttgc ttttagcac ttagtagtta ttccccaag aagagcggga   2640
gagaagttta ttaataatga aactggacag ttcttatca gctctaattg tttgactcaa   2700
tggcttctct tctcattacc atgcagtgct ctgctggctg caatgccttt gaacttcaca   2760
agaaggttag aatttcactg agacattcgg atggtgtggg tgtcagggtg cagctctcac   2820
acatagttga gagtgtaaat tgatacaact ttatggaaaa ttaattggga gtacccattc   2880
acactcctgt ctagcaatct cacttaagg acttgatcct acagaactca ttacatggtg   2940
caaggttcac agtgtggcat tcaaaataga gaagagctgc gggtaactcc catgcccgtt   3000
ggcaggaact ggttgaataa attatggtgc atcagtgctg tggggtatca ttaaaccatt   3060
aaaagaaga gagagtcctg gccttaaaaa aaacttatct gatgtattgt taaacagata   3120
aagcaagttg tagatcaatg tgatttgggg ctaaaaaaat atttctatat aggtgtgaac   3180
atggccatga ctaaggaatc aggaaggaag tacctagatt gtaaccagta acatgtcggg   3240
agtgagatgg gattgagaga cgtaataata gattgagaga aaaagatttt cccatctctt   3300
tttgattttt taagaaaaca gcatgatttt cagtaatttt tacttttgtg tgttttggt   3360
atttttctt tttcttttt ttttttttt ttttgagacg gagtttcact cttgttgccc   3420
aggctggaat gcgatggccc agtcccagct cactgcaacc ttcacttccc aggttcaaga   3480
gattctcctg tctcagcctc ccgagtagct gggattacag gccctgcca ttacgcccag   3540
ctacttttg tatttttagt agagatgggg ttcaccgtgt tggttaggct ggtttgaact   3600
```

```
cctgagctca ggcgatctgc ctacttcagc ctcccaaaat gctgggatta cagccgtgag   3660
ccaccgcccc cagccggtat tttttcaaat caaagaaaaa ataatagagt aaatcatcca   3720
aaactttaga tggtatttag actcagtaaa cttttcatat atgacagatg aagccaaatg   3780
gtctttctgt gcagtcagct agcacacaat tgtgcacccg aggaaaatta gagactgaac   3840
cggggtgtct gtggatgcat ttcctcagca ttcagcctte cttttgcccg tgttctagca   3900
ttacttctgt cctacagcct gggatttgtg aatgaaatag acaggtgcaa aaactccctg   3960
cctgtctgta atatccatag ccccgtgctc tacttgtatt tgcatgtaca aaccataatc   4020
tcctgtaaaa tactctgtga tatttctgaa taataataaa ctctacatcc tacacaaagg   4080
caaaacccct gtatctttca tctttgaaac catagcaaag gtatgaaatt acacctgagc   4140
atgcctggcc tcaaagtcct ggaacggtta tgtctttgac cctcacttca actcaactcc   4200
agaagaagca ggtcttcctt gtaattggat agaaaactca ttgtagagaa gaaagatcta   4260
caggtcaaga aacccacagg tttgctgtaa tccgagcaaa gcactgtagc atttatttta   4320
tattttcact cttcttattt agctcttttt ttttttttt tttgagatg gagtttcatt   4380
cttgtcaccc agcctggagc aatggtgcca tctcggctca ctgcaacctc tgcctcccag   4440
gttcaagtga ttctcctgcc tcagcctcct gagtagctgg ggttacaggc tccaccgcc   4500
acacccagcc aatttttgt atttttagta gagacgggt ttcaccatgt tagccagact   4560
ggtctcaaac tcctggcctt aggtgatcca cccgcctcag catcccaaag tgctgggatt   4620
acaggcgcac cggccttagc tcttttatcc ttaatgaaat gctcctcatt ccctgaggtc   4680
tcacttgaat tcttgcccac ctctgggttg ccttcctctt ctgtctgtgc tttgtaacac   4740
gtggttcctt atgatgtcaa tatttatgca tatgtcttca ttccattact ggattataat   4800
cttgaagcaa cagattttg tctctatatc ccagagccta gaatggattc ttacactggg   4860
cagtaagtac ttaataaatg tatcccaaat caaataaata catttcttct ttttcttttc   4920
tttttttttt tttttgaga cagggttcca ctctgtcacc caggctggag tgtaatgaca   4980
tgatctcagc ttactacagc ctcaatctcc tgggcttaag caatcctccc acctcagcct   5040
cccacatagc taggactaca ggcgctcacc acaacacctc atttttgtat attttttgta   5100
gagattgggg gatctcacta cgttgccccg gctggttttg aacttctggg ctcagacaat   5160
ccacccacct tggcctccca aactgttgag attacaggaa tgagccacca ttccctggcc   5220
aaatacattt ctaaaagcca gtttctggag tatactgtca aataatagat atatgtccac   5280
atttttatac ggacttatat tgtaagaaaa agtaaaaata agtgtgaagt tattacagta   5340
atagtaatta ttttgcagaa aaagaactga gtttaaacag cttttttaga aaacccaac   5400
aggagattca cagtctggta ctaacgttta gacatggatc atcagtaaat gtgttccaaa   5460
gagttacaca gataccagct ttgtcttggg aattcttacc cctgaaaatt gattgactat   5520
cactgactgt gtgacatgag aaagttttgt ggggtttttt ttttgtattt ttttgagacg   5580
tatcttgctc tgtcacccaa gctggagtcc actggcgcga tcttggctca ctacaacctc   5640
tgccgcctgg ttcaagcgat tctcctgcct cagcctccag aatagctgcg attacaggca   5700
cctgccacca tgcccggcta atttttgtat ttttagtaaa gacggggttt catcgtgttg   5760
gccaggatgg tcttgaactc ctgacctcag gtgatctgcc cacctcagcc tcccaaagtg   5820
ctgggattac aggcatgagc caccgtgccc agcctgaaaa agttttgaac ggtctaaatc   5880
catatgctgt gaatcctatt accatcacac acttaggcat ttaaaatcat attttcaagg   5940
ccaggtactg aaatattttc tgcaagcaga gagatcaaac tttagcattg ttattcttgt   6000
```

```
agtagtttca tagtttgagg tcttagattt aagtcttcca ttgattttga tttgatttttt    6060 gtatatggag atagggtct agtttcattc ttttgcatat ggatatccag ttttcccagc      6120
accatttatt gaagagactg tcttttttcac cagtgtatgc tcttggcacc ttcgtcaaaa    6180
atgagttccc tgtaggtgtg tgggtttgct tctggttctc tattctgtcc cattggtcta    6240
agtgtttggt tttatgctac taccatgctg gttggtatag ctctgcagta taacttgaaa    6300
gcaggtaatg tgattccaaa gaagctagtt aagtaattga gctaaactgg aacctcaggt    6360
gtagaagtca taagcgtggg gagcgtttct tctcaggttc tctgcctata atttagtttg    6420
ccacaccaga tgaacagtga caacttggtc ttggtgttcg tggtggtttc caaccaaact    6480
ttggtcataa caggtgaacc agcctggggc atgctttccc attcggttat cctccccata    6540
gtttgcaaag tagcaaagat gaactcttca tgagttggct aagcatagac atttcaagac    6600
caaactaaac gtcctgaaga gcatgtttca cagaaaacta gcccctaagg accagtgggg    6660
ggctgtcaga gaacaaggtt tcaacgtact gagttttaaa gatctaattg cttttaata    6720 acaattcatg aaccaggcac catagtctac aaaatagaca gggtttctgc tgggcactgc    6780
aggacagttg gtttttggaa ggtggcttga gcaggaacaa ggaaaaagca ccgtgccaag    6840
agtggattgg ttaacatcag gggacttcgg gtgactttcc ttctatgggt taaagcaaag    6900
gggacttccc tagcatgtca gctcaggttg actgggcccc tttggattgg ttgctgtgaa    6960
tctcctagtt ttttttgttt tggtttggtt tgggtctttt ggggaaaacg ggccagtttg    7020
gagattcagc tattatttct ctctcctgat atcagaagat cagatcttat gagtacacag    7080
ctgaggtttt gggttggtga tgtggaaccc tggtgtgagt gactccattt tgggttggtc    7140
tattggggtc tcggtgcagg agctcagtcc aaatcagtgg cctctcctca tttttatttg    7200
acttctccat caatctatcc gtgtctcccg tcacatcagt ccattccccc gtgggctgca    7260
cattcagctc ggagctgaga gcttttccca gggtgtgccc tggggtttct gctgcttgca    7320
gcctgatatt aaatctcagg tgtaaatctt cagaggcaac tgttccttag tacccagagc    7380
tttcagctcc ctgagcagaa atgggacttg actgtcagtt tataaactaa ccaaggtgtg    7440
aaattcatgc aacttagccg actttctgtt caaagaattc ttggcagcag ttaatacatt    7500
ttgcccaaat ataagataat tcccttgtac tcacaatgag aaagttttac aaaatggggg    7560
ttttctttag tttacttgaa tataaaacat aggtgttcca ctctgcagta ccttaacagt    7620
tcttaaggag atgtttgaaa caacccatgt ccaggcctca cacctcgcca attaaataaa    7680
tgagaagttc ttcccagcca gtgttaagaa aaattaacat caagttttag gaaggtagac    7740
agattatgca aatgcatacc tatatgattt aagttattac attaatttac acacacatat    7800
ttaaaatcat agattaatct aatttagaga tgctgcattt ttttccatctc tcctgtttca    7860 taaatgttat tcacacggca tttctctgct atccctcggaa tagtgttttgt atcgtgtcac    7920 tctggcacgg ggctctacag aacatgtcga gcgtgttgcc ttccctactg cccacatcgt    7980
ttgagagaac acattttaaa cattttttta ttgtggtaaa atacacataa cataaaagtt    8040
acgattttaa ccttttttaa ctctgtcatc caggctggag tgcagtggcg agatcttggt    8100
tcactgcaac ctccgcctcc taggtccaag tgattctcct gcctcagcct tccgagtagc    8160
tgggattaca ggtgcacacc accacgnccg gctaattttg tatttttagt agatgcgggg    8220
tttcaccatg ttagccaggt tggtctcgaa ctcccgacct caggtgatca gcccgcctcg    8280
cctccccagt gctgggatta caggcgtgcg ccactgtgcc gggcccattt taaccacttt    8340
```

```
taagtgcaca gttcagtggc attaagtata ttcgcggtgt tgtgcgaccg tcaccaccat   8400
tcacctccag aacttctctg tcttcccaaa ctgaaattct gtacccattg aacggtaact   8460
ccccattccc catttctgct tcctaggccc tgacatggag gctgggccaa cggatatctc   8520
acctcccttc aggcttctcc agatttgccc ccgttttcc ccctctttgt cccatctcca    8580
aagaaatggt gtctttcat catcaaggtc catcccttgc tccttgaata cactccaggc    8640
ccagtggaac aggcatcctg tggggtgcac ggacagggtg cctggggaac acccagggca   8700
cagaacccag accggggtt tggagaaggt gtcctagcag aagtgatgtc taagctgagg    8760
ccctacagat aagagaaagt aagcagatga aagggctggg gagggtggca tttcaggcct   8820
acacaaccac acgcgtgttc ttcagccatc tccatggcct cactgcccac ctggtatcag   8880
ccggccacca cccggctaga acggctttca aaatcgctgc tcgtctactc ctcaccaaat   8940
cttgtcttca cttggtgctc aagcccatca cctttctgca agtattattt tttttttttt   9000
ggagatggag tctcgctctg tcacccgggc tggagtgcag tggttcaatg atagctcact   9060
gcaaccttga actcctgggc tcaagatcct cttgccacag cctcccaaag tgctgagatt   9120
acaggcacaa gccaccatgc gtggtccttg ctgcaactt ttttttttttt tttttttttt   9180 ttttgagaca gaatctcgct ctgtcgctca ggctggagtg cagtggtgtg atctcggctc   9240
aatgcaacct ccgcctcccg ggttcaggtg attctcctgc ctcaccctcc tgagtagcta   9300
ggaacacagg cgctcaccac cacatccagc taattttgt gttttagta gagccggggt     9360 tttgccatgt tggccaggct tctctcaaac tcctggacct cgggcgattg gcccgcctcg   9420
gcctcccaaa atgctggaat tacaggcatg agccaccgtg cctggccatt tgctgcaact   9480
tttgacactg ctccccctgc ttttcttccc ctctctgacc tcctttctct gctgtccttt   9540
cgttccttcc tctgccactg aagtgtcctt tcaggtcct tctcaaggtt gtgaccttac    9600
agctgtctct tcacttccag tcatttcttt cataatcact ttgacatcct tattttcatc   9660
tcctgccctg gcctctccca gggaccagga ccatgcattc agctcctggg ggcatctcaa   9720
gcttgttgtg tgtgagcctg cccttgttgt cttctccgtc acctcttcac agcttgctct   9780
gcatttcacc tcctttcctg ttttcccag tgatcgcatc tctacagcgg ctctcacttc    9840
atccccttct ctcctagagg agtgatgcgg agtctcatta atccttgctt atgtcattct   9900 tccccttct ctgtccatca cctccacatg tcctgttccc ccatgcgtcc tacactgtag    9960
ccaggtgggt atttcctgtg ctggtcttag acacccctg aggatacct gcttcaggcg   10020 agagccctca gtgactccct gttgtccgga atgacgtcca gctccttgga cagtcccag   10080 tgtattcacc tgtctcatct ccttctttc gttttgtttg ttttcttaa cttccagccc   10140 gatttctgaa tcatctccct cttgccctc ccattgcctt tgcttaagac taaatgctcc   10200
ttcctcccaa gtccccactg cccagatttc agcagggtcc atctcaaaca tgtctgtctc   10260
caagaaactg cctctgattt ttttcataag aagacacctg tcctctctga cttcatctgt   10320 accctctct tggaagtcac tatcttgtgc cttgcatttt cgttgtttaa gtggtctcca   10380
tttcccagca tatcttgagg tcaagggttc aggtcatttt atctttgtct atgcattgca   10440 atatggggt ttacatat tagctgctca ataaatcggt gttgaataaa ggcatgtgta      10500
tgctttcatt aagactatga aacccacaaa atcagtggt tttcctattt cacccttaga    10560
aaacaaaccc acaacatagc acaacctgat attcagagct aagaacaaag gtcatgcata   10620
ttaatctaaa ttctatcttt atcaactttc acaagtaatt cgtatttccc tgtctgcatc   10680
acggggatga ttctggccag acattgacct tggtaaaatt tcctccagat tatgagaaat   10740
```

```
caagtcaaat atgccaagta acatagtttc tacttagagt caggttcatg ttttagcagg    10800
aacctcaaat accacaaaat ctgtcaagtt ctaacatttg tatctctcga cagtacctga    10860
agttcctgtt tctgtttcct cagcccaggt ttccaattca gtgagcagaa cggtgactgt    10920
gttggtaaaa gagcccacat acctgcccga tcctgcagga gtgttgcaga tgcaaacagg    10980
cgggtctcca catgacctgc ggagtaatga ctagtgtccc taaagtcatg ggcttctgg     11040
ggttagcctt gaaaaaagct aaaggttgca tagagagaga tttctatccg ttcagagact    11100
cactataatt ctctctttct gtctctgtcc ttcatctgtt tctctctttc tctctcactc    11160
tctctctctg atacacacac acacacacac acacacacac actcacactc acacactcct    11220
gagtaaggga atgtgagaa gaaggtaaaa cttcaactaa atgaaaagaa attgtatgaa     11280
ttatggtaag caggttggtt tttagttcca gtaaagatag aaatatttag attacttagg    11340
agaaaagtct agctggtaac acatgggaat gtgcctgtgt gaaaacaaaa caaaacaaaa    11400
aatctaggct tgtggttagg tgaaggtatg tacactgctg agacatggcg atgggtgagc    11460
ttgggatgag gagaaaggct tctctgagaa gattaagaga gaaagattgt ttaaaaatgt    11520
ttaaacatgc tgggcactgt ggctcacacc tgtaatccca cactttggg aggccaaggt     11580
gggcggatca tgaggtcagg agttcgagac catcccggcc aacatggtga aaccctgtct    11640
ctgctaaaaa tacaaaaatt agccaggcgt ggtggcgggt ggctgtagtc ccagctactt    11700
gggaggctga ggcaggagaa tggcgtgaac ccaggaggcg gagatgcagt gagccgagat    11760
tgtgccactg cactccagcc tgggcgacag agcaagactc cgtctcaaaa aaaacaaaaa    11820
aacaaaaaaa aaacacacat tgacaccagg acggagttag cacatcttta caggtgagac    11880
tctcagaccc gagaaaatag aggcacttta gagctgagct aatcccacag ccacctcaac    11940
acacaaacgg ggaatctgag acccgcattg gcaccgtgcc tgaggttcta agcccaggg     12000
cttctgactc gcctcttgtg cttcttcagt actgtgggtg ggggtggggt gggggtgac     12060
attagctgat gagaaagatt ttggttttag aaagatggag ttaacataaa cgaaggtgta    12120
ctgggactgg tctcctctgc tgacttcatg ggaagcacac acacgcacac acacacacac    12180
acacacacac acacacacac atacacacac ctgtccaaga tcagaaaaaa tccctcacat    12240
ccctgtagca tgatcctgat tgtaaaaatg gagccctaat cagaagggca gaagcatgat    12300
tgcctctcaa gagatttgga cgccactttt tcatagttgg ttttagctgc tttgcgatat    12360
atactgaaat aaatagaaaa gggaaagaat tgtaacctgg attgacagac aacaagccct    12420
gacagacaaa aagcagataa gaaataaaat aaggaagata acccataatg taaaataaaa    12480
atagcacatt gttgcatgca ttgataccct ttttttttt tctttgagat cttgctctgt     12540
cttcaggcc gaagtacagt gtctcaatca tagctcactg cagcctccag cttctgggct     12600
caagcaatct tcccatctca gccacccaag tagctgggc tgcaggcacg aactatggtg     12660
cccagctgat aattttaaa aatagggaca ttagtgcatt tagcaaattt gagtgtctgc     12720
tgtgtatcaa gcactgttct gggcactggg acagcacagg gagcaaataa acaaaagccc    12780
ctgcgctcaa ggtgctcgta ttctagaggg agatgctgag ttcacctccc attaaaatgc    12840
cattctcaag atccagtccc tccacccacc ccagccccca gggttttggt ggaaatttaa    12900
ctaagttgga agattgataa tatctccatt cacatttgga tatgatttta atgaaggttg    12960
cttttttggtt tttagggaga agaaaatggc tttccagata gcactggaga tcctcttcca    13020
ggtaaatgat tgattctaaa gctatctggg ctaatagcta gtgtggctga ataaaagata    13080
```

```
atttgaggcc agggtcggtg actcatgcct gtaattccag cactttggga ggccaaggtg    13140
ggcggatcac ctgaggtcag gagttcaaga ccagcctggc caacatggta aaaccccgtc    13200
tctaccaaaa atacaaaaat tagctggttg tggtgggcgc ctgtaatccc agctactcgg    13260
aggctgaggc aggagaatcg cttgaacccg ggaggcggag gttgcagtga gccaagatca    13320
caccactgca ctccagcctg gacaacagag cgaaactcca tctcaaaaaa ttaaattaaa    13380
taaaataaat aatttgagac tatgtttatc attaacttta aaatctgtac tgcagaatag    13440
agcaactttc tacctgcggt gcactgcagg gaaagccgta tcttacaaga cttcacaaaa    13500
gccttcaaag agtattttct ctgcactaac cttcctttgc atgtgagggg cacggcaggg    13560
ttctgaatgg ggcaggttta ggatcaggcc agtcgggact gagtggattc ttcttccctc    13620
tgagttctaa gagccatagc attggtggag aacatgctgt tgttgcttg gtggaaggga    13680
ccagaagcca gctgggtcat ctctctgttt gtgccttggc cacttaggta gccaaggag    13740
ccctcctgac attaggtcag gtgttagtcc ctctcctttt ctgcttttag tgtgtttaag    13800
caaataaaca ttaaagttca tttctccccg ctccccttt ttaatcataa gacagacatg    13860
tttgcaatgt ttaaatttct cattaatcag aagggatagg gagtgaggga gtaagcatta    13920
aaataagcta gcaaatggcc aggtgtggtg gctcacacct gtaatcccag gactttggga    13980
ggccaaggtg ggcagatcac ttgaggccag gagttcaaga ccagcatggc caacatggca    14040
aaactccatc tctactaaaa atacaaaaat tagccaggcg tggtgatggg cacctataat    14100
ctgagctact cgggaggctg aggcagagaa ttgcttgaac ccgggaggca agattgcag    14160
tgagctgaga ctgcaccact gcattccagc ctgggtgaca gagcaagact ccatctcaaa    14220
aaaatgctag caaataata ataataataa taataaaaca tacctcacca acattttcta    14280
catcttgtaa agcatacatt gactgactga agtcaccaga gttttgtttc tttctttctt    14340
aagcagggtg gggaacccgt agagccctca ggggcagcta tcatcagccc aggtaaccaa    14400
gctgaaaaac cagaaggtgc agtgcgtact caacttttc cccttagaaa cacgatatta    14460
gaaaatacac caataccaac atgtgagcaa cagttctctc tggaaggtgc agttctgggt    14520
gattttttt tcattccata gatttttttt ttcttgagac ggagtttcgc actcttgttg    14580
cctaggctgg agtgcaatgg tgcgccacca cgcccggcta ttttttgtat ttttagtaga    14640
gacggggttt caccatgttg gccaggctgg tctcgaactc ctgacctcag gtgatccacc    14700
tgcttcggcc tcctaaagtg ctgggattac aggtgtctca ctatgttgcc taagcttttc    14760
tcgaacccct gagctcaagc ctcctcccac ctcagccatc caaagtgctg ggattacagg    14820
catgagccac cacgcctggt gagtttttat tttcttttca ctatccntat atttctaaaa    14880
tttctaacat gagctggtat cagaactgcc cctccgcatt taatctgtgt atacaaatgt    14940
atatataaca aatgatcaca tgttggtaan gtataccttg ctgcatggtg aaataaccaa    15000
ggaaacttct aaaaggttaa ctgtggttgg cctgggtaat gggagcatta attttttcca    15060
tatgctcatc tgaattttca gatttgctat gacaagcaca tatttatttt ctaattttaa    15120
aaatctatat ttaaactctt taagactaa caccctacac actaatgtgg cacgttagct    15180
aaaataaaaa taaatacaga aatttgttta gaaatatttg taaacccttc aaggactctt    15240
ctgaatgata gtcattatta attagcaggt taatttaat caggcttctg gtcatcttca    15300
aacattttt acttgtgtca aaatgaacca ccagagtgtg gtttttttg ttatttttt    15360
tgtttttttg agacagagtt tcactcttgt tgcccaggct ggagtgcaat ggcgagatct    15420
cggctcactg caacctctgc ctcctgggtt caagcagctc tcctgcctca gcctcctcct    15480
```

```
gagtagctgg gattacaggc gcccaccacc acacccagct aattttttgta tttttagtag   15540 agatgggttt tgccatgttg gccaggttgg tcttgaactc ctcacctcag acgatccacc   15600
cacctcagcc tcccaaagtg ctgggactac agatgcacac caccacaccc ggttaatttt   15660
tgtattttta gtaaggacgg gggttcccca tgttggccag gctggtctca aactcctgac   15720
ctcaagtgat tcacctgcct tggcctccca aagtgctggc attacaggcc tccgccaccg   15780
cacccagccc aacctgggtc cttttgtatg tgagagtttg cttgtttttt tcacgtgctt   15840
tctctactcc agttttattc tatgacaaaa ttgaggccca acatgattta cttgcctgga   15900
tccacccaac ctgtcagtta cttcccagtg ctgctgccaa cttaatgtct ccttaaaagg   15960
atgctttaga gaaaacgaaa tcatgttgtt tttccccttt ggttaagaga tcaaacgccc   16020
accaaaagcc cttgggtcag tttcttagta gataaaaata attcttcgtc actttctgaa   16080
agcggctaac atataaccct tatgatgaat aatgtggtgt gtgtgtgtgt gcgcgcccca   16140
aattccaatg agttatcaaa gccagaaact tatattttaa atatgtttat ttcccaacca   16200
cactggaaac cacacacaga aaaaaaaaaa agcatgatta tacccccttaa ataaccgtta   16260 ctgcagaagg atgtgactct ccttcaacac ttgttggtat tttacagcct ccaaatctga   16320
ccatgtataa ccacctggga tagagttatt ttatttcaga accataatac ttagctatct   16380
cggaagttgc caatataaaa tgtttactct ctaatggttt tgaactaact caagacctgg   16440
ttatcccggg gagcatcctt acaaatgatc tgagagctaa cagtcctctt gcagcagtgg   16500
agggaaacac tcccgtggca atcactctcc aaaagccaga atgtgcaaga taaagggca   16560 ccttccctgc agggaggcac attaagtcag tctgtgatct gctgccaaca tcctgactgg   16620
agccgtttct acgcctaact aatcatgacg tttgtgaatt gtgaagcttg ttgcaattca   16680
caattaactg ttaattgacc catatttat aacccgccag ccatgaactt acaagttaga   16740
tacagacact accagacatt cactattttt ttttacaatt gttttaaatg acattaatga   16800
gcatgcttga ttcctgaact cttctttaca gtataatttt aaaatatttg agtgggatac   16860
gatggagagg agggaggtgg gggaagaaat gccccatgga aaacccactc atcaggttga   16920
gagtgtggag aagccctgtg tatctgagaa ctcttaatca tccacagaca tggtatctct   16980
caaagagaag tgggtgtaat tccaaaatct aattttggca ggcgctcctg actaaatact   17040
taatctggag atgtcttcaa ggcaggcgga ggttttcagt cctggctgca cattagaagt   17100
cccaggggag ctttaaaaaa ttcccacgtc ctccctgcat cccagactaa ttaatcggga   17160
tctccgaggg tgggaccaca catcagggtt ttgtaaattt ccctgggggt ttggtggggt   17220
tgggggtgga ggcgtctatc ctatggccaa ggttgagaac cactgctttt taaaagactg   17280
tttgcttgtt tttgagatgg ggtctcgctc tgtcacccag gctggagtgc agtggcgcaa   17340
tctcagctca ctgcaacctc tgcctcctgg gctcaagcaa ttctcctgaa aaaggctgtt   17400
ggttattaat gcttccccac agctattcta ttcattgttg catgcttctt acgtgtgcta   17460
ggatgggagc tttaaaggat tacctcattt aatcctcaca accaccttgt gagagaggtg   17520
tcattatccc tgtttggaga gtgagacagg ggcttagcaa gctcagtaac ctgtccaagt   17580
cacacatctg catggggtta gctgctgcta aagctcatgc cgttaatctc catggtacac   17640
ggtgtcctct ccatagcaat cttgcggctg ccttgttaac accaaaaaaa cttgcatcag   17700
ctggtttgac aatttctaga taaagagctc ttttcgggct gctaagaagc ctaattttc   17760 atttgatttt cttcttgaac tgtgtcacac tcctcattca tttgatatat tcatcaaata   17820
```

```
cttattgagc acctgctgtg tgcctggtgt gcagcagtga caccagacat ccaaagtcct    17880
tttcctctta gagcttattc tatctgggag agacagataa taaacacaaa atcagtaagt    17940
cattttatat ggtggtaggt gccttgagga agatgagcca ggttaatggg attaagcctg    18000 gtaggggag ggtgccactt tagctcggaa agggtagcga gacccaaaca atgcaaagga     18060
cccggcccgt ggagatctaa gacaggagga tgccagggac aggaagttgc tggggcaaag    18120
cccctgaggc tggactgagc tcagtgttct aggacgggcg tgggcagtga ggagcagcag    18180
aggaggtgag ctgggagata gcctggggac tctttcttct gcctccttca aaaaataaaa    18240
ctagccaggt gtggtggctc acacctgtaa tcccaacaat tgggaagct gatgtaggtg      18300 gattgcttga gtccaggagt tcgagaccag cctgggcaac atagtgagac ccctccccccc   18360 atttctacca aaaaatcaaa aaattagctg gcccgtgg cgtgcgcctg tggtcccagc      18420
tactcaggag gctgaggtgg gagcattgtt tgaacccggg aggtggaggc tgcagtgagg    18480
cgtgattgtg ccactgtact ctagcctggg tgacagagtg agactctgtc tctaaataaa    18540
taagtaaatc tagaacctaa catcttggag tgcagtggca ccaccatggc tcactgcagc    18600
ctcaatctcc tgagctaatc gagcctcccc ttcagcctcc tgagtagctg ggactatagg    18660
cgtgcaccac catacctgaa taatcaaaac ctaacatctt taaagaacat tggcataaga    18720
cttggcaaaa atggcatctt gtccctcatc tcatttagtc caagcgatac aggaaatgct    18780
gccacctcca ttttatagat gaggagtctg acgttcctag aggttcaatg ccctgaaacg    18840
tcaagccttg aggaagttgg agcactggga ttcgaagagc accatccaat acagacccag    18900
aatcaggatg atttgggatt atgcttgtca aggactcagg gcagggctac catacattag    18960
gcacaagaat tttgatagtg ataattactg tgttcattgt cacttcatca tgacagttac    19020
cgtgatgata agaaacctgg cccttcttca cctgacaaag gctttcttcg tttgagccac    19080
tgctcaaacg agactgacca agaataaatc ctcggggctt tggcctttaa aataggaagt    19140
catcataaat gacttgatgt ggtgtgtttc attcttgctt tgcaccagtg gaaaatatac    19200
aggtcaagca tcaaaacatg gcaaatgggg acccccaatta ttagagaatc taagttaatt   19260
tttatgtata attaattatt caacaaccct ctcctctcca aaccaataat taatccatct    19320
tttgtatttt aagaccaatt ctgtagtatt ttccatcaat atctatttac tgctagcaga    19380
tatcagctac attctttctc ctttaataga agttccctct ttaggtatta agattcatta    19440
aacaacaata acaaatctac cttgcctccc agggacaatg cacagttctc attcatttgt    19500
tcatttagca gataattttt gaatttccac tgtacagcag ccctgtgctt gtggttggcc    19560
tgttatttga gaagcatcaa ataataatct catttttttgg ctgggtgtga tagctcacgc   19620
ctgtagtccc agcactttgg gaggctgagg cgggtggatc acttgaggat gggcgttgga    19680
gaccagcctg gctaacatgg tgaaaccctcg tctctattaa aaatacaaaa attagccagg   19740
tgtggtggca gacacctgta atcccagcta ctcgggaggg tgaggcagga gaatcgcttg    19800
aacctgggag gcagaggttg cagtgagccg agatcgcccc attgcactcc agcctgggca    19860
acaagagcga gactccgtct caaaaaacaa aacaaacaa gacaaaaaaa acccaacaa       19920 ataaaataaa taatcccatt tttctccatt tttgagaaag atttctttgg tctgaagtct    19980
ttctctcccc tctccgaggc attacccagt ttaaccttc atgtataata tatatgatag     20040
ttatttaaag tatagcagga caaaatgtat ttgataggag aaaaccttgt ttgctctgtg    20100
ttaagtcctc cagagagcta attagagttt gtgattctaa aaggcaacta tagattcact    20160
tatattagca gttcatgtag attccagtta aggaaatggt ttgtcacttg tgttattgaa    20220
```

```
aacacacaca gggcgagcac tgtggcccat gctggtaatc ccagcgtttt gggaggctga    20280
ggtgggcaga tcacggggtc aggagtttga gatcagcctg gccaacatgg tgaaaacccg    20340
tctctactat aaatacaaaa aattagctgg cagtagtggc aggcgcctct aatctcagct    20400
actcgggagg ctgaggtagg agaatcgctt gaacccagga gtcggaggtt gcagtgagtc    20460
gagatcgcac cattgcactc cagcttgggc aacaagggca agactccgtc tcaaaaaaaa    20520
agaaagaaaa cacacacaca aaaaacttt agtagatctt tcggcatatt attttttaaa    20580
ataaactgat aatggttgat atgattgttc aaagaaataa gagcttttca taaactcagt    20640
ttaaagaaac tttacaggcc gggcgcggtg gctcatgccc gtaatcctag cactttggga    20700
ggccaaggcg ggtggatcac ctgaggtcaa gagttcgaga ccagcctggc caacatggta    20760
aaagcctgtc tctattaaaa aatacaaaaa ttagccaggt gtgttggctg gcgcctgtaa    20820
tctcagcaac tcaggaggct gaagcaggag aatcgctgga acctggtagg cagaggttgc    20880
agtgagacaa aatcgtgcca ttgcactcca gccccagctg acaacagcga gactccatct    20940
caaataaata aataaataaa taaataaata aataaataaa ggagctttac agaaaccttc    21000
tgatgttttt ttcttcttga cgataacatt gccaacactg aatcttacaa agataagaca    21060
agaaagggac cttcagacac cattacatgt aattctggac ttagtggttt aaatccttat    21120
ttttctatga cattaaaaaa atgtatattt taggccaggc acagggctca cacctgtaat    21180
cccagcactt cggaggccg aggcaggtgg attgcttcag cccaggagtt caagagcagc    21240
ctggggaaca tagtgagacc cctgtcccta cagattttt ttttttgttt gagatggagt    21300
tttgctcatg ttgcctaggc tggagtgcag tggcacgatc tcggttcact gcaacctctg    21360
cctcctgggt tcaagcaatt ctcctgcctc agcctcccaa gtagctggga ttacaggcat    21420
gtgccaccac acccggctaa ttttgtattt ttggcagaga ctgggtttct ccatgttggt    21480
caggctggtc ttgaactccc aacctcaggt gatctgcctc cctcagcctc ccaaagtact    21540
gggattacag gcgtgagcca ccttgcccag cctacaaaaa gttttaaaaa attaaaaaat    21600
tagttgggca tggaggtgca tgccagctac tcggaggct gaggcaggag gattgcttga    21660
gcccatgaag tggaggctgc agtgagccat aattgcagca ctgcactcca gcctgggcca    21720
tagagcaaga ccctgtctca aaatatatata tagtatccaa ataaacacaa taattacaga    21780
aaattgaaaa gtgcccataa gcaaaaaaaa aaaaagaaa aaattaatca cctgcgttct    21840
catcacccag aattaaccat tgttaatatt tttgttatag atccttccaa acttttctcc    21900
atgcttgtga ttgtatttat tatacatgat ttacagggat ataaacgact gtattattag    21960
tcattagaag aactggatta tggccgggca cggtggctca cacctgtaat ctcagtactc    22020
tgggaggctg aagtgagcag atcatgaggt caggaaatcg agaccatcct ggctaacaga    22080
gtgaaacccc gtctctacta aaaatacaaa aaattacctg gcgtggtgg caggcgcctg    22140 tagtcccagc tactcgggag gctcaggcag gagcagagat acctatctgt tctcaggatt    22200
ttaaggtgtt gcgcggaaat aagaaaaccg tacagtgttt ctcactacaa agcagggtca    22260
ggagatgcaa acaaactgat gtgggggttc caagtgaggt ggaattccag acaggggccg    22320
ggaagacttc gtgaaaggg agaatctgag gtgggttttc taggatgggt aaagttcatt    22380
agaggaagag aagtgcaaca gaggaagttc ggtgagaggt agagggaagg cgttctgatc    22440
atgaaggaaa cactagaaaa ggtatggaga tagaaaaaga taaggcctga tttttttaacc    22500 taccacttaa aaaaaatcct tgaaaagaga ttttaaaac gaatacttgg tgctgacaaa    22560
```

```
ggtgaaatga ccgggcgcgg tggctcacac ctgtaatctc agcacattgg gaggctgagg    22620
cgggcagatc acttgagctc aggagtttga gaccagcgtg ccaacatgg caaaactcca     22680
tctctactaa aaatataaaa attagacggg tgtgatggtg ggtgcctgta gtcccaacta    22740
ctcaggaggc tgaggcagga gaattgcttg aacccgagag gcggaggttg ctgtgagctg    22800
agattgtgcc actgcactcc agcctggata gcaggatgag actgtctcaa aaaagaaag    22860
aaaaggaaag aaaaaaaaat ccgtactgta aactggtaaa ggctttcttt ctggagagca    22920
atttggggca catgcaccag tagccttaga aggctcatgc ttttgaccta attatcctat    22980
tagtggtgag atgattaaag atgtggcccc aatttatgtg aaaggtatgc atcacatctt    23040
cactcataat caggagagtt ggggaaaacc ctagctgtta atagtttatc caaaatccat    23100
atatatatgt gtgtgtgtgt gtgtgtgtgt gtgtgtatgg atttatatat atatataaat    23160
ggatatatat atatatctgg atggatatat aaatatgata tatatatgtg tgtgtgtgta    23220
tatatatatg tgtatatatg tatatatata tgatggaata ctatttagcc ataaaaagga    23280
atgaattaat ggcattcgca gtaacctgga tggacttgga gaccattatt attttatttt    23340
atttattat ttttgagacg gagtctcgct ctgtcaccca ggctggagtg cagtggctcg    23400
agctcagctc actgcaagct ccacctcccg agttgacgcc attctcctgc ctcagcctcc    23460
tgagtagctg ggactgcagg cgcccgccat cacgcccaga taactttttg tatttttagt    23520
agagactggg tttcaccgtg ttagccggga tggtctccat ctgctgacct catgatccac    23580
ccgcctcggc ctcccaaagt gctgggatta caggcgtgag ccaccgcgcc cagcgagact    23640
gttattctaa gtgaagtaac tcaggaatgg aaaaccaaac atcgtatgtt ctcactcata    23700
agtgggagtt atgctatgag gacgcaaagg cataagaatg atacgataga ctttggggac    23760
tcagggaaaa ggtgggaagg gggtgaagga taaaagatac aaattgggtg cagtgtatac    23820
tgctcgggtg atgggtgcac caaaatctca taaatcacca ctaatgaact tactcatgta    23880
accaaatacc acctgttcct caataaaacca tggaaattaa aaaagaaaaa agaaaaagta    23940
ccctggaaaa aaaatttctc cctggccagt cacggtggct catacctgta atcccagcaa    24000
ttcgagaggc tgaggcagga ggatcacttg agcccagtag ttcaaaacca gccagtgcaa    24060
catagtggga ccctgtctca aataaaatct aaaaattagc caggtgtgtt ggtgcatgtc    24120
tgtggtccca gctactcagg aggctgaggt gagagtattg cttgagccta ggaggttaag    24180
gcggcagtga gccgtgattg tgccactgcc atccaacctg ggcaacaaag caagaccctg    24240
tctcaaaaaa aagaaaaaa aaaacctctc tattcgcctt ttaagaatac ctgggcttct    24300
ctgtgtacac ttaagcttca ttggagtctt tagacttttt ttttgctgta tctgtccagt    24360
taccaagtcc cagcttctac tccatgctcc ccatgctctc ttcctatttt attttccatg    24420
actgcctcgg tataacttgt gctcaaccaa actggactac tcaattccct gcattttctt    24480
ttttaaagtt taatcaaaaa aaaaagaaa actggctggg cacagtgggc ttctgcccac    24540
aatctcggtg ctttgggaaa ctgaggcagg aggattgctt aaggccaaga gttcaagacc    24600
agcctgggta acatagcaag acctccatct ccacaaaaaa atttaaaaat tgactgagtg    24660
tgatggtgtg cacctagtcc cagctgcttg ggaggctgag gcaggagaat tgcttgagcc    24720
caggagttcc aggttatgat gagctatgac tgtgccaccg cactccagcc agggtaacag    24780
agtgggactg tctcaaaaaa caaaacaaaa tccctaatat aatctcagtg tgccttttaa    24840
gtatgccata tatatatata tatatatata tatatatata tatatatc acattttctt    24900
tatccactca ttgatttca tgtagttcta atcgtagaat tcatacattc tttctatctt    24960
```

```
ccatctttca cataacatca caaacatttt ctaggttgcc atattgtctt catagttact    25020
taaataatat tccatcaagt agcacaatca tttatttcac tagtcctcta actgtagaca    25080
ttttggttgt ttttgaaact taataatgta aataacaccg tgataacaat gtttatgtaa    25140
attcatattt tggattatct ccttagggtg gattcccaga agtcacatta gtaggtcaaa    25200
gagtatgagc ctattttcaa ggctcttgtt ttattacctt ttaatttcca cttgcctcaa    25260
tattgctggt ttgctccctt atgatcacca gagttactcc gtcggtccaa attctttacc    25320
ttccgaaact gggaaggcca tgactcaatg ttatatatat agtaaaggct actataacct    25380
tccccagaat tttccaagcc agtggtctct aaagtgacct ttggctgtta aaatctgaat    25440
tcagagggtt catgagactc agtgttgttg tagaatttaa gctccttaat ttgccacgtt    25500
gtttagacac cacttaatac tttattgcaa atgacttgtc aacgcctctc acctacaaac    25560
ttcatcctcc tacaaatata cctcctgcta atcaaatgag gctacagttg agtctttaag    25620
tttcagtaga aagatggccc ttcctctggg gtaggcgcat gctcttcatg ctgaagctca    25680
gctgaaaagc ctcctgctga gttttctgcc tcttcccctc ccactgcaca caccccaggg    25740
tgttggcgcc acttcaaagg gagcctgtgg atgaagaaaa cacaggtaaa ggcagagggc    25800
tcataagggg gccataaatt taaaaagtta agattcctgg cactatcaac tctcacttgt    25860
tttcaaatat gcatatggag tggatattcc agttttcatg tctgtgttgt tgttttaaa    25920 aaaagacctt tcaaagaact gtgcattttt tacaggctga caggctgtgt ttggtgttaa    25980
actgtcaggg ctgactggtc acttggaaag ggcaagggct gaggtgcatg caagtgtcgg    26040
ctggttactc acagacacag cagccccttt taccccggag agagttctgt ttgctggagc    26100
ccttattctg gccagcagtg tcacaaatgc acactgtaag acatagacag tcttggaaag    26160
aaagggaaac tggctttaaa aattcttact ccttctagca aagcaattca tctttggcta    26220
taaagaataa cacagccagg tgcggtggct catgcttgta atcccagcac tttgggaggt    26280
caaggtgggc agatcacttg agtctaggag ttcaagacca gcctgggaaa catggtgaaa    26340
ccccacctct accaaaaaaa aaaaaagaa agaaagaaaa gattagccag gtttggtggt    26400
acgtgcctgt agtcccaggt actcgggaag ctgaggtggg aggatcgctt gagcctggag    26460
ggcggaggtt gcagtgagcc gagatcatgc cactgcactc cagcctgggc aacagagtga    26520
caccctgtat caaaaaaaaa aaaaaaaag aacagtaaca cattattaga aatgagcatt    26580
ctgaggccag gcacggtggc tcatgcctat aatcgcagca ctttgggagg ccgaggcggg    26640
tggatcacaa ggtcaggaga tcgagaccat cctggctaac acggtgaaac cccgtcttta    26700
ctaaaaacac aaaaaattag ccgggtgcag tggcgggtgc ctatagtccc agctactcag    26760
gaggctgagg caggagaatg gcgtgaaccc ctgggaggcg gagcttgcag tgagccgaga    26820
tagtgccact gcactccagc ctgggcgaaa gagcgagact ccatctcaaa aaaaaaaaa    26880 aaaagaaaga aacgagcatt ctgaaatagt cttccatatg atgcttttga caattcagca    26940
ggaaaataaa ggatgtaaga aatgaatgca tatgttaggc ctcttgttga cctgtggact    27000
aaattgtttc tccctgcaga gatcagcaag gacaactcct gcaaagaaaa ctgtacttgt    27060
tcctcctgct tgctccgggc ccccaccata agtgacttgc tcaatgatca ggacttacta    27120
gacgtgatca ggataaagct ggatccgtgt cacccaacgg tgaaaactg gaggaatttt    27180 gcaagcaaat gggggatgtc ctatgacgaa ttgtgcttcc tggagcagag gccacagagc    27240
cccaccttgg agttcttgct ccggaacagt cagaggacgg tgggccagct gatggagctc    27300
```

```
tgcaggctct accacagggc cgacgtggag aaggttctgc gcaggtgggt ggacgaggag   27360
tggcccaagc gggagcgtgg agaccctcc aggcacttct agagctcttc ttcttccttc    27420
attggcctct ccggatgttg aaacaaccac aggtcaagaa ggaatgtgaa tctgttgttt   27480
tataagagtt taggacaagg acgtggaaca gtggacactg gttttcccca aagctggcag   27540
ttttgtggag gggtagcttg tttcggtggt ggatctctgt ttattttgc acatctgtta    27600 taatttaata ttcaaatctg gaattaagaa aacatatttt ctagtatcct ctaagggcca   27660
aagtcctaca atcggaatgg attcatgcca cgttgaagat aaaattatcc tctctctgaa   27720
atacggtaaa gatttaaata ggtcctgaga ctgttgatag ccccagacat acccacagca   27780
ttatatgtaa catctctcct gatcagtgcc attcccacgg tttcaaagaa aacagctaca   27840
aggaatgctt acctgagtgt ctgcagcacc ctccacttct ctcctaggca atgagaccca   27900
gtggctagaa attcaccatg tctattctca agatccatgc cagggagctc tttgactctc   27960
gtgggaatcc cactgttgag gttgatctct tcacctcaga aggtctcttc agagctgctg   28020
tgcccagtgg tgcttcaact ggtatctatg aggtcctaga gctccaggac aatgataaga   28080
ctcgctatat ggggaagggt gtctcaaagc ctgttgagcc catcaataaa actattgcac   28140
ctgtcctggt tagcaagaaa ctgaacgtca cagaacaaga gaagattgac aaacttatga   28200
tagagatgga tggaacagaa ataaatcta aatttggtgc aaatgccatt ctgggagtgt    28260
ccctcgctgc ctgcaaagct agtgctgttg agaagggggt tcccctgtac caccacatcg   28320
ccgacttgtc tggcaactcc aaagtcatct tgccagtccc ggtgttcaat gtcatcaatg   28380
gcagttctca tgctgtcacc aagctggcca tgcaggagtt catggtcctc ccagtcggtg   28440
cagcaaactt cagggaagcc atgcccattg gagcggaggt ttaccacagc ctgaagaatg   28500
tcatcaagga gaaatatggg aaagatgcca ccggtgtggg ggatggaggc gcgtttgctc   28560
ccaacatcct ggagaataaa gaaggcctgg agctgctgaa gactgcgatt gggaaagctg   28620
gctacactga taaggtgatc gtcagcatgg acgtagaggc ctccgagttc ttcaggtctg   28680
gaaagtatga cctggaattc aagtttctcg acgaccccac caggtacatc tcacctgact   28740
gtctggctga cctgtacaag tccttcatca aaaactaccc agtggtgtct actgaagatc   28800
cctttgacca ggatgactgg ggagcttggc agaagttcac ggccagtgca ggaatccagg   28860
tagtggagga tgatctcaga gtgaccaacc caaagaggac agcctcggcc gtgaatgaga   28920
agaagtgcaa ctgcctcctg ctcaaagtga accagattcg ctctgtgact gagtcccttc   28980
aggcgtgcaa gctggcccag gccaatggtt ggtgtgtcat ggtgcctcat cattctgggg   29040
agactgaaaa taccttcatc actgacctgg tggtggggct gtgacctggg cagctcaaga   29100
ctggtgcccc ttgctgatct gagcgcttgg ccaagtacaa ccagctcctc agaattgaag   29160
aggagctggg cagcaaggct aagtttgccg gcaggaactt cagnaacccc ccagccaagt   29220
aagctgtggg caggcaagcc cttcagtcac ctggtggcta attagacccc tccccttgtg   29280
tcaactccgg cagctcaaga cccccgagca acatttgtag gggccgctgc tagttagcta   29340
cccttgccca ccgccgtgga gttcgcacct cttccttaga acttctacag aagcaggttg   29400
cagtgagccg agattgcgcc actgcacacc agtttggaga cagagtgaga gtccgtccca   29460
gaaaaaaaaa aaaaaaaaaa gaacttntac agaagccaag ctccctggag ccctgttggc   29520
agctctagcc ttgcagtcat gtaattggcc caaatcaccg gagccacgtg accctccagt   29580
gtcatctccg gggtggccac aggcaagatc cccagtgatt ttgtgctcaa aataaaaagc   29640
ctcattgacc catgagaaaa aagaaaacag caatgagaag tgaccctgtc ttgttggttt   29700
```

```
attactttt   ttgttataaa   gtactttggt   gaattaacag   gatgctagta   ttacatggtg   29760
atactcttca  gaacacctgc   cccatctttt   ttatgcaagt   atgtttacaa   tcagtggact   29820
atcagtaatg  tcatttgctc   aaatatttt    taaagaccta   cagaaactga   tggttattgg   29880
gaaaacagtc  aggaagtagt   gaggtaatca   aggccatggg   aatagtgttt   gacaaagaga   29940
gtactccaaa  tccctttgg    ttacccagga   ctttaaaaaa   gagagtactc   catcacacct   30000
gtaatcccag  cactttggga   ggccgaggcg   ggtggatcac   gaggtcagga   gatcgagacc   30060
atcatagcta  acatggtgaa   accccgtctc   tactaaaaat   acaaaacatt   agccgggtgt   30120
ggtggcgggc  gcctgtagtc   ccatctactc   aggaggctga   ggcaggagga   tggcttgaac   30180
ccaggaggcg  gacttgcagt   gagccgagat   agcaccactg   cactccagcc   tgggcgacag   30240
agcaagactg  tgtctcaaaa   aaaaaaaaa    aagagtgctc   caaatctcct   ttggttaccc   30300
gggactttaa  aaaatttaat   gtgatagtta   ggccgggtgt   ggttctcacg   cctgtaatcc   30360
tagcactttt  ggaagctgag   gcgggtggat   catttgaggt   caggagttgg   agaccagcct   30420
ggccaacatg  gcgaaacccc   gtctctacta   aaaatacaaa   aattagccag   gcgtggtggt   30480
gggcgcctgt  aatcccagct   cctcgggaaa   ttgaggcact   agaattgctt   gaacccagga   30540
ggtggaggtt  gcagtgagcc   gagattgcgc   cactgcactc   cagcctaggc   aacagagcga   30600
ggttccatct  caaaaaaaaa   aattgtaata   ataataataa   caatgtaata   tttactttt    30660
catcctttat  ataaggctga   gtgcttcacc   cctgagatga   agctcagtta   agaaataaat   30720
gaaaatcccg  taacctattg   gtgaaaggta   accaccccca   gctcctacta   gcccaactta   30780
aaacaggacc  ccatcacact   acacagcagt   ttagccaaga   aaaggggggtc  tttatgtgga   30840
cactgggagg  aagggattc    cttcaaatcc   aaactttaaa   ggatttaaa    caatgaaac    30900
atttggttca  aagaatagct   gatgttttta   tttgatgatt   ttggagaaag   gaaagtgtgg   30960
ggcataatgg  ggtttgttat   tggaaagatc   agattttcta   ggtaatttgg   gtggagaaag   31020
acaaaaggca  aagctttgac   tgacaattcc   atgaaagtgc   tatttggttt   tggttatggg   31080
cttagaaaat  taagacactt   agttcaattt   ggaaggattc   tgtataagtc   cctgattaaa   31140
ataagcaaaa  atgatgaata   acactgattc   agtgcaaccg   aaagattagg   attaactcaa   31200
aagaaagtta  ttttctaaac   caccgtgatt   ttttccactg   acaattacag   cggttttcat   31260
taggttgctg  acacatgaag   tcagcctcac   catcagttgc   aaactctaaa   ctagcaaaat   31320
ctattacaga  gacatactta   tcacttctga   tttagtgcta   atctcaccca   gctcatcttc   31380
tcttgtcaga  tttatgagat   aaatgtcaga   tttatcacca   gatatattga   agtaacagc    31440
cagtaataaa  atgtgagatt   ttaaaaaata   gattctttgg   caaattggtg   ttcagtgagg   31500
caattattaa  acatttttgt   cagccaggtt   ccaggcactg   tacagaagct   gttaggagtt   31560
ctcaccatct  acgaatttga   tttgatgtat   tgtattctca   ttaagctatg   tgtgacacat   31620
tgtcatttat  tagcccagaa   tttaaaaagc   tgtggttgtt   tagtgttggt   ggtagcagac   31680
cccagcagtc  tgatggtctg   cactccttcc   atcctgccac   cccctgggga   tgcaaagact   31740
ggatctcagg  gtgacaatct   tcttgcgcac   gactgcctgg   ccaagtgcct   ccagaaagcc   31800
ccttccttcc  cccatttcca   cccaggccca   cttgtcacct   cagcctaaca   ccagcctgca   31860
cagtctacgg  ccaccatcca   ggcagtggga   gagggaaagg   ggaggagggt   ggaagggaaa   31920
accccttct   atacctctcc   tcagcctgct   ctttcctcct   cccacctctg   agcctccgcc   31980
tcccccagac  agagacagaa   aagatggaag   aacaggtggg   acctccaccc   ccaccccaag   32040
```

```
ccttcatccc ggtggagggg gatgggaaga tttctctcat ttcaagagac tcctccacct   32100
cagactgaca aaaggcagag gcctggcaag aagaaaggge accctgggga agaagggcat   32160
tgaaatagca cctgccgggc cgggcacggt ggctcacgcc tgtaatccca cactttggg    32220 aggccgaggc gcgtggatca cggggtcagg agttcaagac cagcctggcc aagatggtga   32280
aaccccgtct ctactaaaaa tacaaaaagt agccaggcgt ggtagcgggt gcctgtagtc   32340
ccagctactc cggaggctga gacagggaac tgcttgaact gggaaggtgg aggttgcagt   32400
gagccaagat cgtgccatgc actccagcct gggcgacaga gtgagactcc atctcaaaaa   32460
accaaaacag aaatagcacc tgcccccacc ccctgcccgc cctccttccc gccccgtcc    32520 tttcctagac ttcactcaag tcctctgctc agaggaagcc ctgctctact gaaagccaca   32580
aggccattct cggtggcctg gacagcagc ccaagacgtg ggcttctaac tgcctccgaa    32640
ggggccacag cagcaaacat aaataaaaat agtaaaatgt tcttaaatta taaatttaaa   32700
atttggaaaa tttagtgagc acagcttcta ggggcatgt ttccaaaatt ccaaccacaa    32760
aagtgcagtc tcaaaactga ctgtaaaccg aacataccat ctcatctcag acacagctat   32820
tgttcacgag tgtcagtgga actttcctcc cttgagatgg accaaaaacg tcaagcaaga   32880
tgacatttgc tgatttgcag gcttcaggca gataagatac gggcagagtt gagtgtgcgc   32940
ctttacccct aaattcagga atagcaggaa cagcaggaaa aacgtaggac cacagcgtac   33000
gtcccacttg tctttcattt tgatatcatt atttccagag tcctgattgc tagtcatgtc   33060
taacactgga tttattatca tctcattgct agcatggcta ggaaagcttt gaacatcctt   33120
atcattctat tttaattcct attataattg catggggaag ttccagggtg gaaaaatttc   33180 ctttctttc ttttttttt tttaatagga gagttggctg ggcacggtgg ctcacgcctg     33240
tgatcccaac actttgggag gccaaggcgg gtggatcacc tgaggtcagg agttcgagac   33300
caacctggcc aacatagtga aaacctatct ctactaaaaa tacaaagtta gctgggtatg   33360
gtggtgcaca cctatagtcc cagctactgg ggaggctgag acaggagaat cacttgaata   33420
cgggaggcag cagtgagcca agatcatgcc actgcactcc aacctgggag agacagagtg   33480
ccatctcaaa aaaacaaac aaaagagttg atataaattt gctgttataa tttgactgta   33540
ctgtttcttg cacatgttga catctgtaat gactggagtt tatgaaaatt tttgatgagt   33600
aggagcatac cattaacaga gagaaattta atcaaaagat ttttaaagtt ccttcagagt   33660
ccagactttg actaagtgta gtatgattta tatctatgtt gcatacaaaa atatcaaaca   33720
gtaattccca actgaaatac aagtatcaat caattgtgta acaatgcaaa atcatttaat   33780
ttaaagttaa tttatagcaa atgagtactg taatagcata agcatgccga tactttacaa   33840
aggagagagt ggaaaggtag gatattataa ctaattgatc aaatcattgt taaaatttaa   33900
gtttattaat acttttactt ctgtccgtag ggatccatgt taaattgggt atattataaa   33960
cttaactgct aatgatgagg tccttttgct attagaaatc tatttttat ttttcttat    34020 tattttttga ggcagggtct tgctctgttg cccaggctgg agtgcagtgg tgaaattata   34080
gctcactgca gcctcaacct cctgggctca aggaatcctc ctgcctcagc ctcccaagta   34140
atggaaactg cagtcgtata caagcacacc cagcaatttt ttttttttt tttggtaaga   34200 tggggtttag ctatgctgtc caagctggtc tcaaactcct ggcctcaagt gatcctccca   34260 ccttanccte caaagtgctg ggattacagg cgggagccac cattcccagc ctagaatgaa   34320
atatctttag ctaaattaca gggctggatg tggtggctca tgcctgtaat cccagcactt   34380
tgggagactg agggcgggag ggtcacttga gatcaggagt ttgagaccac cctgggcaac   34440
```

```
acagtgagaa ttctgtctct attttaaaaa gagaaaaatc tagggtatat tctcttaaac   34500
aaaactttca tctataatgg tagttgatga ggtcctatgt aatatgcatt tccttggttg   34560
caatagcaaa ttactacaca cacagaaagg aaagccacac tccccgacac atctacacac   34620
aggaggactc acacaggagg gagactcaaa gaaggcacgt gacttttaca ttgttagggc   34680
ttacatggtc ctgggatttc ccaccagtac tcaaaagatc aattgtatga acaagtcacc   34740 tattttacg gcactaaata attattattc aacaacatgg aaaatatgtg gtagcagacc   34800
tggattttcc ttaagagtta tttttatgtg gtactgcccc ctgctggaat ataacatcta   34860
tacacatcct ttctggctgg gctgacatcc taaaaccagc ccaggaccag cctttttatta   34920 atattaattc ttggccaggc gcggtggctc gcctgtaatc ccagtacttt gggagtccag   34980
ggcgggcgga tcacgaggtc aggagttcaa gaccagcctg gccaacatgg tgaaactccg   35040
gctctactaa aaatacaaaa cttagctggg catagtggca cattcctgta atcccagtta   35100
ctcgagaggc tgaggcagga gaattgcctg aaccgggacc cgggaggtgg aggttgcggt   35160
gagccgaaat cgtgccactg cactccagcc tgggctacag agcgagactc cgtctcaaaa   35220
ataaataaat aaaaattaaa attaaaaaat aattcttggt tgtatgctaa aagccttgca   35280
agtagcccca ctggaagata ggaagagtgg ggctgtttta caaatgagca catataagca   35340
gaacgaggcc gccataattg aaatgaaggt ccccgtcccg tggatgtgtt catcgctact   35400
tcaccctgtc attcggatcc aatgtgtgac cagccagctc caataacagt tccatactct   35460
gggaattatt tttaacactc ggcaggatgc tttcttcctg tagttttagg cttagcccct   35520
tgtgcacttt tggtctcttt ccctttcaat ttagcatcca aggaagcggc tgtgaccaaa   35580
ggtagctgtc atgttaaagg acaaagttca tagttacagc aaatattgac ccagagcact   35640
atccttgccc cttcctctat aatgtgcaat gcaaaaatat gttctttttaa gtacaatatt   35700 aataagtaag gtctaggaga ttttcttccc ccttcctttc tcttttagat gagtaaatgt   35760
tttatctagt tttgaggaga ctatccttct tatcacatct ctttccactt ctgctctcct   35820
tgttttataa ttttcctctc ctttgggtcc gtgtcattat ttcgtgtcgc ttgtttttcga   35880 gccatgcact catttatcaa atcagatttc ctccgtatgc cgacggcctt cctctccctg   35940
ccacgggctt cctttttccc tgactatgca gaagcaattt gttcgcttgt gtttcttttt   36000
ttttttgaga cagagtctcg ctctgtcacc caggctggag tgcagtggcg acatctcggc   36060
tcactgcaac ctccgcctgt caggttcaag caattctcat gcgtcagcct ccagagtagc   36120
tgggattaca ggtgtttgcc accaaggctg gctaattttt agtagagacg gggtttcacc   36180
atgttggcca ggcttgtctc gaactcccaa catcagttga tccacccatc tcggccttcc   36240
aaaatgctgg gattataggc atgaaccacc gcatctggcc ttgtctttca tccttaatga   36300
cactttagtc ctaataatgc taaaatcatt ttctactctt tgaattgaaa cacagcttat   36360
ctacatgagc ccaaggcagt agcaacattc acctccattt cttctctgat ctctaccttc   36420
tgaaccctgt ggacttggtt gtaaatggat gagggcaagt cttgcttcct tcccctgtgt   36480
ttacagagga tcgtggctga gatgctgggc cacactctgg gcctgctggc acccctgggc   36540
cggtggctgc tgcccctcag ggtgctcacc acctagacca gaagaaccaa ggtgagggag   36600
agcctgtttt ctttcttcct gtggctgcgg gggctgtgag gcatgggtct agtggctgtg   36660
tttagctggg gatgcctcct agaaatcagc tccaccgttg aagagatcaa agcaatgcac   36720
agtgccactt gaaatgaaac gattgagctt atcagcgctt ttgcaaatgt acaagagggt   36780
```

```
agctcccccg gacatcctga actgagccat gctcttctat tttgtgtaac agcccagtga   36840
cccctgaatc ttcccctgag gcaggtcccc gaagcttcat ggaggatgtt cctcagctga   36900
ccaaggtgag gctcttgagc tcctaaatct ttgtgatact gtttatacat ctttgtgctg   36960
tacttttttaa gctgacttcg tgttatcacc tgtatgattt tatgttttgc ttctaaataa   37020
gtacagatta tttttaaactc taataatggg tgctacaaaa ttaaagatta tgtcaatcac   37080
tgtctctgat gagttatttt atgtagattt caacacaatc attgattcat gtgtactctt   37140
ggtcagtcat cagtcatctg agtacctagt gggtttccaa aatgggtcct ggatgctggg   37200
gatgcaaaga taagcaacac atttctatcc tcaacagcct gtagatgagg gagaatcact   37260
gcggacaatc agggaagtta ccggagagag cagtgcacat gtggtctaga aactggtgga   37320
acaaagttga gaatcactga actaggagga aagacaggtc actgacaatc caaggcacag   37380
tgactcacac tctaatctca gcactttggg aggccaaggc aggaagatcc actgagctca   37440
ggagataaag accagcctgg ctgacctatg gagacccttc tctaccaaaa aaaaaaaaaa   37500
aaaaaaaaac attagcctgg catggtgggg tgtgcctgtg gtaccagcta ttcaggaggc   37560
tgaagtggga ggatcgcttg agcccgggag gtcaagactg cagtgaatca tgatcacacc   37620
attgcactcc agcctaggga agagagcaag aaagaccctg tctcaaaaac agaaaaaaat   37680
ccagtaaaat gtttcagatg ttgttaaagg tgatttcact gttacttttc acctctcctc   37740
attttacatc tctgacctat gcttgtcctc tgacttgcca gacattccta gctatggact   37800
tgatgtctcg acatggaggc tcacaggcac cccaaactca gcctgcccta agctgaaccc   37860
atgatctttc cttccaaact tgtttctcac cagagttccc atcttatcat ccacctagtt   37920
gttcaagtca tccttaagac ctccctctcc ttcactgtct attctacctc cctaatatct   37980
cttaaatcct tccctcctct cccacctcac agccaccatc ctaacctaag cagccaccct   38040
ttctcaccct ataatgacct cctggctgtt ctctatagag ttggtgaatc ctttcgtctt   38100
cagcctgaac cccctttcga gggattctta tatatataca tagatataca caaatatata   38160
tgtacatatg tacatatgtg tgtatatatg tacatatgtg tatggatata catatgtaca   38220
tatgtggatg tacatatgta catgtgtatg ggtgtacata tgtacatgtg tatgggtgta   38280
catatgtaca tatgtgtatg ggtgtacata tgtacatatg tatatgggtg tacatatgta   38340
catgtgtgta tgggtgtaca tatgtacatg tgtgtatggg tgtacatatg tacatgtgtg   38400
tatatatgta catgtgtgta tgtacgcatg tacatatgtg catgtatgtg catgtgtatg   38460
tgtgtgtatg tacacgtgtg catatgtgtg tatatgtgta cacgtacg tgtgtatata    38520
tatatatata tatactggct ggagtgcagt gggaaagttt tggctcacca caaactccac   38580
ctcccaggtt caagtgattc tcctgcctca gtctcctgag tagctgggat tacaggcgtg   38640
caccaccatg cccagctaat ttttgtattt ttagtagaga cggggtttca ccatgttggc   38700
caggctggtc ttgaactcct gacctcaggt gatccaccca cctcggcctc ccaaagtgct   38760
gggattacag gcgtgagcca ccgtgcctgg ccggattcct atcttgaaga cgaagcccca   38820
gaccatcgac acgcctcaa ggccctgcat gacgcctcct gccccaacac ctcgtgtcat   38880
cttgctctcc tctcccgcag ctcctgaggc tttagccacc ctggaattcc aagtccccat   38940
ggtcattttt ttttcctgct caagatatca ccatgtgctg tcccctctgc ccttgtctac   39000
acccacgtgt ccttctcccg ccccggccac actcatgggg cacactgtcc ttccctggct   39060
aatcctccca cactcgatac cactttctct gggatattgc acccgatcct cagccgcagt   39120
tgtcttccta tgacccactc ccacactctc gccacaatgg taattgtttg attcctactt   39180
```

```
gttgtccctg tgagactgca aaccccagag gacaggggcc ctgggttctc cttcgcctct   39240
ggatcatcag cactaactga ataccaggcc tagaagagat gctaacgatg ctgaatgaat   39300
aaataagtgg aaagactctc agtaaagcaa aacctttctt taccatttta tggccgtcaa   39360
ggaggaaaac acattatcag tggaaaacgc aaaatgaggg gatttgctta gcaaacgatg   39420
aattcctctg gcaccctggc agccttggtt tcttttgatg aggtccaccc ccttccatcc   39480
atcttctggg cttaagagat caaagcaaaa catgctgtgg aattcgatac tggtgcaggt   39540
tgcacaacat tgtgactgaa ctaaaagcca ctggatggta caactgaaaa tggtgaattg   39600
cgtgttgcat gaattataac ctaactgggg aaaaaaaggc ttaaaaagag acaaagcttc   39660
ccccacaatg gaaggaagg tataatagaa acagcagctt tcaaaccttg gcaggataat   39720
gaaacccccgt ttctatttt aaaaattagc tgggtacagt ggcacgtgcc tgtagaccca   39780
gctactcggg aggctgaggc tggaagatcg cttgagccca ggagttcaag gctgtggtaa   39840
actataatca cactactgca ctccagcctg ggtgacagag aaagaccctg tctcaaaaaa   39900
ggaaggaaag aaggaaggaa ggaaggaagg agggagggag ggagggaagg agggaaggaa   39960
ggaaggaagg aaggaaatag cagctctgag cttagaaata ggagtctatt tctaagtggg   40020
agatggggag aaggagggaa ctggggaggt gaggaagaag caggtattgt caccagtgag   40080
gactgtgctg ttgtgagccc agctaggcaa ctggcaattc cattctgtta gtgacagcta   40140
caataaccca aagccctctg gagccctgct ttcctctgct ctcttcgtgg cttgactagg   40200
agctgaagat cctgtccctc ttagagcatt ggggcggccc acccccacctc cacccctcctc   40260
cacctgctgc ctcgaggccc ctcccactcc cggggtagac aaaacagttt agaggctgaa   40320
gtcaccgggg ctgtaactgt tggatttgca catgtcatag aaaatcatca tatgttttgt   40380
gtggactcca tgcataacaa caagagaacc aaccagaccc catagacaga agggagtgtg   40440
aattggagac aaaatttaaa ttatgagttg ccttctattc agatttctcc catttttaac   40500
aaaaaggagc ccaaattcct aaatgttatg gttgtttgca gcaacttatc atctttctcc   40560
tttccttcat agccaaggtt tttgaaagag ctatctgagg ccgggaatgg tgactcacgc   40620
ctgtaatcct agcacagagg ctgaggtgag tggatcacct gaggtcagga gttcaagacc   40680
accctggcca acatggcgaa atcccgtctc tactaaaaat acaaaaatta gccgggcatg   40740
gtggcgtgtg cctgtaatcc cagctactca ggaggctgag gcaggagaat cacttgaacc   40800
caggaggtgg aggttgcagt gagccaagat ctcaccactg cactccagcc tgggcaacag   40860
agtgagactc catctaaaac aaaaaaaaaa gtagctgtct gttctttctt ctcgaactct   40920
ttttcccgct ggagtctgtg acctgctgcc gtctgcctca agtgagaggg actagcagat   40980
ctggtgaatt accttctaat gcccgtaccc tgcccatacc agcttcaatc tgtatgtaga   41040
agcttagctt gctccatgca tggcctccag catccactgg tcacaaaata acacaaaata   41100
gcatgagaga gaatggtcgc atggagcgga ggagctgctg agactgaacc caagccaggg   41160
ctactgctgg gtgaactgg acatgccag cccatgggaa agtcttccca cagaagtcat   41220
atttgcaggg gtctcccagg agacagcaca ttctgagcaa aggagtgagg cagagataac   41280
tattcaggaa ccaagagact cgctggaaag aagcagagat tttcagccca gcgtagtgga   41340
tgtttcttga atcttcccct gtggatgccc caaaccttga gatccttcca acaaatagca   41400
cactactaac aaactgtgac tcaaagagag ggaaacatgg tcccctgctc tgtcacaaat   41460
cactgtgaag ctttggcacc ctgactgctc aggtggccac caacacagaa ggaccacgaa   41520
```

```
tggctgagtc aggaagtcac agccgtgtgg ctggaagagg ctctgccttg ctctgggaga    41580
aatgcctatc cccaaggaag ccttagtatc catgggagag aaacactgta gcaatggccc    41640
ccaggactct cgggaagcca cttctggtgg gaggggactc aaaggggtgct gggggacctg   41700 tgtctgcatc tggaagtgag gagccaggaa aattttcttt cagtttcttt cttttttctt    41760
ttcttttttt ttttttttttt ttgagaaagg gccttgccct gtcgctcagg ctgaaacata   41820
gtggtgcgat ctcggctcac tgcaacctcc acctcccagg ttcgagtgat tctcctgcct    41880
cagcctcccg agtagctggg actacaggca tgcaccccca cccacgccca gctaattttt    41940 gtattttttgg tagagatgtg gtttcgccat gttggccagg ctggtctcga actcctggcc   42000
tcaagtgatc ctcccgatgt gctgggatta caggtgtgag ccaccacgcc cggcctcttt    42060
ctgcttcatt taacattaat ggtcatccca cagcatggtg ctgtgcacct gtagtcccag    42120
ctactcaggt ggctgaggtg ggagaatcac ttgcgttcca gctgtagtga gccttgattg    42180
tgtctgtgaa taaatgccac ttctctccag cttgagcaac ataggagac tgtctcttaa     42240 aaaacaaaac aaaacaggct gggctcggtg gcccacgcct acaatcccag cactttggga    42300
ggccaaggca agaggattgc ttgagcccag gaggtcaaga gcagcctggg caaaataggg    42360 agacccatc tctacaaaaa gataaaaaat aaaaaatta actgggcatg gtgatacacc      42420
tgtagtccca gctactctgg aggctgagat aggagtattg cttgagcctg ggaggtcgag    42480
gctgcagcga gccatgatca tgccactaca ctccagtcca ggcagcagag tgagatcccg    42540
cctcaaaaaa ataaaacaaa acaaaactca tctctcccctt ggctcctgag actacaatcc   42600
ctcacggttc tttctactt ctctgttttt ctcttcttgt ctcccttttt ttctggtctc     42660
tctgtcaccc aggctggagt gcagtggtgt gatcatagct cactgcaacc ttgacctcct    42720
gggttcaaga gatcctccca cctcagcctc tcgagtagct aggactacag gctcacacca    42780
ccatgcctag ctaatatttg tagatttgt agagatgggg tcttgctatg ctgtccaggc     42840
tggtctcaag ctcctggcct caagtgatcc acccacctca gccacccaaa gttctgggat    42900
tacaggggtg agccaccgcg cccagccgat aattgttgaa aaatcatttt cagttaaggt    42960
atccagtcaa ggtcagaaaa tgagaaaatg ttaaaaaaaa aaaagctata agtaaaacag    43020
attcagtcgg gacatgatgg ttcacgcctg caatcccagc actttgggag gttgaggtag    43080
gataatcact tgagcccagg agttcgagac cagcctgggc aacatagcga gaccttatcc    43140
atacaaaaaa atttaaaaaa tacccaggca tggtggcata ctcctgcatt ccctgctaat    43200
tggatgggtg aaggggagga tcccttgaaa taggagtaga ggtgcaggaa atatgattgt    43260
gccgtgtaat ccagcctggt tgacagagca agatgttccc cacccccctg aaaaaaaaaa    43320
aaaaacctaa atccaaattt taaaagtttc cttgactctt caacttgctc accctccacc    43380
aaataaaata actacgaagg aggcttattt tttactattt ccagggatac gatatatgtt    43440
tgtcctgaaa atatacatca tggctttact caagccacag tgatgaggcc tcattgtcac    43500
tgtagcctaa ttacgatttt ataactccat ttaaaattca atttaaacac agtttaaaaa    43560
ttcagtccaa gtcaaacatg ctctcagtag ctagaagcaa aactctgttc aggtccttga    43620
tggatctatt tgtactttct ttcatgaaaa cagaaagtcc tttttacac accatgcaac    43680 aggaaaattc ataacggaca ttgttttacc tgttcttggc aaagacaagt gagctcttaa    43740
caagcaaggt aactatggag atgatgtttt gctccaagtt aacacttaca tatttaatta    43800
gaaagatttc aaaggtgggc agattcactg gaaagtttcc aaaagcttca cttgttcaac    43860
aaataatgtt agagagggag caccgtgccc tcgggcccct aggaattagt tccacatggt    43920
```

```
ccggtcctct gtccagtgtg cccagcatcc acttgggaga acagcatggc cttctgtcca    43980
gggcagccca cgccagcact gcctgccctt tcaggcccat ggctcccatt aagtgccatt    44040
tcgagcatac ttagccaagt ttccctacca tggccaacaa agaggttgtt caaaaatgct    44100
tgtcaggtcg ggcatggtgg ctcacgcctg tagtcccggc actttgggag gctgaggcgg    44160
gtggatcacc tgaggtcagg aattcaagac cagcctggcc gacatggtga accccgtctc    44220
ccacaaaaat acaaacatta gttgggcatg atggcgggtg cctgtaatcc cagctgctca    44280
ggaggctgag acaggagaat tgcttgaacc cgggaggtga aggttgcact gagctgagat    44340
cacaccattg cactccagcc tgggcgacag agtgagaatc catctcgaaa aaaaaaaag    44400 tttgtcaacg gtttcactga atccagaata cttttctaaa atgtcaaccc tatagaatac    44460
attttataaa attatgaagg cctggtctgg tgtagtggct cacgcttgta atcccagcac    44520
tttgggcagc caaggcaggt ggatcgcttg aggctgggag tttgagacta gcctggccaa    44580
caaggcaaaa ccctgactct actaaaaaat acaaaaatta ctgggcgtg gtggtgcaca    44640 cctgtaatcc cagctactca ggaggttgag acaggagaat cacttgaacc caggaggtgg    44700
aggttgcagt gagtggagat tgcgccattg cactctagcc tgggtgacag agcaagactc    44760
tatcttcaaa aaatagataa ataaataaaa attaaaacaa aataaaattc tgaaggcctt    44820
aggtcagaga attaccgagg gaatattcaa agttatacct ccaagtatct acaatgaaga    44880
tactttcatc agaaaaaagg agtttacggc caggccctgt ggttcatgcc tataatctca    44940
gcactttggg aagccaaggc tgaggcagga ggatcacttg aggccaggag ttcgagacca    45000
gcctgagcaa aaacgtgaga tcccatttct accaaaaata aaaatgtaag gtaggcatgc    45060
aactgtagtc ccagctactc gagaggctga ggcaagagga tcgcttaaac ccaggactcc    45120
agcctgagca acagagcgag accctgttta taaaaaaaaa agaaaaaaaa aaagaagaag    45180
aagaaggaga agaaaggaaa taaaatttaa gaaaaaaaaa aggacttaat aaggttgaat    45240
gaaggcaaga atattcttag ctctgtttaa gtcaagacct gagtagtagc tctacgtagc    45300
tgtatgtcga taatgttttt gagacagcac tactgataaa ttgttacata ataaactgtt    45360
atggctggat gcagtggctc atgcccataa tcccagcacc ttgggaggcc gaagtgagtg    45420
gatcacctga ggtcaggagt tcgagactag cctgatcaat atggtgaaat cccatttcta    45480
ctaaaaaaat aaaaattagc tgggcatggt ggcgcacctg taatcccagc tactcaggag    45540
gctggggcag gaggattgct tgaacccagg agacagaggt tgcagtgagc cgagattgcg    45600
ccattgcact ccagcctaga agacagagcg agactccatc tcaaataaat aaactgttaa    45660 attaagtttta gcctaaagct accccttac atattttaag ttcagtctaa aggtttccct    45720
gcacatagtg aactgtaacc taactggatg cgtaaacaga ctataaccta ctcttgggcc    45780
agtcactgag ttttggtcaa tcaaaggcag ccaactgttc aaaccaggtt aaaataaggc    45840
agatgctgag ctctaaccag tccagccatt tctgtacctt gcttccattt tctgtccatc    45900
actttccctt ttctgtccat aaatcttcca ccacgtggct gtgctggagc cactgtgaaa    45960
ctattctgtt tcaggggctg cccaattcat gaatcattcc ttgctcaatt aaactctgtt    46020
catttaattt gtctaatatt tttcttttaa tcaaagtaat ttggccgggc acagtggctc    46080
acgcctgtaa tcccaacact cgggaggcc gaggtaggtg gatcacctga ggtcaagggt    46140
tcaagactag cctggccaac atggtgaaac cccgtctcta ctaaaagtac aaaaattagc    46200
cgggtgtggt ggcgggcgcc tgtaatccca gctactcggg aggctgaggg aggagaatcg    46260
```

```
cttgaacccg ggaggtggaa gttgcagtga gctgagattg tgccattgca ctccagcttg    46320
ggcgacaggg caagactctg tctcaaaaaa aaaaaaaaaa ttaattcaga gacctactca    46380
tgtgaagttg tattttttta ttctccatat tacaaaacag aacaattggc acagggatga    46440
agaaatactt tgcaaaacat ctagagaggt taaatgccat gagtctttaa aatgtaagac    46500
tgctttcacc tgagcaatct agtgtccatt tctagagcta gcttaaatgt ccgtgtaaat    46560
ccccgtaatt ggttgggata acaattacct atgttgtata acttgagtca aaaactacgt    46620
ttccactgcc tgccacccct atggatggtt ttctcttaag gtatcaaatt ttactgggaa    46680
agacctagat aaaatacagc gaaaatgagg cggggcgtcc tggcacatgc ctgtaatccc    46740
agcgctttgg gaggctgagt cagaaagatc tttgaattca ggagttcaag accagcctgg    46800
gcaatatagt gaaatcctgt ctttacaaaa aattaaaaat tagccaggca tgggggcatg    46860
ggcctgtagt cccagctact tgggttgggt gactgatgtg ggaggatcac ttgagcccag    46920
gaggttgagg ctgcagtgag ctctgaccat gcccctgcac tccagcctgg gtgacagagc    46980
aagacccagt ctcaaaaaga aagaaaaag agtaatgtta ggtcaaggta gaacctacct    47040
tgactttctg ttactatgga agatattctg gggtatctct gagatccaag tattatggca    47100
cttaagtaat tcctatctat tgttctactt ggttcctcgg gagtaaaagt catattcaaa    47160
ccaaaaaggc tgtgggattt ccagaatttt aaaagcaata atagttaatg ttctcccatg    47220
ggagttactc cacatttta catatgttcc atatgttaac tcatttagac cttacctta    47280 tgaggtaagt cctcttctta tccccacttt agaggtggga aaactgaggc acagaaagag    47340
taagttgctt gcctaaggcc ctgttactag caggtggtga aaccagcatt ccaacccggg    47400
agtctggcaa atgtgtgtga agagcacacg tttggaaatg acagtcatga ggacactgta    47460
agacttctgg aatgtttata atttccactt tgcttgttat ttttcctgtc tgtttcccta    47520
gagtgagctg agtgaaaaaa gaaagaagaa agaaagaaga aagagaaaga gaaagaaagg    47580
agagaaaaag aaaaaagaaa agaaaaacag aaaaagggaa agaaagaaga aatgaaagaa    47640
agaaagaaaa agaagaaaga aagaaagag agaaaggaag gaaggaaggt gggagggagg    47700
gaaaggaaga agaaagaaag aagggggaca gagggaggga atgaaggagg gagagaggga    47760
gggaaggagg aagaaataaa aagatgagga tctgtatgct tgaggggtgg aggtgggggg    47820
cttgggtggg agtgtgggat gggcagaaag ctggaggag ccctggaccg actgcattcc    47880
acagaggatt gtgggtgcaa cgtaggtggc agattgagaa aagcaaacaa acaagctcag    47940
cctttggagc ttcggggaag aaaaaaagct gagcagtgaa tgctggcttc ccacggagaa    48000
ggcaggctgc ttcgccagct cacatccttc cgcgcaccca cttcctcttt ccggaggtca    48060
ctttagattg ctttatggca ggatctccag gtcacaggaa tgttatgttt cgactggggt    48120 ttcccctcc cctgggatgc ctgggccagc tccccaaggg ctagtctctg tcccaggccc    48180
cacactccca tagcactcag caaaagccta gagagagcac cgcaaaatgc caaacgcaac    48240
aggaccgcgt aggaagaaga cgcttggaat gacagggaca ctagaactgc ccatggtcgt    48300
ggtctcaaat ttttgttcca tggtctgaaa tactaaaagt tcttaaacag ctacttgatt    48360
tcatactatt gttttgaaga aaacagtgtt tgtttgttgt tttgtttgtt tgtttgtttg    48420
agacagagtt ttgctcttgt tgccgagttt ggtccatgtt ggtcaggctg gtctcgaact    48480
cctgacatca ggtaatccac ccacctctgc ctcccaaagt gctgggatta caggaaaaca    48540
gttgtttctt taaacaatt atataggctg ggcacggtag ctcatgcctg taatcccagc    48600
actttgggag gctgaggtgg gtgaattacc tgaggtcagc agttcgagac cagcctggcc    48660
```

```
aacatggtga acctccgtct ctactaaaaa tgcaaaaaat tagccgggcg tggtggtgca    48720
ttcctgtaat accaggtact caggaggctg aggcaggaga atcacttgaa cccaggaggt    48780
ggaggttgca gtgagctgag atggcaccac tgcactccag cctgggcaac aagagcaaaa    48840
ctccatctca caatctcaaa aaataaaat aaaataaaat aaaataaatg gttatataag     48900
ctaccttatt gatgcagtta caaatgagcc gctgaaacat ataaatttta agaacaagc     48960 cacatatctt tcatcaccca cagcttcacc aactaaaggt gtatgtagta cttttgtgga    49020
aggcatttcc acatgctttg agggaccttg aaatactgct atgattacat gattttctca    49080
aaaccagact actcctacat tacaagaatt gaaaagttca gagtaaatat ttgtaagacc    49140
tagaaaagat gatgttcttt aaaaaaaacg atgcccatct ttgtagcgaa aagaaagaga    49200
gatcagactg ttactgtgtc tatgtagaaa cagaagacat aagagactcc attttgaaaa    49260
agacctgtac tttaaacaat tgcttttgctg agatgttgtt aatttgtagc tttgccccag   49320
ccactttgac ccaactactt tgacccaacc tggagctcac aaaaatatat gttgtatgaa    49380
atcaaggttt aagggatcta gggctgtgca ggacgtgcct tgttaacaaa atgtttgcaa    49440
gcagtatact tggtaaaagt catcgccatt ctctagtctc aataaaccag gggcacaagg    49500
cactgtggaa agccgcaggg acctctgccc tggaaagcgg ggtgttgtcc aaggtttctc    49560
cccatgtggt agtctgaaat atggcctcgt gggatgagaa agacctgacc atccccagc     49620 ccaacacctg taaagggtct gtgccgaggt ggattagtca aagaggaaag cctcttgcag    49680
ttgagataga ggaaggccac tgtctcctgc ctgcccctgg gaactgaatg tcttggtata    49740
aaacccgatt gtacatttgt tcaattctga gataggagaa aaaccgccct atggcgggag    49800
gcgagacatg tttgcagcaa tgctgccttg ttattcttta ctccaccgag atgtttgggt    49860
ggagagaaac ataaatctgg cttacgtgca cgtccagtca tagtaacttc ccttgaactt    49920
aattatgacg tagattctgt tgctcacatg ttcgttgctg accttctcct tattatcacc    49980
ctgctctcct actacattcc tttttgctga aataacgaag ataataatca ataaaaactg    50040
agggaactca gagatggtgc cggtgcaggt ccttggtatg ctgagcgccg gttccctggg    50100
cccactgttg tttctctata cttttgtctct gtgtttattt tattttctca gtctctcgtc    50160
ccacctgact agaaatatcc acaggtgtgg aggggcaggc cacccttca catcttgtct     50220 ccacttcctt gattaaaaaa aagaaaagaa aaaaaatttt gccgaagttg gattcattca    50280
cagaattcta cacattaaaa atgttgcagg tcgggtgtgg tggcagctcc caaagctgcc    50340
tataatccca gcgctttggg aggcttgagc ccaggaggtc aaggctgcag tgaactgaga    50400
tcgcaccact gcactccagc ctgggcgaca gagcaagacc ctgtctcaaa gaaaaaaaa    50460 aaaacagaaa aaaataacgt tacagaaaaa gtacaatatt tttaatatat atatatat     50520 ttttttttc tgagacagag tgttgctctg tcacccaggc cggagagcta tggctcgatc     50580
tcagctcact gcaacctcca cctcccgggt tcaagcgatt ctcctgcctc agcctcccga    50640
gtagctggga ttacaggcac ccaccaccac gcctggctaa ttttttgtatt tttagtagag   50700 acggggtttc cccatgttgg ccaggctggc ctcgaactcc tgactttatg atccgcctgc    50760
cttggcctcc caaagtgttg ggattacagg tgtgagccac catgcccagc caaaagtaca    50820
atatttttaa tgacatataa agatgttcat tctttgtggt tgccctgggt gagagggact    50880
attgatactc aatagtgttt cttttgtttc tacattgttt ctatagtgaa aatacgcatt    50940
ggctttgtat taaaaaatgt atagtaaaaa tggttttatt aaaaatagca aataactaca    51000
```

```
aaaactccat tgcaatggaa agcagccctt ggattttcta gttgaatgaa acgagtaatt    51060
tatccaatgt tagaaatgtc taaaggctcg ctcaggtttc atgagcagaa caggaattgt    51120
atatccaatt aaatgtgaaa ttgcaatgcc tggtgcggtg gcttatgcct gtaatcccag    51180
cactttggga agccgaggca ggggatcgct tgagcccagg agttcgagac caccatgggt    51240
aacatgggga ggccccatct ctacaaaaaa taaaaatcgt tagccgggca ggttggtgca    51300
tgcttgtgtt cccagctact tgggaggctg aggtggaagg atcctctgag cccaggagga    51360
tgaggctgca gtgagacatg atcgatgcac tccagcctgg atgacagagt gagaccctgt    51420
ctcaaaaaaa aaaaaaaaga aaagaaagta caatcgcaat taaatgtctt tgcgttggtg    51480
gctcctgacc aaattcccta agcaagcagt atgttaatga gcagagggc cacagctcac     51540 cttgctcaat taaaggcagg agcaggccgg gcgtggtggc tcacgcctgt aatcccagca    51600
ctttgggagg ccaaggtggg cggatcacga ggtcaagaga tcgagaccat cctggccaac    51660
atggtgaaac cctgtctgta ctaaaaatac gaaaattaac tgggcatgtg gcatgagcct    51720
gtaatcccag ctactcggga ggctgaggca gaagaattgc ttgaacccgg gaggtggagg    51780
ttgcagtgag ccgagattgc accactgccc tccagcctgg tgacagagcg agacttcatc    51840
ttaaaaaaaa aaaaaaaaa ggcaggagca gtatgggcc agacagaaat caaggtgtaa     51900
attgggcaga tcctcaggcc cagtgctgaa ttttggtttg atgaaataaa acattacatt    51960
tcaaggttgg cagagaggaa tgaaggtgga agaggaatct agggccattt agggaagcca    52020
tgaagcctcc tgcccacact agtgggtaga gtggagccag gcgttttgct agggcttgct    52080
atatctcttg gcagggtgct ctgctgccaa agccaagaat tctaaattag attaaatagc    52140
cagaaagaat gttaaacatt tggacatgat atcctccctc acagattagc tagagtgtag    52200
ttctgctgtg ctagatactt aaataaatac ctccctagct gtgaagcctg cttatcacag    52260
tactatattt taggatgagg tcattatttt cctatgcata cacatgcatt gtataatctt    52320
gccaatgtag gtcagcccaa agaagtgac aaatgtgtag aacacacatt ggactagctt     52380
gggacaaaat tagtatacct aaagatgaca gatttcttaa ctaattttat gagccatgca    52440
gctttgtatt ctagcagaga cagacattag gaatcttata aaatcaaaaa tttaattttt    52500
tgcctgaata gctccaaagg gctaagatct caagcaaatg cgtgtaggtt ttgttttgt      52560 ggttgttgtt gtttttagag acagggtctt gctctgtcac ccatgctgaa gtgcagcggt    52620
gcagtcctag ctcactgcag ccttgacctc tcaggcttaa gtgatcctcc tgccttagcc    52680
tcccgagtag ctgggactac aggcgcatgc caccaccccg agtaattttt tattttttatt    52740 tttacttttg tagagacagg gtctcaata tgttgctcag gctagtatct ttttctttt       52800 tgagacagtc tcgctcaatt gcccaggctg gagtgcagtg gtgccatctc ggctcactgc    52860
aagctccgcc tcccgggttc acgccattct cctgcctcag cctcccgagt agctgggact    52920
acaggcgccc gccaccatgc ccagctaatt ttttttgtat ttttagtaga cggggtttt      52980 caccgtgtta gccaggatgg tctcgatctt ctgacctcgt gatccacccg cctcagcctc    53040
ccaaagtgct gagattacag gcgtgagccc tcgcgcccgg cccagtcttg taacttaact    53100
ttaaagctac ttattcccaa atgaagatgg gatggtacac agattttaag tattagctgg    53160
tttggagctt ctgtctttta aagcaacatt ttactttgcc acagggtggt ggggcggggg    53220
ccatcctaga aagaagagtg tgagtttcat gggatagggt ctggggaggt ggctggagga    53280
gtttaggttc ttttgatatc tgtggctaca cagacagata accaaggaaa atgtccaaac    53340
agtgaaatta agtgctcact gcactaacac agagaaggac cctgatgtct ggccgcaggc    53400
```

```
ctttgttctc attggcttca aagaacttct tgatgtctac cttaatttca ttattattta   53460
cccaggagtc attcaggagc aggttgttca attgccatgt agttatgtgg ttttgagtga   53520
gtttcttaat actgagttct aatttgattg tgctgtggtc tgagacactg tttcgatttc   53580
agttcttttg catttgctga ggaatgtttc atttccaatt atgtggtcga ttttagagta   53640
agtgccacgt gacgctgaga agaatacata ttctgttgat ttcggggggg agagttctgt   53700
agatatctat taggtccact tgatccagag ctgagctcaa gtcttgaata tccttattca   53760
ttttctgtct cgttaatctg tctaatattg acagtgdggt attcaagtct cccactatta   53820
ttgtgtggaa gtttaagtct ctgtgtaggt ctctaaaaac ttgttttatg aatctgggtg   53880
ctcctgtatt gggtgcatat gtatttagga gagttagctc ttcttgttga attgctccct   53940
ttaccattat gtaatgccca tctttgtctt ttttgatctt tgttgggata aaattacatt   54000
ttatgtcccc cttcctatag tttgtcactg agggttggca gaagttgaaa ggaagaagac   54060
atttgggtgt ttggtttggg gttatattag gttataaggt tcattgcctc cacctctttc   54120
aaaacattta gtttctaaat gaatccagct ttaaatgact gcaggagtgc ccatgcacaa   54180
ttttgtttct caaatctttg ggattttttcc ttgaagaata ttcacaggga atggggctgt   54240
cttgcttcat agttactctt ttgtatacat gatctcaaga atcgcctgat cactgctaga   54300
gttaaaccaa tacactaact gcctgaagtg ctgaaaagtc aaatgggggc ttagaacctc   54360
actccagatc ctacacaagc tgatggttct gttcccagaa acaacccagc ttcctcatca   54420
tctatggcca gtgccttgta gcggagctgg agatcaccct ttagtgggct cttcagctgg   54480
atctagaaat caaattgaca ccaggcagat taacaagaga aaagtataca gattttattg   54540
cttttatatg tacttgggaa tctgcacaag ggcaaagtcc gaagaggtgg ccaaagcaag   54600
gtgcttttat acattttag aaaaagagcc aaaaaattgg agaagaaatg ataggacaaa   54660
gaaaatctag ccaggcagta aattttctag gagaatcact aggacatata tgaggaaggg   54720
tgtgtaaaac aggtgaaaga taagggctag ttcattaaac atgtttactc tggtccattg   54780
tagcctctac gataaggagt attttctcgc tctggtgtgg acagggcacg cctcccagag   54840
caacctttat cacttactgc atgcaggaag agacaggtca gcccgccctt cctgaaacta   54900
caatttcttc agtgttttca actcaaaata atcaataccc cccatctggc atatctgggg   54960
atggcacgtc ctttactcct tcaggctctt ctccctgaag gtcctttgca tagttgggaa   55020
tctccaccag gaggggtagc tctttggtct aaacccatgg tggcagagtt tcgacaatat   55080
tcccaactta aatgtttctg attctgagtg gtggttagat ccctttgtac accctgtcc   55140
ccagtgccta cagaatgggc atgttaataa gtgttggctg aacattcaat gatgggataag   55200
gaagaatagg aggcaagaga gacggtggtc tccagtgcca gccccagtg ctaactgggg   55260
tgatttttt tcatgactca ttttcctaaa atcaccctca agggtcctac aaaactcttc   55320
ccaacagcta aatcacagac taatctggcc catcgacgtc ttccctgatt atactaattt   55380
ttttgtgttt tttttttga gatggagtct tgctctgtca cccaggttgg agtgcaatgg   55440
cactatctca gctcacagca acttccacct cctgggttca agcgattctc ctgcctcagc   55500
ctcctgagta gctgggactg ccagcatgcg ccaccatgcc cggctaattt tttttttttt   55560
tttttagta gagatgagat ggggtttcac catgttggcc agggtggtct tgaactcctg   55620
accgcaagtg atccgcttgc ctcggcctcc caaagtgctg ggattacagg tgtgagccac   55680
tgcgcccgac catatattaa tggttttga tgaatttgtt ccatagatta aaatcttgtg   55740
```

```
ccccatcgcg tgtggggctc catcgcatgt ggggcacagg gttcctgagt gtttgtggct   55800
gtcaaaccaa gatgatttct tgcttaatca agcagatttg aaagttcatc tctgctacca   55860
ggaagcactt gctcaactca gaagacaatg tcctatcagt cttcactat cacgcatctg    55920
ttcttcaaga tccgtcaaat tagctccagt gaaacggagg ctaaagtgaa acttttctc    55980
ttatatagat tttattcat aactagggaa aaattaggca cccacagaaa ataataacc     56040
taaaaaaatt aggctgaacg taagaaaaat ttgtgatgaa ataaacattt caatcaacag   56100
aaaatatttt tctgactttt tatgtgccac cattagttac atcattgaga aaacaatatt   56160
tgtattaaaa aaagagctgg tgaaaatctg gcaattggtc gggcatagtg gctcgtgcct   56220
gtaatcccag cactttggaa ggccgaggca ggcggatcac ttgaggtcag gagtttgagg   56280
ccagcctgac ccacgtggtg caacccctc tcaactaaaa atacaaaaat tagctgggcg    56340
tggtggcagg cgcatgtaat cccagctact agggaggtta aggcaggaga attgcttgaa   56400
tctgggagat agaggttgca gtgagccgag actgagccac tgccttccag cctggtgaca   56460
gagcaagact tcatctctct ctctttact tttttaaag acttcttctc aaaaataaaa     56520
agaaagaaag aaaatctggc aatccagtaa aaactggcca ctatggcatg catgtgctat   56580
gcataaacgt aaattgatgc ataaacttaa tttagaact ggaaggaaat ctggagttct    56640
ttaggagcca ggttttacac atgcagaaac ctaacagctt cagttcgat tcgataaaat    56700
ttgactaact aaacttaaga taagcatagt tacgcattag agtattaact ctcaaacttt   56760
taaaaagaa ttcttccttt gcttgttaat tttcttctt tctttttttt ttttttgaga    56820
tagggtcttg ctgtcgtcca ggccgaagtg cagtgacgtc atcatagttc actgcagcct   56880
ctacctcccc ggctcaagta atcctcctgc ctcagcctc tgagtatctg ggactacagg    56940
catgagccac catgcccagc cttttctttt ctttctttc tttctttct ctctctgtct    57000
ctctttcttt cttttttcct cccttcttc ttttttttg atggagtctt gcactatcgc    57060
caggctggaa tgcagtggtg cgatcttggc tcactgcaac ctccgcctcc gggttcaagc   57120
aattctcctg cctcagcctc ctgagtagct gagactacag gtgtgtgcca ccacgccagc   57180
taattttttt attttctag acgggggtt ttaccatgtt ggccaggatg gtcttgatct     57240
cctgacctca ttctccacct gcctaggcct cccgaagtgc tgggattaca ggcatgagcc   57300
accgtacctg gcccttctt tctttttatc aagacaacaa catgtcttta tagtgctccc    57360
aaggctaaag tataccttac gtctatgtaa acactcaacc tgagctttgc aatggcccat   57420
gttggcagta gtgcaaacaa aaacaattat gaaacccatt tcctttgac aaagagaaat    57480
aagtggcaag aattggttct ttctcttagt atgggtctct gaaaagaacc agatcagtca   57540
aaaggggaat attttctga agggataggt ttggcctagt ggcttctacc tcttttagat    57600
gactgctgtt tctcgtttta atgttaaata gacactaata ggagaaatca cattaattca   57660
gtcaacaaac atttactgag cacttcctgt agtcaggccc tctgttaact tctgggaata   57720
caatgacaac tctgacaatc ccaacccaag gagccaacaa gtccgggaat agagacagac   57780
aagaaaacag acaattacaa ctctaccgtt agaataaagg tacattgaga acttgcaaca   57840
atattcctc atcccttatc ttaattattc ataacatgtt taccaccaat aagaatagca    57900
ataacaataa atgcccaact cagacagcaa tgtccattta ccctgtgttt acacagcata   57960
atacaagcaa gctgtggaca gagattctct tgtttagtcc tcacaactct gcaaggtggg   58020
ttttattact ctccatttct agataaagga tctcacctaa tattacatgg gccagtggtc   58080
ttccagttgg ggtatgcaca accctagggg taggtgagga ccctgcctgg ggtcttcagg   58140
```

```
tggggaccat caacctccat ttgtactctt ttctgaacat tggtctgaga cagaaagtcc   58200
ctgcaattaa ggcattaagc tggctctttt tctatttctc atttcataat tgcccttctc   58260
ctgctttacc aaaatctttc accccccatc atatatatat atccccatac atattctata   58320
tatacatacc ctacatatgc atgcacacac atcatatata tgtatgcata tatgatatat   58380
acatatatgc tatgtaaaca tatatagtgt gtatatacat gtgtgtatgt gtatatgtgt   58440
gtatatgtgt atatatacac gtgtgtgtgt acatatatac atcatatatg tgtgtctata   58500
tatgtatata tgggtgtgtc tatatatgtg tatatgtacg caaatacgta tatgtgatgt   58560
atatatataa gatgtgtgtg tgtatatata tgtgtttgca tgtgtgtgtg tatatatata   58620
tagtatatac atattttttg agacagcatc tcactctgtc gcccaggctg aagttcggtg   58680
gctgatgaca gctcactgca cctcccggct caagtgattc ttccacctca gcttcctgaa   58740
tggctgggac tagaggcgtg tgtcaccaca cccagttagt tatttttattt ttcgtagaga   58800 tggtggtctc actgtattgc ccaggctggt ctcgaactcc tgggctcaag cgcttttcca   58860
cctcgacttc ccaaattgct gggattacag gtgtgagcca ctgcaccggc ccatcctttta   58920 tttaaatatt atgcagtgcc ctgagacata taaaaaccc accttcccaa gtaaaggaaa   58980
ttcaagctga tgcctgcaga gccttcttta acaaaggctc tgaaataccc tctctcatta   59040
aaatgatact ttccaataaa attttgttta acaatgattt acaaaatgat aaaatttatt   59100
tattttgatt gtgtatggat catggtaaca ataaaaagac ttgtaaaaat aactaaattg   59160
aaagaatctt gaacatttag agccttaaga ctgtaggaat tgaagaccac agaattatta   59220
atttatatta atattttttgt tgcagagaca taatgaatga tcaacgaaag gcttttaagc   59280
gttaaaaata tattacacta gataaaatta tttgcgggaa tgggatggaa atacattttc   59340
aagagagaaa ggagcaatgt aaaatgaaga tgtaaaatcc ttctgctggt tgtccttggg   59400
gttttctttt aaagaaaagc ttggcagtgt ttttctttt ttccattgga tgatggtgaa   59460
tatcaaatca ctttggtgct aatatttcat ttaatacatt aattttaaaa ttttctgtag   59520
aggtgggatc tcactatgtt gtccaggctg gtttcaaact cctggcctca agcaatctcc   59580
ctgcctcagc ctcccacagt gctgggatta caggtgtgag ccactgcatc cggccccatt   59640
taatacattt aaaagagtgg tgtaacaatt tttatttaaa atgtcatatt tacaatattc   59700
tagaatgtat atcttttcaa ctcattaaac ctaaacatcc ttgtaaaaag tgtgaaaagt   59760
tatatagttt ttcaaaattc gattagcagt tacataagca taaatgttta aagtatgtat   59820
ggtacagcca ggcttcagtt ccctgtctta aacacaaaga tccatatcaa ttccagatac   59880
tgcaatggtt tgctgttttt cctgcttccc ccatctccaa ataaactaaa gcatcaacat   59940
gcctcacctc acataaccct aagttttcag cagttggcag ttacacctgg aaaccattt   60000 tctaaaataa acaacaactg tttgcttacg gatcaaaatg caaaggacca taacatttag   60060
cctcaccttc ctactacaga tcgagtttaa aagtgccatg gtatagctaa attatgaaga   60120
aagatatgaa tataactgca aaagtggaag gagatttggg ataattcttg cccatttttgt   60180 taggccaaat gcatctttgt gcaaattaga aaaaggtggt cttcatccct tcactcctat   60240
ccttttgggg gtggagggge agtggctaaa gtacagacta ggtttcagct accacatcct   60300
ccttcagtta gctgccctcg gcgtgacaga aacatgtgca aacagccctg tgcctttgtc   60360
ttatgttcca gccagccaag aaaaatagtt gtaaaagagc agctgctgtt tggggtaatg   60420
accttggacc ctccccaatt tgttccaagc ctgttttttgt attcattttt cccacattta   60480
```

```
tgttcctgga tggaagcttc catatctgct cttggccta  tttgaaattc  cccagatttc   60540
cttcctggct cctggccttt ggttttcat  gtggctcctg atcccacacg  ctccctgaat   60600
ttggattctc ctgtcatttc aggtgcgagg tttcccacta cagcctcttg  ggcctcacct   60660
ccaatacctc tttcccatca gaacagcccg gaccttcccc tatggtagag  cagagacaga   60720
atttaaatga attctcaaga agtgcttgga ctcatatcta gcaaaattac  atggcattta   60780
acctttgaca caaaaaatgc agcttctagg aatctatcta aagatacact  gtggcaaata   60840
tacaaaaaga agcattattt atcaagcact atttcctaat aaaataattc  ttaggtcagg   60900
cgcaatggct caggcctgta atcccagcac cctgggaggc tgaggaaggc  agatggcttg   60960
agctctggag ttcaggacca gcgtgggtaa catgacaaaa ccccatctct  aacaaaaata   61020
caaaaattag ccgggcatgg tggcatgcac ctgtagtccc agctactcga  gaggctgagg   61080
tgggaggatc gcttgagcct gggaggcaca ggttgcagtg agccaagatc  gcaccactgc   61140
actccagcct gggtgacaga gtgagaccct gtcaaagaaa gagagagaga  gagagaaagg   61200
aagaaagga  agaaaggaag aaagagaaag gaaagagaaa gaaagagaaa  aagaaagaaa   61260
gaaggaaaga aagaaagaaa aaagaaagaa aaagaaagag aaaggagaaa  aagaattctt   61320
actaataaat gcaggagaaa tgatagaatt gaaatatcac cattttcaat  tcctaatgaa   61380
ataacgtatc taggcaatga ccatcaatag ctagatgcta aaatcatctg  atcaaacact   61440
gatgggaact tcgtaacaga tggatcaggc taacaacatc tgaaaccact  aactggtttt   61500
gatgtcataa aaagaaaaac aaccagatat tttctgtctc ctgatgagtt  gcaattggag   61560
ctacatatca cctgtaaagt cttctggcca aaaaattaag cccagccgga  ccttattaaa   61620
cctttaaatc taacaattag ttttgaagct tttacagatt aaatgaagtc  tgagatttgc   61680
ttcaaaatga accagtggtg gggaggaagt gggtgaggtg taggtgaaac  aagattggcc   61740
acgtcgataa ttgctggagc tgggcgatga agcacaggt  atttatcaca  ccatctctct   61800
acttttgtgt gtttttttgt ttgttttggt ttttggtttt aaggagcaga  gagtctaata   61860
ggcaagaaag aaaagagaag gctgaaggaa gacgctcccc cgtacagaga  cagagggagg   61920
gggctccaaa gccgaaagag gaggtcctct tgtgtatgtt ttaaaatact  cccagataaa   61980
atatttttgg aagagtactt ggttggattc aacagctttt tttaattta   aaaaaatcac   62040
ctcaattttt ttgcttgctc taacgtgcca tagaaattcc tgaggttta   cttgttgctt   62100
tacaatgaac tgtgtaaaca caagctggaa gagatcagct atgcgctgga  agggttggtt   62160
aaatattgag actgccttgc tgagggaagc cttttaatga atctcagtaa  ttttgcaaga   62220
gaaaagataa caatgaacac tacattaaac atcattcttt tgcactttgc  taaatatgtg   62280
tatgtaaatt actgtctgac tgttactgga tatatacagc atatacatat  gcacttttt    62340
tactgttttt tttttttttt tttttttttt tttttttaca gagcttgctc  tgtcacctag   62400
gctggagggc agtggcgcag tctcagctca ctgcaatctc cgcctccag   gttcaagcga   62460
ttctcctgtc tcagcctcca aagtagctgg gactacaggc gcctgccacc  gctcctggct   62520
aattttgta  ttttttagtag agacagggt  tcactatgtt gtccaggctg  gtctcgaact   62580
cctgacctcg tgatccatct gcctcggcct cccaaagtgc tgggattaca  ggcataagcc   62640
accgcgcccg gccatgtat  actatttata catttttagt atcattttgt  ctttacatt    62700
tacataattt cagatacatt ttcctcatat caaataattc agcatttttt  agtactaaca   62760
tcatagtctg taagccattc aaaaaatgta tttcacaaaa taggctatct  catccttga   62820
gctattgaga tgaattaatt tatactcctc ctaagatccc tctcgtcact  aagattcttt   62880
```

```
tattttatga caaaaccata gttctagaag cttgtttctc ccacctgaaa agactggatt    62940
tgggacatga tcctgtagaa cttcggaggt aagcctggtg aatcagatca tagggggtct    63000
ggagggtgaa aaaaagggt ttggtgctca tggatggggc tagtattggg gtgtagggga     63060
gattaggtca aagcaagagg attcaaagga gaaatgaatt cctttagatt ggggaagata    63120
atcggaagag gtaaaagaca ccgtccatga cacttcctgg ggaagcagat gtatgtataa    63180
ggatgtgagt attgtggttt tgtaaagaat gcattcctga agatgttgca taatttaaaa    63240
cctacatatt ttgattaatt ttctcatgag aatagcaggg tatgtgttct cggcgctcac    63300
aaatgtataa tccattgtgg caaattttg ctttcacata tttttttta tcattattgt      63360
cacaggttct gtgacggagt tctggtttct aaattcacag cataccaagg cagttcttta    63420
aagttcttga tactctttta tcatatctaa cttgtattcc aaaattattg agttggagca    63480
cattttccca gcacttagca ccgctatttc atggatggtt ggagagggg tccaaaaatt     63540
ttacaattat gttaacaaaa gtaacacagc aacaaaacaa taagcaaaat cactgccaga    63600
gtattcctta gcttgaaaca atacggttca catcgataga atatggcatc tatttctgtt    63660
taatcagtta accctgctaa gtagcaagag cttacaattc atgtctaaaa tcatgatttt    63720
tttactagtt ttttaaaaaa tgtgggctct atatatataa tttaacattt tgcttgtaag    63780
acttaatttt gcctgggtat ggtggctcat gcctgtaatc ctagcacttc aggaggttga    63840
ggcaggagga ctgcttgaac ccaggagttc aagaccagcc tgggcaacac agtgggaccc    63900
catcactacc aaaaaaaaa aaaattagtc aggcatggtg gtgtgcactt gtagtcccag     63960
ctacttggga ggctgaggtg ggaggatcac ttgagcccag gaggtcactg ctgcagtgag    64020
ccattattgt accacaacac tccagcctgg gtaatagagt gagactctgt ctcaaaaaaa    64080
aaaaagact atttctaaat gtgtggctat attataccat ataaatgtgg cttcttgggc     64140
aaggaaagag gacaatatag atgaaaaga aattgatcct accagaagtg atccttttat     64200
ctgcataact ctcaggcagt tgtggcaaat aattggcaat atctattgtt ctgaaactgg    64260
ttttcgcaac tttatttggg aacaccatcc cctctcctgc atgatcagtt tctcctctcc    64320
acggatcatt cacatgagta aagtcagtag cgtgctggta aatgtttaag atcttgttct    64380
ttggggaaa aagttcctaa gttctagcag ttgccctgga taacttcaag gtatcaacat     64440
ggaagttatg tacaaaaatg gctgtcacaa gccagtatga gctaacacca acatactacc    64500
cagtgttctt caaacttcag ctcacagccc attagtgggg cttgcaaaca ttttagtgga    64560
ctataagcag catttttta aaatgaaaaa gtagattgtt ttacacataa caggagtatt     64620
gttttgtaca attttttttt ttttttttt ttttagaca cagtttcact ctgttgccca      64680
ggctggagta cagtggtaca atctcagctc actgcaacct cggccttctg ggttcaagcg    64740
attctcatgc ctcagcctcc cgagtagctg aaattacagg catgcgccac aaggcccagc    64800
taattattgt attttagta gaaacagggt ttcaccatat tggccaggct ggtctcaaac     64860
tcctgacctc aagtgatcca cctgcctcgg cttcccaaag tgctgggatt acaggagtga    64920
gccaacgtgc ctggtcaaaa ttttgtttt cgtaatttta agtatgtgtg tagtaagtct     64980
caatggaaat gtaattctta tggcaggtca cttgaaaaaa aagaagtcta aaagtcacca    65040
atgtagtatc ttctctttaa aaaaaaaaa aaacaacagg agaaacctg aatctgccct      65100
ttgctccact ccttcctcag ctataatgct gcttctccat tcctcctcac agcaaacctt    65160
tctgaaatct ttatagtcat ggtttccacc agttcttcac ctcccatttc tcaacacact    65220
```

```
tcagagtcag agtcagcaat gacatccatg ttcctaagcc cattgcttac ttccgtcctc    65280
cttggcctct cagcacactt ggcacacagg ctgtttctct ttctttggca tctgtgacac    65340
cactctcagc aaattcccct ggttgtccct tctcagtctc atttattggc gttgtcttat    65400
ctccccaggg ctgtccgagg tgattttctc ccactactct cctaggtggt gccatccaat    65460
ctcatgatgt catatcattc ttccctcatg cttcagccat actggttggt ggcctttgtt    65520
tcctgaacac atttaatgca ttctcaagac cctcaggac  tttgcagcag ctgctcgcta    65580
aggctggaat gctcttcccc accatcttca tatggctgtt tcctttcttt cactcaccag    65640
cagcttaaac tttgactcct ctgagagact ttccttgtca cccaactaag gttgccactc    65700
aggtgctccc aatttaatct tctctaaaac acatcactgt atgtgtcctc aactagagta    65760
taagcttcct cgaaacaaga acaatcaaaa ctccttgccc tcatggagtt tatagtctta    65820
tgatgggtga agtaacataa aataaaaagg caccttatat agtatattag catgacaaat    65880
gttagccaga aataaagcaa ggaagagttg ctagggagtg tgtatgagtg tgttttggga    65940
gagtgtttgc aattttaaat attggtggtc aggaagggcc ccactgagaa ctgacatttg    66000
agtagacttg aaaagggaaa aggaaatatt gagtaaagat tttaggatgg gagtgtgaca    66060
ggcctgctag gagaatagca aagtcgctgt ggctgctgca gaaaaagtga aaggaaagt    66120
agtaggagat gaaatcacag tgtgtgagga ttcgggcaga tcaggaagtg ctcgtgtaag    66180
aactggatct ttactcaaag aatgagcaaa aattagtaga cggttggccg gatgcagtgg    66240
ctcacacctg caatcccagg ttacaggagg ccgaggcggg cggatcactt gaggtcagga    66300
gttcaagact agcctgggca acatggtgaa acctcatctc tactaaaaat acaaaactta    66360
gctgggcatg gtggcgcgca cctgtagtcc cagctactca ggaggctgag gcacatgaat    66420
cacttgaaca cggtaggcag aggctgcagt gagctgagaa tgtaacactg tactccactc    66480
caacctgggc aacagagtga gactgcctca aaaaaaaaaa aaagtaggt  tttagtaagg    66540
gattaacatg atctgaatta tgttttgtca tgacttctct ggctgttgtg ttgagactac    66600
attgcagagg ggcaagggca aatataggga gaccgattag gatactgcag taataatgta    66660
agagatgtgg gactctatct agaagggccc atgaggtcct ttgcatgcta gtattcttta    66720
ctgctgtgcc tggccatgat aggcattcag tgaatatttg cttatttaaa ataacacact    66780
gggctaattg aacaacagtg ccaaatgagg gagatatttc taggaataag ttcttaggat    66840
ttatgaacat tttaatccag attttctttg ttaactctgc tctctggccc tttcactcag    66900
ccccgtttgc acctaaatat gacttacaaa agaaacacag catttatgtg tacttatttc    66960
aacttacttt agctttgtaa agaagtacaa ggttgactca gggcccagct tggtgtctca    67020
tgcctgtaat ttcagcattg tgggaggcca aggcaggaag atattgtgag cccaggagtt    67080
tgagaccagc ccgggcaaca cagtggaccc tgtctctaca aaaaaaaatt tttaaattag    67140
ctgggcatag tggtgtgcgt ctatagtccc agctactcct ggggctgagg tgggaggatc    67200
acttgaggga aaccctgtct caaagtggcg gggctggggg gagactcagg cagaattgtg    67260
aagatattca attgctcctg actttatcaa taatctaaca tttcaaccta acattgatat    67320
ctattttatg caaagcatta cactatgcac tggagactgt ataagacaag ttcctttttct    67380
caaactacag tcgagttgga tagataaaac acacaacaca taccaaaaga cagctataaa    67440
tccaaggcag tgtatgtcaa gggtaaattc acctattcag attggatctt gagaagtgca    67500
tcaggcttgg aaaatgggta aggaggagag aaaagcaaca gtgaatcaga acatgagttc    67560
ccagttatgg gacttgtaat gaattcctca attaaaacaa aaaataatga aaacaaaagc    67620
```

```
cagggaggag aaagcccacg ttaatgacac taaaatatat ctttccaaac aaatgtggat   67680
aaaagccaag tagagaagat gagaactttg aggtccctaa cacaaaataa acagtaagca   67740
gccagccatt ccaagtggct gacatgactt tgtttaactt tatttgtatt tctggctggt   67800
gtgtttacag ccataggtc aaactatcag tcagtgtagg gccctgagaa gtcgggtatt    67860
taagagcatc taataggcac agaattgtgc tccatactgc ttaaactgtt ccctaagtgt   67920
ccaatttgga gaaacaccc acacgcagga taaccggcga gtgacgcgga gtggctgcga    67980
gtccaagtta tcactaacgg atggggagct tgggctgggc acagtccagc gtactgaacc   68040
cttcccccac cgtttcacct gcatacagag gtgtgtactg tcaaaaagca gcgcctccaa   68100
gtctcttctg gcactgtctg gacttggatc cgaggcagac gaggaagctg agaaaaccct   68160
ggcgttgacc ccgtggacct gggcgccccg ggaaggccag cgcttggtcc aggcaggcgg   68220
ggcctgtgcg gtgaccaccc tggtcctgaa aagtcccagc cccgagcgcc ctccctccta   68280
gacctggagg cctggaacag ccaggtggac gtcggcccac ctttctttc tttccttccc    68340 attttcctac cacctcccac cccactccgc cttccgggca aaggcagcca gatccaccca   68400
ggacacattc tttgtcctta tccctctgtg ctcgtcccac agcaagccag tcgcggtcca   68460
aggctccaga ggctgtgcag gaggccgagc tgggtggcga tcagcggcgg gtccctgtcc   68520
aaaatccagc agagccgcca gggacgcccc agacacagaa ggcggggcgc ggggagggtg   68580
gggagaccac agcagtgagg cgcgcgagcc gggaagtgaa cgaggactga ctcctgtcgc   68640
ttcccgtagc cgcccacgga cgccagagcc gggaaccctg acggcactta gctgctgaca   68700
aacaacctgc tccgtggagc gcctgaaaca ccagtctttg ggtgagtcgc gcgaccccg    68760 gcctcgggtg gcggggcagt cgctagaggc gtggctgctc tgagggtctc gccagtggag   68820
gatggcattc ggatgtcacg gctcctaaat caccatttga tgggtgggac agtgtccagt   68880
ccaccccgac ccgccggtcc tcaccgcggc agagccgggg ctgggtggcg gggacgctgc   68940
ctctgcaggc gaggcgctcc ggggcataag ggattatcag gagtcgcggc ctttcttgga   69000
catccctggc tggggtcagg ctgtttgccc tggggtgtct cctcgctgca aacccacccc   69060
acctgggctg ctttctcacc tgttccctcc tagcctgagg ccgagcgcca cctccaagtg   69120
gaggaatctg gggaagtttc cttcccggaa tttgtagtga cagtgagtg acctccattg     69180 cgttccctgc ctctaacacg ctctttagga tgccgagtca tttgactgca gtgttaaaca   69240
ttgcaaagcg caagtcatgt gacttccttt gaccgtacgt gaaacttaag tgatggctgc   69300
ttgtgatgca tacgaagtgt tcatgctggc gggacctgtc cctggggata cttcggggt     69360 tgcgtgattt aatgcaagca gatggcttaa attgggtcac tggcttgtta ttatacatgt   69420
gtatggcaac tcggcatcca ttctttttgc tcttgttctt acttcctgaa ttgagtcacg   69480
gagccagagt tttgaggttt tgactaacga attaagttaa tgacatgggg ctatatttag   69540
gtggtaaacc aagagggata cagttttttt tcttaataaa gaaaaagtga tagatttgat   69600
cggtgtgtat tgttggtgtg cagtataatg acagaattgc tggaagtaaa atacaggaag   69660
ctctggtttc atttccccctt tagttctgct taaagtcgag tttttcctgg agctattaaa    69720
tgtagtgtag tgtccatgag tgctttatc ttaaaaaatg tggctgatgc tttccaacac    69780
tcccctgccc tgtgattatt attttttttaa gcaacagaga aaactgtatc ttaatagtat   69840
taaaagtatt ggattttttcc ctactttgat ttgtttaaat tggaggagga agagcaattc   69900
tttctattca caataataat agctaacata gcgcttactc tttcgctgtt ttattaactc   69960
```

```
aatcctcaga acaaaccaat gatgtgaata ctgtaattct cattttatgg aaatgaaaat   70020
ttaaatgaat acctctgata attgtacggg actgtttgat tagtatttac cattaattaa   70080
ttaaattttt ttttttttg agatggagtc tcgttctgtt gcccaggctg gagtgcagtg    70140
gcacaatctc ggctcacttc aacctccgtc tcccaggttc aagcaattgt cctgtctcag   70200
cctcctgagt agctgggact acaggtgcat gccactacgt ctggctaatt tttgtatttt   70260
tagtagggat gggatttcac catattggtc aggctggtct ccaactcctg aacctcaggt   70320
gatccacccg ccttggcctc ccaaagtgct gggattacag gtgtgagcca ccatgcctgg   70380
cctattttag tattttttaat aataaattcc atgttagaaa ttttctactg atgtattttt  70440
taagtcaata tttcctacac tcacaatcca aaattattta gtatatgagc acactggtaa   70500
gaatgggagg cagatcgttg attgtaataa tattctatta tttggtaaat atcagtaaca   70560
taatatataa tttaaatttt aaaataggat atgaagaaaa atgctacatg cttacttttc   70620
ttttcctcta tttttacttt acacagggcc agtgcctcag tttcaatcca ggtaaccttt   70680
aaatgaaact tgcctaaaat cttaggtcat acacagaaga gactccaatc gacaagaagc   70740
tggaaaagaa tgatgttgtc cttaaacaac ctacagaata tcatctataa cccggtaact   70800
gatttctata agataacttt ttacctatgc caggacagat ccaatagaat attaattatc   70860
cattgggaga cagggcaaga ataaaagcca gtgaacatat ttaaagcacc tactatgtaa   70920
tagagatggt ggtgggtgct gattacgaaa cagctcttgt cctctagtgg aggaagaagt   70980
cacaatgata atatgacgtg atgaaacagt gttatgaaca gggaacgtct gggtagagtg   71040
gagggaatgc caacttttgg tgatgggagg aggctcagct aatcataaat tgtagttttt   71100
aaaggaaaat ggatttctta ctctacaagt ttttcatttt cttttttaat tagagctgtc   71160
catgagaagt taatgtctcg atctttccct cagcctttca aatactgctt ggcccttgag   71220
cagggaaaat gtcaaaagcc aatggggaga tggagagtgt gaagtagtaa gggtctcgtg   71280
cagttcaggc aggtcctaga atccctgaat gactgtaatt gctggaaatt gccctgtaat   71340
cctgagcagt aaagagcttg ttttagtttt atgtggtggt gagaatcttt aggaatgtct   71400
agtttccacg tatctgaagc tgaatcctga atcgaggtct gaaaaaggac agccacttt    71460
ttagtaaacc gcctagaaga ttcttgggca aaaggaaggg tgagaatcct taaaatgagg   71520
ccctaaaacca gttttgttag tgtgtgtggg ttcaagtttt tgtcatttac tttatagctg   71580
tatttccttt ttccctaagt tttaatgtca ttgtgtaaga atgaggtatc gctgctgtat   71640
caagcaaagt cagtttttagg agaaatagcc tttcagtggt agtaagtta aaaaagatga   71700
cttcctgaag cggaagcttg tgagacattt aagatgactt tgcgcatgtt agagttaaaa   71760
acatcccaag gttgtaaact gatttcctgc aaagatctta acaacaacaa caacaacaac   71820
aaactaggct gcctgccacg ggtgtctgaa gtatcatctt ggctcaagct gggagaatgg   71880
ataaaggtta cactgttcat ttctgcccctt cacacagaaa agaagataat tttataggta   71940
aaattcgtgc atatcttgat tctagcatac tgctgattcc tgtagtttct ggggtcagta   72000
ctctcaacta ttgaggtgga acaaaaataa gtagacttca tttcttgagg aagggggatct  72060
ggagaagtag ttctgcgcta gagcagaaaa tgccttcagt cttgtggcat gggctggatg   72120
ctgttctgag gataatgcat ttccaaggga gatattttg gcaaatagct ttttttttctt   72180
tcttttcaaa attctctgtt ttattatcag ttctcacaaa agagtcggaa aggttagagg    72240
tagactgaac tgaatggcaa aaacattttg cgctctcttt acgtttcact gctgtaaaat   72300
atttatagta taaagggcct gtattgcact gaatttctct catttgtagc tagttgccct   72360
```

```
ttcaatgttc caaaaaaaag gctgtaaata acttatttta tttattcaat taatttttt    72420
ttttaaattt tttgagatat agtttccctc tggtcaccca ggctggagtg aaatgatgca    72480
atctcggctt actgcaattt ctgcctcccg ggttcaagca attctagtgc ctcagcctcc    72540
tgagtagctg ggactgcagg cacgtgctac catgcccggc taattttgt gttttagta     72600
gatatggggt ttcacagtgt tggccagcct agtctcaaac tcctgacctc aggtgatgtg    72660
cccaccttga cctccaaaag tgctgggatt acaggcgtga ggcaccatgc ctggccaact    72720
tagttattta aagataatca attagtatat tttataagct agacttagga aaactgtttt    72780
cagctgggca tggtggctca cacctgtaat cccagcactt tgggaggccg aggcaggtgg    72840
atcacgaggt caggagttca agaccagcct ggccaagatg gcgaaactcc gtctctactt    72900
aaaaatacaa aacttagcca ggcgtgatgg cagcctcctg taatcccagc tactcgggag    72960
gctgaggcaa gagaatcact tgaacctggg aggcggaggt tgcagtgagc cgagatggtg    73020
ccactgcact ccagcctggg tgacagagcg agactccatc tcaaaaaaa aaaaacccc     73080
cccacacaca aaacctgttt tcttgaatca tggttgtttt gttactgata ggttcaataa    73140
gtaaatatat ttattgtctg ttgtattctt tattaggcat tataaacaca ccgccacttt    73200
ttaatttta tttcattaat gtttccaatt tttttttt ttttttttt tttaagacag        73260
aggctcgctc tgtcatccag gctggagtgg agtggtgcag tcttacccca ctgcaacctc    73320
cacctcctgg gctcagcctt gtaaatagct gggactacag gcatgcacca ccatgcctgg    73380
ctaattttg tatttttt ggtaaagaca gagttttgcc atgttctca gtctggtcaa        73440
gcactcctcc cgcctcggcc tcccaaagtg ttgggattac aggcatgagc caccatgcct    73500
ggcctatttc taatatttg gtccacattg gtgttagacc aactgtccac attaagtttt    73560
cttggaaaag atgaagtaaa tattgcaact ggcctatgta tttttttccc tatttagtat    73620
atttctttga ctagttcaac tgatagaatt ccaagactta aaaagtcag gctctaaggc     73680
tgggtccaga ggctcatgcc tgtaattcca gcactgtggg aggccaaggc tagtggatca    73740
cttgagccca ggagttcaag accagcttga gcaacatagt gagaccttgt ctctctataa    73800
aaatacaaaa attaactggg gattgtggcg catgtctgta gtcccagcta tgaggaagag    73860
tgaggtggga ggattgcttg agcccaggag gttgaggctg cagtgagctg tgagtttgac    73920
actgtgcttc attctgggtg acagagcaag aaccatgttc aaaaataaaa ataaaaagtc    73980
agagtccggg tgctgcggct catgcctgta atcccagcac tttgggaagc cgaggcgaga    74040
ggatcacttg aggtcaggag ttcgagacca gcctgactaa cacagtgaaa ccccgtctct    74100
actaaaaata caaaaattag ccgggcatgg tggcggtggc ctgtaatccc agctacatgg    74160
gaggttgagg caggagaatc acttgaaccc gggaggtgga ggttgtaatg agccaagatt    74220
gcacaactgc actgcatcct gggcgacaga gtgatacttc atctcaaaaa aaaaaaaga    74280
aaaaaaagt taggcttcct tttctgtttt ttttttcttt tttcttctct ttttttttt    74340
tttttaaga gatggaggct tgctctattg cccatgctgg agtgcagtgg tgcaatctcg    74400
gctcactgcc acctttgcct cctgggttct agcaattctc ctgcctcagc ctcccgagta    74460
gctgggacta caggcgcaca ccgccacgcc ccgctaattg ttcttttgta ttttagtaga    74520
gacggggttt caccatgttg gccagcctgg tctcgaactc ctgagctcag gcaatccgcc    74580
cgcctcggcc tcccaaagtg ctaggattat aggcgtgaac caccgtggct ggccacttac    74640
ttttctttct attgaatttg aatgaataat ttggaagaca gtatctttac ttcataccag    74700
```

```
gaatgctgcc agtgaaattt cttgtttggc agttcattat ctacctatat atttaatttt   74760
gctattgttt atagagttct taagatatga ttaaatgcta gctggttaag aaatcattta   74820
gaaatgaaac agaattggtt gttactccaa gttaataagt tgcttgtcaa cataaatcct   74880
acctggtacc cagttttctt aggaaccttg cttccatgtt tatccttttc tgcttagtat   74940
tctaagtact ccttttttac cttacaattt agtcttaaaa cacaacacag tcaagtcttt   75000
cttttgtaac ctgtgaggta ccttctagcc tttgtgctgt ttttcttctt ttttgctgc    75060 ctgccttcct gactgagagt ggatttcctc actaaggctc tgccctctga ttttcactc    75120 tcttttcttt tttggtttta ctagtgaaat tttgtcttta atgtctcttt cttttatgtc   75180
tttaccgatc actcataaat ttttttttcc atatgtatcc agttccaacc tttcacctaa   75240 tgtgaaccc caactctcag ttgctcagcc agcccttcaa gactaggagt tcaaaaccaa    75300
acttgcatct tccttcccaa accagctttc ctcttgcagt tttctgcagc aggatccttc   75360
tgctgtttaa cttttgcctc ctcccttgtt tcctagcacc caatagttgg aagatagtct   75420
gtcttcaaaa ttttaaacta catttatgtc caaaccagtg gcttttcctt ttaaaaaaat   75480
ttaaagataa tatgtgcaaa tcattttttt aaaattcaaa cagtatttaa gagtttcagt   75540
gaaacatgca ttttccttct accctggtac ttagttttac tccccaaggg caatcacttt   75600
ttactggttt ttagaaatat atccttcctg agatacttat gaatatccaa aagtgtgtgt   75660
gttgtgtata tcaccttta tatatcctgt ctctttacgt gcatgcattt taccgtataa    75720
actgttttct accctgcttt ttctatttga cctatttttgg aaatgtcatt ttatttagaa   75780
cttcctcatt tattttaaca gctgcataat tagcagtaaa acttatgtaa gcagtccctt   75840
gtgaagggct gtgtcttttt gcgattatat ccggtgctat agtgtacatc cttgtgtgtg   75900
catcttggtg tgcctgtgct acgtatttct gtaggataaa tctgtaaaag tggaatcact   75960
aggtcagagg gtatggtcca ttttctttac ttatttattt tatttattta ttcatttatt   76020
tttgagacag agtcttgctc tgtcgcccag gctggagtgc agtggcatga tcttggctta   76080
ctgcaagctc cgcctcccgg gttcacacca ttctcctgcc tcagcctccg gagtagctgg   76140
gactacaggc gcccgccacc cacgcctggc taattttttt gtattttttag tagagacggg   76200 gtttcaccat gttagccagg atggtctcga tctcctgacc tcgtgatcca cccatctcag   76260
cctcccaaag tgctgggatt acaggtgtga gccaccgcgc ccggcccat tttattatct    76320 ttatttgctt ggatccttct tagcttcttc aatgttaaag atattgacag ttttcctctt   76380
actgaaattt ataaatccat tgactccctt gatattattg ccctggcctg actgattctt   76440
ctctctcctt tctcttctca ccccatgttg aggtccccaa ggtcacaccc agttttgatg   76500
actcaccagc atagagttgt acttgtgcct atgatttatt gcggtgaaag gatatagagc   76560
aaaattgcaa acggaaaggc acctggggtg aattccaggg gaaatccagt gcaagttcca   76620
aggtcgcctc ccagtggagt cacataggat gtgcttacat cctccagcaa ggagttgtga   76680
caacacttgt gaaatgtgga ctgccaggga agctcatcag agcctcagtg cctagggttt   76740
ttactggagg ctggtcacat aagcaccctc acacatatca aaaaattctg gtcccccaga   76800
aggaaagcag gtgtttagca taaccatatt atttgcatga acagttcagg tacaggaaat   76860
ccccgttacc agttaggttg gtgggtgccc ttctcaaatc ccaagttccc agacaccagc   76920
caggggcctg cctcgtaagg aggcctttcc aggacagcag tcaggcctgc caatgttaat   76980
tcttttctgc atacctccta attttagaaa ccaccgagcc tttgctgcct gacctgtcct   77040
gcttttcgat ttctttatct actttgatat ctttacaaat gatctttacc ctgacttttta  77100
```

```
aatgtgtgct ctggccattc acctagcgtg tggttctgag tctccaagtc ttagcagatt   77160
tgctctcaga tgctctgcca acgcttcaca ccaagtatta caaactaaac tcgtcatctt   77220
cctcctgaaa cctgtctccc aggccaggcg cggtggctca cacttgtaat cccagtactt   77280
tgggaggccg aggtgggtgg atcacctgag gtcaggagtt cgagaccagc ctggccaact   77340
tggtaaaacc ccatctctac gaaaaataca aaaaattag ccaggcgtgg tggcaggcac   77400
ctgtaatccc agctattcag gaggctgagg caggagaatc gcttgaaccc gggaggcgga   77460
gattgcagta agccgagatc acgccattgc actccagcct gggcaacaaa agtgaaactc   77520
catctcaaga aaacaaaaa acaaaaaaca aaaacctgt tttctcccca gctttgtcat   77580
gtatttagtg gccttatgta gacagtttcc tttgaaacat ctcttggact tctctgctct   77640
tccagggcca ttgccaccga cctggaatgt gtccttatcg tttcacgcca ggcttatggc   77700
agcagtcagt cacccagatg acctcctgac ctctggctta tttcacccccc actggactgt   77760 tgttcctaaa cacttctttc gtatgtcact ctaaaatctg accctggctg tacctttctt   77820
taactactcc ctgactgcgt gctgagagaa gatgggtctt gtcttttcct gcctctctgc   77880
ttttgtaaac tgccatttct acctgaagtg gcaactgaaa tcatatcttc ttcataaact   77940
gtctttggct acctcagtta gaattcctta tcccattttc ctgaagcatt tctttgactc   78000
ttctttactg ctccccccacc cttttttttt tctttgagac tgaattttgc ttgttgccca   78060
ggctggagtg caatggcccg atctcggctc attgcaacct ccgcctcctg ggttcaagtg   78120
attctcctgc ctcagcctcc tgagtagctg ggattacagt catgtgccac catgcccggc   78180
taattttgta ttttagtag agatggggtt tctccacgtt ggtcaggctg gtcttcaact   78240
cccaacctca agtgatctgc ccaccttcgc ctcccaaaat gctgggatta caggtgttag   78300
ccactgcgcc tgacccccat ttttttttt tttaaagatg ttgaattggt cagggtttgt   78360
agttacaagc aacagaagcc aactctttaa gcagaaaagg aatttgctaa atgatagtgc   78420
agagttctca gaatctctag caggatgaag aaccaggctt ggagaatagg tagccacaga   78480
tacacaagca tactgtagga cggttcccat gaagaggcat ctgttgtcac cactggacac   78540
agatggtact gtgtctctgc tactctacca atgccactgc tgtctctgac cccagatgta   78600
gctccctctg accctggatg cagctccctc tgaccctgga tgcagctccc tctgaccctc   78660
gatatagctg cccctgaccc cggatgtagc tgcctttgac cccagatgta gctttctcca   78720
aacccagata tagcggctgc ccccttgcca gagtgaatac tgcgtcattg tggcttcttc   78780
ttgtcactgg ttcttactta aaagctgagc tggaagttct aatgggcagt tttgtcacct   78840
gctcttacct tgttgcagtc tagatgaggt ctaatgttca taagctaggg gattttcaga   78900
tatggaaagg gataccaatt ttcagcagcc aaatagagta tcacattttc actccatgtt   78960
tcctgggtgt ctgttatgtt tcctgggtgt ctgactctta ggcttctttc aagctgcagt   79020
ctgcctaata gagagccttg catttaatca tcaaaaaggc aaagcaatat gaatcagcaa   79080
gggtgttttg gcaaataaca gcaaacctga ctgtggcgta agcttgtggt attgtctcca   79140
gtgtgatcag atctgtattt taatttttta aatgtaaatt aataatgatc tgtgaatcac   79200
caaagtagct tggagtagcc tagaaaacaa tgtatgtcct ccgttttcac agaagccaca   79260
tagtcgtggg ttaaatgagt cagcggcagg gcactgtgtc tcatagttaa aaaaaaaaa   79320 aagtattact gaagtaatgc aggatctttt ctgaagtaga aggcatgatg aacccagaaa   79380
actaaagcag caagtggcca ccgttcttag catagttgtt tctcaaactg gaacaaccta   79440
```

```
taaacagttg tgaacaaggt attagaagtg atgggggccg ggtgcggtag cttctcccaa    79500
agctcattac ctcccaaagc aaccccagta ctttgggagg atcactttga gcccaggagt    79560
tccagaccag cccggccaac atggcaaaac cccatctctc taaaactaca aaaaattagc    79620
tgggcatggt ggcacatgcc tgtagtccca gctacttgga tggctgaggc aggagaatcg    79680
cttgaaccgg gaggcagagg ttgcagtgag ctgagatcac gccactgcac tctagcctgg    79740
gggacagagt gagtctctgt ctcaaaaaaa aaaaaaaaa aaaaagtga tgggaataga    79800 ttgttttgtc tcaaaaagct ctttccaaca ctaaatgaa acatataatt aaaaatattt    79860
ttctggctat aaaaatatcg atgcttatta tagacatctg caaagtatga aaatatatga    79920
agaaaaaaat taaaatgcca tcatccccca tgaaaactat tgttatcatt tttgtctgat    79980
ttctttagtg tttctctttt tcttttttta attttttaatt tttttgagta tgtagtatgt    80040
atatctattt atggggtata tggcatattt tgatacagga tacagtgtgt attagcaagg    80100
ttttcttttt aatgtttata tttatttagt tgagatcata ctatatatgg ctctatagat    80160
tactttctct tatattacta acatttgtgt tattaaatat tctgcataaa gataaattta    80220
agatgaaatt tgatgttata aaacttctc attttattaa gagattaacg ctatgaaacc    80280
tgctgctata tattcttgga accagctgtg acccaaaaga tcaatgtagg gatgtaggtc    80340
cttccccatt ctctacacac aaaatcagat actctgatgt gcagctgtag ccccagtcta    80400
cactgtctgt tgtattttt gttttctggt gtcacgtgcc tcccaccctg ctcctagcaa    80460
ttgccatgac aacaaataga taattggctt ccgtaatttc tcatcttatt gcctaaggca    80520
acagagagct tgtgggctca gcttgcggtt cagcagctgc tttgttgcct ctcctctgta    80580
tgtgtgaggc ctgccagagc ccactttcca gacaggtgag agttcattca ttcaccatgc    80640
agttaccgat cgtctcttga cctgtgtcct ggggaggtaa aggtgacgag ccagttctgc    80700
cccatgcagc tcacagtcta ggcaaagcta catgcaaaca aacagaatcc aaagtgctat    80760
catgaaccct ctgagagggg ctgactcagc agcccaggga gcttgaagaa ggctccacag    80820
aggaggctgt gcctcaaggc gatttcggtt taggagccac caatttataa ccacttttct    80880
gtggcccgtc ttatttatt tcttatttct tgacaatcag aagtaccttg ggtaggtttt    80940
accatgcaca tcgtaatttg agtgagctta gtgtgaggct taacggtgtg tgggctgtac    81000
atcctggtca gatgctccag atggaggcag atggttgtga tgcaggagag gcagccacat    81060
agcacaggtc cccagccagt ggactgggaa gacagtgtag tcatctctgg ggaaggggaa    81120
tgacaagatc tggcagtgtg gcaggtccca gaaaaaaagg gctgggttct gggcagtgag    81180
ggtgcaggtt gagacctgaa tactgggtgg agccagctgt cagagtccac gcctgcagac    81240
tggactggtc cacggcaggt ggatgccatg tcttgaagac ccacaggcac ccactcatcc    81300
tcatgatcat gcagttctct ggtttctaac agtgcagtct gggttgcagt ctgggagtcc    81360
agcagagaag agcaggccct ggaatcccag gtgtgggggc gtggcttaac gtggagtttc    81420
cttcagaggc agtgagtgct tgtcattgtc tccgtcagca ttggctttgg gcctagtgtg    81480
gcctcgaacc ttctgttggg atcagcagtg gaacagtagg aaaaggaatg agtagacatg    81540
gcattgcaac aagtcttttt tttttttttct gttagaatta tcatattaag cagaagtttt    81600
gcttcacaaa ctctcagcca aatacaaaat actatgaata gtatttacct tgtgtctctt    81660
tccaaagaac tcatagtggt ttgcagctat tgcagatatc ctggccatgc ggtatgcggt    81720
tccttttttt tgttttttt ttttttttga gacggagcct tgctctgtcg cccaggctgg    81780
agcatagtgg cgcgatctcg gctcactgca agctccgcct cccgggttcg tgccattctc    81840
```

```
ctgcctcagc ctcccgagta gctgggacta caggcgcccg ccaccacacc cggctaattt    81900
ttgtattttt agtagagacg gggtttcacc gtgttagcca ggatggtctc gatctcctga    81960
cctcgtgatc ctcctgcctc ggcctcccaa agtgctggga ttacaggcgt gagccaccgc    82020
gcccggccgc agttcctttt tatagctgtt tgaataggaa agatgacttg gaaaatgctg    82080
gattctgaga tttatgtgca gccttaaaaa gtgtagtttt tctctatcaa taatgagtgt    82140
gggttgtaat tgcttagtaa gtaattttgt ttatgtaaac gtacatttgt taaatttttt    82200
ttcttaggta atcccgtatg ttggcaccat tcccgatcag ctggatcctg aactttgat    82260 tgtgatatgt gggcatgttc ctagtgacgc agacaggtaa aatcactgtg ctaaaggaag    82320
gagcatgaat aggctgtctt tttgtgattg tggaatgata acagagtaag gcgggagaga    82380
ccatttgata ctctgaggcc caattagctt tcatcagcag ccctggccaa ggtgctgagg    82440
agattggaat gaatgactaa ataaaggtta ttgggattta tttcattgct gtaagtctga    82500
tttcagtata aaaaaattag aactatcagc tggatgtggt gacttacaca tacttttcca    82560
gcactttggg aggccaaggc gggaggattg tttgaggcca ggagttcgag accagcctgg    82620
gcaacatagt gagaccccc ccatctgtta aaaaaaaaa aaaattaaa aattaactgg       82680 gcttggtggt gtgcgcctgt agttgtagct actcagggg ctgaggtagg aggatcccctt    82740 gagcccagga gtttgaggtt gcagtgagct gtgatggagc cactgcacta tagcctgggt    82800
gacaaaaaaa aaaaaaaaa aaaaaaaaaa aaagaaaga aaagaattga ggtatgtcat      82860
taaagaaagg aattgtggtc agatgacagg gagagtctag ttttagtctg acattcccac    82920
agcatcacag atctagttca gatggttta ctgaatactt gctttggata caagctgtgg     82980
tatcattagt gttgggctca gctctgtgta cctaacacct gaagagcagt ggtttaagat    83040
gtgaaaatta agtctcaagg agacagccca ggccttttca gttaactcct tcaagtcgtt    83100
agagaagtag actccttcca gcttaccact ctgctatctt gagggtgagg tgaggtcccc    83160
tttcccatta tccttggcag ctagatttcc agccctcact tctgtgcttt gggtagctgg    83220
atgggtgcat gtggtgtttg cggggaaaca gagctggaca aaaggcaagt gcttgctgac    83280
ttttaaggca gtttctagta gccttccctg agcacttcac ttccatctta tcagcagagc    83340
tttagctgca caggcaggcc tagctgcgag ggaggctggg aaaggtaggt ttttattctg    83400
ggcagattca gacccagttc aaactcaggg gctatttac tgaggaagac agaaaagatt     83460
agacagtcag ctcttaggc ctcatagtga atgaatgagg agggattggt cagtcccttg     83520
tcactgggcc tggagtgtag tgcctgctgg gcctttactg gtggctttcc tttctgagca    83580
ctcatgaggc ccctgtgtct tccctcatat agattccagg tggatctgca gaatggcagc    83640
agtgtgaaac ctcgagccga tgtggccttt catttcaatc ctcgtttcaa aagggccggc    83700
tgcattgttt gcaatacttt gataaatgaa aaatggggac gggaagagat cacctatgac    83760
acgcctttca aaagagaaaa gtcttttgag atcgtgatta tggtgctaaa ggacaaattc    83820
caggtaggtt ttggagaggg acaggttgag tcctcattag tgagcaggag tgcacagggg    83880
ggcctttcac atttgtgagc ccagccttgt atttcctaca cctgagatat agtttggctt    83940
tgtagtcttt ctccataaaa ggaccaggaa ggcacctaaa tatgaggggg tggcaccact    84000
actctccagc cagttgttgc catgcagaaa tatggtccac tgtgactaga tcttttttatt   84060 agatcctatt tctcctagca gggctgagtt ctgaattgac acagtattat gttcatgatg    84120
ggagggtaag ttataatata accgtcacca cctgaagaac taacaagggc aatcccagca    84180
```

```
tagaaatcag aagggttttg taaattcaag tcttgccaca agacagttct gtaggatcat   84240
gagattttta gacccagagg acatcctaga aatccttgat gtcagttcca tctctggctt   84300
catggagtgt cttataccta gcgcgcgtgt gtatggttga atttggtccc agaagctctt   84360
acacctgctg gccctctggc ctgtggagct ttcccacagt agaggtttgt accaacgtga   84420
gagaagactc acatgcctct ggcacagatc ctttctgatc ttcgggatac tgctcctgcc   84480
cgaaagtctt tctgaatctc ccaaactcca ttcacctctc ccttctctgg cctttgagc   84540 ccgtgtctgt atcattcttt ttcacagttt ttaacagttg tgctttggct ttatgtgttt   84600
attttgcctc cacaatggga tttaaagctc cttgagtcag agactatatt gtatgctgct   84660
cgcgttttct gcctataacc taacgtggta cctggcattt gagagggagg gagggaggag   84720
gctcgtagcg tgccgaggac ctgcagaagc tactttctcg tcatcttact gtagtctgtt   84780
gaggtagaga ttgttcctac ttcagaataa gaaaaccgaa ttcaaatatg ttgggtaact   84840
tgtccatatt aatttattta gcaaatacaa cagattttga gtgtctgcca catggggtggt   84900 ctccagggac agtgttgtgg ggagctcgca ggcagatctt taacctgggt tcacaatctc   84960
cagggcacct gtgcctgggc ttccaggcga ccttcgaacc cagatgtctc acatgtatgc   85020
agaggcgcac acaagcacac gcacatatac ttatgactgc ctgtttgtct ggggagagac   85080
agttcctggt gcttaatcaa atcaggaact caaaagaagt tcggaagcac tgctggtgtt   85140
ttgggtgctt tcggttacca tttggtcacg tgtgtggaga cctgtgggaa caggtataaa   85200
attggacgca aggaaacatt taaatttgga taataagtta atttattaac tgttttttt   85260 tggtggcggg ggggctctgt cttctgtatc tctctaggtg gctgtaaatg gaaaacatac   85320
tctgctctat ggccacagga tcggcccaga gaaaatagac actctgggca tttatggcaa   85380
agtgaatatt cactcaattg gttttagctt cagctcggtg agtgaccttc cacagcttgg   85440
ggtcttttat gaggatggtt tctgatgaga tggtagaaaa aatcttcaaa taacacttct   85500
attgacataa aaaggacgta tctccctgac tgtagtatta atttttggga agtgaactgt   85560
tcacactagc agaaggctgt ttatcagcca gggcttcatt gtctgtagga tctcaaacct   85620
agtgtggttt aataaaaaca cacacagttt ttagctgggt agcagctatt tcctttgcat   85680
gggcataaaa tggagtattt ctgtaagaca ggttcctagg ctgggagtgt ctgagtcaaa   85740
gagcacagtc atgtgttgca taaggacagt tcagtcaaag atgaaccgca tatacaaccg   85800
tggtcccata agattgtcat atactgtatt tttaccatac cttttctatg tttaggtaag   85860
tttatatgca caaatactta ccatcctgct ctggttgcct acagtatttg gtacagtgcc   85920
tgctgtacag attcactggc caggagctat aggccacacc ctacagccta ggtgtgtagt   85980
tggcagtacc atctaaggtt gttaagtaat attctgtgat gtttgcacga tgacaaaagt   86040
catgtaagga cacatttctc agaacatacc cccttcgtta agcaacacat gactgtcttt   86100
gcattgaaaa ttttgataga tactaactcg cccttcacaa gggtaaaaac agtttgcact   86160
ctcaacagcc atgctcccac cttcttgttg acattacatc ttattctctg taatgtttgc   86220
caatctgatg gggggcggaa aggacccag tgtcaagtat atttttggat catagttttc   86280
aagcatattt ttagtaccat ttataatttt tttatatgtc aaacaggtta tatatagaaa   86340
atattttcta ctggatgtta caaattaatc tttattatct tttctcagga cttacaaagt   86400
acccaagcat ctagtctgga actgacagag ataagtagag aaaatgtaaa tattaaatct   86460
tttaatgagc cactggttta aaaatgttgt tttagctgcc atgttaatga aatggcaaga   86520
aggctgggtt tttgaaaatt atgctttag aacgcaagta atcacttgaa aattgagata   86580
```

```
catacttgtg gtgccaggca cgcagtaagt ttttgctgat gattcacctg tcagtttctg    86640
taactgccac tcactgttct tatgtaaaaa gcactctctc actcttaact gctgaatagt    86700
actgttctgg ggtatttcca aatattgaac atcagccagt gcactggcaa atgaacttcc    86760
atgtgtatct tcaacccctg ggagaataac tgcaatttaa aaatgcgctg ttattaatgg    86820
agaaagtgag gtcttaccga ctggcacgtt cacacctcac agacagaata gaatcttagc    86880
attctggggg caccctggaa aggacaacta agacacgttt gaagttcatg tagtgctggg    86940
tgaaggtggt ggctcaggcc tgtagtccca gcgctttggc tgaggtgggg ggattgcttg    87000
agcctaggag tttgagatca gcctgggcca catagggaga accccatctc tacaaaaaat    87060
taaaaaatta tctgggcatg gtggcgcatg gctgtgatcc cagctttggg tggctgaagt    87120
aggcggatga cttgagccca ggaggttgag gctgcagtga gccatgattg agccactgca    87180
tcccagtgtg gatgacagag taagaccctg tctcttaaaa aaatttcata tagttctatg    87240
aaaaattatt aatttatggt ggaggataaa ggactcagat gaacagggat atcagactct    87300
cttctcaacc cgtgtagccc ttcacaaaca cataccattc cgtcataaag caccagctgc    87360
ctggaggtca caccagagtg gagcaggaac atcccaggct ccggccaggc tcagctcagc    87420
acaaccaaga cttcagatta taaactataa ttcttcccct tctaacattg ttgtgttttg    87480
tttcttttcc aataggttcc aaagtctggc acgcccagc ttgtgagtat ttttgcctgg     87540
gttatttcat gtggaatatt ttataaagtt gcatagaaaa tgaacagttt aaaccgtgga    87600
gggcagcttc attcattcca ttccttactg tagaactgtt tccctacagc ctagtaatag    87660
aggaggagac atttctaaaa tcgcacccag aactgtctac accaagagca aagattcgac    87720
tgtcaatcac acttgactt gcaccaaaat accacctatg aactatgtgt caaaggtttg     87780
aagagcccca aattttctta actctgtata aaaattaagt tgtaatgagc tgttacgagt    87840
aacctgtatc cacaatagaa gcccaaagca gcccccctctg catttgtgtg ccgtccctgg   87900
atggattcga gagtcaacca ggcctgcctc tgagccattc ctgtgtattt cctcagcacc    87960
tccctgcttg gctgcttccc cttcaggcag aacacagtac tgcctcagac cccaggcaca    88020
gggggccttc ctggcgtgtt tcactcatac agagggcatc gggtcccacc ctgtcactca    88080
tttcatcgtc taaaatgtaa tcatgagtgt ttgcttcgag ccaggacag tgctgctgca     88140 ggggacccag ctgggaccaa ggcagactgt ctctcccctc ctgggattta cagggtcatg    88200
gctctgaaac attctgtagt gttctttgga cacgagtttt ccctggagat cgctttctgc    88260
aggcctcttg gtcctgactg tggcttcttt tcagagcctg ccattcgctg caaggttgaa    88320
cacccccatg ggccctggac gaactgtcgt cgttaaagga gaagtgaatg caaatgccaa    88380
aaggtcagta tccttcggta ccagtcacag tgcagatact tccgtgcctg ttaccgcctt    88440
ctacccgtga acgtcctgt gagctggaag tagggctagt gtcagaatct tcatttccaa     88500
agtgagatga ttcaagcagg aggtggttag attgtgaaca gccagtgggc agcagagccg    88560
actaaggccg tgttctgacc tcggcttttt ctggccagac aagagagtag cattttttgtc   88620 cacgaggcct atccttgcct tgtagaactc cagagcagcc ccgtaagatc aggcaacatc    88680 tttcttttt ttttttgaga tggagcctca ctgtgtcacc caggctggag tgcagtgtca     88740
caatcccagc acaccacaac ctccgcttcc tgggtgttca agccattctc ctacctcagc    88800
ctctggagta gctgggatta caggcgcacc accacgccca gctactttt gaatttttgt     88860 attttttagta gagacagggg ttcaccatgt tggccaggct ggtctggaac tcctgacctc    88920
```

```
aagtgatccg cccacttcgc cctcccagtg ctgggattac aggtgtgagt cgccacgccc    88980
agcccaggca acatttttta gggcccctct tgtcatgtga tttagaaaat ttctgcttta    89040 acaactttt ccacagacgt ccagccttct gaaagcttga aattagagct atttcctaga    89100
aagtggcata ctttcaagaa ggaaggaaca cgggtagatg atgaaaagag aatacctgct    89160
tgagaggatc ccaggctcct gcagcctgaa gtagtcattc agtttagcgt taaaccttcc    89220
atttctgtcc aaccacatct cagcctcaat gctgatttta aaggggtttt tttttcgta    89280 tttttatttt gcaagtaacg aattagtgga atgctgactg ggtttaaaat ttcaacttca    89340
cctgcattcc catgtccatg tggatacgtg tgtttcatag agttagaatc atagttcaag    89400
tctggtcact aacattgctg aaattgccac tactctgtcc tacttggtta attaaggttt    89460 ttttttctt tctttctcaa aagctttaat gttgacctac tagcaggaaa atcaaaggat    89520
attgctctac acttgaaccc acgcctgaat attaaagcat ttgtaagaaa ttcttttctt    89580
caggagtcct ggggagaaga agagagaaat attacctctt tcccatttag tcctgggatg    89640
tactttgagg tgaggttcca gttttttgaaa atgggacagc aataagaatc ctgggagcag    89700 gggtggggata agtggtccat ttaaatcaag tcctaactca gtatgtggag gttgtgtatg    89760 tttttttgttt acttggagat tgtaatttgc cccttccttt ttataacgtg ggcaatcagt    89820
ataaatggca aagccagtag agtgtcaaat tatgcacatt ggaattgaca tttgtcatca    89880 tattaaaaatt cctgtgtagc cccatattga taggaattta accaggaagc ttgtctcagg    89940
actggagtca cacatttaat catataagca gacttgagga ctggagaccc taaaactgct    90000
tgcttgcact ggccatcatc tcccatcagg gtaggtggca gtccttctc ctaaggagtt     90060 agtcttgtt atatgtattc aaggaaaaat acatcagtcc cttggaacta aaaggcatgc     90120
agtcctgagt ccccagatag gtgaatattg taacacatac ctttcccgaa atatgtttct    90180
gggatgctga gcagagaata gtctccttgt gatgtggatg ccgggtgttt ggccagcctc    90240
aatcaccagc tcaggtgcca ctgcctcaca cagtcactta gggtcattgg tttaggttat    90300
cattctacag cattttaaac tgacacattg tctggaccat gtgggttctt gaggactcat    90360
caaaacccgt tactaaaagc atgaatatca ggcgaaatag atagcaatgt gacattcgta    90420
tttatcccta agttccagtc taatgcagtg ccctggtatg tggagtgtag acagatgtgg    90480
gctaatcatg gaaggttccc tggaagttgt ggatattggt ttcgaattca gaaagctggg    90540
aaggatgtgg aaggctgaag gttggctttt ctagatttag ggcatgattt gaacaagtcc    90600
ttagaggtgg gaagggcagc acagggttgt tggcttggca agagtcaagg tgcaaagggt    90660
gacttggggt tcactggagg gaaacagaga tgagtgctct agaaggaagt tgagccttgt    90720
ggtgggtgac aggaaaccaa tgatgtaact tgttttgac ctatctgggc cccaagtttg      90780
gatctgctat attaatataa aaaggataa taatgataca ttcaaataat gctgaaaaat     90840
actaagatga aaatacctcc aacttcgtaa ttcaaaccat accattagga ttaggtgaac    90900
cacattccag gcgttttttt gcagagacag tgaaagggat ggctggctga aggaatgaat    90960
agatgaatgt tatatgcttt tgaacaatcg tcttttccat ttaattttct aattcaggag    91020
cagtaattat ccttgtgttg atcactgctg acgattttct atactgatag gtcctttccg    91080
ggggcttcca tctcttgcct tttaaatatg cttgcattga gattatctca ggtctttcca    91140
ttatgccatt actttcattt taaatcttct tgctctttca aatacacttt agttgtatct    91200
acagtgtttt aaaaacaatc tcattcagtg ttgtaatttc atctgtgggc tcttcctctg    91260
gatgaaatcc gtgttcctcc cagctgttcg gcagcatcag atggttgtga gggattctgt    91320
```

```
tgttctgttt tcttctaggc aaaggatgtg ccttcttttc atttgcagta gtctgctcac   91380
ccggaagcat gtcatttctt tgccacttgc ttgtaattca ctggctttgc acttgctctg   91440
atacagtaca ggtaactaat tgactccctc tgctgccaac ttggttttcc ttctgagcta   91500
tagcatcagg ctgtgtgttt tgtgttttct tgagattttg ttaaatatat ctggggtccc   91560
ttctacctgg ttggaactgg gattcccacc attcttgtgg ggatagaatc tcaggttaca   91620
cctatttccc caatcctctg tagccacaga agcttcatct tggccagctc tgttatcaga   91680
gtgcaggact tgggctgaaa tttcctcccc ttcctgattt tccttgacag tccttttccac   91740 tgctcctatc aatcaaaaga atgaaaaccc tcaacttgct gctttgcaga ttcaggtttt   91800
gtgcttcttt ctggcctctc ggggtggggc cgggttagca gcaaggctga gctgcccctc   91860
tttcttctga agccttcatg ggggcgagga gcacaggag agctcagtgc agggcctccc   91920
agtggccttc tcagagtggg tggaaaccca gcctggcact ggcagcgtgg caccagaagt   91980
atgaagtgta ggtgtaaagg tgatgtaaaa ggctagtagg tttttggtt tttcattgtt   92040 tgagttttgg gcatagatga ctgtgaaggg cgaacactgc cgatggatct gaatgaattt   92100
gtagtatgtg caccacttcc aacttacggg atacccagct ttgacggctt tggacaaaca   92160
cactgaggcc aagatgtgct gagcttatca ggatcaggat caccaagcag ctgtaaaaac   92220
cctagcaagt gccttaagct gctgaaattt catattaatt gtctggtttg ttcatggtcc   92280
tagagtttga ggcagaaaag tcaggatcca agtcccttgg ttccaggcta cagctggaaa   92340
cagcatctcg gtgaactaaa gcaaccatat taggagtttt cctgctttag gagagtcccc   92400
agcatcggcg aggaggggc agcactctgg cttttccagga gcaaggggca ggatgcggcc   92460
gagggagagg ggctgtgttg aggaaaggag ggccgcaggc cctggggatg tgtgaggct   92520 ccaaacatgt ccgagtcact tccctgggtg ggatgaggca gacagtgcca ccaccaggga   92580
cactttagtt agattagggt cttggaagtc acagaaggaa gtcagcagca gcaggctgga   92640
acttttctat gtataatcaa atggtttact ctgacaccgt tagcatgtaa caaacacaaa   92700
attttaaact aagggaacc actaatggca tgtttccttt cctttcagat gataaatttac   92760 tgtgatgtta gagaattcaa ggttgcagta aatggcgtac acagcctgga gtacaaacac   92820
agatttaaag agctcagcag tattgacacg ctggaaatta atggagacat ccacttactg   92880
gaagtaagga gctggtagcc tacctacaca gctgctacaa aaaccaaaat acagaatggc   92940
ttctgtgata ctggccttgc tgaaacgcat ctcactgtca ttctattgtt tatattgtta   93000
aaatgagctt gtgcaccatt agatcctgct gggtgttctc agtccttgcc atgaagtatg   93060
gtggtgtcta gcactgaatg gggaaactgg gggcagcaac acttatagcc agttaaagcc   93120
actctgccct ctctcctact ttggctgact cttcaagaat gccattcaac aagtatttat   93180
ggagtaccta ctataataca gtagctaaca tgtattgagc acagattttt tttggtaaaa   93240
ctgtgaggag ctaggatata tacttggtga aacaaaccag tatgttccct gttctcttga   93300
gcttcgactc ttctgtgctc tattgctgcg cactgctttt tctacaggca ttacatcaac   93360
tcctaagggg tcctctggga ttagttaagc agctattaaa tcacccgaag acactaattt   93420
acagaagaca caactccttc cccagtgatc actgtcataa ccagtgctct accgtatccc   93480
atcactgagg actgatgttg actgacatca ttttatcgta ataaacatgt ggctctatta   93540
gctgcaagct ttaccaagta attggcatga catctgagca cagaaattaa ggcaaaaaac   93600
caaagcaaaa caaatacatg gtgctgaaat taacttgatg ccaagcccaa ggcagctgat   93660
```

-continued

```
ttctgtgtat ttgaacttag ggcaaatcag agtctacaca gacgcctaca gaaagtttca    93720
ggaagaggca agatgcattc aatttgaaag atatttatgg gcaacaaagt aaggtcagga    93780
ttagacttca ggcattcata aggcaggcac tatcagaaag tgtacgccaa ctaagggacc    93840
cacaaagcag gcagaggtaa tgcagaaatc tgttttgttc ccatgaaatc accaatcaag    93900
gcctccgttc ttctaaagat tagtccatca tcattagcaa ctgagatcaa agcactcttc    93960
cactttacgt gattaaaatc aaacctgtat cagcaagtta aatggttcca tttctgtgat    94020
ttttctatta tttgagggga gttggcagaa gttccatgta tatgggatct ttacaggtca    94080
gatcttgtta caggaaattt caaaggtttg ggagtgggga gggaaaaaag ctcagtcagt    94140
gaggatcatt ttatcacatt agactggggc agaactctgc caggatttag gaatattttc    94200
agaacagatt ttagatatta tttctatcca tatattgaaa agaataccat tgtcaatctt    94260
atttttttaa aagtactcag tgtagaaatt gctagccctt aattcttttc cagcttttca    94320
tattaatgta tgcagagtct caccaagctc aaagacactg gttgggggtg gagggtgcca    94380
cagggaaagc tgtagaaggc aagaagactc gagaatcccc cagagttatt tttctccata    94440
aagaccatca gagtgcttaa ctgagctgtt ggagactgtg aggcatttag gaaaaaaata    94500
gcccactcac atcattcctt gtaagtctta agttcatttt cattttacgt ggaggaaaaa    94560
aatttaaaaa gctattagta tttattaatg aattttactg agacatttct tagaaatatg    94620
cacttctata ctagcaagct ctgtctctaa aatgcaagtt ggccttttgc ttgccacatt    94680
tctgcattaa acttctatat tagcttcaaa ggcttttaaa ctcaatgcga acattctacg    94740
ggatgttctt agatgccttt aaaaaggggg cagatctaat tttatttgaa ccctcacttt    94800
ccaacttcac catgacccag tactagagat tagggcactt caaagcattg aaaaaaatct    94860
actgatactt actttcttag acaagtagtt cttagttaac caccaatgga actgggttca    94920
ttctgaatcc tggaggagct tcctcgtgcc acccagtgtt tctgggccct ctgtgtgagc    94980
agccaggtat gagctgtttt agaagcagcg tgttgccttc atctctcccg tttcccaaaa    95040
gaacaaagga taaggtgac agtcacactc ctgggttaaa aaaagcattc cagaaccact    95100
tctctttatg ggcacaacaa agaaacgaag gctgaagttc gcctacccaa aatgaaaagt    95160
aggctttaca gtcaaaagta cttctgttga ttgctaaata acttcatttt cttgaaatag    95220
agcaactttg agtgaaatct gcaacatgga taccatgtat ataagatact gctgtacaga    95280
agagttaagg cttacagtgc aaatgaggcg tcagctttgg gtgctaaaat taacaagtct    95340
aatattatta ccatcaatca ggaagagaat aataaatgtt taaacaaaca cagcagtctg    95400
tataaaaata ccgtgtatca tttactcttt ctgcagctct atacgatagg caggagaggc    95460
ttatgtggca gcacaagcca ggtggggatt ttgtaacgaa gtgataaaac atttgtaagt    95520
aatccaagta ggtgtattaa ggcaccaaaa gtaacatggc acccaacacc caaaataaa    95580
aatatgaaat atgagtgtga actctgagta gagtatgaaa caccacagaa agtcttagaa    95640
atagctctgg agtggctctc ccaggacagt ttccagttgc tgaatagtct tttggcactg    95700
atgttctact tcttcacatt catctaaaaa aaaaaaaaaa aaaaatcaaa attaaaatct    95760
gagtcagtct gcctgcctcg gttctcatta gtttaattct taatgccttg cactttccag    95820
caatcattca atcaaaagag tgaaatgaag cacattaaca aagcaggagg cgccacggac    95880
cgcctccctc cacaccgctc cttccgcctt cattccttgc ccacaggctt gcactggaag    95940
ctgaataaga atccccaaaa ctcaaacttc ctagggatgc caccccttta gtagctcaca    96000
cctcccccct ccaagagcta agaaacaaag gagaatgtac ttttgtagct tagataagca    96060
```

```
atgaatcagt aaaggactga tctacttgct ccaccacccc tcccttaata ataacattta    96120
ctgttatttc ctgggcctaa gacttatgtt ccagaactgt cacagctccc catgtcacac    96180
ccactagctt gtgatctttg tcaaataact gaaatctttt aagcctctag tttcttcctt    96240
tgtaaaacag agataaaatg ttgtggtttt aagtgagat  aatccaagta aagcacctaa    96300
catggagtag tgaatgaaca tcggttgcta ctaaaagtgg acatcctacc gcatccttaa    96360
tgccactagg catttccata caatctgggg accaaaactt caatcatata aatgtatgag    96420
gttaattaaa aacactactg taatctgctt gtatgatcac aaaccaccac aaaagaaaag    96480
atcgtgaaga ttacactgta aacggactct caaatgatca ggaggtggtc acttcgcaac    96540
ttgctccctc cacccaactc aaaacaggag ctcgagcctg cctgtatttg agactggagc    96600
tgcctgtatg aggactggat caactgctag tcacgttata tccaaatctg cattatcatt    96660
gggcacattt tcacagaatt ttactgaatt attccttaat tgtttaatgg ttgggaatag    96720
tttgggaatt accttccatc aactctgcta agaaaggaat ggattctggt agcaagacaa    96780
tataattctc ctttagtttt tcagccagtg ctaacacagt aatcaaagca gcaaatcgaa    96840
cctgaaaggg ataaaagagc aaagaaataa aaagtagtgt tactgtattt attatcttaa    96900
gagctgtact gacttgagac aagctctaac tttttaaaca ttagttcaca cgcgtttatt    96960
cacttcatta tgttcattaa gctttcatct tagaatacca gtttcaccat ttgggagctg    97020
tttgtaatat gtgcaacctt ataaatagtt ttttccaaac tgtgtcccag gactgcaaat    97080
ctttaatgtg aaatgtcttt ttataatctc ttcctttaaa aaaaccaat  aaaataaaat    97140
gccacatgca aactcaagtg tgtcaccaga ttttacttca ttggcgctcg ccagcccgcc    97200
aggctggcaa taaagtgcct ccagccacct ctggcaggtc tcctcaccca cagccctga    97260
ctggtcacca ctatagttgt atgaggggcc aggacaatcg cttgggataa actcccatct    97320
cagcactgaa taaaaacat  tctgtgtcac aatatcctag ttttggggct ttaaaaacgt    97380
ctaggtgttc ctcacatgcc ttgtctataa taggaaagc  aagcagtagt tgggtattgt    97440
tagcttttga aacaaaagcc ctactggtct tctaattttg gatattttaa ttaaagaata    97500
tctggacagt acaaagtgaa ttattaaaaa accatttgta actacctaga ttcaatcagg    97560
attttccttga tttgtgcaaa gtaaaatatt acaataaatt tgatactgct acttgtataa    97620
aacctatgg  tttaaaatgt gggggttcat cataatagtc tcattgttag catatcctaa    97680
taaagaattt gaactaataa atcctattaa taaaattctg ctttggtctg ttatagccag    97740
taaagttcta atacaatcat tagtttgaga aatggtgact cattgctaaa acagtttgaa    97800
atttgtaaca cttgggtgtc aaattttgac ttccactcaa cctacccatg ttttatttcc    97860
actgccacca cttactcaac aagatcataa gcctagtatc tataaacaac agaatgtatt    97920
gctctaactc aaaagactat agtgtggata aattcaatgc atttctctct ggagcacaat    97980
gacatttcaa tagcacttaa aaaagaagga attacttcaa atctttgtta tttaaaagta    98040
tttagaaagt attttagtac ttctgcccaa cgcaccattg gggtggggat agggcattgc    98100
tattctttac aaatagccta aagtaaaaa  acaaaatttt cttaggcaca aatttctgcc    98160
taatacaaaa gaccagacct ctagtactgg atgacaaata gcaatgttct tccctgccag    98220
tttactaggg ggcctacatc tgtgaccacc tgcaggctgt ttaggctatg cagtgaaaag    98280
atgcagtttc agtacttgtc acgcagttcc taacctaagg cgaggagtct ctcgtctttta   98340
gcagaatctg gtagttcagt ggtttccaaa gagagtcatc cgccatggcc actgaaaact    98400
```

```
gtgcgatgca tggtatcagg tgctttgtca cccgttcctg gaattctct  tctcccccaa   98460 gcctgttttc cagctaggaa gagtaagaca aagactttga acaacaagtc tcatttcttt   98520
cttctgtttg aaaaaatgtc caacatacaa atattttact atctttcatg atattagcag   98580
gttcaaaaac caggcattat tctaatactc tctagggcaa atgtattgcc ttctagaact   98640
caaatggaat ctcatacccct ttatcatcgc cctttctct ccagcagaac atctcagagg    98700
agctctttgc tccagaggac agccatgctc tgacacgttc tcagtgaggc ccagttaaaa   98760
caaatgaata cattaaccat gacagcttat atcatgtctg tcttttgagc agttaaaaa    98820 ataaaaata aaaataact cagggccagg catggtggct cacgcctgta atcccagcag    98880
tttgggaggc caaggtgggt ggatcacttg aggtcaggag ttcgagacca gcctggccaa   98940
catggcaaaa cctcatccct actaaaaata caaaaattag ccaggtgtgg aggcgggcgc   99000
ctgtgatccc agctattcgg gaggctgagg cacaagaatt gcttgaaccc gggaggtgga   99060
ggttgcagcg agccgagatt gcaccactgc actccagcct gggtgacaga gcaagaccct   99120
gtctcaaaac aacaaaacaa aactcaaatt ccacaatgaa gttatatctt tgaaaaaaca   99180
attttcaaat aaaacatttc attaaaaaga ccagaaaaaa caaccttaca agaaaaatc    99240 ctagcaagct gtcatttgag cagatctaaa acctgccaag ctcgaacagt gatggcttcc   99300
tcagcaacga aagatgattc tgtttggtta cctgatccac cagaggcatc atcaaggctc   99360
ctgctctctc tttacttata aaatgctggg tatcaaaaag gaagattttg tataaacagt   99420
tcaaaataaa ctgcaacagc aagcagcact tttcagggtc attttcagag tcaaaaaatg   99480
cttcatctgt agacgtggga agagtaaaaa tgaaaaaaca ctgaacttaa ccatttaatc   99540
tccaatgttt acattgaaat cactattaaa ataactaaat cagaagagtc taaaatgatc   99600
tagaaatcat aatcaggacg aaggcagaac acaatggatg gtctctcgaa gaatgattcc   99660
ttcttttaga gttaagattc taacactcac tctggcaagt taaattccct caactgtcaa   99720
gtgggtcacg tattagcatt agagaataaa ctaatcttaa ttttgcgtt  ttaaagttac   99780 ttccagtaac tgacagtaac ggccatttac tttattcttt ctcccaagtg aggtgactta   99840
taacattcgc tcatcatgct aaaacaacac ttcactgtct gacaacaatg aagtaaaaaa   99900
ttcaccctcc ttagcttagg acttaagaac ctctaaaatc ttgcttccaa gcactagctt   99960
gtgtcttact ggtaccttgt ataaggcaca caggacaagg gtgacagctg aactgaagcg  100020
accacccacc tgtttggag  atgttcacct ggtccaaggt gtcagcaaaa ggcttcacta  100080
agtggccggc aaacagagta aaaagccctt tcagcttttc agcaatgcaa tctgccaagt  100140
tgtaaaatgt caacaacctg tccttgggg  catcttctgt tttagcccaa tcaaacagct  100200
gaaaggataa gacagtatta gtttcttcga catcttgtca cttaaatctg agcacaaaag  100260
agaggaagag gaagaaagcg tcaccttgaa gaacagggc  ctgaatgtga cctcggaaag  100320
tttgacaacc atggctacta gacagtcaat gatacaattt tccgtttttc caacttcctg  100380
cagatcgttc tgaaaacaga agagcccatt tattagagtg ctgatacctg actgtaaatt  100440
attttggcaa gtaccactgt tacacggcta gattgttctc ggactcttca ataggtggat  100500
aacagcttta ggatttggag gagtgaacct gagcttacct cagagtgctg ggctcggaag  100560
tccagggcct ccaggaaaaa ggcggttagc tgagactgat gggaggtgag ctcttccttc  100620
ttcatcgccc caatatgctc ttgcaagatg ctcataaacg gacccatgtg attctaccaa  100680
taacacagga aaaagatgtg ccattttcaa atgattccta gagttcagcg gtgtgtattt  100740
ttaaaaacta aatcttcttc tttaagtcaa agtttacaca ttgcagtacc acctctcct  100800
```

```
tctccaaagt cttaataccc aataagatct aaccttccag ttcttctcaa tctgcttgta    100860 agttttttg atggcgggca acaggactcg gggtgcaagt gtggtagcca gtgtctttt     100920 aagagatgtg agacggatat tagcctgtga cgcagaaccc atttcactag tgattttctc   100980
cagatgaatc acctacagga atataaaaaa agtgatcagg gccactgcag atcttcgctg   101040
acaaacacac acttacagag aggcttcatg atgaggtact agtgtttgga aaatgcttag   101100 cacttttaa ctacacacag agttcctttt aaagtcagcc ctaaacgtca gtggataaaa    101160
ctgggcagac acctcttgcc caacttgcga tcagggacga aggccgatgg tagacgcaga   101220
cgcacacaca gcacccagac agatgatttt cttagaggac aggaatgcaa gggaccacgg   101280
caagagtcaa gttgctaaaa aactgagaaa gctcctcaga gcacaggccc ctttctctga   101340
gaaggctact tttaaaccct ggctgtggtg taagtgaagc ggtttaatca tttgcccat    101400 ggtaatgaag gctcctaacc ttgtaaatgg caaatgatca acacaatgga acagccaggt   101460
ctcaacactc ttgagcatct tcaatcataa ataccactgg cccctagcgt gttgacagga   101520
aaccgctgac gtgcaataca aaaattctgc tttgcaagat gccttaggat taaacctctc   101580
acagtagaaa cagggcccat caatttccac aagtaataaa aggcggctct accagcccaa   101640
ctccaaagat ctcacagaag aaaaaaaagc cagaatacat tccgcacaat taagaagag    101700 aagcatctcg ctaaaaagtg acccccatat caatttcaag attaagtggc aaggatgatg   101760
gaagagaaaa agtacacatt taataaaagc aagcacatct cttcagaaat aagactcctt   101820
tctgtcaaac ggaaactaac ccttaaagaa aaaacaaaat cactacattt gtgatctttt   101880
accttcccca gccaccctgc gtagcatgtc gtggctatcg tggctcacct gggagagaat   101940
gccttccaga taggggctga tgaagtgcgg gagagtctcc acaaccttct gcagagcagc   102000
caaggcactg agcaggtaga cctcgctgga gaccagctcg ctggtgttct tcattgttgt   102060
cagcaacgat ggcatcaggc tagaaacaaa gtaagagctt tagaagaact tgaagcagaa   102120
acagaggcta gggaatggag tagagggcat tatgaaaaaa accagcaaac tgtgcctatt   102180
acatcgctat ctgcctcata gcctaaaaag cagtgtctat acattttatg tggctaagca   102240
caagaaatct cccagtgcta acagtatgga cacaacagta atttaaaaaa taacaatgtc   102300
tttcattaac tgaacactta ctatgtgtca ggcactatgc aaaactcctt gcaagcactg   102360
ccctacagaa atcctatgag gtagatactg tctctgtttt atagacagca aagctctaac   102420
aggttaagga acatactggc tgtacagtaa ggaactacca cagccaggag cttctaactt   102480
ccaaatttgg cagcagaagg cagctttggc cttgcctaac tgggtgggcc cctctgccaa   102540
gaaccttcac ccactgcttt ttgactatac tagacaaaag gaaggaagaa tggaggacga   102600
ttaacactgc aaagcagtgc atctgaagat aaacgggaag gctgcatctt tctgtttgaa   102660
gattaattat ttttattatt atttctttaa gagacagggt ctcactctgt tgcccaggct   102720
acagtgcagt ggtgcagtca tagctcactg cagcctcaaa ctcctgggct caaatgatct   102780
ccctgccttg gcctcccaaa gtgctgggat tacagccgtg agccaccaca ccctgcaaga   102840
tcaattcttt aacaaattcc aatttatgc aacgtctact cagaggaaaa aaaaaaaag    102900 tcaccaaagt gttattttc aatgtgtgcc aggcggtaac agctcctgtt ccaagtctcc    102960
ggccgcatac ctgggaagct gggggatggc cagcgcctcc agggtggagg tcacctctgc   103020
tatgcacagc agcgcgcttc ccaagacatt cttctcctcc tttctctctg gagcaatcag   103080
tttcacagca gtgctcagca ctgggacaaa aggatctgga ttttctgcac caaaattctt   103140
```

```
gcataaaagc tttaaggtat acaacgctgt ctgtctgttg attgcttgtt cttcttcccc  103200
ttcctttttc ttacgctgca caatggccaa aaggtctgga accagtttta ggaaacgggt  103260
aacctgaagg ggacagccag aatccccaaa tcattaaagc tgcaaaaaat gtttgtccat  103320
tttcccattg tcacagcttg agattgtcta aatggaaatc agactcgggg gtcctgagtc  103380
acacagtcat gctaagcgat gtgcatgttc tagccagtgt ttcacttata caaagcaccc  103440
actgatctgg agtaaaaggg acttagaact atgctaaggc taaggccacg taagctctgt  103500
agtaagcaag aattccacta ggctgaaatt ccattctaag agctcttaca acacacatat  103560
attcccgtta gaattaacgt cacattttaa aacatgtcat ggtattatat tcagataata  103620
atatacttca atttgaaatt gtaccactag agaaattgaa gggagttaaa tgcagctctt  103680
tgataaagca aagtacagta aatgggtgtg tcctgggtct tcactcacta ttgtcttctt  103740
ccaggatata ttttgctgca gcttgttatt caaaaggtcc agcgctttgc ggcgaacaga  103800
tggcagggga ttgcccacca gccctctgat cacaggaatg aatgtctctg tgggcagcaa  103860
ggcattgacc taaagagaaa ttttatattt aacatgaaaa gaaaaacaaa ttaaaaaaaa  103920
aatcaacttc aattaagaca gactgctgtc cactgcacac ctccaggcac caggcacttc  103980
cacacacatt ttcttattta attcttaaaa taacctttca ggtaggcatt accaaccaca  104040
cattatcgaa caaaacaaaa gcctgatgtc aggaggaagt gccaaaggca tgcagctaaa  104100
tgactgagct agatttgaat cagcaatcct aacttcgagg ccagtgatat gtatgtaata  104160
tacttcatac ttttatttta ttccacttga ataaagtaga acagtatata ttatatgact  104220
taattattaa aatatacgag gtacatgttc tcataactgg taaggaaaca attttttcca  104280
gacaaatcta tttctagtca tcaagagatt gtttttctaag aaaaatctga gcttcattat  104340
attcataaaa ggaattgcta agtttattct taaaaacttt acataatttc acaataattt  104400
aaaaaacagc aacaaacag taattccagg gagaaatgaa cacctacctt atctaacagg  104460
tcgtaagctt tactaaggag cgcgcgccag aacttcacgg tgagtttgtc tgcgttcctt  104520
tccatggact gtgcaactgc actgatatag ccgagaacgg tctccagcaa cctgaaacac  104580
agaggctcgc tcagcaaacg gcagctgaag aaactcagag aacttgttca tgtctacctt  104640
atgctaaatg tttcaagtag aaagacgagt taaataattc tgtactaaat tatttcaaaa  104700
actactcgga aagaaaggaa atgagggatt attgccatag acagagatca tcaagaagta  104760
actaggcgct tctgtgcaga agcatcgacc tcgctcagac tctgtgaggt gctgaataag  104820
caacagatgc tgaaagcgtt taaggaactc actcatatct agctcatgct cagtggatct  104880
cactgggctg tccaagtggg gtgttcaggg agttatggcc ctaggttaat ggcaggtgtg  104940
tgcgtgcaca cacacacagg cacacacacg cacacataca catgcacaca caccatacac  105000
catttatata aagagaaata ttaatagaaa tgaacatata acccacttct ttcacattat  105060
taggagacaa aaaaaaagac tacaaacttc aaataacttg taattagaaa agcacacacc  105120
aaattccaac acagctgcca ctggagatcc ccccactgct gccagcctga gggggagct  105180
agagggaaga gtggagacag aagttgacac cgcacagcag aggaggggag aaggggcgc  105240
agacaaaatc agctccaaaa acgaaagtcc tacgcatagc gctacaagtc agcccacagg  105300
actgaaactc agcagctcac attcctggct gcagggcagg cacttccag tggaagggc  105360
aggacagtgg ccctgggaat gccatgcatc tgaaaaggag gtacacagca aggccaggag  105420
gcaaccccg aggacatggg agagaaagga aaattcctgc acccaaatat ataatgcag  105480
catatggatt agaatccacg gaataaagaa ttcatgagcc catagaaatc agggccagat  105540
```

-continued

```
tgagacacta aacagatact gcaactcaat acaatacaca gacttgacat ggatcatgat    105600
gcagaaacac atgcggtgta aaggacagtg ttgggataat tagggagact ggagtatgaa    105660
ctgtagatta catcactgga ttggatcaat gttaaatttt ctgaatttga tcaatgtact    105720
gtggttttat aagaacatct cttattctta gagacataat gtatatgatt tactttcaaa    105780
tggctcagag aaaaaaccct acatagggag aacgctaagg caaatgtggc agaaagtatt    105840
atcaaatggt gaacctggtt gtaaagagta tatgaatttt ctgtactgtt tttccaggtt    105900
ttctataagt ttgaagtcat ttccaaataa aaagtaaaaa aagaaaagga aacatacctc    105960
tcttcaaggc cttttaaaat ctcaggacca ccactctcaa ctacctaatt tttaaagaag    106020
acgtcattag aacggtatgg aagtcaataa taaaagtcat ttcaagtcag ttcaatgaaa    106080
ctcggaccat tcactgaaac cttccacagc aactgttttc tgacattaca atttaatcag    106140
gttcatagca tcttcattat actgtagtaa ctctatttct cttaatttat tttaattata    106200
ttctactggt agtatctaaa aagtactaca atggttcaga aaaatacagc aatcaacact    106260
caattagcac taccgaattc tatgacatgc tgatctggtg agctcacata tcctttgttg    106320
agaagttaaa cattacagat tcagctggaa tcccccaagt actgctcctt ggtcctattc    106380
tccctctacc ccaagcccca caaacaaaac catcatccca aatctgcttc caaatgtttc    106440
aaacactaca tatcacggaa caacatgttt ttctggaaac atattttga gatctatgca    106500 tggtgactta tgttctagtt ccttcatttt aactgcatat gatattcctc tataaatacc    106560
acttatctat ccatttgcct ctgttgttag atgtttagtt tatgtccatt ttttcccctt    106620
ttactaataa tgctagagaa gaacattttt atgtcccttt gatcatcttg ggaagttttt    106680
acagcatata tacctaagga agggaatgac cagatcacag gaattactgg aactttcaac    106740
ctcatg                                                              106746
```

```
<210> SEQ ID NO 2
<211> LENGTH: 5408
<212> TYPE: DNA
<213> ORGANISM: Homo sapiens
<220> FEATURE:
<221> NAME/KEY: CDS
<222> LOCATION: 201..1151
<220> FEATURE:
<221> NAME/KEY: polyA_signal
<222> LOCATION: 1773..1778
<223> OTHER INFORMATION: AATAAA
<220> FEATURE:
<221> NAME/KEY: polyA_signal
<222> LOCATION: 3624..3629
<223> OTHER INFORMATION: AATAAA
<220> FEATURE:
<221> NAME/KEY: polyA_signal
<222> LOCATION: 3828..3833
<223> OTHER INFORMATION: AATAAA
<220> FEATURE:
<221> NAME/KEY: polyA_signal
<222> LOCATION: 5119..5124
<223> OTHER INFORMATION: AATAAA
<220> FEATURE:
<221> NAME/KEY: polyA_signal
<222> LOCATION: 5381..5386
<223> OTHER INFORMATION: AATAAA
<220> FEATURE:
<221> NAME/KEY: polyA_signal
<222> LOCATION: 5386..5391
<223> OTHER INFORMATION: AATAAA
<220> FEATURE:
<221> NAME/KEY: allele
<222> LOCATION: 176
<223> OTHER INFORMATION: 5-1-222 : polymorphic base A or G
```

```
<220> FEATURE:
<221> NAME/KEY: allele
<222> LOCATION: 253
<223> OTHER INFORMATION: 5-2-162 : polymorphic base A or T
<220> FEATURE:
<221> NAME/KEY: allele
<222> LOCATION: 269
<223> OTHER INFORMATION: 5-2-178 : polymorphic base C or T
<220> FEATURE:
<221> NAME/KEY: allele
<222> LOCATION: 303
<223> OTHER INFORMATION: 5-2-213 : polymorphic base C or T
<220> FEATURE:
<221> NAME/KEY: allele
<222> LOCATION: 362
<223> OTHER INFORMATION: 5-3-83 : polymorphic base C or T
<220> FEATURE:
<221> NAME/KEY: allele
<222> LOCATION: 363
<223> OTHER INFORMATION: 5-3-84 : polymorphic base A or G
<220> FEATURE:
<221> NAME/KEY: allele
<222> LOCATION: 527
<223> OTHER INFORMATION: 5-3-248 : polymorphic base A or G
<220> FEATURE:
<221> NAME/KEY: allele
<222> LOCATION: 749
<223> OTHER INFORMATION: 5-7-195 : polymorphic base G or C
<220> FEATURE:
<221> NAME/KEY: allele
<222> LOCATION: 1013
<223> OTHER INFORMATION: 5-10-39 : polymorphic base C or T
<220> FEATURE:
<221> NAME/KEY: allele
<222> LOCATION: 1276
<223> OTHER INFORMATION: 5-10-302 : polymorphic base A or G
<220> FEATURE:
<221> NAME/KEY: allele
<222> LOCATION: 1308
<223> OTHER INFORMATION: 5-10-334 : polymorphic base A or C
<220> FEATURE:
<221> NAME/KEY: allele
<222> LOCATION: 1500
<223> OTHER INFORMATION: 5-11-158 : polymorphic base A or G
<220> FEATURE:
<221> NAME/KEY: allele
<222> LOCATION: 1572
<223> OTHER INFORMATION: 5-11-230 : polymorphic base G or T
<220> FEATURE:
<221> NAME/KEY: allele
<222> LOCATION: 1576
<223> OTHER INFORMATION: 5-11-234 : polymorphic base C or T
<220> FEATURE:
<221> NAME/KEY: allele
<222> LOCATION: 1641
<223> OTHER INFORMATION: 5-11-299 : polymorphic base A or T
<220> FEATURE:
<221> NAME/KEY: allele
<222> LOCATION: 1646
<223> OTHER INFORMATION: 5-11-304 : polymorphic base A or C
<220> FEATURE:
<221> NAME/KEY: allele
<222> LOCATION: 1671
<223> OTHER INFORMATION: 5-11-329 : polymorphic base C or T
<220> FEATURE:
<221> NAME/KEY: allele
<222> LOCATION: 1768
<223> OTHER INFORMATION: 5-12-56 : polymorphic base insertion of CTTT
<220> FEATURE:
<221> NAME/KEY: allele
<222> LOCATION: 1979
<223> OTHER INFORMATION: 5-12-267 : polymorphic base A or C
<220> FEATURE:
<221> NAME/KEY: allele
<222> LOCATION: 2156
<223> OTHER INFORMATION: 5-13-145 : polymorphic base C or T
<220> FEATURE:
<221> NAME/KEY: allele
<222> LOCATION: 2423
```

-continued

```
<223> OTHER INFORMATION: 5-14-44 : polymorphic base C or T
<220> FEATURE:
<221> NAME/KEY: allele
<222> LOCATION: 2471
<223> OTHER INFORMATION: 5-14-93 : polymorphic base A or T
<220> FEATURE:
<221> NAME/KEY: allele
<222> LOCATION: 2522
<223> OTHER INFORMATION: 5-14-144 : polymorphic base insertion of T
<220> FEATURE:
<221> NAME/KEY: allele
<222> LOCATION: 2543
<223> OTHER INFORMATION: 5-14-165 : polymorphic base C or T
<220> FEATURE:
<221> NAME/KEY: allele
<222> LOCATION: 2675
<223> OTHER INFORMATION: 5-14-297 : polymorphic base A or C
<220> FEATURE:
<221> NAME/KEY: allele
<222> LOCATION: 2685
<223> OTHER INFORMATION: 5-14-307 : polymorphic base G or T
<220> FEATURE:
<221> NAME/KEY: allele
<222> LOCATION: 2973
<223> OTHER INFORMATION: 5-15-219 : polymorphic base A or T
<220> FEATURE:
<221> NAME/KEY: allele
<222> LOCATION: 3242
<223> OTHER INFORMATION: 5-16-157 : polymorphic base A or G
<220> FEATURE:
<221> NAME/KEY: allele
<222> LOCATION: 3514
<223> OTHER INFORMATION: 5-17-140 : polymorphic base A or G
<220> FEATURE:
<221> NAME/KEY: allele
<222> LOCATION: 3593
<223> OTHER INFORMATION: 5-18-51 : polymorphic base G or T
<220> FEATURE:
<221> NAME/KEY: allele
<222> LOCATION: 3750
<223> OTHER INFORMATION: 5-18-208 : polymorphic base A or C
<220> FEATURE:
<221> NAME/KEY: allele
<222> LOCATION: 4023
<223> OTHER INFORMATION: 5-300-238 : polymorphic base C or T
<220> FEATURE:
<221> NAME/KEY: allele
<222> LOCATION: 4072
<223> OTHER INFORMATION: 5-300-287 : polymorphic base A or G
<220> FEATURE:
<221> NAME/KEY: allele
<222> LOCATION: 4398
<223> OTHER INFORMATION: 5-262-49 : polymorphic base insertion of C
<220> FEATURE:
<221> NAME/KEY: allele
<222> LOCATION: 4434
<223> OTHER INFORMATION: 5-262-85 : polymorphic base C or T
<220> FEATURE:
<221> NAME/KEY: allele
<222> LOCATION: 4603
<223> OTHER INFORMATION: 5-262-254 : polymorphic base C or T
<220> FEATURE:
<221> NAME/KEY: allele
<222> LOCATION: 5204
<223> OTHER INFORMATION: 5-263-404 : polymorphic base C or T
<220> FEATURE:
<221> NAME/KEY: allele
<222> LOCATION: 5397
<223> OTHER INFORMATION: 5-265-244 : polymorphic base A or G
<220> FEATURE:
<221> NAME/KEY: misc_feature
<222> LOCATION: 708
<223> OTHER INFORMATION: diverging nucleotide G in reference genbank :
      L78132
<220> FEATURE:
<221> NAME/KEY: misc_feature
<222> LOCATION: 709
<223> OTHER INFORMATION: diverging nucleotide T in reference genbank :
      L78132
```

-continued

```
<220> FEATURE:
<221> NAME/KEY: misc_feature
<222> LOCATION: 807
<223> OTHER INFORMATION: diverging nucleotide C in reference genbank :
      L78132
<220> FEATURE:
<221> NAME/KEY: misc_feature
<222> LOCATION: 1230
<223> OTHER INFORMATION: insertion of G in reference genbank : L78132
<220> FEATURE:
<221> NAME/KEY: misc_feature
<222> LOCATION: 1493
<223> OTHER INFORMATION: diverging nucleotide T in reference genbank :
      L78132
<220> FEATURE:
<221> NAME/KEY: misc_feature
<222> LOCATION: 1724
<223> OTHER INFORMATION: diverging nucleotide G in reference genbank :
      L78132
<220> FEATURE:
<221> NAME/KEY: misc_feature
<222> LOCATION: 1845
<223> OTHER INFORMATION: diverging nucleotide C in reference genbank :
      L78132
<220> FEATURE:
<221> NAME/KEY: misc_feature
<222> LOCATION: 1933
<223> OTHER INFORMATION: diverging nucleotide C in reference genbank :
      L78132
<220> FEATURE:
<221> NAME/KEY: misc_feature
<222> LOCATION: 1934
<223> OTHER INFORMATION: diverging nucleotide C in reference genbank :
      L78132
<220> FEATURE:
<221> NAME/KEY: misc_feature
<222> LOCATION: 1935
<223> OTHER INFORMATION: diverging nucleotide C in reference genbank :
      L78132
<220> FEATURE:
<221> NAME/KEY: misc_feature
<222> LOCATION: 1936
<223> OTHER INFORMATION: diverging nucleotide G in reference genbank :
      L78132
<220> FEATURE:
<221> NAME/KEY: misc_feature
<222> LOCATION: 1965
<223> OTHER INFORMATION: deletion of A in reference genbank : L78132
<220> FEATURE:
<221> NAME/KEY: misc_feature
<222> LOCATION: 1981
<223> OTHER INFORMATION: diverging nucleotide C in reference genbank :
      L78132
<220> FEATURE:
<221> NAME/KEY: misc_feature
<222> LOCATION: 2000
<223> OTHER INFORMATION: diverging nucleotide T in reference genbank :
      L78132
<220> FEATURE:
<221> NAME/KEY: misc_feature
<222> LOCATION: 2014
<223> OTHER INFORMATION: diverging nucleotide C in reference genbank :
      L78132
<220> FEATURE:
<221> NAME/KEY: misc_feature
<222> LOCATION: 2404
<223> OTHER INFORMATION: deletion of TTA in reference genbank : L78132
<220> FEATURE:
<221> NAME/KEY: misc_feature
<222> LOCATION: 2407
<223> OTHER INFORMATION: diverging nucleotide C in reference genbank :
      L78132
<220> FEATURE:
<221> NAME/KEY: misc_feature
<222> LOCATION: 2494
<223> OTHER INFORMATION: insertion of G in reference genbank : L78132
<220> FEATURE:
<221> NAME/KEY: misc_feature
<222> LOCATION: 2683
```

-continued

```
<223> OTHER INFORMATION: diverging nucleotide C in reference genbank :
      L78132
<220> FEATURE:
<221> NAME/KEY: misc_feature
<222> LOCATION: 3024
<223> OTHER INFORMATION: insertion of A in reference genbank : L78132
<220> FEATURE:
<221> NAME/KEY: misc_feature
<222> LOCATION: 3058
<223> OTHER INFORMATION: insertion of T in reference genbank : L78132
<220> FEATURE:
<221> NAME/KEY: misc_feature
<222> LOCATION: 3374
<223> OTHER INFORMATION: deletion of AG in reference genbank : L78132
<220> FEATURE:
<221> NAME/KEY: misc_feature
<222> LOCATION: 3379
<223> OTHER INFORMATION: diverging nucleotide A in reference genbank :
      L78132
<220> FEATURE:
<221> NAME/KEY: misc_feature
<222> LOCATION: 3383
<223> OTHER INFORMATION: deletion of G in reference genbank : L78132
<220> FEATURE:
<221> NAME/KEY: misc_feature
<222> LOCATION: 3387
<223> OTHER INFORMATION: deletion of G in reference genbank : L78132
<220> FEATURE:
<221> NAME/KEY: misc_feature
<222> LOCATION: 3402
<223> OTHER INFORMATION: deletion of A in reference genbank : L78132
<220> FEATURE:
<221> NAME/KEY: misc_feature
<222> LOCATION: 3408
<223> OTHER INFORMATION: deletion of A in reference genbank : L78132
<220> FEATURE:
<221> NAME/KEY: misc_feature
<222> LOCATION: 3427
<223> OTHER INFORMATION: deletion of AA in reference genbank : L78132
<220> FEATURE:
<221> NAME/KEY: misc_feature
<222> LOCATION: 3621
<223> OTHER INFORMATION: deletion of A in reference genbank : L78132
<220> FEATURE:
<221> NAME/KEY: misc_feature
<222> LOCATION: 3664
<223> OTHER INFORMATION: deletion of C in reference genbank : L78132
<220> FEATURE:
<221> NAME/KEY: misc_feature
<222> LOCATION: 3672
<223> OTHER INFORMATION: deletion of C in reference genbank : L78132
<220> FEATURE:
<221> NAME/KEY: misc_feature
<222> LOCATION: 3684
<223> OTHER INFORMATION: insertion of TG in reference genbank : L78132
<220> FEATURE:
<221> NAME/KEY: misc_feature
<222> LOCATION: 3688
<223> OTHER INFORMATION: insertion of C in reference genbank : L78132
<220> FEATURE:
<221> NAME/KEY: misc_feature
<222> LOCATION: 3697
<223> OTHER INFORMATION: diverging nucleotide G in reference genbank :
      L78132
<220> FEATURE:
<221> NAME/KEY: misc_feature
<222> LOCATION: 3698
<223> OTHER INFORMATION: diverging nucleotide C in reference genbank :
      L78132
<220> FEATURE:
<221> NAME/KEY: misc_feature
<222> LOCATION: 3787
<223> OTHER INFORMATION: insertion of A in reference genbank : L78132
<220> FEATURE:
<221> NAME/KEY: misc_feature
<222> LOCATION: 3931
<223> OTHER INFORMATION: insertion of G in reference genbank : L78132

<400> SEQUENCE: 2
```

```
agccgcccac ggacgccaga gccgggaacc ctgacggcac ttagctgctg acaaacaacc      60
tgctccgtgg agcgcctgaa acaccagtct ttggggccag tgcctcagtt tcaatccagg     120
taacctttaa atgaaacttg cctaaaatct taggtcatac acagaagaga ctccaatcga     180
caagaagctg gaaagaatg atg ttg tcc tta aac aac cta cag aat atc atc     233
                     Met Leu Ser Leu Asn Asn Leu Gln Asn Ile Ile
                      1               5                      10 tat aac ccg gta atc ccg tat gtt ggc acc att ccc gat cag ctg gat     281
Tyr Asn Pro Val Ile Pro Tyr Val Gly Thr Ile Pro Asp Gln Leu Asp
                15                  20                  25 cct gga act ttg att gtg ata tgt ggg cat gtt cct agt gac gca gac     329
Pro Gly Thr Leu Ile Val Ile Cys Gly His Val Pro Ser Asp Ala Asp
            30                  35                  40 aga ttc cag gtg gat ctg cag aat ggc agc agt gtg aaa cct cga gcc     377
Arg Phe Gln Val Asp Leu Gln Asn Gly Ser Ser Val Lys Pro Arg Ala
        45                  50                  55 gat gtg gcc ttt cat ttc aat cct cgt ttc aaa agg gcc ggc tgc att     425
Asp Val Ala Phe His Phe Asn Pro Arg Phe Lys Arg Ala Gly Cys Ile
60                  65                  70                  75 gtt tgc aat act ttg ata aat gaa aaa tgg gga cgg gaa gag atc acc     473
Val Cys Asn Thr Leu Ile Asn Glu Lys Trp Gly Arg Glu Glu Ile Thr
                80                  85                  90 tat gac acg cct ttc aaa aga gaa aag tct ttt gag atc gtg att atg     521
Tyr Asp Thr Pro Phe Lys Arg Glu Lys Ser Phe Glu Ile Val Ile Met
            95                 100                 105 gtg cta aag gac aaa ttc cag gtg gct gta aat gga aaa cat act ctg     569
Val Leu Lys Asp Lys Phe Gln Val Ala Val Asn Gly Lys His Thr Leu
        110                 115                 120 ctc tat ggc cac agg atc ggc cca gag aaa ata gac act ctg ggc att     617
Leu Tyr Gly His Arg Ile Gly Pro Glu Lys Ile Asp Thr Leu Gly Ile
    125                 130                 135 tat ggc aaa gtg aat att cac tca att ggt ttt agc ttc agc tcg gac     665
Tyr Gly Lys Val Asn Ile His Ser Ile Gly Phe Ser Phe Ser Ser Asp
140                 145                 150                 155 tta caa agt acc caa gca tct agt ctg gaa ctg aca gag ata agt aga     713
Leu Gln Ser Thr Gln Ala Ser Ser Leu Glu Leu Thr Glu Ile Ser Arg
                160                 165                 170 gaa aat gtt cca aag tct ggc acg ccc cag ctt agc ctg cca ttc gct     761
Glu Asn Val Pro Lys Ser Gly Thr Pro Gln Leu Ser Leu Pro Phe Ala
            175                 180                 185 gca agg ttg aac acc ccc atg ggc cct gga cga act gtc gtc gtt aaa     809
Ala Arg Leu Asn Thr Pro Met Gly Pro Gly Arg Thr Val Val Val Lys
        190                 195                 200 gga gaa gtg aat gca aat gcc aaa agc ttt aat gtt gac cta cta gca     857
Gly Glu Val Asn Ala Asn Ala Lys Ser Phe Asn Val Asp Leu Leu Ala
    205                 210                 215 gga aaa tca aag gat att gct cta cac ttg aac cca cgc ctg aat att     905
Gly Lys Ser Lys Asp Ile Ala Leu His Leu Asn Pro Arg Leu Asn Ile
220                 225                 230                 235 aaa gca ttt gta aga aat tct ttt ctt cag gag tcc tgg gga gaa gaa     953
Lys Ala Phe Val Arg Asn Ser Phe Leu Gln Glu Ser Trp Gly Glu Glu
                240                 245                 250 gag aga aat att acc tct ttc cca ttt agt cct ggg atg tac ttt gag    1001
Glu Arg Asn Ile Thr Ser Phe Pro Phe Ser Pro Gly Met Tyr Phe Glu
            255                 260                 265 atg ata att tac tgt gat gtt aga gaa ttc aag gtt gca gta aat ggc    1049
Met Ile Ile Tyr Cys Asp Val Arg Glu Phe Lys Val Ala Val Asn Gly
        270                 275                 280
```

```
gta cac agc ctg gag tac aaa cac aga ttt aaa gag ctc agc agt att     1097
Val His Ser Leu Glu Tyr Lys His Arg Phe Lys Glu Leu Ser Ser Ile
    285                 290                 295 gac acg ctg gaa att aat gga gac atc cac tta ctg gaa gta agg agc     1145
Asp Thr Leu Glu Ile Asn Gly Asp Ile His Leu Leu Glu Val Arg Ser
300                 305                 310                 315 tgg tag cctacctaca cagctgctac aaaaaccaaa atacagaatg cttctgtga       1201
Trp * tactggcctt gctgaaacgc atctcactgt cattctattg tttatattgt taaaatgagc   1261
ttgtgcacca ttagatcctg ctgggtgttc tcagtccttg ccatgaagta tggtggtgtc   1321
tagcactgaa tggggaaact gggggcagca acacttatag ccagttaaag ccactctgcc   1381
ctctctccta ctttggctga ctcttcaaga atgccattca acaagtattt atggagtacc   1441
tactataata cagtagctaa catgtattga gcacagattt tttttggtaa aactgtgagg   1501
agctaggata tatacttggt gaaacaaacc agtatgttcc ctgttctctt gagcttcgac   1561
tcttctgtgc tctattgctg cgcactgctt tttctacagg cattacatca actcctaagg   1621
ggtcctctgg gattagttaa gcagctatta aatcacccga agacactaat ttacagaaga   1681
cacaactcct tccccagtga tcactgtcat aaccagtgct ctaccgtatc ccatcactga   1741
ggactgatgt tgactgacat cattttatcg taataaacat gtggctctat agctgcaag    1801 ctttaccaag taattggcat gacatctgag cacagaaatt aaggcaaaaa accaaagcaa   1861
aacaaataca tggtgctgaa attaacttga tgccaagccc aaggcagctg atttctgtgt   1921
atttgaactt agggcaaatc agagtctaca cagacgccta cagaaagttt caggaagagg   1981
caagatgcat tcaatttgaa agatatttat gggcaacaaa gtaaggtcag gattagactt   2041
caggcattca taaggcaggc actatcagaa agtgtacgcc aactaaggga cccacaaagc   2101
aggcagaggt aatgcagaaa tctgttttgt tcccatgaaa tcaccaatca aggcctccgt   2161
tcttctaaag attagtccat catcattagc aactgagatc aaagcactct tccactttac   2221
gtgattaaaa tcaaacctgt atcagcaagt taaatggttc catttctgtg atttttctat   2281
tatttgaggg gagttggcag aagttccatg tatatgggat ctttacaggt cagatcttgt   2341
tacaggaaat ttcaaaggtt tgggagtggg gagggaaaaa agctcagtca gtgaggatca   2401 tttttatcaca ttagactggg gcagaactct gccaggattt aggaatattt tcagaacaga   2461
ttttagatat tatttctatc catatattga aaagaatacc attgtcaatc ttattttttt   2521
aaaagtactc agtgtagaaa ttgctagccc ttaattcttt tccagctttt catattaatg   2581
tatgcagagt ctcaccaagc tcaaagacac tggttggggg tggagggtgc cacagggaaa   2641
gctgtagaag gcaagaagac tcgagaatcc cccagagtta ttttctcca taaagaccat    2701 cagagtgctt aactgagctg ttggagactg tgaggcattt aggaaaaaaa tagcccactc   2761
acatcattcc ttgtaagtct taagttcatt tcattttac gtggaggaaa aaatttaaa    2821 aagctattag tatttattaa tgaattttac tgagacattt cttagaaata tgcacttcta   2881
tactagcaag ctctgtctct aaaatgcaag ttggccttt gcttgccaca tttctgcatt    2941
aaacttctat attagcttca aaggctttta aactcaatgc gaacattcta cgggatgttc   3001
ttagatgcct ttaaaaaggg ggcagatcta attttatttg aaccctcact ttccaacttc   3061
accatgaccc agtactagag attagggcac ttcaaagcat tgaaaaaaat ctactgatac   3121
ttactttctt agacaagtag ttcttagtta accaccaatg gaactgggtt cattctgaat   3181
cctggaggag cttcctcgtg ccacccagtg tttctgggcc ctctgtgtga gcagccaggt   3241
```

-continued

```
atgagctgtt ttagaagcag cgtgttgcct tcatctctcc cgtttcccaa aagaacaaag    3301
gataaaggtg acagtcacac tcctgggtta aaaaaagcat tccagaacca cttctcttta    3361
tgggcacaac aaagaaacga aggctgaagt tcgcctaccc aaaatgaaaa gtaggcttta    3421
cagtcaaaag tacttctgtt gattgctaaa taacttcatt ttcttgaaat agagcaactt    3481
tgagtgaaat ctgcaacatg gataccatgt atataagata ctgctgtaca gaagagttaa    3541
ggcttacagt gcaaatgagg cgtcagcttt gggtgctaaa attaacaagt ctaatattat    3601
taccatcaat caggaagaga ataataaatg tttaaacaaa cacagcagtc tgtataaaaa    3661
taccgtgtat catttactct ttctgcagct ctatacgata ggcaggagag cttatgtgg     3721 cagcacaagc caggtgggga ttttgtaacg aagtgataaa acatttgtaa gtaatccaag    3781
taggtgtatt aaggcaccaa aagtaacatg cacccaaca cccaaaaata aaatatgaa      3841 atatgagtgt gaactctgag tagagtatga acaccacag aaagtcttag aaatagctct     3901
ggagtggctc tcccaggaca gtttccagtt gctgaatagt cttttggcac tgatgttcta    3961
cttcttcaca ttcatctaaa aaaaaaaaa aaaaaatca aaattaaaat ctgagtcagt      4021
ctgcctgcct cggttctcat tagtttaatt cttaatgcct tgcactttcc agcaatcatt    4081
caatcaaaag agtgaaatga agcacattaa caaagcagga ggcgccacgg accgcctccc    4141
tccacaccgc tccttccgcc ttcattcctt gcccacaggc ttgcactgga agctgaataa    4201
gaatccccaa aactcaaact tcctagggat gccaccccctt tagtagctca cacctccccc   4261
ctccaagagc taagaaacaa aggagaatgt acttttgtag cttagataag caatgaatca    4321
gtaaaggact gatctacttg ctccaccacc cctcccttaa taataacatt tactgttatt    4381
tcctgggcct aagacttatg ttccagaact gtcacagctc cccatgtcac acccactagc    4441
ttgtgatctt tgtcaaataa ctgaaatctt ttaagcctct agtttcttcc tttgtaaaac    4501
agagataaaa tgttgtggtt tttaagtgag ataatccaag taaagcacct aacatggagt    4561
agtgaatgaa catcggttgc tactaaaagt ggacatccta ccgcatcctt aatgccacta    4621
ggcatttcca tacaatctgg ggaccaaaac ttcaatcata taaatgtatg aggttaatta    4681
aaaacactac tgtaatctgc ttgtatgatc acaaccacc acaaagaaa agatcgtgaa      4741 gattacactg taaacggact ctcaaatgat caggaggtgg tcacttcgca acttgctccc    4801
tccacccaac tcaaaacagg agctcgagcc tgcctgtatt tgagactgga gctgcctgta    4861
tgaggactgg atcaactgct agtcacgtta tatccaaatc tgcattatca ttgggcacat    4921
tttcacagaa ttttactgaa ttattcctta attgtttaat ggttgggaat agtttgggaa    4981
ttaccttcca tcaactctgc taagaaagga atggattctg gtagcaagac aatataattc    5041
tcctttagtt tttcagccag tgctaacaca gtaatcaaag cagcaaatcg aacctgaaag    5101
ggataaaaga gcaaagaaat aaaaagtagt gttactgtat ttattatctt aagagctgta    5161
ctgacttgag acaagctcta acttttttaaa cattagttca cacgcgttta ttcacttcat   5221
tatgttcatt aagctttcat cttagaatac cagtttcacc atttgggagc tgtttgtaat    5281
atgtgcaacc ttataaatag tgtttttccaa actgtgtccc aggactgcaa atctttaatg   5341
tgaaatgtct ttttataatc tcttccttta aaaaaaacca ataaaataaa atgccacatg    5401
caaactc                                                              5408
```

<210> SEQ ID NO 3
<211> LENGTH: 5534
<212> TYPE: DNA
<213> ORGANISM: Homo sapiens

```
<220> FEATURE:
<221> NAME/KEY: misc_feature
<222> LOCATION: 201..203
<223> OTHER INFORMATION: ATG
<220> FEATURE:
<221> NAME/KEY: misc_feature
<222> LOCATION: 1275..1277
<223> OTHER INFORMATION: stop :TAG
<220> FEATURE:
<221> NAME/KEY: polyA_signal
<222> LOCATION: 1899..1904
<223> OTHER INFORMATION: AATAAA
<220> FEATURE:
<221> NAME/KEY: polyA_signal
<222> LOCATION: 3750..3755
<223> OTHER INFORMATION: AATAAA
<220> FEATURE:
<221> NAME/KEY: polyA_signal
<222> LOCATION: 3954..3959
<223> OTHER INFORMATION: AATAAA
<220> FEATURE:
<221> NAME/KEY: polyA_signal
<222> LOCATION: 5245..5250
<223> OTHER INFORMATION: AATAAA
<220> FEATURE:
<221> NAME/KEY: polyA_signal
<222> LOCATION: 5507..5512
<223> OTHER INFORMATION: AATAAA
<220> FEATURE:
<221> NAME/KEY: polyA_signal
<222> LOCATION: 5512..5517
<223> OTHER INFORMATION: AATAAA
<220> FEATURE:
<221> NAME/KEY: allele
<222> LOCATION: 176
<223> OTHER INFORMATION: 5-1-222 : polymorphic base A or G
<220> FEATURE:
<221> NAME/KEY: allele
<222> LOCATION: 253
<223> OTHER INFORMATION: 5-2-162 : polymorphic base A or T
<220> FEATURE:
<221> NAME/KEY: allele
<222> LOCATION: 269
<223> OTHER INFORMATION: 5-2-178 : polymorphic base C or T
<220> FEATURE:
<221> NAME/KEY: allele
<222> LOCATION: 303
<223> OTHER INFORMATION: 5-2-213 : polymorphic base C or T
<220> FEATURE:
<221> NAME/KEY: allele
<222> LOCATION: 362
<223> OTHER INFORMATION: 5-3-83 : polymorphic base C or T
<220> FEATURE:
<221> NAME/KEY: allele
<222> LOCATION: 363
<223> OTHER INFORMATION: 5-3-84 : polymorphic base A or G
<220> FEATURE:
<221> NAME/KEY: allele
<222> LOCATION: 527
<223> OTHER INFORMATION: 5-3-248 : polymorphic base A or G
<220> FEATURE:
<221> NAME/KEY: allele
<222> LOCATION: 810
<223> OTHER INFORMATION: 5-202-95 : polymorphic base G or T
<220> FEATURE:
<221> NAME/KEY: allele
<222> LOCATION: 832
<223> OTHER INFORMATION: 5-202-117 : polymorphic base A or T
<220> FEATURE:
<221> NAME/KEY: allele
<222> LOCATION: 875
<223> OTHER INFORMATION: 5-7-195 : polymorphic base G or C
<220> FEATURE:
<221> NAME/KEY: allele
<222> LOCATION: 1139
<223> OTHER INFORMATION: 5-10-39 : polymorphic base C or T
<220> FEATURE:
<221> NAME/KEY: allele
<222> LOCATION: 1402
```

```
<223> OTHER INFORMATION: 5-10-302 : polymorphic base A or G
<220> FEATURE:
<221> NAME/KEY: allele
<222> LOCATION: 1434
<223> OTHER INFORMATION: 5-10-334 : polymorphic base A or C
<220> FEATURE:
<221> NAME/KEY: allele
<222> LOCATION: 1626
<223> OTHER INFORMATION: 5-11-158 : polymorphic base A or G
<220> FEATURE:
<221> NAME/KEY: allele
<222> LOCATION: 1698
<223> OTHER INFORMATION: 5-11-230 : polymorphic base G or T
<220> FEATURE:
<221> NAME/KEY: allele
<222> LOCATION: 1702
<223> OTHER INFORMATION: 5-11-234 : polymorphic base C or T
<220> FEATURE:
<221> NAME/KEY: allele
<222> LOCATION: 1767
<223> OTHER INFORMATION: 5-11-299 : polymorphic base A or T
<220> FEATURE:
<221> NAME/KEY: allele
<222> LOCATION: 1772
<223> OTHER INFORMATION: 5-11-304 : polymorphic base A or C
<220> FEATURE:
<221> NAME/KEY: allele
<222> LOCATION: 1797
<223> OTHER INFORMATION: 5-11-329 : polymorphic base C or T
<220> FEATURE:
<221> NAME/KEY: allele
<222> LOCATION: 1894
<223> OTHER INFORMATION: 5-12-56 : polymorphic base insertion of CTTT
<220> FEATURE:
<221> NAME/KEY: allele
<222> LOCATION: 2105
<223> OTHER INFORMATION: 5-12-267 : polymorphic base A or C
<220> FEATURE:
<221> NAME/KEY: allele
<222> LOCATION: 2282
<223> OTHER INFORMATION: 5-13-145 : polymorphic base C or T
<220> FEATURE:
<221> NAME/KEY: allele
<222> LOCATION: 2549
<223> OTHER INFORMATION: 5-14-44 : polymorphic base C or T
<220> FEATURE:
<221> NAME/KEY: allele
<222> LOCATION: 2597
<223> OTHER INFORMATION: 5-14-93 : polymorphic base A or T
<220> FEATURE:
<221> NAME/KEY: allele
<222> LOCATION: 2648
<223> OTHER INFORMATION: 5-14-144 : polymorphic base insertion of T
<220> FEATURE:
<221> NAME/KEY: allele
<222> LOCATION: 2669
<223> OTHER INFORMATION: 5-14-165 : polymorphic base C or T
<220> FEATURE:
<221> NAME/KEY: allele
<222> LOCATION: 2801
<223> OTHER INFORMATION: 5-14-297 : polymorphic base A or C
<220> FEATURE:
<221> NAME/KEY: allele
<222> LOCATION: 2811
<223> OTHER INFORMATION: 5-14-307 : polymorphic base G or T
<220> FEATURE:
<221> NAME/KEY: allele
<222> LOCATION: 3099
<223> OTHER INFORMATION: 5-15-219 : polymorphic base A or T
<220> FEATURE:
<221> NAME/KEY: allele
<222> LOCATION: 3368
<223> OTHER INFORMATION: 5-16-157 : polymorphic base A or G
<220> FEATURE:
<221> NAME/KEY: allele
<222> LOCATION: 3640
<223> OTHER INFORMATION: 5-17-140 : polymorphic base A or G
<220> FEATURE:
<221> NAME/KEY: allele
```

-continued

```
<222> LOCATION: 3719
<223> OTHER INFORMATION: 5-18-51 : polymorphic base G or T
<220> FEATURE:
<221> NAME/KEY: allele
<222> LOCATION: 3876
<223> OTHER INFORMATION: 5-18-208 : polymorphic base A or C
<220> FEATURE:
<221> NAME/KEY: allele
<222> LOCATION: 4149
<223> OTHER INFORMATION: 5-300-238 : polymorphic base C or T
<220> FEATURE:
<221> NAME/KEY: allele
<222> LOCATION: 4198
<223> OTHER INFORMATION: 5-300-287 : polymorphic base A or G
<220> FEATURE:
<221> NAME/KEY: allele
<222> LOCATION: 4524
<223> OTHER INFORMATION: 5-262-49 : polymorphic base insertion of C
<220> FEATURE:
<221> NAME/KEY: allele
<222> LOCATION: 4560
<223> OTHER INFORMATION: 5-262-85 : polymorphic base C or T
<220> FEATURE:
<221> NAME/KEY: allele
<222> LOCATION: 4729
<223> OTHER INFORMATION: 5-262-254 : polymorphic base C or T
<220> FEATURE:
<221> NAME/KEY: allele
<222> LOCATION: 5330
<223> OTHER INFORMATION: 5-263-404 : polymorphic base C or T
<220> FEATURE:
<221> NAME/KEY: allele
<222> LOCATION: 5523
<223> OTHER INFORMATION: 5-265-244 : polymorphic base A or G
<220> FEATURE:
<221> NAME/KEY: misc_feature
<222> LOCATION: 708
<223> OTHER INFORMATION: diverging nucleotide G in reference genbank :
      L78132
<220> FEATURE:
<221> NAME/KEY: misc_feature
<222> LOCATION: 709
<223> OTHER INFORMATION: diverging nucleotide T in reference genbank :
      L78132
<220> FEATURE:
<221> NAME/KEY: misc_feature
<222> LOCATION: 807
<223> OTHER INFORMATION: diverging nucleotide C in reference genbank :
      L78132
<220> FEATURE:
<221> NAME/KEY: misc_feature
<222> LOCATION: 1356
<223> OTHER INFORMATION: isertion G in reference genbank : L78132
<220> FEATURE:
<221> NAME/KEY: misc_feature
<222> LOCATION: 1619
<223> OTHER INFORMATION: diverging nucleotide T in reference genbank :
      L78132
<220> FEATURE:
<221> NAME/KEY: misc_feature
<222> LOCATION: 1850
<223> OTHER INFORMATION: diverging nucleotide G in reference genbank :
      L78132
<220> FEATURE:
<221> NAME/KEY: misc_feature
<222> LOCATION: 1971
<223> OTHER INFORMATION: diverging nucleotide C in reference genbank :
      L78132
<220> FEATURE:
<221> NAME/KEY: misc_feature
<222> LOCATION: 2059
<223> OTHER INFORMATION: diverging nucleotide C in reference genbank :
      L78132
<220> FEATURE:
<221> NAME/KEY: misc_feature
<222> LOCATION: 2060
<223> OTHER INFORMATION: diverging nucleotide C in reference genbank :
      L78132
<220> FEATURE:
```

-continued

```
<221> NAME/KEY: misc_feature
<222> LOCATION: 2061
<223> OTHER INFORMATION: diverging nucleotide C in reference genbank :
      L78132
<220> FEATURE:
<221> NAME/KEY: misc_feature
<222> LOCATION: 2062
<223> OTHER INFORMATION: diverging nucleotide G in reference genbank :
      L78132
<220> FEATURE:
<221> NAME/KEY: misc_feature
<222> LOCATION: 2091
<223> OTHER INFORMATION: deletion A in reference genbank : L78132
<220> FEATURE:
<221> NAME/KEY: misc_feature
<222> LOCATION: 2107
<223> OTHER INFORMATION: diverging nucleotide C in reference genbank :
      L78132
<220> FEATURE:
<221> NAME/KEY: misc_feature
<222> LOCATION: 2126
<223> OTHER INFORMATION: diverging nucleotide T in reference genbank :
      L78132
<220> FEATURE:
<221> NAME/KEY: misc_feature
<222> LOCATION: 2140
<223> OTHER INFORMATION: diverging nucleotide C in reference genbank :
      L78132
<220> FEATURE:
<221> NAME/KEY: misc_feature
<222> LOCATION: 2530
<223> OTHER INFORMATION: deletion TTA in reference genbank : L78132
<220> FEATURE:
<221> NAME/KEY: misc_feature
<222> LOCATION: 2533
<223> OTHER INFORMATION: diverging nucleotide C in reference genbank :
      L78132
<220> FEATURE:
<221> NAME/KEY: misc_feature
<222> LOCATION: 2620
<223> OTHER INFORMATION: isertion G in reference genbank : L78132
<220> FEATURE:
<221> NAME/KEY: misc_feature
<222> LOCATION: 2809
<223> OTHER INFORMATION: diverging nucleotide C in reference genbank :
      L78132
<220> FEATURE:
<221> NAME/KEY: misc_feature
<222> LOCATION: 3150
<223> OTHER INFORMATION: isertion A in reference genbank : L78132
<220> FEATURE:
<221> NAME/KEY: misc_feature
<222> LOCATION: 3184
<223> OTHER INFORMATION: isertion T in reference genbank : L78132
<220> FEATURE:
<221> NAME/KEY: misc_feature
<222> LOCATION: 3500
<223> OTHER INFORMATION: deletion AG in reference genbank : L78132
<220> FEATURE:
<221> NAME/KEY: misc_feature
<222> LOCATION: 3505
<223> OTHER INFORMATION: diverging nucleotide A in reference genbank :
      L78132
<220> FEATURE:
<221> NAME/KEY: misc_feature
<222> LOCATION: 3509
<223> OTHER INFORMATION: deletion G in reference genbank : L78132
<220> FEATURE:
<221> NAME/KEY: misc_feature
<222> LOCATION: 3513
<223> OTHER INFORMATION: deletion G in reference genbank : L78132
<220> FEATURE:
<221> NAME/KEY: misc_feature
<222> LOCATION: 3528
<223> OTHER INFORMATION: deletion A in reference genbank : L78132
<220> FEATURE:
<221> NAME/KEY: misc_feature
<222> LOCATION: 3534
<223> OTHER INFORMATION: deletion A in reference genbank : L78132
```

```
<220> FEATURE:
<221> NAME/KEY: misc_feature
<222> LOCATION: 3553
<223> OTHER INFORMATION: deletion AA in reference genbank : L78132
<220> FEATURE:
<221> NAME/KEY: misc_feature
<222> LOCATION: 3747
<223> OTHER INFORMATION: deletion A in reference genbank : L78132
<220> FEATURE:
<221> NAME/KEY: misc_feature
<222> LOCATION: 3790
<223> OTHER INFORMATION: deletion C in reference genbank : L78132
<220> FEATURE:
<221> NAME/KEY: misc_feature
<222> LOCATION: 3798
<223> OTHER INFORMATION: deletion C in reference genbank : L78132
<220> FEATURE:
<221> NAME/KEY: misc_feature
<222> LOCATION: 3810
<223> OTHER INFORMATION: isertion TG in reference genbank : L78132
<220> FEATURE:
<221> NAME/KEY: misc_feature
<222> LOCATION: 3814
<223> OTHER INFORMATION: isertion C in reference genbank : L78132
<220> FEATURE:
<221> NAME/KEY: misc_feature
<222> LOCATION: 3823
<223> OTHER INFORMATION: diverging nucleotide G in reference genbank :
      L78132
<220> FEATURE:
<221> NAME/KEY: misc_feature
<222> LOCATION: 3824
<223> OTHER INFORMATION: diverging nucleotide C in reference genbank :
      L78132
<220> FEATURE:
<221> NAME/KEY: misc_feature
<222> LOCATION: 3913
<223> OTHER INFORMATION: isertion A in reference genbank : L78132
<220> FEATURE:
<221> NAME/KEY: misc_feature
<222> LOCATION: 4057
<223> OTHER INFORMATION: isertion G in reference genbank : L78132

<400> SEQUENCE: 3
agccgcccac ggacgccaga gccgggaacc ctgacggcac ttagctgctg acaaacaacc      60
tgctccgtgg agcgcctgaa acaccagtct ttggggccag tgcctcagtt tcaatccagg     120
taacctttaa atgaaacttg cctaaaatct taggtcatac acagaagaga ctccaatcga     180
caagaagctg gaaagaatg atg ttg tcc tta aac aac cta cag aat atc atc     233
                    Met Leu Ser Leu Asn Asn Leu Gln Asn Ile Ile
                     1               5                  10 tat aac ccg gta atc ccg tat gtt ggc acc att ccc gat cag ctg gat      281
Tyr Asn Pro Val Ile Pro Tyr Val Gly Thr Ile Pro Asp Gln Leu Asp
         15                  20                  25 cct gga act ttg att gtg ata tgt ggg cat gtt cct agt gac gca gac      329
Pro Gly Thr Leu Ile Val Ile Cys Gly His Val Pro Ser Asp Ala Asp
     30                  35                  40 aga ttc cag gtg gat ctg cag aat ggc agc agt gtg aaa cct cga gcc      377
Arg Phe Gln Val Asp Leu Gln Asn Gly Ser Ser Val Lys Pro Arg Ala
 45                  50                  55 gat gtg gcc ttt cat ttc aat cct cgt ttc aaa agg gcc ggc tgc att      425
Asp Val Ala Phe His Phe Asn Pro Arg Phe Lys Arg Ala Gly Cys Ile
 60                  65                  70                  75 gtt tgc aat act ttg ata aat gaa aaa tgg gga cgg gaa gag atc acc      473
Val Cys Asn Thr Leu Ile Asn Glu Lys Trp Gly Arg Glu Glu Ile Thr
                 80                  85                  90 tat gac acg cct ttc aaa aga gaa aag tct ttt gag atc gtg att atg      521
Tyr Asp Thr Pro Phe Lys Arg Glu Lys Ser Phe Glu Ile Val Ile Met
             95                 100                 105
```

-continued

| | | |
|---|---|---|
| gtg cta aag gac aaa ttc cag gtg gct gta aat gga aaa cat act ctg<br>Val Leu Lys Asp Lys Phe Gln Val Ala Val Asn Gly Lys His Thr Leu<br>    110                  115                  120 | 569 |
| ctc tat ggc cac agg atc ggc cca gag aaa ata gac act ctg ggc att<br>Leu Tyr Gly His Arg Ile Gly Pro Glu Lys Ile Asp Thr Leu Gly Ile<br>125                  130                  135 | 617 |
| tat ggc aaa gtg aat att cac tca att ggt ttt agc ttc agc tcg gac<br>Tyr Gly Lys Val Asn Ile His Ser Ile Gly Phe Ser Phe Ser Ser Asp<br>140                  145                  150                  155 | 665 |
| tta caa agt acc caa gca tct agt ctg gaa ctg aca gag ata agt aga<br>Leu Gln Ser Thr Gln Ala Ser Ser Leu Glu Leu Thr Glu Ile Ser Arg<br>                160                  165                  170 | 713 |
| gaa aat gtt cca aag tct ggc acg ccc cag ctt cct agt aat aga gga<br>Glu Asn Val Pro Lys Ser Gly Thr Pro Gln Leu Pro Ser Asn Arg Gly<br>                    175                  180                  185 | 761 |
| gga gac att tct aaa atc gca ccc aga act gtc tac acc aag agc aaa<br>Gly Asp Ile Ser Lys Ile Ala Pro Arg Thr Val Tyr Thr Lys Ser Lys<br>                190                  195                  200 | 809 |
| gat tcg act gtc aat cac act ttg act tgc acc aaa ata cca cct atg<br>Asp Ser Thr Val Asn His Thr Leu Thr Cys Thr Lys Ile Pro Pro Met<br>205                  210                  215 | 857 |
| aac tat gtg tca aag agc ctg cca ttc gct gca agg ttg aac acc ccc<br>Asn Tyr Val Ser Lys Ser Leu Pro Phe Ala Ala Arg Leu Asn Thr Pro<br>220                  225                  230                  235 | 905 |
| atg ggc cct gga cga act gtc gtc gtt aaa gga gaa gtg aat gca aat<br>Met Gly Pro Gly Arg Thr Val Val Val Lys Gly Glu Val Asn Ala Asn<br>                240                  245                  250 | 953 |
| gcc aaa agc ttt aat gtt gac cta cta gca gga aaa tca aag gat att<br>Ala Lys Ser Phe Asn Val Asp Leu Leu Ala Gly Lys Ser Lys Asp Ile<br>                    255                  260                  265 | 1001 |
| gct cta cac ttg aac cca cgc ctg aat att aaa gca ttt gta aga aat<br>Ala Leu His Leu Asn Pro Arg Leu Asn Ile Lys Ala Phe Val Arg Asn<br>                270                  275                  280 | 1049 |
| tct ttt ctt cag gag tcc tgg gga gaa gaa gag aga aat att acc tct<br>Ser Phe Leu Gln Glu Ser Trp Gly Glu Glu Glu Arg Asn Ile Thr Ser<br>285                  290                  295 | 1097 |
| ttc cca ttt agt cct ggg atg tac ttt gag atg ata att tac tgt gat<br>Phe Pro Phe Ser Pro Gly Met Tyr Phe Glu Met Ile Ile Tyr Cys Asp<br>300                  305                  310                  315 | 1145 |
| gtt aga gaa ttc aag gtt gca gta aat ggc gta cac agc ctg gag tac<br>Val Arg Glu Phe Lys Val Ala Val Asn Gly Val His Ser Leu Glu Tyr<br>                320                  325                  330 | 1193 |
| aaa cac aga ttt aaa gag ctc agc agt att gac acg ctg gaa att aat<br>Lys His Arg Phe Lys Glu Leu Ser Ser Ile Asp Thr Leu Glu Ile Asn<br>                335                  340                  345 | 1241 |
| gga gac atc cac tta ctg gaa gta agg agc tgg tag cctacctaca<br>Gly Asp Ile His Leu Leu Glu Val Arg Ser Trp *<br>                350                  355 | 1287 |
| cagctgctac aaaaaccaaa atacagaatg gcttctgtga tactggcctt gctgaaacgc | 1347 |
| atctcactgt cattctattg tttatattgt taaaatgagc ttgtgcacca ttagatcctg | 1407 |
| ctgggtgttc tcagtccttg ccatgaagta tggtggtgtc tagcactgaa tggggaaact | 1467 |
| gggggcagca acacttatag ccagttaaag ccactctgcc ctctctccta ctttggctga | 1527 |
| ctcttcaaga atgccattca acaagtattt atggagtacc tactataata cagtagctaa | 1587 |
| catgtattga gcacagattt ttttggtaa aactgtgagg agctaggata tatacttggt | 1647 |
| gaaacaaacc agtatgttcc ctgttctctt gagcttcgac tcttctgtgc tctattgctg | 1707 |
| cgcactgctt tttctacagg cattacatca actcctaagg ggtcctctgg gattagttaa | 1767 |

```
gcagctatta aatcacccga agacactaat ttacagaaga cacaactcct tccccagtga   1827
tcactgtcat aaccagtgct ctaccgtatc ccatcactga ggactgatgt tgactgacat   1887
cattttatcg taataaacat gtggctctat tagctgcaag ctttaccaag taattggcat   1947
gacatctgag cacagaaatt aaggcaaaaa accaaagcaa acaaataca tggtgctgaa    2007 attaacttga tgccaagccc aaggcagctg atttctgtgt atttgaactt agggcaaatc   2067
agagtctaca cagacgccta cagaaagttt caggaagagg caagatgcat tcaatttgaa   2127
agatatttat gggcaacaaa gtaaggtcag gattagactt caggcattca taaggcaggc   2187
actatcagaa agtgtacgcc aactaaggga cccacaaagc aggcagaggt aatgcagaaa   2247
tctgttttgt tcccatgaaa tcaccaatca aggcctccgt tcttctaaag attagtccat   2307
catcattagc aactgagatc aaagcactct tccactttac gtgattaaaa tcaaacctgt   2367
atcagcaagt taaatggttc catttctgtg attttttctat tatttgaggg gagttggcag   2427
aagttccatg tatatgggat ctttacaggt cagatcttgt tacaggaaat ttcaaaggtt   2487
tgggagtggg gagggaaaaa agctcagtca gtgaggatca ttttatcaca ttagactggg   2547
gcagaactct gccaggattt aggaatattt tcagaacaga ttttagatat tatttctatc   2607
catatattga aaagaatacc attgtcaatc ttatttttttt aaaagtactc agtgtagaaa   2667
ttgctagccc ttaattcttt tccagctttt catattaatg tatgcagagt ctcaccaagc   2727
tcaaagacac tggttggggg tggagggtgc cacaggaaa gctgtagaag caagaagac    2787 tcgagaatcc cccagagtta tttttctcca taaagaccat cagagtgctt aactgagctg   2847
ttggagactg tgaggcattt aggaaaaaaa tagcccactc acatcattcc ttgtaagtct   2907
taagttcatt ttcattttac gtggaggaaa aaaatttaaa aagctattag tatttattaa   2967
tgaattttac tgagacattt cttagaaata tgcacttcta tactagcaag ctctgtctct   3027
aaaatgcaag ttggcctttt gcttgccaca tttctgcatt aaacttctat attagcttca   3087
aaggctttta aactcaatgc gaacattcta cgggatgttc ttagatgcct ttaaaaaggg   3147
ggcagatcta attttatttg aaccctcact ttccaacttc accatgaccc agtactagag   3207
attagggcac ttcaaagcat tgaaaaaaat ctactgatac ttactttctt agacaagtag   3267
ttcttagtta accaccaatg gaactgggtt cattctgaat cctggaggag cttcctcgtg   3327
ccacccagtg tttctgggcc ctctgtgtga gcagccaggt atgagctgtt ttagaagcag   3387
cgtgttgcct tcatctctcc cgtttcccaa aagaacaaag gataaaggtg acagtcacac   3447
tcctgggtta aaaaaagcat tccagaacca cttctcttta tgggcacaac aaagaaacga   3507
aggctgaagt tcgcctaccc aaaatgaaaa gtaggcttta cagtcaaaag tacttctgtt   3567
gattgctaaa taacttcatt ttcttgaaat agagcaactt tgagtgaaat ctgcaacatg   3627
gataccatgt atataagata ctgctgtaca gaagagttaa ggcttacagt gcaaatgagg   3687
cgtcagcttt gggtgctaaa attaacaagt ctaatattat taccatcaat caggaagaga   3747
ataataaatg tttaaacaaa cacagcagtc tgtataaaaa taccgtgtat catttactct   3807
ttctgcagct ctatacgata ggcaggagag gcttatgtgg cagcacaagc caggtgggga   3867
ttttgtaacg aagtgataaa acatttgtaa gtaatccaag taggtgtatt aaggcaccaa   3927
aagtaacatg gcacccaaca cccaaaaata aaaatatgaa atatgagtgt gaactctgag   3987
tagagtatga acaccacag aaagtcttag aaatagctct ggagtggctc tcccaggaca   4047
gtttccagtt gctgaatagt ctttttggcac tgatgttcta cttcttcaca ttcatctaaa   4107
```

```
aaaaaaaaaa aaaaaaatca aaattaaaat ctgagtcagt ctgcctgcct cggttctcat    4167
tagtttaatt cttaatgcct tgcactttcc agcaatcatt caatcaaaag agtgaaatga    4227
agcacattaa caaagcagga ggcgccacgg accgcctccc tccacaccgc tccttccgcc    4287
ttcattcctt gcccacaggc ttgcactgga agctgaataa gaatcccaa aactcaaact    4347 tcctagggat gccacccctt tagtagctca cacctccccc ctccaagagc taagaaacaa    4407
aggagaatgt acttttgtag cttagataag caatgaatca gtaaaggact gatctacttg    4467
ctccaccacc cctcccttaa taataacatt tactgttatt tcctgggcct aagacttatg    4527
ttccagaact gtcacagctc cccatgtcac acccactagc ttgtgatctt tgtcaaataa    4587
ctgaaatctt ttaagcctct agtttcttcc tttgtaaaac agagataaaa tgttgtggtt    4647
tttaagtgag ataatccaag taaagcacct aacatggagt agtgaatgaa catcggttgc    4707
tactaaaagt ggacatccta ccgcatcctt aatgccacta ggcatttcca tacaatctgg    4767
ggaccaaaac ttcaatcata taatgtatg aggttaatta aaaacactac tgtaatctgc    4827
ttgtatgatc acaaccacc acaaagaaa agatcgtgaa gattacactg taaacggact    4887
ctcaaatgat caggaggtgg tcacttcgca acttgctccc tccacccaac tcaaaacagg    4947
agctcgagcc tgcctgtatt tgagactgga gctgcctgta tgaggactgg atcaactgct    5007
agtcacgtta tatccaaatc tgcattatca ttgggcacat tttcacagaa ttttactgaa    5067
ttattcctta attgtttaat ggttgggaat agtttgggaa ttaccttcca tcaactctgc    5127
taagaaagga atggattctg gtagcaagac aatataattc tcctttagtt tttcagccag    5187
tgctaacaca gtaatcaaag cagcaaatcg aacctgaaag ggataaaaga gcaaagaaat    5247
aaaaagtagt gttactgtat ttattatctt aagagctgta ctgacttgag acaagctcta    5307 acttttaaa cattagttca cacgcgttta ttcacttcat tatgttcatt aagctttcat    5367
cttagaatac cagtttcacc atttgggagc tgtttgtaat atgtgcaacc ttataaatag    5427
tgttttccaa actgtgtccc aggactgcaa atctttaatg tgaaatgtct ttttataatc    5487
tcttccttta aaaaaaacca ataaaataaa atgccacatg caaactc                 5534
```

<210> SEQ ID NO 4
<211> LENGTH: 2471
<212> TYPE: DNA
<213> ORGANISM: Homo sapiens
<220> FEATURE:
<221> NAME/KEY: misc_feature
<222> LOCATION: 201..203
<223> OTHER INFORMATION: ATG
<220> FEATURE:
<221> NAME/KEY: misc_feature
<222> LOCATION: 1305..1307
<223> OTHER INFORMATION: stop :TAG
<220> FEATURE:
<221> NAME/KEY: polyA_signal
<222> LOCATION: 2182..2187
<223> OTHER INFORMATION: AATAAA
<220> FEATURE:
<221> NAME/KEY: polyA_signal
<222> LOCATION: 2444..2449
<223> OTHER INFORMATION: AATAAA
<220> FEATURE:
<221> NAME/KEY: polyA_signal
<222> LOCATION: 2449..2454
<223> OTHER INFORMATION: AATAAA
<220> FEATURE:
<221> NAME/KEY: allele
<222> LOCATION: 176
<223> OTHER INFORMATION: 5-1-222 : polymorphic base A or G
<220> FEATURE:
<221> NAME/KEY: allele

```
<222> LOCATION: 253
<223> OTHER INFORMATION: 5-2-162 : polymorphic base A or T
<220> FEATURE:
<221> NAME/KEY: allele
<222> LOCATION: 269
<223> OTHER INFORMATION: 5-2-178 : polymorphic base C or T
<220> FEATURE:
<221> NAME/KEY: allele
<222> LOCATION: 303
<223> OTHER INFORMATION: 5-2-213 : polymorphic base C or T
<220> FEATURE:
<221> NAME/KEY: allele
<222> LOCATION: 362
<223> OTHER INFORMATION: 5-3-83 : polymorphic base C or T
<220> FEATURE:
<221> NAME/KEY: allele
<222> LOCATION: 363
<223> OTHER INFORMATION: 5-3-84 : polymorphic base A or G
<220> FEATURE:
<221> NAME/KEY: allele
<222> LOCATION: 527
<223> OTHER INFORMATION: 5-3-248 : polymorphic base A or G
<220> FEATURE:
<221> NAME/KEY: allele
<222> LOCATION: 749
<223> OTHER INFORMATION: 5-7-195 : polymorphic base G or C
<220> FEATURE:
<221> NAME/KEY: allele
<222> LOCATION: 1013
<223> OTHER INFORMATION: 5-10-39 : polymorphic base C or T
<220> FEATURE:
<221> NAME/KEY: allele
<222> LOCATION: 1461
<223> OTHER INFORMATION: 5-262-49 : polymorphic base insertion of C
<220> FEATURE:
<221> NAME/KEY: allele
<222> LOCATION: 1497
<223> OTHER INFORMATION: 5-262-85 : polymorphic base C or T
<220> FEATURE:
<221> NAME/KEY: allele
<222> LOCATION: 1666
<223> OTHER INFORMATION: 5-262-254 : polymorphic base C or T
<220> FEATURE:
<221> NAME/KEY: allele
<222> LOCATION: 2267
<223> OTHER INFORMATION: 5-263-404 : polymorphic base C or T
<220> FEATURE:
<221> NAME/KEY: allele
<222> LOCATION: 2460
<223> OTHER INFORMATION: 5-265-244 : polymorphic base A or G
<220> FEATURE:
<221> NAME/KEY: misc_feature
<222> LOCATION: 708
<223> OTHER INFORMATION: diverging nucleotide G in reference genbank :
      L78132
<220> FEATURE:
<221> NAME/KEY: misc_feature
<222> LOCATION: 709
<223> OTHER INFORMATION: diverging nucleotide T in reference genbank :
      L78132
<220> FEATURE:
<221> NAME/KEY: misc_feature
<222> LOCATION: 807
<223> OTHER INFORMATION: diverging nucleotide C in reference genbank :
      L78132
<220> FEATURE:
<221> NAME/KEY: misc_feature
<222> LOCATION: 1013
<223> OTHER INFORMATION: diverging nucleotide T in reference genbank :
      L78132

<400> SEQUENCE: 4
agccgcccac ggacgccaga gccgggaacc ctgacggcac ttagctgctg acaaacaacc     60
tgctccgtgg agcgcctgaa acaccagtct ttggggccag tgcctcagtt tcaatccagg    120
taacctttaa atgaaacttg cctaaaatct taggtcatac acagaagaga ctccaatcga    180
```

```
caagaagctg aaaagaatg atg ttg tcc tta aac aac cta cag aat atc atc      233
                    Met Leu Ser Leu Asn Asn Leu Gln Asn Ile Ile
                     1               5                  10 tat aac ccg gta atc ccg tat gtt ggc acc att ccc gat cag ctg gat      281
Tyr Asn Pro Val Ile Pro Tyr Val Gly Thr Ile Pro Asp Gln Leu Asp
            15                  20                  25 cct gga act ttg att gtg ata tgt ggg cat gtt cct agt gac gca gac      329
Pro Gly Thr Leu Ile Val Ile Cys Gly His Val Pro Ser Asp Ala Asp
        30                  35                  40 aga ttc cag gtg gat ctg cag aat ggc agc agt gtg aaa cct cga gcc      377
Arg Phe Gln Val Asp Leu Gln Asn Gly Ser Ser Val Lys Pro Arg Ala
 45                  50                  55 gat gtg gcc ttt cat ttc aat cct cgt ttc aaa agg gcc ggc tgc att      425
Asp Val Ala Phe His Phe Asn Pro Arg Phe Lys Arg Ala Gly Cys Ile
 60                  65                  70                  75 gtt tgc aat act ttg ata aat gaa aaa tgg gga cgg gaa gag atc acc      473
Val Cys Asn Thr Leu Ile Asn Glu Lys Trp Gly Arg Glu Glu Ile Thr
                80                  85                  90 tat gac acg cct ttc aaa aga gaa aag tct ttt gag atc gtg att atg      521
Tyr Asp Thr Pro Phe Lys Arg Glu Lys Ser Phe Glu Ile Val Ile Met
            95                 100                 105 gtg cta aag gac aaa ttc cag gtg gct gta aat gga aaa cat act ctg      569
Val Leu Lys Asp Lys Phe Gln Val Ala Val Asn Gly Lys His Thr Leu
        110                 115                 120 ctc tat ggc cac agg atc ggc cca gag aaa ata gac act ctg ggc att      617
Leu Tyr Gly His Arg Ile Gly Pro Glu Lys Ile Asp Thr Leu Gly Ile
    125                 130                 135 tat ggc aaa gtg aat att cac tca att ggt ttt agc ttc agc tcg gac      665
Tyr Gly Lys Val Asn Ile His Ser Ile Gly Phe Ser Phe Ser Ser Asp
140                 145                 150                 155 tta caa agt acc caa gca tct agt ctg gaa ctg aca gag ata agt aga      713
Leu Gln Ser Thr Gln Ala Ser Ser Leu Glu Leu Thr Glu Ile Ser Arg
                160                 165                 170 gaa aat gtt cca aag tct ggc acg ccc cag ctt agc ctg cca ttc gct      761
Glu Asn Val Pro Lys Ser Gly Thr Pro Gln Leu Ser Leu Pro Phe Ala
            175                 180                 185 gca agg ttg aac acc ccc atg ggc cct gga cga act gtc gtc gtt aaa      809
Ala Arg Leu Asn Thr Pro Met Gly Pro Gly Arg Thr Val Val Val Lys
        190                 195                 200 gga gaa gtg aat gca aat gcc aaa agc ttt aat gtt gac cta cta gca      857
Gly Glu Val Asn Ala Asn Ala Lys Ser Phe Asn Val Asp Leu Leu Ala
    205                 210                 215 gga aaa tca aag gat att gct cta cac ttg aac cca cgc ctg aat att      905
Gly Lys Ser Lys Asp Ile Ala Leu His Leu Asn Pro Arg Leu Asn Ile
220                 225                 230                 235 aaa gca ttt gta aga aat tct ttt ctt cag gag tcc tgg gga gaa gaa      953
Lys Ala Phe Val Arg Asn Ser Phe Leu Gln Glu Ser Trp Gly Glu Glu
                240                 245                 250 gag aga aat att acc tct ttc cca ttt agt cct ggg atg tac ttt gag     1001
Glu Arg Asn Ile Thr Ser Phe Pro Phe Ser Pro Gly Met Tyr Phe Glu
            255                 260                 265 atg ata att tac tgt gat gtt aga gaa ttc aag gtt gca gta aat ggc     1049
Met Ile Ile Tyr Cys Asp Val Arg Glu Phe Lys Val Ala Val Asn Gly
        270                 275                 280 gta cac agc ctg gag tac aaa cac aga ttt aaa gag ctc agc agt att     1097
Val His Ser Leu Glu Tyr Lys His Arg Phe Lys Glu Leu Ser Ser Ile
    285                 290                 295 gac acg ctg gaa att aat gga gac atc cac tta ctg gaa caa tca ttc     1145
Asp Thr Leu Glu Ile Asn Gly Asp Ile His Leu Leu Glu Gln Ser Phe
300                 305                 310                 315
```

```
aat caa aag agt gaa atg aag cac att aac aaa gca gga ggc gcc acg      1193
Asn Gln Lys Ser Glu Met Lys His Ile Asn Lys Ala Gly Gly Ala Thr
            320                 325                 330 gac cgc ctc cct cca cac cgc tcc ttc cgc ctt cat tcc ttg ccc aca      1241
Asp Arg Leu Pro Pro His Arg Ser Phe Arg Leu His Ser Leu Pro Thr
        335                 340                 345 ggc ttg cac tgg aag ctg aat aag aat ccc caa aac tca aac ttc cta      1289
Gly Leu His Trp Lys Leu Asn Lys Asn Pro Gln Asn Ser Asn Phe Leu
    350                 355                 360 ggg atg cca ccc ctt tag tagctcacac ctccccctc caagagctaa              1337
Gly Met Pro Pro Leu  *
365 gaaacaaagg agaatgtact tttgtagctt agataagcaa tgaatcagta aaggactgat    1397 ctacttgctc caccacccct cccttaataa taacatttac tgttatttcc tgggcctaag    1457 acttatgttc cagaactgtc acagctcccc atgtcacacc cactagcttg tgatctttgt    1517 caaataactg aaatctttta agcctctagt ttcttccttt gtaaaacaga gataaaatgt    1577 tgtggttttt aagtgagata atccaagtaa agcacctaac atggagtagt gaatgaacat    1637 cggttgctac taaaagtgga catcctaccg catccttaat gccactaggc atttccatac    1697 aatctgggga ccaaaacttc aatcatataa atgtatgagg ttaattaaaa acactactgt    1757 aatctgcttg tatgatcaca aaccaccaca aaagaaaaga tcgtgaagat tacactgtaa    1817 acggactctc aaatgatcag gaggtggtca cttcgcaact tgctccctcc acccaactca    1877 aaacaggagc tcgagcctgc ctgtatttga gactggagct gcctgtatga ggactggatc    1937 aactgctagt cacgttatat ccaaatctgc attatcattg ggcacatttt cacagaattt    1997 tactgaatta ttccttaatt gtttaatggt tgggaatagt ttgggaatta ccttccatca    2057 actctgctaa gaaaggaatg gattctggta gcaagacaat ataattctcc tttagttttt    2117 cagccagtgc taacacagta atcaaagcag caaatcgaac ctgaaaggga taaaagagca    2177 aagaaataaa aagtagtgtt actgtattta ttatcttaag agctgtactg acttgagaca    2237 agctctaact tttttaaacat tagttcacac gcgtttattc acttcattat gttcattaag    2297 cttccatctt agaataccag tttcaccatt tgggagctgt ttgtaatatg tgcaacctta    2357 taaatagtgt tttccaaact gtgtcccagg actgcaaatc tttaatgtga aatgtctttt    2417 tataatctct tcctttaaaa aaaaccaata aaataaaatg ccacatgcaa actc          2471

<210> SEQ ID NO 5
<211> LENGTH: 316
<212> TYPE: PRT
<213> ORGANISM: Homo sapiens
<220> FEATURE:
<221> NAME/KEY: VARIANT
<222> LOCATION: 18
<223> OTHER INFORMATION: 5-2-162 : polymorphic amino acid Tyr or Phe
<220> FEATURE:
<221> NAME/KEY: VARIANT
<222> LOCATION: 35
<223> OTHER INFORMATION: 5-2-213 : polymorphic amino acid Cys or Arg
<220> FEATURE:
<221> NAME/KEY: VARIANT
<222> LOCATION: 55
<223> OTHER INFORMATION: 5-3-84 : polymorphic amino acid Val or Met
<220> FEATURE:
<221> NAME/KEY: VARIANT
<222> LOCATION: 183
<223> OTHER INFORMATION: 5-7-195 : polymorphic amino acid Ser or Arg

<400> SEQUENCE: 5
```

-continued

Met Leu Ser Leu Asn Asn Leu Gln Asn Ile Ile Tyr Asn Pro Val Ile
1               5                   10                  15

Pro Tyr Val Gly Thr Ile Pro Asp Gln Leu Asp Pro Gly Thr Leu Ile
            20                  25                  30

Val Ile Cys Gly His Val Pro Ser Asp Ala Asp Arg Phe Gln Val Asp
        35                  40                  45

Leu Gln Asn Gly Ser Ser Val Lys Pro Arg Ala Asp Val Ala Phe His
50                  55                  60

Phe Asn Pro Arg Phe Lys Arg Ala Gly Cys Ile Val Cys Asn Thr Leu
65                  70                  75                  80

Ile Asn Glu Lys Trp Gly Arg Glu Glu Ile Thr Tyr Asp Thr Pro Phe
                85                  90                  95

Lys Arg Glu Lys Ser Phe Glu Ile Val Ile Met Val Leu Lys Asp Lys
                100                 105                 110

Phe Gln Val Ala Val Asn Gly Lys His Thr Leu Leu Tyr Gly His Arg
            115                 120                 125

Ile Gly Pro Glu Lys Ile Asp Thr Leu Gly Ile Tyr Gly Lys Val Asn
130                 135                 140

Ile His Ser Ile Gly Phe Ser Phe Ser Ser Asp Leu Gln Ser Thr Gln
145                 150                 155                 160

Ala Ser Ser Leu Glu Leu Thr Glu Ile Ser Arg Glu Asn Val Pro Lys
            165                 170                 175

Ser Gly Thr Pro Gln Leu Ser Leu Pro Phe Ala Ala Arg Leu Asn Thr
            180                 185                 190

Pro Met Gly Pro Gly Arg Thr Val Val Lys Gly Glu Val Asn Ala
            195                 200                 205

Asn Ala Lys Ser Phe Asn Val Asp Leu Leu Ala Gly Lys Ser Lys Asp
210                 215                 220

Ile Ala Leu His Leu Asn Pro Arg Leu Asn Ile Lys Ala Phe Val Arg
225                 230                 235                 240

Asn Ser Phe Leu Gln Glu Ser Trp Gly Glu Glu Arg Asn Ile Thr
            245                 250                 255

Ser Phe Pro Phe Ser Pro Gly Met Tyr Phe Glu Met Ile Ile Tyr Cys
            260                 265                 270

Asp Val Arg Glu Phe Lys Val Ala Val Asn Gly Val His Ser Leu Glu
            275                 280                 285

Tyr Lys His Arg Phe Lys Glu Leu Ser Ser Ile Asp Thr Leu Glu Ile
            290                 295                 300

Asn Gly Asp Ile His Leu Leu Glu Val Arg Ser Trp
305                 310                 315

<210> SEQ ID NO 6
<211> LENGTH: 358
<212> TYPE: PRT
<213> ORGANISM: Homo sapiens
<220> FEATURE:
<221> NAME/KEY: VARIANT
<222> LOCATION: 18
<223> OTHER INFORMATION: 5-2-162 : polymorphic amino acid Tyr or Phe
<220> FEATURE:
<221> NAME/KEY: VARIANT
<222> LOCATION: 35
<223> OTHER INFORMATION: 5-2-213 : polymorphic amino acid Cys or Arg
<220> FEATURE:
<221> NAME/KEY: VARIANT
<222> LOCATION: 55
<223> OTHER INFORMATION: 5-3-84 : polymorphic amino acid Val or Met
<220> FEATURE:
<221> NAME/KEY: VARIANT

```
<222> LOCATION: 204
<223> OTHER INFORMATION: 5-202-95 : polymorphic amino acid Asp or Tyr
<220> FEATURE:
<221> NAME/KEY: VARIANT
<222> LOCATION: 211
<223> OTHER INFORMATION: 5-202-117 : polymorphic amino acid Leu or Stop
<220> FEATURE:
<221> NAME/KEY: VARIANT
<222> LOCATION: 225
<223> OTHER INFORMATION: 5-7-195 : polymorphic amino acid Ser or Arg

<400> SEQUENCE: 6
```

Met Leu Ser Leu Asn Asn Leu Gln Asn Ile Ile Tyr Asn Pro Val Ile
1               5                   10                  15

Pro Tyr Val Gly Thr Ile Pro Asp Gln Leu Asp Pro Gly Thr Leu Ile
            20                  25                  30

Val Ile Cys Gly His Val Pro Ser Asp Ala Asp Arg Phe Gln Val Asp
        35                  40                  45

Leu Gln Asn Gly Ser Ser Val Lys Pro Arg Ala Asp Val Ala Phe His
    50                  55                  60

Phe Asn Pro Arg Phe Lys Arg Ala Gly Cys Ile Val Cys Asn Thr Leu
65                  70                  75                  80

Ile Asn Glu Lys Trp Gly Arg Glu Glu Ile Thr Tyr Asp Thr Pro Phe
                85                  90                  95

Lys Arg Glu Lys Ser Phe Glu Ile Val Ile Met Val Leu Lys Asp Lys
            100                 105                 110

Phe Gln Val Ala Val Asn Gly Lys His Thr Leu Leu Tyr Gly His Arg
        115                 120                 125

Ile Gly Pro Glu Lys Ile Asp Thr Leu Gly Ile Tyr Gly Lys Val Asn
    130                 135                 140

Ile His Ser Ile Gly Phe Ser Phe Ser Ser Asp Leu Gln Ser Thr Gln
145                 150                 155                 160

Ala Ser Ser Leu Glu Leu Thr Glu Ile Ser Arg Glu Asn Val Pro Lys
                165                 170                 175

Ser Gly Thr Pro Gln Leu Pro Ser Asn Arg Gly Gly Asp Ile Ser Lys
            180                 185                 190

Ile Ala Pro Arg Thr Val Tyr Thr Lys Ser Lys Asp Ser Thr Val Asn
        195                 200                 205

His Thr Leu Thr Cys Thr Lys Ile Pro Pro Met Asn Tyr Val Ser Lys
    210                 215                 220

Ser Leu Pro Phe Ala Ala Arg Leu Asn Thr Pro Met Gly Pro Gly Arg
225                 230                 235                 240

Thr Val Val Lys Gly Glu Val Asn Ala Asn Ala Lys Ser Phe Asn
                245                 250                 255

Val Asp Leu Leu Ala Gly Lys Ser Lys Asp Ile Ala Leu His Leu Asn
            260                 265                 270

Pro Arg Leu Asn Ile Lys Ala Phe Val Arg Asn Ser Phe Leu Gln Glu
        275                 280                 285

Ser Trp Gly Glu Glu Glu Arg Asn Ile Thr Ser Phe Pro Phe Ser Pro
    290                 295                 300

Gly Met Tyr Phe Glu Met Ile Ile Tyr Cys Asp Val Arg Glu Phe Lys
305                 310                 315                 320

Val Ala Val Asn Gly Val His Ser Leu Glu Tyr Lys His Arg Phe Lys
                325                 330                 335

Glu Leu Ser Ser Ile Asp Thr Leu Glu Ile Asn Gly Asp Ile His Leu
            340                 345                 350

Leu Glu Val Arg Ser Trp
         355

<210> SEQ ID NO 7
<211> LENGTH: 368
<212> TYPE: PRT
<213> ORGANISM: Homo sapiens
<220> FEATURE:
<221> NAME/KEY: VARIANT
<222> LOCATION: 18
<223> OTHER INFORMATION: 5-2-162 : polymorphic amino acid Tyr or Phe
<220> FEATURE:
<221> NAME/KEY: VARIANT
<222> LOCATION: 35
<223> OTHER INFORMATION: 5-2-213 : polymorphic amino acid Cys or Arg
<220> FEATURE:
<221> NAME/KEY: VARIANT
<222> LOCATION: 55
<223> OTHER INFORMATION: 5-3-84 : polymorphic amino acid Val or Met
<220> FEATURE:
<221> NAME/KEY: VARIANT
<222> LOCATION: 183
<223> OTHER INFORMATION: 5-7-195 : polymorphic amino acid Ser or Arg

<400> SEQUENCE: 7

Met Leu Ser Leu Asn Asn Leu Gln Asn Ile Ile Tyr Asn Pro Val Ile
1               5                   10                  15

Pro Tyr Val Gly Thr Ile Pro Asp Gln Leu Asp Pro Gly Thr Leu Ile
            20                  25                  30

Val Ile Cys Gly His Val Pro Ser Asp Ala Asp Arg Phe Gln Val Asp
        35                  40                  45

Leu Gln Asn Gly Ser Ser Val Lys Pro Arg Ala Asp Val Ala Phe His
    50                  55                  60

Phe Asn Pro Arg Phe Lys Arg Ala Gly Cys Ile Val Cys Asn Thr Leu
65                  70                  75                  80

Ile Asn Glu Lys Trp Gly Arg Glu Glu Ile Thr Tyr Asp Thr Pro Phe
                85                  90                  95

Lys Arg Glu Lys Ser Phe Glu Ile Val Ile Met Val Leu Lys Asp Lys
            100                 105                 110

Phe Gln Val Ala Val Asn Gly Lys His Thr Leu Leu Tyr Gly His Arg
        115                 120                 125

Ile Gly Pro Glu Lys Ile Asp Thr Leu Gly Ile Tyr Gly Lys Val Asn
    130                 135                 140

Ile His Ser Ile Gly Phe Ser Phe Ser Ser Asp Leu Gln Ser Thr Gln
145                 150                 155                 160

Ala Ser Ser Leu Glu Leu Thr Glu Ile Ser Arg Glu Asn Val Pro Lys
                165                 170                 175

Ser Gly Thr Pro Gln Leu Ser Leu Pro Phe Ala Ala Arg Leu Asn Thr
            180                 185                 190

Pro Met Gly Pro Gly Arg Thr Val Val Lys Gly Glu Val Asn Ala
        195                 200                 205

Asn Ala Lys Ser Phe Asn Val Asp Leu Leu Ala Gly Lys Ser Lys Asp
    210                 215                 220

Ile Ala Leu His Leu Asn Pro Arg Leu Asn Ile Lys Ala Phe Val Arg
225                 230                 235                 240

Asn Ser Phe Leu Gln Glu Ser Trp Gly Glu Glu Arg Asn Ile Thr
                245                 250                 255

Ser Phe Pro Phe Ser Pro Gly Met Tyr Phe Glu Met Ile Ile Tyr Cys
            260                 265                 270

Asp Val Arg Glu Phe Lys Val Ala Val Asn Gly Val His Ser Leu Glu

```
                      275                 280                 285
Tyr Lys His Arg Phe Lys Glu Leu Ser Ser Ile Asp Thr Leu Glu Ile
            290                 295                 300

Asn Gly Asp Ile His Leu Leu Glu Gln Ser Phe Asn Gln Lys Ser Glu
305                 310                 315                 320

Met Lys His Ile Asn Lys Ala Gly Ala Thr Asp Arg Leu Pro Pro
            325                 330                 335

His Arg Ser Phe Arg Leu His Ser Leu Pro Thr Gly Leu His Trp Lys
            340                 345                 350

Leu Asn Lys Asn Pro Gln Asn Ser Asn Phe Leu Gly Met Pro Pro Leu
            355                 360                 365

<210> SEQ ID NO 8
<211> LENGTH: 1738
<212> TYPE: DNA
<213> ORGANISM: Mus musculus

<400> SEQUENCE: 8
gagtgttact accaccgggg acaagttttt actttgagta atccttaaat gaagagtggg      60
taaagtgtgt atacggaaga gagactccaa tcaacaatat caataagttg aaaaagaaaa     120 atg ttg tcc tta aat aac cta caa aat atc atc tat aac ccg ata atc      168
Met Leu Ser Leu Asn Asn Leu Gln Asn Ile Ile Tyr Asn Pro Ile Ile
1               5                   10                  15 ccc tat gtt ggc acc att act gag caa ttg aag cct ggc tct ctg att      216
Pro Tyr Val Gly Thr Ile Thr Glu Gln Leu Lys Pro Gly Ser Leu Ile
                20                  25                  30 gta atc cgt ggg cat gtc cct aaa gat tca gaa aga ttc cag gtt gac      264
Val Ile Arg Gly His Val Pro Lys Asp Ser Glu Arg Phe Gln Val Asp
            35                  40                  45 ttt cag ctg ggc aac agc ctg aag cca aga gca gac gtg gcc ttc cac      312
Phe Gln Leu Gly Asn Ser Leu Lys Pro Arg Ala Asp Val Ala Phe His
        50                  55                  60 ttt aac cct cgg ttc aaa agg tct agc tgc att gtt tgt aac aca ctg      360
Phe Asn Pro Arg Phe Lys Arg Ser Ser Cys Ile Val Cys Asn Thr Leu
65                  70                  75                  80 aca cag gag aag tgg ggc tgg gag gag atc acc tac gac atg ccc ttc      408
Thr Gln Glu Lys Trp Gly Trp Glu Glu Ile Thr Tyr Asp Met Pro Phe
                85                  90                  95 aga aaa gaa aag tcc ttt gag atc gtg ttc atg gtg ctc aag aac aaa      456
Arg Lys Glu Lys Ser Phe Glu Ile Val Phe Met Val Leu Lys Asn Lys
                100                 105                 110 ttc cag gtg gct gtg aac gga agg cat gtt ctg ctg tac gcc cac agg      504
Phe Gln Val Ala Val Asn Gly Arg His Val Leu Leu Tyr Ala His Arg
            115                 120                 125 atc agc ccg gag cag atc gac aca gtg ggc atc tac ggc aaa gtg aac      552
Ile Ser Pro Glu Gln Ile Asp Thr Val Gly Ile Tyr Gly Lys Val Asn
        130                 135                 140 atc cac tcc atc ggg ttc aga ttc agc tcg gat tta cag agt atg gaa      600
Ile His Ser Ile Gly Phe Arg Phe Ser Ser Asp Leu Gln Ser Met Glu
145                 150                 155                 160 aca tct gct ctg gga ctg aca cag ata aac aga gag aat ata caa aag      648
Thr Ser Ala Leu Gly Leu Thr Gln Ile Asn Arg Glu Asn Ile Gln Lys
                165                 170                 175 cca ggc aag ctc cag ctg agc ctg cca ttt gaa gca agg ttg aat gcc      696
Pro Gly Lys Leu Gln Leu Ser Leu Pro Phe Glu Ala Arg Leu Asn Ala
                180                 185                 190 tcc atg ggt cct gga cga acc gtt gtc att aaa ggg gaa gtg aac acc      744
Ser Met Gly Pro Gly Arg Thr Val Val Ile Lys Gly Glu Val Asn Thr
```

```
                 195                 200                 205
aat gcc cga agc ttt aat gtt gac cta gtg gca gga aaa aca agg gat     792
Asn Ala Arg Ser Phe Asn Val Asp Leu Val Ala Gly Lys Thr Arg Asp
    210                 215                 220 atc gct ctg cac ttg aac cca cgc ctc aat gtg aaa gca ttt gta aga     840
Ile Ala Leu His Leu Asn Pro Arg Leu Asn Val Lys Ala Phe Val Arg
225                 230                 235                 240 aat tcc ttt ctt cag gat gcc tgg gga gaa gag gag aga aat att acc     888
Asn Ser Phe Leu Gln Asp Ala Trp Gly Glu Glu Glu Arg Asn Ile Thr
                245                 250                 255 tgc ttc cca ttt agt tct ggg atg tac ttt gag atg ata atc tac tgt     936
Cys Phe Pro Phe Ser Ser Gly Met Tyr Phe Glu Met Ile Ile Tyr Cys
                260                 265                 270 gat gtc cgg gaa ttc aag gtt gct ata aat ggt gtg cac agc ctg gag     984
Asp Val Arg Glu Phe Lys Val Ala Ile Asn Gly Val His Ser Leu Glu
            275                 280                 285 tac aaa cac aga ttt aaa gac cta agc agt att gat aca cta tca gtc    1032
Tyr Lys His Arg Phe Lys Asp Leu Ser Ser Ile Asp Thr Leu Ser Val
        290                 295                 300 gat ggt gat atc cgt ttg ctg gat gta agg agc tgg tag ctaccatgac     1081
Asp Gly Asp Ile Arg Leu Leu Asp Val Arg Ser Trp *
305                 310                 315 tgccaaaacc cccgaaatac aaaatggctt atccggtact ggccatgtca atgcatctc   1141 gctttcacca tattgtttat attgctaagt tgagctcctc aacatcaag tcctactggt   1201 gttgtcaggt ctggccatgc agtacattca gaggaacaga gccggggcaa tcacagctca  1261
ctgccagaga ggctctgcac actgggtccc tcttataaac cacactcagc aaatatttaa  1321
gtgcctaata tactacatat actagctaat agggatggca agcatacttc ctttgtatat  1381
tctctgagcc gggcacagac atggcagggc ccagaacttg tgtggtccat gttttctagc  1441
acttcgtacc agtttctggc ctcctaatgt agggtcttct tgctggcatt gcattaaccc  1501 cactagggc ctttgcagtt aaggtcagaa aaatatacta atggatggca acactactt   1561 ccccagcaac ccttttcata atcagcattc tatcatatct cataattgaa gactgcatag  1621
catttactta gctctcaccg ctttaaactt tataaaatgt atgatgctga acacagcaga  1681
aaaactgagg ccaaaaccct gaattatgac aaaacaagtg ttctgctcca agcagat     1738
```

<210> SEQ ID NO 9
<211> LENGTH: 316
<212> TYPE: PRT
<213> ORGANISM: Mus musculus

<400> SEQUENCE: 9

```
Met Leu Ser Leu Asn Asn Leu Gln Asn Ile Ile Tyr Asn Pro Ile Ile
1               5                   10                  15

Pro Tyr Val Gly Thr Ile Thr Glu Gln Leu Lys Pro Gly Ser Leu Ile
            20                  25                  30

Val Ile Arg Gly His Val Pro Lys Asp Ser Glu Arg Phe Gln Val Asp
        35                  40                  45

Phe Gln Leu Gly Asn Ser Leu Lys Pro Arg Ala Asp Val Ala Phe His
    50                  55                  60

Phe Asn Pro Arg Phe Lys Arg Ser Ser Cys Ile Val Cys Asn Thr Leu
65                  70                  75                  80

Thr Gln Glu Lys Trp Gly Trp Glu Glu Ile Thr Tyr Asp Met Pro Phe
                85                  90                  95

Arg Lys Glu Lys Ser Phe Glu Ile Val Phe Met Val Leu Lys Asn Lys
```

```
                100                 105                 110
Phe Gln Val Ala Val Asn Gly Arg His Val Leu Leu Tyr Ala His Arg
        115                 120                 125

Ile Ser Pro Glu Gln Ile Asp Thr Val Gly Ile Tyr Gly Lys Val Asn
130                 135                 140

Ile His Ser Ile Gly Phe Arg Phe Ser Ser Asp Leu Gln Ser Met Glu
145                 150                 155                 160

Thr Ser Ala Leu Gly Leu Thr Gln Ile Asn Arg Glu Asn Ile Gln Lys
                165                 170                 175

Pro Gly Lys Leu Gln Leu Ser Leu Pro Phe Glu Ala Arg Leu Asn Ala
        180                 185                 190

Ser Met Gly Pro Gly Arg Thr Val Val Ile Lys Gly Glu Val Asn Thr
        195                 200                 205

Asn Ala Arg Ser Phe Asn Val Asp Leu Val Ala Gly Lys Thr Arg Asp
210                 215                 220

Ile Ala Leu His Leu Asn Pro Arg Leu Asn Val Lys Ala Phe Val Arg
225                 230                 235                 240

Asn Ser Phe Leu Gln Asp Ala Trp Gly Glu Glu Arg Asn Ile Thr
                245                 250                 255

Cys Phe Pro Phe Ser Ser Gly Met Tyr Phe Glu Met Ile Ile Tyr Cys
                260                 265                 270

Asp Val Arg Glu Phe Lys Val Ala Ile Asn Gly Val His Ser Leu Glu
        275                 280                 285

Tyr Lys His Arg Phe Lys Asp Leu Ser Ser Ile Asp Thr Leu Ser Val
        290                 295                 300

Asp Gly Asp Ile Arg Leu Leu Asp Val Arg Ser Trp
305                 310                 315

<210> SEQ ID NO 10
<211> LENGTH: 18
<212> TYPE: DNA
<213> ORGANISM: Artificial Sequence
<220> FEATURE:
<223> OTHER INFORMATION: sequencing oligonucleotide PrimerPU

<400> SEQUENCE: 10
tgtaaaacga cggccagt                                                 18

<210> SEQ ID NO 11
<211> LENGTH: 18
<212> TYPE: DNA
<213> ORGANISM: Artificial Sequence
<220> FEATURE:
<223> OTHER INFORMATION: sequencing oligonucleotide PrimerRP

<400> SEQUENCE: 11
caggaaacag ctatgacc                                                 18

<210> SEQ ID NO 12
<211> LENGTH: 106746
<212> TYPE: DNA
<213> ORGANISM: Homo sapiens
<220> FEATURE:
<221> NAME/KEY: misc_feature
<222> LOCATION: 1..68647
<223> OTHER INFORMATION: 5'regulation  region
<220> FEATURE:
<221> NAME/KEY: misc_feature
<222> LOCATION: 66647..68647
<223> OTHER INFORMATION: promoter
<220> FEATURE:
```

-continued

```
<221> NAME/KEY: misc_feature
<222> LOCATION: 97156..106746
<223> OTHER INFORMATION: 3'regulation region
<220> FEATURE:
<221> NAME/KEY: exon
<222> LOCATION: 68648..68741
<223> OTHER INFORMATION: exon0
<220> FEATURE:
<221> NAME/KEY: exon
<222> LOCATION: 70647..70794
<223> OTHER INFORMATION: exon1
<220> FEATURE:
<221> NAME/KEY: exon
<222> LOCATION: 82208..82296
<223> OTHER INFORMATION: exon2
<220> FEATURE:
<221> NAME/KEY: exon
<222> LOCATION: 83613..83823
<223> OTHER INFORMATION: exon3
<220> FEATURE:
<221> NAME/KEY: exon
<222> LOCATION: 85298..85417
<223> OTHER INFORMATION: exon4
<220> FEATURE:
<221> NAME/KEY: exon
<222> LOCATION: 86389..86445
<223> OTHER INFORMATION: exon5
<220> FEATURE:
<221> NAME/KEY: exon
<222> LOCATION: 87496..87522
<223> OTHER INFORMATION: exon6
<220> FEATURE:
<221> NAME/KEY: exon
<222> LOCATION: 87650..87775
<223> OTHER INFORMATION: exon6bis
<220> FEATURE:
<221> NAME/KEY: exon
<222> LOCATION: 88295..88383
<223> OTHER INFORMATION: exon7
<220> FEATURE:
<221> NAME/KEY: exon
<222> LOCATION: 89484..89649
<223> OTHER INFORMATION: exon8
<220> FEATURE:
<221> NAME/KEY: exon
<222> LOCATION: 92749..97155
<223> OTHER INFORMATION: exon9
<220> FEATURE:
<221> NAME/KEY: exon
<222> LOCATION: 92749..92883
<223> OTHER INFORMATION: exon9bis
<220> FEATURE:
<221> NAME/KEY: exon
<222> LOCATION: 95821..97155
<223> OTHER INFORMATION: exon9ter
<220> FEATURE:
<221> NAME/KEY: misc_feature
<222> LOCATION: 70647..70794
<223> OTHER INFORMATION: homology with genset EST : A241850
<220> FEATURE:
<221> NAME/KEY: misc_feature
<222> LOCATION: 68648..68741
<223> OTHER INFORMATION: homology with genset EST : A241850
<220> FEATURE:
<221> NAME/KEY: misc_feature
<222> LOCATION: 82208..82229
<223> OTHER INFORMATION: homology with genset EST : A241850
<220> FEATURE:
<221> NAME/KEY: allele
<222> LOCATION: 278
<223> OTHER INFORMATION: 99-1601-278 : polymorphic base A or C
<220> FEATURE:
<221> NAME/KEY: allele
<222> LOCATION: 402
<223> OTHER INFORMATION: 99-1601-402 : polymorphic base w= A or T
<220> FEATURE:
<221> NAME/KEY: allele
<222> LOCATION: 472
<223> OTHER INFORMATION: 99-1601-472 : polymorphic base A or T
```

```
<220> FEATURE:
<221> NAME/KEY: allele
<222> LOCATION: 2955
<223> OTHER INFORMATION: 99-13801-100 : polymorphic base T or C
<220> FEATURE:
<221> NAME/KEY: allele
<222> LOCATION: 12167
<223> OTHER INFORMATION: 99-13806-166 : polymorphic base G or A
<220> FEATURE:
<221> NAME/KEY: allele
<222> LOCATION: 12536
<223> OTHER INFORMATION: 99-13799-376 : polymorphic base T or G
<220> FEATURE:
<221> NAME/KEY: allele
<222> LOCATION: 17593
<223> OTHER INFORMATION: 99-13798-297 : polymorphic base T or C
<220> FEATURE:
<221> NAME/KEY: allele
<222> LOCATION: 17606
<223> OTHER INFORMATION: 99-13798-284 : polymorphic base T or C
<220> FEATURE:
<221> NAME/KEY: allele
<222> LOCATION: 22079
<223> OTHER INFORMATION: 99-1602-200 : polymorphic base G or C
<220> FEATURE:
<221> NAME/KEY: allele
<222> LOCATION: 28964
<223> OTHER INFORMATION: 99-13794-186 : polymorphic base T or C
<220> FEATURE:
<221> NAME/KEY: allele
<222> LOCATION: 29003
<223> OTHER INFORMATION: 99-13794-147 : polymorphic base C or G
<220> FEATURE:
<221> NAME/KEY: allele
<222> LOCATION: 31077
<223> OTHER INFORMATION: 99-13812-384 : polymorphic base T or C
<220> FEATURE:
<221> NAME/KEY: allele
<222> LOCATION: 31766
<223> OTHER INFORMATION: 99-13805-313 : polymorphic base T or C
<220> FEATURE:
<221> NAME/KEY: allele
<222> LOCATION: 34791
<223> OTHER INFORMATION: 99-1587-281 : polymorphic base A or G
<220> FEATURE:
<221> NAME/KEY: allele
<222> LOCATION: 45751
<223> OTHER INFORMATION: 99-1582-430 : polymorphic base C or T
<220> FEATURE:
<221> NAME/KEY: allele
<222> LOCATION: 49847
<223> OTHER INFORMATION: 99-1585-465 : polymorphic base T or C
<220> FEATURE:
<221> NAME/KEY: allele
<222> LOCATION: 49855
<223> OTHER INFORMATION: 99-1585-457 : polymorphic base T or C
<220> FEATURE:
<221> NAME/KEY: allele
<222> LOCATION: 49886
<223> OTHER INFORMATION: 99-1585-426 : polymorphic base G or A
<220> FEATURE:
<221> NAME/KEY: allele
<222> LOCATION: 49900
<223> OTHER INFORMATION: 99-1585-412 : polymorphic base G or A
<220> FEATURE:
<221> NAME/KEY: allele
<222> LOCATION: 49906
<223> OTHER INFORMATION: 99-1585-406 : polymorphic base C or A
<220> FEATURE:
<221> NAME/KEY: allele
<222> LOCATION: 49921
<223> OTHER INFORMATION: 99-1585-391 : polymorphic base C or A
<220> FEATURE:
<221> NAME/KEY: allele
<222> LOCATION: 49939
<223> OTHER INFORMATION: 99-1585-373 : polymorphic base G or A
<220> FEATURE:
<221> NAME/KEY: allele
<222> LOCATION: 50256
```

-continued

```
<223> OTHER INFORMATION: 99-1585-55 : polymorphic base C or A
<220> FEATURE:
<221> NAME/KEY: allele
<222> LOCATION: 54955
<223> OTHER INFORMATION: 99-1607-373 : polymorphic base T or C
<220> FEATURE:
<221> NAME/KEY: allele
<222> LOCATION: 64239
<223> OTHER INFORMATION: 99-1577-105 : polymorphic base A or G
<220> FEATURE:
<221> NAME/KEY: allele
<222> LOCATION: 65436
<223> OTHER INFORMATION: 99-1591-235 : polymorphic base A or G
<220> FEATURE:
<221> NAME/KEY: allele
<222> LOCATION: 65496
<223> OTHER INFORMATION: 99-1591-295 : polymorphic base G or T
<220> FEATURE:
<221> NAME/KEY: allele
<222> LOCATION: 66967
<223> OTHER INFORMATION: 99-1572-315 : polymorphic base C or T
<220> FEATURE:
<221> NAME/KEY: allele
<222> LOCATION: 66987
<223> OTHER INFORMATION: 99-1572-335 : polymorphic base A or G
<220> FEATURE:
<221> NAME/KEY: allele
<222> LOCATION: 67092
<223> OTHER INFORMATION: 99-1572-440 : polymorphic base C or T
<220> FEATURE:
<221> NAME/KEY: allele
<222> LOCATION: 67129
<223> OTHER INFORMATION: 99-1572-477 : polymorphic base A or T
<220> FEATURE:
<221> NAME/KEY: allele
<222> LOCATION: 67229
<223> OTHER INFORMATION: 99-1572-578 : polymorphic base C or T
<220> FEATURE:
<221> NAME/KEY: allele
<222> LOCATION: 67433
<223> OTHER INFORMATION: 5-264-188 : polymorphic base A or G
<220> FEATURE:
<221> NAME/KEY: allele
<222> LOCATION: 67723
<223> OTHER INFORMATION: 5-169-97 : polymorphic base G or C
<220> FEATURE:
<221> NAME/KEY: allele
<222> LOCATION: 67834
<223> OTHER INFORMATION: 5-169-208 : polymorphic base A or G
<220> FEATURE:
<221> NAME/KEY: allele
<222> LOCATION: 67955
<223> OTHER INFORMATION: 5-169-331 : polymorphic base C or T
<220> FEATURE:
<221> NAME/KEY: allele
<222> LOCATION: 68213
<223> OTHER INFORMATION: 5-170-238 : polymorphic base A or G
<220> FEATURE:
<221> NAME/KEY: allele
<222> LOCATION: 68263
<223> OTHER INFORMATION: 5-170-288 : polymorphic base A or C
<220> FEATURE:
<221> NAME/KEY: allele
<222> LOCATION: 68375
<223> OTHER INFORMATION: 5-170-400 : polymorphic base G or C
<220> FEATURE:
<221> NAME/KEY: allele
<222> LOCATION: 68477
<223> OTHER INFORMATION: 5-171-156 : polymorphic base G or T
<220> FEATURE:
<221> NAME/KEY: allele
<222> LOCATION: 68525
<223> OTHER INFORMATION: 5-171-204 : polymorphic base C or T
<220> FEATURE:
<221> NAME/KEY: allele
<222> LOCATION: 68594
<223> OTHER INFORMATION: 5-171-273 : polymorphic base A or G
<220> FEATURE:
<221> NAME/KEY: allele
```

```
<222> LOCATION: 68610
<223> OTHER INFORMATION: 5-171-289 : polymorphic base C or T
<220> FEATURE:
<221> NAME/KEY: allele
<222> LOCATION: 70566
<223> OTHER INFORMATION: 5-1-60 : polymorphic base C or T
<220> FEATURE:
<221> NAME/KEY: allele
<222> LOCATION: 70728
<223> OTHER INFORMATION: 5-1-222 : polymorphic base A or G
<220> FEATURE:
<221> NAME/KEY: allele
<222> LOCATION: 80038
<223> OTHER INFORMATION: 99-1578-99 : polymorphic base G or T
<220> FEATURE:
<221> NAME/KEY: allele
<222> LOCATION: 80118
<223> OTHER INFORMATION: 99-1578-179 : polymorphic base A or T
<220> FEATURE:
<221> NAME/KEY: allele
<222> LOCATION: 80170
<223> OTHER INFORMATION: 99-1578-231 : insertion AC
<220> FEATURE:
<221> NAME/KEY: allele
<222> LOCATION: 80183
<223> OTHER INFORMATION: 99-1578-245 : deletion AT
<220> FEATURE:
<221> NAME/KEY: allele
<222> LOCATION: 80435
<223> OTHER INFORMATION: 99-1578-496 : polymorphic base C or T
<220> FEATURE:
<221> NAME/KEY: allele
<222> LOCATION: 82090
<223> OTHER INFORMATION: 5-2-30 : insertion CAG
<220> FEATURE:
<221> NAME/KEY: allele
<222> LOCATION: 82165
<223> OTHER INFORMATION: 5-2-109 : polymorphic base G or T
<220> FEATURE:
<221> NAME/KEY: allele
<222> LOCATION: 82169
<223> OTHER INFORMATION: 5-2-113 : deletion GTTT
<220> FEATURE:
<221> NAME/KEY: allele
<222> LOCATION: 82218
<223> OTHER INFORMATION: 5-2-162 : polymorphic base A or T
<220> FEATURE:
<221> NAME/KEY: allele
<222> LOCATION: 82234
<223> OTHER INFORMATION: 5-2-178 : polymorphic base C or T
<220> FEATURE:
<221> NAME/KEY: allele
<222> LOCATION: 82268
<223> OTHER INFORMATION: 5-2-213 : polymorphic base C or T
<220> FEATURE:
<221> NAME/KEY: allele
<222> LOCATION: 82393
<223> OTHER INFORMATION: 99-1605-112 : polymorphic base T or C
<220> FEATURE:
<221> NAME/KEY: allele
<222> LOCATION: 83587
<223> OTHER INFORMATION: 5-3-27 : polymorphic base A or G
<220> FEATURE:
<221> NAME/KEY: allele
<222> LOCATION: 83643
<223> OTHER INFORMATION: 5-3-83 : polymorphic base C or T
<220> FEATURE:
<221> NAME/KEY: allele
<222> LOCATION: 83644
<223> OTHER INFORMATION: 5-3-84 : polymorphic base A or G
<220> FEATURE:
<221> NAME/KEY: allele
<222> LOCATION: 83808
<223> OTHER INFORMATION: 5-3-248 : polymorphic base A or G
<220> FEATURE:
<221> NAME/KEY: allele
<222> LOCATION: 83881
<223> OTHER INFORMATION: 5-3-321 : polymorphic base G or T
<220> FEATURE:
```

```
<221> NAME/KEY: allele
<222> LOCATION: 83884
<223> OTHER INFORMATION: 5-3-324 : polymorphic base C or T
<220> FEATURE:
<221> NAME/KEY: allele
<222> LOCATION: 83909
<223> OTHER INFORMATION: 5-4-313 : polymorphic base A or G
<220> FEATURE:
<221> NAME/KEY: allele
<222> LOCATION: 83937
<223> OTHER INFORMATION: 5-3-377 : insertion TTTG
<220> FEATURE:
<221> NAME/KEY: allele
<222> LOCATION: 83947
<223> OTHER INFORMATION: 5-4-351 : polymorphic base C or T
<220> FEATURE:
<221> NAME/KEY: allele
<222> LOCATION: 83982
<223> OTHER INFORMATION: 5-4-386 : polymorphic base A or G
<220> FEATURE:
<221> NAME/KEY: allele
<222> LOCATION: 83988
<223> OTHER INFORMATION: 5-4-392 : polymorphic base GGG or TA
<220> FEATURE:
<221> NAME/KEY: allele
<222> LOCATION: 84047
<223> OTHER INFORMATION: 5-260-255 : polymorphic base C or T
<220> FEATURE:
<221> NAME/KEY: allele
<222> LOCATION: 84092
<223> OTHER INFORMATION: 5-260-300 : polymorphic base C or T
<220> FEATURE:
<221> NAME/KEY: allele
<222> LOCATION: 84145
<223> OTHER INFORMATION: 5-260-353 : polymorphic base C or T
<220> FEATURE:
<221> NAME/KEY: allele
<222> LOCATION: 85202
<223> OTHER INFORMATION: 5-9-50 : polymorphic base C or T
<220> FEATURE:
<221> NAME/KEY: allele
<222> LOCATION: 86259
<223> OTHER INFORMATION: 5-5-21 : polymorphic base A or G
<220> FEATURE:
<221> NAME/KEY: allele
<222> LOCATION: 86323
<223> OTHER INFORMATION: 5-5-85 : polymorphic base TATAAAATATT or
      ACAGGTTATATA
<220> FEATURE:
<221> NAME/KEY: allele
<222> LOCATION: 87713
<223> OTHER INFORMATION: 5-202-95 : polymorphic base G or T
<220> FEATURE:
<221> NAME/KEY: allele
<222> LOCATION: 87735
<223> OTHER INFORMATION: 5-202-117 : polymorphic base A or T
<220> FEATURE:
<221> NAME/KEY: allele
<222> LOCATION: 87787
<223> OTHER INFORMATION: 5-202-169 : polymorphic base A or C
<220> FEATURE:
<221> NAME/KEY: allele
<222> LOCATION: 87806
<223> OTHER INFORMATION: 5-202-188 : polymorphic base A or G
<220> FEATURE:
<221> NAME/KEY: allele
<222> LOCATION: 87860
<223> OTHER INFORMATION: 5-202-242 : polymorphic base A or G
<220> FEATURE:
<221> NAME/KEY: allele
<222> LOCATION: 87902
<223> OTHER INFORMATION: 5-202-284 : polymorphic base C or T
<220> FEATURE:
<221> NAME/KEY: allele
<222> LOCATION: 87980
<223> OTHER INFORMATION: 5-202-362 : deletion CC
<220> FEATURE:
<221> NAME/KEY: allele
<222> LOCATION: 88012
```

-continued

```
<223> OTHER INFORMATION: 5-202-394 : polymorphic base C or T
<220> FEATURE:
<221> NAME/KEY: allele
<222> LOCATION: 88215
<223> OTHER INFORMATION: 5-7-113 : polymorphic base C or T
<220> FEATURE:
<221> NAME/KEY: allele
<222> LOCATION: 88283
<223> OTHER INFORMATION: 5-7-181 : polymorphic base G or C
<220> FEATURE:
<221> NAME/KEY: allele
<222> LOCATION: 88297
<223> OTHER INFORMATION: 5-7-195 : polymorphic base G or C
<220> FEATURE:
<221> NAME/KEY: allele
<222> LOCATION: 88442
<223> OTHER INFORMATION: 5-7-340 : polymorphic base C or T
<220> FEATURE:
<221> NAME/KEY: allele
<222> LOCATION: 88471
<223> OTHER INFORMATION: 5-7-369 : polymorphic base A or T
<220> FEATURE:
<221> NAME/KEY: allele
<222> LOCATION: 88480
<223> OTHER INFORMATION: 5-7-378 : polymorphic base C or T
<220> FEATURE:
<221> NAME/KEY: allele
<222> LOCATION: 89394
<223> OTHER INFORMATION: 5-181-57 : polymorphic base A or G
<220> FEATURE:
<221> NAME/KEY: allele
<222> LOCATION: 89464
<223> OTHER INFORMATION: 5-181-127 : polymorphic base C or T
<220> FEATURE:
<221> NAME/KEY: allele
<222> LOCATION: 89471
<223> OTHER INFORMATION: 5-181-134 : polymorphic base C or T
<220> FEATURE:
<221> NAME/KEY: allele
<222> LOCATION: 89658
<223> OTHER INFORMATION: 5-181-321 : polymorphic base A or C
<220> FEATURE:
<221> NAME/KEY: allele
<222> LOCATION: 92760
<223> OTHER INFORMATION: 5-10-39 : polymorphic base C or T
<220> FEATURE:
<221> NAME/KEY: allele
<222> LOCATION: 93023
<223> OTHER INFORMATION: 5-10-302 : polymorphic base A or G
<220> FEATURE:
<221> NAME/KEY: allele
<222> LOCATION: 93055
<223> OTHER INFORMATION: 5-10-334 : polymorphic base A or C
<220> FEATURE:
<221> NAME/KEY: allele
<222> LOCATION: 93247
<223> OTHER INFORMATION: 5-11-158 : polymorphic base A or G
<220> FEATURE:
<221> NAME/KEY: allele
<222> LOCATION: 93319
<223> OTHER INFORMATION: 5-11-230 : polymorphic base G or T
<220> FEATURE:
<221> NAME/KEY: allele
<222> LOCATION: 93323
<223> OTHER INFORMATION: 5-11-234 : polymorphic base C or T
<220> FEATURE:
<221> NAME/KEY: allele
<222> LOCATION: 93388
<223> OTHER INFORMATION: 5-11-299 : polymorphic base A or T
<220> FEATURE:
<221> NAME/KEY: allele
<222> LOCATION: 93393
<223> OTHER INFORMATION: 5-11-304 : polymorphic base A or C
<220> FEATURE:
<221> NAME/KEY: allele
<222> LOCATION: 93418
<223> OTHER INFORMATION: 5-11-329 : polymorphic base C or T
<220> FEATURE:
<221> NAME/KEY: allele
```

```
<222> LOCATION: 93515
<223> OTHER INFORMATION: 5-12-56 : insertion CTTT
<220> FEATURE:
<221> NAME/KEY: allele
<222> LOCATION: 93726
<223> OTHER INFORMATION: 5-12-267 : polymorphic base A or C
<220> FEATURE:
<221> NAME/KEY: allele
<222> LOCATION: 93903
<223> OTHER INFORMATION: 5-13-145 : polymorphic base C or T
<220> FEATURE:
<221> NAME/KEY: allele
<222> LOCATION: 94170
<223> OTHER INFORMATION: 5-14-44 : polymorphic base C or T
<220> FEATURE:
<221> NAME/KEY: allele
<222> LOCATION: 94218
<223> OTHER INFORMATION: 5-14-93 : polymorphic base A or T
<220> FEATURE:
<221> NAME/KEY: allele
<222> LOCATION: 94269
<223> OTHER INFORMATION: 5-14-144 : insertion T
<220> FEATURE:
<221> NAME/KEY: allele
<222> LOCATION: 94290
<223> OTHER INFORMATION: 5-14-165 : polymorphic base C or T
<220> FEATURE:
<221> NAME/KEY: allele
<222> LOCATION: 94422
<223> OTHER INFORMATION: 5-14-297 : polymorphic base A or C
<220> FEATURE:
<221> NAME/KEY: allele
<222> LOCATION: 94432
<223> OTHER INFORMATION: 5-14-307 : polymorphic base G or T
<220> FEATURE:
<221> NAME/KEY: allele
<222> LOCATION: 94720
<223> OTHER INFORMATION: 5-15-219 : polymorphic base A or T
<220> FEATURE:
<221> NAME/KEY: allele
<222> LOCATION: 94989
<223> OTHER INFORMATION: 5-16-157 : polymorphic base A or G
<220> FEATURE:
<221> NAME/KEY: allele
<222> LOCATION: 95261
<223> OTHER INFORMATION: 5-17-140 : polymorphic base A or G
<220> FEATURE:
<221> NAME/KEY: allele
<222> LOCATION: 95340
<223> OTHER INFORMATION: 5-18-51 : polymorphic base G or T
<220> FEATURE:
<221> NAME/KEY: allele
<222> LOCATION: 95497
<223> OTHER INFORMATION: 5-18-208 : polymorphic base A or C
<220> FEATURE:
<221> NAME/KEY: allele
<222> LOCATION: 95770
<223> OTHER INFORMATION: 5-300-238 : polymorphic base C or T
<220> FEATURE:
<221> NAME/KEY: allele
<222> LOCATION: 95819
<223> OTHER INFORMATION: 5-300-287 : polymorphic base A or G
<220> FEATURE:
<221> NAME/KEY: allele
<222> LOCATION: 96145
<223> OTHER INFORMATION: 5-262-49 : insertion C
<220> FEATURE:
<221> NAME/KEY: allele
<222> LOCATION: 96181
<223> OTHER INFORMATION: 5-262-85 : polymorphic base C or T
<220> FEATURE:
<221> NAME/KEY: allele
<222> LOCATION: 96350
<223> OTHER INFORMATION: 5-262-254 : polymorphic base C or T
<220> FEATURE:
<221> NAME/KEY: allele
<222> LOCATION: 96951
<223> OTHER INFORMATION: 5-263-404 : polymorphic base C or T
<220> FEATURE:
```

-continued

```
<221> NAME/KEY: allele
<222> LOCATION: 97144
<223> OTHER INFORMATION: 5-265-244 : polymorphic base A or G
<220> FEATURE:
<221> NAME/KEY: allele
<222> LOCATION: 97276
<223> OTHER INFORMATION: 5-265-376 : polymorphic base A or G
<220> FEATURE:
<221> NAME/KEY: allele
<222> LOCATION: 102267
<223> OTHER INFORMATION: 99-7183-338 : polymorphic base C or T
<220> FEATURE:
<221> NAME/KEY: allele
<222> LOCATION: 105937
<223> OTHER INFORMATION: 99-7207-138 : polymorphic base A or G
<220> FEATURE:
<221> NAME/KEY: misc_binding
<222> LOCATION: 258..277
<223> OTHER INFORMATION: 99-1601-278.mis1
<220> FEATURE:
<221> NAME/KEY: misc_binding
<222> LOCATION: 279..298
<223> OTHER INFORMATION: 99-1601-278.mis2 complement
<220> FEATURE:
<221> NAME/KEY: misc_binding
<222> LOCATION: 382..401
<223> OTHER INFORMATION: 99-1601-402.mis1
<220> FEATURE:
<221> NAME/KEY: misc_binding
<222> LOCATION: 403..422
<223> OTHER INFORMATION: 99-1601-402.mis2 complement
<220> FEATURE:
<221> NAME/KEY: misc_binding
<222> LOCATION: 452..471
<223> OTHER INFORMATION: 99-1601-472.mis1
<220> FEATURE:
<221> NAME/KEY: misc_binding
<222> LOCATION: 473..492
<223> OTHER INFORMATION: 99-1601-472.mis2 complement
<220> FEATURE:
<221> NAME/KEY: misc_binding
<222> LOCATION: 2935..2954
<223> OTHER INFORMATION: 99-13801-100.mis2
<220> FEATURE:
<221> NAME/KEY: misc_binding
<222> LOCATION: 2956..2975
<223> OTHER INFORMATION: 99-13801-100.mis1 complement
<220> FEATURE:
<221> NAME/KEY: misc_binding
<222> LOCATION: 12147..12166
<223> OTHER INFORMATION: 99-13806-166.mis2
<220> FEATURE:
<221> NAME/KEY: misc_binding
<222> LOCATION: 12168..12187
<223> OTHER INFORMATION: 99-13806-166.mis1 complement
<220> FEATURE:
<221> NAME/KEY: misc_binding
<222> LOCATION: 12516..12535
<223> OTHER INFORMATION: 99-13799-376.mis2
<220> FEATURE:
<221> NAME/KEY: misc_binding
<222> LOCATION: 12537..12556
<223> OTHER INFORMATION: 99-13799-376.mis1 complement
<220> FEATURE:
<221> NAME/KEY: misc_binding
<222> LOCATION: 17573..17592
<223> OTHER INFORMATION: 99-13798-297.mis2
<220> FEATURE:
<221> NAME/KEY: misc_binding
<222> LOCATION: 17594..17613
<223> OTHER INFORMATION: 99-13798-297.mis1 complement
<220> FEATURE:
<221> NAME/KEY: misc_binding
<222> LOCATION: 17586..17605
<223> OTHER INFORMATION: 99-13798-284.mis2
<220> FEATURE:
<221> NAME/KEY: misc_binding
<222> LOCATION: 17607..17626
<223> OTHER INFORMATION: 99-13798-284.mis1 complement
```

```
<220> FEATURE:
<221> NAME/KEY: misc_binding
<222> LOCATION: 22059..22078
<223> OTHER INFORMATION: 99-1602-200.mis1
<220> FEATURE:
<221> NAME/KEY: misc_binding
<222> LOCATION: 22080..22099
<223> OTHER INFORMATION: 99-1602-200.mis2 complement
<220> FEATURE:
<221> NAME/KEY: misc_binding
<222> LOCATION: 28944..28963
<223> OTHER INFORMATION: 99-13794-186.mis2
<220> FEATURE:
<221> NAME/KEY: misc_binding
<222> LOCATION: 28965..28984
<223> OTHER INFORMATION: 99-13794-186.mis1 complement
<220> FEATURE:
<221> NAME/KEY: misc_binding
<222> LOCATION: 28983..29002
<223> OTHER INFORMATION: 99-13794-147.mis2
<220> FEATURE:
<221> NAME/KEY: misc_binding
<222> LOCATION: 29004..29023
<223> OTHER INFORMATION: 99-13794-147.mis1 complement
<220> FEATURE:
<221> NAME/KEY: misc_binding
<222> LOCATION: 31057..31076
<223> OTHER INFORMATION: 99-13812-384.mis2
<220> FEATURE:
<221> NAME/KEY: misc_binding
<222> LOCATION: 31078..31097
<223> OTHER INFORMATION: 99-13812-384.mis1 complement
<220> FEATURE:
<221> NAME/KEY: misc_binding
<222> LOCATION: 31746..31765
<223> OTHER INFORMATION: 99-13805-313.mis2
<220> FEATURE:
<221> NAME/KEY: misc_binding
<222> LOCATION: 31767..31786
<223> OTHER INFORMATION: 99-13805-313.mis1 complement
<220> FEATURE:
<221> NAME/KEY: misc_binding
<222> LOCATION: 34771..34790
<223> OTHER INFORMATION: 99-1587-281.mis1
<220> FEATURE:
<221> NAME/KEY: misc_binding
<222> LOCATION: 34792..34811
<223> OTHER INFORMATION: 99-1587-281.mis2 complement
<220> FEATURE:
<221> NAME/KEY: misc_binding
<222> LOCATION: 45731..45750
<223> OTHER INFORMATION: 99-1582-430.mis1
<220> FEATURE:
<221> NAME/KEY: misc_binding
<222> LOCATION: 45752..45771
<223> OTHER INFORMATION: 99-1582-430.mis2 complement
<220> FEATURE:
<221> NAME/KEY: misc_binding
<222> LOCATION: 49827..49846
<223> OTHER INFORMATION: 99-1585-465.mis2
<220> FEATURE:
<221> NAME/KEY: misc_binding
<222> LOCATION: 49848..49867
<223> OTHER INFORMATION: 99-1585-465.mis1 complement
<220> FEATURE:
<221> NAME/KEY: misc_binding
<222> LOCATION: 49835..49854
<223> OTHER INFORMATION: 99-1585-457.mis2
<220> FEATURE:
<221> NAME/KEY: misc_binding
<222> LOCATION: 49856..49875
<223> OTHER INFORMATION: 99-1585-457.mis1 complement
<220> FEATURE:
<221> NAME/KEY: misc_binding
<222> LOCATION: 49866..49885
<223> OTHER INFORMATION: 99-1585-426.mis2
<220> FEATURE:
<221> NAME/KEY: misc_binding
<222> LOCATION: 49887..49906
```

-continued

```
<223> OTHER INFORMATION: 99-1585-426.mis1 complement
<220> FEATURE:
<221> NAME/KEY: misc_binding
<222> LOCATION: 49880..49899
<223> OTHER INFORMATION: 99-1585-412.mis2
<220> FEATURE:
<221> NAME/KEY: misc_binding
<222> LOCATION: 49901..49920
<223> OTHER INFORMATION: 99-1585-412.mis1 complement
<220> FEATURE:
<221> NAME/KEY: misc_binding
<222> LOCATION: 49886..49905
<223> OTHER INFORMATION: 99-1585-406.mis2
<220> FEATURE:
<221> NAME/KEY: misc_binding
<222> LOCATION: 49907..49926
<223> OTHER INFORMATION: 99-1585-406.mis1 complement
<220> FEATURE:
<221> NAME/KEY: misc_binding
<222> LOCATION: 49901..49920
<223> OTHER INFORMATION: 99-1585-391.mis2
<220> FEATURE:
<221> NAME/KEY: misc_binding
<222> LOCATION: 49922..49941
<223> OTHER INFORMATION: 99-1585-391.mis1 complement
<220> FEATURE:
<221> NAME/KEY: misc_binding
<222> LOCATION: 49919..49938
<223> OTHER INFORMATION: 99-1585-373.mis2
<220> FEATURE:
<221> NAME/KEY: misc_binding
<222> LOCATION: 49940..49959
<223> OTHER INFORMATION: 99-1585-373.mis1 complement
<220> FEATURE:
<221> NAME/KEY: misc_binding
<222> LOCATION: 50236..50255
<223> OTHER INFORMATION: 99-1585-55.mis2
<220> FEATURE:
<221> NAME/KEY: misc_binding
<222> LOCATION: 50257..50276
<223> OTHER INFORMATION: 99-1585-55.mis1 complement
<220> FEATURE:
<221> NAME/KEY: misc_binding
<222> LOCATION: 54935..54954
<223> OTHER INFORMATION: 99-1607-373.mis2
<220> FEATURE:
<221> NAME/KEY: misc_binding
<222> LOCATION: 54956..54975
<223> OTHER INFORMATION: 99-1607-373.mis1 complement
<220> FEATURE:
<221> NAME/KEY: misc_binding
<222> LOCATION: 64219..64238
<223> OTHER INFORMATION: 99-1577-105.mis1
<220> FEATURE:
<221> NAME/KEY: misc_binding
<222> LOCATION: 64240..64259
<223> OTHER INFORMATION: 99-1577-105.mis2 complement
<220> FEATURE:
<221> NAME/KEY: misc_binding
<222> LOCATION: 65416..65435
<223> OTHER INFORMATION: 99-1591-235.mis1
<220> FEATURE:
<221> NAME/KEY: misc_binding
<222> LOCATION: 65437..65456
<223> OTHER INFORMATION: 99-1591-235.mis2 complement
<220> FEATURE:
<221> NAME/KEY: misc_binding
<222> LOCATION: 65476..65495
<223> OTHER INFORMATION: 99-1591-295.mis1
<220> FEATURE:
<221> NAME/KEY: misc_binding
<222> LOCATION: 65497..65516
<223> OTHER INFORMATION: 99-1591-295.mis2 complement
<220> FEATURE:
<221> NAME/KEY: misc_binding
<222> LOCATION: 66947..66966
<223> OTHER INFORMATION: 99-1572-315.mis1
<220> FEATURE:
<221> NAME/KEY: misc_binding
```

```
<222> LOCATION: 66968..66987
<223> OTHER INFORMATION: 99-1572-315.mis2 complement
<220> FEATURE:
<221> NAME/KEY: misc_binding
<222> LOCATION: 66967..66986
<223> OTHER INFORMATION: 99-1572-335.mis1
<220> FEATURE:
<221> NAME/KEY: misc_binding
<222> LOCATION: 66988..67007
<223> OTHER INFORMATION: 99-1572-335.mis2 complement
<220> FEATURE:
<221> NAME/KEY: misc_binding
<222> LOCATION: 67072..67091
<223> OTHER INFORMATION: 99-1572-440.mis1
<220> FEATURE:
<221> NAME/KEY: misc_binding
<222> LOCATION: 67093..67112
<223> OTHER INFORMATION: 99-1572-440.mis2 complement
<220> FEATURE:
<221> NAME/KEY: misc_binding
<222> LOCATION: 67109..67128
<223> OTHER INFORMATION: 99-1572-477.mis1
<220> FEATURE:
<221> NAME/KEY: misc_binding
<222> LOCATION: 67130..67149
<223> OTHER INFORMATION: 99-1572-477.mis2 complement
<220> FEATURE:
<221> NAME/KEY: misc_binding
<222> LOCATION: 67209..67228
<223> OTHER INFORMATION: 99-1572-578.mis1
<220> FEATURE:
<221> NAME/KEY: misc_binding
<222> LOCATION: 67230..67249
<223> OTHER INFORMATION: 99-1572-578.mis2 complement
<220> FEATURE:
<221> NAME/KEY: misc_binding
<222> LOCATION: 67413..67432
<223> OTHER INFORMATION: 5-264-188.mis1
<220> FEATURE:
<221> NAME/KEY: misc_binding
<222> LOCATION: 67434..67453
<223> OTHER INFORMATION: 5-264-188.mis2 complement
<220> FEATURE:
<221> NAME/KEY: misc_binding
<222> LOCATION: 67703..67722
<223> OTHER INFORMATION: 5-169-97.mis1
<220> FEATURE:
<221> NAME/KEY: misc_binding
<222> LOCATION: 67724..67743
<223> OTHER INFORMATION: 5-169-97.mis2 complement
<220> FEATURE:
<221> NAME/KEY: misc_binding
<222> LOCATION: 67814..67833
<223> OTHER INFORMATION: 5-169-208.mis1
<220> FEATURE:
<221> NAME/KEY: misc_binding
<222> LOCATION: 67835..67854
<223> OTHER INFORMATION: 5-169-208.mis2 complement
<220> FEATURE:
<221> NAME/KEY: misc_binding
<222> LOCATION: 67935..67954
<223> OTHER INFORMATION: 5-169-331.mis1
<220> FEATURE:
<221> NAME/KEY: misc_binding
<222> LOCATION: 67956..67975
<223> OTHER INFORMATION: 5-169-331.mis2 complement
<220> FEATURE:
<221> NAME/KEY: misc_binding
<222> LOCATION: 68193..68212
<223> OTHER INFORMATION: 5-170-238.mis1
<220> FEATURE:
<221> NAME/KEY: misc_binding
<222> LOCATION: 68214..68233
<223> OTHER INFORMATION: 5-170-238.mis2 complement
<220> FEATURE:
<221> NAME/KEY: misc_binding
<222> LOCATION: 68243..68262
<223> OTHER INFORMATION: 5-170-288.mis1
<220> FEATURE:
```

```
<221> NAME/KEY: misc_binding
<222> LOCATION: 68264..68283
<223> OTHER INFORMATION: 5-170-288.mis2 complement
<220> FEATURE:
<221> NAME/KEY: misc_binding
<222> LOCATION: 68355..68374
<223> OTHER INFORMATION: 5-170-400.mis1
<220> FEATURE:
<221> NAME/KEY: misc_binding
<222> LOCATION: 68376..68395
<223> OTHER INFORMATION: 5-170-400.mis2 complement
<220> FEATURE:
<221> NAME/KEY: misc_binding
<222> LOCATION: 68457..68476
<223> OTHER INFORMATION: 5-171-156.mis1
<220> FEATURE:
<221> NAME/KEY: misc_binding
<222> LOCATION: 68478..68497
<223> OTHER INFORMATION: 5-171-156.mis2 complement
<220> FEATURE:
<221> NAME/KEY: misc_binding
<222> LOCATION: 68505..68524
<223> OTHER INFORMATION: 5-171-204.mis1
<220> FEATURE:
<221> NAME/KEY: misc_binding
<222> LOCATION: 68526..68545
<223> OTHER INFORMATION: 5-171-204.mis2 complement
<220> FEATURE:
<221> NAME/KEY: misc_binding
<222> LOCATION: 68574..68593
<223> OTHER INFORMATION: 5-171-273.mis1
<220> FEATURE:
<221> NAME/KEY: misc_binding
<222> LOCATION: 68595..68614
<223> OTHER INFORMATION: 5-171-273.mis2 complement
<220> FEATURE:
<221> NAME/KEY: misc_binding
<222> LOCATION: 68590..68609
<223> OTHER INFORMATION: 5-171-289.mis1
<220> FEATURE:
<221> NAME/KEY: misc_binding
<222> LOCATION: 68611..68630
<223> OTHER INFORMATION: 5-171-289.mis2 complement
<220> FEATURE:
<221> NAME/KEY: misc_binding
<222> LOCATION: 70546..70565
<223> OTHER INFORMATION: 5-1-60.mis1
<220> FEATURE:
<221> NAME/KEY: misc_binding
<222> LOCATION: 70567..70586
<223> OTHER INFORMATION: 5-1-60.mis2 complement
<220> FEATURE:
<221> NAME/KEY: misc_binding
<222> LOCATION: 70708..70727
<223> OTHER INFORMATION: 5-1-222.mis1
<220> FEATURE:
<221> NAME/KEY: misc_binding
<222> LOCATION: 70729..70748
<223> OTHER INFORMATION: 5-1-222.mis2 complement
<220> FEATURE:
<221> NAME/KEY: misc_binding
<222> LOCATION: 80018..80037
<223> OTHER INFORMATION: 99-1578-99.mis1
<220> FEATURE:
<221> NAME/KEY: misc_binding
<222> LOCATION: 80039..80058
<223> OTHER INFORMATION: 99-1578-99.mis2 complement
<220> FEATURE:
<221> NAME/KEY: misc_binding
<222> LOCATION: 80098..80117
<223> OTHER INFORMATION: 99-1578-179.mis1
<220> FEATURE:
<221> NAME/KEY: misc_binding
<222> LOCATION: 80119..80138
<223> OTHER INFORMATION: 99-1578-179.mis2 complement
<220> FEATURE:
<221> NAME/KEY: misc_binding
<222> LOCATION: 80150..80169
<223> OTHER INFORMATION: 99-1578-231.mis1
```

```
<220> FEATURE:
<221> NAME/KEY: misc_binding
<222> LOCATION: 80171..80190
<223> OTHER INFORMATION: 99-1578-231.mis2 complement
<220> FEATURE:
<221> NAME/KEY: misc_binding
<222> LOCATION: 80163..80182
<223> OTHER INFORMATION: 99-1578-245.mis1
<220> FEATURE:
<221> NAME/KEY: misc_binding
<222> LOCATION: 80184..80203
<223> OTHER INFORMATION: 99-1578-245.mis2 complement
<220> FEATURE:
<221> NAME/KEY: misc_binding
<222> LOCATION: 80415..80434
<223> OTHER INFORMATION: 99-1578-496.mis1
<220> FEATURE:
<221> NAME/KEY: misc_binding
<222> LOCATION: 80436..80455
<223> OTHER INFORMATION: 99-1578-496.mis2 complement
<220> FEATURE:
<221> NAME/KEY: misc_binding
<222> LOCATION: 82070..82089
<223> OTHER INFORMATION: 5-2-30.mis1
<220> FEATURE:
<221> NAME/KEY: misc_binding
<222> LOCATION: 82091..82110
<223> OTHER INFORMATION: 5-2-30.mis2 complement
<220> FEATURE:
<221> NAME/KEY: misc_binding
<222> LOCATION: 82145..82164
<223> OTHER INFORMATION: 5-2-109.mis1
<220> FEATURE:
<221> NAME/KEY: misc_binding
<222> LOCATION: 82166..82185
<223> OTHER INFORMATION: 5-2-109.mis2 complement
<220> FEATURE:
<221> NAME/KEY: misc_binding
<222> LOCATION: 82149..82168
<223> OTHER INFORMATION: 5-2-113.mis1
<220> FEATURE:
<221> NAME/KEY: misc_binding
<222> LOCATION: 82170..82189
<223> OTHER INFORMATION: 5-2-113.mis2 complement
<220> FEATURE:
<221> NAME/KEY: misc_binding
<222> LOCATION: 82198..82217
<223> OTHER INFORMATION: 5-2-162.mis1
<220> FEATURE:
<221> NAME/KEY: misc_binding
<222> LOCATION: 82219..82238
<223> OTHER INFORMATION: 5-2-162.mis2 complement
<220> FEATURE:
<221> NAME/KEY: misc_binding
<222> LOCATION: 82214..82233
<223> OTHER INFORMATION: 5-2-178.mis1
<220> FEATURE:
<221> NAME/KEY: misc_binding
<222> LOCATION: 82235..82254
<223> OTHER INFORMATION: 5-2-178.mis2 complement
<220> FEATURE:
<221> NAME/KEY: misc_binding
<222> LOCATION: 82248..82267
<223> OTHER INFORMATION: 5-2-213.mis1
<220> FEATURE:
<221> NAME/KEY: misc_binding
<222> LOCATION: 82269..82288
<223> OTHER INFORMATION: 5-2-213.mis2 complement
<220> FEATURE:
<221> NAME/KEY: misc_binding
<222> LOCATION: 82373..82392
<223> OTHER INFORMATION: 99-1605-112.mis2
<220> FEATURE:
<221> NAME/KEY: misc_binding
<222> LOCATION: 82394..82413
<223> OTHER INFORMATION: 99-1605-112.mis1 complement
<220> FEATURE:
<221> NAME/KEY: misc_binding
<222> LOCATION: 83567..83586
```

```
<223> OTHER INFORMATION: 5-3-27.mis1
<220> FEATURE:
<221> NAME/KEY: misc_binding
<222> LOCATION: 83588..83607
<223> OTHER INFORMATION: 5-3-27.mis2 complement
<220> FEATURE:
<221> NAME/KEY: misc_binding
<222> LOCATION: 83623..83642
<223> OTHER INFORMATION: 5-3-83.mis1
<220> FEATURE:
<221> NAME/KEY: misc_binding
<222> LOCATION: 83644..83663
<223> OTHER INFORMATION: 5-3-83.mis2 complement
<220> FEATURE:
<221> NAME/KEY: misc_binding
<222> LOCATION: 83624..83643
<223> OTHER INFORMATION: 5-3-84.mis1
<220> FEATURE:
<221> NAME/KEY: misc_binding
<222> LOCATION: 83645..83664
<223> OTHER INFORMATION: 5-3-84.mis2 complement
<220> FEATURE:
<221> NAME/KEY: misc_binding
<222> LOCATION: 83788..83807
<223> OTHER INFORMATION: 5-3-248.mis1
<220> FEATURE:
<221> NAME/KEY: misc_binding
<222> LOCATION: 83809..83828
<223> OTHER INFORMATION: 5-3-248.mis2 complement
<220> FEATURE:
<221> NAME/KEY: misc_binding
<222> LOCATION: 83861..83880
<223> OTHER INFORMATION: 5-3-321.mis1
<220> FEATURE:
<221> NAME/KEY: misc_binding
<222> LOCATION: 83882..83901
<223> OTHER INFORMATION: 5-3-321.mis2 complement
<220> FEATURE:
<221> NAME/KEY: misc_binding
<222> LOCATION: 83864..83883
<223> OTHER INFORMATION: 5-3-324.mis1
<220> FEATURE:
<221> NAME/KEY: misc_binding
<222> LOCATION: 83885..83904
<223> OTHER INFORMATION: 5-3-324.mis2 complement
<220> FEATURE:
<221> NAME/KEY: misc_binding
<222> LOCATION: 83889..83908
<223> OTHER INFORMATION: 5-4-313.mis1
<220> FEATURE:
<221> NAME/KEY: misc_binding
<222> LOCATION: 83910..83929
<223> OTHER INFORMATION: 5-4-313.mis2 complement
<220> FEATURE:
<221> NAME/KEY: misc_binding
<222> LOCATION: 83917..83936
<223> OTHER INFORMATION: 5-3-377.mis1
<220> FEATURE:
<221> NAME/KEY: misc_binding
<222> LOCATION: 83938..83957
<223> OTHER INFORMATION: 5-3-377.mis2 complement
<220> FEATURE:
<221> NAME/KEY: misc_binding
<222> LOCATION: 83927..83946
<223> OTHER INFORMATION: 5-4-351.mis1
<220> FEATURE:
<221> NAME/KEY: misc_binding
<222> LOCATION: 83948..83967
<223> OTHER INFORMATION: 5-4-351.mis2 complement
<220> FEATURE:
<221> NAME/KEY: misc_binding
<222> LOCATION: 83962..83981
<223> OTHER INFORMATION: 5-4-386.mis1
<220> FEATURE:
<221> NAME/KEY: misc_binding
<222> LOCATION: 83983..84002
<223> OTHER INFORMATION: 5-4-386.mis2 complement
<220> FEATURE:
<221> NAME/KEY: misc_binding
```

```
<222> LOCATION: 83968..83987
<223> OTHER INFORMATION: 5-4-392.mis1
<220> FEATURE:
<221> NAME/KEY: misc_binding
<222> LOCATION: 83989..84008
<223> OTHER INFORMATION: 5-4-392.mis2 complement
<220> FEATURE:
<221> NAME/KEY: misc_binding
<222> LOCATION: 84027..84046
<223> OTHER INFORMATION: 5-260-255.mis1
<220> FEATURE:
<221> NAME/KEY: misc_binding
<222> LOCATION: 84048..84067
<223> OTHER INFORMATION: 5-260-255.mis2 complement
<220> FEATURE:
<221> NAME/KEY: misc_binding
<222> LOCATION: 84072..84091
<223> OTHER INFORMATION: 5-260-300.mis1
<220> FEATURE:
<221> NAME/KEY: misc_binding
<222> LOCATION: 84093..84112
<223> OTHER INFORMATION: 5-260-300.mis2 complement
<220> FEATURE:
<221> NAME/KEY: misc_binding
<222> LOCATION: 84125..84144
<223> OTHER INFORMATION: 5-260-353.mis1
<220> FEATURE:
<221> NAME/KEY: misc_binding
<222> LOCATION: 84146..84165
<223> OTHER INFORMATION: 5-260-353.mis2 complement
<220> FEATURE:
<221> NAME/KEY: misc_binding
<222> LOCATION: 85182..85201
<223> OTHER INFORMATION: 5-9-50.mis1
<220> FEATURE:
<221> NAME/KEY: misc_binding
<222> LOCATION: 85203..85222
<223> OTHER INFORMATION: 5-9-50.mis2 complement
<220> FEATURE:
<221> NAME/KEY: misc_binding
<222> LOCATION: 86239..86258
<223> OTHER INFORMATION: 5-5-21.mis1
<220> FEATURE:
<221> NAME/KEY: misc_binding
<222> LOCATION: 86260..86279
<223> OTHER INFORMATION: 5-5-21.mis2 complement
<220> FEATURE:
<221> NAME/KEY: misc_binding
<222> LOCATION: 86303..86322
<223> OTHER INFORMATION: 5-5-85.mis1
<220> FEATURE:
<221> NAME/KEY: misc_binding
<222> LOCATION: 86324..86343
<223> OTHER INFORMATION: 5-5-85.mis2 complement
<220> FEATURE:
<221> NAME/KEY: misc_binding
<222> LOCATION: 87693..87712
<223> OTHER INFORMATION: 5-202-95.mis1
<220> FEATURE:
<221> NAME/KEY: misc_binding
<222> LOCATION: 87714..87733
<223> OTHER INFORMATION: 5-202-95.mis2 complement
<220> FEATURE:
<221> NAME/KEY: misc_binding
<222> LOCATION: 87715..87734
<223> OTHER INFORMATION: 5-202-117.mis1
<220> FEATURE:
<221> NAME/KEY: misc_binding
<222> LOCATION: 87736..87755
<223> OTHER INFORMATION: 5-202-117.mis2 complement
<220> FEATURE:
<221> NAME/KEY: misc_binding
<222> LOCATION: 87767..87786
<223> OTHER INFORMATION: 5-202-169.mis1
<220> FEATURE:
<221> NAME/KEY: misc_binding
<222> LOCATION: 87788..87807
<223> OTHER INFORMATION: 5-202-169.mis2 complement
<220> FEATURE:
```

-continued

```
<221> NAME/KEY: misc_binding
<222> LOCATION: 87786..87805
<223> OTHER INFORMATION: 5-202-188.mis1
<220> FEATURE:
<221> NAME/KEY: misc_binding
<222> LOCATION: 87807..87826
<223> OTHER INFORMATION: 5-202-188.mis2 complement
<220> FEATURE:
<221> NAME/KEY: misc_binding
<222> LOCATION: 87840..87859
<223> OTHER INFORMATION: 5-202-242.mis1
<220> FEATURE:
<221> NAME/KEY: misc_binding
<222> LOCATION: 87861..87880
<223> OTHER INFORMATION: 5-202-242.mis2 complement
<220> FEATURE:
<221> NAME/KEY: misc_binding
<222> LOCATION: 87882..87901
<223> OTHER INFORMATION: 5-202-284.mis1
<220> FEATURE:
<221> NAME/KEY: misc_binding
<222> LOCATION: 87903..87922
<223> OTHER INFORMATION: 5-202-284.mis2 complement
<220> FEATURE:
<221> NAME/KEY: misc_binding
<222> LOCATION: 87960..87979
<223> OTHER INFORMATION: 5-202-362.mis1
<220> FEATURE:
<221> NAME/KEY: misc_binding
<222> LOCATION: 87981..88000
<223> OTHER INFORMATION: 5-202-362.mis2 complement
<220> FEATURE:
<221> NAME/KEY: misc_binding
<222> LOCATION: 87992..88011
<223> OTHER INFORMATION: 5-202-394.mis1
<220> FEATURE:
<221> NAME/KEY: misc_binding
<222> LOCATION: 88013..88032
<223> OTHER INFORMATION: 5-202-394.mis2 complement
<220> FEATURE:
<221> NAME/KEY: misc_binding
<222> LOCATION: 88195..88214
<223> OTHER INFORMATION: 5-7-113.mis1
<220> FEATURE:
<221> NAME/KEY: misc_binding
<222> LOCATION: 88216..88235
<223> OTHER INFORMATION: 5-7-113.mis2 complement
<220> FEATURE:
<221> NAME/KEY: misc_binding
<222> LOCATION: 88263..88282
<223> OTHER INFORMATION: 5-7-181.mis1
<220> FEATURE:
<221> NAME/KEY: misc_binding
<222> LOCATION: 88284..88303
<223> OTHER INFORMATION: 5-7-181.mis2 complement
<220> FEATURE:
<221> NAME/KEY: misc_binding
<222> LOCATION: 88277..88296
<223> OTHER INFORMATION: 5-7-195.mis1
<220> FEATURE:
<221> NAME/KEY: misc_binding
<222> LOCATION: 88298..88317
<223> OTHER INFORMATION: 5-7-195.mis2 complement
<220> FEATURE:
<221> NAME/KEY: misc_binding
<222> LOCATION: 88422..88441
<223> OTHER INFORMATION: 5-7-340.mis1
<220> FEATURE:
<221> NAME/KEY: misc_binding
<222> LOCATION: 88443..88462
<223> OTHER INFORMATION: 5-7-340.mis2 complement
<220> FEATURE:
<221> NAME/KEY: misc_binding
<222> LOCATION: 88451..88470
<223> OTHER INFORMATION: 5-7-369.mis1
<220> FEATURE:
<221> NAME/KEY: misc_binding
<222> LOCATION: 88472..88491
<223> OTHER INFORMATION: 5-7-369.mis2 complement
```

```
<220> FEATURE:
<221> NAME/KEY: misc_binding
<222> LOCATION: 88460..88479
<223> OTHER INFORMATION: 5-7-378.mis1
<220> FEATURE:
<221> NAME/KEY: misc_binding
<222> LOCATION: 88481..88500
<223> OTHER INFORMATION: 5-7-378.mis2 complement
<220> FEATURE:
<221> NAME/KEY: misc_binding
<222> LOCATION: 89374..89393
<223> OTHER INFORMATION: 5-181-57.mis1
<220> FEATURE:
<221> NAME/KEY: misc_binding
<222> LOCATION: 89395..89414
<223> OTHER INFORMATION: 5-181-57.mis2 complement
<220> FEATURE:
<221> NAME/KEY: misc_binding
<222> LOCATION: 89444..89463
<223> OTHER INFORMATION: 5-181-127.mis1
<220> FEATURE:
<221> NAME/KEY: misc_binding
<222> LOCATION: 89465..89484
<223> OTHER INFORMATION: 5-181-127.mis2 complement
<220> FEATURE:
<221> NAME/KEY: misc_binding
<222> LOCATION: 89451..89470
<223> OTHER INFORMATION: 5-181-134.mis1
<220> FEATURE:
<221> NAME/KEY: misc_binding
<222> LOCATION: 89472..89491
<223> OTHER INFORMATION: 5-181-134.mis2 complement
<220> FEATURE:
<221> NAME/KEY: misc_binding
<222> LOCATION: 89638..89657
<223> OTHER INFORMATION: 5-181-321.mis1
<220> FEATURE:
<221> NAME/KEY: misc_binding
<222> LOCATION: 89659..89678
<223> OTHER INFORMATION: 5-181-321.mis2 complement
<220> FEATURE:
<221> NAME/KEY: misc_binding
<222> LOCATION: 92740..92759
<223> OTHER INFORMATION: 5-10-39.mis1
<220> FEATURE:
<221> NAME/KEY: misc_binding
<222> LOCATION: 92761..92780
<223> OTHER INFORMATION: 5-10-39.mis2 complement
<220> FEATURE:
<221> NAME/KEY: misc_binding
<222> LOCATION: 93003..93022
<223> OTHER INFORMATION: 5-10-302.mis1
<220> FEATURE:
<221> NAME/KEY: misc_binding
<222> LOCATION: 93024..93043
<223> OTHER INFORMATION: 5-10-302.mis2 complement
<220> FEATURE:
<221> NAME/KEY: misc_binding
<222> LOCATION: 93035..93054
<223> OTHER INFORMATION: 5-10-334.mis1
<220> FEATURE:
<221> NAME/KEY: misc_binding
<222> LOCATION: 93056..93075
<223> OTHER INFORMATION: 5-10-334.mis2 complement
<220> FEATURE:
<221> NAME/KEY: misc_binding
<222> LOCATION: 93227..93246
<223> OTHER INFORMATION: 5-11-158.mis1
<220> FEATURE:
<221> NAME/KEY: misc_binding
<222> LOCATION: 93248..93267
<223> OTHER INFORMATION: 5-11-158.mis2 complement
<220> FEATURE:
<221> NAME/KEY: misc_binding
<222> LOCATION: 93299..93318
<223> OTHER INFORMATION: 5-11-230.mis1
<220> FEATURE:
<221> NAME/KEY: misc_binding
<222> LOCATION: 93320..93339
```

-continued

```
<223> OTHER INFORMATION: 5-11-230.mis2 complement
<220> FEATURE:
<221> NAME/KEY: misc_binding
<222> LOCATION: 93303..93322
<223> OTHER INFORMATION: 5-11-234.mis1
<220> FEATURE:
<221> NAME/KEY: misc_binding
<222> LOCATION: 93324..93343
<223> OTHER INFORMATION: 5-11-234.mis2 complement
<220> FEATURE:
<221> NAME/KEY: misc_binding
<222> LOCATION: 93368..93387
<223> OTHER INFORMATION: 5-11-299.mis1
<220> FEATURE:
<221> NAME/KEY: misc_binding
<222> LOCATION: 93389..93408
<223> OTHER INFORMATION: 5-11-299.mis2 complement
<220> FEATURE:
<221> NAME/KEY: misc_binding
<222> LOCATION: 93373..93392
<223> OTHER INFORMATION: 5-11-304.mis1
<220> FEATURE:
<221> NAME/KEY: misc_binding
<222> LOCATION: 93394..93413
<223> OTHER INFORMATION: 5-11-304.mis2 complement
<220> FEATURE:
<221> NAME/KEY: misc_binding
<222> LOCATION: 93398..93417
<223> OTHER INFORMATION: 5-11-329.mis1
<220> FEATURE:
<221> NAME/KEY: misc_binding
<222> LOCATION: 93419..93438
<223> OTHER INFORMATION: 5-11-329.mis2 complement
<220> FEATURE:
<221> NAME/KEY: misc_binding
<222> LOCATION: 93495..93514
<223> OTHER INFORMATION: 5-12-56.mis1
<220> FEATURE:
<221> NAME/KEY: misc_binding
<222> LOCATION: 93516..93535
<223> OTHER INFORMATION: 5-12-56.mis2 complement
<220> FEATURE:
<221> NAME/KEY: misc_binding
<222> LOCATION: 93706..93725
<223> OTHER INFORMATION: 5-12-267.mis1
<220> FEATURE:
<221> NAME/KEY: misc_binding
<222> LOCATION: 93727..93746
<223> OTHER INFORMATION: 5-12-267.mis2 complement
<220> FEATURE:
<221> NAME/KEY: misc_binding
<222> LOCATION: 93883..93902
<223> OTHER INFORMATION: 5-13-145.mis1
<220> FEATURE:
<221> NAME/KEY: misc_binding
<222> LOCATION: 93904..93923
<223> OTHER INFORMATION: 5-13-145.mis2 complement
<220> FEATURE:
<221> NAME/KEY: misc_binding
<222> LOCATION: 94150..94169
<223> OTHER INFORMATION: 5-14-44.mis1
<220> FEATURE:
<221> NAME/KEY: misc_binding
<222> LOCATION: 94171..94190
<223> OTHER INFORMATION: 5-14-44.mis2 complement
<220> FEATURE:
<221> NAME/KEY: misc_binding
<222> LOCATION: 94198..94217
<223> OTHER INFORMATION: 5-14-93.mis1
<220> FEATURE:
<221> NAME/KEY: misc_binding
<222> LOCATION: 94219..94238
<223> OTHER INFORMATION: 5-14-93.mis2 complement
<220> FEATURE:
<221> NAME/KEY: misc_binding
<222> LOCATION: 94249..94268
<223> OTHER INFORMATION: 5-14-144.mis1
<220> FEATURE:
<221> NAME/KEY: misc_binding
```

```
<222> LOCATION: 94270..94289
<223> OTHER INFORMATION: 5-14-144.mis2 complement
<220> FEATURE:
<221> NAME/KEY: misc_binding
<222> LOCATION: 94270..94289
<223> OTHER INFORMATION: 5-14-165.mis1
<220> FEATURE:
<221> NAME/KEY: misc_binding
<222> LOCATION: 94291..94310
<223> OTHER INFORMATION: 5-14-165.mis2 complement
<220> FEATURE:
<221> NAME/KEY: misc_binding
<222> LOCATION: 94402..94421
<223> OTHER INFORMATION: 5-14-297.mis1
<220> FEATURE:
<221> NAME/KEY: misc_binding
<222> LOCATION: 94423..94442
<223> OTHER INFORMATION: 5-14-297.mis2 complement
<220> FEATURE:
<221> NAME/KEY: misc_binding
<222> LOCATION: 94412..94431
<223> OTHER INFORMATION: 5-14-307.mis1
<220> FEATURE:
<221> NAME/KEY: misc_binding
<222> LOCATION: 94433..94452
<223> OTHER INFORMATION: 5-14-307.mis2 complement
<220> FEATURE:
<221> NAME/KEY: misc_binding
<222> LOCATION: 94700..94719
<223> OTHER INFORMATION: 5-15-219.mis1
<220> FEATURE:
<221> NAME/KEY: misc_binding
<222> LOCATION: 94721..94740
<223> OTHER INFORMATION: 5-15-219.mis2 complement
<220> FEATURE:
<221> NAME/KEY: misc_binding
<222> LOCATION: 94969..94988
<223> OTHER INFORMATION: 5-16-157.mis1
<220> FEATURE:
<221> NAME/KEY: misc_binding
<222> LOCATION: 94990..95009
<223> OTHER INFORMATION: 5-16-157.mis2 complement
<220> FEATURE:
<221> NAME/KEY: misc_binding
<222> LOCATION: 95241..95260
<223> OTHER INFORMATION: 5-17-140.mis1
<220> FEATURE:
<221> NAME/KEY: misc_binding
<222> LOCATION: 95262..95281
<223> OTHER INFORMATION: 5-17-140.mis2 complement
<220> FEATURE:
<221> NAME/KEY: misc_binding
<222> LOCATION: 95320..95339
<223> OTHER INFORMATION: 5-18-51.mis1
<220> FEATURE:
<221> NAME/KEY: misc_binding
<222> LOCATION: 95341..95360
<223> OTHER INFORMATION: 5-18-51.mis2 complement
<220> FEATURE:
<221> NAME/KEY: misc_binding
<222> LOCATION: 95477..95496
<223> OTHER INFORMATION: 5-18-208.mis1
<220> FEATURE:
<221> NAME/KEY: misc_binding
<222> LOCATION: 95498..95517
<223> OTHER INFORMATION: 5-18-208.mis2 complement
<220> FEATURE:
<221> NAME/KEY: misc_binding
<222> LOCATION: 95750..95769
<223> OTHER INFORMATION: 5-300-238.mis1
<220> FEATURE:
<221> NAME/KEY: misc_binding
<222> LOCATION: 95771..95790
<223> OTHER INFORMATION: 5-300-238.mis2 complement
<220> FEATURE:
<221> NAME/KEY: misc_binding
<222> LOCATION: 95799..95818
<223> OTHER INFORMATION: 5-300-287.mis1
<220> FEATURE:
```

-continued

```
<221> NAME/KEY: misc_binding
<222> LOCATION: 95820..95839
<223> OTHER INFORMATION: 5-300-287.mis2 complement
<220> FEATURE:
<221> NAME/KEY: misc_binding
<222> LOCATION: 96125..96144
<223> OTHER INFORMATION: 5-262-49.mis1
<220> FEATURE:
<221> NAME/KEY: misc_binding
<222> LOCATION: 96146..96165
<223> OTHER INFORMATION: 5-262-49.mis2 complement
<220> FEATURE:
<221> NAME/KEY: misc_binding
<222> LOCATION: 96161..96180
<223> OTHER INFORMATION: 5-262-85.mis1
<220> FEATURE:
<221> NAME/KEY: misc_binding
<222> LOCATION: 96182..96201
<223> OTHER INFORMATION: 5-262-85.mis2 complement
<220> FEATURE:
<221> NAME/KEY: misc_binding
<222> LOCATION: 96330..96349
<223> OTHER INFORMATION: 5-262-254.mis1
<220> FEATURE:
<221> NAME/KEY: misc_binding
<222> LOCATION: 96351..96370
<223> OTHER INFORMATION: 5-262-254.mis2 complement
<220> FEATURE:
<221> NAME/KEY: misc_binding
<222> LOCATION: 96931..96950
<223> OTHER INFORMATION: 5-263-404.mis1
<220> FEATURE:
<221> NAME/KEY: misc_binding
<222> LOCATION: 96952..96971
<223> OTHER INFORMATION: 5-263-404.mis2 complement
<220> FEATURE:
<221> NAME/KEY: misc_binding
<222> LOCATION: 97124..97143
<223> OTHER INFORMATION: 5-265-244.mis1
<220> FEATURE:
<221> NAME/KEY: misc_binding
<222> LOCATION: 97145..97164
<223> OTHER INFORMATION: 5-265-244.mis2 complement
<220> FEATURE:
<221> NAME/KEY: misc_binding
<222> LOCATION: 97256..97275
<223> OTHER INFORMATION: 5-265-376.mis1
<220> FEATURE:
<221> NAME/KEY: misc_binding
<222> LOCATION: 97277..97296
<223> OTHER INFORMATION: 5-265-376.mis2 complement
<220> FEATURE:
<221> NAME/KEY: misc_binding
<222> LOCATION: 102247..102266
<223> OTHER INFORMATION: 99-7183-338.mis2
<220> FEATURE:
<221> NAME/KEY: misc_binding
<222> LOCATION: 102268..102287
<223> OTHER INFORMATION: 99-7183-338.mis1 complement
<220> FEATURE:
<221> NAME/KEY: misc_binding
<222> LOCATION: 105917..105936
<223> OTHER INFORMATION: 99-7207-138.mis2
<220> FEATURE:
<221> NAME/KEY: misc_binding
<222> LOCATION: 105938..105957
<223> OTHER INFORMATION: 99-7207-138.mis1 complement
<220> FEATURE:
<221> NAME/KEY: misc_binding
<222> LOCATION: 255..301
<223> OTHER INFORMATION: 99-1601-278.probe
<220> FEATURE:
<221> NAME/KEY: misc_binding
<222> LOCATION: 379..425
<223> OTHER INFORMATION: 99-1601-402.probe
<220> FEATURE:
<221> NAME/KEY: misc_binding
<222> LOCATION: 449..495
<223> OTHER INFORMATION: 99-1601-472.probe
```

-continued

```
<220> FEATURE:
<221> NAME/KEY: misc_binding
<222> LOCATION: 2932..2978
<223> OTHER INFORMATION: 99-13801-100.probe
<220> FEATURE:
<221> NAME/KEY: misc_binding
<222> LOCATION: 12144..12190
<223> OTHER INFORMATION: 99-13806-166.probe
<220> FEATURE:
<221> NAME/KEY: misc_binding
<222> LOCATION: 12513..12559
<223> OTHER INFORMATION: 99-13799-376.probe
<220> FEATURE:
<221> NAME/KEY: misc_binding
<222> LOCATION: 17570..17616
<223> OTHER INFORMATION: 99-13798-297.probe
<220> FEATURE:
<221> NAME/KEY: misc_binding
<222> LOCATION: 17583..17629
<223> OTHER INFORMATION: 99-13798-284.probe
<220> FEATURE:
<221> NAME/KEY: misc_binding
<222> LOCATION: 22056..22102
<223> OTHER INFORMATION: 99-1602-200.probe
<220> FEATURE:
<221> NAME/KEY: misc_binding
<222> LOCATION: 28941..28987
<223> OTHER INFORMATION: 99-13794-186.probe
<220> FEATURE:
<221> NAME/KEY: misc_binding
<222> LOCATION: 28980..29026
<223> OTHER INFORMATION: 99-13794-147.probe
<220> FEATURE:
<221> NAME/KEY: misc_binding
<222> LOCATION: 31054..31100
<223> OTHER INFORMATION: 99-13812-384.probe
<220> FEATURE:
<221> NAME/KEY: misc_binding
<222> LOCATION: 31743..31789
<223> OTHER INFORMATION: 99-13805-313.probe
<220> FEATURE:
<221> NAME/KEY: misc_binding
<222> LOCATION: 34768..34814
<223> OTHER INFORMATION: 99-1587-281.probe
<220> FEATURE:
<221> NAME/KEY: misc_binding
<222> LOCATION: 45728..45774
<223> OTHER INFORMATION: 99-1582-430.probe
<220> FEATURE:
<221> NAME/KEY: misc_binding
<222> LOCATION: 49824..49870
<223> OTHER INFORMATION: 99-1585-465.probe
<220> FEATURE:
<221> NAME/KEY: misc_binding
<222> LOCATION: 49832..49878
<223> OTHER INFORMATION: 99-1585-457.probe
<220> FEATURE:
<221> NAME/KEY: misc_binding
<222> LOCATION: 49863..49909
<223> OTHER INFORMATION: 99-1585-426.probe
<220> FEATURE:
<221> NAME/KEY: misc_binding
<222> LOCATION: 49877..49923
<223> OTHER INFORMATION: 99-1585-412.probe
<220> FEATURE:
<221> NAME/KEY: misc_binding
<222> LOCATION: 49883..49929
<223> OTHER INFORMATION: 99-1585-406.probe
<220> FEATURE:
<221> NAME/KEY: misc_binding
<222> LOCATION: 49898..49944
<223> OTHER INFORMATION: 99-1585-391.probe
<220> FEATURE:
<221> NAME/KEY: misc_binding
<222> LOCATION: 49916..49962
<223> OTHER INFORMATION: 99-1585-373.probe
<220> FEATURE:
<221> NAME/KEY: misc_binding
<222> LOCATION: 50233..50279
```

```
<223> OTHER INFORMATION: 99-1585-55.probe
<220> FEATURE:
<221> NAME/KEY: misc_binding
<222> LOCATION: 54932..54978
<223> OTHER INFORMATION: 99-1607-373.probe
<220> FEATURE:
<221> NAME/KEY: misc_binding
<222> LOCATION: 64216..64262
<223> OTHER INFORMATION: 99-1577-105.probe
<220> FEATURE:
<221> NAME/KEY: misc_binding
<222> LOCATION: 65413..65459
<223> OTHER INFORMATION: 99-1591-235.probe
<220> FEATURE:
<221> NAME/KEY: misc_binding
<222> LOCATION: 65473..65519
<223> OTHER INFORMATION: 99-1591-295.probe
<220> FEATURE:
<221> NAME/KEY: misc_binding
<222> LOCATION: 66944..66990
<223> OTHER INFORMATION: 99-1572-315.probe
<220> FEATURE:
<221> NAME/KEY: misc_binding
<222> LOCATION: 66964..67010
<223> OTHER INFORMATION: 99-1572-335.probe
<220> FEATURE:
<221> NAME/KEY: misc_binding
<222> LOCATION: 67069..67115
<223> OTHER INFORMATION: 99-1572-440.probe
<220> FEATURE:
<221> NAME/KEY: misc_binding
<222> LOCATION: 67106..67152
<223> OTHER INFORMATION: 99-1572-477.probe
<220> FEATURE:
<221> NAME/KEY: misc_binding
<222> LOCATION: 67206..67252
<223> OTHER INFORMATION: 99-1572-578.probe
<220> FEATURE:
<221> NAME/KEY: misc_binding
<222> LOCATION: 67410..67456
<223> OTHER INFORMATION: 5-264-188.probe
<220> FEATURE:
<221> NAME/KEY: misc_binding
<222> LOCATION: 67700..67746
<223> OTHER INFORMATION: 5-169-97.probe
<220> FEATURE:
<221> NAME/KEY: misc_binding
<222> LOCATION: 67811..67857
<223> OTHER INFORMATION: 5-169-208.probe
<220> FEATURE:
<221> NAME/KEY: misc_binding
<222> LOCATION: 67932..67978
<223> OTHER INFORMATION: 5-169-331.probe
<220> FEATURE:
<221> NAME/KEY: misc_binding
<222> LOCATION: 68190..68236
<223> OTHER INFORMATION: 5-170-238.probe
<220> FEATURE:
<221> NAME/KEY: misc_binding
<222> LOCATION: 68240..68286
<223> OTHER INFORMATION: 5-170-288.probe
<220> FEATURE:
<221> NAME/KEY: misc_binding
<222> LOCATION: 68352..68398
<223> OTHER INFORMATION: 5-170-400.probe
<220> FEATURE:
<221> NAME/KEY: misc_binding
<222> LOCATION: 68454..68500
<223> OTHER INFORMATION: 5-171-156.probe
<220> FEATURE:
<221> NAME/KEY: misc_binding
<222> LOCATION: 68502..68548
<223> OTHER INFORMATION: 5-171-204.probe
<220> FEATURE:
<221> NAME/KEY: misc_binding
<222> LOCATION: 68571..68617
<223> OTHER INFORMATION: 5-171-273.probe
<220> FEATURE:
<221> NAME/KEY: misc_binding
```

```
<222> LOCATION: 68587..68633
<223> OTHER INFORMATION: 5-171-289.probe
<220> FEATURE:
<221> NAME/KEY: misc_binding
<222> LOCATION: 70543..70589
<223> OTHER INFORMATION: 5-1-60.probe
<220> FEATURE:
<221> NAME/KEY: misc_binding
<222> LOCATION: 70705..70751
<223> OTHER INFORMATION: 5-1-222.probe
<220> FEATURE:
<221> NAME/KEY: misc_binding
<222> LOCATION: 80015..80061
<223> OTHER INFORMATION: 99-1578-99.probe
<220> FEATURE:
<221> NAME/KEY: misc_binding
<222> LOCATION: 80095..80141
<223> OTHER INFORMATION: 99-1578-179.probe
<220> FEATURE:
<221> NAME/KEY: misc_binding
<222> LOCATION: 80147..80193
<223> OTHER INFORMATION: 99-1578-231.probe
<220> FEATURE:
<221> NAME/KEY: misc_binding
<222> LOCATION: 80160..80206
<223> OTHER INFORMATION: 99-1578-245.probe
<220> FEATURE:
<221> NAME/KEY: misc_binding
<222> LOCATION: 80412..80458
<223> OTHER INFORMATION: 99-1578-496.probe
<220> FEATURE:
<221> NAME/KEY: misc_binding
<222> LOCATION: 82067..82113
<223> OTHER INFORMATION: 5-2-30.probe
<220> FEATURE:
<221> NAME/KEY: misc_binding
<222> LOCATION: 82142..82188
<223> OTHER INFORMATION: 5-2-109.probe
<220> FEATURE:
<221> NAME/KEY: misc_binding
<222> LOCATION: 82146..82192
<223> OTHER INFORMATION: 5-2-113.probe
<220> FEATURE:
<221> NAME/KEY: misc_binding
<222> LOCATION: 82195..82241
<223> OTHER INFORMATION: 5-2-162.probe
<220> FEATURE:
<221> NAME/KEY: misc_binding
<222> LOCATION: 82211..82257
<223> OTHER INFORMATION: 5-2-178.probe
<220> FEATURE:
<221> NAME/KEY: misc_binding
<222> LOCATION: 82245..82291
<223> OTHER INFORMATION: 5-2-213.probe
<220> FEATURE:
<221> NAME/KEY: misc_binding
<222> LOCATION: 82370..82416
<223> OTHER INFORMATION: 99-1605-112.probe
<220> FEATURE:
<221> NAME/KEY: misc_binding
<222> LOCATION: 83564..83610
<223> OTHER INFORMATION: 5-3-27.probe
<220> FEATURE:
<221> NAME/KEY: misc_binding
<222> LOCATION: 83620..83666
<223> OTHER INFORMATION: 5-3-83.probe
<220> FEATURE:
<221> NAME/KEY: misc_binding
<222> LOCATION: 83621..83667
<223> OTHER INFORMATION: 5-3-84.probe
<220> FEATURE:
<221> NAME/KEY: misc_binding
<222> LOCATION: 83785..83831
<223> OTHER INFORMATION: 5-3-248.probe
<220> FEATURE:
<221> NAME/KEY: misc_binding
<222> LOCATION: 83858..83904
<223> OTHER INFORMATION: 5-3-321.probe
<220> FEATURE:
```

-continued

```
<221> NAME/KEY: misc_binding
<222> LOCATION: 83861..83907
<223> OTHER INFORMATION: 5-3-324.probe
<220> FEATURE:
<221> NAME/KEY: misc_binding
<222> LOCATION: 83886..83932
<223> OTHER INFORMATION: 5-4-313.probe
<220> FEATURE:
<221> NAME/KEY: misc_binding
<222> LOCATION: 83914..83960
<223> OTHER INFORMATION: 5-3-377.probe
<220> FEATURE:
<221> NAME/KEY: misc_binding
<222> LOCATION: 83924..83970
<223> OTHER INFORMATION: 5-4-351.probe
<220> FEATURE:
<221> NAME/KEY: misc_binding
<222> LOCATION: 83959..84005
<223> OTHER INFORMATION: 5-4-386.probe
<220> FEATURE:
<221> NAME/KEY: misc_binding
<222> LOCATION: 83965..84011
<223> OTHER INFORMATION: 5-4-392.probe
<220> FEATURE:
<221> NAME/KEY: misc_binding
<222> LOCATION: 84024..84070
<223> OTHER INFORMATION: 5-260-255.probe
<220> FEATURE:
<221> NAME/KEY: misc_binding
<222> LOCATION: 84069..84115
<223> OTHER INFORMATION: 5-260-300.probe
<220> FEATURE:
<221> NAME/KEY: misc_binding
<222> LOCATION: 84122..84168
<223> OTHER INFORMATION: 5-260-353.probe
<220> FEATURE:
<221> NAME/KEY: misc_binding
<222> LOCATION: 85179..85225
<223> OTHER INFORMATION: 5-9-50.probe
<220> FEATURE:
<221> NAME/KEY: misc_binding
<222> LOCATION: 86236..86282
<223> OTHER INFORMATION: 5-5-21.probe
<220> FEATURE:
<221> NAME/KEY: misc_binding
<222> LOCATION: 86300..86346
<223> OTHER INFORMATION: 5-5-85.probe
<220> FEATURE:
<221> NAME/KEY: misc_binding
<222> LOCATION: 87690..87736
<223> OTHER INFORMATION: 5-202-95.probe
<220> FEATURE:
<221> NAME/KEY: misc_binding
<222> LOCATION: 87712..87758
<223> OTHER INFORMATION: 5-202-117.probe
<220> FEATURE:
<221> NAME/KEY: misc_binding
<222> LOCATION: 87764..87810
<223> OTHER INFORMATION: 5-202-169.probe
<220> FEATURE:
<221> NAME/KEY: misc_binding
<222> LOCATION: 87783..87829
<223> OTHER INFORMATION: 5-202-188.probe
<220> FEATURE:
<221> NAME/KEY: misc_binding
<222> LOCATION: 87837..87883
<223> OTHER INFORMATION: 5-202-242.probe
<220> FEATURE:
<221> NAME/KEY: misc_binding
<222> LOCATION: 87879..87925
<223> OTHER INFORMATION: 5-202-284.probe
<220> FEATURE:
<221> NAME/KEY: misc_binding
<222> LOCATION: 87957..88003
<223> OTHER INFORMATION: 5-202-362.probe
<220> FEATURE:
<221> NAME/KEY: misc_binding
<222> LOCATION: 87989..88035
<223> OTHER INFORMATION: 5-202-394.probe
```

```
<220> FEATURE:
<221> NAME/KEY: misc_binding
<222> LOCATION: 88192..88238
<223> OTHER INFORMATION: 5-7-113.probe
<220> FEATURE:
<221> NAME/KEY: misc_binding
<222> LOCATION: 88260..88306
<223> OTHER INFORMATION: 5-7-181.probe
<220> FEATURE:
<221> NAME/KEY: misc_binding
<222> LOCATION: 88274..88320
<223> OTHER INFORMATION: 5-7-195.probe
<220> FEATURE:
<221> NAME/KEY: misc_binding
<222> LOCATION: 88419..88465
<223> OTHER INFORMATION: 5-7-340.probe
<220> FEATURE:
<221> NAME/KEY: misc_binding
<222> LOCATION: 88448..88494
<223> OTHER INFORMATION: 5-7-369.probe
<220> FEATURE:
<221> NAME/KEY: misc_binding
<222> LOCATION: 88457..88503
<223> OTHER INFORMATION: 5-7-378.probe
<220> FEATURE:
<221> NAME/KEY: misc_binding
<222> LOCATION: 89371..89417
<223> OTHER INFORMATION: 5-181-57.probe
<220> FEATURE:
<221> NAME/KEY: misc_binding
<222> LOCATION: 89441..89487
<223> OTHER INFORMATION: 5-181-127.probe
<220> FEATURE:
<221> NAME/KEY: misc_binding
<222> LOCATION: 89448..89494
<223> OTHER INFORMATION: 5-181-134.probe
<220> FEATURE:
<221> NAME/KEY: misc_binding
<222> LOCATION: 89635..89681
<223> OTHER INFORMATION: 5-181-321.probe
<220> FEATURE:
<221> NAME/KEY: misc_binding
<222> LOCATION: 92737..92783
<223> OTHER INFORMATION: 5-10-39.probe
<220> FEATURE:
<221> NAME/KEY: misc_binding
<222> LOCATION: 93000..93046
<223> OTHER INFORMATION: 5-10-302.probe
<220> FEATURE:
<221> NAME/KEY: misc_binding
<222> LOCATION: 93032..93078
<223> OTHER INFORMATION: 5-10-334.probe
<220> FEATURE:
<221> NAME/KEY: misc_binding
<222> LOCATION: 93224..93270
<223> OTHER INFORMATION: 5-11-158.probe
<220> FEATURE:
<221> NAME/KEY: misc_binding
<222> LOCATION: 93296..93342
<223> OTHER INFORMATION: 5-11-230.probe
<220> FEATURE:
<221> NAME/KEY: misc_binding
<222> LOCATION: 93300..93346
<223> OTHER INFORMATION: 5-11-234.probe
<220> FEATURE:
<221> NAME/KEY: misc_binding
<222> LOCATION: 93365..93411
<223> OTHER INFORMATION: 5-11-299.probe
<220> FEATURE:
<221> NAME/KEY: misc_binding
<222> LOCATION: 93370..93416
<223> OTHER INFORMATION: 5-11-304.probe
<220> FEATURE:
<221> NAME/KEY: misc_binding
<222> LOCATION: 93395..93441
<223> OTHER INFORMATION: 5-11-329.probe
<220> FEATURE:
<221> NAME/KEY: misc_binding
<222> LOCATION: 93492..93538
```

```
<223> OTHER INFORMATION: 5-12-56.probe
<220> FEATURE:
<221> NAME/KEY: misc_binding
<222> LOCATION: 93703..93749
<223> OTHER INFORMATION: 5-12-267.probe
<220> FEATURE:
<221> NAME/KEY: misc_binding
<222> LOCATION: 93880..93926
<223> OTHER INFORMATION: 5-13-145.probe
<220> FEATURE:
<221> NAME/KEY: misc_binding
<222> LOCATION: 94147..94193
<223> OTHER INFORMATION: 5-14-44.probe
<220> FEATURE:
<221> NAME/KEY: misc_binding
<222> LOCATION: 94195..94241
<223> OTHER INFORMATION: 5-14-93.probe
<220> FEATURE:
<221> NAME/KEY: misc_binding
<222> LOCATION: 94246..94292
<223> OTHER INFORMATION: 5-14-144.probe
<220> FEATURE:
<221> NAME/KEY: misc_binding
<222> LOCATION: 94267..94313
<223> OTHER INFORMATION: 5-14-165.probe
<220> FEATURE:
<221> NAME/KEY: misc_binding
<222> LOCATION: 94399..94445
<223> OTHER INFORMATION: 5-14-297.probe
<220> FEATURE:
<221> NAME/KEY: misc_binding
<222> LOCATION: 94409..94455
<223> OTHER INFORMATION: 5-14-307.probe
<220> FEATURE:
<221> NAME/KEY: misc_binding
<222> LOCATION: 94697..94743
<223> OTHER INFORMATION: 5-15-219.probe
<220> FEATURE:
<221> NAME/KEY: misc_binding
<222> LOCATION: 94966..95012
<223> OTHER INFORMATION: 5-16-157.probe
<220> FEATURE:
<221> NAME/KEY: misc_binding
<222> LOCATION: 95238..95284
<223> OTHER INFORMATION: 5-17-140.probe
<220> FEATURE:
<221> NAME/KEY: misc_binding
<222> LOCATION: 95317..95363
<223> OTHER INFORMATION: 5-18-51.probe
<220> FEATURE:
<221> NAME/KEY: misc_binding
<222> LOCATION: 95474..95520
<223> OTHER INFORMATION: 5-18-208.probe
<220> FEATURE:
<221> NAME/KEY: misc_binding
<222> LOCATION: 95747..95793
<223> OTHER INFORMATION: 5-300-238.probe
<220> FEATURE:
<221> NAME/KEY: misc_binding
<222> LOCATION: 95796..95842
<223> OTHER INFORMATION: 5-300-287.probe
<220> FEATURE:
<221> NAME/KEY: misc_binding
<222> LOCATION: 96122..96168
<223> OTHER INFORMATION: 5-262-49.probe
<220> FEATURE:
<221> NAME/KEY: misc_binding
<222> LOCATION: 96158..96204
<223> OTHER INFORMATION: 5-262-85.probe
<220> FEATURE:
<221> NAME/KEY: misc_binding
<222> LOCATION: 96327..96373
<223> OTHER INFORMATION: 5-262-254.probe
<220> FEATURE:
<221> NAME/KEY: misc_binding
<222> LOCATION: 96928..96974
<223> OTHER INFORMATION: 5-263-404.probe
<220> FEATURE:
<221> NAME/KEY: misc_binding
```

```
<222> LOCATION: 97121..97167
<223> OTHER INFORMATION: 5-265-244.probe
<220> FEATURE:
<221> NAME/KEY: misc_binding
<222> LOCATION: 97253..97299
<223> OTHER INFORMATION: 5-265-376.probe
<220> FEATURE:
<221> NAME/KEY: misc_binding
<222> LOCATION: 102244..102290
<223> OTHER INFORMATION: 99-7183-338.probe
<220> FEATURE:
<221> NAME/KEY: misc_binding
<222> LOCATION: 105914..105960
<223> OTHER INFORMATION: 99-7207-138.probe
<220> FEATURE:
<221> NAME/KEY: misc_binding
<222> LOCATION: 1..18
<223> OTHER INFORMATION: 99-1601.pu
<220> FEATURE:
<221> NAME/KEY: misc_binding
<222> LOCATION: 486..506
<223> OTHER INFORMATION: 99-1601.rp complement
<220> FEATURE:
<221> NAME/KEY: misc_binding
<222> LOCATION: 2607..2627
<223> OTHER INFORMATION: 99-13801.rp
<220> FEATURE:
<221> NAME/KEY: misc_binding
<222> LOCATION: 3035..3054
<223> OTHER INFORMATION: 99-13801.pu complement
<220> FEATURE:
<221> NAME/KEY: misc_binding
<222> LOCATION: 11883..11902
<223> OTHER INFORMATION: 99-13806.rp
<220> FEATURE:
<221> NAME/KEY: misc_binding
<222> LOCATION: 12313..12331
<223> OTHER INFORMATION: 99-13806.pu complement
<220> FEATURE:
<221> NAME/KEY: misc_binding
<222> LOCATION: 12379..12399
<223> OTHER INFORMATION: 99-13799.rp
<220> FEATURE:
<221> NAME/KEY: misc_binding
<222> LOCATION: 12889..12909
<223> OTHER INFORMATION: 99-13799.pu complement
<220> FEATURE:
<221> NAME/KEY: misc_binding
<222> LOCATION: 17442..17462
<223> OTHER INFORMATION: 99-13798.rp
<220> FEATURE:
<221> NAME/KEY: misc_binding
<222> LOCATION: 17868..17887
<223> OTHER INFORMATION: 99-13798.pu complement
<220> FEATURE:
<221> NAME/KEY: misc_binding
<222> LOCATION: 21881..21899
<223> OTHER INFORMATION: 99-1602.pu
<220> FEATURE:
<221> NAME/KEY: misc_binding
<222> LOCATION: 22487..22506
<223> OTHER INFORMATION: 99-1602.rp complement
<220> FEATURE:
<221> NAME/KEY: misc_binding
<222> LOCATION: 28669..28689
<223> OTHER INFORMATION: 99-13794.rp
<220> FEATURE:
<221> NAME/KEY: misc_binding
<222> LOCATION: 29131..29149
<223> OTHER INFORMATION: 99-13794.pu complement
<220> FEATURE:
<221> NAME/KEY: misc_binding
<222> LOCATION: 30941..30961
<223> OTHER INFORMATION: 99-13812.rp
<220> FEATURE:
<221> NAME/KEY: misc_binding
<222> LOCATION: 31437..31457
<223> OTHER INFORMATION: 99-13812.pu complement
<220> FEATURE:
```

```
<221> NAME/KEY: misc_binding
<222> LOCATION: 31560..31579
<223> OTHER INFORMATION: 99-13805.rp
<220> FEATURE:
<221> NAME/KEY: misc_binding
<222> LOCATION: 32057..32075
<223> OTHER INFORMATION: 99-13805.pu complement
<220> FEATURE:
<221> NAME/KEY: misc_binding
<222> LOCATION: 34515..34535
<223> OTHER INFORMATION: 99-1587.pu
<220> FEATURE:
<221> NAME/KEY: misc_binding
<222> LOCATION: 34890..34909
<223> OTHER INFORMATION: 99-1587.rp complement
<220> FEATURE:
<221> NAME/KEY: misc_binding
<222> LOCATION: 45325..45343
<223> OTHER INFORMATION: 99-1582.pu
<220> FEATURE:
<221> NAME/KEY: misc_binding
<222> LOCATION: 46000..46018
<223> OTHER INFORMATION: 99-1582.rp complement
<220> FEATURE:
<221> NAME/KEY: misc_binding
<222> LOCATION: 49765..49784
<223> OTHER INFORMATION: 99-1585.rp
<220> FEATURE:
<221> NAME/KEY: misc_binding
<222> LOCATION: 50291..50310
<223> OTHER INFORMATION: 99-1585.pu complement
<220> FEATURE:
<221> NAME/KEY: misc_binding
<222> LOCATION: 54726..54746
<223> OTHER INFORMATION: 99-1607.rp
<220> FEATURE:
<221> NAME/KEY: misc_binding
<222> LOCATION: 55307..55325
<223> OTHER INFORMATION: 99-1607.pu complement
<220> FEATURE:
<221> NAME/KEY: misc_binding
<222> LOCATION: 64135..64153
<223> OTHER INFORMATION: 99-1577.pu
<220> FEATURE:
<221> NAME/KEY: misc_binding
<222> LOCATION: 64518..64536
<223> OTHER INFORMATION: 99-1577.rp complement
<220> FEATURE:
<221> NAME/KEY: misc_binding
<222> LOCATION: 65202..65219
<223> OTHER INFORMATION: 99-1591.pu
<220> FEATURE:
<221> NAME/KEY: misc_binding
<222> LOCATION: 65815..65834
<223> OTHER INFORMATION: 99-1591.rp complement
<220> FEATURE:
<221> NAME/KEY: misc_binding
<222> LOCATION: 66653..66671
<223> OTHER INFORMATION: 99-1572.pu
<220> FEATURE:
<221> NAME/KEY: misc_binding
<222> LOCATION: 67275..67295
<223> OTHER INFORMATION: 99-1572.rp complement
<220> FEATURE:
<221> NAME/KEY: misc_binding
<222> LOCATION: 67627..67646
<223> OTHER INFORMATION: 5-169.pu
<220> FEATURE:
<221> NAME/KEY: misc_binding
<222> LOCATION: 68024..68043
<223> OTHER INFORMATION: 5-169.rp complement
<220> FEATURE:
<221> NAME/KEY: misc_binding
<222> LOCATION: 67246..67263
<223> OTHER INFORMATION: 5-264.pu
<220> FEATURE:
<221> NAME/KEY: misc_binding
<222> LOCATION: 67678..67696
<223> OTHER INFORMATION: 5-264.rp complement
```

-continued

```
<220> FEATURE:
<221> NAME/KEY: misc_binding
<222> LOCATION: 67977..67994
<223> OTHER INFORMATION: 5-170.pu
<220> FEATURE:
<221> NAME/KEY: misc_binding
<222> LOCATION: 68406..68424
<223> OTHER INFORMATION: 5-170.rp complement
<220> FEATURE:
<221> NAME/KEY: misc_binding
<222> LOCATION: 68322..68340
<223> OTHER INFORMATION: 5-171.pu
<220> FEATURE:
<221> NAME/KEY: misc_binding
<222> LOCATION: 68725..68742
<223> OTHER INFORMATION: 5-171.rp complement
<220> FEATURE:
<221> NAME/KEY: misc_binding
<222> LOCATION: 70507..70524
<223> OTHER INFORMATION: 5-1.pu
<220> FEATURE:
<221> NAME/KEY: misc_binding
<222> LOCATION: 70909..70928
<223> OTHER INFORMATION: 5-1.rp complement
<220> FEATURE:
<221> NAME/KEY: misc_binding
<222> LOCATION: 79940..79957
<223> OTHER INFORMATION: 99-1578.pu
<220> FEATURE:
<221> NAME/KEY: misc_binding
<222> LOCATION: 80557..80575
<223> OTHER INFORMATION: 99-1578.rp complement
<220> FEATURE:
<221> NAME/KEY: misc_binding
<222> LOCATION: 82057..82077
<223> OTHER INFORMATION: 99-1605.rp
<220> FEATURE:
<221> NAME/KEY: misc_binding
<222> LOCATION: 82484..82504
<223> OTHER INFORMATION: 99-1605.pu complement
<220> FEATURE:
<221> NAME/KEY: misc_binding
<222> LOCATION: 82058..82077
<223> OTHER INFORMATION: 5-2.pu
<220> FEATURE:
<221> NAME/KEY: misc_binding
<222> LOCATION: 82473..82492
<223> OTHER INFORMATION: 5-2.rp complement
<220> FEATURE:
<221> NAME/KEY: misc_binding
<222> LOCATION: 83561..83578
<223> OTHER INFORMATION: 5-3.pu
<220> FEATURE:
<221> NAME/KEY: misc_binding
<222> LOCATION: 83965..83982
<223> OTHER INFORMATION: 5-3.rp complement
<220> FEATURE:
<221> NAME/KEY: misc_binding
<222> LOCATION: 83597..83616
<223> OTHER INFORMATION: 5-4.pu
<220> FEATURE:
<221> NAME/KEY: misc_binding
<222> LOCATION: 83999..84017
<223> OTHER INFORMATION: 5-4.rp complement
<220> FEATURE:
<221> NAME/KEY: misc_binding
<222> LOCATION: 83793..83812
<223> OTHER INFORMATION: 5-260.pu
<220> FEATURE:
<221> NAME/KEY: misc_binding
<222> LOCATION: 84148..84167
<223> OTHER INFORMATION: 5-260.rp complement
<220> FEATURE:
<221> NAME/KEY: misc_binding
<222> LOCATION: 85153..85170
<223> OTHER INFORMATION: 5-9.pu
<220> FEATURE:
<221> NAME/KEY: misc_binding
<222> LOCATION: 85559..85576
```

```
<223> OTHER INFORMATION: 5-9.rp complement
<220> FEATURE:
<221> NAME/KEY: misc_binding
<222> LOCATION: 86239..86257
<223> OTHER INFORMATION: 5-5.pu
<220> FEATURE:
<221> NAME/KEY: misc_binding
<222> LOCATION: 86519..86539
<223> OTHER INFORMATION: 5-5.rp complement
<220> FEATURE:
<221> NAME/KEY: misc_binding
<222> LOCATION: 87619..87638
<223> OTHER INFORMATION: 5-202.pu
<220> FEATURE:
<221> NAME/KEY: misc_binding
<222> LOCATION: 88033..88050
<223> OTHER INFORMATION: 5-202.rp complement
<220> FEATURE:
<221> NAME/KEY: misc_binding
<222> LOCATION: 88104..88122
<223> OTHER INFORMATION: 5-7.pu
<220> FEATURE:
<221> NAME/KEY: misc_binding
<222> LOCATION: 88519..88536
<223> OTHER INFORMATION: 5-7.rp complement
<220> FEATURE:
<221> NAME/KEY: misc_binding
<222> LOCATION: 89338..89357
<223> OTHER INFORMATION: 5-181.pu
<220> FEATURE:
<221> NAME/KEY: misc_binding
<222> LOCATION: 89739..89758
<223> OTHER INFORMATION: 5-181.rp complement
<220> FEATURE:
<221> NAME/KEY: misc_binding
<222> LOCATION: 92722..92741
<223> OTHER INFORMATION: 5-10.pu
<220> FEATURE:
<221> NAME/KEY: misc_binding
<222> LOCATION: 93124..93142
<223> OTHER INFORMATION: 5-10.rp complement
<220> FEATURE:
<221> NAME/KEY: misc_binding
<222> LOCATION: 93090..93108
<223> OTHER INFORMATION: 5-11.pu
<220> FEATURE:
<221> NAME/KEY: misc_binding
<222> LOCATION: 93490..93509
<223> OTHER INFORMATION: 5-11.rp complement
<220> FEATURE:
<221> NAME/KEY: misc_binding
<222> LOCATION: 93460..93478
<223> OTHER INFORMATION: 5-12.pu
<220> FEATURE:
<221> NAME/KEY: misc_binding
<222> LOCATION: 93862..93881
<223> OTHER INFORMATION: 5-12.rp complement
<220> FEATURE:
<221> NAME/KEY: misc_binding
<222> LOCATION: 93759..93776
<223> OTHER INFORMATION: 5-13.pu
<220> FEATURE:
<221> NAME/KEY: misc_binding
<222> LOCATION: 94175..94192
<223> OTHER INFORMATION: 5-13.rp complement
<220> FEATURE:
<221> NAME/KEY: misc_binding
<222> LOCATION: 94127..94144
<223> OTHER INFORMATION: 5-14.pu
<220> FEATURE:
<221> NAME/KEY: misc_binding
<222> LOCATION: 94535..94554
<223> OTHER INFORMATION: 5-14.rp complement
<220> FEATURE:
<221> NAME/KEY: misc_binding
<222> LOCATION: 94504..94521
<223> OTHER INFORMATION: 5-15.pu
<220> FEATURE:
<221> NAME/KEY: misc_binding
```

-continued

```
<222> LOCATION: 94904..94921
<223> OTHER INFORMATION: 5-15.rp complement
<220> FEATURE:
<221> NAME/KEY: misc_binding
<222> LOCATION: 94833..94850
<223> OTHER INFORMATION: 5-16.pu
<220> FEATURE:
<221> NAME/KEY: misc_binding
<222> LOCATION: 95232..95251
<223> OTHER INFORMATION: 5-16.rp complement
<220> FEATURE:
<221> NAME/KEY: misc_binding
<222> LOCATION: 95124..95142
<223> OTHER INFORMATION: 5-17.pu
<220> FEATURE:
<221> NAME/KEY: misc_binding
<222> LOCATION: 95542..95561
<223> OTHER INFORMATION: 5-17.rp complement
<220> FEATURE:
<221> NAME/KEY: misc_binding
<222> LOCATION: 95290..95308
<223> OTHER INFORMATION: 5-18.pu
<220> FEATURE:
<221> NAME/KEY: misc_binding
<222> LOCATION: 95689..95708
<223> OTHER INFORMATION: 5-18.rp complement
<220> FEATURE:
<221> NAME/KEY: misc_binding
<222> LOCATION: 95533..95551
<223> OTHER INFORMATION: 5-300.pu
<220> FEATURE:
<221> NAME/KEY: misc_binding
<222> LOCATION: 95934..95952
<223> OTHER INFORMATION: 5-300.rp complement
<220> FEATURE:
<221> NAME/KEY: misc_binding
<222> LOCATION: 96097..96115
<223> OTHER INFORMATION: 5-262.pu
<220> FEATURE:
<221> NAME/KEY: misc_binding
<222> LOCATION: 96574..96591
<223> OTHER INFORMATION: 5-262.rp complement
<220> FEATURE:
<221> NAME/KEY: misc_binding
<222> LOCATION: 96548..96565
<223> OTHER INFORMATION: 5-263.pu
<220> FEATURE:
<221> NAME/KEY: misc_binding
<222> LOCATION: 96982..97001
<223> OTHER INFORMATION: 5-263.rp complement
<220> FEATURE:
<221> NAME/KEY: misc_binding
<222> LOCATION: 96901..96918
<223> OTHER INFORMATION: 5-265.pu
<220> FEATURE:
<221> NAME/KEY: misc_binding
<222> LOCATION: 97292..97309
<223> OTHER INFORMATION: 5-265.rp complement
<220> FEATURE:
<221> NAME/KEY: misc_binding
<222> LOCATION: 102156..102176
<223> OTHER INFORMATION: 99-7183.rp
<220> FEATURE:
<221> NAME/KEY: misc_binding
<222> LOCATION: 102584..102604
<223> OTHER INFORMATION: 99-7183.pu complement
<220> FEATURE:
<221> NAME/KEY: misc_binding
<222> LOCATION: 105570..105588
<223> OTHER INFORMATION: 99-7207.rp
<220> FEATURE:
<221> NAME/KEY: misc_binding
<222> LOCATION: 106056..106074
<223> OTHER INFORMATION: 99-7207.pu complement
<220> FEATURE:
<221> NAME/KEY: misc_feature
<222> LOCATION: 86434
<223> OTHER INFORMATION: diverging nucleotide G in reference genbank :
    L78132
```

```
<220> FEATURE:
<221> NAME/KEY: misc_feature
<222> LOCATION: 86435
<223> OTHER INFORMATION: diverging nucleotide T in reference genbank :
      L78132
<220> FEATURE:
<221> NAME/KEY: misc_feature
<222> LOCATION: 88355
<223> OTHER INFORMATION: diverging nucleotide C in reference genbank :
      L78132
<220> FEATURE:
<221> NAME/KEY: misc_feature
<222> LOCATION: 92976
<223> OTHER INFORMATION: insertion of G in reference genbank : L78132
<220> FEATURE:
<221> NAME/KEY: misc_feature
<222> LOCATION: 93240
<223> OTHER INFORMATION: diverging nucleotide T in reference genbank :
      L78132
<220> FEATURE:
<221> NAME/KEY: misc_feature
<222> LOCATION: 93471
<223> OTHER INFORMATION: diverging nucleotide G in reference genbank :
      L78132
<220> FEATURE:
<221> NAME/KEY: misc_feature
<222> LOCATION: 93592
<223> OTHER INFORMATION: diverging nucleotide C in reference genbank :
      L78132
<220> FEATURE:
<221> NAME/KEY: misc_feature
<222> LOCATION: 93680
<223> OTHER INFORMATION: diverging nucleotide C in reference genbank :
      L78132
<220> FEATURE:
<221> NAME/KEY: misc_feature
<222> LOCATION: 93681
<223> OTHER INFORMATION: diverging nucleotide C in reference genbank :
      L78132
<220> FEATURE:
<221> NAME/KEY: misc_feature
<222> LOCATION: 93682
<223> OTHER INFORMATION: diverging nucleotide C in reference genbank :
      L78132
<220> FEATURE:
<221> NAME/KEY: misc_feature
<222> LOCATION: 93683
<223> OTHER INFORMATION: diverging nucleotide G in reference genbank :
      L78132
<220> FEATURE:
<221> NAME/KEY: misc_feature
<222> LOCATION: 93712
<223> OTHER INFORMATION: deletion of A in reference genbank : L78132
<220> FEATURE:
<221> NAME/KEY: misc_feature
<222> LOCATION: 93728
<223> OTHER INFORMATION: diverging nucleotide C in reference genbank :
      L78132
<220> FEATURE:
<221> NAME/KEY: misc_feature
<222> LOCATION: 93747
<223> OTHER INFORMATION: diverging nucleotide T in reference genbank :
      L78132
<220> FEATURE:
<221> NAME/KEY: misc_feature
<222> LOCATION: 93761
<223> OTHER INFORMATION: diverging nucleotide C in reference genbank :
      L78132
<220> FEATURE:
<221> NAME/KEY: misc_feature
<222> LOCATION: 94151
<223> OTHER INFORMATION: deletion of TTA in reference genbank : L78132
<220> FEATURE:
<221> NAME/KEY: misc_feature
<222> LOCATION: 94154
<223> OTHER INFORMATION: diverging nucleotide C in reference genbank :
      L78132
<220> FEATURE:
<221> NAME/KEY: misc_feature
```

```
<222> LOCATION: 94241
<223> OTHER INFORMATION: insertion of G in reference genbank : L78132
<220> FEATURE:
<221> NAME/KEY: misc_feature
<222> LOCATION: 94430
<223> OTHER INFORMATION: diverging nucleotide C in reference genbank :
      L78132
<220> FEATURE:
<221> NAME/KEY: misc_feature
<222> LOCATION: 94771
<223> OTHER INFORMATION: insertion of A in reference genbank : L78132
<220> FEATURE:
<221> NAME/KEY: misc_feature
<222> LOCATION: 94805
<223> OTHER INFORMATION: insertion of T in reference genbank : L78132
<220> FEATURE:
<221> NAME/KEY: misc_feature
<222> LOCATION: 95121
<223> OTHER INFORMATION: deletion of AG in reference genbank : L78132
<220> FEATURE:
<221> NAME/KEY: misc_feature
<222> LOCATION: 95126
<223> OTHER INFORMATION: diverging nucleotide A in reference genbank :
      L78132
<220> FEATURE:
<221> NAME/KEY: misc_feature
<222> LOCATION: 95130
<223> OTHER INFORMATION: deletion of G in reference genbank : L78132
<220> FEATURE:
<221> NAME/KEY: misc_feature
<222> LOCATION: 95134
<223> OTHER INFORMATION: deletion of G in reference genbank : L78132
<220> FEATURE:
<221> NAME/KEY: misc_feature
<222> LOCATION: 95149
<223> OTHER INFORMATION: deletion of A in reference genbank : L78132
<220> FEATURE:
<221> NAME/KEY: misc_feature
<222> LOCATION: 95155
<223> OTHER INFORMATION: deletion of A in reference genbank : L78132
<220> FEATURE:
<221> NAME/KEY: misc_feature
<222> LOCATION: 95174
<223> OTHER INFORMATION: deletion of AA in reference genbank : L78132
<220> FEATURE:
<221> NAME/KEY: misc_feature
<222> LOCATION: 95368
<223> OTHER INFORMATION: deletion of A in reference genbank : L78132
<220> FEATURE:
<221> NAME/KEY: misc_feature
<222> LOCATION: 95411
<223> OTHER INFORMATION: deletion of C in reference genbank : L78132
<220> FEATURE:
<221> NAME/KEY: misc_feature
<222> LOCATION: 95419
<223> OTHER INFORMATION: deletion of C in reference genbank : L78132
<220> FEATURE:
<221> NAME/KEY: misc_feature
<222> LOCATION: 95431
<223> OTHER INFORMATION: insertion of TG in reference genbank : L78132
<220> FEATURE:
<221> NAME/KEY: misc_feature
<222> LOCATION: 95435
<223> OTHER INFORMATION: insertion of C in reference genbank : L78132
<220> FEATURE:
<221> NAME/KEY: misc_feature
<222> LOCATION: 95444
<223> OTHER INFORMATION: diverging nucleotide G in reference genbank :
      L78132
<220> FEATURE:
<221> NAME/KEY: misc_feature
<222> LOCATION: 95445
<223> OTHER INFORMATION: diverging nucleotide C in reference genbank :
      L78132
<220> FEATURE:
<221> NAME/KEY: misc_feature
<222> LOCATION: 95534
<223> OTHER INFORMATION: insertion of A in reference genbank : L78132
<220> FEATURE:
```

-continued

```
<221> NAME/KEY: misc_feature
<222> LOCATION: 95678
<223> OTHER INFORMATION: insertion of G in reference genbank : L78132
<220> FEATURE:
<221> NAME/KEY: primer_bind
<222> LOCATION: 67820..67850
<223> OTHER INFORMATION: 5-169-208_A_AS complement
<220> FEATURE:
<221> NAME/KEY: primer_bind
<222> LOCATION: 67820..67848
<223> OTHER INFORMATION: 5-169-208_A_S
<220> FEATURE:
<221> NAME/KEY: primer_bind
<222> LOCATION: 67820..67850
<223> OTHER INFORMATION: 5-169-208_G_AS complement
<220> FEATURE:
<221> NAME/KEY: primer_bind
<222> LOCATION: 67820..67848
<223> OTHER INFORMATION: 5-169-208_G_S
<220> FEATURE:
<221> NAME/KEY: primer_bind
<222> LOCATION: 67941..67969
<223> OTHER INFORMATION: 5-169-331_C_AS complement
<220> FEATURE:
<221> NAME/KEY: primer_bind
<222> LOCATION: 67940..67969
<223> OTHER INFORMATION: 5-169-331_C_S
<220> FEATURE:
<221> NAME/KEY: primer_bind
<222> LOCATION: 67941..67969
<223> OTHER INFORMATION: 5-169-331_T_AS complement
<220> FEATURE:
<221> NAME/KEY: primer_bind
<222> LOCATION: 67940..67969
<223> OTHER INFORMATION: 5-169-331_T_S
<220> FEATURE:
<221> NAME/KEY: primer_bind
<222> LOCATION: 67709..67738
<223> OTHER INFORMATION: 5-169-97_C_AS complement
<220> FEATURE:
<221> NAME/KEY: primer_bind
<222> LOCATION: 67707..67737
<223> OTHER INFORMATION: 5-169-97_C_S
<220> FEATURE:
<221> NAME/KEY: primer_bind
<222> LOCATION: 67709..67738
<223> OTHER INFORMATION: 5-169-97_G_AS complement
<220> FEATURE:
<221> NAME/KEY: primer_bind
<222> LOCATION: 67707..67737
<223> OTHER INFORMATION: 5-169-97_G_S
<220> FEATURE:
<221> NAME/KEY: primer_bind
<222> LOCATION: 68199..68228
<223> OTHER INFORMATION: 5-170-238_A_AS complement
<220> FEATURE:
<221> NAME/KEY: primer_bind
<222> LOCATION: 68198..68227
<223> OTHER INFORMATION: 5-170-238_A_S
<220> FEATURE:
<221> NAME/KEY: primer_bind
<222> LOCATION: 68199..68228
<223> OTHER INFORMATION: 5-170-238_G_AS complement
<220> FEATURE:
<221> NAME/KEY: primer_bind
<222> LOCATION: 68198..68227
<223> OTHER INFORMATION: 5-170-238_G_S
<220> FEATURE:
<221> NAME/KEY: primer_bind
<222> LOCATION: 68249..68277
<223> OTHER INFORMATION: 5-170-288_A_AS complement
<220> FEATURE:
<221> NAME/KEY: primer_bind
<222> LOCATION: 68247..68277
<223> OTHER INFORMATION: 5-170-288_A_S
<220> FEATURE:
<221> NAME/KEY: primer_bind
<222> LOCATION: 68249..68277
<223> OTHER INFORMATION: 5-170-288_C_AS complement
```

```
<220> FEATURE:
<221> NAME/KEY: primer_bind
<222> LOCATION: 68247..68277
<223> OTHER INFORMATION: 5-170-288_C_S
<220> FEATURE:
<221> NAME/KEY: primer_bind
<222> LOCATION: 68463..68492
<223> OTHER INFORMATION: 5-171-156_G_AS complement
<220> FEATURE:
<221> NAME/KEY: primer_bind
<222> LOCATION: 68463..68491
<223> OTHER INFORMATION: 5-171-156_G_S
<220> FEATURE:
<221> NAME/KEY: primer_bind
<222> LOCATION: 68463..68492
<223> OTHER INFORMATION: 5-171-156_T_AS complement
<220> FEATURE:
<221> NAME/KEY: primer_bind
<222> LOCATION: 68463..68491
<223> OTHER INFORMATION: 5-171-156_T_S
<220> FEATURE:
<221> NAME/KEY: primer_bind
<222> LOCATION: 68511..68539
<223> OTHER INFORMATION: 5-171-204_C_AS complement
<220> FEATURE:
<221> NAME/KEY: primer_bind
<222> LOCATION: 68511..68539
<223> OTHER INFORMATION: 5-171-204_C_S
<220> FEATURE:
<221> NAME/KEY: primer_bind
<222> LOCATION: 68511..68539
<223> OTHER INFORMATION: 5-171-204_T_AS complement
<220> FEATURE:
<221> NAME/KEY: primer_bind
<222> LOCATION: 68511..68539
<223> OTHER INFORMATION: 5-171-204_T_S
<220> FEATURE:
<221> NAME/KEY: primer_bind
<222> LOCATION: 68580..68608
<223> OTHER INFORMATION: 5-171-273_A_AS complement
<220> FEATURE:
<221> NAME/KEY: primer_bind
<222> LOCATION: 68580..68608
<223> OTHER INFORMATION: 5-171-273_A_S
<220> FEATURE:
<221> NAME/KEY: primer_bind
<222> LOCATION: 68580..68608
<223> OTHER INFORMATION: 5-171-273_G_AS complement
<220> FEATURE:
<221> NAME/KEY: primer_bind
<222> LOCATION: 68580..68608
<223> OTHER INFORMATION: 5-171-273_G_S
<220> FEATURE:
<221> NAME/KEY: primer_bind
<222> LOCATION: 68596..68626
<223> OTHER INFORMATION: 5-171-289_C_AS complement
<220> FEATURE:
<221> NAME/KEY: primer_bind
<222> LOCATION: 68596..68624
<223> OTHER INFORMATION: 5-171-289_C_S
<220> FEATURE:
<221> NAME/KEY: primer_bind
<222> LOCATION: 68596..68626
<223> OTHER INFORMATION: 5-171-289_T_AS complement
<220> FEATURE:
<221> NAME/KEY: primer_bind
<222> LOCATION: 68596..68624
<223> OTHER INFORMATION: 5-171-289_T_S
<220> FEATURE:
<221> NAME/KEY: primer_bind
<222> LOCATION: 68361..68389
<223> OTHER INFORMATION: 5-171-54_C_AS complement
<220> FEATURE:
<221> NAME/KEY: primer_bind
<222> LOCATION: 68360..68389
<223> OTHER INFORMATION: 5-171-54_C_S
<220> FEATURE:
<221> NAME/KEY: primer_bind
<222> LOCATION: 68361..68389
```

```
<223> OTHER INFORMATION: 5-171-54_G_AS complement
<220> FEATURE:
<221> NAME/KEY: primer_bind
<222> LOCATION: 68360..68389
<223> OTHER INFORMATION: 5-171-54_G_S
<220> FEATURE:
<221> NAME/KEY: primer_bind
<222> LOCATION: 66953..66983
<223> OTHER INFORMATION: 99-1572-315_C_AS complement
<220> FEATURE:
<221> NAME/KEY: primer_bind
<222> LOCATION: 66951..66981
<223> OTHER INFORMATION: 99-1572-315_C_S
<220> FEATURE:
<221> NAME/KEY: primer_bind
<222> LOCATION: 66953..66983
<223> OTHER INFORMATION: 99-1572-315_T_AS complement
<220> FEATURE:
<221> NAME/KEY: primer_bind
<222> LOCATION: 66951..66981
<223> OTHER INFORMATION: 99-1572-315_T_S
<220> FEATURE:
<221> NAME/KEY: primer_bind
<222> LOCATION: 66973..67002
<223> OTHER INFORMATION: 99-1572-335_A_AS complement
<220> FEATURE:
<221> NAME/KEY: primer_bind
<222> LOCATION: 66973..67001
<223> OTHER INFORMATION: 99-1572-335_A_S
<220> FEATURE:
<221> NAME/KEY: primer_bind
<222> LOCATION: 66973..67002
<223> OTHER INFORMATION: 99-1572-335_G_AS complement
<220> FEATURE:
<221> NAME/KEY: primer_bind
<222> LOCATION: 66973..67001
<223> OTHER INFORMATION: 99-1572-335_G_S
<220> FEATURE:
<221> NAME/KEY: primer_bind
<222> LOCATION: 67078..67106
<223> OTHER INFORMATION: 99-1572-440_C_AS complement
<220> FEATURE:
<221> NAME/KEY: primer_bind
<222> LOCATION: 67078..67106
<223> OTHER INFORMATION: 99-1572-440_C_S
<220> FEATURE:
<221> NAME/KEY: primer_bind
<222> LOCATION: 67078..67106
<223> OTHER INFORMATION: 99-1572-440_T_AS complement
<220> FEATURE:
<221> NAME/KEY: primer_bind
<222> LOCATION: 67078..67106
<223> OTHER INFORMATION: 99-1572-440_T_S
<220> FEATURE:
<221> NAME/KEY: primer_bind
<222> LOCATION: 67115..67144
<223> OTHER INFORMATION: 99-1572-477_A_AS complement
<220> FEATURE:
<221> NAME/KEY: primer_bind
<222> LOCATION: 67113..67143
<223> OTHER INFORMATION: 99-1572-477_A_S
<220> FEATURE:
<221> NAME/KEY: primer_bind
<222> LOCATION: 67115..67144
<223> OTHER INFORMATION: 99-1572-477_T_AS complement
<220> FEATURE:
<221> NAME/KEY: primer_bind
<222> LOCATION: 67113..67143
<223> OTHER INFORMATION: 99-1572-477_T_S
<220> FEATURE:
<221> NAME/KEY: primer_bind
<222> LOCATION: 67215..67247
<223> OTHER INFORMATION: 99-1572-578_C_AS complement
<220> FEATURE:
<221> NAME/KEY: primer_bind
<222> LOCATION: 67212..67243
<223> OTHER INFORMATION: 99-1572-578_C_S
<220> FEATURE:
<221> NAME/KEY: primer_bind
```

```
<222> LOCATION: 67215..67247
<223> OTHER INFORMATION: 99-1572-578_T_AS complement
<220> FEATURE:
<221> NAME/KEY: primer_bind
<222> LOCATION: 67212..67243
<223> OTHER INFORMATION: 99-1572-578_T_S
<220> FEATURE:
<221> NAME/KEY: misc_feature
<222> LOCATION: 8187,14867,14970,29204,29487,34266
<223> OTHER INFORMATION: n=a, g, c or t
<220> FEATURE:
<221> NAME/KEY: misc_feature
<222> LOCATION: (8187)..(34266)
<223> OTHER INFORMATION: n=a, g, c or t
<220> FEATURE:
<221> NAME/KEY: misc_feature
<222> LOCATION: (67092,68525, 82234, 82393)..()
<223> OTHER INFORMATION: polymorphic base; y=C or T

<400> SEQUENCE: 12
```

| | | | | | |
|---|---|---|---|---|---|
| ttggcttggc | agggcaacca | gctcaccaga | ctctctgcag | acccgaagtc | attacataca | 60 |
| gtatgataac | agggaatgga | cccgaccagc | atttgctgga | gatgatatct | ggtgtcagcc | 120 |
| cgacaggccc | ctacctgctt | ctcttgatat | gcaggaatcc | cttcaagctc | aacaagatc | 180 |
| tgtttaatag | actggagagt | cctttagttc | cttcctctaa | gggaaaatca | gatcgttctg | 240 |
| gtttgcttgg | taactcctta | cttcatccct | gatgggaagt | ttatagaatg | aggaaccagg | 300 |
| gctattacat | gaaactataa | aactgcctag | agcacatact | tggtattttt | aacattgttg | 360 |
| agagggactc | acttaattca | gccttgcagc | tattgcattc | cwgtccaaac | caacggcagg | 420 |
| ttctcaaaac | aagcggtgaa | agggttcctg | ttgcagagct | gtctggacat | ttaaagaagg | 480 |
| gagaggaaat | ctcaagggt | cggttgcact | ggaatagaaa | tcgcctgttc | ttttttttg | 540 |
| agacggagtc | tcgctctgtc | acccaggctg | gagagcagtt | gcgcgatctt | tgctcactgc | 600 |
| aacctctgcc | tcccgggttc | acgccattct | cctgcctcag | cctcctgaat | agctgggact | 660 |
| acaggcgccc | gccaccacgt | ctggctcatt | ttttgtattt | ttagtagaga | tggagtttca | 720 |
| ccatttagc | caggatggtc | tcgatctgct | gaccttgtaa | tccacccgcc | tcggcctccc | 780 |
| aaagtacagg | gattataggc | gtgagccacc | gcgcccaggt | gcctgttcct | tttttaagag | 840 |
| tctcactctg | tcgcccaggc | tggcgtgcag | tggcgcgatc | tctgcttact | gcagtctccg | 900 |
| tctcctgagt | tcaaatcaag | cgagaaatca | cttgttctct | tctgtgaacg | gaagcatcgc | 960 |
| agatctctct | tggcctcaca | ctcctccatc | tccctgattc | ctctgttctt | catttaccta | 1020 |
| ccttcccagc | agtctgcaga | gctggccgct | cactcacctc | tagtaagggg | atggagggtc | 1080 |
| ctgtgttgga | ataactcact | gaccgctaga | aagttaaaaa | taaatgggta | atgccaggag | 1140 |
| aacttggctg | gtgccttaaa | agccatagaa | cttctctttc | catctgtaga | taactgtaga | 1200 |
| caattttgtc | caaaacagat | aatgatctga | ttctacctcc | cattggtatt | tcccttcctc | 1260 |
| ggcctgtgac | atctcacttt | ctctagactg | aactttatcc | cagactgtga | ccttgccatg | 1320 |
| accttcctcc | tgcgtgtgcc | tctgccacca | caggaatggc | cacgcctcag | atcatgtcac | 1380 |
| cgctgggaac | aaaccctcta | cctgcgactc | tgaagttccc | tctctgaccc | tcttttcttt | 1440 |
| cttcccctcc | ccctcccct | cactccctct | gcacctgtgt | ttcgctgtca | cgctcccaac | 1500 |
| tcatccctgt | agagctggtg | aagagatgct | gatgtagttc | ttgaccttga | acccagccc | 1560 |
| tgcagccgtc | ctgtggcctc | actgacccag | cgtcatgccc | tggtcaagca | ttttggtgat | 1620 |
| gctcttggtg | attttcaatg | ggacctgcct | tgccaagccc | tgggcttagg | tgaaccagga | 1680 |
| ccacctgcat | tctatgtttt | tgattgctgg | aaaaaaaatca | tgaaatgtca | actgttgttc | 1740 |

```
tcattttttcc cactgccagt tcctgctacc caacctccgc cctcatttca aggccttgag    1800
tactttttt  ctatagtgaa gtctcccaaa aatgatattt ttttaaaaaa gaaaagccat    1860
agtactctga tttgatgtgg tctgttaata cctatgggct ttgacttgtt tctgctttta    1920
gacctagaca aaataaaata tctgtggtaa acatattca  agtttaccgg gcacgggggc    1980
tcacgcctgt aatcccagca ctttgggagg ctggggcagg cagatcactt gagcccagga    2040
gtttgagacc agcctgggca acagggtgaa acaacatctc tacaaaaata caaaaaatac    2100
ctgggcattg tggtgcatgc ctgtagtcgc agctactcgg gagactgagg tgggaggatg    2160
gcttgagctc tggaggcgga ggtcatagtg agccaagatc gtgccactga actccagcct    2220
gggcaacaga ggcagattct ttctctctaa aaaacataaa ataaaaaaag gccaggcgca    2280
gtggctcaca cctgtaatcc cagcactttg ggaggctgag gggggcggac gaagaggtca    2340
ggagatagag accatcctgg ccaacatggt gaaaccctgc ctctactaaa aatacaaaaa    2400
ttagccgggt gtagtggtgc atgcctgtaa tctcaactac tcaggaggct gaggcaggaa    2460
aatcgcttga acccaggagg cggaggctgc agtgagccaa gatcgcacca ctgcactcca    2520
gcctgggtga cagagcaaga ctctgtcccc caccaaaaaa aataaataaa taaatcaggc    2580
caaagggcaa aaatgcttgc ttttttagcac ttagtagtta tttccccaag aagagcggga    2640
gagaagttta ttaataatga aactggacag ttctttatca gctctaattg tttgactcaa    2700
tggcttctct tctcattacc atgcagtgct ctgctggctg caatgccttt gaacttcaca    2760
agaaggttag aatttcactg agacattcgg atggtgtggg tgtcagggtg cagctctcac    2820
acatagttga gagtgtaaat tgatacaact ttatggaaaa ttaattggga gtacccattc    2880
acactcctgt ctagcaatct cactttaagg acttgatcct acagaactca ttacatggtg    2940
caaggttcac agtgtggcat tcaaaataga gaagagctgc gggtaactcc catgcccgtt    3000
ggcaggaact ggttgaataa attatggtgc atcagtgctg tggggtatca ttaaaccatt    3060
aaaaagaaga gagagtcctg gccttaaaaa aaacttatct gatgtattgt taaacagata    3120
aagcaagttg tagatcaatg tgatttgggg ctaaaaaaat atttctatat aggtgtgaac    3180
atggccatga ctaaggaatc aggaaggaag tacctagatt gtaaccagta acatgtcggg    3240
agtgagatgg gattgagaga cgtaataata gattgagaga aaaagatttt cccatctctt    3300
tttgattttt taagaaaaca gcatgatttt cagtaatttt tacttttgtg tgttttttggt   3360
attttttctt tttctttttt tttttttttt ttttgagacg gagtttcact cttgttgccc    3420
aggctggaat gcgatggccc agtcccagct cactgcaacc ttcacttccc aggttcaaga    3480
gattctcctg tctcagcctc ccgagtagct gggattacag gcccctgcca ttacgcccag    3540
ctactttttg tatttttagt agagatgggg ttcaccgtgt tggttaggct ggtttgaact    3600
cctgagctca ggcgatctgc ctacttcagc ctcccaaaat gctgggatta cagccgtgag    3660
ccaccgcccc cagccggtat ttttttcaaat caaagaaaaa ataatagagt aaatcatcca    3720
aaactttaga tggtatttag actcagtaaa cttttcatat atgacagatg aagccaaatg    3780
gtctttctgt gcagtcagct agcacacaat tgtgcacccg aggaaaatta gagactgaac    3840
cggggtgtct gtggatgcat ttcctcagca ttcagccttc cttttgcccg tgttctagca    3900
ttacttctgt cctacagcct gggatttgtg aatgaaatag acaggtgcaa aaactccctg    3960
cctgtctgta atatccatag ccccgtgctc tacttgtatt tgcatgtaca aaccataatc    4020
tcctgtaaaa tactctgtga tatttctgaa taataataaa ctctcatccc tacacaaagg    4080
caaaacccct gtatctttca tctttgaaac catagcaaag gtatgaaatt acacctgagc    4140
```

```
atgcctggcc tcaaagtcct ggaacggtta tgtctttgac cctcacttca actcaactcc   4200
agaagaagca ggtcttcctt gtaattggat agaaaactca ttgtagagaa gaaagatcta   4260
caggtcaaga aacccacagg tttgctgtaa tccgagcaaa gcactgtagc atttatttta   4320
tattttcact cttcttattt agctcttttt tttttttttt ttttgagatg gagtttcatt   4380
cttgtcaccc agcctggagc aatggtgcca tctcggctca ctgcaacctc tgcctcccag   4440
gttcaagtga ttctcctgcc tcagcctcct gagtagctgg ggttacaggc tccaccgcc   4500 acacccagcc aatttttttgt attttttagta gagacgggt ttcaccatgt tagccagact   4560
ggtctcaaac tcctggcctt aggtgatcca cccgcctcag catcccaaag tgctgggatt   4620
acaggcgcac cggccttagc tcttttatcc ttaatgaaat gctcctcatt ccctgaggtc   4680
tcacttgaat tcttgcccac ctctgggttg ccttcctctt ctgtctgtgc tttgtaacac   4740
gtggttcctt atgatgtcaa tatttatgca tatgtcttca ttccattact ggattataat   4800
cttgaagcaa cagatttttg tctctatatc ccagagccta gaatggattc ttacactggg   4860
cagtaagtac ttaataaatg tatcccaaat caaataaata catttcttct ttttcttttc   4920
tttttttttt tttttttgaga cagggttcca ctctgtcacc caggctggag tgtaatgaca   4980
tgatctcagc ttactacagc ctcaatctcc tgggcttaag caatcctccc acctcagcct   5040
cccacatagc taggactaca ggcgctcacc acaacacctc atttttgtat attttttgta   5100
gagattgggg gatctcacta cgttgccccg gctggttttg aacttctggg ctcagacaat   5160
ccacccacct tggcctccca aactgttgag attacaggaa tgagccacca ttccctggcc   5220
aaatacattt ctaaaagcca gtttctggag tatactgtca aataatagat atatgtccac   5280 attttttatac ggacttatat tgtaagaaaa agtaaaaata agtgtgaagt tattacagta   5340
atagtaatta ttttgcagaa aaagaactga gtttaaacag gcttttttaga aaaacccaac   5400 aggagattca cagtctggta ctaacgttta gacatggatc atcagtaaat gtgttccaaa   5460
gagttacaca gataccagct ttgtcttggg aattcttacc cctgaaaatt gattgactat   5520
cactgactgt gtgacatgag aaagttttgt ggggtttttt ttttgtattt ttttgagacg   5580
tatcttgctc tgtcacccaa gctggagtcc actggcgcga tcttggctca ctacaacctc   5640
tgccgcctgg ttcaagcgat tctcctgcct cagcctccag aatagctgcg attacaggca   5700
cctgccacca tgcccggcta attttttgtat ttttagtaaa gacggggttt catcgtgttg   5760
gccaggatgt tcttgaactc ctgacctcag gtgatctgcc cacctcagcc tcccaaagtg   5820
ctgggattac aggcatgagc caccgtgccc agcctgaaaa agttttgaac ggtctaaatc   5880
catatgctgt gaatcctatt accatcacac acttaggcat ttaaaatcat attttcaagg   5940
ccaggtactg aaatattttc tgcaagcaga gagatcaaac tttagcattg ttattcttgt   6000
agtagtttca tagtttgagg tcttagattt aagtcttcca ttgatttga tttgattttt   6060 gtatatggag ataggggtct agtttcattc ttttttgcatat ggatatccag ttttcccagc   6120
accatttatt gaagagactg tctttttcac cagtgtatgc tcttggcacc ttcgtcaaaa   6180
atgagttccc tgtaggtgtg tgggtttgct tctggttctc tattctgtcc cattggtcta   6240
agtgtttggt tttatgctac taccatgctg gttggtatag ctctgcagta taacttgaaa   6300
gcaggtaatg tgattccaaa gaagctagtt aagtaattga gctaaactgg aacctcaggt   6360
gtagaagtca taagcgtggg gagcgtttct tctcaggttc tctgcctata atttagtttg   6420
ccacaccaga tgaacagtga caacttggtc ttggtgttcg tggtggtttc caaccaaact   6480
```

```
ttggtcataa caggtgaacc agcctggggc atgctttccc attcggttat cctccccata   6540
gtttgcaaag tagcaaagat gaactcttca tgagttggct aagcatagac atttcaagac   6600
caaactaaac gtcctgaaga gcatgtttca cagaaaacta gcccctaagg gaccagtggg   6660
ggctgtcaga gaacaaggtt tcaacgtact gagttttaaa gatctaattg cttttaata    6720 acaattcatg aaccaggcac catagtctac aaaatagaca gggtttctgc tgggcactgc   6780
aggacagttg gttttggaa ggtggcttga gcaggaacaa ggaaaaagca ccgtgccaag    6840
agtggattgg ttaacatcag gggacttcgg gtgactttcc ttctatgggt taaagcaaag   6900
gggacttccc tagcatgtca gctcaggttg actgggcccc tttggattgg ttgctgtgaa   6960
tctcctagtt ttttttgttt tggtttggtt tgggtctttt ggggaaaacg ggccagtttg   7020
gagattcagc tattatttct ctctcctgat atcagaagat cagatcttat gagtacacag   7080
ctgaggtttt gggttggtga tgtggaaccc tggtgtgagt gactccattt tgggttggtc   7140
tattggggtc tcggtgcagg agctcagtcc aaatcagtgg cctctcctca tttttatttg   7200
acttctccat caatctatcc gtgtctcccg tcacatcagt ccattccccc gtgggctgca   7260
cattcagctc ggagctgaga ctttttccca gggtgtgccc tggggtttct gctgcttgca   7320
gcctgatatt aaatctcagg tgtaaatctt cagaggcaac tgttccttag tacccagagc   7380
tttcagctcc ctgagcagaa atgggacttg actgtcagtt tataaactaa ccaaggtgtg   7440
aaattcatgc aacttagccg actttctgtt caaagaattc ttggcagcag ttaatacatt   7500
ttgcccaaat ataagataat tcccttgtac tcacaatgag aaagttttac aaaatggggg   7560
ttttctttag tttacttgaa tataaaacat aggtgttcca ctctgcagta ccttaacagt   7620
tcttaaggag atgtttgaaa caacccatgt ccaggcctca cacctcgcca attaaataaa   7680
tgagaagttc ttcccagcca gtgttaagaa aaattaacat caagttttag gaaggtagac   7740
agattatgca aatgcatacc tatatgattt aagttattac attaatttac acacacatat   7800
ttaaaatcat agattaatct aatttagaga tgctgcattt tttccatctc tcctgtttca   7860
taaatgttat tcacacggca tttctctgct atcctcggaa tagtgtttgt atcgtgtcac   7920
tctggcacgg ggctctacag aacatgtcga gcgtgttgcc ttccctactg cccacatcgt   7980
ttgagagaac acattttaaa catttttta ttgtggtaaa atacacataa cataaaagtt    8040 acgatttaa cctttttaa ctctgtcatc caggctggag tgcagtggcg agatcttggt     8100
tcactgcaac ctccgcctcc taggtccaag tgattctcct gcctcagcct tccgagtagc   8160
tgggattaca ggtgcacacc accacgnccg gctaattttg tatttttagt agatgcgggg   8220
tttcaccatg ttagccaggt tggtctcgaa ctcccgacct caggtgatca gcccgcctcg   8280
cctccccagt gctgggatta caggcgtgcg ccactgtgcc gggcccattt taaccacttt   8340
taagtgcaca gttcagtggc attaagtata ttcgcggtgt tgtgcgaccg tcaccaccat   8400
tcacctccag aacttctctg tcttcccaaa ctgaaattct gtacccattg aacggtaact   8460
ccccattccc catttctgct tctaggcccc tgacatggag gctgggccaa cggatatctc   8520
acctcccttc aggcttctcc agatttgccc ccgttttct ccctctttgt cccatctcca    8580
aagaaatggt gtcttttcat catcaaggtc catcccttgc tccttgaata cactccaggc   8640
ccagtggaac aggcatcctg tggggtgcac ggacagggtg cctggggaac acccagggca   8700
cagaacccag accggggggtt tggagaaggt gtcctagcag aagtgatgtc taagctgagg   8760
ccctacagat aagagaaagt aagcagatga aagggctggg gagggtggca tttcaggcct   8820
acacaaccac acgcgtgttc ttcagccatc tccatggcct cactgcccac ctggtatcag   8880
```

```
ccggccacca cccggctaga acggctttca aaatcgctgc tcgtctactc ctcaccaaat    8940
cttgtcttca cttggtgctc aagcccatca cctttctgca agtattattt tttttttttt    9000
ggagatggag tctcgctctg tcacccgggc tggagtgcag tggttcaatg atagctcact    9060
gcaaccttga actcctgggc tcaagatcct cttgccacag cctcccaaag tgctgagatt    9120
acaggcacaa gccaccatgc gtggtccttg ctgcaacttt tttttttttt tttttttttt    9180
ttttgagaca gaatctcgct ctgtcgctca ggctggagtg cagtggtgtg atctcggctc    9240
aatgcaacct ccgcctcccg ggttcaggtg attctcctgc ctcaccctcc tgagtagcta    9300
ggaacacagg cgctcaccac cacatccagc taattttgt gttttagta gagccggggt     9360
tttgccatgt tggccaggct tctctcaaac tcctggacct cgggcgattg ccccgcctcg    9420
gcctcccaaa atgctggaat tacaggcatg agccaccgtg cctggccatt tgctgcaact    9480
tttgacactg ctcccctgc ttttcttccc ctctctgacc tcctttctct gctgtccttt     9540
cgttccttcc tctgccactg aagtgtcctt ctcaggtcct tctcaaggtt gtgaccttac    9600
agctgtctct tcacttccag tcatttcttt cataatcact ttgacatcct tattttcatc    9660
tcctgccctg gcctctccca gggaccagga ccatgcattc agctcctggg ggcatctcaa    9720
gcttgttgtg tgtgagcctg cccttgttgt cttctccgtc acctcttcac agcttgctct    9780
gcatttcacc tcctttcctg ttttccccag tgatcgcatc tctacagcgg ctctcacttc    9840
atcccctcct ctcctagagg agtgatgcgg agtctcatta atccttgctt atgtcattct    9900
tccccttct ctgtccatca cctccacatg tcctgttccc ccatgcgtcc tacactgtag     9960
ccaggtgggt atttcctgtg ctggtcttag acaccccctg aggataccct gcttcaggcg   10020
agagccctca gtgactccct gttgtccgga atgacgtcca gctccttgga cagtcccag    10080
tgtattcacc tgtctcatct ccttctttc gttttgtttg ttttcttaa cttccagccc    10140
gatttctgaa tcatctccct cttgcccctc ccattgcctt tgcttaagac taaatgctcc   10200
ttcctcccaa gtccccactg cccagatttc agcagggtcc atctcaaaca tgtctgtctc   10260
caagaaactg cctctgattt ttttcataag aagacacctg tcctctctga cttcatctgt   10320
accctctct tggaagtcac tatcttgtgc cttgcatttt cgttgtttaa gtggtctcca   10380
tttcccagca tatcttgagg tcaagggttc aggtcatttt atctttgtct atgcattgca   10440
atatgggggt ttttacatat tagctgctca ataaatcggt gttgaataaa ggcatgtgta   10500
tgctttcatt aagactatga aacccacaaa aatcagtggt tttcctattt caccccttaga  10560
aaacaaaccc acaacatagc acaacctgat attcagagct aagaacaaag gtcatgcata   10620
ttaatctaaa ttctatcttt atcaactttc acaagtaatt cgtatttccc tgtctgcatc   10680
acggggatga ttctggccag acattgacct tggtaaaatt tcctccagat tatgagaaat   10740
caagtcaaat atgccaagta acatagtttc tacttagagt caggttcatg ttttagcagg   10800
aacctcaaat accacaaaat ctgtcaagtt ctaacatttg tatctctcga cagtacctga   10860
agttcctgtt tctgtttcct cagcccaggt ttccaattca gtgagcagaa cggtgactgt   10920
gttggtaaaa gagcccacat acctgcccga tcctgcagga gtgttgcaga tgcaaacagg   10980
cgggtctcca catgacctgc ggagtaatga ctagtgtccc taaagtcatg gggcttctgg   11040
ggttagcctt gaaaaaagct aaaggttgca tagagagaga tttctatccg ttcagagact   11100
cactataatt ctctctttct gtctctgtcc ttcatctgtt tctctctttc tctctcactc   11160
tctctctctg atacacacac acacacacac acacacacac actcacactc acacactcct   11220
```

```
gagtaaggga aatgtgagaa gaaggtaaaa cttcaactaa atgaaaagaa attgtatgaa   11280
ttatggtaag caggttggtt tttagttcca gtaaagatag aaatatttag attacttagg   11340
agaaaagtct agctggtaac acatgggaat gtgcctgtgt gaaaacaaaa caaaacaaaa   11400
aatctaggct tgtggttagg tgaaggtatg tacactgctg agacatggcg atgggtgagc   11460
ttgggatgag gagaaaggct tctctgaaga gattaagaga gaaagattgt ttaaaaatgt   11520
ttaaacatgc tgggcactgt ggctcacacc tgtaatccca cactttggg aggccaaggt   11580 gggcggatca tgaggtcagg agttcgagac catcccggcc aacatggtga aaccctgtct   11640
ctgctaaaaa tacaaaaatt agccaggcgt ggtggcgggt ggctgtagtc ccagctactt   11700
gggaggctga ggcaggagaa tggcgtgaac ccaggaggcg gagatgcagt gagccgagat   11760
tgtgccactg cactccagcc tgggcgacag agcaagactc cgtctcaaaa aaaacaaaaa   11820
aacaaaaaaa aaacacacat tgacaccagg acggagttag cacatcttta caggtgagac   11880
tctcagaccc gagaaaatag aggcacttta gagctgagct aatcccacag ccacctcaac   11940
acacaaacgg ggaatctgag acccgcattg gcaccgtgcc tgaggttcta agcccaggg   12000 cttctgactc gcctcttgtg cttcttcagt actgtgggtg ggggtggggt gggggtgac   12060 attagctgat gagaaagatt ttggttttag aaagatggag ttaacataaa cgaaggtgta   12120
ctgggactgg tctcctctgc tgacttcatg ggaagcacac acacgcacac acacacacac   12180
acacacacac acacacacac atacacacac ctgtccaaga tcagaaaaaa tccctcacat   12240
ccctgtagca tgatcctgat tgtaaaaatg gagccctaat cagaagggca gaagcatgat   12300
tgcctctcaa gagatttgga cgccactttt tcatagttgg ttttagctgc tttgcgatat   12360
atactgaaat aaatagaaaa gggaaagaat tgtaacctgg attgacagac aacaagccct   12420
gacagacaaa aagcagataa gaaataaaat aaggaagata acccataatg taaaataaaa   12480
atagcacatt gttgcatgca ttgatacct ttttttttt tctttgagat cttgctctgt   12540 cttttcaggcc gaagtacagt gtctcaatca tagctcactg cagcctccag cttctgggct   12600
caagcaatct tcccatctca gccacccaag tagctgggc tgcaggcacg aactatggtg   12660
cccagctgat aattttaaa aataggaca ttagtgcatt tagcaaattt gagtgtctgc   12720
tgtgtatcaa gcactgttct gggcactggg acagcacagg gagcaaataa acaaagccc   12780 ctgcgctcaa ggtgctcgta ttctagaggg agatgctgag ttcacctccc attaaaatgc   12840
cattctcaag atccagtccc tccacccacc ccagccccca gggttttggt ggaaatttaa   12900
ctaagttgga agattgataa tatctccatt cacatttgga tatgattta atgaaggttg   12960 cttttttggtt tttagggaga agaaaatggc tttccagata gcactggaga tcctcttcca   13020
ggtaaatgat tgattctaaa gctatctggg ctaatagcta gtgtggctga ataaaagata   13080
atttgaggcc agggtcggtg actcatgcct gtaattccag cactttggga ggccaaggtg   13140
ggcggatcac ctgaggtcag gagttcaaga ccagcctggc caacatggta aaccccgtc   13200 tctaccaaaa atacaaaaat tagctggttg tggtgggcgc ctgtaatccc agctactcgg   13260
aggctgaggc aggagaatcg cttgaacccg ggaggcggag gttgcagtga gccaagatca   13320
caccactgca ctccagcctg gacaacagag cgaaactcca tctcaaaaaa ttaaattaaa   13380
taaaataaat aatttgagac tatgtttatc attaacttta aaatctgtac tgcagaatag   13440
agcaactttc tacctgcggt gcactgcagg gaaagccgta tcttacaaga cttcacaaaa   13500
gccttcaaag agtattttct ctgcactaac cttcctttgc atgtgagggg cacggcaggg   13560
ttctgaatgg ggcaggttta ggatcaggcc agtcgggact gagtggattc ttcttccctc   13620
```

```
tgagttctaa gagccatagc attggtggag aacatgctgt tgttgcttg gtggaaggga    13680 ccagaagcca gctgggtcat ctctctgttt gtgccttggc cacttaggta gccaaaggag    13740
ccctcctgac attaggtcag gtgttagtcc ctctccttt ctgcttttag tgtgtttaag    13800
caaataaaca ttaaagttca tttctccccg ctccccttt ttaatcataa gacagacatg    13860
tttgcaatgt ttaaatttct cattaatcag aagggatagg gagtgaggga gtaagcatta    13920
aaataagcta gcaaatggcc aggtgtggtg gctcacacct gtaatcccag actttggga    13980 ggccaaggtg ggcagatcac ttgaggccag gagttcaaga ccagcatggc caacatggca    14040
aaactccatc tctactaaaa atacaaaaat tagccaggcg tggtgatggg cacctataat    14100
ctgagctact cgggaggctg aggcagagaa ttgcttgaac ccgggaggca agattgcag    14160 tgagctgaga ctgcaccact gcattccagc ctgggtgaca gagcaagact ccatctcaaa    14220
aaaatgctag caaataata ataataataa taataaaaca tacctcacca acattttcta    14280
catcttgtaa agcatacatt gactgactga agtcaccaga gttttgtttc tttctttctt    14340
aagcagggtg gggaacccgt agagccctca ggggcagcta tcatcagccc aggtaaccaa    14400
gctgaaaaac cagaaggtgc agtgcgtact caacttttc cccttagaaa cacgatatta    14460
gaaaatacac caataccaac atgtgagcaa cagttctctc tggaaggtgc agttctgggt    14520
gatttttttt tcattccata gatttttttt ttcttgagac ggagtttcgc actcttgttg    14580
cctaggctgg agtgcaatgg tgcgccacca cgcccggcta attttgtat ttttagtaga    14640 gacgggggttt caccatgttg gccaggctgg tctcgaactc ctgacctcag gtgatccacc    14700
tgcttcggcc tcctaaagtg ctgggatgac aggtgtctca ctatgttgcc taagcttttc    14760
tcgaacccct gagctcaagc ctcctcccac ctcagccatc caaagtgctg ggattacagg    14820
catgagccac cacgcctggt gagttttat tttctttcca ctatccntat atttctaaaa    14880
tttctaacat gagctggtat cagaactgcc cctccgcatt taatctgtgt atacaaatgt    14940
atatataaca aatgatcaca tgttggtaan gtataccttg ctgcatggtg aaataaccaa    15000
ggaaacttct aaaaggttaa ctgtggttgg cctgggtaat gggagcatta atttttcca    15060 tatgctcatc tgaattttca gatttgctat gacaagcaca tatttatttt ctaatttaa    15120 aaatctatat ttaaactctt taaagactaa cacactacac actaatgtgg cacgttagct    15180
aaaataaaaa taaatacaga aatttgttta gaaatatttg taaacccttc aaggactctt    15240
ctgaatgata gtcattatta attagcaggt taatttaat caggcttctg gtcatcttca    15300 aacattttt acttgtgtca aaatgaacca ccagagtgtg gtttttttg ttatttttt    15360 tgtttttttg agacagagtt tcactcttgt tgcccaggct ggagtgcaat ggcgagatct    15420
cggctcactg caacctctgc ctcctgggtt caagcagctc tcctgcctca gcctcctcct    15480
gagtagctgg gattacaggc gcccaccacc acacccagct aattttttgta ttttagtag    15540 agatgggttt tgccatgttg gccaggttgg tcttgaactc ctcacctcag acgatccacc    15600
cacctcagcc tcccaaagtg ctgggactac agatgcacac caccacaccc ggttaattt    15660 tgtattttta gtaaggacgg gggttcccca tgttggccag gctggtctca aactcctgac    15720
ctcaagtgat tcacctgcct tggcctccca aagtgctggc attacaggcc tccgccaccg    15780
cacccagccc aacctgggtc cttttgtatg tgagagtttg cttgtttttt tcacgtgctt    15840
tctctactcc agttttattc tatgacaaaa ttgaggccca acatgattta cttgcctgga    15900
tccacccaac ctgtcagtta cttcccagtg ctgctgccaa cttaatgtct ccttaaaagg    15960
```

```
atgctttaga gaaaacgaaa tcatgttgtt tttcccctttt ggttaagaga tcaaacgccc   16020
accaaaagcc cttgggtcag tttcttagta gataaaaata attcttcgtc actttctgaa   16080
agcggctaac atataaccct tatgatgaat aatgtggtgt gtgtgtgtgt gcgcgcccca   16140
aattccaatg agttatcaaa gccagaaact tatattttaa atatgtttat ttcccaacca   16200
cactggaaac cacacacaga aaaaaaaaaa agcatgatta taccccctta ataaccgtta   16260
ctgcagaagg atgtgactct ccttcaacac ttgttggtat tttacagcct ccaaatctga   16320
ccatgtataa ccacctggga tagagttatt ttatttcaga accataatac ttagctatct   16380
cggaagttgc caatataaaa tgtttactct ctaatggttt tgaactaact caagacctgg   16440
ttatcccggg gagcatcctt acaaatgatc tgagagctaa cagtcctctt gcagcagtgg   16500
agggaaacac tcccgtggca atcactctcc aaaagccaga atgtgcaaga taaagggca   16560
ccttccctgc agggaggcac attaagtcag tctgtgatct gctgccaaca tcctgactgg   16620
agccgtttct acgcctaact aatcatgacg tttgtgaatt gtgaagcttg ttgcaattca   16680
caattaactg ttaattgacc catattttat aacccgccag ccatgaactt acaagttaga   16740
tacagacact accagacatt cactattttt ttttacaatt gttttaaatg acattaatga   16800
gcatgcttga ttcctgaact cttctttaca gtataatttt aaaatatttg agtgggatac   16860
gatgagagag agggaggtgg gggaagaaat gccccatgga aaacccactc atcaggttga   16920
gagtgtggag aagccctgtg tatctgagaa ctcttaatca tccacagaca tggtatctct   16980
caaagagaag tgggtgtaat tccaaaatct aattttggca ggcgctcctg actaaatact   17040
taatctggag atgtcttcaa ggcaggcgga ggttttcagt cctggctgca cattagaagt   17100
cccagggggag cttaaaaaaa ttcccacgtc ctccctgcat cccagactaa ttaatcggga   17160
tctccgaggg tgggaccaca catcagggtt ttgtaaattt ccctgggggt ttggtggggt   17220
tgggggtgga ggcgtctatc ctatggccaa ggttgagaac cactgctttt taaaagactg   17280
tttgcttgtt tttgagatgg ggtctcgctc tgtcacccag gctggagtgc agtggcgcaa   17340
tctcagctca ctgcaacctc tgcctcctgg gctcaagcaa ttctcctgaa aaaggctgtt   17400
ggttattaat gcttccccac agctattcta ttcattgttg catgcttctt acgtgtgcta   17460
ggatgggagc tttaaaggat tacctcattt aatcctcaca accaccttgt gagagaggtg   17520
tcattatccc tgtttggaga gtgagacagg ggcttagcaa gctcagtaac ctgtccaagt   17580
cacacatctg catggggtta gctgctgcta aagctcatgc cgttaatctc catggtacac   17640
ggtgtcctct ccatagcaat cttgcggctg ccttgttaac accaaaaaaa cttgcatcag   17700
ctggtttgac aatttctaga taaagagctc ttttcgggct gctaagaagc ctaattttc   17760
atttgatttt cttcttgaac tgtgtcacac tcctcattca tttgatatat tcatcaaata   17820
cttattgagc acctgctgtg tgcctggtgt gcagcagtga caccagacat ccaaagtcct   17880
tttcctctta gagcttattc tatctgggag agacagataa taaacacaaa atcagtaagt   17940
catttatat ggtggtaggt gccttgagga agatgagcca ggttaatggg attaagcctg   18000
gtagggggag ggtgccactt tagctcgaa aggtagcga acccaaaca atgcaaagga   18060
cccggcccgt ggagatctaa gacaggagga tgccagggac aggaagttgc tggggcaaag   18120
cccctgaggc tggactgagc tcagtgttct aggacgggcg tgggcagtga ggagcagcag   18180
aggaggtgag ctgggagata gcctgggac tctttcttct gcctccttca aaaaataaaa   18240
ctagccaggt gtggtggctc acacctgtaa tcccaacaat ttgggaagct gatgtaggtg   18300
gattgcttga gtccaggagt tcgagaccag cctgggcaac atagtgagac ccctccccc   18360
```

```
atttctacca aaaaatcaaa aaattagctg ggcccggtgg cgtgcgcctg tggtcccagc   18420
tactcaggag gctgaggtgg gagcattgtt tgaacccggg aggtggaggc tgcagtgagg   18480
cgtgattgtg ccactgtact ctagcctggg tgacagagtg agactctgtc tctaaataaa   18540
taagtaaatc tagaacctaa catcttggag tgcagtggca ccaccatggc tcactgcagc   18600
ctcaatctcc tgagctaatc gagcctcccc ttcagcctcc tgagtagctg ggactatagg   18660
cgtgcaccac catacctgaa taatcaaaac ctaacatctt taaagaacat tggcataaga   18720
cttggcaaaa atggcatctt gtccctcatc tcatttagtc caagcgatac aggaaatgct   18780
gccacctcca ttttatagat gaggagtctg acgttcctag aggttcaatg ccctgaaacg   18840
tcaagccttg aggaagttgg agcactggga ttcgaagagc accatccaat acagacccag   18900
aatcaggatg atttgggatt atgcttgtca aggactcagg gcagggctac catacattag   18960
gcacaagaat tttgatagtg ataattactg tgttcattgt cacttcatca tgacagttac   19020
cgtgatgata agaaacctgg cccttcttca cctgacaaag gctttcttcg tttgagccac   19080
tgctcaaacg agactgacca agaataaatc ctcggggctt tggcctttaa ataggaagt    19140 catcataaat gacttgatgt ggtgtgtttc attcttgctt tgcaccagtg gaaaatatac   19200
aggtcaagca tcaaaacatg gcaaatgggg accccaatta ttagagaatc taagttaatt   19260
tttatgtata attaattatt caacaaccct ctcctctcca aaccaataat taatccatct   19320
tttgtatttt aagaccaatt ctgtagtatt ttccatcaat atctatttac tgctagcaga   19380
tatcagctac attctttctc ctttaataga agttccctct ttaggtatta agattcatta   19440
aacaacaata acaaatctac cttgcctccc agggacaatg cacagttctc attcatttgt   19500
tcatttagca gataattttt gaatttccac tgtacagcag ccctgtgctt gtggttggcc   19560
tgttatttga gaagcatcaa ataataatct cattttttgg ctgggtgtga tagctcacgc   19620
ctgtagtccc agcactttgg gaggctgagg cgggtggatc acttgaggat gggcgttgga   19680
gaccagcctg gctaacatgg tgaaaccctcg tctctattaa aaatacaaaa attagccagg   19740
tgtggtggca gacacctgta atcccagcta ctcggggagg gtgaggcagga gaatcgcttg   19800 aacctgggag gcagaggttg cagtgagccg agatcgcccc attgcactcc agcctgggca   19860
acaagagcga gactccgtct caaaaaacaa aacaaaacaa gacaaaaaaa aacccaacaa   19920
ataaaataaa taatcccatt tttctccatt tttgagaaag atttctttgg tctgaagtct   19980
ttctctcccc tctccgaggc attacccagt ttaacctttc atgtataata tatatgatag   20040
ttatttaaag tatagcagga caaaatgtat ttgataggag aaaaccttgt ttgctctgtg   20100
ttaagtcctc cagagagcta attagagttt gtgattctaa aaggcaacta tagattcact   20160
tatattagca gttcatgtag attccagtta aggaaatggt ttgtcacttg tgttattgaa   20220
aacacacaca gggcgagcac tgtggcccat gctggtaatc ccagcgtttt gggaggctga   20280
ggtgggcaga tcacggggtc aggagtttga gatcagcctg gccaacatgg tgaaacccg    20340 tctctactat aaatacaaaa aattagctgg cagtagtggc aggcgcctct aatctcagct   20400
actcgggagg ctgaggtagg agaatcgctt gaacccagga gtcggaggtt gcagtgagtc   20460
gagatcgcac cattgcactc cagcttgggc aacaagggca agactccgtc tcaaaaaaaa   20520
agaaagaaaa cacacacaca aaaaaacttt agtagatctt tcggcatatt atttttttaaa  20580 ataaactgat aatggttgat atgattgttc aaagaaataa gagcttttca taaactcagt   20640
ttaaagaaac tttacaggcc gggcgcggtg gctcatgccc gtaatcctag cactttggga   20700
```

```
ggccaaggcg ggtggatcac ctgaggtcaa gagttcgaga ccagcctggc caacatggta    20760
aaagcctgtc tctattaaaa aatacaaaaa ttagccaggt gtgttggctg gcgcctgtaa    20820
tctcagcaac tcaggaggct gaagcaggag aatcgctgga acctggtagg cagaggttgc    20880
agtgagacaa aatcgtgcca ttgcactcca gccccagctg acaacagcga gactccatct    20940
caaataaata aataaataaa taaataaata aataaataaa ggagctttac agaaaccttc    21000
tgatgttttt ttcttcttga cgataacatt gccaacactg aatcttacaa agataagaca    21060
agaaagggac cttcagacac cattacatgt aattctggac ttagtggttt aaatccttat    21120
ttttctatga cattaaaaaa atgtatattt taggccaggc acagggctca cacctgtaat    21180
cccagcactt cgggaggccg aggcaggtgg attgcttcag cccaggagtt caagagcagc    21240
ctggggaaca tagtgagacc cctgtcccta cagatttttt tttttttgttt gagatggagt    21300 tttgctcatg ttgcctaggc tggagtgcag tggcacgatc tcggttcact gcaacctctg    21360
cctcctgggt tcaagcaatt ctcctgcctc agcctcccaa gtagctggga ttacaggcat    21420
gtgccaccac acccggctaa ttttgtattt ttggcagaga ctgggtttct ccatgttggt    21480
caggctggtc ttgaactccc aacctcaggt gatctgcctc cctcagcctc ccaaagtact    21540
gggattacag gcgtgagcca ccttgcccag cctacaaaaa gttttaaaaa attaaaaaat    21600
tagttgggca tggaggtgca tgccagctac tcgggaggct gaggcaggag gattgcttga    21660
gcccatgaag tggaggctgc agtgagccat aattgcagca ctgcactcca gcctgggcca    21720
tagagcaaga ccctgtctca aaatatata tagtatccaa ataaacacaa taattacaga    21780
aaattgaaaa gtgcccataa gcaaaaaaaa aaaaagaaa aaattaatca cctgcgttct    21840
catcacccag aattaaccat tgttaatatt tttgttatag atccttccaa acttttctcc    21900
atgcttgtga ttgtatttat tatacatgat ttacagggat ataaacgact gtattattag    21960
tcattagaag aactggatta tggccgggca cggtggctca cacctgtaat ctcagtactc    22020
tgggaggctg aagtgagcag atcatgaggt caggaaatcg agaccatcct ggctaacaga    22080
gtgaaacccc gtctctacta aaaatacaaa aaattacctg ggcgtggtgg caggcgcctg    22140
tagtcccagc tactcgggag gctcaggcag gagcagagat acctatctgt tctcaggatt    22200
ttaaggtgtt gcgcggaaat aagaaaaccg tacagtgttt ctcactacaa agcagggtca    22260
ggagatgcaa acaaactgat gtgggggttc caagtgaggt ggaattccag acaggggccg    22320
ggaagacttc gtggaaaggg agaatctgag gtgggttttc taggatgggt aaagttcatt    22380
agaggaagag aagtgcaaca gaggaagttc ggtgagaggt agagggaagg cgttctgatc    22440
atgaaggaaa cactagaaaa ggtatggaga tagaaaaaga taaggcctga tttttttaacc    22500 taccacttaa aaaaaatcct tgaaaagaga tttttaaaac gaatacttgg tgctgacaaa    22560
ggtgaaatga ccgggcgcgg tggctcacac ctgtaatctc agcacattgg gaggctgagg    22620
cgggcagatc acttgagctc aggagtttga ccagcgtgg ccaacatgg caaaactcca    22680 tctctactaa aaatataaaa attagacggg tgtgatggtg ggtgcctgta gtcccaacta    22740
ctcaggaggc tgaggcagga gaattgcttg aacccgagag gcgaggttg ctgtgagctg    22800 agattgtgcc actgcactcc agcctggata gcaggatgag actgtctcaa aaaagaaag    22860 aaaaggaaag aaaaaaaaat ccgtactgta aactggtaaa ggctttcttt ctggagagca    22920
atttggggca catgcaccag tagccttaga aggctcatgc ttttgaccta attatcctat    22980
tagtggtgag atgattaaag atgtggcccc aattttatgtg aaaggtatgc atcacatctt    23040
cactcataat caggagagtt ggggaaaacc ctagctgtta atagtttatc caaaatccat    23100
```

```
atatatatgt gtgtgtgtgt gtgtgtgtgt gtgtgtatgg atttatatat atatataaat   23160
ggatatatat atatatctgg atggatatat aaatatgata tatatatgtg tgtgtgtgta   23220
tatatatatg tgtatatatg tatatatata tgatggaata ctatttagcc ataaaaagga   23280
atgaattaat ggcattcgca gtaacctgga tggacttgga gaccattatt attttatttt   23340
atttatttat ttttgagacg gagtctcgct ctgtcaccca ggctgagtg cagtggctcg    23400
agctcagctc actgcaagct ccacctcccg agttgacgcc attctcctgc ctcagcctcc   23460
tgagtagctg ggactgcagg cgcccgccat cacgcccaga taacttttg tattttttagt   23520
agagactggg tttcaccgtg ttagccggga tggtctccat ctgctgacct catgatccac   23580
ccgcctcggc ctcccaaagt gctgggatta caggcgtgag ccaccgcgcc cagcgagact   23640
gttattctaa gtgaagtaac tcaggaatgg aaaaccaaac atcgtatgtt ctcactcata   23700
agtgggagtt atgctatgag gacgcaaagg cataagaatg atacgataga ctttggggac   23760
tcagggaaaa ggtgggaagg gggtgaagga taaaagatac aaattgggtg cagtgtatac   23820
tgctcgggtg atgggtgcac caaaatctca taaatcacca ctaatgaact tactcatgta   23880
accaaatacc acctgttcct caataaacca tggaaattaa aaagaaaaa agaaaaagta    23940
ccctggaaaa aaaatttctc cctggccagt cacggtggct catacctgta atcccagcaa   24000
ttcgagaggc tgaggcagga ggatcacttg agcccagtag ttcaaaacca gccagtgcaa   24060
catagtggga ccctgtctca aataaaatct aaaaattagc caggtgtgtt ggtgcatgtc   24120
tgtggtccca gctactcagg aggctgaggt gagagtattg cttgagccta ggaggttaag   24180
gcggcagtga gccgtgattg tgccactgcc atccaacctg gcaacaaag caagaccctg    24240
tctcaaaaaa aaagaaaaaa aaaacctctc tattcgcctt ttaagaatac ctgggcttct   24300
ctgtgtacac ttaagcttca ttggagtctt tagacttttt ttttgctgta tctgtccagt   24360
taccaagtcc cagcttctac tccatgctcc ccatgctctc ttcctattt attttccatg    24420
actgcctcgg tataacttgt gctcaaccaa actggactac tcaattccct gcatttttctt  24480
ttttaaagtt taatcaaaaa aaaaaagaaa actggctggg cacagtgggc ttctgcccac   24540
aatctcggtg ctttgggaaa ctgaggcagg aggattgctt aaggccaaga gttcaagacc   24600
agcctgggta acatagcaag acctccatct ccacaaaaaa atttaaaaat tgactgagtg   24660
tgatggtgtg cacctagtcc cagctgcttg ggaggctgag gcaggagaat tgcttgagcc   24720
caggagttcc aggttatgat gagctatgac tgtgccaccg cactccagcc agggtaacag   24780
agtgggactg tctcaaaaaa caaaacaaaa tccctaatat aatctcagtg tgccttttaa   24840
gtatgccata tatatatata tatatatata tatatatata tatatatc acattttctt    24900
tatccactca ttgattttca tgtagttcta atcgtagaat tcatacattc tttctatctt   24960
ccatctttca cataacatca caaacatttt ctaggttgcc atattgtctt catagttact   25020
taaataatat tccatcaagt agcacaatca tttatttcac tagtcctcta actgtagaca   25080
ttttggttgt ttttgaaact taataatgta aataacaccg tgataacaat gtttatgtaa   25140
attcatattt tggattatct ccttagggtg gattcccaga agtcacatta gtaggtcaaa   25200
gagtatgagc ctattttcaa ggctcttgtt ttattacctt taatttcca cttgcctcaa    25260
tattgctggt ttgctcccttt atgatcacca gagttactcc gtcggtccaa attctttacc  25320
ttccgaaact gggaaggcca tgactcaatg ttatatatat agtaaaggct actataacct   25380
tccccagaat tttccaagcc agtggtctct aaagtgacct ttggctgtta aaatctgaat   25440
```

```
tcagagggtt catgagactc agtgttgttg tagaatttaa gctccttaat ttgccacgtt   25500
gtttagacac cacttaatac tttattgcaa atgacttgtc aacgcctctc acctacaaac   25560
ttcatcctcc tacaaatata cctcctgcta atcaaatgag gctacagttg agtctttaag   25620
tttcagtaga aagatggccc ttcctctggg gtaggcgcat gctcttcatg ctgaagctca   25680
gctgaaaagc ctcctgctga gttttctgcc tctttccctc ccactgcaca caccccaggg   25740
tgttggcgcc acttcaaagg gagcctgtgg atgaagaaaa cacaggtaaa ggcagagggc   25800
tcataagggg gccataaatt taaaaagtta agattcctgg cactatcaac tctcacttgt   25860
tttcaaatat gcatatggag tggatattcc agttttcatg tctgtgttgt tgtttttaaa   25920
aaaagacctt tcaaagaact gtgcatttt tacaggctga caggctgtgt ttggtgttaa   25980
actgtcaggg ctgactggtc acttggaaag ggcaagggct gaggtgcatg caagtgtcgg   26040
ctggttactc acagacacag cagccccttt taccccggag agagttctgt ttgctggagc   26100
ccttattctg gccagcagtg tcacaaatgc acactgtaag acatagacag tcttggaaag   26160
aaagggaaac tggctttaaa aattcttact ccttctagca aagcaattca tctttggcta   26220
taaagaataa cacagccagg tgcggtggct catgcttgta atcccagcac tttgggaggt   26280
caaggtgggc agatcacttg agtctaggag ttcaagacca gcctgggaaa catggtgaaa   26340
ccccacctct accaaaaaaa aaaaaagaa agaaagaaaa gattagccag gtttggtggt   26400
acgtgcctgt agtcccaggt actcgggaag ctgaggtggg aggatcgctt gagcctggag   26460
ggcggaggtt gcagtgagcc gagatcatgc cactgcactc cagcctgggc aacagagtga   26520
caccctgtat caaaaaaaa aaaaaaaag aacagtaaca cattattaga aatgagcatt   26580
ctgaggccag gcacggtggc tcatgcctat aatcgcagca ctttgggagg ccgaggcggg   26640
tggatcacaa ggtcaggaga tcgagaccat cctggctaac acggtgaaac cccgtcttta   26700
ctaaaaacac aaaaaattag ccgggtgcag tggcgggtgc ctatagtccc agctactcag   26760
gaggctgagg caggagaatg gcgtgaaccc ctgggaggcg gagcttgcag tgagccgaga   26820
tagtgccact gcactccagc ctgggcgaaa gagcgagact ccatctcaaa aaaaaaaaa   26880 aaaagaaaga aacgagcatt ctgaaatagt cttccatatg atgcttttga caattcagca   26940
ggaaaataaa ggatgtaaga aatgaatgca tatgttaggc ctcttgttga cctgtggact   27000
aaattgtttc tccctgcaga gatcagcaag gacaactcct gcaaagaaaa ctgtacttgt   27060
tcctcctgct tgctccgggc ccccaccata agtgacttgc tcaatgatca ggacttacta   27120
gacgtgatca ggataaagct ggatccgtgt cacccaacgg tgaaaactg gaggaatttt   27180 gcaagcaaat gggggatgtc ctatgacgaa ttgtgcttcc tggagcagag gccacagagc   27240
cccaccttgg agttcttgct ccggaacagt cagaggacgt tgggccagct gatggagctc   27300
tgcaggctct accacagggc cgacgtggag aaggttctgc gcaggtgggt ggacgaggag   27360
tggcccaagc gggagcgtgg agaccctcc aggcacttct agagctcttc ttcttccttc   27420
attggcctct ccggatgttg aaacaaccac aggtcaagaa ggaatgtgaa tctgttgttt   27480
tataagagtt taggacaagg acgtggaaca gtggacactg gttttcccca aagctggcag   27540
ttttgtggag gggtagcttg tttcggtggt ggatctctgt ttatttttgc acatctgtta   27600
taatttaata ttcaaatctg gaattaagaa aacatatttt ctagtatcct ctaagggcca   27660
aagtcctaca atcggaatgg attcatgcca cgttgaagat aaaattatcc tctctctgaa   27720
atacggtaaa gatttaaata ggtcctgaga ctgttgatag ccccagacat acccacagca   27780
ttatatgtaa catctctcct gatcagtgcc attcccacgg tttcaaagaa aacagctaca   27840
```

```
aggaatgctt acctgagtgt ctgcagcacc ctccacttct ctcctaggca atgagaccca   27900
gtggctagaa attcaccatg tctattctca agatccatgc cagggagctc tttgactctc   27960
gtgggaatcc cactgttgag gttgatctct tcacctcaga aggtctcttc agagctgctg   28020
tgcccagtgg tgcttcaact ggtatctatg aggtcctaga gctccaggac aatgataaga   28080
ctcgctatat ggggaagggt gtctcaaagc ctgttgagcc catcaataaa actattgcac   28140
ctgtcctggt tagcaagaaa ctgaacgtca cagaacaaga gaagattgac aaacttatga   28200
tagagatgga tggaacagaa aataaatcta aatttggtgc aaatgccatt ctgggagtgt   28260
ccctcgctgc ctgcaaagct agtgctgttg agaagggggt tcccctgtac caccacatcg   28320
ccgacttgtc tggcaactcc aaagtcatct tgccagtccc ggtgttcaat gtcatcaatg   28380
gcagttctca tgctgtcacc aagctggcca tgcaggagtt catggtcctc ccagtcggtg   28440
cagcaaactt cagggaagcc atgcccattg agcggaggt ttaccacagc ctgaagaatg   28500
tcatcaagga gaaatatggg aaagatgcca ccggtgtggg ggatggaggc gcgtttgctc   28560
ccaacatcct ggagaataaa gaaggcctgg agctgctgaa gactgcgatt gggaaagctg   28620
gctacactga taaggtgatc gtcagcatgg acgtagaggc ctccgagttc ttcaggtctg   28680
gaaagtatga cctggaattc aagttttctcg acgaccccac caggtacatc tcacctgact   28740
gtctggctga cctgtacaag tccttcatca aaaactaccc agtggtgtct actgaagatc   28800
cctttgacca ggatgactgg ggagcttggc agaagttcac ggccagtgca ggaatccagg   28860
tagtggagga tgatctcaga gtgaccaacc caaagaggac agcctcggcc gtgaatgaga   28920
agaagtgcaa ctgcctcctg ctcaaagtga accagattcg ctctgtgact gagtcccttc   28980
aggcgtgcaa gctggcccag gccaatggtt ggtgtgtcat ggtgcctcat cattctgggg   29040
agactgaaaa taccttcatc actgacctgg tggtggggct gtgacctggg cagctcaaga   29100
ctggtgcccc ttgctgatct gagcgcttgg ccaagtacaa ccagctcctc agaattgaag   29160
aggagctggg cagcaaggct aagtttgccg gcaggaactt cagnaacccc ccagccaagt   29220
aagctgtggg caggcaagcc cttcagtcac ctggtggcta attagacccc tccccttgtg   29280
tcaactccgg cagctcaaga cccccgagca acatttgtag gggccgctgc tagttagcta   29340
cccttgccca ccgccgtgga gttcgcacct cttccttaga acttctacag aagcaggttg   29400
cagtgagccg agattgcgcc actgcacacc agtttggaga cagagtgaga gtccgtccca   29460
gaaaaaaaaa aaaaaaaaaa gaacttntac agaagccaag ctccctggag ccctgttggc   29520
agctctagcc ttgcagtcat gtaattggcc caaatcaccg gagccacgtg accctccagt   29580
gtcatctccg gggtggccac aggcaagatc cccagtgatt ttgtgctcaa aataaaaagc   29640
ctcattgacc catgagaaaa aagaaaacag caatgagaag tgaccctgtc ttgttggttt   29700 attactttt ttgttataaa gtactttggt gaattaacag gatgctagta ttacatggtg   29760
atactcttca gaacacctgc cccatctttt ttatgcaagt atgtttacaa tcagtggact   29820
atcagtaatg tcatttgctc aaatattttt taaagaccta cagaaactga tggttattgg   29880
gaaaacagtc aggaagtagt gaggtaatca aggccatggg aatagtgttt gacaaagaga   29940
gtactccaaa tccttttggg ttacccagga ctttaaaaaa gagagtactc catcacacct   30000
gtaatcccag cactttggga ggccgaggcg ggtggatcac gaggtcagga gatcgagacc   30060
atcatagcta acatggtgaa accccgtctc tactaaaaat acaaaacatt agccgggtgt   30120
ggtggcgggc gcctgtagtc ccatctactc aggaggctga ggcaggagga tggcttgaac   30180
```

```
ccaggaggcg gacttgcagt gagccgagat agcaccactg cactccagcc tgggcgacag   30240
agcaagactg tgtctcaaaa aaaaaaaaaa aagagtgctc caaatctcct ttggttaccc   30300
gggactttaa aaaatttaat gtgatagtta ggccgggtgt ggttctcacg cctgtaatcc   30360
tagcactttt ggaagctgag gcgggtggat catttgaggt caggagttgg agaccagcct   30420
ggccaacatg gcgaaacccc gtctctacta aaaatacaaa aattagccag gcgtggtggt   30480
gggcgcctgt aatcccagct cctcgggaaa ttgaggcact agaattgctt gaacccagga   30540
ggtggaggtt gcagtgagcc gagattgcgc cactgcactc cagcctaggc aacagagcga   30600
ggttccatct caaaaaaaaa aattgtaata ataataataa caatgtaata tttactttt    30660
catcctttat ataaggctga gtgcttcacc cctgagatga agctcagtta agaaataaat   30720
gaaaatcccg taacctattg gtgaaaggta accaccccca gctcctacta gcccaactta   30780
aaacaggacc ccatcacact acacagcagt ttagccaaga aaggggggtc tttatgtgga   30840
cactgggagg gaagggattc cttcaaatcc aaactttaaa ggatttaaa caatgaaac    30900
atttggttca agaatagct gatgttttta tttgatgatt ttggagaaag gaaagtgtgg    30960
ggcataatgg ggtttgttat tggaaagatc agatttcta ggtaatttgg gtggagaaag    31020
acaaaaggca aagctttgac tgacaattcc atgaaagtgc tatttggttt tggttatggg   31080
cttagaaaat taagacactt agttcaattt ggaaggattc tgtataagtc cctgattaaa   31140
ataagcaaaa atgatgaata acactgattc agtgcaaccg aaagattagg attaactcaa   31200
aagaaagtta ttttctaaac caccgtgatt ttttccactg acaattacag cggttttcat   31260
taggttgctg acacatgaag tcagcctcac catcagttgc aaactctaaa ctagcaaaat   31320
ctattacaga gacatactta tcacttctga tttagtgcta atctcaccca gctcatcttc   31380
tcttgtcaga tttatgagat aaatgtcaga tttatcacca gatatattga agtaacagc    31440
cagtaataaa atgtgagatt ttaaaaaata gattctttgg caaattggtg ttcagtgagg   31500
caattattaa acattttgt cagccaggtt ccaggcactg tacagaagct gttaggagtt    31560
ctcaccatct acgaatttga tttgatgtat tgtattctca ttaagctatg tgtgacacat   31620
tgtcatttat tagcccagaa tttaaaaagc tgtggttgtt tagtgttggt ggtagcagac   31680
cccagcagtc tgatggtctg cactccttcc atcctgccac cccctgggga tgcaaagact   31740
ggatctcagg gtgacaatct tcttgcgcac gactgcctgg ccaagtgcct ccagaaagcc   31800
ccttccttcc cccatttcca cccaggccca cttgtcacct cagcctaaca ccagcctgca   31860
cagtctacgg ccaccatcca ggcagtggga gagggaaagg ggaggagggt ggaagggaaa   31920
acccctttct atacctctcc tcagcctgct ctttcctcct cccacctctg agcctccgcc   31980
tcccccagac agagacagaa aagatggaag aacaggtggg acctccaccc ccaccccaag   32040
ccttcatccc ggtggagggg gatgggaaga tttctctcat ttcaagagac tcctccacct   32100
cagactgaca aaaggcagag gcctggcaag aagaaagggc accctgggga agaagggcat   32160
tgaaatagca cctgccgggc cgggcacggt ggctcacgcc tgtaatccca cactttggg    32220
aggccgaggc gcgtggatca cggggtcagg agttcaagac cagcctggcc aagatggtga   32280
aaccccgtct ctactaaaaa tacaaaaagt agccaggcgt ggtagcgggt gcctgtagtc   32340
ccagctactc cggaggctga gcagggaac tgcttgaact gggaaggtgg aggttgcagt    32400
gagccaagat cgtgccatgc actccagcct gggcgacaga gtgagactcc atctcaaaaa   32460
accaaaacag aaatagcacc tgcccccacc ccctgcccgc cctccttccc gccccgtcc    32520
tttcctagac ttcactcaag tcctctgctc agaggaagcc ctgctctact gaaagccaca   32580
```

```
aggccattct cggtggcctg ggacagcagc ccaagacgtg ggcttctaac tgcctccgaa   32640
ggggccacag cagcaaacat aaataaaaat agtaaaatgt tcttaaatta taaatttaaa   32700
atttggaaaa tttagtgagc acagcttcta gggggcatgt ttccaaaatt ccaaccacaa   32760
aagtgcagtc tcaaaactga ctgtaaaccg aacataccat ctcatctcag acacagctat   32820
tgttcacgag tgtcagtgga actttcctcc cttgagatgg accaaaaacg tcaagcaaga   32880
tgacatttgc tgatttgcag gcttcaggca gataagatac gggcagagtt gagtgtgcgc   32940
ctttacccct aaaattcagga atagcaggaa cagcaggaaa aacgtaggac cacagcgtac   33000
gtcccacttg tctttcattt tgatatcatt atttccagag tcctgattgc tagtcatgtc   33060
taacactgga tttattatca tctcattgct agcatggcta ggaaagcttt gaacatcctt   33120
atcattctat tttaattcct attataattg catggggaag ttccagggtg gaaaaatttc   33180 ctttctttc tttttttttt tttaatagga gagttggctg ggcacggtgg ctcacgcctg   33240
tgatcccaac actttgggag gccaaggcgg gtggatcacc tgaggtcagg agttcgagac   33300
caacctggcc aacatagtga aaacctatct ctactaaaaa tacaaagtta gctgggtatg   33360
gtggtgcaca cctatagtcc cagctactgg ggaggctgag acaggagaat cacttgaata   33420
cgggaggcag cagtgagcca agatcatgcc actgcactcc aacctgggag agacagagtg   33480
ccatctcaaa aaaacaaac aaaagagttg atataaattt gctgttataa tttgactgta   33540
ctgtttcttg cacatgttga catctgtaat gactggagtt tatgaaaatt tttgatgagt   33600
aggagcatac cattaacaga gagaaattta atcaaaagat tttaaagtt ccttcagagt   33660 ccagactttg actaagtgta gtatgattta tatctatgtt gcatacaaaa atatcaaaca   33720
gtaattccca actgaaatac aagtatcaat caattgtgta acaatgcaaa atcatttaat   33780
ttaaagttaa tttatagcaa atgagtactg taatagcata agcatgccga tactttacaa   33840
aggagagagt ggaaaggtag gatattataa ctaattgatc aaatcattgt taaaatttaa   33900
gtttattaat acttttactt ctgtccgtag ggatccatgt taaattgggt atattataaa   33960
cttaactgct aatgatgagg tccttttgct attagaaatc tatttttat ttttctttat   34020 tattttttga ggcagggtct tgctctgttg cccaggctgg agtgcagtgg tgaaattata   34080
gctcactgca gcctcaacct cctgggctca aggaatcctc ctgcctcagc ctcccaagta   34140
atggaaactg cagtcgtata caagcacacc cagcaatttt tttttttttt tttggtaaga   34200
tggggtttag ctatgctgtc caagctggtc tcaaactcct ggcctcaagt gatcctccca   34260
ccttancctc caaagtgctg ggattacagg cgggagccac cattcccagc ctagaatgaa   34320
atatctttag ctaaattaca gggctggatg tggtggctca tgcctgtaat cccagcactt   34380
tgggagactg agggcgggag ggtcacttga gatcaggagt ttgagaccac cctgggcaac   34440
acagtgagaa ttctgtctct attttaaaaa gagaaaatc tagggtatat tctcttaaac   34500
aaaactttca tctataatgg tagttgatga ggtcctatgt aatatgcatt tccttggttg   34560
caatagcaaa ttactacaca cacagaaagg aaagccacac tccccgacac atctacacac   34620
aggaggactc acacaggagg gagactcaaa gaaggcacgt gactttaca ttgttagggc   34680 ttacatggtc ctgggatttc ccaccagtac tcaaaagatc aattgtatga acaagtcacc   34740 tattttacg gcactaaata attattattc aacaacatgg aaaatatgtg gtagcagacc   34800
tggattttcc ttaagagtta ttttatgtg gtactgcccc ctgctggaat ataacatcta   34860
tacacatcct ttctggctgg gctgacatcc taaaaccagc ccaggaccag ccttttatta   34920
```

```
atattaattc ttggccaggc gcggtggctc gcctgtaatc ccagtacttt gggagtccag    34980
ggcgggcgga tcacgaggtc aggagttcaa gaccagcctg gccaacatgg tgaaactccg    35040
gctctactaa aaatacaaaa cttagctggg catagtggca cattcctgta atcccagtta    35100
ctcgagaggc tgaggcagga gaattgcctg aaccgggacc cggaggtgg aggttgcggt     35160
gagccgaaat cgtgccactg cactccagcc tgggctacag agcgagactc cgtctcaaaa    35220
ataaataaat aaaaattaaa attaaaaaat aattcttggt tgtatgctaa aagccttgca    35280
agtagcccca ctggaagata ggaagagtgg ggctgtttta caaatgagca catataagca    35340
gaacgaggcc gccataattg aaatgaaggt ccccgtcccg tggatgtgtt catcgctact    35400
tcaccctgtc attcggatcc aatgtgtgac cagccagctc caataacagt tccatactct    35460
gggaattatt tttaacactc ggcaggatgc tttcttcctg tagttttagg cttagcccct    35520
tgtgcacttt tggtctcttt ccctttcaat ttagcatcca aggaagcggc tgtgaccaaa    35580
ggtagctgtc atgttaaagg acaaagttca tagttacagc aaatattgac ccagagcact    35640
atccttgccc cttcctctat aatgtgcaat gcaaaaatat gttctttaa gtacaatatt     35700
aataagtaag gtctaggaga ttttcttccc ccttcctttc tcttttagat gagtaaatgt    35760
tttatctagt tttgaggaga ctatccttct tatcacatct cttttccactt ctgctctcct   35820
tgttttataa ttttcctctc ctttgggtcc gtgtcattat ttcgtgtcgc ttgttttcga    35880
gccatgcact catttatcaa atcagatttc ctccgtatgc cgacggcctt cctctccctg    35940
ccacgggctt cctttttccc tgactatgca gaagcaattt gttcgcttgt gtttcttttt    36000
tttttgaga cagagtctcg ctctgtcacc caggctggag tgcagtggcg acatctcggc    36060
tcactgcaac ctccgcctgt caggttcaag caattctcat cgtcagcct ccagagtagc     36120
tgggattaca ggtgtttgcc accaaggctg gctaattttt agtagagacg gggtttcacc    36180
atgttggcca ggcttgtctc gaactcccaa catcagttga tccacccatc tcggccttcc    36240
aaaatgctgg gattataggc atgaaccacc gcatctggcc ttgtctttca tccttaatga    36300
cactttagtc ctaataatgc taaaatcatt ttctactctt tgaattgaaa cacagcttat    36360
ctacatgagc ccaaggcagt agcaacattc acctccattt cttctctgat ctctaccttc    36420
tgaaccctgt ggacttggtt gtaaatggat gagggcaagt cttgcttcct tcccctgtgt    36480
ttacagagga tcgtggctga gatgctgggc cacactctgg gcctgctggc accccctgggc   36540
cggtggctgc tgcccctcag ggtgctcacc acctagacca gaagaaccaa ggtgagggag    36600
agcctgtttt ctttcttcct gtggctgcgg gggctgtgag gcatgggtct agtggctgtg    36660
tttagctggg gatgcctcct agaaatcagc tccaccgttg aagagatcaa agcaatgcac    36720
agtgccactt gaaatgaaac gattgagctt atcagcgctt ttgcaaatgt acaagagggt    36780
agctcccccg gacatcctga actgagccat gctcttctat tttgtgtaac agcccagtga    36840
cccctgaatc ttcccctgag gcaggtcccc gaagcttcat ggaggatgtt cctcagctga    36900
ccaaggtgag gctcttgagc tcctaaatct ttgtgatact gtttatacat ctttgtgctg    36960
tacttttaa gctgacttcg tgttatcacc tgtatgattt tatgttttgc ttctaaataa     37020
gtacagatta ttttaaactc taataatggg tgctacaaaa ttaaagatta tgtcaatcac    37080
tgtctctgat gagttatttt atgtagattt caacacaatc attgattcat gtgtactctt    37140
ggtcagtcat cagtcatctg agtacctagt gggtttccaa aatgggtcct ggatgctggg    37200
gatgcaaaga taagcaacac atttctatcc tcaacagcct gtagatgagg gagaatcact    37260
gcggacaatc agggaagtta ccggagagag cagtgcacat gtggtctaga aactggtgga    37320
```

```
acaaagttga gaatcactga actaggagga aagacaggtc actgacaatc caaggcacag  37380
tgactcacac tctaatctca gcactttggg aggccaaggc aggaagatcc actgagctca  37440
ggagataaag accagcctgg ctgacctatg gagacccttc tctaccaaaa aaaaaaaaaa  37500
aaaaaaaaac attagcctgg catggtgggg tgtgcctgtg gtaccagcta ttcaggaggc  37560
tgaagtggga ggatcgcttg agcccgggag gtcaagactg cagtgaatca tgatcacacc  37620
attgcactcc agcctaggga agagagcaag aaagaccctg tctcaaaaac agaaaaaaat  37680
ccagtaaaat gtttcagatg ttgttaaagg tgatttcact gttacttttc acctctcctc  37740
attttacatc tctgacctat gcttgtcctc tgacttgcca gacattccta gctatggact  37800
tgatgtctcg acatggaggc tcacaggcac cccaaactca gcctgcccta agctgaaccc  37860
atgatctttc cttccaaact tgtttctcac cagagttccc atcttatcat ccacctagtt  37920
gttcaagtca tccttaagac ctccctctcc ttcactgtct attctacctc cctaatatct  37980
cttaaatcct tccctcctct cccacctcac agccaccatc ctaacctaag cagccaccct  38040
ttctcaccct ataatgacct cctggctgtt ctctatagag ttggtgaatc ctttcgtctt  38100
cagcctgaac cccctttcga gggattctta tatatataca tagatataca caaatatata  38160
tgtacatatg tacatatgtg tgtatatatg tacatatgtg tatggatata catatgtaca  38220
tatgtggatg tacatatgta catgtgtatg ggtgtacata tgtacatgtg tatgggtgta  38280
catatgtaca tatgtgtatg ggtgtacata tgtacatatg tatatgggtg tacatatgta  38340
catgtgtgta tgggtgtaca tatgtacatg tgtgtatggg tgtacatatg tacatgtgtg  38400
tatatatgta catgtgtgta tgtacgcatg tacatatgtg catgtatgtg catgtgtatg  38460
tgtgtgtatg tacacgtgtg catatgtgtg tatatgtgta cacgtgtacg tgtgtatata  38520
tatatatata tatactggct ggagtgcagt gggaaagttt tggctcacca caaactccac  38580
ctcccaggtt caagtgattc tcctgcctca gtctcctgag tagctgggat tacaggcgtg  38640
caccaccatg cccagctaat ttttgtattt ttagtagaga cggggtttca ccatgttggc  38700
caggctggtc ttgaactcct gacctcaggt gatccaccca cctcggcctc ccaaagtgct  38760
gggattacag gcgtgagcca ccgtgcctgg ccggattcct atcttgaaga cgaagcccca  38820
gaccatcgac acgcctcaa ggccctgcat gacgcctcct gccccaacac ctcgtgtcat  38880
cttgctctcc tctcccgcag ctcctgaggc tttagccacc ctggaattcc aagtccccat  38940
ggtcattttt ttttcctgct caagatatca ccatgtgctg tcccctctgc ccttgtctac  39000
acccacgtgt ccttctcccg ccccggccac actcatgggg cacactgtcc ttccctggct  39060
aatcctccca cactcgatac cactttctct gggatattgc acccgatcct cagccgcagt  39120
tgtcttccta tgacccactc ccacactctc gccacaatgg taattgtttg attcctactt  39180
gttgtccctg tgagactgca aaccccagag gacaggggcc ctgggttctc cttcgcctct  39240
ggatcatcag cactaactga atacctggcc tagaagagat gctaacgatg ctgaatgaat  39300
aaataagtgg aaagactctc agtaaagcaa aacctttctt taccatttta tggccgtcaa  39360
ggaggaaaac acattatcag tggaaaacgc aaaatgaggg gatttgctta gcaaacgatg  39420
aattcctctg gcaccctggc agccttggtt tcttttgatg aggtccaccc ccttccatcc  39480
atcttctggg cttaagagat caaagcaaaa catgctgtgg aattcgatac tggtgcaggt  39540
tgcacaacat tgtgactgaa ctaaaagcca ctggatggta caactgaaaa tggtgaattg  39600
cgtgttgcat gaattataac ctaactgggg aaaaaaaggc ttaaaaagag acaaagcttc  39660
```

```
ccccacaatg gaaaggaagg tataatagaa acagcagctt tcaaaccttg gcaggataat    39720
gaaaccccgt ttctattttt aaaaattagc tgggtacagt ggcacgtgcc tgtagaccca    39780
gctactcggg aggctgaggc tggaagatcg cttgagccca ggagttcaag gctgtggtaa    39840
actataatca cactactgca ctccagcctg ggtgacagag aaagaccctg tctcaaaaaa    39900
ggaaggaaag aaggaaggaa ggaaggaagg agggagggag ggagggaagg agggaaggaa    39960
ggaaggaagg aaggaaatag cagctctgag cttagaaata ggagtctatt tctaagtggg    40020
agatggggag aaggagggaa ctggggaggt gaggaagaag caggtattgt caccagtgag    40080
gactgtgctg ttgtgagccc agctaggcaa ctggcaattc cattctgtta gtgacagcta    40140
caataaccca aagccctctg gagccctgct ttcctctgct ctcttcgtgg cttgactagg    40200
agctgaagat cctgtccctc ttagagcatt ggggcggccc accccacctc caccctcctc    40260
cacctgctgc ctcgaggccc ctcccactcc cggggtagac aaaacagttt agaggctgaa    40320
gtcaccgggc tgtaactgt tggatttgca catgtcatag aaaatcatca tatgttttgt     40380
gtggactcca tgcataacaa caagagaacc aaccagaccc catagacaga agggagtgtg    40440
aattggagac aaaatttaaa ttatgagttg ccttctattc agatttctcc cattttaac     40500
aaaaaggagc ccaaattcct aaatgttatg gttgtttgca gcaacttatc atctttctcc    40560
tttccttcat agccaaggtt tttgaaagag ctatctgagg ccgggaatgg tgactcacgc    40620
ctgtaatcct agcacagagg ctgaggtgag tgatcacct gaggtcagga gttcaagacc     40680
accctggcca acatggcgaa atcccgtctc tactaaaaat acaaaaatta gccgggcatg    40740
gtggcgtgtg cctgtaatcc cagctactca ggaggctgag gcaggagaat cacttgaacc    40800
caggaggtgg aggttgcagt gagccaagat ctcaccactg cactccagcc tgggcaacag    40860
agtgagactc catctaaaac aaaaaaaaaa gtagctgtct gttctttctt ctcgaactct    40920
ttttcccgct gggagtctgtg acctgctgcc gtctgcctca agtgagaggg actagcagat    40980
ctggtgaatt accttctaat gcccgtaccc tgcccatacc agcttcaatc tgtatgtaga    41040
agcttagctt gctccatgca tggcctccag catccactgg tcacaaaata acacaaaata    41100
gcatgagaga gaatggtcgc atggagcgga ggagctgctg agactgaacc caagccaggg    41160
ctactgctgg gtggaactgg acatgccag cccatgggaa agtcttccca cagaagtcat     41220
atttgcaggg gtctcccagg agacagcaca ttctgagcaa aggagtgagg cagagataac    41280
tattcaggaa ccaagagact cgctggaaag aagcagagat tttcagccca gcgtagtgga    41340
tgtttcttga atcttcccct gtggatgccc caaaccttga gatccttcca acaaatagca    41400
cactactaac aaactgtgac tcaaagagag ggaaacatgg tccctgctc tgtcacaaat     41460
cactgtgaag ctttggcacc ctgactgctc aggtggccac caacacagaa ggaccacgaa    41520
tggctgagtc aggaagtcac agccgtgtgg ctggaagagg ctctgccttg ctctgggaga    41580
aatgcctatc cccaaggaag ccttagtatc catgggagag aaacactgta gcaatggccc    41640
ccaggactct cgggaagcca cttctggtgg gaggggactc aaagggtgct gggggacctg    41700
tgtctgcatc tggaagtgag gagccaggaa aattttcttt cagttctttt cttttttctt    41760
ttctttttt ttttttttt ttgagaaagg gccttgccct gtcgctcagg ctgaaacata      41820
gtggtgcgat ctcggctcac tgcaacctcc acctcccagg ttcgagtgat tctcctgcct    41880
cagcctcccg agtagctggg actacaggca tgcaccccca cccacgccca gctaatttt    41940
gtatttttgg tagagatgtg gtttcgccat gttggccagg ctggtctcga actcctggcc    42000
tcaagtgatc ctcccgatgt gctgggatta caggtgtgag ccaccacgcc cggcctcttt    42060
```

```
ctgcttcatt taacattaat ggtcatccca cagcatggtg ctgtgcacct gtagtcccag   42120
ctactcaggt ggctgaggtg ggagaatcac ttgcgttcca gctgtagtga gccttgattg   42180
tgtctgtgaa taaatgccac ttctctccag cttgagcaac ataggagac tgtctcttaa    42240
aaaacaaaac aaaacaggct gggctcggtg cccacgcct acaatcccag cactttggga    42300
ggccaaggca agaggattgc ttgagcccag gaggtcaaga gcagcctggg caaaataggg   42360
agaccccatc tctacaaaaa gataaaaaat aaaaaaatta actgggcatg gtgatacacc   42420
tgtagtccca gctactctgg aggctgagat aggagtattg cttgagcctg ggaggtcgag   42480
gctgcagcga gccatgatca tgccactaca ctccagtcca ggcagcagag tgagatcccg   42540
cctcaaaaaa ataaaacaaa acaaaactca tctctcccttt ggctcctgag actacaatcc  42600
ctcacggttc ttttctactt ctctgttttt tcttcttgt ctcccttttt ttctggtctc    42660
tctgtcaccc aggctggagt gcagtggtgt gatcatagct cactgcaacc ttgacctcct   42720
gggttcaaga gatcctccca cctcagcctc tcgagtagct aggactacag gctcacacca   42780
ccatgcctag ctaatatttg tagattttgt agagatgggg tcttgctatg ctgtccaggc   42840
tggtctcaag ctcctggcct caagtgatcc acccacctca gccacccaaa gttctgggat   42900
tacaggggtg agccaccgcg cccagccgat aattgttgaa aaatcatttt cagttaaggt   42960
atccagtcaa ggtcagaaaa tgagaaaatg ttaaaaaaaa aaaagctata agtaaaacag   43020
attcagtcgg gacatgatgg ttcacgcctg caatcccagc actttgggag gttgaggtag   43080
gataatcact tgagcccagg agttcgagac cagcctgggc aacatagcga gaccttatcc   43140
atacaaaaaa atttaaaaaa tacccaggca tggtggcata ctcctgcatt ccctgctaat   43200
tggatgggtg aaggggagga tcccttgaaa taggagtaga ggtgcaggaa atatgattgt   43260
gccgtgtaat ccagcctggt tgacagagca agatgttccc cacccccctg aaaaaaaaaa   43320
aaaaacctaa atccaaattt taaaagtttc cttgactctt caacttgctc accctccacc   43380
aaataaaata actacgaagg aggcttattt tttactattt ccagggatac gatatatgtt   43440
tgtcctgaaa atatacatca tggctttact caagccacag tgatgaggcc tcattgtcac   43500
tgtagcctaa ttacgatttt ataactccat ttaaaattca atttaaacac agtttaaaaa   43560
ttcagtccaa gtcaaacatg ctctcagtag ctagaagcaa aactctgttc aggtccttga   43620
tggatctatt tgtactttct ttcatgaaaa cagaaagtcc ttttttacac accatgcaac   43680
aggaaaattc ataacggaca ttgttttacc tgttcttggc aaagacaagt gagctcttaa   43740
caagcaaggt aactatggag atgatgtttt gctccaagtt aacacttaca tatttaatta   43800
gaaagatttc aaaggtgggc agattcactg gaaagtttcc aaaagcttca cttgttcaac   43860
aaataatgtt agagagggag caccgtgccc tcgggcccct aggaattagt tccacatggt   43920
ccggtcctct gtccagtgtg cccagcatcc acttgggaga acagcatggc cttctgtcca   43980
gggcagccca cgccagcact gcctgccctt tcaggcccat ggctcccatt aagtgccatt   44040
tcgagcatac ttagccaagt ttccctacca tggccaacaa agaggttgtt caaaaatgct   44100
tgtcaggtcg ggcatggtgg ctcacgcctg tagtcccggc actttgggag gctgaggcgg   44160
gtggatcacc tgaggtcagg aattcaagac cagcctggcc gacatggtga accccgtct   44220
ccacaaaaat acaaacatta gttgggcatg atggcgggtg cctgtaatcc cagctgctca   44280
ggaggctgag acaggagaat tgcttgaacc cgggaggtga aggttgcact gagctgagat   44340
cacaccattg cactccagcc tgggcgacag agtgagaatc catctcgaaa aaaaaaaaag   44400
```

```
tttgtcaacg gtttcactga atccagaata cttttctaaa atgtcaaccc tatagaatac   44460
attttataaa attatgaagg cctggtctgg tgtagtggct cacgcttgta atcccagcac   44520
tttgggcagc caaggcaggt ggatcgcttg aggctgggag tttgagacta gcctggccaa   44580
caaggcaaaa ccctgactct actaaaaaat acaaaaatta actgggcgtg gtggtgcaca   44640
cctgtaatcc cagctactca ggaggttgag acaggagaat cacttgaacc caggaggtgg   44700
aggttgcagt gagtggagat tgcgccattg cactctagcc tgggtgacag agcaagactc   44760
tatcttcaaa aaatagataa ataaataaaa attaaaacaa aataaaattc tgaaggcctt   44820
aggtcagaga attaccgagg gaatattcaa agttatacct ccaagtatct acaatgaaga   44880
tactttcatc agaaaaaagg agtttacggc caggccctgt ggttcatgcc tataatctca   44940
gcactttggg aagccaaggc tgaggcagga ggatcacttg aggccaggag ttcgagacca   45000
gcctgagcaa aaacgtgaga tcccatttct accaaaaata aaaatgtaag gtaggcatgc   45060
aactgtagtc ccagctactc gagaggctga ggcaagagga tcgcttaaac ccaggactcc   45120
agcctgagca acagagcgag accctgttta taaaaaaaaa agaaaaaaaa aagaagaag   45180 aagaaggaga agaaaggaaa taaaatttaa gaaaaaaaaa aggacttaat aaggttgaat   45240
gaaggcaaga atattcttag ctctgtttaa gtcaagacct gagtagtagc tctacgtagc   45300
tgtatgtcga taatgttttt gagacagcac tactgataaa ttgttacata ataaactgtt   45360
atggctggat gcagtggctc atgcccataa tcccagcacc ttgggaggcc gaagtgagtg   45420
gatcacctga ggtcaggagt tcgagactag cctgatcaat atggtgaaat cccatttcta   45480
ctaaaaaaat aaaaattagc tgggcatggt ggcgcacctg taatcccagc tactcaggag   45540
gctggggcag gaggattgct tgaacccagg agacagaggt tgcagtgagc cgagattgcg   45600
ccattgcact ccagcctaga agacagagcg agactccatc tcaaataaat aaactgttaa   45660
attaagttta gcctaaagct accccttac atatttaag ttcagtctaa aggtttccct   45720
gcacatagtg aactgtaacc taactggatg cgtaaacaga ctataaccta ctcttgggcc   45780
agtcactgag ttttggtcaa tcaaaggcag ccaactgttc aaaccaggtt aaaataaggc   45840
agatgctgag ctctaaccag tccagccatt tctgtacctt gcttccattt tctgtccatc   45900
actttccctt ttctgtccat aaatcttcca ccacgtggct gtgctggagc cactgtgaaa   45960
ctattctgtt tcagggctg cccaattcat gaatcattcc ttgctcaatt aaactctgtt   46020
catttaattt gtctaatatt tttctttaa tcaaagtaat ttggccgggc acagtggctc   46080
acgcctgtaa tcccaacact tcgggaggcc gaggtaggtg atcacctga ggtcaagggt   46140 tcaagactag cctggccaac atggtgaaac cccgtctcta ctaaaagtac aaaaattagc   46200
cgggtgtggt ggcgggcgcc tgtaatccca gctactcggg aggctgaggg aggagaatcg   46260
cttgaacccg ggaggtggaa gttgcagtga gctgagattg tgccattgca ctccagcttg   46320
ggcgacaggg caagactctg tctcaaaaaa aaaaaaaaaa ttaattcaga gacctactca   46380
tgtgaagttg tattttttta ttctccatat tacaaaacag aacaattggc acagggatga   46440
agaaatactt tgcaaaacat ctagagaggt taaatgccat gagtctttaa aatgtaagac   46500
tgctttcacc tgagcaatct agtgtccatt tctagagcta gcttaaatgt ccgtgtaaat   46560
ccccgtaatt ggttgggata acaattacct atgttgtata acttgagtca aaactacgt   46620 ttccactgcc tgccacccct atggatggtt ttctcttaag gtatcaaatt ttactgggaa   46680
agacctagat aaaatacagc gaaaatgagg cggggcgtcc tggcacatgc ctgtaatccc   46740
agcgctttgg gaggctgagt cagaaagatc tttgaattca ggagttcaag accagcctgg   46800
```

```
gcaatatagt gaaatcctgt ctttacaaaa aattaaaaat tagccaggca tgggggcatg   46860
ggcctgtagt cccagctact tgggttgggt gactgatgtg ggaggatcac ttgagcccag   46920
gaggttgagg ctgcagtgag ctctgaccat gcccctgcac tccagcctgg gtgacagagc   46980
aagacccagt ctcaaaaaga aaagaaaaag agtaatgtta ggtcaaggta gaacctacct   47040
tgactttctg ttactatgga agatattctg gggtatctct gagatccaag tattatggca   47100
cttaagtaat tcctatctat tgttctactt ggttcctcgg gagtaaaagt catattcaaa   47160
ccaaaaaggc tgtgggattt ccagaatttt aaaagcaata atagttaatg ttctcccatg   47220
ggagttactc cacatttta catatgttcc atatgttaac tcatttagac cttacccttta   47280 tgaggtaagt cctcttctta tccccacttt agaggtggga aaactgaggc acagaaagag   47340
taagttgctt gcctaaggcc ctgttactag caggtggtga aaccagcatt ccaacccggg   47400
agtctggcaa atgtgtgtga agagcacacg tttggaaatg acagtcatga ggacactgta   47460
agacttctgg aatgtttata atttcacctt tgcttgttat ttttcctgtc tgtttcccta   47520
gagtgagctg agtgaaaaaa gaaagaagaa agaaagaaga aagagaaaga gaaagaaagg   47580
agagaaaaag aaaaagaaa agaaaaacag aaaaagggaa agaaagaaga aatgaaagaa   47640 agaaagaaa agaagaaaga aaagaaagag agaaaggaag gaaggaaggt gggaggggag   47700
gaaaggaaga agaaagaaag aaggggggaca gagggaggga atgaaggagg gagagaggga   47760
gggaaggagg aagaaataaa aagatgagga tctgtatgct tgaggggtgg aggtggggga   47820
cttgggtggg agtgtgggat gggcagaaag ctggaggag ccctggaccg actgcattcc   47880
acagaggatt gtgggtgcaa cgtaggtggc agattgagaa aagcaaacaa acaagctcag   47940
cctttggagc ttcggggaag aaaaaaagct gagcagtgaa tgctggcttc ccacggagaa   48000
ggcaggctgc ttcgccagct cacatccttc cgcgcaccca cttcctcttt ccggaggtca   48060
ctttagattg cttttatggca ggatctccag gtcacaggaa tgttatgttt cgactggggt   48120
ttccccctcc cctgggatgc ctgggccagc tccccaaggg ctagtctctg tcccaggccc   48180
cacactccca tagcactcag caaaagccta gagagagcac cgcaaaatgc caaacgcaac   48240
aggaccgcgt aggaagaaga cgcttggaat gacagggaca ctagaactgc ccatggtcgt   48300
ggtctcaaat ttttgttcca tggtctgaaa tactaaaagt tcttaaacag ctacttgatt   48360
tcatactatt gttttgaaga aaacagtgtt tgtttgttgt tttgtttgtt tgtttgtttg   48420
agacagagtt ttgctcttgt tgccgagttt ggtccatgtt ggtcaggctg gtctcgaact   48480
cctgacatca ggtaatccac ccacctctgc ctcccaaagt gctgggatta caggaaaaca   48540
gttgtttctt taaaacaatt atataggctg ggcacggtag ctcatgcctg taatcccagc   48600
actttgggag gctgaggtgg gtgaattacc tgaggtcagc agttcgagac cagcctggcc   48660
aacatggtga acctccgtct ctactaaaaa tgcaaaaaat tagccgggcg tggtggtgca   48720
ttcctgtaat accaggtact caggaggctg aggcaggaga atcacttgaa cccaggaggt   48780
ggaggttgca gtgagctgag atggcaccac tgcactccag cctgggcaac aagagcaaaa   48840
ctccatctca caatctcaaa aaaataaaat aaaataaaat aaaataaatg gttatataag   48900
ctaccttatt gatgcagtta caaatgagcc gctgaaacat ataaaatttta aagaacaagc   48960 cacatatctt tcatcaccca cagcttcacc aactaaaggt gtatgtagta ctttttgtgga   49020 aggcatttcc acatgctttg agggaccttg aaatactgct atgattacat gattttctta   49080
aaaccagact actcctacat tacaagaatt gaaaagttca gagtaaatat ttgtaagacc   49140
```

```
tagaaaagat gatgttcttt aaaaaaaacg atgcccatct ttgtagcgaa aagaaagaga  49200
gatcagactg ttactgtgtc tatgtagaaa cagaagacat aagagactcc attttgaaaa  49260
agacctgtac tttaaacaat tgctttgctg agatgttgtt aatttgtagc tttgccccag  49320
ccactttgac ccaactactt tgacccaacc tggagctcac aaaaatatat gttgtatgaa  49380
atcaaggttt aagggatcta gggctgtgca ggacgtgcct tgttaacaaa atgtttgcaa  49440
gcagtatact tggtaaaagt catcgccatt ctctagtctc aataaaccag ggcacaagg  49500 cactgtggaa agccgcaggg acctctgccc tggaaagcgg ggtgttgtcc aaggtttctc  49560
cccatgtggt agtctgaaat atggcctcgt gggatgagaa agacctgacc atcccccagc  49620
ccaacacctg taagggtct gtgccgaggt ggattagtca aagaggaaag cctcttgcag  49680
ttgatataga ggaaggccac tgtctcctgc ctgcccctgg gaactgaatg tcttggtata  49740
aaacccgatt gtacatttgt tcaattctga gataggagaa aaaccgccct atggcgggag  49800
gcgagacatg tttgcagcaa tgctgccttg ttattcttta ctccaccgag atgtttgggt  49860
ggagagaaac ataaatctgg cttacgtgca cgtccagtca tagtaacttc ccttgaactt  49920
aattatgacg tagattctgt tgctcacatg ttcgttgctg accttctcct tattatcacc  49980
ctgctctcct actacattcc ttttgctga aataacgaag ataataatca ataaaaactg  50040
agggaactca gagatggtgc cggtgcaggt ccttggtatg ctgagcgccg gttccctggg  50100
cccactgttg tttctctata ctttgtctct gtgttttatt tattttctca gtctctcgtc  50160
ccacctgact agaaatatcc acaggtgtgg aggggcaggc cacccttca catcttgtct  50220 ccacttcctt gattaaaaaa aagaaaagaa aaaaaattt gccgaagttg gattcattca  50280
cagaattcta cacattaaaa atgttgcagg tcgggtgtgg tggcagctcc caaagctgcc  50340
tataatccca gcgctttggg aggcttgagc ccaggaggtc aaggctgcag tgaactgaga  50400
tcgcaccact gcactccagc ctgggcgaca gagcaagacc ctgtctcaaa gaaaaaaaa  50460 aaaacagaaa aaaataacgt tacagaaaaa gtacaatatt tttaatatat atatatatat  50520 ttttttttc tgagacagag tgttgctctg tcacccaggc cggagagcta tggctcgatc  50580
tcagctcact gcaacctcca cctcccgggt tcaagcgatt ctcctgcctc agcctcccga  50640
gtagctggga ttacaggcac ccaccaccac gcctggctaa ttttttgtatt tttagtagag  50700 acggggtttc cccatgttgg ccaggctggc ctcgaactcc tgactttatg atccgcctgc  50760
cttggcctcc caaagtgttg ggattacagg tgtgagccac catgcccagc caaaagtaca  50820 atattttaa tgacatataa agatgttcat tctttgtggt tgccctgggt gagagggact  50880
attgatactc aatagtgttt cttttgtttc tacattgttt ctatagtgaa aatacgcatt  50940
ggctttgtat taaaaatgt atagtaaaaa tggttttatt aaaaatagca ataactaca  51000 aaaactccat tgcaatggaa agcagcccct tggattttcta gttgaatgaa acgagtaatt  51060
tatccaatgt tagaaatgtc taaaggctcg ctcaggtttc atgagcagaa caggaattgt  51120
atatccaatt aaatgtgaaa ttgcaatgcc tggtgcggtg cttatgcct gtaatcccag  51180 cactttggga agccgaggca ggggatcgct tgagcccagg agttcgagac caccatgggt  51240
aacatgggga ggccccatct ctacaaaaaa taaaaatcgt tagccgggca ggttggtgca  51300
tgcttgtgtt cccagctact tgggaggctg aggtggaagg atcctctgag cccaggagga  51360
tgaggctgca gtgagacatg atcgatgcac tccagcctgg atgacagagt gagaccctgt  51420
ctcaaaaaaa aaaaaaaaga aaagaaagta caatcgcaat taaatgtctt tgcgttggtg  51480
gctcctgacc aaaattccta agcaagcagt atgttaatga gcagaggggc cacagctcac  51540
```

```
cttgctcaat taaaggcagg agcaggccgg gcgtggtggc tcacgcctgt aatcccagca   51600
ctttgggagg ccaaggtggg cggatcacga ggtcaagaga tcgagaccat cctggccaac   51660
atggtgaaac cctgtctgta ctaaaaatac gaaaattaac tgggcatgtg gcatgagcct   51720
gtaatcccag ctactcggga ggctgaggca gaagaattgc ttgaacccgg gaggtggagg   51780
ttgcagtgag ccgagattgc accactgccc tccagcctgg tgacagagcg agacttcatc   51840
ttaaaaaaaa aaaaaaaaa ggcaggagca agtatgggcc agacagaaat caaggtgtaa   51900
attgggcaga tcctcaggcc cagtgctgaa ttttggtttg atgaaataaa acattacatt   51960
tcaaggttgg cagagaggaa tgaaggtgga agaggaatct agggccattt agggaagcca   52020
tgaagcctcc tgcccacact agtgggtaga gtggagccag gcgttttgct agggcttgct   52080
atatctcttg gcagggtgct ctgctgccaa agccaagaat tctaaattag attaaatagc   52140
cagaaagaat gttaaacatt tggacatgat atcctccctc acagattagc tagagtgtag   52200
ttctgctgtg ctagatactt aaataaatac ctccctagct gtgaagcctg cttatcacag   52260
tactatattt taggatgagg tcattatttt cctatgcata cacatgcatt gtataatctt   52320
gccaatgtag gtcagcccaa agaagtgac aaatgtgtag aacacacatt ggactagctt   52380
gggacaaaat tagtatacct aaagatgaca gatttcttaa ctaattttat gagccatgca   52440
gctttgtatt ctagcagaga cagacattag gaatcttata aaatcaaaaa ttttaatttt   52500
tgcctgaata gctccaaagg gctaagatct caagcaaatg cgtgtaggtt ttgttttttgt   52560
ggttgttgtt gttttagag acagggtctt gctctgtcac ccatgctgaa gtgcagcggt   52620
gcagtcctag ctcactgcag ccttgacctc tcaggcttaa gtgatcctcc tgccttagcc   52680
tcccgagtag ctgggactac aggcgcatgc caccaccccg agtaattttt tatttttatt   52740
tttacttttg tagagacagg ggtctcaata tgttgctcag gctagtatct tttttctttt   52800
tgagacagtc tcgctcaatt gcccaggctg gagtgcagtg gtgccatctc ggctcactgc   52860
aagctccgcc tcccgggttc acgccattct cctgcctcag cctcccgagt agctgggact   52920
acaggcgccc gccaccatgc ccagctaatt ttttttgtat ttttagtaga cgggggttt    52980
caccgtgtta gccaggatgg tctcgatctt ctgacctcgt gatccacccg cctcagcctc   53040
ccaaagtgct gagattacag gcgtgagccc tcgcgcccgg cccagtcttg taacttaact   53100
ttaaagctac ttattcccaa atgaagatgg gatggtacac agattttaag tattagctgg   53160
tttggagctt ctgtctttta aagcaacatt ttactttgcc acagggtggt ggggcggggg   53220
ccatcctaga aagaagagtg tgagtttcat gggatagggt ctggggaggt ggctggagga   53280
gtttaggttc ttttgatatc tgtggctaca cagacagata accaaggaaa atgtccaaac   53340
agtgaaatta agtgctcact gcactaacac agagaaggac cctgatgtct ggccgcaggc   53400
ctttgttctc attggcttca aagaacttct tgatgtctac cttaatttca ttattattta   53460
cccaggagtc attcaggagc aggttgttca attgccatgt agttatgtgg ttttgagtga   53520
gtttcttaat actgagttct aatttgattg tgctgtggtc tgagacactg tttcgatttc   53580
agttcttttg catttgctga ggaatgtttc atttccaatt atgtggtcga ttttagagta   53640
agtgccacgt gacgctgaga agaatacata ttctgttgat ttcgggggggg agagttctgt   53700
agatatctat taggtccact tgatccagag ctgagctcaa gtcttgaata tccttattca   53760
ttttctgtct cgttaatctg tctaatattg acagtggggt attcaagtct cccactatta   53820
ttgtgtggaa gtttaagtct ctgtgtaggt ctctaaaaac ttgttttatg aatctgggtg   53880
```

```
ctcctgtatt gggtgcatat gtatttagga gagttagctc ttcttgttga attgctccct  53940
ttaccattat gtaatgccca tctttgtctt ttttgatctt tgttgggata aaattacatt  54000
ttatgtcccc cttcctatag tttgtcactg agggttggca gaagttgaaa ggaagaagac  54060
atttgggtgt ttggtttggg gttatattag gttataaggt tcattgcctc cacctctttc  54120
aaaacattta gtttctaaat gaatccagct ttaaatgact gcaggagtgc ccatgcacaa  54180
ttttgtttct caaatctttg ggattttttcc ttgaagaata ttcacaggga atggggctgt  54240
cttgcttcat agttactctt ttgtatacat gatctcaaga atcgctgat cactgctaga  54300
gttaaaccaa tacactaact gcctgaagtg ctgaaaagtc aaatgggggc ttagaacctc  54360
actccagatc ctacacaagc tgatggttct gttcccagaa acaacccagc ttcctcatca  54420
tctatggcca gtgccttgta gcggagctgg agatcaccct ttagtgggct cttcagctgg  54480
atctagaaat caaattgaca ccaggcagat taacaagaga aagtataca gatttttattg  54540
cttttatatg tacttgggaa tctgcacaag ggcaaagtcc gaagaggtgg ccaaagcaag  54600
gtgctttat acatttttag aaaagagcc aaaaattgg agaagaaatg ataggacaaa  54660
gaaaatctag ccaggcagta aattttctag gagaatcact aggacatata tgaggaaggg  54720
tgtgtaaaac aggtgaaaga taagggctag ttcattaaac atgtttactc tggtccattg  54780
tagcctctac gataaggagt attttctcgc tctggtgtgg acagggcacg cctcccagag  54840
caacctttat cacttactgc atgcaggaag agacaggtca gcccgcccctt cctgaaacta  54900
caatttcttc agtgttttca actcaaaata atcaatccc cccatctggc atatctgggg  54960
atggcacgtc ctttactcct tcaggctctt ctccctgaag gtcctttgca tagttgggaa  55020
tctccaccag gaggggtagc tctttggtct aaacccatgg tggcagagtt tcgacaatat  55080
tcccaactta aatgtttctg attctgagtg gtggttagat cccttttgtac accctgtcc  55140
ccagtgccta cagaatgggc atgttaataa gtgttggctg aacattcaat gatggataag  55200
gaagaatagg aggcaagaga gacggtggtc tccagtgcca gccccagtg ctaactgggg  55260
tgatttttttt tcatgactca ttttcctaaa atcaccctca agggtcctac aaaactcttc  55320
ccaacagcta aatcacagac taatctggcc catcgacgtc ttccctgatt atactaattt  55380
ttttgtgttt tttttttttga gatggagtct tgctctgtca cccaggttgg agtgcaatgg  55440
cactatctca gctcacagca acttccacct cctgggttca agcgattctc ctgcctcagc  55500
ctcctgagta gctgggactg ccagcatgcg ccaccatgcc cggctaattt ttttttttttt  55560
tttttagta gagatgagat gggggtttcac catgttggcc agggtggtct tgaactcctg  55620
accgcaagtg atccgcttgc ctcggcctcc caaagtgctg ggattacagg tgtgagccac  55680
tgcgcccgac catatattaa tggttttttga tgaatttgtt ccatagatta aaatcttgtg  55740
ccccatcgcg tgtggggctc catcgcatgt ggggcacagg gttcctgagt gtttgtggct  55800
gtcaaaccaa gatgatttct tgcttaatca agcagatttg aaagttcatc tctgctacca  55860
ggaagcactt gctcaactca gaagacaatg tcctatcagt ctttcactat cacgcatctg  55920
ttcttcaaga tccgtcaaat tagctccagt gaaacggagg ctaaagtgaa acttttttctc  55980
ttatatagat ttttattcat aactagggaa aaattaggca cccacagaaa ataataacc  56040
taaaaaaatt aggctgaacg taagaaaaat ttgtgatgaa ataaacattt caatcaacag  56100
aaaatatttt tctgactttt tatgtgccac cattagttac atcattgaga aaacaatatt  56160
tgtattaaaa aaagagctgg tgaaaatctg gcaattggtc gggcatagtg gctcgtgcct  56220
gtaatcccag cactttggaa ggccgaggca ggcggatcac ttgaggtcag gagtttgagg  56280
```

```
ccagcctgac ccacgtggtg caaccccctc tcaactaaaa atacaaaaat tagctgggcg   56340
tggtggcagg cgcatgtaat cccagctact agggaggtta aggcaggaga attgcttgaa   56400
tctgggagat agaggttgca gtgagccgag actgagccac tgccttccag cctggtgaca   56460
gagcaagact tcatctctct ctcttttact tttttaaag acttcttctc aaaaataaaa   56520
agaaagaaag aaaatctggc aatccagtaa aaactggcca ctatggcatg catgtgctat   56580
gcataaacgt aaattgatgc ataaacttaa ttttagaact ggaaggaaat ctggagttct   56640
ttaggagcca ggttttacac atgcagaaac ctaacagctt cagtttcgat tcgataaaat   56700
ttgactaact aaacttaaga taagcatagt tacgcattag agtattaact ctcaaacttt   56760
taaaaaagaa ttcttccttt gcttgttaat tttctttctt tcttttttt tttttgaga    56820 tagggtcttg ctgtcgtcca ggccgaagtg cagtgacgtc atcatagttc actgcagcct   56880
ctacctcccc ggctcaagta atcctcctgc ctcagcctc tgagtatctg ggactacagg    56940
catgagccac catgcccagc ctttctttt cttttctttc ttttctttct ctctctgtct    57000
ctcttctttt cttttttcct cccttctttc tttttttttg atggagtctt gcactatcgc   57060
caggctggaa tgcagtggtg cgatcttggc tcactgcaac ctccgcctcc gggttcaagc   57120
aattctcctg cctcagcctc ctgagtagct gagactacag gtgtgtgcca ccacgccagc   57180 taatttttt attttctag acacgggtt ttaccatgtt ggccaggatg gtcttgatct      57240
cctgacctca ttctccacct gcctaggcct cccgaagtgc tgggattaca ggcatgagcc   57300
accgtacctg gcccttcctt tcttttatc aagacaacaa catgtctta tagtgctccc     57360 aaggctaaag tataccttac gtctatgtaa acactcaacc tgagctttgc aatggcccat   57420
gttggcagta gtgcaaacaa aaacaattat gaaacccatt tcctttgac aaagagaaat    57480 aagtggcaag aattggttct ttctcttagt atgggtctct gaaagaacc agatcagtca    57540 aaaggggaat attttctga agggataggt ttggcctagt ggcttctacc tcttttagat    57600
gactgctgtt tctcgttta atgttaaata gacactaata ggagaaatca cattaattca    57660
gtcaacaaac atttactgag cacttcctgt agtcaggccc tctgttaact tctgggaata   57720
caatgacaac tctgacaatc ccaacccaag gagccaacaa gtccgggaat agagacagac   57780
aagaaaacag acaattacaa ctctaccgtt agaataaagg tacattgaga acttgcaaca   57840
aatattcctc atcccttatc ttaattattc ataacatgtt taccaccaat aagaatagca   57900
ataacaataa atgcccaact cagacagcaa tgtccattta ccctgtgttt acacagcata   57960
atacaagcaa gctgtggaca gagattctct tgtttagtcc tcacaactct gcaaggtggg   58020
ttttattact ctccatttct agataaagga tctcacctaa tattacatgg gccagtggtc   58080
ttccagttgg ggtatgcaca accctagggg taggtgagga ccctgcctgg ggtcttcagg   58140
tggggaccat caacctccat ttgtactctt ttctgaacat tggtctgaga cagaaagtcc   58200
ctgcaattaa ggcattaagc tggctctttt tctatttctc atttcataat tgcccttctc   58260
ctgctttacc aaaatctttc acccccatc atatatatat atcccatac atattctata    58320 tatacatacc ctacatatgc atgcacacac atcatatata tgtatgcata tatgatatat   58380
acatatatgc tatgtaaaca tatatagtgt gtatatacat gtgtatatgt gtatatgtgt   58440
gtatatgtgt atatatacac gtgtgtgtgt acatatatac atcatatatg tgtgtctata   58500
tatgtatata tgggtgtgtc tatatatgtg tatatgtacg caaatacgta tatgtgatgt   58560
atatatataa gatgtgtgtg tgtatatata tgtgtttgca tgtgtgtgtg tatatatata   58620
```

```
tagtatatac atatttttg agacagcatc tcactctgtc gcccaggctg aagttcggtg   58680
gctgatgaca gctcactgca cctcccggct caagtgattc ttccacctca gcttcctgaa   58740
tggctgggac tagaggcgtg tgtcaccaca cccagttagt tatttatttt ttcgtagaga   58800
tggtggtctc actgtattgc ccaggctggt ctcgaactcc tgggctcaag cgcttttcca   58860
cctcgacttc ccaaattgct gggattacag gtgtgagcca ctgcaccggc ccatcctta   58920
ttttaatatt atgcagtgcc ctgagacata taaaaaccc accttcccaa gtaaaggaaa   58980
ttcaagctga tgcctgcaga gccttcttta acaaaggctc tgaaatacc tctctcatta   59040
aaatgatact ttccaataaa attttgttta acaatgattt acaaaatgat aaaatttatt   59100
tattttgatt gtgtatggat catggtaaca ataaaaagac ttgtaaaaat aactaaattg   59160
aaagaatctt gaacatttag agccttaaga ctgtaggaat tgaagaccac agaattatta   59220
atttatatta atatttttgt tgcagagaca taatgaatga tcaacgaaag gcttttaagc   59280
gttaaaaata tattcacta gataaaatta tttgcgggaa tgggatggaa atacattttc   59340
aagagagaaa ggagcaatgt aaaatgaaga tgtaaaatcc ttctgctggt tgtccttggg   59400
gttttctttt aaagaaaagc ttggcagtgt ttttctttt ttccattgga tgatggtgaa   59460
tatcaaatca ctttggtgct aatatttcat ttaatacatt aattttaaaa ttttctgtag   59520
aggtgggatc tcactatgtt gtccaggctg gtttcaaact cctggcctca gcaatctcc   59580
ctgcctcagc ctcccacagt gctgggatta caggtgtgag ccactgcatc cggccccatt   59640
taatacattt aaaagagtgg tgtaacaatt tttatttaaa atgtcatatt tacaatattc   59700
tagaatgtat atcttttcaa ctcattaaac ctaaacatcc ttgtaaaaag tgtgaaaagt   59760
tatatagttt ttcaaaattc gattagcagt tacataagca taaatgttta aagtatgtat   59820
ggtacagcca ggcttcagtt ccctgtctta aacacaaaga tccatatcaa ttccagatac   59880
tgcaatggtt tgctgttttt cctgcttccc ccatctccaa ataaactaaa gcatcaacat   59940
gcctcacctc ataaccct aagttttcag cagttggcag ttacacctgg aaaccatttt   60000
tctaaaataa acaacaactg tttgcttacg gatcaaaatg caaaggacca taacatttag   60060
cctcaccttc ctactacaga tcgagtttaa aagtgccatg gtatagctaa attatgaaga   60120
aagatatgaa tataactgca aaagtggaag gagatttggg ataattcttg cccattttgt   60180
taggccaaat gcatctttgt gcaaattaga aaaaggtggt cttcatccct tcactcctat   60240
cctttggggg gtggaggggc agtggctaaa gtacagacta ggtttcagct accacatcct   60300
ccttcagtta gctgccctcg gcgtgacaga aacatgtgca aacagccctg tgcctttgtc   60360
ttatgttcca gccagccaag aaaaatagtt gtaaaagagc agctgctgtt tggggtaatg   60420
accttggacc ctccccaatt tgttccaagc ctgtttttgt attcattttt cccacattta   60480
tgttcctgga tggaagcttc catatctgct cttggcccta tttgaaattc cccagatttc   60540
cttcctggct cctggccttt ggttttcat gtggctcctg atcccacacg ctcctgaat   60600
ttggattctc ctgtcatttc aggtgcgagg tttcccacta cagcctcttg ggcctcacct   60660
ccaataccte tttcccatca gaacagcccg gaccttcccc tatggtagag cagagacaga   60720
atttaaatga attctcaaga agtgcttgga ctcatatcta gcaaaattac atggcattta   60780
acctttgaca caaaaatgc agcttctagg aatctatcta aagatacact gtggcaaata   60840
tacaaaagaa agcattattt atcaagcact atttcctaat aaaataattc ttaggtcagg   60900
cgcaatggct caggcctgta atcccagcac cctgggaggc tgaggaaggc agatggcttg   60960
agctctggag ttcaggacca gcgtgggtaa catgacaaaa ccccatctct aacaaaaata   61020
```

```
caaaaattag ccgggcatgg tggcatgcac ctgtagtccc agctactcga gaggctgagg    61080
tgggaggatc gcttgagcct gggaggcaca ggttgcagtg agccaagatc gcaccactgc    61140
actccagcct gggtgacaga gtgagaccct gtcaaagaaa gagagagaga gagagaaagg    61200
aaagaaagga agaaaggaag aaagagaaag gaaagagaaa gaaagagaaa aagaaagaaa    61260
gaaggaaaga aagaaagaaa aaagaaagaa aaagaaagag aaaggagaaa aagaattctt    61320
actaataaat gcaggagaaa tgatagaatt gaaatatcac cattttcaat tcctaatgaa    61380
ataacgtatc taggcaatga ccatcaatag ctagatgcta aaatcatctg atcaaacact    61440
gatgggaact tcgtaacaga tggatcaggc taacaacatc tgaaaccact aactggtttt    61500
gatgtcataa aaagaaaaac aaccagatat tttctgtctc ctgatgagtt gcaattggag    61560
ctacatatca cctgtaaagt cttctggcca aaaaattaag cccagccgga ccttattaaa    61620
cctttaaatc taacaattag ttttgaagct tttacagatt aaatgaagtc tgagatttgc    61680
ttcaaaatga accagtggtg gggaggaagt gggtgaggtg taggtgaaac aagattggcc    61740
acgtcgataa ttgctggagc tgggcgatga agcacaggt atttatcaca ccatctctct    61800
acttttgtgt gtttttttgt ttgtttttgg ttttggtttt aaggagcaga gagtctaata    61860
ggcaagaaag aaaagagaag gctgaaggaa gacgctcccc cgtacagaga cagagggagg    61920
gggctccaaa gccgaaagag gaggtcctct tgtgtatgtt ttaaaatact cccagataaa    61980
atattttggg aagagtactt ggttggattc aacagctttt ttttaattta aaaaaatcac    62040
ctcaattttt ttgcttgctc taacgtgcca tagaaattcc tgaggttttta cttgttgctt    62100 tacaatgaac tgtgtaaaca caagctggaa gagatcagct atgcgctgga agggttggtt    62160
aaatattgag actgccttgc tgagggaagc cttttaatga atctcagtaa ttttgcaaga    62220
gaaaagataa caatgaacac tacattaaac atcattcttt tgcactttgc taaatatgtg    62280
tatgtaaatt actgtctgac tgttactgga tatatacagc atatacatat gcactttttt    62340
tactgttttt ttttttttt ttttttttt tttttttaca gagcttgctc tgtcacctag    62400
gctggagggc agtggcgcag tctcagctca ctgcaatctc cgcctccag gttcaagcga    62460 ttctcctgtc tcagcctcca agtagctggg gactacaggc gcctgccacc gctcctggct    62520 aattttgta ttttagtag agacaggt tcactatgtt gtccaggctg gtctcgaact    62580
cctgacctcg tgatccatct gcctcggcct cccaaagtgc tgggattaca ggcataagcc    62640
accgcgcccg gcccatgtat actatttata cattttagt atcatttgt ctttacattt    62700 tacataattt cagatacatt ttcctcatat caaataattc agcatttttt agtactaaca    62760
tcatagtctg taagccattc aaaaaatgta tttcacaaaa taggctatct catcctttga    62820
gctattgaga tgaattaatt tatactcctc ctaagatccc tctcgtcact aagattcttt    62880
tattttatga caaaaccata gttctagaag cttgtttctc ccacctgaaa agactggatt    62940
tgggacatga tcctgtagaa cttcggaggt aagcctggtg aatcagatca taggggtct    63000 ggagggtgaa aaaaagggt ttggtgctca tggatgggc tagtattggg gtgtagggga    63060
gattaggtca aagcaagagg attcaaagga gaaatgaatt cctttagatt ggggaagata    63120
atcggaagag gtaaaagaca ccgtccatga cacttcctgg ggaagcagat gtatgtataa    63180
ggatgtgagt attgtggttt tgtaaagaat gcattcctga agatgttgca taatttaaaa    63240
cctacatatt ttgattaatt ttctcatgag aatagcaggg tatgtgttct cggcgctcac    63300
aaatgtataa tccattgtgg caaatttttg ctttcacata ttttttttta tcattattgt    63360
```

```
cacaggttct gtgacggagt tctggtttct aaattcacag cataccaagg cagttcttta    63420
aagttcttga tactctttta tcatatctaa cttgtattcc aaaattattg agttggagca    63480
cattttccca gcacttagca ccgctatttc atggatggtt ggagaggggg tccaaaaatt    63540
ttacaattat gttaacaaaa gtaacacagc aacaaaacaa taagcaaaat cactgccaga    63600
gtattcctta gcttgaaaca atacggttca catcgataga atatggcatc tatttctgtt    63660
taatcagtta accctgctaa gtagcaagag cttacaattc atgtctaaaa tcatgatttt    63720
tttactagtt tttaaaaaa tgtgggctct atatatataa tttaacattt tgcttgtaag    63780
acttaatttt gcctgggtat ggtggctcat gcctgtaatc ctagcacttc aggaggttga    63840
ggcaggagga ctgcttgaac ccaggagttc aagaccagcc tgggcaacac agtgggaccc    63900
catcactacc aaaaaaaaaa aaaattagtc aggcatggtg gtgtgcactt gtagtcccag    63960
ctacttggga ggctgaggtg ggaggatcac ttgagcccag gaggtcactg ctgcagtgag    64020
ccattattgt accacaacac tccagcctgg gtaatagagt gagactctgt ctcaaaaaaa    64080
aaaaaagact atttctaaat gtgtggctat attataccat ataaatgtgg cttcttgggc    64140
aaggaaagag gacaatatag atgaaaaaga aattgatcct accagaagtg atccttttat    64200
ctgcataact ctcaggcagt tgtggcaaat aattggcaat atctattgtt ctgaaactgg    64260
ttttcgcaac ttttattggg aacaccatcc cctctcctgc atgatcagtt tctcctctcc    64320
acggatcatt cacatgagta aagtcagtag cgtgctggta aatgtttaag atcttgttct    64380
ttggggaaa aagttcctaa gttctagcag ttgccctgga taacttcaag gtatcaacat    64440
ggaagttatg tacaaaaatg gctgtcacaa gccagtatga gctaacacca acatactacc    64500
cagtgttctt caaacttcag ctcacagccc attagtgggg cttgcaaaca ttttagtgga    64560
ctataagcag cattttttta aaatgaaaaa gtagattgtt ttacacataa caggagtatt    64620
gttttgtaca atttttttt tttttttttt tttttagaca cagtttcact ctgttgccca    64680
ggctggagta cagtggtaca atctcagctc actgcaacct cggccttctg ggttcaagcg    64740
attctcatgc ctcagcctcc cgagtagctg aaattacagg catgcgccac aaggcccagc    64800
taattattgt atttttagta gaaacagggt ttcaccatat tggccaggct ggtctcaaac    64860
tcctgacctc aagtgatcca cctgcctcgg cttcccaaag tgctgggatt acaggagtga    64920
gccaacgtgc ctggtcaaaa ttttgtttt cgtaatttta agtatgtgtg tagtaagtct    64980
caatggaaat gtaattctta tggcaggtca cttgaaaaaa aagaagtcta aaagtcacca    65040
atgtagtatc ttctctttaa aaaaaaaaa aaacaacagg agaaacctg aatctgccct    65100
ttgctccact ccttcctcag ctataatgct gcttctccat tcctcctcac agcaaacctt    65160
tctgaaatct ttatagtcat ggtttccacc agttcttcac ctcccatttc tcaacacact    65220
tcagagtcag agtcagcaat gacatccatg ttcctaagcc cattgcttac ttccgtcctc    65280
cttggcctct cagcacactt ggcacacagg ctgtttctct ttctttggca tctgtgacac    65340
cactctcagc aaattcccct ggttgtccct tctcagtctc atttattggc gttgtcttat    65400
ctccccaggg ctgtccgagg tgattttctc ccactactct cctaggtggt gccatccaat    65460
ctcatgatgt catatcattc ttccctcatg cttcagccat actggttggt ggcctttgtt    65520
tcctgaacac atttaatgca ttctcaagac cctcaggac tttgcagcag ctgctcgcta    65580
aggctggaat gctcttcccc accatcttca tatggctgtt ccttctcttt cactcaccag    65640
cagcttaaac tttgactcct ctgagagact ttccttgtca cccaactaag gttgccactc    65700
aggtgctccc aatttaatct tctctaaaac acatcactgt atgtgtcctc aactagagta    65760
```

```
taagcttcct cgaaacaaga acaatcaaaa ctccttgccc tcatggagtt tatagtctta   65820
tgatgggtga agtaacataa aataaaaagg caccttatat agtatattag catgacaaat   65880
gttagccaga aataaagcaa ggaagagttg ctagggagtg tgtatgagtg tgttttggga   65940
gagtgtttgc aattttaaat attggtggtc aggaagggcc ccactgagaa ctgacatttg   66000
agtagacttg aaaagggaaa aggaaatatt gagtaaagat tttaggatgg gagtgtgaca   66060
ggcctgctag gagaatagca aagtcgctgt ggctgctgca gaaaagtga aaggaaagt    66120 agtaggagat gaaatcacag tgtgtgagga ttcgggcaga tcaggaagtg ctcgtgtaag   66180
aactggatct ttactcaaag aatgagcaaa aattagtaga cggttggccg gatgcagtgg   66240
ctcacacctg caatcccagg ttacaggagg ccgaggcggg cggatcactt gaggtcagga   66300
gttcaagact agcctgggca acatggtgaa acctcatctc tactaaaaat acaaaactta   66360
gctgggcatg gtggcgcgca cctgtagtcc cagctactca ggaggctgag gcacatgaat   66420
cacttgaaca cggtaggcag aggctgcagt gagctgagaa tgtaacactg tactccactc   66480
caacctgggc aacagagtga gactgcctca aaaaaaaaa aaagtaggt tttagtaagg    66540 gattaacatg atctgaatta tgttttgtca tgacttctct ggctgttgtg ttgagactac   66600
attgcagagg ggcaagggca aatataggga gaccgattag gatactgcag taataatgta   66660
agagatgtgg gactctatct agaagggccc atgaggtcct ttgcatgcta gtattcttta   66720
ctgctgtgcc tggccatgat aggcattcag tgaatatttg cttatttaaa ataacacact   66780
gggctaattg aacaacagtg ccaaatgagg gagatatttc taggaataag ttcttaggat   66840
ttatgaacat tttaatccag attttctttg ttaactctgc tctctggccc tttcactcag   66900
ccccgtttgc acctaaatat gacttacaaa agaaacacag catttatgtg tacttatttc   66960
aacttacttt agctttgtaa agaagtacaa ggttgactca gggcccagct tggtgtctca   67020
tgcctgtaat ttcagcattg tgggaggcca aggcaggaag atattgtgag cccaggagtt   67080
tgagaccagc cygggcaaca cagtggaccc tgtctctaca aaaaaaaatt tttaaattag   67140
ctgggcatag tggtgtgcgt ctatagtccc agctactcct ggggctgagg tgggaggatc   67200
acttgaggga aaccctgtct caaagtggcg gggctggggg gagactcagg cagaattgtg   67260
aagatattca attgctcctg actttatcaa taatctaaca tttcaaccta acattgatat   67320
ctattttatg caaagcatta cactatgcac tggagactgt ataagacaag ttccttttct   67380
caaactacag tcgagttgga tagataaaac acacaacaca taccaaaaga cagctataaa   67440
tccaaggcag tgtatgtcaa gggtaaattc acctattcag attggatctt gagaagtgca   67500
tcaggcttgg aaaatgggta aggaggagag aaaagcaaca gtgaatcaga acatgagttc   67560
ccagttatgg gacttgtaat gaattcctca attaaaacaa aaaataatga aacaaaagc    67620 cagggaggag aaagcccacg ttaatgacac taaaatatat cttccaaac aaatgtggat    67680 aaaagccaag tagagaagat gagaactttg aggtccctaa cacaaaataa acagtaagca   67740
gccagccatt ccaagtggct gacatgactt tgtttaactt tatttgtatt tctggctggt   67800
gtgtttacag ccaataggtc aaactatcag tcagtgtagg gccctgagaa gtcgggtatt   67860
taagagcatc taataggcac agaattgtgc tccatactgc ttaaactgtt ccctaagtgt   67920
ccaatttgga gaaaacaccc acacgcagga taaccggcga gtgacgcgga gtggctgcga   67980
gtccaagtta tcactaacgg atggggagct tgggctgggc acagtccagc gtactgaacc   68040
cttcccccac cgtttcacct gcatacagag gtgtgtactg tcaaaaagca gcgcctccaa   68100
```

```
gtctcttctg gcactgtctg gacttggatc cgaggcagac gaggaagctg agaaaaccct    68160
ggcgttgacc ccgtggacct gggcgccccg ggaaggccag cgcttggtcc aggcaggcgg    68220
ggcctgtgcg gtgaccaccc tggtcctgaa aagtcccagc cccgagcgcc ctccctccta    68280
gacctggagg cctggaacag ccaggtggac gtcggcccac ctttcttttc tttccttccc    68340
attttcctac cacctcccac cccactccgc cttccgggca aaggcagcca gatccaccca    68400
ggacacattc tttgtcctta tccctctgtg ctcgtcccac agcaagccag tcgcggtcca    68460
aggctccaga ggctgtgcag gaggccgagc tgggtggcga tcagcggcgg gtccctgtcc    68520
aaaayccagc agagccgcca gggacgcccc agacacagaa ggcggggcgc ggggagggtg    68580
gggagaccac agcagtgagg cgcgcgagcc gggaagtgaa cgaggactga ctcctgtcgc    68640
ttcccgtagc cgcccacgga cgccagagcc gggaaccctg acggcactta gctgctgaca    68700
aacaacctgc tccgtggagc gcctgaaaca ccagtctttg ggtgagtcgc gcgaccccg     68760 gcctcgggtg gcggggcagt cgctagaggc gtggctgctc tgagggtctc gccagtggag    68820
gatggcattc ggatgtcacg gctcctaaat caccatttga tgggtgggac agtgtccagt    68880
ccaccccgac ccgccggtcc tcaccgcggc agagccgggg ctgggtggcg gggacgctgc    68940
ctctgcaggc gaggcgctcc ggggcataag ggattatcag gagtcgcggc ctttcttgga    69000
catccctggc tggggtcagg ctgtttgccc tggggtgtct cctcgctgca aacccacccc    69060
acctgggctg ctttctcacc tgttccctcc tagcctgagg ccgagcgcca cctccaagtg    69120
gaggaatctg gggaagtttc cttcccggaa tttgtagtga cagtggagtg acctccattg    69180
cgttccctgc ctctaacacg ctctttagga tgccgagtca tttgactgca gtgttaaaca    69240
ttgcaaagcg caagtcatgt gacttccttt gaccgtacgt gaaacttaag tgatggctgc    69300
ttgtgatgca tacgaagtgt tcatgctggc gggacctgtc cctggggata cttcggggt     69360 tgcgtgattt aatgcaagca gatggcttaa attgggtcac tggcttgtta ttatacatgt    69420
gtatggcaac tcggcatcca ttcttttgc tcttgttctt acttcctgaa ttgagtcacg      69480
gagccagagt tttgaggttt tgactaacga attaagttaa tgacatgggg ctatatttag    69540
gtggtaaacc aagagggata cagtttttt tcttaataaa gaaaaagtga tagatttgat      69600
cggtgtgtat tgttggtgtg cagtataatg acagaattgc tggaagtaaa atacaggaag    69660
ctctggtttc atttcccctt tagttctgct taaagtcgag ttttttcctgg agctattaaa   69720 tgtagtgtag tgtccatgag tgcttttatc ttaaaaaatg tggctgatgc tttccaacac    69780 tccctgccc tgtgattatt atttttttaa gcaacagaga aaactgtatc ttaatagtat      69840
taaaagtatt ggattttttcc ctactttgat ttgtttaaat tggaggagga agagcaattc   69900
tttctattca caataataat agctaacata gcgcttactc tttcgctgtt ttattaactc    69960
aatcctcaga acaaaccaat gatgtgaata ctgtaattct catttatgg aaatgaaaat     70020 ttaaatgaat acctctgata attgtacggg actgtttgat tagtatttac cattaattaa    70080 ttaaatttt ttttttttg agatggagtc tcgttctgtt gcccaggctg gagtgcagtg      70140
gcacaatctc ggctcacttc aacctccgtc tcccaggttc aagcaattgt cctgtctcag    70200
cctcctgagt agctgggact acaggtgcat gccactacgt ctggctaatt tttgtatttt    70260
tagtagggat gggatttcac catattggtc aggctggtct ccaactcctg aacctcaggt    70320
gatccacccg ccttggcctc ccaaagtgct gggattacag gtgtgagcca ccatgcctgg    70380
cctattttag tatttttaat aataaattcc atgttagaaa ttttctactg atgtattttt    70440
taagtcaata tttcctacac tcacaatcca aaattattta gtatatgagc acactggtaa    70500
```

```
gaatgggagg cagatcgttg attgtaataa tattctatta tttggtaaat atcagtaaca      70560
taatatataa tttaaatttt aaaataggat atgaagaaaa atgctacatg cttactttttc     70620 ttttcctcta tttttactttt acacagggcc agtgcctcag tttcaatcca ggtaaccttt    70680
aaatgaaact tgcctaaaat cttaggtcat acacagaaga gactccaatc gacaagaagc     70740
tggaaaagaa tgatgttgtc cttaaacaac ctacagaata tcatctataa cccggtaact     70800
gatttctata agataacttt ttacctatgc caggacagat ccaatagaat attaattatc     70860
cattgggaga cagggcaaga ataaaagcca gtgaacatat ttaaagcacc tactatgtaa     70920
tagagatggt ggtgggtgct gattacgaaa cagctcttgt cctctagtgg aggaagaagt     70980
cacaatgata atatgacgtg atgaaacagt gttatgaaca gggaacgtct gggtagagtg    71040
gagggaatgc caacttttgg tgatgggagg aggctcagct aatcataaat tgtagttttt    71100
aaaggaaaat ggatttctta ctctacaagt ttttcatttt ctttttttaat tagagctgtc    71160 catgagaagt taatgtctcg atctttccct cagcctttca aatactgctt ggcccttgag    71220
cagggaaaat gtcaaaagcc aatgggggaga tggagagtgt gaagtagtaa gggtctcgtg   71280
cagttcaggc aggtcctaga atccctgaat gactgtaatt gctggaaatt gccctgtaat   71340
cctgagcagt aaagagcttg ttttagtttt atgtggtggt gagaatcttt aggaatgtct    71400
agtttccacg tatctgaagc tgaatcctga atcgaggtct gaaaaaggac agccactttt   71460
ttagtaaacc gcctagaaga ttcttgggca aaggaaggg tgagaatcct taaaatgagg     71520
ccctaaacca gttttgttag tgtgtgtggg ttcaagtttt tgtcatttac tttatagctg   71580
tatttccttt ttccctaagt tttaatgtca ttgtgtaaga atgaggtatc gctgctgtat   71640
caagcaaagt cagtttttagg agaaatagcc tttcagtggt agtaagttta aaaagatga    71700 cttcctgaag cggaagcttg tgagacattt aagatgactt tgcgcatgtt agagttaaaa   71760
acatcccaag gttgtaaact gatttcctgc aaagatctta acaacaacaa caacaacaac   71820
aaactaggct gcctgccacg ggtgtctgaa gtatcatctt ggctcaagct gggagaatgg    71880
ataaaggtta cactgttcat ttctgccctt cacacagaaa agaagataat tttatagtta   71940
aaattcgtgc atatcttgat tctagcatac tgctgattcc tgtagttttct ggggtcagta    72000 ctctcaacta ttgaggtgga acaaaaataa gtagacttca tttcttgagg aaggggatct   72060
ggagaagtag ttctgcgcta gagcagaaaa tgccttcagt cttgtggcat gggctggatg   72120
ctgttctgag gataatgcat ttccaaggga gatattttttg gcaaatagct ttttttttctt  72180 tcttttcaaa attctctgtt ttattatcag ttctcacaaa agagtcggaa aggttagagg   72240
tagactgaac tgaatggcaa aaacattttg cgctctcttt acgtttcact gctgtaaaat    72300
atttatagta taaagggcct gtattgcact gaatttctct catttgtagc tagttgccct   72360
ttcaatgttc caaaaaaaag gctgtaaata acttattttta tttattcaat taattttttt   72420
ttttaaattt tttgagatat agtttccctc tggtcaccca ggctggagtg aaatgatgca   72480
atctcggctt actgcaatttt ctgcctcccg ggttcaagca attctagtgc ctcagcctcc   72540
tgagtagctg ggactgcagg cacgtgctac catgcccggc taatttttgt gttttttagta   72600 gatatgggt ttcacagtgt tggccagcct agtctcaaac tcctgacctc aggtgatgtg     72660
cccaccttga cctccaaaag tgctgggatt acaggcgtga ggcaccatgc ctggccaact   72720 tagttatttta aagataatca attagtatat tttataagct agacttagga aaactgttttt  72780 cagctgggca tggtggctca cacctgtaat cccagcactt tgggaggccg aggcaggtgg   72840
```

```
atcacgaggt caggagttca agaccagcct ggccaagatg gcgaaactcc gtctctactt   72900
aaaaatacaa aacttagcca ggcgtgatgg cagcctcctg taatcccagc tactcgggag   72960
gctgaggcaa gagaatcact tgaacctggg aggcggaggt tgcagtgagc cgagatggtg   73020
ccactgcact ccagcctggg tgacagagcg agactccatc tcaaaaaaaa aaaaccccc    73080 cccacacaca aaacctgttt tcttgaatca tggttgtttt gttactgata ggttcaataa   73140
gtaaatatat ttattgtctg ttgtattctt tattaggcat tataaacaca ccgccacttt   73200 ttaatttta tttcattaat gtttccaatt tttttttttt tttttttttt tttaagacag    73260
aggctcgctc tgtcatccag gctggagtgg agtggtgcag tcttacccca ctgcaacctc   73320
cacctcctgg gctcagcctt gtaaatagct gggactacag gcatgcacca ccatgcctgg   73380 ctaattttg tatttttttt ggtaaagaca gagttttgcc atgtttctca gtctggtcaa    73440
gcactcctcc cgcctcggcc tcccaaagtg ttgggattac aggcatgagc caccatgcct   73500
ggcctatttc taatattttg gtccacattg gtgttagacc aactgtccac attaagtttt   73560
cttggaaaag atgaagtaaa tattgcaact ggcctatgta ttttttttccc tatttagtat   73620 atttctttga ctagttcaac tgatagaatt ccaagactta aaaagtcag gctctaaggc    73680 tgggtccaga ggctcatgcc tgtaattcca gcactgtggg aggccaaggc tagtggatca   73740
cttgagccca ggagttcaag accagcttga gcaacatagt gagaccttgt ctctctataa   73800
aaatacaaaa attaactggg gattgtggcg catgtctgta gtcccagcta tgaggaagag   73860
tgaggtggga ggattgcttg agcccaggag gttgaggctg cagtgagctg tgagtttgac   73920
actgtgcttc attctgggtg acagagcaag aaccatgttc aaaaataaaa ataaaaagtc   73980
agagtccggg tgctgcggct catgcctgta atcccagcac tttgggaagc cgaggcgaga   74040
ggatcacttg aggtcaggag ttcgagacca gcctgactaa cacagtgaaa ccccgtctct   74100
actaaaaata caaaaattag ccgggcatgg tggcggtggc ctgtaatccc agctacatgg   74160
gaggttgagg caggagaatc acttgaaccc gggaggtgga ggttgtaatg agccaagatt   74220
gcacaactgc actgcatcct gggcgacaga gtgatacttc atctcaaaaa aaaaaaaga   74280 aaaaaaagt taggcttcct tttctgtttt ttttttcttt ttcttctct ttttttttt    74340 ttttttaaga gatggaggct tgctctattg cccatgctgg agtgcagtgg tgcaatctcg   74400
gctcactgcc acctttgcct cctgggttct agcaattctc ctgcctcagc ctcccgagta   74460
gctgggacta caggcgcaca ccgccacgcc ccgctaattg ttcttttgta ttttagtaga   74520
gacggggttt caccatgttg gccagcctgg tctcgaactc ctgagctcag gcaatccgcc   74580
cgcctcggcc tcccaaagtg ctaggattat aggcgtgaac caccgtggct ggccacttac   74640
ttttctttct attgaatttg aatgaataat ttggaagaca gtatctttac ttcataccag   74700
gaatgctgcc agtgaaattt cttgtttggc agttcattat ctacctatat atttaatttt   74760
gctattgttt atagagttct taagatatga ttaaatgcta gctggttaag aaatcattta   74820
gaaatgaaac agaattggtt gttactccaa gttaataagt tgcttgtcaa cataaatcct   74880
acctggtacc cagttttctt aggaaccttg cttccatgtt tatcctttc tgcttagtat    74940 tctaagtact ccttttttac cttacaattt agtcttaaaa cacaacacag tcaagtcttt   75000
cttttgtaac ctgtgaggta ccttctagcc tttgtgctgt ttttcttctt ttttgctgc    75060 ctgccttcct gactgagagt ggatttcctc actaaggctc tgccctctga ttttcactc    75120 tcttttcttt tttggtttta ctagtgaaat ttgtctttta atgtctcttt cttttatgtc   75180
tttaccgatc actcataaat ttttttttcc atatgtatcc agttccaacc tttcacctaa   75240
```

-continued

```
tgtgaacccc caactctcag ttgctcagcc agcccttcaa gactaggagt tcaaaaccaa   75300
acttgcatct tccttcccaa accagctttc ctcttgcagt tttctgcagc aggatccttc   75360
tgctgtttaa cttttgcctc ctcccttgtt tcctagcacc caatagttgg aagatagtct   75420
gtcttcaaaa ttttaaacta catttatgtc caaaccagtg gcttttcctt ttaaaaaaat   75480
ttaaagataa tatgtgcaaa tcattttttt aaaattcaaa cagtatttaa gagtttcagt   75540
gaaacatgca ttttccttct accctggtac ttagttttac tccccaaggg caatcacttt   75600
ttactggttt ttagaaatat atccttcctg agatacttat gaatatccaa aagtgtgtgt   75660
gttgtgtata tcaccttttα tatatcctgt ctctttacgt gcatgcattt taccgtataa   75720
actgttttct accctgcttt ttctatttga cctattttgg aaatgtcatt ttatttagaa   75780
cttcctcatt tattttaaca gctgcataat tagcagtaaa acttatgtaa gcagtccctt   75840
gtgaagggct gtgtcttttt gcgattatat ccggtgctat agtgtacatc cttgtgtgtg   75900
catcttggtg tgcctgtgct acgtatttct gtaggataaa tctgtaaaag tggaatcact   75960
aggtcagagg gtatggtcca ttttctttac ttatttattt tatttattta ttcatttatt   76020
tttgagacag agtcttgctc tgtcgcccag gctggagtgc agtggcatga tcttggctta   76080
ctgcaagctc cgcctcccgg gttcacacca ttctcctgcc tcagcctccg gagtagctgg   76140
gactacaggc gcccgccacc cacgcctggc taattttttt gtattttαg tagagacggg   76200 gtttcaccat gttagccagg atggtctcga tctcctgacc tcgtgatcca cccatctcag   76260
cctcccaaag tgctgggatt acaggtgtga gccaccgcgc ccggcccat tttattatct   76320 ttatttgctt ggatccttct tagcttcttc aatgttaaag atattgacag ttttcctctt   76380
actgaaattt ataaatccat tgactccctt gatattattg ccctggcctg actgattctt   76440
ctctctcctt tctcttctca ccccatgttg aggtccccaa ggtcacaccc agttttgatg   76500
actcaccagc atagagttgt acttgtgcct atgatttatt gcggtgaaag gatatagagc   76560
aaaattgcaa acggaaaggc acctgggtg aattccaggg gaaatccagt gcaagttcca   76620
aggtcgcctc ccagtggagt cacataggat gtgcttacat cctccagcaa ggagttgtga   76680
caacacttgt gaaatgtgga ctgccaggga agctcatcag agcctcagtg cctagggttt   76740
ttactggagg ctggtcacat aagcaccctc acacatatca aaaaattctg gtcccccaga   76800
aggaaagcag gtgtttagca taaccatatt atttgcatga acagttcagg tacaggaaat   76860
ccccgttacc agttaggttg gtgggtgccc ttctcaaatc ccaagttccc agacaccagc   76920
caggggcctg cctcgtaagg aggcctttcc aggacagcag tcaggcctgc caatgttaat   76980
tcttttctgc atacctccta attttagaaa ccaccgagcc tttgctgcct gacctgtcct   77040
gcttttcgat ttcttttatct actttgatat ctttacaaat gatctttacc ctgacttta   77100 aatgtgtgct ctggccattc acctagcgtg tggttctgag tctccaagtc ttagcagatt   77160
tgctctcaga tgctctgcca acgcttcaca ccaagtatta caaactaaac tcgtcatctt   77220
cctcctgaaa cctgtctccc aggccaggcg cggtggctca cacttgtaat cccagtactt   77280
tgggaggccg aggtgggtgg atcacctgag gtcaggagtt cgagaccagc ctggccaact   77340
tggtaaaacc ccatctctac gaaaaataca aaaaattag ccaggcgtgg tggcaggcac   77400
ctgtaatccc agctattcag gaggctgagg caggagaatc gcttgaaccc gggaggcgga   77460
gattgcagta agccgagatc acgccattgc actccagcct gggcaacaaa agtgaaactc   77520
catctcaaga aaacaaaaa acaaaaaaca aaaaacctgt tttctcccca gctttgtcat   77580
```

```
gtatttagtg gccttatgta gacagtttcc tttgaaacat ctcttggact tctctgctct   77640
tccagggcca ttgccaccga cctggaatgt gtccttatcg tttcacgcca ggcttatggc   77700
agcagtcagt cacccagatg acctcctgac ctctggctta tttcaccccc actggactgt   77760
tgttcctaaa cacttctttc gtatgtcact ctaaaatctg accctggctg taccttcctt   77820
taactactcc ctgactgcgt gctgagagaa gatgggtctt gtcttttcct gcctctctgc   77880
ttttgtaaac tgccatttct acctgaagtg gcaactgaaa tcatatcttc ttcataaact   77940
gtctttggct acctcagtta gaattcctta tcccatttc ctgaagcatt tctttgactc   78000
ttctttactg ctcccccacc cttttttttt tctttgagac tgaattttgc ttgttgccca   78060
ggctggagtg caatggcccg atctcggctc attgcaacct ccgcctcctg ggttcaagtg   78120
attctcctgc ctcagcctcc tgagtagctg ggattacagt catgtgccac catgcccggc   78180
taattttgta ttttagtag atgggggtt tctccacgtt ggtcaggctg gtcttcaact     78240
cccaacctca agtgatctgc ccaccttcgc ctcccaaaat gctgggatta caggtgttag   78300
ccactgcgcc tgacccccat tttttttttt tttaagatg ttgaattggt cagggtttgt    78360
agttacaagc aacagaagcc aactctttaa gcagaaaagg aatttgctaa atgatagtgc   78420
agagttctca gaatctctag caggatgaag aaccaggctt ggagaatagg tagccacaga   78480
tacacaagca tactgtagga cggttcccat gaagaggcat ctgttgtcac cactggacac   78540
agatggtact gtgtctctgc tactctacca atgccactgc tgtctctgac cccagatgta   78600
gctccctctg accctggatg cagctccctc tgaccctgga tgcagctccc tctgaccctc   78660
gatatagctg cccctgaccc cggatgtagc tgccttgac cccagatgta gctttctcca    78720
aacccagata tagcggctgc ccccttgcca gagtgaatac tgcgtcattg tggcttcttc   78780
ttgtcactgg ttcttactta aaagctgagc tggaagttct aatgggcagt tttgtcacct   78840
gctcttacct tgttgcagtc tagatgaggt ctaatgttca taagctaggg gatttcaga    78900 tatggaaagg gataccaatt ttcagcagcc aaatagagta tcacatttc actccatgtt    78960 tcctgggtgt ctgttatgtt tcctgggtgt ctgactctta ggcttctttc aagctgcagt   79020
ctgcctaata gagagccttg catttaatca tcaaaaaggc aaagcaatat gaatcagcaa   79080
gggtgttttg gcaaataaca gcaaacctga ctgtggcgta agcttgtggt attgtctcca   79140
gtgtgatcag atctgtattt taattttta aatgtaaatt aataatgatc tgtgaatcac    79200
caaagtagct tggagtagcc tagaaaacaa tgtatgtcct ccgttttcac agaagccaca   79260
tagtcgtggg ttaaatgagt cagcggcagg gcactgtgtc tcatagttaa aaaaaaaaa    79320 aagtattact gaagtaatgc aggatctttt ctgaagtaga aggcatgatg aacccagaaa   79380
actaaagcag caagtggcca ccgttcttag catagttgtt tctcaaactg gaacaaccta   79440
taaacagttg tgaacaaggt attagaagtg atggggccg ggtgcggtag cttctcccaa     79500
agctcattac ctcccaaagc aaccccagta ctttgggagg atcactttga gcccaggagt   79560
tccagaccag cccggccaac atggcaaaac ccatctctc taaaactaca aaaattagc     79620 tgggcatggt ggcacatgcc tgtagtccca gctacttgga tggctgaggc aggagaatcg   79680
cttgaaccgg gaggcagagg ttgcagtgag ctgagatcac gccactgcac tctagcctgg   79740
gggacagagt gagtctctgt ctcaaaaaaa aaaaaaaaa aaaaaagtga tgggaataga    79800
ttgttttgtc tcaaaaagct ctttccaaca ctaaatgaa acatataatt aaaaatattt     79860
ttctggctat aaaaatatcg atgcttatta tagcacatctg caaagtatga aaatatatga  79920 agaaaaaat taaaatgcca tcatcccca tgaaaactat tgttatcatt tttgtctgat     79980
```

-continued

```
ttctttagtg tttctctttt tctttttta attttaatt ttttgagta tgtagtatgt   80040
atatctattt atggggtata tggcatattt tgatacagga tacagtgtgt attagcaagg  80100
ttttctttt  aatgtttata tttatttagt tgagatcata ctatatatgg ctctatagat  80160
tactttctct tatattacta acatttgtgt tattaaatat tctgcataaa gataaattta  80220
agatgaaatt tgatgttata aaacttctc  attttattaa gagattaacg ctatgaaacc  80280
tgctgctata tattcttgga accagctgtg acccaaaaga tcaatgtagg gatgtaggtc  80340
cttccccatt ctctacacac aaaatcagat actctgatgt gcagctgtag ccccagtcta  80400
cactgtctgt tgtatttttt gttttctggt gtcacgtgcc tcccaccctg ctcctagcaa  80460
ttgccatgac aacaaataga taattggctt ccgtaatttc tcatcttatt gcctaaggca  80520
acagagagct tgtgggctca gcttgcggtt cagcagctgc tttgttgcct ctcctctgta  80580
tgtgtgaggc ctgccagagc ccactttcca gacaggtgag agttcattca ttcaccatgc  80640
agttaccgat cgtctcttga cctgtgtcct ggggaggtaa aggtgacgag ccagttctgc  80700
cccatgcagc tcacagtcta ggcaaagcta catgcaaaca aacagaatcc aaagtgctat  80760
catgaaccct ctgagagggg ctgactcagc agcccaggga gcttgaagaa ggctccacag  80820
aggaggctgt gcctcaaggc gatttcggtt taggagccac caatttataa ccactttct   80880
gtggcccgtc ttatttatt  tcttatttct tgacaatcag aagtaccttg ggtaggtttt  80940
accatgcaca tcgtaatttg agtgagctta gtgtgaggct taacggtgtg tgggctgtac  81000
atcctggtca gatgctccag atggaggcag atggttgtga tgcaggagag gcagccacat  81060
agcacaggtc cccagccagt ggactgggaa gacagtgtag tcatctctgg gaaggggaa   81120
tgacaagatc tggcagtgtg gcaggtccca gaaaaaaagg gctgggttct gggcagtgag  81180
ggtgcaggtt gagacctgaa tactgggtgg agccagctgt cagagtccac gcctgcagac  81240
tggactggtc cacggcaggt ggatgccatg tcttgaagac ccacaggcac ccactcatcc  81300
tcatgatcat gcagttctct ggtttctaac agtgcagtct gggttgcagt ctgggagtcc  81360
agcagagaag agcaggccct ggaatcccag gtgtgggggc gtggcttaac gtggagtttc  81420
cttcagaggc agtgagtgct tgtcattgtc tccgtcagca ttggctttgg gcctagtgtg  81480
gcctcgaacc ttctgttggg atcagcagtg gaacagtagg aaaaggaatg agtagacatg  81540
gcattgcaac aagtcttttt ttttttttct gttagaatta tcatattaag cagaagtttt  81600
gcttcacaaa ctctcagcca aatacaaaat actatgaata gtatttacct tgtgtctctt  81660
tccaaagaac tcatagtggt ttgcagctat tgcagatatc ctggccatgc ggtatgcggt  81720
tccttttttt tgtttttttt ttttttttga gacggagcct tgctctgtcg cccaggctgg  81780
agcatagtgg cgcgatctcg gctcactgca agctccgcct cccgggttcg tgccattctc  81840
ctgcctcagc ctcccgagta gctgggacta caggcgcccg ccaccacacc cggctaattt  81900
ttgtattttt agtagagacg gggtttcacc gtgttagcca ggatggtctc gatctcctga  81960
cctcgtgatc ctcctgcctc ggcctcccaa agtgctggga ttacaggcgt gagccaccgc  82020
gcccggccgc agttcctttt tatagctgtt tgaataggaa agatgacttg gaaaatgctg  82080
gattctgaga tttatgtgca gccttaaaaa gtgtagtttt tctctatcaa taatgagtgt  82140
gggttgtaat tgcttagtaa gtaattttgt ttatgtaaac gtacatttgt taaatttttt  82200
ttcttaggta atcccgtatg ttggcaccat tccygatcag ctggatcctg aactttgat   82260
tgtgatatgt gggcatgttc ctagtgacgc agacaggtaa aatcactgtg ctaaaggaag  82320
```

```
gagcatgaat aggctgtctt tttgtgattg tggaatgata acagagtaag gcggagaga      82380 ccatttgata ctytgaggcc caattagctt tcatcagcag ccctggccaa ggtgctgagg      82440
agattggaat gaatgactaa ataaaggtta ttgggattta tttcattgct gtaagtctga      82500
tttcagtata aaaaaattag aactatcagc tggatgtggt gacttacaca tactttttcca     82560 gcactttggg aggccaaggc gggaggattg tttgaggcca ggagttcgag accagcctgg      82620
gcaacatagt gagaccccc ccatctgtta aaaaaaaaa aaaaattaaa aattaactgg        82680
gcttggtggt gtgcgcctgt agttgtagct actcaggggg ctgaggtagg aggatccctt     82740
gagcccagga gtttgaggtt gcagtgagct gtgatggagc cactgcacta tagcctgggt      82800
gacaaaaaaa aaaaaaaaa aaaaaaaaa aaagaaaga aaaagaatta ggtatgtcat        82860
taaagaaagg aattgtggtc agatgacagg gagagtctag ttttagtctg acattcccac     82920
agcatcacag atctagttca gatggtttta ctgaatactt gctttggata caagctgtgg     82980
tatcattagt gttgggctca gctctgtgta cctaacacct gaagagcagt ggtttaagat     83040
gtgaaaatta agtctcaagg agacagccca ggccttttca gttaactcct tcaagtcgtt    83100
agagaagtag actccttcca gcttaccact ctgctatctt gagggtgagg tgaggtcccc     83160
tttcccatta tccttggcag ctagatttcc agccctcact tctgtgcttt gggtagctgg    83220
atgggtgcat gtggtgtttg cggggaaaca gagctggaca aaaggcaagt gcttgctgac    83280 tttaaggca gtttctagta gccttcctg agcacttcac ttccatctta tcagcagagc      83340
tttagctgca caggcaggcc tagctgcgag ggaggctggg aaaggtaggt ttttattctg    83400
ggcagattca gacccagttc aaactcaggg gctattttac tgaggaagac agaaaagatt    83460
agacagtcag ctctttaggc ctcatagtga atgaatgagg agggattggt cagtcccttg    83520
tcactgggcc tggagtgtag tgcctgctgg gcctttactg gtggctttcc tttctgagca   83580
ctcatgaggc ccctgtgtct tccctcatat agattccagg tggatctgca gaatggcagc   83640
agtgtgaaac ctcgagccga tgtggccttt catttcaatc ctcgtttcaa aagggccggc   83700
tgcattgttt gcaatacttt gataaatgaa aaatggggac gggaagagat cacctatgac   83760
acgcctttca aaagagaaaa gtcttttgag atcgtgatta tggtgctaaa ggacaaattc   83820
caggtaggtt ttggagaggg acaggttgag tcctcattag tgagcaggag tgcacagggg   83880
ggcctttcac atttgtgagc ccagccttgt atttcctaca cctgagatat agtttggctt   83940
tgtagtcttt ctccataaaa ggaccaggaa ggcacctaaa tatgaggggg tggcaccact   84000
actctccagc cagttgttgc catgcagaaa tatggtccac tgtgactaga tctttttatt    84060
agatcctatt tctcctagca gggctgagtt ctgaattgac acagtattat gttcatgatg   84120
ggagggtaag ttataatata accgtcacca cctgaagaac taacaagggc aatcccagca   84180
tagaaatcag aagggttttg taaattcaag tcttgccaca agacagttct gtaggatcat   84240 gagatttta gacccagagg acatcctaga aatccttgat gtcagttcca tctctggctt    84300
catggagtgt cttataccta gcgcgcgtgt gtatggttga atttggtccc agaagctctt    84360
acacctgctg gccctctggc ctgtggagct ttcccacagt agaggtttgt accaacgtga    84420
gagaagactc acatgcctct ggcacagatc ctttctgatc ttcgggatac tgctcctgcc    84480
cgaaagtctt tctgaatctc ccaaactcca ttcacctctc ccttctctgg cctttgagc    84540 ccgtgtctgt atcattcttt ttcacagttt ttaacagttg tgctttggct ttatgtgttt    84600
attttgcctc cacaatggga tttaaagctc cttgagtcag agactatatt gtatgctgct   84660
cgcgttttct gcctataacc taacgtggta cctggcattt gagagggagg gagggaggag   84720
```

```
gctcgtagcg tgccgaggac ctgcagaagc tactttctcg tcatcttact gtagtctgtt    84780
gaggtagaga ttgttcctac ttcagaataa gaaaaccgaa ttcaaatatg ttgggtaact    84840
tgtccatatt aatttattta gcaaatacaa cagattttga gtgtctgcca catgggtggt    84900
ctccagggac agtgttgtgg ggagctcgca ggcagatctt taacctgggt tcacaatctc    84960
cagggcacct gtgcctgggc ttccaggcga ccttcgaacc cagatgtctc acatgtatgc    85020
agaggcgcac acaagcacac gcacatatac ttatgactgc ctgtttgtct ggggagagac    85080
agttcctggt gcttaatcaa atcaggaact caaaagaagt tcggaagcac tgctggtgtt    85140
ttgggtgctt tcggttacca tttggtcacg tgtgtggaga cctgtgggaa caggtataaa    85200
attggacgca aggaaacatt taaatttgga taataagtta atttattaac tgttttttt     85260 tggtggcggg ggggctctgt cttctgtatc tctctaggtg gctgtaaatg gaaaacatac    85320
tctgctctat ggccacagga tcggcccaga gaaaatagac actctgggca tttatggcaa    85380
agtgaatatt cactcaattg gttttagctt cagctcggtg agtgaccttc cacagcttgg    85440
ggtcttttat gaggatggtt tctgatgaga tggtagaaaa aatcttcaaa taacacttct    85500
attgacataa aaaggacgta tctccctgac tgtagtatta atttttggga agtgaactgt    85560
tcacactagc agaaggctgt ttatcagcca gggcttcatt gtctgtagga tctcaaacct    85620
agtgtggttt taataaaaca cacacagttt ttagctgggt agcagctatt tcctttgcat    85680
gggcataaaa tggagtattt ctgtaagaca ggttcctagg ctgggagtgt ctgagtcaaa    85740
gagcacagtc atgtgttgca taaggacagt tcagtcaaag atgaaccgca tatacaaccg    85800
tggtcccata agattgtcat atactgtatt tttaccatac cttttctatg tttaggtaag    85860
tttatatgca caaatactta ccatcctgct ctggttgcct acagtatttg gtacagtgcc    85920
tgctgtacag attcactggc caggagctat aggccacacc ctacagccta ggtgtgtagt    85980
tggcagtacc atctaaggtt gttaagtaat attctgtgat gtttgcacga tgacaaaagt    86040
catgtaagga cacatttctc agaacatacc cccttcgtta agcaacacat gactgtcttt    86100
gcattgaaaa ttttgataga tactaactcg cccttcacaa gggtaaaaac agtttgcact    86160
ctcaacagcc atgctcccac cttcttgttg acattacatc ttattctctg taatgtttgc    86220
caatctgatg gggggcggaa aggacccag tgtcaagtat attttggat catagttttc      86280 aagcatattt ttagtaccat ttataatttt tttatatgtc aaacaggtta tatatagaaa    86340
atattttcta ctggatgtta caaattaatc tttattatct tttctcagga cttacaaagt    86400
acccaagcat ctagtctgga actgacagag ataagtagag aaaatgtaaa tattaaatct    86460
tttaatgagc cactggttta aaaatgttgt tttagctgcc atgttaatga aatggcaaga    86520
aggctgggtt tttgaaaatt atgcttttag aacgcaagta atcacttgaa aattgagata    86580
catacttgtg gtgccaggca cgcagtaagt ttttgctgat gattcacctg tcagtttctg    86640
taactgccac tcactgttct tatgtaaaaa gcactctctc actcttaact gctgaatagt    86700
actgttctgg ggtatttcca aatattgaac atcagccagt gcactggcaa atgaacttcc    86760
atgtgtatct tcaacccctg ggagaataac tgcaatttaa aaatgcgctg ttattaatgg    86820
agaaagtgag gtcttaccga ctggcacgtt cacacctcac agacagaata gaatcttagc    86880
attctggggg caccctggaa aggacaacta agacacgttt gaagttcatg tagtgctggg    86940
tgaaggtggt ggctcaggcc tgtagtccca gcgctttggc tgaggtgggg ggattgcttg    87000
agcctaggag tttgagatca gcctgggcca cataggggaga accccatctc tacaaaaat    87060
```

```
taaaaaatta tctgggcatg gtggcgcatg gctgtgatcc cagctttggg tggctgaagt    87120
aggcggatga cttgagccca ggaggttgag gctgcagtga gccatgattg agccactgca    87180
tcccagtgtg gatgacagag taagaccctg tctcttaaaa aaatttcata tagttctatg    87240
aaaaattatt aatttatggt ggaggataaa ggactcagat gaacagggat atcagactct    87300
cttctcaacc cgtgtagccc ttcacaacac cataccattc cgtcataaag caccagctgc    87360
ctggaggtca caccagagtg gagcaggaac atcccaggct ccggccaggc tcagctcagc    87420
acaaccaaga cttcagatta taaactataa ttcttcccct tctaacattg ttgtgttttg    87480
tttcttttcc aataggttcc aaagtctggc acgccccagc ttgtgagtat ttttgcctgg    87540
gttatttcat gtggaatatt ttataaagtt gcatagaaaa tgaacagttt aaaccgtgga    87600
gggcagcttc attcattcca ttccttactg tagaactgtt tccctacagc ctagtaatag    87660
aggaggagac atttctaaaa tcgcacccag aactgtctac accaagagca aagattcgac    87720
tgtcaatcac actttgactt gcaccaaaat accacctatg aactatgtgt caaaggtttg    87780
aagagcccca aattttctta actctgtata aaaattaagt tgtaatgagc tgttacgagt    87840
aacctgtatc cacaatagaa gcccaaagca gcccctctg catttgtgtg ccgtccctgg    87900
atggattcga gagtcaacca ggcctgcctc tgagccattc ctgtgtattt cctcagcacc    87960
tccctgcttg gctgcttccc cttcaggcag aacacagtac tgcctcagac cccaggcaca    88020
gggggccttc ctggcgtgtt tcactcatac agagggcatc gggtcccacc ctgtcactca    88080
tttcatcgtc taaatgtaa tcatgagtgt ttgcttcgag ccagggacag tgctgctgca    88140
ggggacccag ctgggaccaa ggcagactgt ctctcccctc ctgggattta cagggtcatg    88200
gctctgaaac attctgtagt gttctttgga cacgagtttt ccctggagat cgctttctgc    88260
aggcctcttg gtcctgactg tggcttcttt tcagagcctg ccattcgctg caaggttgaa    88320
caccccatg ggcctggac gaactgtcgt cgttaaagga gaagtgaatg caaatgccaa    88380
aaggtcagta tccttcggta ccagtcacag tgcagatact tccgtgcctg ttaccgcctt    88440
ctacccgtga acggtcctgt gagctggaag tagggctagt gtcagaatct tcatttccaa    88500
agtgagatga ttcaagcagg aggtggttag attgtgaaca gccagtgggc agcagagccg    88560
actaaggccg tgttctgacc tcggcttttt ctggccagac aagagagtag cattttttgtc    88620
cacgaggcct atccttgcct tgtagaactc cagagcagcc ccgtaagatc aggcaacatc    88680
tttttctttt tttttgaga tggagcctca ctgtgtcacc caggctggag tgcagtgtca    88740
caatcccagc acaccacaac ctccgcttcc tgggtgttca agccattctc ctacctcagc    88800
ctctggagta gctgggatta caggcgcacc accacgccca gctacttttt gaattttgt    88860
attttagta gagacagggg ttcaccatgt tggccaggct ggtctggaac tcctgacctc    88920
aagtgatccg cccacttcgc cctcccagtg ctgggattac aggtgtgagt cgccacgccc    88980
agcccaggca acatttttta gggcccctct tgtcatgtga tttagaaaat ttctgcttta    89040
acaacttttt ccacagacgt ccagccttct gaaagcttga aattagagct atttcctaga    89100
aagtggcata ctttcaagaa ggaaggaaca cgggtagatg atgaaaagag aatacctgct    89160
tgagaggatc ccaggctcct gcagcctgaa gtagtcattc agtttagcgt taaaccttcc    89220
atttctgtcc aaccacatct cagcctcaat gctgatttta aagggttttt ttttttcgta    89280
ttttttatttt gcaagtaacg aattagtgga atgctgactg ggtttaaaat ttcaacttca    89340
cctgcattcc catgtccatg tggatacgtg tgtttcatag agttagaatc atagttcaag    89400
tctggtcact aacattgctg aaattgccac tactctgtcc tacttggtta attaaggttt    89460
```

```
tttttttctt tctttctcaa aagctttaat gttgacctac tagcaggaaa atcaaaggat    89520
attgctctac acttgaaccc acgcctgaat attaaagcat ttgtaagaaa ttcttttctt    89580
caggagtcct ggggagaaga agagagaaat attacctctt tcccatttag tcctgggatg    89640
tactttgagg tgaggttcca gttttttgaaa atgggacagc aataagaatc ctgggagcag    89700 gggtggggata agtggtccat ttaaatcaag tcctaactca gtatgtggag gttgtgtatg    89760
ttttttgttt acttggagat tgtaatttgc cccttccttt ttataacgtg ggcaatcagt    89820
ataaatggca aagccagtag agtgtcaaat tatgcacatt ggaattgaca tttgtcatca    89880
tattaaaatt cctgtgtagc cccatattga taggaattta accaggaagc ttgtctcagg    89940
actggagtca cacatttaat catataagca gacttgagga ctggagaccc taaaactgct    90000
tgcttgcact ggccatcatc tcccatcagg gtaggtggca gtcctttctc ctaaggagtt    90060
agtcttgttt atatgtattc aaggaaaaat acatcagtcc cttggaacta aaaggcatgc    90120
agtcctgagt ccccagatag gtgaatattg taacacatac cttttcccgaa atatgtttct    90180 gggatgctga gcagagaata gtctccttgt gatgtggatg ccgggtgttt ggccagcctc    90240
aatcaccagc tcaggtgcca ctgcctcaca cagtcactta gggtcattgg tttaggttat    90300
cattctacag cattttaaac tgacacattg tctggaccat gtgggttctt gaggactcat    90360
caaaacccgt tactaaaagc atgaatatca ggcgaaatag atagcaatgt gacattcgta    90420
tttatcccta agttccagtc taatgcagtg ccctggtatg tggagtgtag acagatgtgg    90480
gctaatcatg gaaggttccc tggaagttgt ggatattggt ttcgaattca gaaagctggg    90540
aaggatgtgg aaggctgaag gttggctttt ctagatttag ggcatgattt gaacaagtcc    90600
ttagaggtgg gaagggcagc acagggttgt tggcttggca agagtcaagg tgcaaagggt    90660
gacttggggt tcactggagg gaaacagaga tgagtgctct agaaggaagt tgagccttgt    90720
ggtgggtgac aggaaaccaa tgatgtaact tgttttttgac ctatctgggc cccaagtttg    90780
gatctgctat attaatataa aaaaggataa taatgataca ttcaaataat gctgaaaaat    90840
actaagatga aaatacctcc aacttcgtaa ttcaaaccat accattagga ttaggtgaac    90900
cacattccag gcgttttttt gcagagacag tgaaagggat ggctggctga aggaatgaat    90960
agatgaatgt tatatgcttt tgaacaatcg tcttttccat ttaattttct aattcaggag    91020
cagtaattat cctgtgttg atcactgctg acgattttct atactgatag gtcctttccg    91080
ggggcttcca tctcttgcct tttaaatatg cttgcattga gattatctca ggtctttcca    91140
ttatgccatt acttcatttt taaatcttct tgctcttttca aatacacttt agttgtatct    91200
acagtgtttt aaaaacaatc tcattcagtg ttgtaatttc atctgtgggc tcttcctctg    91260
gatgaaatcc gtgttcctcc cagctgttcg gcagcatcag atggttgtga gggattctgt    91320
tgttctgttt tcttctaggc aaaggatgtg ccttcttttc atttgcagta gtctgctcac    91380
ccggaagcat gtcatttctt tgccacttgc ttgtaattca ctggctttgc acttgctctg    91440
atacagtaca ggtaactaat tgactccctc tgctgccaac ttggttttcc ttctgagcta    91500
tagcatcagg ctgtgtgttt tgtgttttct tgagattttg ttaaatatat ctggggtccc    91560
ttctacctgg ttgaactgg gattcccacc attcttgtgg ggatagaatc tcaggttaca    91620
cctatttccc caatcctctg tagccacaga agcttcatct tggccagctc tgttatcaga    91680
gtgcaggact tgggctgaaa tttcctcccc ttcctgattt tccttgacag tcctttccac    91740
tgctcctatc aatcaaaaga atgaaaaccc tcaacttgct gctttgcaga ttcaggtttt    91800
```

```
gtgcttcttt ctggcctctc ggggtggggc cgggttagca gcaaggctga gctgccccte   91860 tttcttctga agccttcatg ggggcgagga gcacagggag agctcagtgc agggcctccc   91920
agtggccttc tcagagtggg tggaaaccca gcctggcact ggcagcgtgg caccagaagt   91980
atgaagtgta ggtgtaaagg tgatgtaaaa ggctagtagg ttttttggtt tttcattgtt   92040
tgagttttgg gcatagatga ctgtgaaggg cgaacactgc cgatggatct gaatgaattt   92100
gtagtatgtg caccacttcc aacttacggg atacccagct ttgacggctt tggacaaaca   92160
cactgaggcc aagatgtgct gagcttatca ggatcaggat caccaagcag ctgtaaaaac   92220
cctagcaagt gccttaagct gctgaaattt catattaatt gtctggtttg ttcatggtcc   92280
tagagtttga ggcagaaaag tcaggatcca agtcccttgg ttccaggcta cagctggaaa   92340
cagcatctcg gtgaactaaa gcaaccatat taggagtttt cctgctttag gagagtcccc   92400
agcatcggcg aggaggggc agcactctgg ctttccagga gcaaggggca ggatgcggcc   92460
gagggagagg ggctgtgttg aggaaaggag ggccgcaggc cctggggatg gtgtgaggct   92520
ccaaacatgt ccgagtcact tccctgggtg ggatgaggca gacagtgcca ccaccaggga   92580
cactttagtt agattagggt cttggaagtc acagaaggaa gtcagcagca gcaggctgga   92640 actttctat gtataatcaa atggtttact ctgacaccgt tagcatgtaa caaacacaaa   92700
attttaaact aagggaacc actaatggca tgtttccttt cctttcagat gataatttac   92760
tgtgatgtta gagaattcaa ggttgcagta aatggcgtac acagcctgga gtacaaacac   92820
agatttaaag agctcagcag tattgacacg ctggaaatta atggagacat ccacttactg   92880
gaagtaagga gctggtagcc tacctacaca gctgctacaa aaaccaaaat acagaatggc   92940
ttctgtgata ctggccttgc tgaaacgcat ctcactgtca ttctattgtt tatattgtta   93000
aaatgagctt gtgcaccatt agatcctgct gggtgttctc agtccttgcc atgaagtatg   93060
gtggtgtcta gcactgaatg gggaaactgg gggcagcaac acttatagcc agttaaagcc   93120
actctgccct ctctcctact ttggctgact cttcaagaat gccattcaac aagtatttat   93180
ggagtaccta ctataataca gtagctaaca tgtattgagc acagattttt tttggtaaaa   93240
ctgtgaggag ctaggatata tacttggtga aacaaaccag tatgttccct gttctcttga   93300
gcttcgactc ttctgtgctc tattgctgcg cactgctttt tctacaggca ttacatcaac   93360
tcctaagggg tcctctggga ttagttaagc agctattaaa tcacccgaag acactaattt   93420
acagaagaca caactccttc cccagtgatc actgtcataa ccagtgctct accgtatccc   93480
atcactgagg actgatgttg actgacatca ttttatcgta ataaacatgt ggctctatta   93540
gctgcaagct ttaccaagta attggcatga catctgagca cagaaattaa ggcaaaaaac   93600
caaagcaaaa caaatacatg gtgctgaaat taacttgatg ccaagcccaa ggcagctgat   93660
ttctgtgtat ttgaacttag ggcaaatcag agtctacaca gacgcctaca gaaagtttca   93720
ggaagaggca agatgcattc aatttgaaag atatttatgg gcaacaaagt aaggtcagga   93780
ttagacttca ggcattcata aggcaggcac tatcagaaag tgtacgccaa ctaagggacc   93840
cacaaagcag gcagaggtaa tgcagaaatc tgttttgttc ccatgaaatc accaatcaag   93900
gcctccgttc ttctaaagat tagtccatca tcattagcaa ctgagatcaa agcactcttc   93960
cactttacgt gattaaaatc aaacctgtat cagcaagtta aatggttcca tttctgtgat   94020
ttttctatta tttgagggga gttggcagaa gttccatgta tatgggatct ttacaggtca   94080
gatcttgtta caggaaattt caaaggtttg ggagtgggga gggaaaaaag ctcagtcagt   94140
gaggatcatt ttatcacatt agactggggc agaactctgc caggatttag gaatattttc   94200
```

```
agaacagatt ttagatatta tttctatcca tatattgaaa agaataccat tgtcaatctt    94260
atttttttaa aagtactcag tgtagaaatt gctagcccct aattctttc cagctttca    94320 tattaatgta tgcagagtct caccaagctc aaagacactg gttggggtg gagggtgcca    94380 cagggaaagc tgtagaaggc aagaagactc gagaatcccc cagagttatt tttctccata    94440
aagaccatca gagtgcttaa ctgagctgtt ggagactgtg aggcatttag gaaaaaaata    94500
gcccactcac atcattcctt gtaagtctta agttcatttt cattttacgt ggaggaaaaa    94560
aatttaaaaa gctattagta tttattaatg aattttactg agacatttct tagaaatatg    94620
cacttctata ctagcaagct ctgtctctaa aatgcaagtt ggccttttgc ttgccacatt    94680
tctgcattaa acttctatat tagcttcaaa ggcttttaaa ctcaatgcga acattctacg    94740
ggatgttctt agatgccttt aaaaagggg cagatctaat tttatttgaa ccctcacttt    94800
ccaacttcac catgacccag tactagagat tagggcactt caaagcattg aaaaaaatct    94860
actgatactt actttcttag acaagtagtt cttagttaac caccaatgga actgggttca    94920
ttctgaatcc tggaggagct tcctcgtgcc acccagtgtt tctgggccct ctgtgtgagc    94980
agccaggtat gagctgtttt agaagcagcg tgttgccttc atctctcccg tttcccaaaa    95040
gaacaaagga taaggtgac agtcacactc ctgggttaaa aaaagcattc cagaaccact    95100
tctctttatg ggcacaacaa agaaacgaag gctgaagttc gcctacccaa aatgaaaagt    95160
aggctttaca gtcaaagta cttctgttga ttgctaaata acttcatttt cttgaaatag    95220
agcaactttg agtgaaatct gcaacatgga taccatgtat ataagatact gctgtacaga    95280
agagttaagg cttacagtgc aaatgaggcg tcagctttgg gtgctaaaat taacaagtct    95340
aatattatta ccatcaatca ggaagagaat aataaatgtt taaacaaaca cagcagtctg    95400
tataaaaata ccgtgtatca tttactcttt ctgcagctct atacgatagg caggagaggc    95460
ttatgtggca gcacaagcca ggtggggatt ttgtaacgaa gtgataaaac atttgtaagt    95520
aatccaagta ggtgtattaa ggcaccaaaa gtaacatggc acccaacacc caaaaataaa    95580
aatatgaaat atgagtgtga actctgagta gagtatgaaa caccacagaa agtcttagaa    95640
atagctctgg agtggctctc ccaggacagt ttccagttgc tgaatagtct tttggcactg    95700
atgttctact tcttcacatt catctaaaaa aaaaaaaaa aaaaatcaaa attaaaatct    95760
gagtcagtct gcctgcctcg gttctcatta gtttaattct taatgccttg cactttccag    95820
caatcattca atcaaaagag tgaaatgaag cacattaaca aagcaggagg cgccacggac    95880
cgcctccctc cacaccgctc cttccgcctt cattccttgc ccacaggctt gcactggaag    95940
ctgaataaga atccccaaaa ctcaaacttc ctagggatgc caccccttta gtagctcaca    96000 cctccccct ccaagagcta agaaacaaag gagaatgtac ttttgtagct tagataagca    96060
atgaatcagt aaaggactga tctacttgct ccaccacccc tcccttaata ataacattta    96120
ctgttatttc ctgggcctaa gacttatgtt ccagaactgt cacagctccc catgtcacac    96180
ccactagctt gtgatctttg tcaaataact gaaatctttt aagcctctag tttcttcctt    96240
tgtaaaacag agataaaatg ttgtggtttt taagtgagat aatccaagta aagcacctaa    96300
catggagtag tgaatgaaca tcggttgcta ctaaaagtgg acatcctacc gcatccttaa    96360
tgccactagg catttccata caatctgggg accaaaactt caatcatata aatgtatgag    96420
gttaattaaa aacactactg taatctgctt gtatgatcac aaaccaccac aaaagaaaag    96480
atcgtgaaga ttcactgta aacggactct caaatgatca ggaggtggtc acttcgcaac    96540
```

```
ttgctccctc cacccaactc aaaacaggag ctcgagcctg cctgtatttg agactggagc    96600
tgcctgtatg aggactggat caactgctag tcacgttata tccaaatctg cattatcatt    96660
gggcacattt tcacagaatt ttactgaatt attccttaat tgtttaatgg ttgggaatag    96720
tttgggaatt accttccatc aactctgcta agaaaggaat ggattctggt agcaagacaa    96780
tataattctc ctttagtttt tcagccagtg ctaacacagt aatcaaagca gcaaatcgaa    96840
cctgaaaggg ataaaagagc aaagaaataa aaagtagtgt tactgtattt attatcttaa    96900
gagctgtact gacttgagac aagctctaac ttttttaaaca ttagttcaca cgcgtttatt    96960
cacttcatta tgttcattaa gctttcatct tagaatacca gtttcaccat tgggagctg    97020 tttgtaatat gtgcaacctt ataaatagtg ttttccaaac tgtgtcccag gactgcaaat    97080
ctttaatgtg aaatgtcttt ttataatctc ttcctttaaa aaaaaccaat aaaataaaat    97140
gccacatgca aactcaagtg tgtcaccaga ttttacttca ttggcgctcg ccagcccgcc    97200
aggctggcaa taaagtgcct ccagccacct ctggcaggtc tcctcaccca cagcccctga    97260
ctggtcacca ctatagttgt atgaggggcc aggacaatcg cttgggataa actcccatct    97320
cagcactgaa taaaaacat tctgtgtcac aatatcctag ttttgggct ttaaaaacgt    97380 ctaggtgttc ctcacatgcc ttgtctataa taaggaaagc aagcagtagt tgggtattgt    97440
tagcttttga aacaaaagcc ctactggtct tctaatttg gatatttaa ttaaagaata    97500 tctggacagt acaaagtgaa ttattaaaaa accatttgta actacctaga ttcaatcagg    97560
atttccttga tttgtgcaaa gtaaaatatt acaataaatt tgatactgct acttgtataa    97620
aaacctatgg tttaaaatgt gggggttcat cataatagtc tcattgttag catatcctaa    97680
taaagaattt gaactaataa atcctattaa taaaattctg ctttggtctg ttatagccag    97740
taaagttcta atacaatcat tagtttgaga aatggtgact cattgctaaa acagtttgaa    97800
atttgtaaca cttgggtgtc aaattttgac ttccactcaa cctacccatg ttttatttcc    97860
actgccacca cttactcaac aagatcataa gcctagtatc tataaacaac agaatgtatt    97920
gctctaactc aaaagactat agtgtggata aattcaatgc atttctctct ggagcacaat    97980
gacatttcaa tagcacttaa aaaagaagga attacttcaa atctttgtta tttaaaagta    98040
tttagaaagt attttagtac ttctgcccaa cgcaccattg gggtggggat agggcattgc    98100
tattctttac aaatagccta taagtaaaaa acaaaatttt cttaggcaca aatttctgcc    98160
taatacaaaa gaccagacct ctagtactgg atgacaaata gcaatgttct tccctgccag    98220
tttactaggg ggcctacatc tgtgaccacc tgcaggctgt ttaggctatg cagtgaaaag    98280
atgcagtttc agtacttgtc acgcagttcc taaccttagg cgaggagtct ctcgtcttta    98340
gcagaatctg gtagttcagt ggtttccaaa gagagtcatc cgccatggcc actgaaaact    98400
gtgcgatgca tggtatcagg tgctttgtca cccgttcctg gaatttctct tctcccccaa    98460
gcctgttttc cagctaggaa gagtaagaca aagactttga acaacaagtc tcatttcttt    98520
cttctgtttg aaaaaatgtc caacatacaa atatttact atctttcatg atattagcag    98580
gttcaaaaac caggcattat tctaatactc tctaggcaa atgtattgcc ttctagaact    98640
caaatggaat ctcataccct ttatcatcgc ccctttctct ccagcagaac atctcagagg    98700
agctctttgc tccagaggac agccatgctc tgacacgttc tcagtgaggc ccagttaaaa    98760
caaatgaata cattaaccat gacagcttat atcatgtctg tcttttgagc agtttaaaaa    98820
ataaaaaata aaaaataact cagggccagg catggtggct cacgcctgta atcccagcag    98880
tttgggaggc caaggtgggt ggatcacttg aggtcaggag ttcgagacca gcctggccaa    98940
```

```
catggcaaaa cctcatccct actaaaaata caaaaattag ccaggtgtgg aggcgggcgc   99000
ctgtgatccc agctattcgg gaggctgagg cacaagaatt gcttgaaccc gggaggtgga   99060
ggttgcagcg agccgagatt gcaccactgc actccagcct gggtgacaga gcaagaccct   99120
gtctcaaaac aacaaaacaa aactcaaatt ccacaatgaa gttatatctt tgaaaaaaca   99180
attttcaaat aaaacatttc attaaaaaga ccagaaaaaa caaccttaca agaaaaatc    99240 ctagcaagct gtcatttgag cagatctaaa acctgccaag ctcgaacagt gatggcttcc   99300
tcagcaacga aagatgattc tgtttggtta cctgatccac cagaggcatc atcaaggctc   99360
ctgctctctc tttacttata aaatgctggg tatcaaaaag gaagattttg tataaacagt   99420
tcaaaataaa ctgcaacagc aagcagcact tttcagggtc attttcagag tcaaaaaatg   99480
cttcatctgt agacgtggga agagtaaaaa tgaaaaaaca ctgaacttaa ccatttaatc   99540
tccaatgttt acattgaaat cactattaaa ataactaaat cagaagagtc taaaatgatc   99600
tagaaatcat aatcaggacg aaggcagaac acaatggatg gtctctcgaa gaatgattcc   99660
ttcttttaga gttaagattc taacactcac tctggcaagt taaattccct caactgtcaa   99720
gtgggtcacg tattagcatt agagaataaa ctaatcttaa ttttttgcgtt ttaaagttac   99780 ttccagtaac tgacagtaac ggccatttac tttattcttt ctcccaagtg aggtgactta   99840
taacattcgc tcatcatgct aaaacaacac ttcactgtct gacaacaatg aagtaaaaaa   99900
ttcaccctcc ttagcttagg acttaagaac ctctaaaatc ttgcttccaa gcactagctt   99960
gtgtcttact ggtaccttgt ataaggcaca caggacaagg gtgacagctg aactgaagcg  100020
accacccacc tgttttggag atgttcacct ggtccaaggt gtcagcaaaa ggcttcacta  100080
agtggccggc aaacagagta aaaagccctt tcagcttttc agcaatgcaa tctgccaagt  100140
tgtaaaatgt caacaacctg tcctttgggg catcttctgt tttagcccaa tcaaacagct  100200
gaaaggataa gacagtatta gtttcttcga catcttgtca cttaaatctg agcacaaaag  100260
agaggaagag gaagaaagcg tcaccttgaa gaacaggggc ctgaatgtga cctcggaaag  100320
tttgacaacc atggctacta gacagtcaat gatacaattt tccgtttttc caacttcctc  100380
cagatcgttc tgaaaacaga gagcccatt  tattagagtg ctgatacctg actgtaaatt  100440
attttggcaa gtaccactgt tacacggcta gattgttctc ggactcttca ataggtggat  100500
aacagcttta ggatttggag gagtgaacct gagcttacct cagagtgctg ggctcggaag  100560
tccagggcct ccaggaaaaa ggcggttagc tgagactgat gggaggtgag ctcttccttc  100620
ttcatcgccc caatatgctc ttgcaagatg ctcataaacg gacccatgtg attctaccaa  100680
taacacagga aaaagatgtg ccattttcaa atgattccta gagttcagcg gtgtgtattt  100740
ttaaaaacta atcttcttc  tttaagtcaa agtttacaca ttgcagtacc acctctccct  100800
tctccaaagt cttaatacccc aataagatct aaccttccag ttcttctcaa tctgcttgta  100860 agttttttg atggcgggca acaggactcg gggtgcaagt gtggtagcca gtgtcttttt   100920
aagagatgtg agacggatat tagcctgtga cgcagaaccc atttcactag tgattttctc  100980
cagatgaatc acctacagga atataaaaaa agtgatcagg gccactgcag atcttcgctg  101040
acaaacacac acttacagag aggcttcatg atgaggtact agtgtttgga aaatgcttag  101100
cactttttaa ctacacacag agttcctttt aaagtcagcc ctaaacgtca gtggataaaa  101160
ctgggcagac acctcttgcc caacttgcga tcagggacga aggccgatgg tagacgcaga  101220
cgcacacaca gcacccagac agatgatttt cttagaggac aggaatgcaa gggaccacgg  101280
```

```
caagagtcaa gttgctaaaa aactgagaaa gctcctcaga gcacaggccc ctttctctga   101340
gaaggctact tttaaaccct ggctgtggtg taagtgaagc ggtttaatca tttgccccat   101400
ggtaatgaag gctcctaacc ttgtaaatgg caaatgatca acacaatgga acagccaggt   101460
ctcaacactc ttgagcatct tcaatcataa ataccactgg cccctagcgt gttgacagga   101520
aaccgctgac gtgcaataca aaaattctgc tttgcaagat gccttaggat taaacctctc   101580
acagtagaaa cagggcccat caatttccac aagtaataaa aggcggctct accagcccaa   101640
ctccaaagat ctcacagaag aaaaaaaagc cagaatacat tccgcacaat taaagaagag   101700
aagcatctcg ctaaaaagtg acccccatat caatttcaag attaagtggc aaggatgatg   101760
gaagagaaaa agtacacatt taataaaagc aagcacatct cttcagaaat aagactcctt   101820
tctgtcaaac ggaaactaac ccttaaagaa aaaacaaaat cactacattt gtgatctttt   101880
accttcccca gccaccctgc gtagcatgtc gtggctatcg tggctcacct gggagagaat   101940
gccttccaga taggggctga tgaagtgcgg gagagtctcc acaaccttct gcagagcagc   102000
caaggcactg agcaggtaga cctcgctgga gaccagctcg ctggtgttct tcattgttgt   102060
cagcaacgat ggcatcaggc tagaaacaaa gtaagagctt tagaagaact tgaagcagaa   102120
acagaggcta gggaatggag tagagggcat tatgaaaaaa accagcaaac tgtgcctatt   102180
acatcgctat ctgcctcata gcctaaaaag cagtgtctat acattttatg tggctaagca   102240
caagaaatct cccagtgcta acagtatgga cacaacagta atttaaaaaa taacaatgtc   102300
tttcattaac tgaacactta ctatgtgtca ggcactatgc aaaactcctt gcaagcactg   102360
ccctacagaa atcctatgag gtagatactg tctctgtttt atagacagca aagctctaac   102420
aggttaagga acatactggc tgtacagtaa ggaactacca cagccaggag cttctaactt   102480
ccaaatttgg cagcagaagg cagctttggc cttgcctaac tgggtgggcc cctctgccaa   102540
gaaccttcac ccactgcttt ttgactatac tagacaaaag gaaggaagaa tggaggacga   102600
ttaacactgc aaagcagtgc atctgaagat aaacgggaag gctgcatctt tctgtttgaa   102660
gattaattat ttttattatt atttctttaa gagacagggt ctcactctgt tgcccaggct   102720
acagtgcagt ggtgcagtca tagctcactg cagcctcaaa ctcctgggct caaatgatct   102780
ccctgccttg gcctcccaaa gtgctgggat cacagccgtg agccaccaca ccctgcaaga   102840
tcaattcttt aacaaattcc aatttttatgc aacgtctact cagaggaaaa aaaaaaaaag   102900
tcaccaaagt gttattttttc aatgtgtgcc aggcggtaac agctcctgtt ccaagtctcc   102960
ggccgcatac ctgggaagct gggggatggc cagcgcctcc agggtggagg tcacctctgc   103020
tatgcacagc agcgcgcttc ccaagacatt cttctcctcc tttctctctg gagcaatcag   103080
tttcacagca gtgctcagca ctgggacaaa aggatctgga ttttctgcac caaaattctt   103140
gcataaaagc tttaaggtat acaacgctgt ctgtctgttg attgcttgtt cttcttcccc   103200 ttccttttttc ttacgctgca caatggccaa aaggtctgga accagtttta ggaaacgggt   103260
aacctgaagg ggacagccag aatccccaaa tcattaaagc tgcaaaaaat gtttgtccat   103320
tttcccattg tcacagcttg agattgtcta aatggaaatc agactcgggg gtcctgagtc   103380
acacagtcat gctaagcgat gtgcatgttc tagccagtgt ttcacttata caaagcaccc   103440
actgatctgg agtaaaaggg acttagaact atgctaaggc taaggccacg taagctctgt   103500
agtaagcaag aattccacta ggctgaaatt ccattctaag agctcttaca acacacatat   103560
attcccgtta gaattaacgt cacatttaaa aacatgtcat ggtattatat tcagataata   103620
atatacttca atttgaaatt gtaccactag agaaattgaa gggagttaaa tgcagctctt   103680
```

```
tgataaagca aagtacagta aatgggtgtg tcctgggtct tcactcacta ttgtcttctt 103740
ccaggatata ttttgctgca gcttgttatt caaaaggtcc agcgctttgc ggcgaacaga 103800
tggcagggga ttgcccacca gccctctgat cacaggaatg aatgtctctg tgggcagcaa 103860
ggcattgacc taaagagaaa ttttatattt aacatgaaaa gaaaaacaaa ttaaaaaaaa 103920
aatcaacttc aattaagaca gactgctgtc cactgcacac ctccaggcac caggcacttc 103980
cacacacatt ttcttattta attcttaaaa taacctttca ggtaggcatt accaaccaca 104040
cattatcgaa caaacaaaa gcctgatgtc aggaggaagt gccaaaggca tgcagctaaa 104100
tgactgagct agatttgaat cagcaatcct aacttcgagg ccagtgatat gtatgtaata 104160
tacttcatac ttttatttta ttccacttga ataaagtaga acagtatata ttatatgact 104220
taattattaa aatatacgag gtacatgttc tcataactgg taaggaaaca attttttcca 104280
gacaaatcta tttctagtca tcaagagatt gttttctaag aaaaatctga gcttcattat 104340
attcataaaa ggaattgcta agtttattct taaaaacttt acataatttc acaataattt 104400
aaaaaacagc aacaaaacag taattccagg gagaaatgaa cacctacctt atctaacagg 104460
tcgtaagctt tactaaggag cgcgcgccag aacttcacgg tgagtttgtc tgcgttcctt 104520
tccatggact gtgcaactgc actgatatag ccgagaacgg tctccagcaa cctgaaacac 104580
agaggctcgc tcagcaaacg gcagctgaag aaactcagag aacttgttca tgtctacctt 104640
atgctaaatg tttcaagtag aaagacgagt taaataattc tgtactaaat tatttcaaaa 104700
actactcgga aagaaaggaa atgagggatt attgccatag acagagatca tcaagaagta 104760
actaggcgct tctgtgcaga agcatcgacc tcgctcagac tctgtgaggt gctgaataag 104820
caacagatgc tgaaagcgtt taaggaactc actcatatct agctcatgct cagtggatct 104880
cactgggctg tccaagtggg gtgttcaggg agttatggcc ctaggttaat ggcaggtgtg 104940
tgcgtgcaca cacacacagg cacacacacg cacacataca catgcacaca caccatacac 105000
catttatata aagagaaata ttaatagaaa tgaacatata acccacttct ttcacattat 105060
taggagacaa aaaaaaagac tacaaacttc aaataacttg taattagaaa agcacacacc 105120
aaattccaac acagctgcca ctggagatcc ccccactgct gccagcctga gggggagct 105180 agagggaaga gtggagacag aagttgacac cgcacagcag aggaggggag aagggggcgc 105240
agacaaaatc agctccaaaa acgaaagtcc tacgcatagc gctacaagtc agcccacagg 105300
actggaactc agcagctcac attcctggct gcagggcagg cactttccag tggaagggc 105360 aggacagtgg ccctgggaat gccatgcatc tgaaaaggag gtacacagca aggccaggag 105420
gcaaaccccg aggacatggg agagaaagga aaattcctgc acccaaatat ataatggcag 105480
catatggatt agaatccacg gaataaagaa ttcatgagcc catagaaatc agggccagat 105540
tgagacacta aacagatact gcaactcaat acaatacaca gacttgacat ggatcatgat 105600
gcagaaacac atgcggtgta aaggacagtg ttgggataat tagggagact ggagtatgaa 105660
ctgtagatta catcactgga ttggatcaat gttaaatttt ctgaatttga tcaatgtact 105720
gtggttttat aagaacatct cttattctta gagacataat gtatatgatt tactttcaaa 105780
tggctcagag aaaaaaccct acatagggag aacgctaagg caaatgtggc agaaagtatt 105840
atcaaatggt gaacctggtt gtaaagagta tatgaatttt ctgtactgtt tttccaggtt 105900
ttctataagt ttgaagtcat ttccaaataa aaagtaaaaa aagaaaagga aacatacctc 105960
tcttcaaggc cttttaaaat ctcaggacca ccactctcaa ctacctaatt tttaaagaag 106020
```

```
acgtcattag aacggtatgg aagtcaataa taaaagtcat ttcaagtcag ttcaatgaaa    106080
ctcggaccat tcactgaaac cttccacagc aactgttttc tgacattaca atttaatcag    106140
gttcatagca tcttcattat actgtagtaa ctctatttct cttaatttat tttaattata    106200
ttctactggt agtatctaaa aagtactaca atggttcaga aaaatacagc aatcaacact    106260
caattagcac taccgaattc tatgacatgc tgatctggtg agctcacata tcctttgttg    106320
agaagttaaa cattacagat tcagctggaa tcccccaagt actgctcctt ggtcctattc    106380
tccctctacc ccaagcccca caaacaaaac catcatccca aatctgcttc caaatgtttc    106440
aaacactaca tatcacggaa caacatgttt ttctggaaac atattttga gatctatgca     106500 tggtgactta tgttctagtt ccttcatttt aactgcatat gatattcctc tataaatacc    106560
acttatctat ccatttgcct ctgttgttag atgtttagtt tatgtccatt ttttcccctt    106620
ttactaataa tgctagagaa gaacattttt atgtcccttt gatcatcttg ggaagttttt    106680
acagcatata tacctaagga agggaatgac cagatcacag gaattactgg aactttcaac    106740
ctcatg                                                                106746

<210> SEQ ID NO 13
<211> LENGTH: 132
<212> TYPE: PRT
<213> ORGANISM: Homo sapiens
<220> FEATURE:
<221> NAME/KEY: MISC_FEATURE
<222> LOCATION: (1)..(132)
<223> OTHER INFORMATION: amino acid sequence of leg2

<400> SEQUENCE: 13

Met Thr Gly Glu Leu Glu Val Lys Asn Met Asp Met Lys Pro Gly Ser
1               5                   10                  15

Thr Leu Lys Ile Thr Gly Ser Ile Ala Asp Gly Thr Asp Gly Phe Val
            20                  25                  30

Ile Asn Leu Gly Gln Gly Thr Asp Lys Leu Asn Leu His Phe Asn Pro
        35                  40                  45

Arg Phe Ser Glu Ser Thr Ile Val Cys Asn Ser Leu Asp Gly Ser Asn
    50                  55                  60

Trp Gly Gln Glu Gln Arg Glu Asp His Leu Cys Phe Ser Pro Gly Ser
65                  70                  75                  80

Glu Val Lys Phe Thr Val Thr Phe Glu Ser Asp Lys Phe Lys Val Lys
                85                  90                  95

Leu Pro Asp Gly His Glu Leu Thr Phe Pro Asn Arg Leu Gly His Ser
            100                 105                 110

His Leu Ser Tyr Leu Ser Val Arg Gly Gly Phe Asn Met Ser Ser Phe
        115                 120                 125

Lys Leu Lys Glu
    130

<210> SEQ ID NO 14
<211> LENGTH: 134
<212> TYPE: PRT
<213> ORGANISM: Homo sapiens
<220> FEATURE:
<221> NAME/KEY: MISC_FEATURE
<222> LOCATION: (1)..(134)
<223> OTHER INFORMATION: amino acid sequence of leg1

<400> SEQUENCE: 14

Ala Cys Gly Leu Val Ala Ser Asn Leu Asn Leu Lys Pro Gly Glu Cys
1               5                   10                  15
```

-continued

```
Leu Arg Val Arg Gly Glu Val Ala Pro Asp Ala Lys Ser Phe Val Leu
         20                  25                  30

Asn Leu Gly Lys Asp Ser Asn Asn Leu Cys Leu His Phe Asn Pro Arg
     35                  40                  45

Phe Asn Ala His Gly Asp Ala Asn Thr Ile Val Cys Asn Ser Lys Asp
 50                  55                  60

Gly Gly Ala Trp Gly Thr Glu Gln Arg Glu Ala Val Phe Pro Phe Gln
 65                  70                  75                  80

Pro Gly Ser Val Ala Glu Val Cys Ile Thr Phe Asp Gln Ala Asn Leu
             85                  90                  95

Thr Val Lys Leu Pro Asp Gly Tyr Glu Phe Lys Phe Pro Asn Arg Leu
            100                 105                 110

Asn Leu Glu Ala Ile Asn Tyr Met Ala Ala Asp Gly Asp Phe Lys Ile
            115                 120                 125

Lys Cys Val Ala Phe Asp
        130
```

<210> SEQ ID NO 15
<211> LENGTH: 316
<212> TYPE: PRT
<213> ORGANISM: Homo sapiens
<220> FEATURE:
<221> NAME/KEY: MISC_FEATURE
<222> LOCATION: (1)..(316)
<223> OTHER INFORMATION: amino acid sequence of PCTA

<400> SEQUENCE: 15

```
Met Leu Ser Leu Asn Asn Leu Gln Asn Ile Ile Tyr Asn Pro Val Ile
 1               5                  10                  15

Pro Tyr Val Gly Thr Ile Pro Asp Gln Leu Asp Pro Gly Thr Leu Ile
             20                  25                  30

Val Ile Cys Gly His Val Pro Ser Asp Ala Asp Arg Phe Gln Val Asp
             35                  40                  45

Leu Gln Asn Gly Ser Ser Val Lys Pro Arg Ala Asp Val Ala Phe His
 50                  55                  60

Phe Asn Pro Arg Phe Lys Arg Ala Gly Cys Ile Val Cys Asn Thr Leu
 65                  70                  75                  80

Ile Asn Glu Lys Trp Gly Arg Glu Glu Ile Thr Tyr Asp Thr Pro Phe
                 85                  90                  95

Lys Arg Glu Lys Ser Phe Glu Ile Val Ile Met Val Leu Lys Asp Lys
            100                 105                 110

Phe Gln Val Ala Val Asn Gly Lys His Thr Leu Leu Tyr Gly His Arg
            115                 120                 125

Ile Gly Pro Glu Lys Ile Asp Thr Leu Gly Ile Tyr Gly Lys Val Asn
        130                 135                 140

Ile His Ser Ile Gly Phe Ser Phe Ser Ser Asp Leu Gln Ser Thr Gln
145                 150                 155                 160

Ala Ser Ser Leu Glu Leu Thr Glu Ile Ser Arg Glu Asn Val Pro Lys
                165                 170                 175

Ser Gly Thr Pro Gln Leu Ser Leu Pro Phe Ala Ala Arg Leu Asn Thr
            180                 185                 190

Pro Met Gly Pro Gly Arg Thr Val Val Lys Gly Glu Val Asn Ala
            195                 200                 205

Asn Ala Lys Ser Phe Asn Val Asp Leu Leu Ala Gly Lys Ser Lys Asp
        210                 215                 220
```

```
Ile Ala Leu His Leu Asn Pro Arg Leu Asn Ile Lys Ala Phe Val Arg
225                 230                 235                 240

Asn Ser Phe Leu Gln Glu Ser Trp Gly Glu Glu Arg Asn Ile Thr
            245                 250                 255

Ser Phe Pro Phe Ser Pro Gly Met Tyr Phe Glu Met Ile Ile Tyr Cys
            260                 265                 270

Asp Val Arg Glu Phe Lys Val Ala Val Asn Gly Val His Ser Leu Glu
            275                 280                 285

Tyr Lys His Arg Phe Lys Glu Leu Ser Ser Ile Asp Thr Leu Glu Ile
            290                 295                 300

Asn Gly Asp Ile His Leu Leu Glu Val Arg Ser Trp
305                 310                 315

<210> SEQ ID NO 16
<211> LENGTH: 358
<212> TYPE: PRT
<213> ORGANISM: Homo sapiens
<220> FEATURE:
<221> NAME/KEY: MISC_FEATURE
<222> LOCATION: (1)..(358)
<223> OTHER INFORMATION: amino acid sequence of PCTA.var

<400> SEQUENCE: 16

Met Leu Ser Leu Asn Asn Leu Gln Asn Ile Ile Tyr Asn Pro Val Ile
1               5                   10                  15

Pro Tyr Val Gly Thr Ile Pro Asp Gln Leu Asp Pro Gly Thr Leu Ile
            20                  25                  30

Val Ile Cys Gly His Val Pro Ser Asp Ala Asp Arg Phe Gln Val Asp
            35                  40                  45

Leu Gln Asn Gly Ser Ser Val Lys Pro Arg Ala Asp Val Ala Phe His
        50                  55                  60

Phe Asn Pro Arg Phe Lys Arg Ala Gly Cys Ile Val Cys Asn Thr Leu
65                  70                  75                  80

Ile Asn Glu Lys Trp Gly Arg Glu Glu Ile Thr Tyr Asp Thr Pro Phe
                85                  90                  95

Lys Arg Glu Lys Ser Phe Glu Ile Val Ile Met Val Leu Lys Asp Lys
            100                 105                 110

Phe Gln Val Ala Val Asn Gly Lys His Thr Leu Leu Tyr Gly His Arg
        115                 120                 125

Ile Gly Pro Glu Lys Ile Asp Thr Leu Gly Ile Tyr Gly Lys Val Asn
130                 135                 140

Ile His Ser Ile Gly Phe Ser Phe Ser Ser Asp Leu Gln Ser Thr Gln
145                 150                 155                 160

Ala Ser Ser Leu Glu Leu Thr Glu Ile Ser Arg Glu Asn Val Pro Lys
                165                 170                 175

Ser Gly Thr Pro Gln Leu Pro Ser Asn Arg Gly Gly Asp Ile Ser Lys
            180                 185                 190

Ile Ala Pro Arg Thr Val Tyr Thr Lys Ser Lys Asp Ser Thr Val Asn
        195                 200                 205

His Thr Leu Thr Cys Thr Lys Ile Pro Pro Met Asn Tyr Val Ser Lys
210                 215                 220

Ser Leu Pro Phe Ala Ala Arg Leu Asn Thr Pro Met Gly Pro Gly Arg
225                 230                 235                 240

Thr Val Val Val Lys Gly Glu Val Asn Ala Asn Ala Lys Ser Phe Asn
                245                 250                 255

Val Asp Leu Leu Ala Gly Lys Ser Lys Asp Ile Ala Leu His Leu Asn
```

-continued

```
                260                 265                 270
Pro Arg Leu Asn Ile Lys Ala Phe Val Arg Asn Ser Phe Leu Gln Glu
            275                 280                 285

Ser Trp Gly Glu Glu Arg Asn Ile Thr Ser Phe Pro Phe Ser Pro
        290                 295                 300

Gly Met Tyr Phe Glu Met Ile Ile Tyr Cys Asp Val Arg Glu Phe Lys
305                 310                 315                 320

Val Ala Val Asn Gly Val His Ser Leu Glu Tyr Lys His Arg Phe Lys
                325                 330                 335

Glu Leu Ser Ser Ile Asp Thr Leu Glu Ile Asn Gly Asp Ile His Leu
            340                 345                 350

Leu Glu Val Arg Ser Trp
            355

<210> SEQ ID NO 17
<211> LENGTH: 315
<212> TYPE: PRT
<213> ORGANISM: Mus musculus
<220> FEATURE:
<221> NAME/KEY: MISC_FEATURE
<222> LOCATION: (1)..(315)
<223> OTHER INFORMATION: amino acid sequence of PCTA.mus

<400> SEQUENCE: 17

Met Leu Ser Leu Asn Asn Leu Gln Asn Ile Ile Tyr Asn Pro Ile Ile
1               5                   10                  15

Pro Tyr Val Gly Thr Ile Thr Glu Gln Leu Lys Pro Gly Ser Leu Ile
            20                  25                  30

Val Ile Arg Gly His Val Pro Lys Asp Ser Glu Arg Phe Gln Val Asp
        35                  40                  45

Phe Gln Leu Gly Asn Ser Leu Lys Pro Arg Ala Asp Val Ala Phe His
    50                  55                  60

Phe Asn Pro Arg Phe Lys Arg Ser Ser Cys Ile Val Cys Asn Thr Leu
65                  70                  75                  80

Thr Gln Glu Lys Trp Gly Trp Glu Glu Ile Thr Tyr Asp Met Pro Phe
                85                  90                  95

Arg Lys Glu Lys Ser Phe Glu Ile Val Phe Met Val Leu Lys Asn Lys
            100                 105                 110

Phe Gln Val Ala Val Asn Gly Arg His Val Leu Leu Tyr Ala His Arg
        115                 120                 125

Ile Ser Pro Glu Gln Ile Asp Thr Val Gly Ile Tyr Gly Lys Val Asn
    130                 135                 140

Ile His Ser Ile Gly Phe Arg Phe Ser Ser Asp Leu Gln Ser Met Glu
145                 150                 155                 160

Thr Ser Ala Leu Gly Leu Thr Gln Ile Asn Arg Glu Asn Ile Gln Lys
                165                 170                 175

Pro Gly Lys Leu Gln Leu Ser Leu Pro Phe Glu Ala Arg Leu Asn Ala
            180                 185                 190

Ser Met Gly Pro Gly Arg Thr Val Val Ile Lys Gly Glu Val Asn Thr
        195                 200                 205

Asn Ala Arg Ser Phe Asn Val Asp Leu Val Ala Gly Lys Thr Arg Asp
    210                 215                 220

Ile Ala Leu His Leu Asn Pro Arg Leu Asn Lys Ala Phe Val Arg Asn
225                 230                 235                 240

Ser Phe Leu Gln Asp Ala Trp Gly Glu Glu Arg Asn Ile Thr Cys
                245                 250                 255
```

-continued

```
Phe Pro Phe Ser Ser Gly Met Tyr Phe Glu Met Ile Ile Tyr Cys Asp
            260                 265                 270

Val Arg Glu Phe Lys Val Ala Ile Asn Gly Val His Ser Leu Glu Tyr
        275                 280                 285

Lys His Arg Phe Lys Asp Leu Ser Ser Ile Asp Thr Leu Ser Val Asp
    290                 295                 300

Gly Asp Ile Arg Leu Leu Asp Val Arg Ser Trp
305                 310                 315

<210> SEQ ID NO 18
<211> LENGTH: 355
<212> TYPE: PRT
<213> ORGANISM: Homo sapiens
<220> FEATURE:
<221> NAME/KEY: MISC_FEATURE
<222> LOCATION: (1)..(355)
<223> OTHER INFORMATION: amino acid sequence of gal9-1

<400> SEQUENCE: 18

Met Ala Phe Ser Gly Ser Gln Ala Pro Tyr Leu Ser Pro Ala Val Pro
1               5                   10                  15

Phe Ser Gly Thr Ile Gln Gly Gly Leu Gln Asp Gly Leu Gln Ile Thr
            20                  25                  30

Val Asn Gly Thr Val Leu Ser Ser Ser Gly Thr Arg Phe Ala Val Asn
        35                  40                  45

Phe Gln Thr Gly Phe Ser Gly Asn Asp Ile Ala Phe His Phe Asn Pro
    50                  55                  60

Arg Phe Glu Asp Gly Gly Tyr Val Val Cys Asn Thr Arg Gln Asn Gly
65                  70                  75                  80

Ser Trp Gly Pro Glu Glu Arg Lys Thr His Met Pro Phe Gln Lys Gly
                85                  90                  95

Met Pro Phe Asp Leu Cys Phe Leu Val Gln Ser Ser Asp Phe Lys Val
            100                 105                 110

Met Val Asn Gly Ile Leu Phe Val Gln Tyr Phe His Arg Val Pro Phe
        115                 120                 125

His Arg Val Asp Thr Ile Ser Val Asn Gly Ser Val Gln Leu Ser Tyr
    130                 135                 140

Ile Ser Phe Gln Asn Pro Arg Thr Val Pro Val Gln Pro Ala Phe Ser
145                 150                 155                 160

Thr Val Pro Phe Ser Gln Pro Val Cys Phe Pro Pro Arg Pro Arg Gly
                165                 170                 175

Arg Arg Gln Lys Pro Pro Gly Val Trp Pro Ala Asn Pro Ala Pro Ile
            180                 185                 190

Thr Gln Thr Val Ile His Thr Val Gln Ser Ala Pro Gly Gln Met Phe
        195                 200                 205

Ser Thr Pro Ala Ile Pro Pro Met Met Tyr Pro His Pro Ala Tyr Pro
    210                 215                 220

Met Pro Phe Ile Thr Thr Ile Leu Gly Gly Leu Tyr Pro Ser Lys Ser
225                 230                 235                 240

Ile Leu Leu Ser Gly Thr Val Leu Pro Ser Ala Gln Arg Phe His Ile
                245                 250                 255

Asn Leu Cys Ser Gly Asn His Ile Ala Phe His Leu Asn Pro Arg Phe
            260                 265                 270

Asp Glu Asn Ala Val Val Arg Asn Thr Gln Ile Asp Asn Ser Trp Gly
        275                 280                 285
```

-continued

Ser Glu Glu Arg Ser Leu Pro Arg Lys Met Pro Phe Val Arg Gly Gln
        290                 295                 300

Ser Phe Ser Val Trp Ile Leu Cys Glu Ala His Cys Leu Lys Val Ala
305                 310                 315                 320

Val Asp Gly Gln His Leu Phe Glu Tyr Tyr His Arg Leu Arg Asn Leu
                325                 330                 335

Pro Thr Ile Asn Arg Leu Glu Val Gly Gly Asp Ile Gln Leu Thr His
            340                 345                 350

Val Gln Thr
        355

<210> SEQ ID NO 19
<211> LENGTH: 323
<212> TYPE: PRT
<213> ORGANISM: Homo sapiens
<220> FEATURE:
<221> NAME/KEY: MISC_FEATURE
<222> LOCATION: (1)..(323)
<223> OTHER INFORMATION: amino acid sequence of gal

<400> SEQUENCE: 19

Met Ala Phe Ser Gly Ser Gln Ala Pro Tyr Leu Ser Pro Ala Val Pro
1               5                   10                  15

Phe Ser Gly Thr Ile Gln Gly Gly Leu Gln Asp Gly Leu Gln Ile Thr
                20                  25                  30

Val Asn Gly Thr Val Leu Ser Ser Gly Thr Arg Phe Ala Val Asn
            35                  40                  45

Phe Gln Thr Gly Phe Ser Gly Asn Asp Ile Ala Phe His Phe Asn Pro
        50                  55                  60

Arg Phe Glu Asp Gly Gly Tyr Val Val Cys Asn Thr Arg Gln Asn Gly
65                  70                  75                  80

Ser Trp Gly Pro Glu Glu Arg Arg Thr His Met Pro Phe Gln Lys Gly
                85                  90                  95

Met Pro Phe Asp Leu Cys Phe Leu Val Gln Ser Ser Asp Phe Lys Val
                100                 105                 110

Met Val Asn Gly Ile Leu Phe Val Gln Tyr Phe His Arg Val Pro Phe
            115                 120                 125

His Arg Val Asp Thr Ile Phe Val Asn Gly Ser Val Gln Leu Ser Tyr
        130                 135                 140

Ile Ser Phe Gln Pro Pro Gly Val Trp Pro Ala Asn Pro Ala Pro Ile
145                 150                 155                 160

Thr Gln Thr Val Ile His Thr Val Gln Ser Ala Pro Gly Gln Met Phe
                165                 170                 175

Ser Thr Pro Ala Ile Pro Pro Met Met Tyr Pro His Pro Ala Tyr Pro
            180                 185                 190

Met Pro Phe Ile Thr Thr Ile Leu Gly Gly Leu Tyr Pro Ser Lys Ser
        195                 200                 205

Ile Leu Leu Ser Gly Thr Val Leu Pro Ser Ala Gln Arg Phe His Ile
210                 215                 220

Asn Leu Cys Ser Gly Asn His Ile Ala Phe His Leu Asn Leu Arg Phe
225                 230                 235                 240

Asp Glu Asn Ala Val Val Arg Asn Thr Gln Ile Asp Asn Ser Trp Gly
                245                 250                 255

Ser Glu Glu Arg Ser Leu Pro Arg Lys Met Pro Phe Val Arg Gly Gln
            260                 265                 270

Ser Phe Ser Val Trp Ile Leu Cys Gly Ala His Cys Leu Lys Val Ala

```
                275                 280                 285
Val Asp Gly Gln His Leu Phe Glu Tyr Tyr His Arg Leu Arg Asn Leu
    290                 295                 300
Pro Thr Ile Asn Arg Leu Glu Val Gly Gly Asp Ile Gln Leu Thr His
305                 310                 315                 320
Val Gln Thr

<210> SEQ ID NO 20
<211> LENGTH: 135
<212> TYPE: PRT
<213> ORGANISM: Homo sapiens
<220> FEATURE:
<221> NAME/KEY: MISC_FEATURE
<222> LOCATION: (1)..(135)
<223> OTHER INFORMATION: amino acid sequence of leg7

<400> SEQUENCE: 20

Ser Asn Val Pro His Lys Ser Ser Leu Pro Glu Gly Ile Arg Pro Gly
1               5                   10                  15

Thr Val Leu Arg Ile Arg Gly Leu Val Pro Pro Asn Ala Ser Arg Phe
            20                  25                  30

His Val Asn Leu Leu Cys Gly Glu Glu Gln Gly Ser Asp Ala Ala Leu
        35                  40                  45

His Phe Asn Pro Arg Leu Asp Thr Ser Glu Val Val Phe Asn Ser Lys
    50                  55                  60

Glu Gln Gly Ser Trp Gly Arg Glu Glu Arg Gly Pro Gly Val Pro Phe
65                  70                  75                  80

Gln Arg Gly Gln Pro Phe Glu Val Leu Ile Ile Ala Ser Asp Asp Gly
                85                  90                  95

Phe Lys Ala Val Val Gly Asp Ala Gln Tyr His His Phe Arg His Arg
            100                 105                 110

Leu Pro Leu Ala Arg Val Arg Leu Val Glu Val Gly Gly Asp Val Gln
        115                 120                 125

Leu Asp Ser Val Arg Ile Phe
    130                 135

<210> SEQ ID NO 21
<211> LENGTH: 323
<212> TYPE: PRT
<213> ORGANISM: Homo sapiens
<220> FEATURE:
<221> NAME/KEY: MISC_FEATURE
<222> LOCATION: (1)..(323)
<223> OTHER INFORMATION: amino acid sequence of gal4

<400> SEQUENCE: 21

Met Ala Tyr Val Pro Ala Pro Gly Tyr Gln Pro Thr Tyr Asn Pro Thr
1               5                   10                  15

Leu Pro Tyr Tyr Gln Pro Ile Pro Gly Gly Leu Asn Val Gly Met Ser
            20                  25                  30

Val Tyr Ile Gln Gly Val Ala Ser Glu His Met Lys Arg Phe Phe Val
        35                  40                  45

Asn Phe Val Val Gly Gln Asp Pro Gly Ser Asp Val Ala Phe His Phe
    50                  55                  60

Asn Pro Arg Phe Asp Gly Trp Asp Lys Val Val Phe Asn Thr Leu Gln
65                  70                  75                  80

Gly Gly Lys Trp Gly Ser Glu Glu Arg Lys Arg Ser Met Pro Phe Lys
                85                  90                  95
```

```
Lys Gly Ala Ala Phe Glu Leu Val Phe Ile Val Leu Ala Glu His Tyr
                100                 105                 110

Lys Val Val Asn Gly Asn Pro Phe Tyr Glu Tyr Gly His Arg Leu
            115                 120                 125

Pro Leu Gln Met Val Thr His Leu Gln Val Asp Gly Asp Leu Gln Leu
    130                 135                 140

Gln Ser Ile Asn Phe Ile Gly Gly Pro Leu Arg Pro Gln Gly Pro
145                 150                 155                 160

Pro Met Met Pro Pro Tyr Pro Gly Pro Gly His Cys His Gln Gln Leu
                165                 170                 175

Asn Ser Leu Pro Thr Met Glu Gly Pro Pro Thr Phe Asn Pro Pro Val
            180                 185                 190

Pro Tyr Phe Gly Arg Leu Gln Gly Gly Leu Thr Ala Arg Arg Thr Ile
    195                 200                 205

Ile Ile Lys Gly Tyr Val Pro Pro Thr Gly Lys Ser Phe Ala Ile Asn
210                 215                 220

Phe Lys Val Gly Ser Ser Gly Asp Ile Ala Leu His Ile Asn Pro Arg
225                 230                 235                 240

Met Gly Asn Gly Thr Val Val Arg Asn Ser Leu Leu Asn Gly Ser Trp
                245                 250                 255

Gly Ser Glu Glu Lys Lys Ile Thr His Asn Pro Phe Gly Pro Gly Gln
                260                 265                 270

Phe Phe Asp Leu Ser Ile Arg Cys Gly Leu Asp Arg Phe Lys Val Tyr
            275                 280                 285

Ala Asn Gly Gln His Leu Phe Asp Phe Ala His Arg Leu Ser Ala Phe
    290                 295                 300

Gln Arg Val Asp Thr Leu Glu Ile Gln Gly Asp Val Thr Leu Ser Tyr
305                 310                 315                 320

Val Gln Ile

<210> SEQ ID NO 22
<211> LENGTH: 466
<212> TYPE: PRT
<213> ORGANISM: Artificial Sequence
<220> FEATURE:
<223> OTHER INFORMATION: conserved sequence among SEQ ID NOs. 13-21
<220> FEATURE:
<221> NAME/KEY: MISC_FEATURE
<222> LOCATION: (1)..(113)
<223> OTHER INFORMATION: Xaa = no concensus amino acid found among
      sequences
<220> FEATURE:
<221> NAME/KEY: MISC_FEATURE
<222> LOCATION: (115)..(116)
<223> OTHER INFORMATION: Xaa = no concensus amino acid found among
      sequences
<220> FEATURE:
<221> NAME/KEY: MISC_FEATURE
<222> LOCATION: (118)..(121)
<223> OTHER INFORMATION: Xaa = no concensus amino acid found among
      sequences
<220> FEATURE:
<221> NAME/KEY: MISC_FEATURE
<222> LOCATION: (124)..(124)
<223> OTHER INFORMATION: Xaa = no concensus amino acid found among
      sequences
<220> FEATURE:
<221> NAME/KEY: MISC_FEATURE
<222> LOCATION: (127)..(127)
<223> OTHER INFORMATION: Xaa = no concensus amino acid found among
      sequences
<220> FEATURE:
<221> NAME/KEY: MISC_FEATURE
<222> LOCATION: (130)..(133)
```

```
<223> OTHER INFORMATION: Xaa = no concensus amino acid found among
      sequences
<220> FEATURE:
<221> NAME/KEY: MISC_FEATURE
<222> LOCATION: (135)..(135)
<223> OTHER INFORMATION: Xaa = no concensus amino acid found among
      sequences
<220> FEATURE:
<221> NAME/KEY: MISC_FEATURE
<222> LOCATION: (137)..(137)
<223> OTHER INFORMATION: Xaa = no concensus amino acid found among
      sequences
<220> FEATURE:
<221> NAME/KEY: MISC_FEATURE
<222> LOCATION: (139)..(139)
<223> OTHER INFORMATION: Xaa = no concensus amino acid found among
      sequences
<220> FEATURE:
<221> NAME/KEY: MISC_FEATURE
<222> LOCATION: (141)..(142)
<223> OTHER INFORMATION: Xaa = no concensus amino acid found among
      sequences
<220> FEATURE:
<221> NAME/KEY: MISC_FEATURE
<222> LOCATION: (144)..(144)
<223> OTHER INFORMATION: Xaa = no concensus amino acid found among
      sequences
<220> FEATURE:
<221> NAME/KEY: MISC_FEATURE
<222> LOCATION: (147)..(147)
<223> OTHER INFORMATION: Xaa = no concensus amino acid found among
      sequences
<220> FEATURE:
<221> NAME/KEY: MISC_FEATURE
<222> LOCATION: (151)..(152)
<223> OTHER INFORMATION: Xaa = no concensus amino acid found among
      sequences
<220> FEATURE:
<221> NAME/KEY: MISC_FEATURE
<222> LOCATION: (154)..(158)
<223> OTHER INFORMATION: Xaa = no concensus amino acid found among
      sequences
<220> FEATURE:
<221> NAME/KEY: MISC_FEATURE
<222> LOCATION: (160)..(160)
<223> OTHER INFORMATION: Xaa = no concensus amino acid found among
      sequences
<220> FEATURE:
<221> NAME/KEY: MISC_FEATURE
<222> LOCATION: (162)..(162)
<223> OTHER INFORMATION: Xaa = no concensus amino acid found among
      sequences
<220> FEATURE:
<221> NAME/KEY: MISC_FEATURE
<222> LOCATION: (171)..(178)
<223> OTHER INFORMATION: Xaa = no concensus amino acid found among
      sequences
<220> FEATURE:
<221> NAME/KEY: MISC_FEATURE
<222> LOCATION: (184)..(186)
<223> OTHER INFORMATION: Xaa = no concensus amino acid found among
      sequences
<220> FEATURE:
<221> NAME/KEY: MISC_FEATURE
<222> LOCATION: (188)..(188)
<223> OTHER INFORMATION: Xaa = no concensus amino acid found among
      sequences
<220> FEATURE:
<221> NAME/KEY: MISC_FEATURE
<222> LOCATION: (191)..(191)
<223> OTHER INFORMATION: Xaa = no concensus amino acid found among
      sequences
<220> FEATURE:
<221> NAME/KEY: MISC_FEATURE
<222> LOCATION: (195)..(198)
<223> OTHER INFORMATION: Xaa = no concensus amino acid found among
      sequences
<220> FEATURE:
<221> NAME/KEY: MISC_FEATURE
```

```
<222> LOCATION: (201)..(202)
<223> OTHER INFORMATION: Xaa = no concensus amino acid found among
      sequences
<220> FEATURE:
<221> NAME/KEY: MISC_FEATURE
<222> LOCATION: (204)..(205)
<223> OTHER INFORMATION: Xaa = no concensus amino acid found among
      sequences
<220> FEATURE:
<221> NAME/KEY: MISC_FEATURE
<222> LOCATION: (208)..(211)
<223> OTHER INFORMATION: Xaa = no concensus amino acid found among
      sequences
<220> FEATURE:
<221> NAME/KEY: MISC_FEATURE
<222> LOCATION: (213)..(214)
<223> OTHER INFORMATION: Xaa = no concensus amino acid found among
      sequences
<220> FEATURE:
<221> NAME/KEY: MISC_FEATURE
<222> LOCATION: (216)..(216)
<223> OTHER INFORMATION: Xaa = no concensus amino acid found among
      sequences
<220> FEATURE:
<221> NAME/KEY: MISC_FEATURE
<222> LOCATION: (220)..(220)
<223> OTHER INFORMATION: Xaa = no concensus amino acid found among
      sequences
<220> FEATURE:
<221> NAME/KEY: MISC_FEATURE
<222> LOCATION: (224)..(228)
<223> OTHER INFORMATION: Xaa = no concensus amino acid found among
      sequences
<220> FEATURE:
<221> NAME/KEY: MISC_FEATURE
<222> LOCATION: (230)..(230)
<223> OTHER INFORMATION: Xaa = no concensus amino acid found among
      sequences
<220> FEATURE:
<221> NAME/KEY: MISC_FEATURE
<222> LOCATION: (234)..(234)
<223> OTHER INFORMATION: Xaa = no concensus amino acid found among
      sequences
<220> FEATURE:
<221> NAME/KEY: MISC_FEATURE
<222> LOCATION: (237)..(238)
<223> OTHER INFORMATION: Xaa = no concensus amino acid found among
      sequences
<220> FEATURE:
<221> NAME/KEY: MISC_FEATURE
<222> LOCATION: (240)..(243)
<223> OTHER INFORMATION: Xaa = no concensus amino acid found among
      sequences
<220> FEATURE:
<221> NAME/KEY: MISC_FEATURE
<222> LOCATION: (245)..(245)
<223> OTHER INFORMATION: Xaa = no concensus amino acid found among
      sequences
<220> FEATURE:
<221> NAME/KEY: MISC_FEATURE
<222> LOCATION: (251)..(251)
<223> OTHER INFORMATION: Xaa = no concensus amino acid found among
      sequences
<220> FEATURE:
<221> NAME/KEY: MISC_FEATURE
<222> LOCATION: (254)..(254)
<223> OTHER INFORMATION: Xaa = no concensus amino acid found among
      sequences
<220> FEATURE:
<221> NAME/KEY: MISC_FEATURE
<222> LOCATION: (256)..(333)
<223> OTHER INFORMATION: Xaa = no concensus amino acid found among
      sequences
<220> FEATURE:
<221> NAME/KEY: MISC_FEATURE
<222> LOCATION: (335)..(352)
<223> OTHER INFORMATION: Xaa = no concensus amino acid found among
      sequences
<220> FEATURE:
```

```
<221> NAME/KEY: MISC_FEATURE
<222> LOCATION: (354)..(354)
<223> OTHER INFORMATION: Xaa = no concensus amino acid found among
      sequences
<220> FEATURE:
<221> NAME/KEY: MISC_FEATURE
<222> LOCATION: (356)..(361)
<223> OTHER INFORMATION: Xaa = no concensus amino acid found among
      sequences
<220> FEATURE:
<221> NAME/KEY: MISC_FEATURE
<222> LOCATION: (363)..(373)
<223> OTHER INFORMATION: Xaa = no concensus amino acid found among
      sequences
<220> FEATURE:
<221> NAME/KEY: MISC_FEATURE
<222> LOCATION: (376)..(376)
<223> OTHER INFORMATION: Xaa = no concensus amino acid found among
      sequences
<220> FEATURE:
<221> NAME/KEY: MISC_FEATURE
<222> LOCATION: (378)..(378)
<223> OTHER INFORMATION: Xaa = no concensus amino acid found among
      sequences
<220> FEATURE:
<221> NAME/KEY: MISC_FEATURE
<222> LOCATION: (380)..(380)
<223> OTHER INFORMATION: Xaa = no concensus amino acid found among
      sequences
<220> FEATURE:
<221> NAME/KEY: MISC_FEATURE
<222> LOCATION: (382)..(387)
<223> OTHER INFORMATION: Xaa = no concensus amino acid found among
      sequences
<220> FEATURE:
<221> NAME/KEY: MISC_FEATURE
<222> LOCATION: (391)..(396)
<223> OTHER INFORMATION: Xaa = no concensus amino acid found among
      sequences
<220> FEATURE:
<221> NAME/KEY: MISC_FEATURE
<222> LOCATION: (399)..(399)
<223> OTHER INFORMATION: Xaa = no concensus amino acid found among
      sequences
<220> FEATURE:
<221> NAME/KEY: MISC_FEATURE
<222> LOCATION: (402)..(408)
<223> OTHER INFORMATION: Xaa = no concensus amino acid found among
      sequences
<220> FEATURE:
<221> NAME/KEY: MISC_FEATURE
<222> LOCATION: (411)..(412)
<223> OTHER INFORMATION: Xaa = no concensus amino acid found among
      sequences
<220> FEATURE:
<221> NAME/KEY: MISC_FEATURE
<222> LOCATION: (414)..(415)
<223> OTHER INFORMATION: Xaa = no concensus amino acid found among
      sequences
<220> FEATURE:
<221> NAME/KEY: MISC_FEATURE
<222> LOCATION: (417)..(419)
<223> OTHER INFORMATION: Xaa = no concensus amino acid found among
      sequences
<220> FEATURE:
<221> NAME/KEY: MISC_FEATURE
<222> LOCATION: (421)..(421)
<223> OTHER INFORMATION: Xaa = no concensus amino acid found among
      sequences
<220> FEATURE:
<221> NAME/KEY: MISC_FEATURE
<222> LOCATION: (423)..(427)
<223> OTHER INFORMATION: Xaa = no concensus amino acid found among
      sequences
<220> FEATURE:
<221> NAME/KEY: MISC_FEATURE
<222> LOCATION: (430)..(432)
<223> OTHER INFORMATION: Xaa = no concensus amino acid found among
      sequences
```

-continued

```
<220> FEATURE:
<221> NAME/KEY: MISC_FEATURE
<222> LOCATION: (434)..(434)
<223> OTHER INFORMATION: Xaa = no concensus amino acid found among
      sequences
<220> FEATURE:
<221> NAME/KEY: MISC_FEATURE
<222> LOCATION: (436)..(440)
<223> OTHER INFORMATION: Xaa = no concensus amino acid found among
      sequences
<220> FEATURE:
<221> NAME/KEY: MISC_FEATURE
<222> LOCATION: (443)..(451)
<223> OTHER INFORMATION: Xaa = no concensus amino acid found among
      sequences
<220> FEATURE:
<221> NAME/KEY: MISC_FEATURE
<222> LOCATION: (453)..(455)
<223> OTHER INFORMATION: Xaa = no concensus amino acid found among
      sequences
<220> FEATURE:
<221> NAME/KEY: MISC_FEATURE
<222> LOCATION: (458)..(459)
<223> OTHER INFORMATION: Xaa = no concensus amino acid found among
      sequences
<220> FEATURE:
<221> NAME/KEY: MISC_FEATURE
<222> LOCATION: (461)..(462)
<223> OTHER INFORMATION: Xaa = no concensus amino acid found among
      sequences
<220> FEATURE:
<221> NAME/KEY: MISC_FEATURE
<222> LOCATION: (464)..(466)
<223> OTHER INFORMATION: Xaa = no concensus amino acid found among
      sequences

<400> SEQUENCE: 22

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa Xaa Xaa Xaa Xaa Xaa Xaa Xaa Xaa
                85                  90                  95

Xaa Xaa Xaa Xaa Xaa Xaa Xaa Xaa Xaa Xaa Xaa Xaa Xaa Xaa Xaa Xaa
            100                 105                 110

Xaa Pro Xaa Xaa Pro Xaa Xaa Xaa Xaa Ile Pro Xaa Gly Leu Xaa Pro
        115                 120                 125

Gly Xaa Xaa Xaa Xaa Ile Xaa Gly Xaa Val Xaa Pro Xaa Xaa Ala Xaa
    130                 135                 140

Arg Phe Xaa Val Asn Leu Xaa Xaa Gly Xaa Xaa Xaa Xaa Xaa Gly Xaa
145                 150                 155                 160

Asp Xaa Ala Phe His Phe Asn Pro Arg Phe Xaa Xaa Xaa Xaa Xaa Xaa
                165                 170                 175

Xaa Xaa Val Val Cys Asn Thr Xaa Xaa Xaa Gly Xaa Trp Gly Xaa Glu
            180                 185                 190

Glu Arg Xaa Xaa Xaa Xaa Pro Phe Xaa Xaa Gly Xaa Xaa Phe Glu Xaa
        195                 200                 205

Xaa Xaa Xaa Val Xaa Xaa Asp Xaa Phe Lys Val Xaa Val Asn Gly Xaa
    210                 215                 220
```

```
Xaa Xaa Xaa Xaa Tyr Xaa His Arg Leu Xaa Pro Leu Xaa Xaa Val Xaa
225                 230             235              240

Xaa Xaa Xaa Val Xaa Gly Asp Val Gln Leu Xaa Ser Ile Xaa Phe Xaa
            245             250              255

Xaa Xaa Xaa Xaa Xaa Xaa Xaa Xaa Xaa Xaa Xaa Xaa Xaa Xaa Xaa Xaa
            260             265             270

Xaa Xaa Xaa Xaa Xaa Xaa Xaa Xaa Xaa Xaa Xaa Xaa Xaa Xaa Xaa Xaa
        275             280             285

Xaa Xaa Xaa Xaa Xaa Xaa Xaa Xaa Xaa Xaa Xaa Xaa Xaa Xaa Xaa Xaa
    290             295             300

Xaa Xaa Xaa Xaa Xaa Xaa Xaa Xaa Xaa Xaa Xaa Xaa Xaa Xaa Xaa Xaa
305             310             315                 320

Xaa Xaa Xaa Xaa Xaa Xaa Xaa Xaa Xaa Xaa Xaa Xaa Pro Xaa Xaa
                325             330             335

Xaa Xaa Xaa Xaa Xaa Xaa Xaa Xaa Xaa Xaa Xaa Xaa Xaa Xaa Xaa
            340             345             350

Gly Xaa Val Xaa Xaa Xaa Xaa Xaa Xaa Phe Xaa Xaa Xaa Xaa Xaa Xaa
        355             360             365

Xaa Xaa Xaa Xaa Xaa Ile Ala Xaa His Xaa Asn Xaa Arg Xaa Xaa Xaa
    370             375             380

Xaa Xaa Xaa Val Arg Asn Xaa Xaa Xaa Xaa Xaa Trp Gly Xaa Glu
385             390             395                 400

Glu Xaa Xaa Xaa Xaa Xaa Xaa Xaa Pro Phe Xaa Xaa Gly Xaa Xaa Phe
            405             410             415

Xaa Xaa Xaa Ile Xaa Cys Xaa Xaa Xaa Xaa Xaa Lys Val Xaa Xaa Xaa
            420             425             430

Gly Xaa His Xaa Xaa Xaa Xaa Xaa His Arg Xaa Xaa Xaa Xaa Xaa Xaa
        435             440             445

Xaa Xaa Xaa Leu Xaa Xaa Xaa Gly Asp Xaa Xaa Leu Xaa Xaa Val Xaa
    450             455             460

Xaa Xaa
465
```

POLYMORPHIC MARKERS OF PROSTATE CARCINOMA TUMOR ANTIGEN -1(PCTA-1)

RELATED APPLICATIONS

This application is a divisional of U.S. application Ser. No. 09/326,402, filed Jun. 4, 1999, now U.S. Pat. No. 6,759,192, which claims priority to U.S. Provisional Patent Application Ser. No. 60/088,187, filed Jun. 5, 1998, abandoned, and U.S. Provisional Patent Application Ser. No. 60/102,324, filed Sep. 28, 1998, abandoned, the disclosures of which are incorporated herein by reference in their entireties.

The Sequence Listing for this application is on duplicate compact discs labeled "Copy 1" and "Copy 2." Copy 1 and Copy 2 each contain only one file named "GEN-T112XCD1-seqlist.txt" which was created on Apr. 7, 2004, and is 444 KB. The entire contents of each of the computer discs are incorporated herein by reference in their entireties.

FIELD OF THE INVENTION

The invention concerns the genomic and cDNA sequences of the PCTA-1 gene, biallelic markers of the PCTA-1 gene and the association established between these markers and prostate cancer. The invention provides means to determine the predisposition of individuals to prostate cancer as well as means for the diagnosis of this cancer and for the prognosis/detection of an eventual treatment response to therapeutic agents acting against prostate cancer.

BACKGROUND OF THE INVENTION

Prostate Cancer

The incidence of prostate cancer has dramatically increased over the last decades. It averages 30-50/100,000 males in Western European countries as well as within the US White male population. In these countries, it has recently become the most commonly diagnosed malignancy, being one of every four cancers diagnosed in American males. Prostate cancer's incidence is very much population specific, since it varies from 2/100,000 in China, to over 80/100,000 among African-American males.

In France, the incidence of prostate cancer is 35/100,000 males and it is increasing by 10/100,000 per decade. Mortality due to prostate cancer is also growing accordingly. It is the second cause of cancer death among French males, and the first one among French males aged over 70. This makes prostate cancer a serious burden in terms of public health.

Prostate cancer is a latent disease. Many men carry prostate cancer cells without overt signs of disease. Autopsies of individuals dying of other causes show prostate cancer cells in 30% of men at age 50 and in 60% of men at age 80. Furthermore, prostate cancer can take up to 10 years to kill a patient after the initial diagnosis.

The progression of the disease usually goes from a well-defined mass within the prostate to a breakdown and invasion of the lateral margins of the prostate, followed by metastasis to regional lymph nodes, and metastasis to the bone marrow. Cancer metastasis to bone is common and often associated with uncontrollable pain.

Unfortunately, in 80% of cases, diagnosis of prostate cancer is established when the disease has already metastasized to the bones. Of special interest is the observation that prostate cancers frequently grow more rapidly in sites of metastasis than within the prostate itself.

Early-stage diagnosis of prostate cancer mainly relies today on Prostate Specific Antigen (PSA) dosage, and allows the detection of prostate cancer seven years before clinical symptoms become apparent. The effectiveness of PSA dosage diagnosis is however limited, due to its inability to discriminate between malignant and non-malignant affections of the organ and because not all prostate cancers give rise to an elevated serum PSA concentration. Furthermore, PSA dosage and other currently available approaches such as physical examination, tissue biopsy and bone scans are of limited value in predicting disease progression.

Therefore, there is a strong need for a reliable diagnostic procedure which would enable a more systematic early-stage prostate cancer prognosis.

Although an early-stage prostate cancer prognosis is important, the possibility of measuring the period of time during which treatment can be deferred is also interesting as currently available medicaments are expensive and generate important adverse effects. However, the aggressiveness of prostate tumors varies widely. Some tumors are relatively aggressive, doubling every six months whereas others are slow-growing, doubling once every five years. In fact, the majority of prostate cancers grow relatively slowly and never becomes clinically manifest. Very often, affected patients are among the elderly and die from another disease before prostate cancer actually develops. Thus, a significant question in treating prostate carcinoma is how to discriminate between tumors that will progress and those that will not progress during the expected lifetime of the patient.

Hence, there is also a strong need for detection means which may be used to evaluate the aggressiveness or the development potential of prostate cancer tumors once diagnosed.

Furthermore, at the present time, there is no means to predict prostate cancer susceptibility. It would also be very beneficial to detect individual susceptibility to prostate cancer. This could allow preventive treatment and a careful follow up of the development of the tumor.

A further consequence of the slow growth rate of prostate cancer is that few cancer cells are actively dividing at any one time, rendering prostate cancer generally resistant to radiation and chemotherapy. Surgery is the mainstay of treatment but it is largely ineffective and removes the ejaculatory ducts, resulting in impotence. Oral oestrogens and luteinizing releasing hormone analogs are also used for treatment of prostate cancer. These hormonal treatments provide marked improvement for many patients, but they only provide temporary relief. Indeed, most of these cancers soon relapse with the development of hormone-resistant tumor cells and the oestrogen treatment can lead to serious cardiovascular complications. Consequently, there is a strong need for preventive and curative treatment of prostate cancer.

Efficacy/tolerance prognosis could be precious in prostate cancer therapy. Indeed, hormonal therapy, the main treatment currently available, presents important side effects. The use of chemotherapy is limited because of the small number of patients with chemosensitive tumors. Furthermore the age profile of the prostate cancer patient and intolerance to chemotherapy make the systematic use of this treatment very difficult.

Therefore, a valuable assessment of the eventual efficacy of a medicament to be administered to a prostate cancer patient as well as the patient's eventual tolerance to it may allow the benefit/risk ratio of prostate cancer treatment to be enhanced.

Prostate Carcinoma Tumor Antigen—1 (PCTA-1)

WO 96/21671 describes a new protein, named PCTA-1. The document describes the cloning and sequencing of a cDNA encoding PCTA-1 (GenBank L78132). This cDNA has 3.85 kb in length and presents about 80% sequence homology with rat galectin-8.

WO 96/21671 mentions that the PCTA-1 protein retains a number of conserved structural motifs that are found in most members of the galectin gene family. On the basis of its predicted amino acid sequence, PCTA-1 is said to appear to be a human homologue of rat galectin-8. The galectins display wide tissue distribution, clear developmental regulation, and differential levels in specific tissues, supporting the hypothesis that they contribute to many physiologically important processes in mammalian cells. Of direct relevance to cancer is the finding that the galectins can mediate both cell-cell and cell-matrix interactions.

SUMMARY OF THE INVENTION

The inventors have characterized the genomic sequence of the PCTA-1 gene, including its regulatory regions, and, through an association study, have shown that alleles of some biallelic markers of PCTA-1 are associated with prostate cancer.

Therefore, the present invention concerns the identification and characterization of the genomic sequence of the PCTA-1 gene, of new cDNA sequences and the proteins encoded by these cDNAs. The invention also concerns biallelic markers located in such sequences, as well as the selection of significant polymorphisms associated with prostate cancer.

Oligonucleotide probes and primers hybridizing specifically with a genomic sequence of PCTA-1 are also part of the invention. A further object of the invention consists of recombinant vectors comprising any of the nucleic acid sequences described in the present invention, and in particular of recombinant vectors comprising the regulatory region of PCTA-1 or a sequence encoding a PCTA-1 protein, as well as cell hosts comprising said nucleic acid sequences or recombinant vectors.

The selected polymorphisms are used in the design of assays for the reliable detection of genetic susceptibility to prostate cancer, of an early onset of prostate cancer, of the aggressiveness of prostate cancer tumors, of a modified or forthcoming expression of the PCTA-1 gene, of a modified or forthcoming production of the PCTA-1 protein, or of the production of a modified PCTA-1 protein. They can be used for diagnosis, staging, prognosis, and monitoring of such a disease, which processes can be further included within treatment approaches. The selected polymorphisms can also be used in the design of drug screening protocols to provide an accurate and efficient evaluation of the therapeutic and side-effect potential of new or already existing medicaments.

The invention also encompasses methods of screening of molecules which modulate or inhibit the expression of the PCTA-1 gene and more preferably of agent acting against prostate cancer.

BRIEF DESCRIPTION OF THE DRAWINGS

FIGS. 7A-D is an alignment of the mouse and human PCTA-1 proteins. The amino acid sequences provided in the alignment are presented as SEQ ID NO: 13 (leg2), SEQ ID NO: 14 (leg1), SEQ ID NO: 15 (PCTA), SEQ ID NO: 16 (PCTA.var), SEQ ID NO: 17 (PCTA.mus), SEQ ID NO: 18 (gal9-1), SEQ ID NO: 19 (gal), 20 (leg7), SEQ ID NO: 21 (gal4), and SEQ ID NO: 22 (consensus sequence).

BRIEF DESCRIPTION OF THE SEQUENCES PROVIDED IN THE SEQUENCE LISTING

Figure 1A:
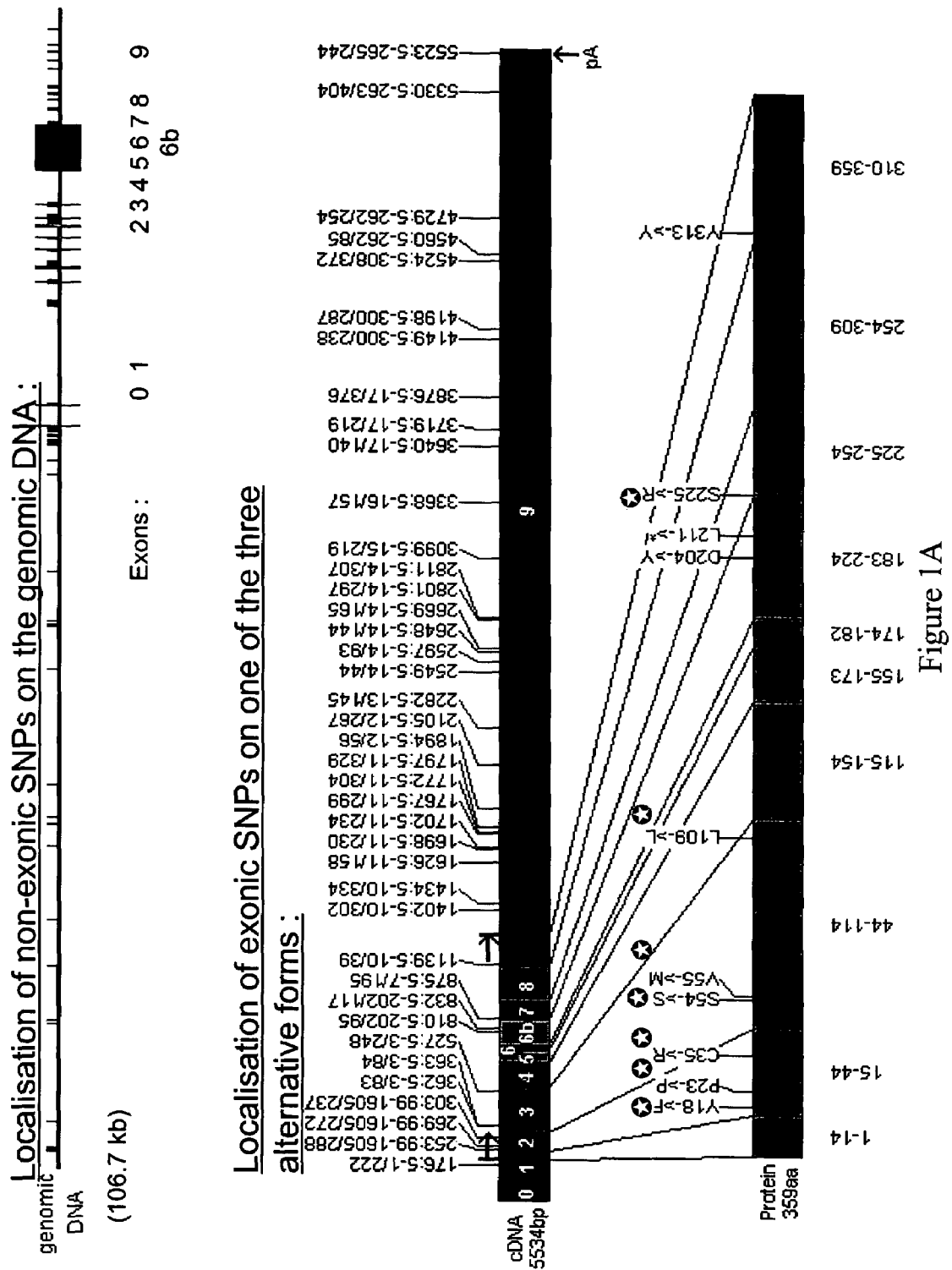
FIG. 1A is a diagram of the PCTA-1 gene with an indication of the relative position of the biallelic markers of the present invention. The upper line refers to the genomic sequence of PCTA-1. The middle line refers to the alternative cDNA comprising the exon 6bis with the biallelic markers localization. The lower line refers the PCTA-1 protein with the polymorphic amino acids due to the biallelic markers. refers to frequent SNP (detected on pool of hundred DNA).
Figure 1B:
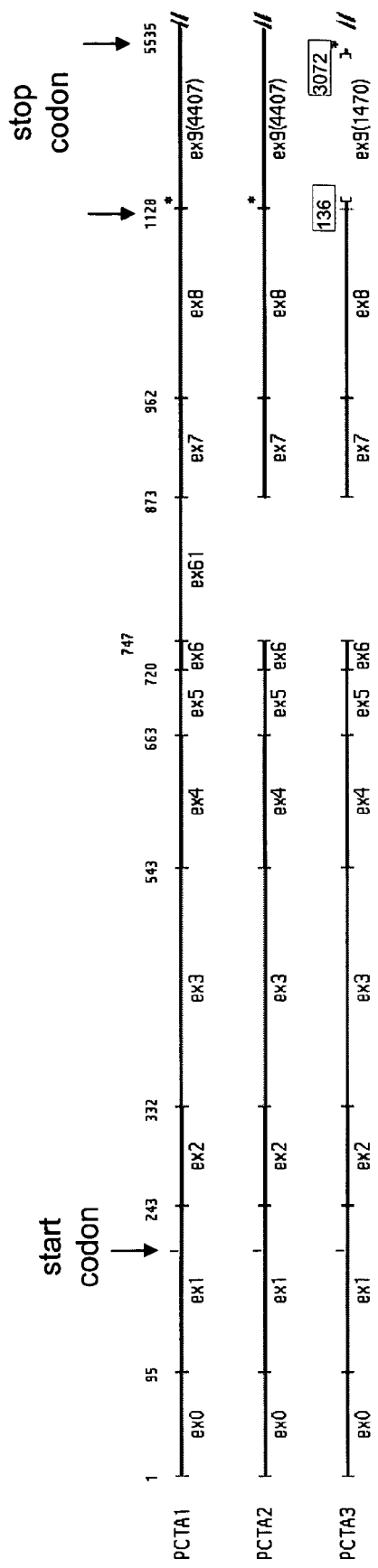
FIG. 1B is a diagram of the 3 alternative cDNAs of PCTA-1.
Figure 2:
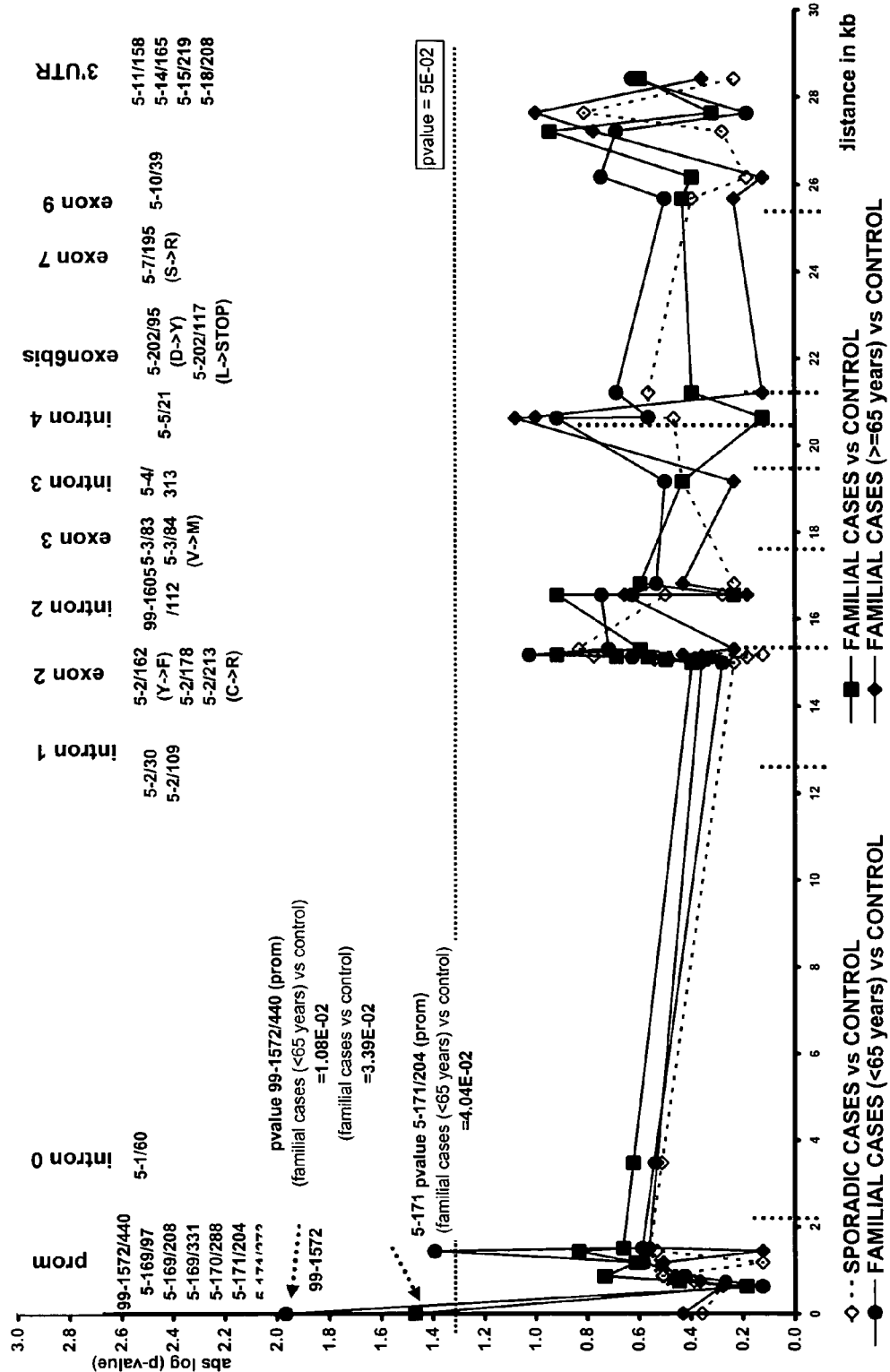
FIG. 2 is a graph demonstrating the association between some of the biallelic markers of the invention and prostate cancer with the absolute value of the logarithm (base 10) of the p-value of the chi-square values for each marker shown on the y-axis and a rough estimate of the position of each marker with respect to the PCTA-1 gene elements on the x-axis.

SEQ ID No 1 contains a genomic sequence of PCTA-1 comprising the 5' regulatory region (upstream untranscribed region), the exons (0, 1, 2, 3, 4, 5, 6, 6bis, 7, 8, 9, 9bis, and 9ter) and introns, and the 3' regulatory region (downstream untranscribed region).

SEQ ID No 2 contains a cDNA sequence of PCTA-1 comprising the exons 0, 1, 2, 3, 4, 5, 6, 7, 8, and 9.

SEQ ID No 3 contains a cDNA sequence of PCTA-1 comprising the exons 0, 1, 2, 3, 4, 5, 6, 6bis, 7, 8, and 9.

SEQ ID No 4 contains a cDNA sequence of PCTA-1 comprising the exons 0, 1, 2, 3, 4, 5, 6, 7, 8, 9bis and 9ter.

SEQ ID No 5 contains the amino acid sequence encoded by the cDNA of SEQ ID No 2.

SEQ ID No 6 contains the amino acid sequence encoded by the cDNA of SEQ ID No 3.

SEQ ID No 7 contains the amino acid sequence encoded by the cDNA of SEQ ID No 4.

SEQ ID No 8 contains a murine cDNA sequence of PCTA-1.

SEQ ID No 9 contains the amino acid sequence encoded by the cDNA of SEQ ID No 8.

SEQ ID No 10 contains a primer containing the additional PU 5' sequence described further in Example 2.

SEQ ID No 11 contains a primer containing the additional RP 5' sequence described further in Example 2.

SEQ ID No 12 is a version of the polynucleotide sequence of the PCTA-1 gene of SEQ ID NO: 1 that provides symbols appropriate for indicated allelic substitutions at nucleotide positions 402, 67092, 68525, 82234, and 82393.

DETAILED DESCRIPTION OF THE INVENTION

Definitions

Before describing the invention in greater detail, the following definitions are set forth to illustrate and define the meaning and scope of the terms used to describe the invention herein.

The term "PCTA-1 gene" is intended to define an entity which can comprise some or all the following elements: exons, introns, promoter, regulatory regions, 5'UTR, 3' UTR and regions never transcribed and located either upstream or downstream of the coding sequence of PCTA-1. The term "PCTA-1 gene", when used herein, encompasses genomic, mRNA and cDNA sequences encoding a PCTA-1 protein.

The term "heterologous protein", when used herein, is intended to designate any protein or polypeptide other than the PCTA-1 protein. More particularly, the heterologous protein is a compound which can be used as a marker in further experiments with a PCTA-1 regulatory region or as a toxin to certain cells in which it is intended to be produced, preferably a toxin to prostate cancer cells.

As used herein, the term "toxin gene" refers to a polynucleotide sequence which encodes a polypeptide that, when expressed in a eukaryotic cell, typically a mammalian cell, kills or disables the cell or causes the cell to exhibit apoptosis, cytostasis or senescence.

The term "isolated" requires that the material be removed from its original environment (e.g., the natural environment if it is naturally occurring). For example, a naturally-occurring polynucleotide or polypeptide present in a living animal is not isolated, but the same polynucleotide or DNA or polypeptide, separated from some or all of the coexisting materials in the natural system, is isolated. Such polynucleotide could be part of a vector and/or such polynucleotide or polypeptide could be part of a composition, and still be isolated in that the vector or composition is not part of its natural environment.

The term "purified" does not require absolute purity; rather, it is intended as a relative definition. Purification of starting material or natural material to at least one order of magnitude, preferably two or three orders, and more preferably four or five orders of magnitude is expressly contemplated. As an example, purification from 0.1% concentration to 10% concentration is two orders of magnitude. The term "purified" is used herein to describe a polynucleotide or polynucleotide vector of the invention which has been separated from other compounds including, but not limited to other nucleic acids, carbohydrates, lipids and proteins (such as the enzymes used in the synthesis of the polynucleotide), or the separation of covalently closed polynucleotides from linear polynucleotides. A polynucleotide is substantially pure when at least about 50%, preferably 60 to 75% of a sample exhibits a single polynucleotide sequence and conformation (linear versus covalently closed). A substantially pure polynucleotide typically comprises about 50%, preferably 60 to 90% weight/weight of a nucleic acid sample, more usually about 95%, and preferably is over about 99% pure. Polynucleotide purity or homogeneity is indicated by a number of means well known in the art, such as agarose or polyacrylamide gel electrophoresis of a sample, followed by visualizing a single polynucleotide band upon staining the gel. For certain purposes higher resolution can be provided by using HPLC or other means well known in the art.

As used interchangeably herein, the terms "nucleic acids", "oligonucleotides", and "polynucleotides" include RNA, DNA, or RNA/DNA hybrid sequences of more than one nucleotide in either single chain or duplex form. The term "nucleotide" as used herein as an adjective to describe molecules comprising RNA, DNA, or RNA/DNA hybrid sequences of any length in single-stranded or duplex form. The term "nucleotide" is also used herein as a noun to refer to individual nucleotides or varieties of nucleotides, meaning a molecule, or individual unit in a larger nucleic acid molecule, comprising a purine or pyrimidine, a ribose or deoxyribose sugar moiety, and a phosphate group, or phosphodiester linkage in the case of nucleotides within an oligonucleotide or polynucleotide. Although the term "nucleotide" is also used herein to encompass "modified nucleotides" which comprise at least one modifications (a) an alternative linking group, (b) an analogous form of purine, (c) an analogous form of pyrimidine, or (d) an analogous sugar, for examples of analogous linking groups, purine, pyrimidines, and sugars see for example PCT publication No. WO 95/04064. This may be especially oligonucleotides with α or β anomers, oligonucleotides with inter-nucleotide linkage of the phosphorothioate or methyl phosphonate type, or alternatively oligothionucleotide. The polynucleotide sequences of the invention may be prepared by any known method, including synthetic, recombinant, ex vivo generation, or a combination thereof, as well as utilizing any purification methods known in the art.

Throughout the present specification, the expression "nucleotide sequence" may be employed to designate indifferently a polynucleotide or a nucleic acid. More precisely, the expression "nucleotide sequence" encompasses the nucleic material itself and is thus not restricted to the sequence information (i.e. the succession of letters chosen among the four base letters) that biochemically characterizes a specific DNA or RNA molecule.

A "promoter" refers to a DNA sequence recognized by the synthetic machinery of the cell required to initiate the specific transcription of a gene.

A sequence which is "operably linked" to a regulatory sequence such as a promoter means that said regulatory element is in the correct location and orientation in relation to the nucleic acid to control RNA polymerase initiation and expression of the nucleic acid of interest. As used herein, the term "operably linked" refers to a linkage of polynucleotide elements in a functional relationship. For instance, a promoter or enhancer is operably linked to a coding sequence if it affects the transcription of the coding sequence. More precisely, two DNA molecules (such as a polynucleotide containing a promoter region and a polynucleotide encoding a desired polypeptide or polynucleotide) are said to be "operably linked" if the nature of the linkage between the two polynucleotides does not (1) result in the introduction of a frame-shift mutation or (2) interfere with the ability of the polynucleotide containing the promoter to direct the transcription of the coding polynucleotide.

The term "primer" denotes a specific oligonucleotide sequence which is complementary to a target nucleotide sequence and used to hybridize to the target nucleotide sequence. A primer serves as an initiation point for nucleotide polymerization catalyzed by either DNA polymerase, RNA polymerase or reverse transcriptase.

The term "probe" denotes a defined nucleic acid segment (or nucleotide analog segment, e.g., polynucleotide as defined herein) which can be used to identify a specific polynucleotide sequence present in samples, said nucleic acid segment comprising a nucleotide sequence complementary of the specific polynucleotide sequence to be identified.

The terms "base paired" and "Watson & Crick base paired" are used interchangeably herein to refer to nucleotides which can be hydrogen bonded to one another by virtue of their sequence identities in a manner like that found in double-helical DNA with thymine or uracil residues linked to adenine residues by two hydrogen bonds and cytosine and guanine residues linked by three hydrogen bonds (See Stryer, L., *Biochemistry*, 4$^{th}$, edition, 1995).

The terms "complementary" or "complement thereof" are used herein to refer to the sequences of polynucleotides which are capable of forming Watson & Crick base pairing with another specified polynucleotide throughout the entirety of the complementary region. For the purpose of the present invention, a first polynucleotide is deemed to be complementary to a second polynucleotide when each base in the first polynucleotide is paired with its complementary base. Complementary bases are, generally, A and T (or A and U), or C and G. "Complement" is used herein as a synonym of "complementary polynucleotide", "complementary nucleic acid" and "complementary nucleotide sequence". These terms are applied to pairs of polynucleotides based solely upon their sequences and not any particular set of conditions under which the two polynucleotides would actually bind.

The term "polypeptide" refers to a polymer of amino acids without regard to the length of the polymer; thus, peptides, oligopeptides, and proteins are included within the definition of polypeptide. This term also does not specify or exclude post-expression modifications of polypeptides, for example, polypeptides which include the covalent attachment of glycosyl groups, acetyl groups, phosphate groups, lipid groups and the like are expressly encompassed by the term polypeptide. Also included within the definition are polypeptides which contain one or more analogs of an amino acid (including, for example, non-naturally occurring amino acids, amino acids which only occur naturally in an unrelated biological system, modified amino acids from mammalian systems etc.), polypeptides with substituted linkages, as well as other modifications known in the art, both naturally occurring and non-naturally occurring.

The term "recombinant polypeptide" is used herein to refer to polypeptides that have been artificially designed and which comprise at least two polypeptide sequences that are not found as contiguous polypeptide sequences in their initial natural environment, or to refer to polypeptides which have been expressed from a recombinant polynucleotide.

The term "purified" is used herein to describe a polypeptide of the invention which has been separated from other compounds including, but not limited to nucleic acids, lipids, carbohydrates and other proteins. A polypeptide is substantially pure when at least about 50%, preferably 60 to 75% of a sample exhibits a single polypeptide sequence. A substantially pure polypeptide typically comprises about 50%, preferably 60 to 90% weight/weight of a protein sample, more usually about 95%, and preferably is over about 99% pure. Polypeptide purity or homogeneity is indicated by a number of means well known in the art, such as agarose or polyacrylamide gel electrophoresis of a sample, followed by visualizing a single polypeptide band upon staining the gel. For certain purposes higher resolution can be provided by using HPLC or other means well known in the art.

As used herein, the term "non-human animal" refers to any non-human vertebrate, birds and more usually mammals, preferably primates, farm animals such as swine, goats, sheep, donkeys, and horses, rabbits or rodents, more preferably rats or mice. As used herein, the term "animal" is used to refer to any vertebrate, preferable a mammal. Both the terms "animal" and "mammal" expressly embrace human subjects unless preceded with the term "non-human".

As used herein, the term "antibody" refers to a polypeptide or group of polypeptides which are comprised of at least one binding domain, where an antibody binding domain is formed from the folding of variable domains of an antibody molecule to form three-dimensional binding spaces with an internal surface shape and charge distribution complementary to the features of an antigenic determinant of an antigen, which allows an immunological reaction with the antigen. Antibodies include recombinant proteins comprising the binding domains, as wells as fragments, including Fab, Fab', F(ab)$_2$, and F(ab')$_2$ fragments.

As used herein, an "antigenic determinant" is the portion of an antigen molecule, in this case a PCTA-1 polypeptide, that determines the specificity of the antigen-antibody reaction. An "epitope" refers to an antigenic determinant of a polypeptide. An epitope can comprise as few as 3 amino acids in a spatial conformation which is unique to the epitope. Generally an epitope consists of at least 6 such amino acids, and more usually at least 8-10 such amino acids. Methods for determining the amino acids which make up an epitope include x-ray crystallography, 2-dimensional nuclear magnetic resonance, and epitope mapping e.g. the Pepscan method described by Geysen et al. 1984; PCT Publication No. WO 84/03564; and PCT Publication No. WO 84/03506, the disclosures of which are incorporated herein by reference in their entireties.

The term "allele" is used herein to refer to variants of a nucleotide sequence. A biallelic polymorphism has two forms. Diploid organisms may be homozygous or heterozygous for an allelic form.

The term "heterozygosity rate" is used herein to refer to the incidence of individuals in a population which are heterozygous at a particular allele. In a biallelic system, the heterozygosity rate is on average equal to $2P_a(1-P_a)$, where $P_a$ is the frequency of the least common allele. In order to be useful in genetic studies, a genetic marker should have an adequate level of heterozygosity to allow a reasonable probability that a randomly selected person will be heterozygous.

The term "genotype" as used herein refers the identity of the alleles present in an individual or a sample. In the context of the present invention, a genotype preferably refers to the description of the biallelic marker alleles present in an individual or a sample. The term "genotyping" a sample or an individual for a biallelic marker consists of determining the specific allele or the specific nucleotide carried by an individual at a biallelic marker.

The term "mutation" as used herein refers to a difference in DNA sequence between or among different genomes or individuals which has a frequency below 1%.

The term "haplotype" refers to a combination of alleles present in an individual or a sample. In the context of the present invention, a haplotype preferably refers to a combination of biallelic marker alleles found in a given individual and which may be associated with a phenotype.

The term "polymorphism" as used herein refers to the occurrence of two or more alternative genomic sequences or alleles between or among different genomes or individuals. "Polymorphic" refers to the condition in which two or more variants of a specific genomic sequence can be found in a population. A "polymorphic site" is the locus at which the variation occurs. A single nucleotide polymorphism is a single base pair change. Typically a single nucleotide polymorphism is the replacement of one nucleotide by another nucleotide at the polymorphic site. Deletion of a single nucleotide or insertion of a single nucleotide, also give rise to single nucleotide polymorphisms. In the context of the present invention "single nucleotide polymorphism" preferably refers to a single nucleotide substitution. However, the polymorphism can also involve an insertion or a deletion of at least one nucleotide, preferably between 1 and 5 nucleotides. The nucleotide modification can also involve the presence of several adjacent single base polymorphisms. This type of nucleotide modification is usually called a "variable motif". Generally, a "variable motif" involves the presence of 2 to 10 adjacent single base polymorphisms. In some instances, series of two or more single base polymorphisms can be interrupted by single bases which are not polymorphic. This is also globally considered to be a "variable motif". Typically, between different genomes or between different individuals, the polymorphic site may be occupied by two different nucleotides.

The term "biallelic polymoriphism" and "biallelic marker" are used interchangeably herein to refer to a polymorphism, usually a single nucleotide, having two alleles at a fairly high frequency in the population. A "biallelic marker allele" refers to the nucleotide variants present at a biallelic marker site. Typically, the frequency of the less common allele of the biallelic markers of the present invention has been validated to be greater than 1%, preferably the frequency is greater than 10%, more preferably the frequency is at least 20% (i.e. heterozygosity rate of at least 0.32), even more preferably the frequency is at least 30% (i.e. heterozygosity rate of at least 0.42). A biallelic marker wherein the frequency of the less common allele is 30% or more is termed a "high quality biallelic marker".

As used herein the terminology "defining a biallelic marker" means that a sequence includes a polymorphic base from a biallelic marker. The sequences defining a biallelic marker may be of any length consistent with their intended use, provided that they contain a polymorphic base from a biallelic marker. The sequence has between 2 and 100, preferably between 20, 30, or 40 and 60, and more preferably about 47 nucleotides in length. Likewise, the term "marker" or "biallelic marker" requires that the sequence is of sufficient length to practically (although not necessarily unambiguously) identify the polymorphic allele, which usually implies a length of at least 4, 5, 6, 10, 15, 20, 25, or 40 nucleotides.

As used herein the term "PCTA-1-related biallelic marker" or "biallelic marker of the PCTA-1 gene" relates to a set of biallelic markers in linkage disequilibrium with the PCTA-1 gene. The term PCTA-1-related biallelic marker encompasses all of the biallelic markers A1 to A125 disclosed in Table 2.

The location of nucleotides in a polynucleotide with respect to the center of the polynucleotide are described herein in the following manner. When a polynucleotide has an odd number of nucleotides, the nucleotide at an equal distance from the 3' and 5' ends of the polynucleotide is considered to be "at the center" of the polynucleotide, and any nucleotide immediately adjacent to the nucleotide at the center, or the nucleotide at the center itself is considered to be "within 1 nucleotide of the center." With an odd number of nucleotides in a polynucleotide any of the five nucleotides positions in the middle of the polynucleotide would be considered to be within 2 nucleotides of the center, and so on. When a polynucleotide has an even number of nucleotides, there would be a bond and not a nucleotide at the center of the polynucleotide. Thus, either of the two central nucleotides would be considered to be "within 1 nucleotide of the center" and any of the four nucleotides in the middle of the polynucleotide would be considered to be "within 2 nucleotides of the center", and so on. For polymorphisms which involve the substitution, insertion or deletion of 1 or more nucleotides, the polymorphism, allele or biallelic marker is "at the center" of a polynucleotide if the difference between the distance from the substituted, inserted, or deleted polynucleotides of the polymorphism and the 3' end of the polynucleotide, and the distance from the substituted, inserted, or deleted polynucleotides of the polymorphism and the 5' end of the polynucleotide is zero or one nucleotide. If this difference is 0 to 3, then the polymorphism is considered to be "within 1 nucleotide of the center." If the difference is 0 to 5, the polymorphism is considered to be "within 2 nucleotides of the center." If the difference is 0 to 7, the polymorphism is considered to be "within 3 nucleotides of the center," and so on.

The terms "trait" and "phenotype" are used interchangeably herein and refer to any visible, detectable or otherwise measurable property of an organism such as symptoms of, or susceptibility to a disease for example. Preferably, the term "trait" or "phenotype", when used herein, encompasses, but is not limited to, prostate cancer, an early onset of prostate cancer, a beneficial response to or side effects related to treatment or a vaccination against prostate cancer, a susceptibility to prostate cancer, the level of aggressiveness of prostate cancer tumors, a modified or forthcoming expression of the PCTA-1 gene, a modified or forthcoming production of the PCTA-1 protein, or the production of a modified PCTA-1 protein. However, the term "trait" or "phenotype" can refer to other types of cancer.

The term "susceptibility to prostate cancer" is used herein to designate a strong likelihood for an individual to develop in his lifetime a form of prostate cancer, particularly a form of prostate cancer in which a PCTA-1 protein is expressed. This likelihood is strongly related to the association established between the biallelic markers of the present invention and prostate cancer or other more specific characteristics which can lead to the development of the prostate cancer such as the modified expression of the PCTA-1 gene, the modified production of the PCTA-1 protein or the production of a modified PCTA-1 protein.

The term "aggressiveness" of prostate cancer tumors refers to the metastatic potential of these tumors.

The term "treatment of prostate cancer" when used herein is intended to designate the administration of substances either for prophylactic or curative purposes. When administered for prophylactic purposes, the treatment is provided in advance of the appearance of biologically or clinically significant cancer symptoms. When administered for curative purposes, the treatment is provided to attenuate the pathological symptoms of prostate cancer, to decrease the size or growth of cancer tumors or metastases or to remove them.

The terms "an agent acting against prostate cancer" refers to any drug or compound that is capable of reducing the growth rate, rate of metastasis, or viability of tumor cells in a mammal, is capable of reducing the size or eliminating tumors in a mammal, or is capable of increasing the average life span of a mammal or human with cancer. Agents acting against prostate cancer also include compounds which are able to reduce the risk of cancer developing in a population, particularly a high risk population. Examples of agents acting against prostate cancer include hormonal therapeutic agents (for example, medroxyprogesterone acetate, estramustine phosphate, gonadotrophin releasing hormone (GnRH) agonists, anti-androgens such as flutamide, nilutamide, groserelin, and cyprosterone acetate, anti-gonadotropic agents such as stilboestrol and other oestrogenic agents, progestogens such as megestrol acetate) or chemotherapeutic agents (for example, carboplatin, cisplatin, methotrexate, mitomycin, epirubicin, vinblastine, 5-fluorouracyl, mitozantrone, cyclophosphamide, interferon, N-(4-hydroxyphenyl) retinamide (4HPR)). These agents can be used in combination.

The term "side effects to an agent acting against prostate cancer" refers to adverse effects of therapy resulting from extensions of the principal pharmacological action of the drug or to idiosyncratic adverse reactions resulting from an interaction of the drug with unique host factors. These side effects include, but are not limited to, adverse reactions such as dermatological, hematological or hepatological toxicities and further includes gastric and intestinal ulceration, disturbance in platelet function, renal injury, nephritis, vasomotor rhinitis with profuse watery secretions, angioneurotic edema, generalized urticaria, and bronchial asthma to laryngeal edema and bronchoconstriction, hypotension, sexual dysfunction, and shock. More particularly, the side effects can be nausea/vomiting, cardiovascular side effects such as deep vein thrombosis and fluid retention, and gynaecomastia.

The term "response to an agent acting against prostate cancer" refers to drug efficacy, including but not limited to ability to metabolize a compound, to the ability to convert a pro-drug to an active drug, and to the pharmacokinetics (absorption, distribution, elimination) and the pharmacodynamics (receptor-related) of a drug in an individual.

In the context of the present invention, a "positive response" to a medicament can be defined as comprising a reduction of the symptoms related to the disease, an increase of survival time or condition to be treated.

In the context of the present invention, a "negative response" to a medicament can be defined as comprising either a lack of positive response to the medicament which does not lead to a symptom reduction or an increase of survival time, or which leads to a side-effect observed following administration of the medicament.

Variants and Fragments

1—Polynucleotides

The invention also relates to variants and fragments of the polynucleotides described herein, particularly of a PCTA-1 gene containing one or more biallelic markers according to the invention.

Variants of polynucleotides, as the term is used herein, are polynucleotides that differ from a reference polynucleotide. A variant of a polynucleotide may be a naturally occurring variant such as a naturally occurring allelic variant, or it may be a variant that is not known to occur naturally. Such non-naturally occurring variants of the polynucleotide may be made by mutagenesis techniques, including those applied to polynucleotides, cells or organisms. Generally, differences are limited so that the nucleotide sequences of the reference and the variant are closely similar overall and, in many regions, identical.

Variants of polynucleotides according to the invention include, without being limited to, nucleotide sequences which are at least 95% identical to a polynucleotide selected from the group consisting of the nucleotide sequences of SEQ ID Nos 1, 2, 3, 4, 8 or to any polynucleotide fragment of at least 8 consecutive nucleotides of a polynucleotide selected from the group consisting of the nucleotide sequences of SEQ ID Nos 1, 2, 3, 4, 8, and preferably at least 99% identical, more particularly at least 99.5% identical, and most preferably at least 99.8% identical to a polynucleotide selected from the group consisting of the nucleotide sequences of SEQ ID Nos 1, 2, 3, 4, 8 or to any polynucleotide fragment of at least 8 consecutive nucleotides of a polynucleotide selected from the group consisting of the nucleotide sequences of SEQ ID Nos 1, 2, 3, 4, 8.

Nucleotide changes present in a variant polynucleotide may be silent, which means that they do not alter the amino acids encoded by the polynucleotide. However, nucleotide changes may also result in amino acid substitutions, additions, deletions, fusions and truncations in the polypeptide encoded by the reference sequence. The substitutions, deletions or additions may involve one or more nucleotides. The variants may be altered in coding or non-coding regions or both. Alterations in the coding regions may produce conservative or non-conservative amino acid substitutions, deletions or additions.

In the context of the present invention, particularly preferred embodiments are those in which the polynucleotides encode polypeptides which retain substantially the same biological function or activity as the mature PCTA-1 protein, or those in which the polynucleotides encode polypeptides which maintain or increase a particular biological activity, while reducing a second biological activity.

A polynucleotide fragment is a polynucleotide having a sequence that entirely is the same as part but not all of a given nucleotide sequence, preferably the nucleotide sequence of a PCTA-1 gene, and variants thereof. The fragment can be a portion of an exon or of an intron of a PCTA-1 gene. It can also be a portion of the regulatory sequences of the PCTA-1 gene, preferably of the promoter. Preferably, such fragments comprise at least one of the biallelic markers A1 to A125, and the complements thereof, or a biallelic marker in linkage disequilibrium therewith.

Such fragments may be "free-standing", i.e. not part of or fused to other polynucleotides, or they may be comprised within a single larger polynucleotide of which they form a part or region. However, several fragments may be comprised within a single larger polynucleotide.

As representative examples of polynucleotide fragments of the invention, there may be mentioned those which have from about 4, 6, 8, 15, 20, 25, 40, 10 to 30, 30 to 55, 50 to 100, 75 to 100 or 100 to 200 nucleotides in length. Preferred are those fragments having about 47 nucleotides in length, such as those of P1 to P125 and the complementary sequences thereto, and containing at least one of the biallelic markers of the PCTA-1 gene which are described herein. It will of course be understood that the polynucleotides P1 to P125 and the complementary sequences thereto can be shorter or longer, although it is preferred that they at least contain the biallelic marker of the primer which can be located at one end of the fragment.

2—Polypeptides

The invention also relates to variants, fragments, analogs and derivatives of the polypeptides described herein, including mutated PCTA-1 proteins.

The variant may be 1) one in which one or more of the amino acid residues are substituted with a conserved or non-conserved amino acid residue and such substituted amino acid residue may or may not be one encoded by the genetic code, or 2) one in which one or more of the amino acid residues includes a substituent group, or 3) one in which the PCTA-1 protein is fused with another compound, such as a compound to increase the half-life of the polypeptide (for example, polyethylene glycol), or 4) one in which the additional amino acids are fused to the PCTA-1 protein, such as a leader or secretory sequence or a sequence which is employed for purification of the PCTA-1 protein or a preprotein sequence. Such variants are deemed to be within the scope of those skilled in the art.

A polypeptide fragment is a polypeptide having a sequence that entirely is the same as part but not all of a given polypeptide sequence, preferably a polypeptide encoded by a PCTA-1 gene and variants thereof. Preferred fragments include those of the active region of the PCTA-1 protein that may play a role in prostate cancer and those regions possessing antigenic properties and which can be used to raise antibodies against the PCTA-1 protein.

In the case of an amino acid substitution in the amino acid sequence of a polypeptide according to the invention, one or several amino acids can be replaced by "equivalent" amino acids. The expression "equivalent" amino acid is used herein to designate any amino acid that may be substituted for one of the amino acids having similar properties, such that one skilled in the art of peptide chemistry would expect the secondary structure and hydropathic nature of the polypeptide to be substantially unchanged. Generally, the following groups of amino acids represent equivalent changes: (1) Ala, Pro, Gly, Glu, Asp, Gln, Asn, Ser, Thr; (2) Cys, Ser, Tyr, Thr; (3) Val, Ile, Leu, Met, Ala, Phe; (4) Lys, Arg, His; (5) Phe, Tyr, Trp, His.

A specific embodiment of a modified PCTA-1 peptide molecule of interest according to the present invention, includes, but is not limited to, a peptide molecule which is resistant to proteolysis, is a peptide in which the —CONH— peptide bond is modified and replaced by a ($CH_2NH$) reduced bond, a (NHCO) retro inverso bond, a ($CH_2$—O) methylene-oxy bond, a ($CH_2$—S) thiomethylene bond, a ($CH_2CH_2$) carba bond, a (CO—$CH_2$) cetomethylene bond, a (CHOH—$CH_2$) hydroxyethylene bond), a (N—N) bound, a E-alcene bond or also a —CH=CH— bond. The invention also encompasses a human PCTA-1 polypeptide or a fragment or a variant thereof in which at least one peptide bound has been modified as described above.

Such fragments may be "free-standing", i.e. not part of or fused to other polypeptides, or they may be comprised within a single larger polypeptide of which they form a part or region. However, several fragments may be comprised within a single larger polypeptide.

As representative examples of polypeptide fragments of the invention, there may be mentioned those which have from about 5, 6, 7, 8, 9 or 10 to 15, 10 to 20, 15 to 40, or 30 to 55 amino acids long. Preferred are those fragments containing at least one amino acid mutation in the PCTA-1 protein.

Identity Between Nucleic Acids or Polypeptides

The terms "percentage of sequence identity" and "percentage homology" are used interchangeably herein to refer to comparisons among polynucleotides and polypeptides, and are determined by comparing two optimally aligned sequences over a comparison window, wherein the portion of the polynucleotide or polypeptide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity. Homology is evaluated using any of the variety of sequence comparison algorithms and programs known in the art. Such algorithms and programs include, but are by no means limited to, TBLASTN, BLASTP, FASTA, TFASTA, and CLUSTALW (Pearson and Lipman, 1988; Altschul et al., 1990; Thompson et al., 1994; Higgins et al., 1996; Altschul et al., 1993). In a particularly preferred embodiment, protein and nucleic acid sequence homologies are evaluated using the Basic Local Alignment Search Tool ("BLAST") which is well known in the art (see, e.g., Karlin and Altschul, 1990; Altschul et al., 1990, 1993, 1997). In particular, five specific BLAST programs are used to perform the following task:

(1) BLASTP and BLAST3 compare an amino acid query sequence against a protein sequence database;

(2) BLASTN compares a nucleotide query sequence against a nucleotide sequence database;

(3) BLASTX compares the six-frame conceptual translation products of a query nucleotide sequence (both strands) against a protein sequence database;

(4) TBLASTN compares a query protein sequence against a nucleotide sequence database translated in all six reading frames (both strands); and (5) TBLASTX compares the six-frame translations of a nucleotide query sequence against the six-frame translations of a nucleotide sequence database.

The BLAST programs identify homologous sequences by identifying similar segments, which are referred to herein as "high-scoring segment pairs," between a query amino or nucleic acid sequence and a test sequence which is preferably obtained from a protein or nucleic acid sequence database. High-scoring segment pairs are preferably identified (i.e., aligned) by means of a scoring matrix, many of which are known in the art. Preferably, the scoring matrix used is the BLOSUM62 matrix (Gonnet et al., 1992; Henikoff and Henikoff, 1993). Less preferably, the PAM or PAM250 matrices may also be used (see, e.g., Schwartz and Dayhoff, eds., 1978). The BLAST programs evaluate the statistical significance of all high-scoring segment pairs identified, and preferably selects those segments which satisfy a user-specified threshold of significance, such as a user-specified percent homology. Preferably, the statistical significance of a high-scoring segment pair is evaluated using the statistical significance formula of Karlin (see, e.g., Karlin and Altschul, 1990).

Stringent Hybridization Conditions

By way of example and not limitation, procedures using conditions of high stringency are as follows: Prehybridization of filters containing DNA is carried out for 8 h to overnight at 65° C. in buffer composed of 6×SSC, 50 mM Tris-HCl (pH 7.5), 1 mM EDTA, 0.02% PVP, 0.02% Ficoll, 0.02% BSA, and 500 µg/ml denatured salmon sperm DNA. Filters are hybridized for 48 h at 65° C., the preferred hybridization temperature, in prehybridization mixture containing 100 µg/ml denatured salmon sperm DNA and 5-20×10$^6$ cpm of $^{32}$P-labeled probe. Alternatively, the hybridization step can be performed at 65° C. in the presence of SSC buffer, 1×SSC corresponding to 0.15M NaCl and 0.05 M Na citrate. Subsequently, filter washes can be done at 37° C. for 1 h in a solution containing 2×SSC, 0.01% PVP, 0.01% Ficoll, and 0.01% BSA, followed by a wash in 0.1×SSC at 50° C. for 45 min. Alternatively, filter washes can be performed in a solution containing 2×SSC and 0.1% SDS, or 0.5×SSC and 0.1% SDS, or 0.1×SSC and 0.1% SDS at 68° C. for 15 minute intervals. Following the wash steps, the hybridized probes are detectable by autoradiography. Other conditions of high stringency which may be used are well known in the art and as cited in Sambrook et al., 1989; and Ausubel et al., 1989. These hybridization conditions are suitable for a nucleic acid molecule of about 20 nucleotides in length. There is no need to say that the hybridization conditions described above are to be adapted according to the length of the desired nucleic acid, following techniques well known to the one skilled in the art. The suitable hybridization conditions may for example be adapted according to the teachings disclosed in the book of Hames and Higgins (1985) or in Sambrook et al.(1989).

Genomic Sequence of the PCTA-1 Gene

The present invention relates to a purified and/or isolated nucleic acid corresponding to the genomic sequence of the PCTA-1 gene. Preferably, this genomic PCTA-1 sequence comprises the nucleotide sequence of SEQ ID No 1, a sequence complementary thereto, a fragment or a variant thereof.

The present invention encompasses the genomic sequence of PCTA-1. The PTCA-1 gene sequence comprises a coding sequence including 13 exons included in SEQ ID No 1, namely exon 0, exon 1, exon 2, exon 3, exon 4, exon 5, exon 6, exon 6bis, exon 7, exon 8, exon 9, exon 9bis and exon 9ter, the intronic regions, the promoter, the 5'UTR, the 3'UTR, and regulatory regions located upstream and downstream of the coding region.

The localization of the exons and introns of the PCTA-1 gene is detailed in Table A and is described as feature in SEQ ID No 1.

TABLE A

| | Position range in SEQ ID No 1 | | | Position range in SEQ ID No 1 | |
|---|---|---|---|---|---|
| Exon | Beginning | End | Intron | Beginning | End |
| 0 | 68648 | 68741 | 0 | 68742 | 70646 |
| 1 | 70647 | 70794 | 1 | 70795 | 82207 |
| 2 | 82208 | 82296 | 2 | 82297 | 83612 |
| 3 | 83613 | 83823 | 3 | 83824 | 85297 |
| 4 | 85298 | 85417 | 4 | 85418 | 86388 |
| 5 | 86389 | 86445 | 5 | 86446 | 87495 |
| 6 | 87496 | 87522 | 6 | 87523 | 87649 |
| 6bis | 87650 | 87775 | 6bis | 87776 | 88294 |
| 7 | 88295 | 88383 | 7 | 88384 | 89483 |
| 8 | 89484 | 89649 | 8 | 89650 | 92748 |
| 9 | 92749 | 97155 | 9bis | 92884 | 95820 |
| 9bis | 92749 | 92883 | | | |
| 9ter | 95821 | 97155 | | | |

Intron 0 refers to the nucleotide sequence located between Exon 0 and Exon 1, and so on. The intron 6 refers to the nucleotide sequence located between Exon 6 and Exon 6bis. The intron 6bis refers to the nucleotide sequence located between Exon 6bis and Exon 7. The intron 8 refers to the nucleotide sequence located between Exon 8 and Exon 9 or 9bis. The intron 9bis refers to the nucleotide sequence located between Exon 9bis and Exon 9ter.

The invention also encompasses a purified, isolated, or recombinant polynucleotide comprising a nucleotide sequence having at least 70, 75, 80, 85, 90, or 95% nucleotide identity with a nucleotide sequence of SEQ ID No 1 or a complementary sequence thereto or a fragment thereof. The nucleotide differences as regards to the nucleotide sequence of SEQ ID No 1 may be generally randomly distributed throughout the entire nucleic acid. Nevertheless, preferred nucleic acids are those wherein the nucleotide differences as regards to the nucleotide sequence of SEQ ID No 1 are predominantly located outside the coding sequences contained in the exons. These nucleic acids, as well as their fragments and variants, may be used as oligonucleotide primers or probes in order to detect the presence of a copy of the PCTA-1 gene in a test sample, or alternatively in order to amplify a target nucleotide sequence within the PCTA-1 sequences.

Another object of the invention consists of a purified, isolated, or recombinant nucleic acid that hybridizes with the nucleotide sequence of SEQ ID No 1 or a complementary sequence thereto or a variant thereof, under the stringent hybridization conditions as defined above.

Particularly preferred nucleic acids of the invention include isolated, purified, or recombinant polynucleotides comprising a contiguous span of at least 12, 15, 18, 20, 25, 30, 35, 40, 50, 60, 70, 80, 90, 100, 150, 200, 500, or 1000 nucleotides of SEQ ID No 1 or the complements thereof, wherein said contiguous span comprises at least 1, 2, 3, 5, or 10 of the following nucleotide positions of SEQ ID No 1:1-70715, 70795-82207, 82297-83612, 83824-85297, 85418-86388, 86446-87495, 87523-88294, 88384-89483, 89650-92748, 97156-98309, 98476-99329, 99491-100026, 100212-100281, 100396-100538, 100682-100833, 100995-101920, 102087-102970, 103264-103724, and 103753-106746. Additional preferred nucleic acids of the invention include isolated, purified, or recombinant polynucleotides comprising a contiguous span of at least 12, 15, 18, 20, 25, 30, 35, 40, 50, 60, 70, 80, 90, 100, 150, 200, 500, or 1000 nucleotides of SEQ ID No 1 or the complements thereof, wherein said contiguous span comprises at least one nucleotide selected from the group consisting of a nucleotide G at positions 70728, 87860, 88297, 94432, and 95340 of SEQ ID No 1; a nucleotide A at positions 82218, 83644, 83808, 87787, 87806, 94218, and 97144 of SEQ ID No 1; a nucleotide C at positions 87902, 88215, 88283, 92760, 93726, and 94422 of SEQ ID No 1; and a nucleotide T at positions 93903, and 94170 of SEQ ID No 1. Other preferred nucleic acids of the invention include isolated, purified, or recombinant polynucleotides comprising a contiguous span of at least 12, 15, 18, 20, 25, 30, 35, 40, 50, 60, 70, 80, 90, 100, 150, 200, 500, or 1000 nucleotides of SEQ ID No 1 or the complements thereof, wherein said contiguous span comprises at least one nucleotide selected from the group consisting of a nucleotide G at positions 86435, 93592, 93680, 93681, 93682, 93728, 93761, and 95445 of SEQ ID No 1; a nucleotide A at positions 86434, 88355, 93240, 93471, and 93747 of SEQ ID No 1; a nucleotide C at positions 93683, 95126, and 95444 of SEQ ID No 1; and a nucleotide T at positions 94154, and 94430 of SEQ ID No 1. Other preferred nucleic acids of the invention include isolated, purified, or recombinant polynucleotides comprising a contiguous span of at least 12, 15, 18, 20, 25, 30, 35, 40, 50, 60, 70, 80, 90, 100, 150, 200, 500, or 1000 nucleotides of SEQ ID No 1 or the complements thereof, wherein said contiguous span comprises nucleotide positions selected from the group consisting of the nucleotide positions of SEQ ID No 1: 92975-92977, 93711-93715, 94151-94153, 94240-94243, 94770-94773, 94804-94808, 95121-95122, 95129-95135, 95148-95153, 95154-95159, 95173-95178, 95367-95374, 95410-95413, 95418-95420, 95430-95436, 95533-95535, and 95677-95677. It should be noted that nucleic acid fragments of any size and sequence may also be comprised by the polynucleotides described in this section.

A preferred aspect of the present invention is a purified and/or isolated and/or recombined PCTA-1 gene or a fragment thereof comprising at least one of the biallelic polymorphisms described below, a sequence complementary thereto, a fragment or a variant thereof. In some embodiments, the PCTA-1 gene or a fragment thereof may comprise at least one of the nucleotide sequences of P1 to P125, a sequence complementary thereto, a fragment or a variant thereof. In a preferred embodiment, the PCTA-1 gene or a fragment thereof comprises a biallelic marker selected from the group consisting of A1 to A125 and the complements thereof.

While this section is entitled "Genomic Sequences of The PCTA-1 Gene", it should be noted that nucleic acid fragments of any size and sequence may also be comprised by the polynucleotides described in this section, flanking the genomic sequences of PCTA-1 on either side or between two or more such genomic sequences.

PCTA-1 cDNA Sequences

The invention also concerns a purified and/or isolated cDNA encoding a PCTA-1 protein. Preferably, the cDNA comprises a nucleotide sequence selected from the group consisting of SEQ ID Nos 2, 3, 4, sequences complementary thereto and functional fragments and variants thereof. Moreover, preferred polynucleotides of the invention include purified, isolated, or recombinant PCTA-1 cDNAs consisting of, consisting essentially of, or comprising a sequence selected from the group consisting of SEQ ID Nos 2, 3, 4 and the complementary sequence thereto.

The invention also pertains to a purified or isolated nucleic acid comprising a polynucleotide having at least 95% nucleotide identity with a polynucleotide selected from the group consisting of SEQ ID Nos 2, 3, 4, advantageously 99% nucleotide identity, preferably 99.5% nucleotide identity and most preferably 99.8% nucleotide identity with a polynucleotide selected from the group consisting of SEQ ID Nos 2, 3, 4, or a sequence complementary thereto or a biologically active fragment thereof.

Another object of the invention consists of purified, isolated or recombinant nucleic acids comprising a polynucleotide that hybridizes, under the stringent hybridization conditions defined herein, with a polynucleotide selected from the group consisting of the nucleotide sequences of SEQ ID Nos 2, 3, 4, or a sequence complementary thereto or a variant thereof or a biologically active fragment thereof.

The 5'UTR and 3'UTR regions of a gene are of particular importance in that they often comprise regulatory elements which can play a role in providing appropriate expression levels, particularly through the control of mRNA stability. The inventors have cloned a complete PCTA-1 cDNA (SEQ ID No 2) in which the 5'UTR is carried by exon 0 and a portion of exon 1 and the 3'UTR is carried by a portion of exon 9. Moreover, they have characterized a 5'EST, which is located as a feature in SEQ ID No 1, comprising the exons 0 and 1, and partially exon 2. Since an ATG codon is located at the beginning of the partial exon 1 disclosed in WO 96/21671, one could assume that the promoter of the PCTA-1 gene would be located immediately upstream of this codon. However, the inventors unexpectedly found that the PCTA-1 genomic DNA contains further exonic sequences upstream of the partial exon 1 disclosed in WO 96/21671. Without the knowledge of such sequences, the identification by the skilled person of the PCTA-1 promoter was extremely unlikely. Only the full genomic sequence of PCTA-1 and access by the inventors to a proprietary 5'EST database rendered possible the identification of a full cDNA sequence and of the PCTA-1 promoter. The invention concern the nucleotide sequence of 5' EST consisting of the position range 1-266 in the SEQ ID No 2.

The main characteristics of the PCTA-1 cDNA comprising exons 0, 1, 2, 3, 4, 5, 6, 7, 8, and 9 are detailed in Table B. The invention concerns the purified and/or isolated sequence of the 5'UTR and 3'UTR as described in Table B or a complementary sequence thereto or an allelic variant thereof set forth in SEQ ID No 2. Particularly preferred nucleic acids of the invention include isolated, purified, or recombinant polynucleotides comprising a contiguous span of at least 12, 15, 18, 20, 25, 30, 35, 40, 50, 60, 70, 80, 90, 100, 150, 200, 500, or 1000 nucleotides of SEQ ID No 2 or the complements thereof, wherein said contiguous span comprises at least 1, 2, 3, 5, or 10 of the nucleotide positions 1-162 of SEQ ID No 2. Further preferred nucleic acids of the invention include isolated, purified, or recombinant polynucleotides comprising a contiguous span of at least 12, 15, 18, 20, 25, 30, 35, 40, 50, 60, 70, 80, 90, 100, 150, 200, 500, or 1000 nucleotides of SEQ ID No 2 or the complements thereof, wherein said contiguous span comprises at least one nucleotide selected from the group consisting of a nucleotide A at positions 253, 363, 527, 2471, and 5397 of SEQ ID No 2; a nucleotide C at positions 1013, 1979, and 2675 of SEQ ID No 2; a nucleotide G at positions 176, 749, 2685, 3593 of SEQ ID No 2; and a nucleotide T at positions 2156, and 2423 of SEQ ID No 2. Additional preferred nucleic acids of the invention include isolated, purified, or recombinant polynucleotides comprising a contiguous span of at least 12, 15, 18, 20, 25, 30, 35, 40, 50, 60, 70, 80, 90, 100, 150, 200, 500, or 1000 nucleotides of SEQ ID No 2 or the complements thereof, wherein said contiguous span comprises at least one nucleotide selected from the group consisting of a nucleotide A at positions 708, 807, 1493, 1724, and 2000; a nucleotide C at positions 1936, 3379, and 3697; a nucleotide G at positions 709, 1845, 1933, 1934, 1935, 1981, 2014, and 3698; and a nucleotide T at positions 2407, and 2683 of SEQ ID No 2. Other preferred nucleic acids of the invention include isolated, purified, or recombinant polynucleotides comprising a contiguous span of at least 12, 15, 18, 20, 25, 30, 35, 40, 50, 60, 70, 80, 90, 100, 150, 200, 500, or 1000 nucleotides of SEQ ID No 2 or the complements thereof, wherein said contiguous span comprises nucleotide positions selected from the group consisting of the nucleotide positions of SEQ ID No 2: 1229-1231, 1964-1968, 2404-2406, 2493-2496, 3023-3026, 3057-3061, 3374-3375, 3382-3388, 3401-3406, 3407-3412, 3426-3431, 3620-3627, 3663-3666, 3671-3673, 3683-3689, 3786-3788 and 3930-3932. It should be noted that nucleic acid fragments of any size and sequence may also be comprised by the polynucleotides described in this section.

The majority of interrupted genes are transcribed into an RNA that gives rise to a single type of spliced mRNA. But the RNAs of some genes follow patterns of alternative splicing, wherein a single gene gives rise to more than one mRNA species. In some cases, the ultimate pattern of expression is dictated by the primary transcript, because the use of different startpoints or termination sequences alters the splicing pattern. In other cases, a single primary transcript is spliced in more than one way, and internal exons are substituted, added or deleted. In some cases, the multiple products all are made in the same cell, but in others, the process is regulated so that particular splicing patterns occur only under particular conditions.

At least three PCTA-1 cDNAs are produced by alternative splicing. The inventors have identified a minor species of PCTA-1 cDNA, disclosed in SEQ ID No 3, and comprising an additional exon 6bis which encodes 42 additional amino acids. In a further embodiment, the present invention concerns the additional exon of the PCTA-1 gene located between exon 6 and exon 7, namely exon 6bis, detailed as a feature in SEQ ID No 1 and in Table A, a sequence complementary thereto, and a fragment or variant thereof. The present invention embodies a PCTA-1 cDNA comprising the exon 6bis disclosed in SEQ ID No 1.

The main characteristics of this second PCTA-1 cDNA comprising exons 0, 1, 2, 3, 4, 5, 6, 6bis, 7, 8, and 9 are detailed in Table B. The amino acid sequence of this new PCTA-1 protein is disclosed in SEQ ID No 6. Particularly preferred nucleic acids of the invention include isolated, purified, or recombinant polynucleotides comprising a contiguous span of at least 12, 15, 18, 20, 25, 30, 35, 40, 50, 60, 70, 80, 90, 100, 150, 200, 500, or 1000 nucleotides of SEQ ID No 3 or the complements thereof, wherein said contiguous span comprises at least 1, 2, 3, 5, or 10 of the following nucleotide positions of SEQ ID No 3: 1-162 and 747-872. Further preferred nucleic acids of the invention include isolated, purified, or recombinant polynucleotides comprising a contiguous span of at least 12, 15, 18, 20, 25, 30, 35, 40, 50, 60, 70, 80, 90, 100, 150, 200, 500, or 1000 nucleotides of SEQ ID No 3 or the complements thereof, wherein said contiguous span comprises at least one nucleotide selected from the group consisting of a nucleotide A at positions 253, 363, 527, 2597, and 5523 of SEQ ID No 3; a nucleotide C at positions 1139, 2105, and 2801 of SEQ ID No 3; a nucleotide G at positions 176, 875, 2811, 3719 of SEQ ID No 3; and a nucleotide T at positions 2282, and 2549 of SEQ ID No 3. Additional preferred nucleic acids of the invention include isolated, purified, or recombinant polynucleotides comprising a contiguous span of at least 12, 15, 18, 20, 25, 30, 35, 40, 50, 60, 70, 80, 90, 100, 150, 200, 500, or 1000 nucleotides of SEQ ID No 3 or the complements thereof, wherein said contiguous span comprises at least one nucleotide selected from the group consisting of a nucleotide A at positions 708, 807, 1619, 1850, and 2126; a nucleotide C at positions 2062, 3505, and 3823; a nucleotide G at positions 709, 1971, 2059, 2060, 2061, 2107, 2140, and 3824; and a nucleotide T at positions 2533, and 2809 of SEQ ID No 3. Other preferred nucleic acids of the invention include isolated, purified, or recombinant polynucleotides comprising a contiguous span of at least 12, 15, 18, 20, 25, 30, 35, 40, 50, 60, 70, 80, 90, 100, 150, 200, 500, or 1000 nucleotides of SEQ ID No 3 or the complements thereof, wherein said contiguous span comprises nucleotide positions selected from the group consisting of the nucleotide positions of SEQ ID No 3: 1355-1357, 1892-1894, 2090-2094, 2530-2532, 2619-2622, 3149-3152, 3183-3187, 3500-3501, 3508-3514, 3527-3532, 3533-3538, 3552-3557, 3746-3749, 3789-3792, 3797-3799, 3809-3815, 3912-3914 and 4056-4058. It should be noted that nucleic acid fragments of any size and sequence may also be comprised by the polynucleotides described in this section.

The inventors have also identified a species of PCTA-1 cDNA comprising alternative exons to exon 9 which are called exons 9bis and 9ter. Its sequence is disclosed in SEQ ID No 4. The exon 9bis and 9ter correspond respectively to the beginning and the ends of the exon 9. The polynucleotide of the exon 9 located between exons 9bis and 9ter is spliced or deleted. The combination of exons 9bis and 9ter extends the ORF of the PCTA-1 gene.

The main characteristics of this second PCTA-1 cDNA comprising exons 0, 1, 2, 3, 4, 5, 6, 7, 8, 9bis and 9ter are detailed in Table B. The amino acid sequence of the new PCTA-1 protein encoded by this cDNA is disclosed in SEQ ID No 7. Particularly preferred nucleic acids of the invention include isolated, purified, or recombinant polynucleotides comprising a contiguous span of at least 12, 15, 18, 20, 25, 30, 35, 40, 50, 60, 70, 80, 90, 100, 150, 200, 500, or 1000 nucleotides of SEQ ID No 4 or the complements thereof, wherein said contiguous span comprises at least 1, 2, 3, 5, or 10 of the nucleotide positions 1-162 of SEQ ID No 4. Further preferred nucleic acids of the invention include isolated, purified, or recombinant polynucleotides comprising a contiguous span of at least 12, 15, 18, 20, 25, 30, 35, 40, 50, 60, 70, 80, 90, 100, 150, 200, 500, or 1000 nucleotides of SEQ ID No 4 or the complements thereof, wherein said contiguous span comprises at least one nucleotide selected from the group consisting of a nucleotide A at positions 253, 363, 527 and 2460 of SEQ ID No 4; a nucleotide C at position 1013 of SEQ ID No 4 and a nucleotide G at positions 176, and 749 of SEQ ID No 4. Additionally preferred nucleic acids of the invention include isolated, purified, or recombinant polynucleotides comprising a contiguous span of at least 12, 15, 18, 20, 25, 30, 35, 40, 50, 60, 70, 80, 90, 100, 150, 200, 500, or 1000 nucleotides of SEQ ID No 4 or the complements thereof, wherein said contiguous span comprises at least one nucleotide selected from the group consisting of a nucleotide A at positions 708 and 807 and a nucleotide G at position 709 of SEQ No 4. Other preferred nucleic acids of the invention include isolated, purified, or recombinant polynucleotides comprising a contiguous span of at least 12, 15, 18, 20, 25, 30, 35, 40, 50, 60, 70, 80, 90, 100, 150, 200, 500, or 1000 nucleotides of SEQ ID No 4 or the complements thereof, wherein said contiguous span comprises the pairs of nucleotide positions 1136-1137 of SEQ ID No 4. It should be noted that nucleic acid fragments of any size and sequence may also be comprised by the polynucleotides described in this section.

The invention further embodies purified, isolated, or recombinant polynucleotides comprising a nucleotide sequence selected from the group consisting of the 13 exons of the PCTA-1 gene, or a sequence complementary thereto. The invention also deals with purified, isolated, or recombinant nucleic acids comprising a combination of at least two exons of the PCTA-1 gene, wherein the polynucleotides are arranged within the nucleic acid, from the 5'-end to the 3'-end of said nucleic acid, in the same order as in SEQ ID No 1. In this specific embodiment of a purified or isolated nucleic acid according to the invention, said nucleic acid preferably comprises the exon 0 at its 5' end and the exon 9 or 9ter at its 3' end.

The 3'UTR sequence of PCTA-1 appears to include several polyadenylation sites. These polyadenylation sites could have an influence on the stability of the mRNA resulting from the transcription of the PCTA-1 genomic DNA.

The invention also concerns a purified and/or isolated cDNA sequence encoding a mouse PCTA-1 protein, particularly a cDNA comprising the nucleotide sequence of SEQ ID No 8, a sequence complementary thereto or a fragment and variant thereof. The main characteristics of the murine cDNA are detailed in Table B. Moreover, preferred polynucleotides of the invention include purified, isolated, or recombinant PCTA-1 cDNAs consisting of, consisting essentially of, or comprising the sequence of SEQ ID No 8 and the complementary sequence thereto.

The invention also pertains to a purified or isolated nucleic acid comprising a polynucleotide having at least 95% nucleotide identity with a polynucleotide of SEQ ID No 8, advantageously 99% nucleotide identity, preferably 99.5% nucleotide identity and most preferably 99.8% nucleotide identity with a polynucleotide of SEQ ID No 8, or a sequence complementary thereto or a biologically active fragment thereof.

Another object of the invention consists of purified, isolated or recombinant nucleic acids comprising a polynucleotide that hybridizes, under the stringent hybridization conditions defined herein, with a polynucleotide of SEQ ID No 8, or a sequence complementary thereto or a variant thereof or a biologically active fragment thereof.

Particularly preferred nucleic acids of the invention include isolated, purified, or recombinant polynucleotides comprising a contiguous span of at least 12, 15, 18, 20, 25, 30, 35, 40, 50, 60, 70, 80, 90, 100, 150, 200, 500, or 1000 nucleotides of SEQ ID No 8 or the complements thereof, wherein said contiguous span comprises at least 1, 2, 3, 5, or 10 of the following nucleotide positions of SEQ ID No 8: 1-500, 501-1000, 1001-1500, and 1501-1738.

TABLE B

| cDNA | Position range of 5'UTR | Position range of ORF | | Position range of 3'UTR | Position range of polyadenylation sites |
|---|---|---|---|---|---|
| | | ATG | STOP | | |
| SEQ ID No 2 | 1-200 | 201-203 | 1149-1151 | 1152-5408 | 1773-1778, 3624-3629, 3828-3833, 5119-5124, 5381-5386, 5386-5391 |
| SEQ ID No 3 | 1-200 | 201-203 | 1275-1277 | 1278-5534 | 1899-1904, 3750-3755, 3954-3959, 5245-5250, 5507-5512, 5512-5517 |
| SEQ ID No 4 | 1-200 | 201-203 | 1305-1307 | 1308-2471 | 2182-2187, 2444-2449, 2449-2454 |
| SEQ ID No 8 | 1-120 | 121-123 | 1068-1070 | 1071-1738 | |

While this section is entitled "PCTA-1 cDNA Sequences," it should be noted that nucleic acid fragments of any size and sequence may also be comprised by the polynucleotides described in this section, flanking the genomic sequences of PCTA-1 on either side or between two or more such genomic sequences.

Coding Regions

The invention also concerns a nucleotide sequence encoding the human PCTA-1 protein selected from the group consisting of SEQ ID No 5, 6, 7, sequences complementary thereto and fragments and variants thereof. The present invention embodies isolated, purified, and recombinant polynucleotides which encode polypeptides comprising a contiguous span of at least 6 amino acids, preferably at least 8 or 10 amino acids, more preferably at least 12, 15, 20, 25, 30, 40, 50, or 100 amino acids of SEQ ID No 5, wherein said contiguous span includes:
  a serine residue at amino acid position 170 and/or a lysine residue at amino acid position 203 in SEQ ID No 5; and/or
  at least one residue selected from the group consisting of a tyrosine residue at amino acid position 18, a cysteine residue at amino acid position 35, a methionine residue at amino acid position 55 and an arginine residue at amino acid position 183 in SEQ ID No 5.

The present invention also embodies isolated, purified, and recombinant polynucleotides which encode polypeptides comprising a contiguous span of at least 6 amino acids, preferably at least 8 or 10 amino acids, more preferably at least 12, 15, 20, 25, 30, 40, 50, or 100 amino acids of SEQ ID No 6, wherein said contiguous span includes:
  a serine residue at amino acid position 170 and/or a lysine residue at amino acid position 245 in SEQ ID No 6; and/or
  at least one residue selected from the group consisting of a tyrosine residue at amino acid position 18, a cysteine residue at amino acid position 35, a methionine residue at amino acid position 55 and an arginine residue at amino acid position 225 in SEQ ID No 6; and/or
  at least 1, 2, 3, 5 or 10 of the amino acid encoded by the exon 6bis, more particularly at least 1, 2, 3, 5 or 10 of the amino acid positions 183-224 of the SEQ ID No 6.

The present invention further embodies isolated, purified, and recombinant polynucleotides which encode polypeptides comprising a contiguous span of at least 6 amino acids, preferably at least 8 or 10 amino acids, more preferably at least 12, 15, 20, 25, 30, 40, 50, or 100 amino acids of SEQ ID No 7, wherein said contiguous span includes:
  a serine residue at amino acid position 170 and/or a lysine residue at amino acid position 203 in SEQ ID No 7; and/or
  at least one residue selected from the group consisting of a tyrosine residue at amino acid position 18, a cysteine residue at amino acid position 35, a methionine residue at amino acid position 55 and an arginine residue at amino acid position 183 in SEQ ID No 7; and/or
  at least 1, 2, 3, 5 or 10 of the amino acid encoded by the exons 9bis and 9ter, more particularly at least 1, 2, 3, 5 or 10 of the amino acid positions 313-368 of the SEQ ID No 7.

The invention also concerns a nucleotide sequence encoding the murine PCTA-1 protein of SEQ ID No 9, sequences complementary thereto and fragments and variants thereof. More particularly, the present invention embodies isolated, purified, and recombinant polynucleotides which encode polypeptides comprising a contiguous span of at least 6 amino acids, preferably at least 8 or 10 amino acids, more preferably at least 12, 15, 20, 25, 30, 40, 50, or 100 amino acids of SEQ ID No 9, wherein said contiguous span comprises at least 1, 2, 3, 5, or 10 of the following amino acid positions of SEQ ID No 9: 1-50, 51-100, 101-150, 151-200, 201-250, and 251-316.

The above disclosed polynucleotide that contains the coding sequence of the PCTA-1 gene may be expressed in a desired host cell or a desired host organism, when this polynucleotide is placed under the control of suitable expression signals. The expression signals may be either the expression signals contained in the regulatory regions in the PCTA-1 gene of the invention or in contrast the signals may be exogenous regulatory nucleic sequences. Such a polynucleotide, when placed under the suitable expression signals, may also be inserted in a vector for its expression and/or amplification.

Regulatory Sequences of the PCTA-1 Gene

The present invention also concerns the purified and/or isolated sequences of the upstream regulatory region (5' regulatory region) of the PCTA-1 gene, sequences complementary thereto, and fragments or variants thereof, particularly the nucleotide sequence located between positions 1 and 68647 of SEQ ID No 1, as well as any sequence of 8 to 3000 consecutive nucleotides, preferably of 8 to 500 consecutive nucleotides, included therein. More particularly, the invention further includes specific elements within this regulatory region. These elements include a promoter region. The promoter region appears to be located in the 10 kb region, preferably in the 5 kb region, more preferably in the 2 kb region, still more preferably in the 1 kb region, and more particularly in the 500 bp, upstream of the first exon of the PCTA-1 gene. Preferably, the promoter region has a nucleotide sequence located between positions 66647 and 68647 of SEQ ID No 1 as well as any functional sequence of at least 8 consecutive nucleotide, preferably 8 to 400 consecutive nucleotides, more preferably of 8 to 300 nucleotides included therein, sequences complementary thereto and fragments and variants thereof. Further comments are provided below on this region which is of a particular importance in the present invention.

Also included in the invention are regulatory sequences downstream of the PCTA-1 coding sequence (3' regulatory region) such as those included in the nucleotide sequence located between positions 97156 and 106746 of SEQ ID No 1, sequences complementary thereto and fragments and variants thereof.

In order to identify the relevant biologically active polynucleotide fragments or variants of the 5' or 3' regulatory region, the one skilled in the art will refer to the book of Sambrook et al. (Sambrook et al., 1989) which describes the use of a recombinant vector carrying a marker gene (i.e. beta galactosidase, chloramphenicol acetyl transferase, etc.) the expression of which will be detected when placed under the control of a biologically active polynucleotide fragments or variants of the 5' or 3' regulatory region. Genomic sequences located upstream of the first exon of the PCTA-1 gene are cloned into a suitable promoter reporter vector, such as the pSEAP-Basic, pSEAP-Enhancer, pβgal-Basic, pβgal-Enhancer, or pEGFP-1 Promoter Reporter vectors available from Clontech, or pGL2-basic or pGL3-basic promoterless luciferase reporter gene vector from Promega. Briefly, each of these promoter reporter vectors include multiple cloning sites positioned upstream of a reporter gene encoding a readily assayable protein such as secreted alkaline phosphatase, luciferase, beta galactosidase, or green fluorescent protein. The sequences upstream the PCTA-1 coding region are inserted into the cloning sites upstream of the reporter gene in both orientations and introduced into an appropriate host cell. The level of reporter protein is assayed and compared to the level obtained from a vector which lacks an insert in the cloning site. The presence of an elevated expression level in the vector containing the insert with respect to the control vector indicates the presence of a promoter in the insert. If necessary, the upstream sequences can be cloned into vectors which contain an enhancer for increasing transcription levels from weak promoter sequences. A significant level of expression above that observed with the vector lacking an insert indicates that a promoter sequence is present in the inserted upstream sequence.

Promoter sequences within the upstream genomic DNA may be further defined by constructing nested 5' and/or 3' deletions in the upstream DNA using conventional techniques such as Exonuclease III or appropriate restriction endonuclease digestion. The resulting deletion fragments can be inserted into the promoter reporter vector to determine whether the deletion has reduced or obliterated promoter activity. In this way, the boundaries of the promoters may be defined. If desired, potential individual regulatory sites within the promoter may be identified using site directed mutagenesis or linker scanning to obliterate potential transcription factor binding sites within the promoter individually or in combination. The effects of these mutations on transcription levels may be determined by inserting the mutations into cloning sites in promoter reporter vectors. This type of assay is well-known to those skilled in the art and is described in WO 97/17359, U.S. Pat. No. 5,374,544, EP 582,796, U.S. Pat. No. 5,698,389, U.S. Pat. No. 5,643,746, U.S. Pat. No. 5,502,176, and U.S. Pat. No. 5,266,488, the disclosures of which are incorporated herein by reference in their entireties.

The strength and the specificity of the promoter of the PCTA-1 gene can be assessed through the expression levels of a detectable polynucleotide operably linked to the PCTA-1 promoter in different types of cells and tissues. The detectable polynucleotide may be either a polynucleotide that specifically hybridizes with a predefined oligonucleotide probe, or a polynucleotide encoding a detectable protein, including a PCTA-1 polypeptide or a fragment or a variant thereof. This type of assay is well-known to those skilled in the art and is described in U.S. Pat. No. 5,502,176, and U.S. Pat. No. 5,266,488, the disclosures of which are incorporated herein by reference in their entireties. In one embodiment, the efficacy of the promoter of the PCTA-1 gene is assessed in normal and cancer cells. In a preferred embodiment, the efficacy of the promoter of the PCTA-1 gene is assessed in normal cells and in cancer cells which can present different degrees of malignancy, more preferably cells from prostate tissue. Some of the methods are discussed in more detail below.

Polynucleotides carrying the regulatory elements located at the 5' end and at the 3' end of the PCTA-1 coding region may be advantageously used to control the transcriptional and translational activity of an heterologous polynucleotide of interest.

Thus, the present invention also concerns a purified or isolated nucleic acid comprising a polynucleotide which is selected from the group consisting of the 5' and 3' regulatory regions, or a sequence complementary thereto or a biologically active fragment or variant thereof. "5' regulatory region" refers to the nucleotide sequence located between positions 1 and 68647 of SEQ ID No 1. "3' regulatory region" refers to the nucleotide sequence located between positions 97156 and 106746 of SEQ ID No 1.

The invention also pertains to a purified or isolated nucleic acid comprising a polynucleotide having at least 95% nucleotide identity with a polynucleotide selected from the group consisting of the 5' and 3' regulatory regions, advantageously 99% nucleotide identity, preferably 99.5% nucleotide identity and most preferably 99.8% nucleotide identity with a polynucleotide selected from the group consisting of the 5' and 3' regulatory regions, or a sequence complementary thereto or a biologically active fragment thereof.

Another object of the invention consists of purified, isolated or recombinant nucleic acids comprising a polynucleotide that hybridizes, under the stringent hybridization conditions defined herein, with a polynucleotide selected from the group consisting of the nucleotide sequences of the 5'- and 3' regulatory regions, or a sequence complementary thereto or a variant thereof or a biologically active fragment thereof.

Preferred nucleic acids of the invention include isolated, purified, or recombinant polynucleotides comprising a contiguous span of at least 12, 15, 18, 20, 25, 30, 35, 40, 50, 60, 70, 80, 90, 100, 150, 200, 500, or 1000 nucleotides of SEQ ID No 1 or the complements thereof, wherein said contiguous span comprises at least 1, 2, 3, 5, or 10 of the following nucleotide positions of SEQ ID No 1: 1-4000, 4001-8000, 8001-12000, 12001-16000, 16001-20000, 20001-24000, 24001-28000, 28001-32000, 32001-36000, 36001-40000, 40001-44000, 44001-48000, 48001-52000, 52001-56000, 56001-60000, 60001-64000, 64001-68647. Particularly preferred nucleic acids of the invention include isolated, purified, or recombinant polynucleotides comprising a contiguous span of at least 12, 15, 18, 20, 25, 30, 35, 40, 50, 60, 70, 80, 90, 100, 150, 200, 500, or 1000 nucleotides of SEQ ID No 1 or the complements thereof, wherein said contiguous span comprises at least 1, 2, 3, 5, or 10 of the following nucleotide positions of SEQ ID No 1: 66647-68647.

"Biologically active" polynucleotide derivatives of SEQ ID No 1 are polynucleotides comprising or alternatively consisting of a fragment of said polynucleotide which is functional as a regulatory region for expressing a recombinant polypeptide or a recombinant polynucleotide in a recombinant cell host. It could act either as an enhancer or as a repressor.

For the purpose of the invention, a nucleic acid or polynucleotide is "functional" as a regulatory region for expressing a recombinant polypeptide or a recombinant polynucleotide if said regulatory polynucleotide contains nucleotide sequences which contain transcriptional and translational regulatory information, and such sequences are "operably linked" to nucleotide sequences which encode the desired polypeptide or the desired polynucleotide.

The regulatory polynucleotides of the invention may be prepared from the nucleotide sequence of SEQ ID No 1 by cleavage using suitable restriction enzymes, as described for example in the book of Sambrook et al.(1989). The regulatory polynucleotides may also be prepared by digestion of SEQ ID No 1 by an exonuclease enzyme, such as Bal31 (Wabiko et al., 1986). These regulatory polynucleotides can also be prepared by nucleic acid chemical synthesis, as described elsewhere in the specification.

A preferred 5'-regulatory polynucleotide of the invention includes the 5'-untranslated region (5'-UTR) of the PCTA-1 cDNA, or a biologically active fragment or variant thereof. A preferred 3'-regulatory polynucleotide of the invention includes the 3'-untranslated region (3'-UTR) of the PCTA-1 cDNA, or a biologically active fragment or variant thereof.

A further object of the invention consists of a purified or isolated nucleic acid comprising:
  a) a nucleic acid comprising a regulatory nucleotide sequence selected from the group consisting of:
    (i) a nucleotide sequence comprising a polynucleotide of the 5' regulatory region or a complementary sequence thereto;
    (ii) a nucleotide sequence comprising a polynucleotide having at least 95% of nucleotide identity with the nucleotide sequence of the 5' regulatory region or a complementary sequence thereto;
    (iii) a nucleotide sequence comprising a polynucleotide that hybridizes under stringent hybridization conditions with the nucleotide sequence of the 5' regulatory region or a complementary sequence thereto; and
    (iv) a biologically active fragment or variant of the polynucleotides in (i), (ii) and (iii);
  b) a polynucleotide encoding a desired polypeptide or a nucleic acid of interest, operably linked to the nucleic acid defined in (a) above; and
  c) Optionally, a nucleic acid comprising a 3'-regulatory polynucleotide, preferably a 3'-regulatory polynucleotide of the PCTA-1 gene.

In a specific embodiment of the nucleic acid defined above, said nucleic acid includes the 5'-untranslated region (5'-UTR) of the PCTA-1 cDNA, or a biologically active fragment or variant thereof. In a second specific embodiment of the nucleic acid defined above, said nucleic acid includes the 3'-untranslated region (3'-UTR) of the PCTA-1 cDNA, or a biologically active fragment or variant thereof.

The regulatory polynucleotide of the 5' regulatory region, or its biologically active fragments or variants, is operably linked at the 5'-end of the polynucleotide encoding the desired polypeptide or polynucleotide.

The regulatory polynucleotide of the 3' regulatory region, or its biologically active fragments or variants, is advantageously operably linked at the 3'-end of the polynucleotide encoding the desired polypeptide or polynucleotide.

The desired polypeptide encoded by the above-described nucleic acid may be of various nature or origin, encompassing proteins of prokaryotic or eukaryotic origin. Among the polypeptides expressed under the control of a PCTA-1 regulatory region include bacterial, fungal or viral antigens. Also encompassed are eukaryotic proteins such as intracellular proteins, like "house keeping" proteins, membrane-bound proteins, like receptors, and secreted proteins like endogenous mediators such as cytokines. The desired polypeptide may be the PCTA-1 protein, especially the protein of a amino acid sequence selected from the group consisting of SEQ ID Nos 5, 6, 7, 9, or a fragment or a variant thereof.

The desired nucleic acids encoded by the above-described polynucleotide, usually an RNA molecule, may be complementary to a desired coding polynucleotide, for example to a PCTA-1 coding sequence, and thus useful as an antisense polynucleotide.

Such a polynucleotide may be included in a recombinant expression vector in order to express the desired polypeptide or the desired nucleic acid in host cell or in a host organism. Suitable recombinant vectors that contain a polynucleotide such as described herein are disclosed elsewhere in the specification.

Polynucleotide Constructs

The terms "polynucleotide construct" and "recombinant polynucleotide" are used interchangeably herein to refer to linear or circular, purified or isolated polynucleotides that have been artificially designed and which comprise at least two nucleotide sequences that are not found as contiguous nucleotide sequences in their initial natural environment.

DNA Construct that Enables Directing Temporal and Spatial PCTA-1 Gene Expression in Recombinant Cell Hosts and in Transgenic Animals.

In order to study the physiological and phenotypic consequences of a lack of synthesis of the PCTA-1 protein, both at the cell level and at the multi cellular organism level, the invention also encompasses DNA constructs and recombinant vectors enabling a conditional expression of a specific allele of the PCTA-1 genomic sequence or cDNA and also of a copy of this genomic sequence or cDNA harboring substitutions, deletions, or additions of one or more bases as regards to the PCTA-1 nucleotide sequence of SEQ ID Nos 1, 2, 3, 4, 8, or a fragment thereof, these base substitutions, deletions or additions being located either in an exon, an intron or a regulatory sequence, but preferably in the 5'-regulatory sequence or in an exon of the PCTA-1 genomic sequence or within a PCTA-1 cDNA of SEQ ID Nos 2, 3, 4, or 8. In a preferred embodiment, the PCTA-1 sequence comprises a biallelic marker of the present invention. In a preferred embodiment, the PCTA-1 sequence comprises a biallelic marker of the present invention, preferably one of the biallelic markers A1 to A125 and the complements thereof.

The present invention embodies recombinant vectors comprising any one of the polynucleotides described in the present invention. More particularly, the polynucleotide constructs according to the present invention can comprise any of the polynucleotides described in the "PCTA-1 cDNA Sequences" section, the "Coding Regions" section, and the "Oligonucleotide Probes And Primers" section.

A first preferred DNA construct is based on the tetracycline resistance operon tet from *E. coli* transposon Tn10 for controlling the PCTA-1 gene expression, such as described by Gossen et al.(1992, 1995) and Furth et al.(1994). Such a DNA construct contains seven tet operator sequences from Tn10 (tetop) that are fused to either a minimal promoter or a 5'-regulatory sequence of the PCTA-1 gene, said minimal promoter or said PCTA-1 regulatory sequence being operably linked to a polynucleotide of interest that codes either for a sense or an antisense oligonucleotide or for a polypeptide, including a PCTA-1 polypeptide or a peptide fragment thereof. This DNA construct is functional as a conditional expression system for the nucleotide sequence of interest when the same cell also comprises a nucleotide sequence coding for either the wild type (tTA) or the mutant (rTA) repressor fused to the activating domain of viral protein VP16 of herpes simplex virus, placed under the control of a promoter, such as the HCMVIE1 enhancer/promoter or the MMTV-LTR. Indeed, a preferred DNA construct of the invention comprise both the polynucleotide containing the tet operator sequences and the polynucleotide containing a sequence coding for the tTA or the rTA repressor.

In a specific embodiment, the conditional expression DNA construct contains the sequence encoding the mutant tetracycline repressor rTA, the expression of the polynucleotide of interest is silent in the absence of tetracycline and induced in its presence.

DNA Constructs Allowing Homologous Recombination: Replacement Vectors

A second preferred DNA construct will comprise, from 5'-end to 3'-end: (a) a first nucleotide sequence that is comprised in the PCTA-1 genomic sequence; (b) a nucleotide sequence comprising a positive selection marker, such as the marker for neomycine resistance (neo); and (c) a second nucleotide sequence that is comprised in the PCTA-1 genomic sequence, and is located on the genome downstream the first PCTA-1 nucleotide sequence (a).

In a preferred embodiment, this DNA construct also comprises a negative selection marker located upstream the nucleotide sequence (a) or downstream the nucleotide sequence (c). Preferably, the negative selection marker consists of the thymidine kinase (tk) gene (Thomas et al., 1986), the hygromycine beta gene (Te Riele et al., 1990), the hprt gene (Van der Lugt et al., 1991; Reid et al., 1990) or the Diphteria toxin A fragment (Dt-A) gene (Nada et al., 1993; Yagi et al.1990). Preferably, the positive selection marker is located within a PCTA-I exon sequence so as to interrupt the sequence encoding a PCTA-1 protein. These replacement vectors are described, for example, by Thomas et al.(1986; 1987), Mansour et al.(1988) and Koller et al.(1992).

The first and second nucleotide sequences (a) and (c) may be indifferently located within a PCTA-1 regulatory sequence, an intronic sequence, an exon sequence or a sequence containing both regulatory and/or intronic and/or exon sequences. The size of the nucleotide sequences (a) and (c) ranges from 1 to 50 kb, preferably from 1 to 10 kb, more preferably from 2 to 6 kb and most preferably from 2 to 4 kb.

DNA Constructs Allowing Homologous Recombination: Cre-LoxP System.

These new DNA constructs make use of the site specific recombination system of the P1 phage. The P1 phage possesses a recombinase called Cre which interacts specifically with a 34 base pairs loxP site. The loxP site is composed of two palindromic sequences of 13 bp separated by a 8 bp conserved sequence (Hoess et al., 1986). The recombination by the Cre enzyme between two loxP sites having an identical orientation leads to the deletion of the DNA fragment.

The Cre-loxP system used in combination with a homologous recombination technique has been first described by Gu et al.(1993, 1994). Briefly, a nucleotide sequence of interest to be inserted in a targeted location of the genome harbors at least two loxP sites in the same orientation and located at the respective ends of a nucleotide sequence to be excised from the recombinant genome. The excision event requires the presence of the recombinase (Cre) enzyme within the nucleus of the recombinant cell host. The recombinase enzyme may be brought at the desired time either by (a) incubating the recombinant cell hosts in a culture medium containing this enzyme, by injecting the Cre enzyme directly into the desired cell, such as described by Araki et al.(1995), or by lipofection of the enzyme into the cells, such as described by Baubonis et al.(1993); (b)transfecting the cell host with a vector comprising the Cre coding sequence operably linked to a promoter functional in the recombinant cell host, which promoter being optionally inducible, said vector being introduced in the recombinant cell host, such as described by Gu et al.(1993) and Sauer et al.(1988); (c) introducing in the genome of the cell host a polynucleotide comprising the Cre coding sequence operably linked to a promoter functional in the recombinant cell host, which promoter is optionally inducible, and said polynucleotide being inserted in the genome of the cell host either by a random insertion event or an homologous recombination event, such as described by Gu et al. (1994).

In a specific embodiment, the vector containing the sequence to be inserted in the PCTA-1 gene by homologous recombination is constructed in such a way that selectable markers are flanked by loxP sites of the same orientation, it is possible, by treatment by the Cre enzyme, to eliminate the selectable markers while leaving the PCTA-1 sequences of interest that have been inserted by an homologous recombination event. Again, two selectable markers are needed: a positive selection marker to select for the recombination event and a negative selection marker to select for the homologous recombination event. Vectors and methods using the Cre-loxP system are described by Zou et al.(1994).

Thus, a third preferred DNA construct of the invention comprises, from 5'-end to 3'-end: (a) a first nucleotide sequence that is comprised in the PCTA-1 genomic sequence; (b) a nucleotide sequence comprising a polynucleotide encoding a positive selection marker, said nucleotide sequence comprising additionally two sequences defining a site recognized by a recombinase, such as a loxP site, the two sites being placed in the same orientation; and (c) a second nucleotide sequence that is comprised in the PCTA-1 genomic sequence, and is located on the genome downstream of the first PCTA-1 nucleotide sequence (a).

The sequences defining a site recognized by a recombinase, such as a loxP site, are preferably located within the nucleotide sequence (b) at suitable locations bordering the nucleotide sequence for which the conditional excision is sought. In one specific embodiment, two loxP sites are located at each side of the positive selection marker sequence, in order to allow its excision at a desired time after the occurrence of the homologous recombination event.

In a preferred embodiment of a method using the third DNA construct described above, the excision of the polynucleotide fragment bordered by the two sites recognized by a recombinase, preferably two loxP sites, is performed at a desired time, due to the presence within the genome of the recombinant host cell of a sequence encoding the Cre enzyme operably linked to a promoter sequence, preferably an inducible promoter, more preferably a tissue-specific promoter sequence and most preferably a promoter sequence which is both inducible and tissue-specific, such as described by Gu et al.(1994).

The presence of the Cre enzyme within the genome of the recombinant cell host may result of the breeding of two transgenic animals, the first transgenic animal bearing the PCTA-1-derived sequence of interest containing the loxP sites as described above and the second transgenic animal bearing the Cre coding sequence operably linked to a suitable promoter sequence, such as described by Gu et al.(1994).

Spatio-temporal control of the Cre enzyme expression may also be achieved with an adenovirus based vector that contains the Cre gene thus allowing infection of cells, or in vivo infection of organs, for delivery of the Cre enzyme, such as described by Anton and Graham (1995) and Kanegae et al. (1995).

The DNA constructs described above may be used to introduce a desired nucleotide sequence of the invention, preferably a PCTA-1 genomic sequence or a PCTA-1 cDNA sequence, and most preferably an altered copy of a PCTA-1 genomic or cDNA sequence, within a predetermined location of the targeted genome, leading either to the generation of an altered copy of a targeted gene (knock-out homologous recombination) or to the replacement of a copy of the targeted gene by another copy sufficiently homologous to allow an homologous recombination event to occur (knock-in homologous recombination). In a specific embodiment, the DNA constructs described above may be used to introduce a PCTA-1 genomic sequence or a PCTA-1 cDNA sequence comprising at least one biallelic marker of the present invention, preferably at least one biallelic marker selected from the group consisting of A1 to A125 and the complements thereof.

Oligonucleotide Probes and Primers

Polynucleotides derived from the PCTA-1 gene are useful in order to detect the presence of at least a copy of a nucleotide sequence of SEQ ID No 1, or a fragment, complement, or variant thereof in a test sample.

Particularly preferred probes and primers of the invention include isolated, purified, or recombinant polynucleotides comprising a contiguous span of at least 12, 15, 18, 20, 25, 30, 35, 40, 50, 60, 70, 80, 90, 100, 150, 200, 500, or 1000 nucleotides of SEQ ID No 1 or the complements thereof, wherein said contiguous span comprises at least 1, 2, 3, 5, or 10 of the following nucleotide positions of SEQ ID No 1: 1-70715, 70795-82207, 82297-83612, 83824-85297, 85418-86388, 86446-87495, 87523-88294, 88384-89483, 89650-92748, 97156-98309, 98476-99329, 99491-100026, 100212-100281, 100396-100538, 100682-100833, 100995-101920, 102087-102970, 103264-103724, and 103753-106746. Additional preferred probes and primers of the invention include isolated, purified, or recombinant polynucleotides comprising a contiguous span of at least 12, 15, 18, 20, 25, 30, 35, 40, 50, 60, 70, 80, 90, 100, 150, 200, 500, or 1000 nucleotides of SEQ ID No 1 or the complements thereof, wherein said contiguous span comprises at least one nucleotide selected from the group consisting of a nucleotide G at positions 70728, 87860, 88297, 94432, and 95340 of SEQ ID No 1; a nucleotide A at positions 82218, 83644, 83808, 87787, 87806, 94218, and 97144 of SEQ ID No 1; a nucleotide C at positions 87902, 88215, 88283, 92760, 93726, and 94422 of SEQ ID No 1; and a nucleotide T at positions 93903, and 94170 of SEQ ID No 1. Other preferred probes and primers of the invention include isolated, purified, or recombinant polynucleotides comprising a contiguous span of at least 12, 15, 18, 20, 25, 30, 35, 40, 50, 60, 70, 80, 90, 100, 150, 200, 500, or 1000 nucleotides of SEQ ID No 1 or the complements thereof, wherein said contiguous span comprises at least one nucleotide selected from the group consisting of a nucleotide G at positions 86435, 93592, 93680, 93681, 93682, 93728, 93761, and 95445 of SEQ ID No 1; a nucleotide A at positions 86434, 88355, 93240, 93471, and 93747 of SEQ ID No 1; a nucleotide C at positions 93683, 95126, and 95444 of SEQ ID No 1; and a nucleotide T at positions 94154, and 94430 of SEQ ID No 1. Other preferred probes and primers of the invention include isolated, purified, or recombinant polynucleotides comprising a contiguous span of at least 12, 15, 18, 20, 25, 30, 35, 40, 50, 60, 70, 80, 90, 100, 150, 200, 500, or 1000 nucleotides of SEQ ID No 1 or the complements thereof, wherein said contiguous span comprises nucleotide positions selected from the group consisting of the nucleotide positions of SEQ ID No 1: 92975-92977, 93711-93715, 94151-94153, 94240-94243, 94770-94773, 94804-94808, 95121-95122, 95129-95135, 95148-95153, 95154-95159, 95173-95178, 95367-95374, 95410-95413, 95418-95420, 95430-95436, 95533-95535, and 95677-95677.

Another object of the invention is a purified, isolated, or recombinant polynucleotide comprising the nucleotide sequence of SEQ ID No 2, complementary sequences thereto, as well as allelic variants, and fragments thereof. Particularly preferred probes and primers of the invention include isolated, purified, or recombinant polynucleotides comprising a contiguous span of at least 12, 15, 18, 20, 25, 30, 35, 40, 50, 60, 70, 80, 90, 100, 150, 200, 500, or 1000 nucleotides of SEQ ID No 2 or the complements thereof, wherein said contiguous span comprises at least 1, 2, 3, 5, or 10 of the nucleotide positions 1-162 of SEQ ID No 2. Additional preferred probes and primers of the invention include isolated, purified, or recombinant polynucleotides comprising a contiguous span of at least 12, 15, 18, 20, 25, 30, 35, 40, 50, 60, 70, 80, 90, 100, 150, 200, 500, or 1000 nucleotides of SEQ ID No 2 or the complements thereof, wherein said contiguous span comprises at least one nucleotide selected from the group consisting of a nucleotide A at positions 253, 363, 527, 2471, and 5397 of SEQ ID No 2; a nucleotide C at positions 1013, 1979, and 2675 of SEQ ID No 2; a nucleotide G at positions 176, 749, 2685, 3593 of SEQ ID No 2; and a nucleotide T at positions 2156, and 2423 of SEQ ID No 2. Particularly preferred probes and primers of the invention include isolated, purified, or recombinant polynucleotides comprising a contiguous span of at least 12, 15, 18, 20, 25, 30, 35, 40, 50, 60, 70, 80, 90, 100, 150, 200, 500, or 1000 nucleotides of SEQ ID No 2 or the complements thereof, wherein said contiguous span comprises at least one nucleotide selected from the group consisting of a nucleotide A at positions 708, 807, 1493, 1724, and 2000; a nucleotide C at positions 1936, 3379, and 3697; a nucleotide G at positions 709, 1845, 1933, 1934, 1935, 1981, 2014, and 3698; and a nucleotide T at positions 2407, and 2683 of SEQ ID No 2. Other preferred probes and primers of the invention include isolated, purified, or recombinant polynucleotides comprising a contiguous span of at least 12, 15, 18, 20, 25, 30, 35, 40, 50, 60, 70, 80, 90, 100, 150, 200, 500, or 1000 nucleotides of SEQ ID No 2 or the complements thereof, wherein said contiguous span comprises nucleotide positions selected from the group consisting of the nucleotide positions of SEQ ID No 2: 1229-1231, 1964-1968, 2404-2406, 2493-2496, 3023-3026, 3057-3061, 3374-3375, 3382-3388, 3401-3406, 3407-3412, 3426-3431, 3620-3627, 3663-3666, 3671-3673, 3683-3689, 3786-3788 and 3930-3932.

A further object of the invention is a purified, isolated, or recombinant polynucleotide comprising the nucleotide sequence of SEQ ID No 3, complementary sequences thereto, as well as allelic variants, and fragments thereof. Particularly preferred probes and primers of the invention include isolated, purified, or recombinant polynucleotides comprising a contiguous span of at least 12, 15, 18, 20, 25, 30, 35, 40, 50, 60, 70, 80, 90, 100, 150, 200, 500, or 1000 nucleotides of SEQ ID No 3 or the complements thereof, wherein said contiguous span comprises at least 1, 2, 3, 5, or 10 of the following nucleotide positions of SEQ ID No 3: 1-162 and 747-872. Additional preferred probes and primers of the invention include isolated, purified, or recombinant polynucleotides comprising a contiguous span of at least 12, 15, 18, 20, 25, 30, 35, 40, 50, 60, 70, 80, 90, 100, 150, 200, 500, or 1000 nucleotides of SEQ ID No 3 or the complements thereof, wherein said contiguous span comprises at least one nucleotide selected from the group consisting of a nucleotide A at positions 253, 363, 527, 2597, and 5523 of SEQ ID No 3; a nucleotide C at positions 1139, 2105, and 2801 of SEQ ID No 3; a nucleotide G at positions 176, 875, 2811, 3719 of SEQ ID No 3; and a nucleotide T at positions 2282, and 2549 of SEQ ID No 3. Additional preferred probes and primers of the invention include isolated, purified, or recombinant polynucleotides comprising a contiguous span of at least 12, 15, 18, 20, 25, 30, 35, 40, 50, 60, 70, 80, 90, 100, 150, 200, 500, or 1000 nucleotides of SEQ ID No 3 or the complements thereof, wherein said contiguous span comprises at least one nucleotide selected from the group consisting of a nucleotide A at positions 708, 807, 1619, 1850, and 2126; a nucleotide C at positions 2062, 3505, and 3823; a nucleotide G at positions 709, 1971, 2059, 2060, 2061, 2107, 2140, and 3824; and a nucleotide T at positions 2533, and 2809 of SEQ ID No 3. Other preferred probes and primers of the invention include isolated, purified, or recombinant polynucleotides comprising a contiguous span of at least 12, 15, 18, 20, 25, 30, 35, 40, 50, 60, 70, 80, 90, 100, 150, 200, 500, or 1000 nucleotides of SEQ ID No 3 or the complements thereof, wherein said contiguous span comprises nucleotide positions selected from the group consisting of the nucleotide positions of SEQ ID No 3: 1355-1357, 1892-1894,2090-2094, 2530-2532, 2619-2622, 3149-3152,3183-3187, 3500-3501,3508-3514, 3527-3532, 3533-3538, 3552-3557, 3746-3749, 3789-3792, 3797-3799, 3809-3815, 3912-3914 and 40564058.

An additional object of the invention is a purified, isolated, or recombinant polynucleotide comprising the nucleotide sequence of SEQ ID No 4, complementary sequences thereto, as well as allelic variants, and fragments thereof. Particularly preferred probes and primers of the invention include isolated, purified, or recombinant polynucleotides comprising a contiguous span of at least 12, 15, 18, 20, 25, 30, 35, 40, 50, 60, 70, 80, 90, 100, 150, 200, 500, or 1000 nucleotides of SEQ ID No 4 or the complements thereof, wherein said contiguous span comprises at least 1, 2, 3, 5, or 10 of the nucleotide positions 1-162 of SEQ ID No 4. Additional preferred probes and primers of the invention include isolated, purified, or recombinant polynucleotides comprising a contiguous span of at least 12, 15, 18, 20, 25, 30, 35, 40, 50, 60, 70, 80, 90, 100, 150, 200, 500, or 1000 nucleotides of SEQ ID No 4 or the complements thereof, wherein said contiguous span comprises at least one nucleotide selected from the group consisting of a nucleotide A at positions 253, 363, 527 and 2460 of SEQ ID No 4; a nucleotide C at position 1013 of SEQ ID No 4; and a nucleotide G at positions 176 and 749 of SEQ ID No 4. Additionally preferred probes and primers of the invention include isolated, purified, or recombinant polynucleotides comprising a contiguous span of at least 12, 15, 18, 20, 25, 30, 35, 40, 50, 60, 70, 80, 90, 100, 150, 200, 500, or 1000 nucleotides of SEQ ID No 4 or the complements thereof, wherein said contiguous span comprises at least one nucleotide selected from the group consisting of a nucleotide A at positions 708 and 807 and a nucleotide G at position 709 of SEQ ID No 4. Other preferred probes and primers of the invention include isolated, purified, or recombinant polynucleotides comprising a contiguous span of at least 12, 15, 18, 20, 25, 30, 35, 40, 50, 60, 70, 80, 90, 100, 150, 200, 500, or 1000 nucleotides of SEQ ID No 4 or the complements thereof, wherein said contiguous span comprises the pairs of nucleotide positions 1136-1137 of SEQ ID No 4.

One more object of the invention is a purified, isolated, or recombinant polynucleotide comprising the nucleotide sequence of SEQ ID No 8, complementary sequences thereto, as well as allelic variants, and fragments thereof. Particularly preferred nucleic acids of the invention include isolated, purified, or recombinant polynucleotides comprising a contiguous span of at least 12, 15, 18, 20, 25, 30, 35, 40, 50, 60, 70, 80, 90, 100, 150, 200, 500, or 1000 nucleotides of SEQ ID No 8 or the complements thereof, wherein said contiguous span comprises at least 1, 2, 3, 5, or 10 of the following nucleotide positions of SEQ ID No 8: 1-500, 501-1000, 1001-1500, and 1501-1738.

Thus, the invention also relates to nucleic acid probes characterized in that they hybridize specifically, under the stringent hybridization conditions defined above, with a nucleic acid selected from the group consisting of the nucleotide sequences:

a) 1-70715, 70795-82207, 82297-83612, 83824-85297, 85418-86388, 86446-87495, 87523-88294, 88384-89483, 89650-92748, 97156-98309, 98476-99329, 99491-100026, 100212-100281, 100396-100538, 100682-100833, 100995-101920, 102087-102970, 103264-103724, and 103753-106746 of SEQ ID No 1 or a variant thereof or a sequence complementary thereto;

b) 1-162 of SEQ ID No 2 or a variant thereof or a sequence complementary thereto;

c) 1-162 and 747-872 of SEQ ID No 3 or a variant thereof or a sequence complementary thereto;

d) 1-162 of SEQ ID No 4 or a variant thereof or a sequence complementary thereto; and e) SEQ ID No 8 or a variant thereof or a sequence complementary thereto.

In a preferred embodiment, the oligonucleotides of the invention can hybridize with at least a portion of an intron or of the regulatory sequences of the PCTA-1 gene. Particularly preferred oligonucleotides of the invention hybridize with a sequence comprised in an intron or in the regulatory sequences of the PCTA-1 gene. In an other preferred embodiment, the oligonucleotides of the invention can hybridize with at least a portion of an exon selected from the group of exons 0, 1, 6bis, 9, and 9ter.

The present invention also concerns oligonucleotides and groups of oligonucleotides for the detection of alleles of biallelic markers of the PCTA-1 gene, preferably those associated with cancer, preferably with prostate cancer, with an early onset of prostate cancer, with a susceptibility to prostate cancer, with the level of aggressiveness of prostate cancer tumors, with a modified or forthcoming expression of the PCTA-1 gene, with a modified or forthcoming production of the PCTA-1 protein, or with the production of a modified PCTA-1 protein. These oligonucleotides are characterized in that they can hybridize with a PCTA-1 gene, preferably with a polymorphic PCTA-1 gene and more preferably with a region of a PCTA-1 gene comprising a polymorphic site containing a specific allele associated with prostate cancer, with the level of aggressiveness of prostate cancer tumors or with modifications in the regulation of expression of the PCTA-1 gene. These oligonucleotides are useful either as primers for use in various processes such as DNA amplification and microsequencing or as probes for DNA recognition in hybridization analyses.

Therefore, another preferred embodiment of a probe according to the invention consists of a nucleic acid comprising a biallelic marker selected from the group consisting of A1 to A125 or the complements thereof, for which the respective locations in the sequence listing are provided in Table 2. In some embodiments, the oligonucleotides comprise the polymorphic base of a sequence selected from P1 to P125, and the complementary sequences thereto. In other embodiments, the oligonucleotides have a 3' terminus immediately adjacent to a polymorphic base in the PCTA-1 gene, such as a polymorphic base comprised in one of the sequences P1 to P125, and the complementary sequence thereto. In other embodiments, the oligonucleotide is capable of discriminating between different alleles of a biallelic marker in the PCTA-1 gene, including the biallelic markers A1 to A125 and the complements thereof.

In one embodiment the invention encompasses isolated, purified, and recombinant polynucleotides consisting of, or consisting essentially of a contiguous span of 8 to 50 nucleotides of any one of SEQ ID Nos 1, 2, 3, 4 and the complement thereof, wherein said span includes a PCTA-1-related biallelic marker in said sequence; optionally, wherein said PCTA-1-related biallelic marker is selected from the group consisting of A1 to A125, and the complements thereof, or optionally the biallelic markers in linkage disequilibrium therewith; optionally, wherein said PCTA-1-related biallelic marker is selected from the group consisting of A1 to A44, A46 to A53, A57, A58, A62 to A76, A81, A82, A86 to A91, A107, A118, and A123 to A125, and the complements thereof, or optionally the biallelic markers in linkage disequilibrium therewith; optionally, wherein said PCTA-1-related biallelic marker is selected from the group consisting of A45, A54, A60, A61, A77 to A80, A83 to A85, A93, A102 to A106, A109, A110, A114, and A122, and the complements thereof, or optionally the biallelic markers in linkage disequilibrium therewith; optionally, wherein said PCTA-1-related biallelic marker is selected from the group consisting of A55, A56, A59, A92, A94 to A101, A108, A111 to A113, A115 to A117, and A119 to A121, and the complements thereof, or optionally the biallelic markers in linkage disequilibrium therewith; optionally, wherein said contiguous span is 18 to 47 nucleotides in length and said biallelic marker is within 4 nucleotides of the center of said polynucleotide; optionally, wherein said polynucleotide consists of said contiguous span and said contiguous span is 25 nucleotides in length and said biallelic marker is at the center of said polynucleotide; optionally, wherein said polynucleotide consists of said contiguous span and said contiguous span is 47 nucleotides in length and said biallelic marker is at the center of said polynucleotide; optionally, wherein the 3' end of said contiguous span is present at the 3' end of said polynucleotide; and optionally, wherein the 3' end of said contiguous span is located at the 3' end of said polynucleotide and said biallelic marker is present at the 3' end of said polynucleotide. In a preferred embodiment, said probes comprises, consists of, or consists essentially of a sequence selected from the following sequences: P1 to P125 and the complementary sequences thereto.

In another embodiment the invention encompasses isolated, purified and recombinant polynucleotides comprising, consisting of, or consisting essentially of a contiguous span of 8 to 50 nucleotides of SEQ ID Nos 1, 2, 3, 4, or the complements thereof, wherein the 3' end of said contiguous span is located at the 3' end of said polynucleotide, and wherein the 3' end of said polynucleotide is located within 20 nucleotides upstream of a PCTA-1-related biallelic marker in said sequence; optionally, wherein said PCTA-1-related biallelic marker is selected from the group consisting of A1 to A125, and the complements thereof, or optionally the biallelic markers in linkage disequilibrium therewith; optionally, wherein said PCTA-1-related biallelic marker is selected from the group consisting of A1 to A44, A46 to A53, A57, A58, A62 to A76, A81, A82, A86 to A91, A107, A118, and A123 to A125, and the complements thereof, or optionally the biallelic markers in linkage disequilibrium therewith; optionally, wherein said PCTA-1-related biallelic marker is selected from the group consisting of A45, A54, A60, A61, A77 to A80, A83 to A85, A93, A102 to A106, A109, A110, A114, and A122, and the complements thereof, or optionally the biallelic markers in linkage disequilibrium therewith; optionally, wherein said PCTA-1-related biallelic marker is selected from the group consisting of A55, A56, A59, A92, A94 to A101, A108, A111 to A113, A115 to A117, and A119 to A121, and the complements thereof, or optionally the biallelic markers in linkage disequilibrium therewith; optionally, wherein the 3' end of said polynucleotide is located 1 nucleotide upstream of said PCTA-1-related biallelic marker in said sequence; and optionally, wherein said polynucleotide consists essentially of a sequence selected from the following sequences: D1 to D125 and E1 to E125.

In a further embodiment, the invention encompasses isolated, purified, or recombinant polynucleotides comprising, consisting of, or consisting essentially of a sequence selected from the following sequences: B1 to B47 and C1 to C47.

In an additional embodiment, the invention encompasses polynucleotides for use in hybridization assays, sequencing assays, and enzyme-based mismatch detection assays for determining the identity of the nucleotide at a PCTA-1-related biallelic marker in SEQ ID Nos 1, 2, 3, 4, or the complements thereof, as well as polynucleotides for use in amplifying segments of nucleotides comprising a PCTA-1-related biallelic marker in SEQ ID Nos 1, 2, 3, 4, or the complements thereof; optionally, wherein said PCTA-1-related biallelic marker is selected from the group consisting of A1 to A125, and the complements thereof, or optionally the biallelic markers in linkage disequilibrium therewith; optionally, wherein said PCTA-1-related biallelic marker is selected from the group consisting of A1 to A44, A46 to A53, A57, A58, A62 to A76, A81, A82, A86 to A91, A107, A118, and A123 to A125, and the complements thereof, or optionally the biallelic markers in linkage disequilibrium therewith; optionally, wherein said PCTA-1-related biallelic marker is selected from the group consisting of A45, A54, A60, A61, A77 to A80, A83 to A85, A93, A102 to A106, A109, A110, A114, and A122, and the complements thereof, or optionally the biallelic markers in linkage disequilibrium therewith; optionally, wherein said PCTA-1-related biallelic marker is selected from the group consisting of A55, A56, A59, A92, A94 to A101, A108, A111 to A113, A115 to A117, and A119 to A121, and the complements thereof, or optionally the biallelic markers in linkage disequilibrium therewith.

The formation of stable hybrids depends on the melting temperature (Tm) of the DNA. The Tm depends on the length of the primer or probe, the ionic strength of the solution and the G+C content. The higher the G+C content of the primer or probe, the higher is the melting temperature because G:C pairs are held by three H bonds whereas A:T pairs have only two. The GC content in the probes of the invention usually ranges between 10 and 75%, preferably between 35 and 60%, and more preferably between 40 and 55%.

A probe or a primer according to the invention has between 8 and 1000 nucleotides in length, or is specified to be at least 12, 15, 18, 20, 25, 35, 40, 50, 60, 70, 80, 100, 250, 500 or 1000 nucleotides in length. More particularly, the length of these probes and primers can range from 8, 10, 15, 20, or 30 to 100 nucleotides, preferably from 10 to 50, more preferably from 15 to 30 nucleotides. Shorter probes and primers tend to lack specificity for a target nucleic acid sequence and generally require cooler temperatures to form sufficiently stable hybrid complexes with the template. Longer probes and primers are expensive to produce and can sometimes self-hybridize to form hairpin structures. The appropriate length for primers and probes under a particular set of assay conditions may be empirically determined by one of skill in the art. A preferred probe or primer consists of a nucleic acid comprising a polynucleotide selected from the group of the nucleotide sequences of P1 to P125 and the complementary sequence thereto, B1 to B47, C1 to C47, D1 to D125, E1 to E125, for which the respective locations in the sequence listing are provided in Tables 1, 2, 3 and 4.

The primers and probes can be prepared by any suitable method, including, for example, cloning and restriction of appropriate sequences and direct chemical synthesis by a method such as the phosphodiester method of Narang et al.(1979), the phosphodiester method of Brown et al.(1979), the diethylphosphoramidite method of Beaucage et al.(1981) and the solid support method described in EP 0 707 592, the disclosure of which is incorporated herein by reference in its entirety.

Detection probes are generally nucleic acid sequences or uncharged nucleic acid analogs such as, for example peptide nucleic acids which are disclosed in International Patent Application WO 92/20702, morpholino analogs which are described in U.S. Pat. Nos. 5,185,444; 5,034,506 and 5,142,047, the disclosures of which are incorporated herein by reference in their entireties. The probe may have to be rendered "non-extendable" in that additional dNTPs cannot be added to the probe. In and of themselves analogs usually are non-extendable and nucleic acid probes can be rendered non-extendable by modifying the 3' end of the probe such that the hydroxyl group is no longer capable of participating in elongation. For example, the 3' end of the probe can be functionalized with the capture or detection label to thereby consume or otherwise block the hydroxyl group. Alternatively, the 3' hydroxyl group simply can be cleaved, replaced or modified, U.S. patent application Ser. No. 07/049,061 filed Apr. 19, 1993 describes modifications, which can be used to render a probe non-extendable.

Any of the polynucleotides of the present invention can be labeled, if desired, by incorporating any label known in the art to be detectable by spectroscopic, photochemical, biochemical, immunochemical, or chemical means. For example, useful labels include radioactive substances (including, $^{32}P$, $^{35}S$, $^{3}H$, $^{125}I$), fluorescent dyes (including, 5-bromodesoxyuridin, fluorescein, acetylaminofluorene, digoxigenin) or biotin. Preferably, polynucleotides are labeled at their 3' and 5' ends. Examples of non-radioactive labeling of nucleic acid fragments are described in the French patent No. FR-7810975 or by Urdea et al (1988) or Sanchez-Pescador et al (1988), the disclosures of which are incorporated herein by reference in their entireties. In addition, the probes according to the present invention may have structural characteristics such that they allow the signal amplification, such structural characterists being, for example, branched DNA probes as those described by Urdea et al. in 1991 or in the European patent No. EP 0 225 807 (Chiron), the disclosures of which are incorporated herein by reference in their entireties.

A label can also be used to capture the primer, so as to facilitate the immobilization of either the primer or a primer extension product, such as amplified DNA, on a solid support. A capture label is attached to the primers or probes and can be a specific binding member which forms a binding pair with the solid's phase reagent's specific binding member (e.g. biotin and streptavidin). Therefore depending upon the type of label carried by a polynucleotide or a probe, it may be employed to capture or to detect the target DNA. Further, it will be understood that the polynucleotides, primers or probes provided herein, may, themselves, serve as the capture label. For example, in the case where a solid phase reagent's binding member is a nucleic acid sequence, it may be selected such that it binds a complementary portion of a primer or probe to thereby immobilize the primer or probe to the solid phase. In cases where a polynucleotide probe itself serves as the binding member, those skilled in the art will recognize that the probe will contain a sequence or "tail" that is not complementary to the target. In the case where a polynucleotide primer itself serves as the capture label, at least a portion of the primer will be free to hybridize with a nucleic acid on a solid phase. DNA Labeling techniques are well known to the skilled technician.

The probes of the present invention are useful for a number of purposes. They can be notably used in Southern hybridization to genomic DNA. The probes can also be used to detect PCR amplification products. They may also be used to detect mismatches in the PCTA-1 gene or mRNA using other techniques.

Any of the polynucleotides, primers and probes of the present invention can be conveniently immobilized on a solid support. Solid supports are known to those skilled in the art and include the walls of wells of a reaction tray, test tubes, polystyrene beads, magnetic beads, nitrocellulose strips, membranes, microparticles such as latex particles, sheep (or other animal) red blood cells, duracytes and others. The solid support is not critical and can be selected by one skilled in the art. Thus, latex particles, microparticles, magnetic or non-magnetic beads, membranes, plastic tubes, walls of microtiter wells, glass or silicon chips, sheep (or other suitable animal's) red blood cells and duracytes are all suitable examples. Suitable methods for immobilizing nucleic acids on solid phases include ionic, hydrophobic, covalent interactions and the like. A solid support, as used herein, refers to any material which is insoluble, or can be made insoluble by a subsequent reaction. The solid support can be chosen for its intrinsic ability to attract and immobilize the capture reagent. Alternatively, the solid phase can retain an additional receptor which has the ability to attract and immobilize the capture reagent. The additional receptor can include a charged substance that is oppositely charged with respect to the capture reagent itself or to a charged substance conjugated to the capture reagent. As yet another alternative, the receptor molecule can be any specific binding member which is immobilized upon (attached to) the solid support and which has the ability to immobilize the capture reagent through a specific binding reaction. The receptor molecule enables the indirect binding of the capture reagent to a solid support material before the performance of the assay or during the performance of the assay. The solid phase thus can be a plastic, derivatized plastic, magnetic or non-magnetic metal, glass or silicon surface of a test tube, microtiter well, sheet, bead, microparticle, chip, sheep (or other suitable animal's) red blood cells, duracytes® and other configurations known to those of ordinary skill in the art. The polynucleotides of the invention can be attached to or immobilized on a solid support individually or in groups of at least 2, 5, 8, 10, 12, 15, 20, or 25 distinct polynucleotides of the invention to a single solid support. In addition, polynucleotides other than those of the invention may be attached to the same solid support as one or more polynucleotides of the invention.

Consequently, the invention also deals with a method for detecting the presence of a nucleic acid comprising a nucleotide sequence selected from a group consisting of SEQ ID Nos 1, 2, 3, 4, 8, a fragment or a variant thereof and a complementary sequence thereto in a sample, said method comprising the following steps of:

a) bringing into contact a nucleic acid probe or a plurality of nucleic acid probes which can hybridize with a nucleotide sequence included in a nucleic acid selected form the group consisting of the nucleotide sequences of SEQ ID Nos 1, 2, 3, 4, 8, a fragment or a variant thereof and a complementary sequence thereto and the sample to be assayed; and b) detecting the hybrid complex formed between the probe and a nucleic acid in the sample.

The invention further concerns a kit for detecting the presence of a nucleic acid comprising a nucleotide sequence selected from a group consisting of SEQ ID Nos 1, 2, 3, 4, 8, a fragment thereof or a variant thereof and a complementary sequence thereto in a sample, said kit comprising:

a) a nucleic acid probe or a plurality of nucleic acid probes which can hybridize with a nucleotide sequence included in a nucleic acid selected form the group consisting of the nucleotide sequences of SEQ ID Nos 1, 2, 3, 4, 8, a fragment or a variant thereof and a complementary sequence thereto; and b) optionally, the reagents necessary for performing the hybridization reaction.

In a first preferred embodiment of this detection method and kit, said nucleic acid probe or the plurality of nucleic acid probes are labeled with a detectable molecule. In a second preferred embodiment of said method and kit, said nucleic acid probe or the plurality of nucleic acid probes has been immobilized on a substrate. In a third preferred embodiment, the nucleic acid probe or the plurality of nucleic acid probes comprise either a sequence which is selected from the group consisting of the nucleotide sequences of P1 to P125 and the complementary sequence thereto, B1 to B47, C1 to C47, D1 to D125, E1 to E125 or a biallelic marker selected from the group consisting of A1 to A125 and the complements thereto.

Oligonucleotide Arrays

A substrate comprising a plurality of oligonucleotide primers or probes of the invention may be used either for detecting or amplifying targeted sequences in the PCTA-1 gene and may also be used for detecting mutations in the coding or in the non-coding sequences of the PCTA-1 gene.

Any polynucleotide provided herein may be attached in overlapping areas or at random locations on the solid support. Alternatively the polynucleotides of the invention may be attached in an ordered array wherein each polynucleotide is attached to a distinct region of the solid support which does not overlap with the attachment site of any other polynucleotide. Preferably, such an ordered array of polynucleotides is designed to be "addressable" where the distinct locations are recorded and can be accessed as part of an assay procedure. Addressable polynucleotide arrays typically comprise a plurality of different oligonucleotide probes that are coupled to a surface of a substrate in different known locations. The knowledge of the precise location of each polynucleotides location makes these "addressable" arrays particularly useful in hybridization assays. Any addressable array technology known in the art can be employed with the polynucleotides of the invention. One particular embodiment of these polynucleotide arrays is known as the Genechips™, and has been generally described in U.S. Pat. No. 5,143,854; PCT publications WO 90/15070 and 92/10092, the disclosures of which are incorporated herein by reference in their entireties. These arrays may generally be produced using mechanical synthesis methods or light directed synthesis methods which incorporate a combination of photolithographic methods and solid phase oligonucleotide synthesis (Fodor et al., 1991). The immobilization of arrays of oligonucleotides on solid supports has been rendered possible by the development of a technology generally identified as "Very Large Scale Immobilized Polymer Synthesis" (VLSIPS™) in which, typically, probes are immobilized in a high density array on a solid surface of a chip. Examples of VLSIPS™ technologies are provided in U.S. Pat. Nos. 5,143,854; and 5,412,087 and in PCT Publications WO 90/15070, WO 92/10092 and WO 95/11995, the disclosures of which are incorporated herein by reference in their entireties, which describe methods for forming oligonucleotide arrays through techniques such as light-directed synthesis techniques. In designing strategies aimed at providing arrays of nucleotides immobilized on solid supports, further presentation strategies were developed to order and display the oligonucleotide arrays on the chips in an attempt to maximize hybridization patterns and sequence information. Examples of such presentation strategies are disclosed in PCT Publications WO 94/12305, WO 94/11530, WO 97/29212 and WO 97/31256.

In another embodiment of the oligonucleotide arrays of the invention, an oligonucleotide probe matrix may advantageously be used to detect mutations occurring in the PCTA-1 gene and preferably in its regulatory region. For this particular purpose, probes are specifically designed to have a nucleotide sequence allowing their hybridization to the genes that carry known mutations (either by deletion, insertion or substitution of one or several nucleotides). By known mutations, it is meant, mutations on the PCTA-1 gene that have been identified according, for example to the technique used by Huang et al.(1996) or Samson et al.(1996).

Another technique that is used to detect mutations in the PCTA-1 gene is the use of a high-density DNA array. Each oligonucleotide probe constituting a unit element of the high density DNA array is designed to match a specific subsequence of the PCTA-1 genomic DNA or cDNA. Thus, an array consisting of oligonucleotides complementary to subsequences of the target gene sequence is used to determine the identity of the target sequence with the wild gene sequence, measure its amount, and detect differences between the target sequence and the reference wild gene sequence of the PCTA-1 gene. In one such design, termed 4L tiled array, is implemented a set of four probes (A, C, G, T), preferably 15-nucleotide oligomers. In each set of four probes, the perfect complement will hybridize more strongly than mismatched probes. Consequently, a nucleic acid target of length L is scanned for mutations with a tiled array containing 4L probes, the whole probe set containing all the possible mutations in the known wild reference sequence. The hybridization signals of the 15-mer probe set tiled array are perturbed by a single base change in the target sequence. As a consequence, there is a characteristic loss of signal or a "footprint" for the probes flanking a mutation position. This technique was described by Chee et al. in 1996.

Consequently, the invention concerns an array of nucleic acid molecules comprising at least one polynucleotide described above as probes and primers. Preferably, the invention concerns an array of nucleic acid comprising at least two polynucleotides described above as probes and primers.

A further object of the invention consists of an array of nucleic acid sequences comprising either at least one of the sequences selected from the group consisting of P1 to P125, B1 to B47, C1 to C47, D1 to D125, E1 to E125, the sequences complementary thereto, a fragment thereof of at least 8, 10, 12, 15, 18, 20, 25, 30, or 40 consecutive nucleotides thereof, and at least one sequence comprising a biallelic marker selected from the group consisting of A1 to A125 and the complements thereto.

The invention also pertains to an array of nucleic acid sequences comprising either at least two of the sequences selected from the group consisting of P1 to P 125, B1 to B47, C1 to C47, D1 to D125, E1 to E125, the sequences complementary thereto, a fragment thereof of at least 8 consecutive nucleotides thereof, and at least two sequences comprising a biallelic marker selected from the group consisting of A1 to A125 and the complements thereof.

PCTA-1 Proteins and Polypeptide Fragments Thereof

The term "PCTA-1 polypeptides" is used herein to embrace all of the proteins and polypeptides of the present invention. Also forming part of the invention are polypeptides encoded by the polynucleotides of the invention, as well as fusion polypeptides comprising such polypeptides.

The invention embodies PCTA-1 proteins from humans, including isolated or purified PCTA-1 proteins consisting, consisting essentially, or comprising the sequence of SEQ ID No 5. It should be noted the PCTA-1 proteins of the invention are based on the naturally-occurring variant of the amino acid sequence of human PCTA-1, wherein the valine residue of amino acid position 170 has been replaced with a serine residue and the glutamine residue of amino acid position 203 has been replaced with a lysine residue. This variant protein and the fragments thereof which contain a serine at the amino acid position 170 and a lysine at the amino acid position 203 of SEQ ID No 5 are collectively referred to herein as "170-Ser 203-Lys variants." In another embodiment, the present invention concerns a purified and/or isolated nucleic acid encoding the PCTA-1 protein of SEQ ID No 5 or variant or fragment thereof.

The invention also concerns a purified and/or isolated PCTA-1 protein comprising a sequence selected from the group consisting of SEQ ID Nos 6, 7 and variants and functional fragments thereof. In another embodiment, the present invention concerns a purified and/or isolated nucleic acid encoding the PCTA-1 protein comprising a sequence selected from the group consisting of SEQ ID Nos 6, 7 or a variant or a fragment thereof.

The invention also encompasses the amino acid sequence of a murine PCTA-1 protein, such as that of SEQ ID No 9, fragments and variants thereof. The invention also concerns a nucleotide sequence encoding the murine PCTA-1 protein of SEQ ID No 9, sequences complementary thereto and fragments and variants thereof.

The invention also relates to modified human and mouse PCTA-1 proteins and to fragments and variants thereof. The term "modified PCTA-1 protein" is intended to designate a PCTA-1 protein which, when compared to a native PCTA-1 protein of SEQ ID No 5, 6, or 7, bears at least one amino acid substitution, deletion or addition. More particularly, preferred modified PCTA-1 proteins include the proteins bearing at least one of the following amino acid substitutions:

a substitution from F to Y at position 18, a substitution from R to C at position 35, a substitution from V to M at position 55 and a substitution from S to R at position 183 in SEQ ID No 5;

a substitution from F to Y at position 18, a substitution from R to C at position 35, a substitution from V to M at position 55, a substitution from D to Y at position 204 and a substitution from S to R at position 225 in SEQ ID No 6; and a substitution from F to Y at position 18, a substitution from R to C at position 35, a substitution from V to M at position 55 and a substitution from S to R at position 183 in SEQ ID No 7.

Modified proteins bearing two or more of such substitutions also fall within the scope of the present invention. Other preferred embodiments include regions of the modified PCTA-1 proteins of the invention, and particularly those regions bearing at least one of the substitutions described above. Particularly preferred regions are those possessing antigenic properties and which can be used in vaccine agents or to raise antibodies against the PCTA-1 protein, and which most preferably comprise at least one of the particular substitutions referred to above.

The term "modified PCTA-1 protein" also designates a truncated PCTA-1 protein consisting of the amino acid sequence 1-211 of SEQ ID No 7.

The present invention embodies isolated, purified, and recombinant polypeptides comprising a contiguous span of at least 6 amino acids, preferably at least 8 to 10 amino acids, more preferably at least 12, 15, 20, 25, 30, 40, 50, or 100 amino acids of SEQ ID No 5, wherein said contiguous span includes:

a serine residue at amino acid position 170 and/or a lysine residue at amino acid position 203 in SEQ ID No 5; and/or at least one residue selected from the group consisting of a tyrosine residue at amino acid position 18, a cysteine residue at amino acid position 35, a methionine residue at amino acid position 55 and an arginine residue at amino acid position 183 in SEQ ID No 5.

The present invention embodies isolated, purified, and recombinant polypeptides comprising a contiguous span of at least 6 amino acids, preferably at least 8 to 10 amino acids, more preferably at least 12, 15, 20, 25, 30, 40, 50, or 100 amino acids of SEQ ID No 6, wherein said contiguous span includes:

a serine residue at amino acid position 170 and/or a lysine residue at amino acid position 245 in SEQ ID No 6; and/or at least one residue selected from the group consisting of a tyrosine residue at amino acid position 18, a cysteine residue at amino acid position 35, a methionine residue at amino acid position 55 and an arginine residue at amino acid position 225 in SEQ ID No 6; and/or at least 1, 2, 3, 5 or 10 of the amino acid encoded by the exon 6bis, more particularly at least 1, 2, 3, 5 or 10 of the amino acid positions 183-224 of the SEQ ID No 6.

The present invention embodies isolated, purified, and recombinant polypeptides comprising a contiguous span of at least 6 amino acids, preferably at least 8 to 10 amino acids, more preferably at least 12, 15, 20, 25, 30, 40, 50, or 100 amino acids of SEQ ID No 7, wherein said contiguous span includes:

a serine residue at amino acid position 170 and/or a lysine residue at amino acid position 203 in SEQ ID No 7; and/or at least one residue selected from the group consisting of a tyrosine residue at amino acid position 18, a cysteine residue at amino acid position 35, a methionine residue at amino acid position 55 and an arginine residue at amino acid position 183 in SEQ ID No 7; and/or at least 1, 2, 3, 5 or 10 of the amino acid encoded by the exons 9bis and 9ter, more particularly at least 1, 2, 3, 5 or 10 of the amino acid positions 313-368 of the SEQ ID No 7.

The invention also concerns the truncated PCTA-1 protein consisting essentially of or consisting of the amino acid positions 1-211 of SEQ ID No 7.

In other preferred embodiments the contiguous stretch of amino acids from SEQ ID Nos 5, 6, 7 comprises the site of a mutation or functional mutation, including a deletion, addition, swap or truncation of the amino acids in the PCTA-1 protein sequence.

The present invention embodies isolated, purified, and recombinant polypeptides comprising a contiguous span of at least 6 amino acids, preferably at least 8 to 10 amino acids, more preferably at least 12, 15, 20, 25, 30, 40, 50, or 100 amino acids of SEQ ID No 9.

PCTA-1 proteins are preferably isolated from human or mammalian tissue samples or expressed from human or mammalian genes. The PCTA-1 polypeptides of the invention can be made using routine expression methods known in the art. The polynucleotide encoding the desired polypeptide, is ligated into an expression vector suitable for any convenient host. Both eukaryotic and prokaryotic host systems is used in forming recombinant polypeptides, and a summary of some of the more common systems. The polypeptide is then isolated from lysed cells or from the culture medium and purified to the extent needed for its intended use. Purification is by any technique known in the art, for example, differential extraction, salt fractionation, chromatography, centrifugation, and the like. See, for example, Methods in Enzymology for a variety of methods for purifying proteins.

In addition, shorter protein fragments is produced by chemical synthesis. Alternatively the proteins of the invention is extracted from cells or tissues of humans or non-human animals. Methods for purifying proteins are known in the art, and include the use of detergents or chaotropic agents to disrupt particles followed by differential extraction and separation of the polypeptides by ion exchange chromatography, affinity chromatography, sedimentation according to density, and gel electrophoresis.

Any PCTA-1 cDNA, including SEQ ID Nos 2, 3, 4, 8, is used to express PCTA-1 proteins and polypeptides. The nucleic acid encoding a PCTA-1 protein or polypeptide to be expressed is operably linked to a promoter in an expression vector using conventional cloning technology. The PCTA-1 insert in the expression vector may comprise the full coding sequence for a PCTA-1 protein or a fragment thereof. For example, the PCTA-1 derived insert may encode a polypeptide as described above.

The expression vector is any of the mammalian, yeast, insect or bacterial expression systems known in the art. Commercially available vectors and expression systems are available from a variety of suppliers including Genetics Institute (Cambridge, Mass.), Stratagene (La Jolla, Calif.), Promega (Madison, Wis.), and Invitrogen (San Diego, Calif.). If desired, to enhance expression and facilitate proper protein folding, the codon context and codon pairing of the sequence is optimized for the particular expression organism in which the expression vector is introduced, as explained by Hatfield, et al., U.S. Pat. No. 5,082,767, the disclosure of which is incorporated herein by reference in its entirety.

In one embodiment, the entire coding sequence of a PCTA-1 cDNA through the poly A signal of the cDNA are operably linked to a promoter in the expression vector. Alternatively, if the nucleic acid encoding a fragment of the PCTA-1 protein lacks a methionine to serve as the initiation site, an initiating methionine can be introduced next to the first codon of the nucleic acid using conventional techniques. Similarly, if the insert from a PCTA-1 cDNA lacks a poly A signal, this sequence can be added to the construct by, for example, splicing out the Poly A signal from pSG5 (Stratagene) using BglI and SalI restriction endonuclease enzymes and incorporating it into the mammalian expression vector pXT1 (Stratagene). pXT1 contains the LTRs and a portion of the gag gene from Moloney Murine Leukemia Virus. The position of the LTRs in the construct allow efficient stable transfection. The vector includes the Herpes Simplex Thymidine Kinase promoter and the selectable neomycin gene. The nucleic acid encoding a PCTA-1 protein or a fragment thereof is obtained by PCR from a bacterial vector containing a PCTA-1 cDNA selected from the group consisting of SEQ ID Nos 2, 3, 4, and 8 using oligonucleotide primers complementary to the PCTA-1 cDNA or fragment thereof and containing restriction endonuclease sequences for Pst I incorporated into the 5'primer and BglII at the 5' end of the corresponding cDNA 3' primer, taking care to ensure that the sequence encoding the PCTA-1 protein or a fragment thereof is positioned properly with respect to the poly A signal. The purified fragment obtained from the resulting PCR reaction is digested with PstI, blunt ended with an exonuclease, digested with Bgl II, purified and ligated to pXT1, now containing a poly A signal and digested with BglII.

The ligated product is transfected into mouse NIH 3T3 cells using Lipofectin (Life Technologies, Inc., Grand Island, N.Y.) under conditions outlined in the product specification. Positive transfectants are selected after growing the transfected cells in 600 ug/ml G418 (Sigma, St. Louis, Mo.).

Alternatively, the nucleic acids encoding the PCTA-1 protein or a fragment thereof is cloned into pED6dpc2 (Genetics Institute, Cambridge, Mass.). The resulting pED6dpc2 constructs is transfected into a suitable host cell, such as COS I cells. Methotrexate resistant cells are selected and expanded.

The above procedures may also be used to express a mutant PCTA-1 protein responsible for a detectable phenotype or a fragment thereof.

The expressed proteins is purified using conventional purification techniques such as ammonium sulfate precipitation or chromatographic separation based on size or charge. The protein encoded by the nucleic acid insert may also be purified using standard immunochromatography techniques. In such procedures, a solution containing the expressed PCTA-1 protein or fragment thereof, such as a cell extract, is applied to a column having antibodies against the PCTA-1 protein or fragment thereof is attached to the chromatography matrix. The expressed protein is allowed to bind the immunochromatography column. Thereafter, the column is washed to remove non-specifically bound proteins. The specifically bound expressed protein is then released from the column and recovered using standard techniques.

To confirm expression of a PCTA-1 protein or a fragment thereof, the proteins expressed from host cells containing an expression vector containing an insert encoding a PCTA-1 protein or a fragment thereof can be compared to the proteins expressed in host cells containing the expression vector without an insert. The presence of a band in samples from cells containing the expression vector with an insert which is absent in samples from cells containing the expression vector without an insert indicates that the PCTA-1 protein or a fragment thereof is being expressed. Generally, the band will have the mobility expected for the PCTA-1 protein or fragment thereof. However, the band may have a mobility different than that expected as a result of modifications such as glycosylation, ubiquitination, or enzymatic cleavage.

Antibodies capable of specifically recognizing the expressed PCTA-1 protein or a fragment thereof are described below.

If antibody production is not possible, the nucleic acids encoding the PCTA-1 protein or a fragment thereof is incorporated into expression vectors designed for use in purification schemes employing chimeric polypeptides. In such strategies the nucleic acid encoding the PCTA-1 protein or a fragment thereof is inserted in frame with the gene encoding the other half of the chimera. The other half of the chimera is β-globin or a nickel binding polypeptide encoding sequence. A chromatography matrix having antibody to β-globin or nickel attached thereto is then used to purify the chimeric protein. Protease cleavage sites is engineered between the β-globin gene or the nickel binding polypeptide and the PCTA-1 protein or fragment thereof. Thus, the two polypeptides of the chimera is separated from one another by protease digestion.

One useful expression vector for generating β-globin chimeric proteins is pSG5 (Stratagene), which encodes rabbit β-globin. Intron II of the rabbit β-globin gene facilitates splicing of the expressed transcript, and the polyadenylation signal incorporated into the construct increases the level of expression. These techniques are well known to those skilled in the art of molecular biology. Standard methods are published in methods texts such as Davis et al., (1986) and many of the methods are available from Stratagene, Life Technologies, Inc., or Promega. Polypeptide may additionally be produced from the construct using in vitro translation systems such as the In vitro Express™ Translation Kit (Stratagene).

Antibodies that Bind PCTA-1 Polypeptides of the Invention

Any PCTA-1 polypeptide or whole protein may be used to generate antibodies capable of specifically binding to an expressed PCTA-1 protein or fragments thereof as described.

One antibody composition of the invention is capable of specifically binding or specifically bind to the 170-Ser 203-Lys variant of the PCTA-1 protein of SEQ ID No 5. An other antibody composition of the invention is capable of specifically binding or specifically bind to the PCTA-1 protein selected from the group consisting of amino acid sequences of SEQ ID Nos 6, 7, 9. For an antibody composition to specifically bind to a first variant of PCTA-1, it must demonstrate at least a 5%, 10%, 15%, 20%, 25%, 50%, or 100% greater binding affinity for a full length first variant of the PCTA-1 protein than for a full length second variant of the PCTA-1 protein in an ELISA, RIA, or other antibody-based binding assay.

In a preferred embodiment, the invention concerns antibody compositions, either polyclonal or monoclonal, capable of selectively binding, or selectively bind to an epitope-containing any one of the following polypeptides:

a) a polypeptide comprising a contiguous span of at least 6 amino acids, preferably at least 8 to 10 amino acids, more preferably at least 12, 15, 20, 25, 30, 40, 50, or 100 amino acids of SEQ ID No 5, wherein said epitope comprises:
  i) a serine residue at amino acid position 170 and/or a lysine residue at amino acid position 203 in SEQ ID No 5; and/or
  ii) at least one residue selected from the group consisting of a tyrosine residue at amino acid position 18, a cysteine residue at amino acid position 35, a methionine residue at amino acid position 55 and an arginine residue at amino acid position 183 in SEQ ID No 5;

b) a polypeptide comprising a contiguous span of at least 6 amino acids, preferably at least 8 to 10 amino acids, more preferably at least 12, 15, 20, 25, 30, 40, 50, or 100 amino acids of SEQ ID No 6, wherein said epitope comprises:
  i) a serine residue at amino acid position 170 and/or a lysine residue at amino acid position 245 in SEQ ID No 6; and/or
  ii) at least one residue selected from the group consisting of a tyrosine residue at amino acid position 18, a cysteine residue at amino acid position 35, a methionine residue at amino acid position 55 and an arginine residue at amino acid position 225 in SEQ ID No 6; and/or
  iii) at least 1, 2, 3, 5 or 10 of the amino acid encoded by the exon 6bis, more particularly at least 1, 2, 3, 5 or 10 of the amino acid positions 183-224 of the SEQ ID No 6;

c) a polypeptide comprising a contiguous span of at least 6 amino acids, preferably at least 8 to 10 amino acids, more preferably at least 12, 15, 20, 25, 30, 40, 50, or 100 amino acids of SEQ ID No 7, wherein said epitope comprises:
  i) a serine residue at amino acid position 170 and/or a lysine residue at amino acid position 203 in SEQ ID No 7; and/or
  ii) at least one residue selected from the group consisting of a tyrosine residue at amino acid position 18, a cysteine residue at amino acid position 35, a methionine residue at amino acid position 55 and an arginine residue at amino acid position 183 in SEQ ID No 7; and/or
  iii) at least 1, 2, 3, 5 or 10 of the amino acid encoded by the exons 9bis and 9ter, more particularly at least 1, 2, 3, 5 or 10 of the amino acid positions 313-368 of the SEQ ID No 7; and d) a polypeptide comprising a contiguous span of at least 6 amino acids, preferably at least 8 to 10 amino acids, more preferably at least 12, 15, 20, 25, 30, 40, 50, or 100 amino acids of SEQ ID No 9.

The invention also concerns a purified or isolated antibody capable of specifically binding to a mutated PCTA-1 protein or to a fragment or variant thereof comprising an epitope of the mutated PCTA-1 protein. In another preferred embodiment, the present invention concerns an antibody capable of binding to a polypeptide comprising at least 10 consecutive amino acids of a PCTA-1 protein and including at least one of the amino acids which can be encoded by the trait causing mutations.

In a preferred embodiment, the invention concerns the use of any one of the following polypeptides in the manufacture of antibodies:

a) a polypeptide comprising a contiguous span of at least 6 amino acids, preferably at least 8 to 10 amino acids, more preferably at least 12, 15, 20, 25, 30, 40, 50, or 100 amino acids of SEQ ID No 5, wherein said contigous span comprises:
  i) a serine residue at amino acid position 170 and/or a lysine residue at amino acid position 203 in SEQ ID No 5; and/or
  ii) at least one residue selected from the group consisting of a tyrosine residue at amino acid position 18, a cysteine residue at amino acid position 35, a methionine residue at amino acid position 55 and an arginine residue at amino acid position 183 in SEQ ID No 5;

b) a polypeptide comprising a contiguous span of at least 6 amino acids, preferably at least 8 to 10 amino acids, more preferably at least 12, 15, 20, 25, 30, 40, 50, or 100 amino acids of SEQ ID No 6, wherein said contigous span comprises:
  i) a serine residue at amino acid position 170 and/or a lysine residue at amino acid position 245 in SEQ ID No 6; and/or
  i) at least one residue selected from the group consisting of a tyrosine residue at amino acid position 18, a cysteine residue at amino acid position 35, a methionine residue at amino acid position 55 and an arginine residue at amino acid position 225 in SEQ ID No 6; and/or
  ii) at least 1, 2, 3, 5 or 10 of the amino acid encoded by the exon 6bis, more particularly at least 1, 2, 3, 5 or 10 of the amino acid positions 183-224 of the SEQ ID No 6;

c) a polypeptide comprising a contiguous span of at least 6 amino acids, preferably at least 8 to 10 amino acids, more preferably at least 12, 15, 20, 25, 30, 40, 50, or 100 amino acids of SEQ ID No 7, wherein said contigous span comprises:

) a serine residue at amino acid position 170 and/or a lysine residue at amino acid position 203 in SEQ ID No 7; and/or i) at least one residue selected from the group consisting of a tyrosine residue at amino acid position 18, a cysteine residue at amino acid position 35, a methionine residue at amino acid position 55 and an arginine residue at amino acid position 183 in SEQ ID No 7; and/or ii) at least 1, 2, 3, 5 or 10 of the amino acid encoded by the exons 9bis and 9ter, more particularly at least 1, 2, 3, 5 or 10 of the amino acid positions 313-368 of the SEQ ID No 7; and d) a polypeptide comprising a contiguous span of at least 6 amino acids, preferably at least 8 to 10 amino acids, more preferably at least 12, 15, 20, 25, 30, 40, 50, or 100 amino acids of SEQ ID No 9.

Non-human animals or mammals, whether wild-type or transgenic, which express a different species of PCTA-1 than the one to which antibody binding is desired, and animals which do not express PCTA-1 (i.e. a PCTA-1 knock out animal as described in herein) are particularly useful for preparing antibodies. PCTA-1 knock out animals will recognize all or most of the exposed regions of a PCTA-1 protein as foreign antigens, and therefore produce antibodies with a wider array of PCTA-1 epitopes. Moreover, smaller polypeptides with only 10 to 30 amino acids may be useful in obtaining specific binding to any one of the PCTA-1 proteins. In addition, the humoral immune system of animals which produce a species of PCTA-1 that resembles the antigenic sequence will preferentially recognize the differences between the animal's native PCTA-1 species and the antigen sequence, and produce antibodies to these unique sites in the antigen sequence. Such a technique will be particularly useful in obtaining antibodies that specifically bind to any one of the PCTA-1 proteins.

Antibody preparations prepared according to either protocol are useful in quantitative immunoassays which determine concentrations of antigen-bearing substances in biological samples; they are also used semi-quantitatively or qualitatively to identify the presence of antigen in a biological sample. The antibodies may also be used in therapeutic compositions for killing cells expressing the protein or reducing the levels of the protein in the body.

The antibodies of the invention may be labeled by any one of the radioactive, fluorescent or enzymatic labels known in the art.

Consequently, the invention is also directed to a method for detecting specifically the presence of a PCTA-1 polypeptide according to the invention in a biological sample, said method comprising the following steps:

a) bringing into contact the biological sample with a polyclonal or monoclonal antibody that specifically binds a PCTA-1 polypeptide comprising an amino acid sequence selected from the group consisting of SEQ ID Nos 5, 6, 7, 9, or to a peptide fragment or variant thereof; and b) detecting the antigen-antibody complex formed.

The invention also concerns a diagnostic kit for detecting in vitro the presence of a PCTA-1 polypeptide according to the present invention in a biological sample, wherein said kit comprises:

a) a polyclonal or monoclonal antibody that specifically binds a PCTA-1 polypeptide comprising an amino acid sequence selected from the group consisting of SEQ ID Nos 5, 6, 7, 9, or to a peptide fragment or variant thereof, optionally labeled;

b) a reagent allowing the detection of the antigen-antibody complexes formed, said reagent carrying optionally a label, or being able to be recognized itself by a labeled reagent, more particularly in the case when the above-mentioned monoclonal or polyclonal antibody is not labeled by itself.

PCTA-1-Related Biallelic markers

Advantages of the Biallelic Markers of the Present Invention

The PCTA-1-related biallelic markers of the present invention offer a number of important advantages over other genetic markers such as RFLP (Restriction fragment length polymorphism) and VNTR (Variable Number of Tandem Repeats) markers.

The first generation of markers, were RFLPs, which are variations that modify the length of a restriction fragment. But methods used to identify and to type RFLPs are relatively wasteful of materials, effort, and time. The second generation of genetic markers were VNTRs, which can be categorized as either minisatellites or microsatellites. Minisatellites are tandemly repeated DNA sequences present in units of 5-50 repeats which are distributed along regions of the human chromosomes ranging from 0.1 to 20 kilobases in length. Since they present many possible alleles, their informative content is very high. Minisatellites are scored by performing Southern blots to identify the number of tandem repeats present in a nucleic acid sample from the individual being tested. However, there are only $10^4$ potential VNTRs that can be typed by Southern blotting. Moreover, both RFLP and VNTR markers are costly and time-consuming to develop and assay in large numbers.

Single nucleotide polymorphism or biallelic markers can be used in the same manner as RFLPs and VNTRs but offer several advantages. SNP are densely spaced in the human genome and represent the most frequent type of variation. An estimated number of more than $10^7$ sites are scattered along the $3\times10^9$ base pairs of the human genome. Therefore, SNP occur at a greater frequency and with greater uniformity than RFLP or VNTR markers which means that there is a greater probability that such a marker will be found in close proximity to a genetic locus of interest. SNP are less variable than VNTR markers but are mutationally more stable.

Also, the different forms of a characterized single nucleotide polymorphism, such as the biallelic markers of the present invention, are often easier to distinguish and can therefore be typed easily on a routine basis. Biallelic markers have single nucleotide based alleles and they have only two common alleles, which allows highly parallel detection and automated scoring. The biallelic markers of the present invention offer the possibility of rapid, high throughput genotyping of a large number of individuals.

Biallelic markers are densely spaced in the genome, sufficiently informative and can be assayed in large numbers. The combined effects of these advantages make biallelic markers extremely valuable in genetic studies. Biallelic markers can be used in linkage studies in families, in allele sharing methods, in linkage disequilibrium studies in populations, in association studies of case-control populations or of trait positive and trait negative populations. An important aspect of the present invention is that biallelic markers allow association studies to be performed to identify genes involved in complex traits. Association studies examine the frequency of marker alleles in unrelated case- and control-populations and are generally employed in the detection of polygenic or sporadic traits. Association studies may be conducted within the general population and are not limited to studies performed on related individuals in affected families (linkage studies). Biallelic markers in different genes can be screened in parallel for direct association with disease or response to a treatment. This multiple gene approach is a powerful tool for a variety of human genetic studies as it provides the necessary statistical power to examine the synergistic effect of multiple genetic factors on a particular phenotype, drug response, sporadic trait, or disease state with a complex genetic etiology.

PCTA-1-Related Biallelic Markers and Polynucleotides Related Thereto

The invention also concerns a purified and/or isolated PCTA-1-related biallelic marker located in the sequence of the PCTA-1 gene, preferably a biallelic marker comprising an allele associated with prostate cancer, with an early onset of prostate cancer, with a response to a prophylactic or therapeutic agent administered for cancer treatment, particularly prostate cancer, with the level of aggressiveness of prostate cancer tumors, with a modified or forthcoming expression of the PCTA-1 gene, with a modified or forthcoming production of the PCTA-1 protein, or with the production of a modified PCTA-1 protein. The term PCTA-1-related biallelic marker includes the biallelic markers designated A1 to A125. The invention also concerns sets of these biallelic markers. 125 biallelic markers were identified. They include 3 deletions, 6 insertions and 2 variable motifs. 40 biallelic markers, namely A45, A54 to A56, A59 to A61, A75, A76, A85, A93 to A122, were located in exonic region. 39 biallelic markers, namely A44, A46 to A53, A57 to A58, A62 to A74, A77 to A84, A86 to A92, were localized in intronic region of the PCTA-1 gene. 3 biallelic markers A123, A124 and A125 were in the 3' regulatory region. 43 biallelic markers, namely A1 to A43, were located in the 5' regulatory region. More particularly, 16 of them, namely A28 to A43, were in the promoter of the PCTA-1 gene.

Among the exonic biallelic markers, 6 of them change the amino acid sequence of a PCTA-1 protein. First, the biallelic marker A54 encodes either a residue tyrosine or phenylalanine. The biallelic marker A56 encodes either a residue cysteine or arginine. The marker A60 encodes either a residue valine or methionine. The marker A75 encodes either a residue aspartic acid or tyrosine. The marker A76 encodes either a leucine residue or a STOP. Finally, the biallelic marker A85 encodes either a residue serine or arginine.

The invention also relates to a purified and/or isolated nucleotide sequence comprising a polymorphic base of a PCTA-1-related biallelic marker, preferably of a biallelic marker selected from the group consisting of A1 to A125, and the complements thereof. The sequence has between 8 and 1000 nucleotides in length, and preferably comprises at least 8, 10, 12, 15, 18, 20, 25, 35, 40, 50, 60, 70, 80, 100, 250, 500 or 1000 contiguous nucleotides, to the extent that such lengths are consistent with the specific sequence, of a nucleotide sequence selected from the group consisting of SEQ ID Nos 1, 2, 3, 4, or a variant thereof or a complementary sequence thereto. These nucleotide sequences comprise the polymorphic base of either allele 1 or allele 2 of the considered biallelic marker. Optionally, said biallelic marker may be within 6, 5, 4, 3, 2, or 1 nucleotides of the center of said polynucleotide or at the center of said polynucleotide. Optionally, the 3' end of said contiguous span may be present at the 3' end of said polynucleotide. Optionally, biallelic marker may be present at the 3' end of said polynucleotide. Optionally, the 3' end of said polynucleotide may be located within or at least 2, 4, 6, 8, 10, 12, 15, 18, 20, 25, 50, 100, 250, 500, or 1000 nucleotides upstream of a PCTA-1-related biallelic marker in said sequence. Optionally, the 3' end of said polynucleotide may be located 1 nucleotide upstream of a PCTA-1-related biallelic marker in said sequence. Optionally, said polynucleotide may further comprise a label. Optionally, said polynucleotide can be attached to solid support. In a further embodiment, the polynucleotides defined above can be used alone or in any combination.

In a preferred embodiment, the sequences comprising a polymorphic base of one of the biallelic markers listed in Table 2 are selected from the group consisting of the nucleotide sequences that have a contiguous span of, that consist of, that are comprised in, or that comprises a polynucleotide having one of the sequences set forth as the amplicons listed in Table 1 or a variant thereof or a complementary sequence thereto.

The invention further concerns a nucleic acid encoding a PCTA-1 protein, wherein said nucleic acid comprises a polymorphic base of a biallelic marker selected from the group consisting of A1 to A125 and the complements thereof.

The invention also relates to a purified and/or isolated nucleotide sequence comprising a sequence defining a biallelic marker located in the sequence of the PCTA-1 gene. Preferably, the sequences defining a biallelic marker include the polymorphic base of one of the sequences P1 to P125 or the complementary sequence thereto. In some embodiments, the sequences defining a biallelic marker comprise one of the sequences selected from the group consisting of P1 to P125, or a fragment or variant thereof or a complementary sequence thereto, said fragment comprising the polymorphic base.

The invention also concerns a set of the purified and/or isolated nucleotide sequences defined above. More particularly, the set of purified and/or isolated nucleotide sequences comprises a group of sequences defining a combination of biallelic markers located in the sequence of the PCTA-1 gene, preferably wherein alleles of said biallelic markers or the combinations thereof are associated with prostate cancer, with the level of aggressiveness of prostate cancer tumors, or with a level of expression of the PCTA-1 gene.

In a preferred embodiment, the invention relates to a set of purified and/or isolated nucleotide sequences, each sequence comprising a sequence defining a biallelic marker located in the sequence of the PCTA-1 gene, wherein the set is characterized in that between about 30 and 100%, preferably between about 40 and 60%, more preferably between 50 and 60%, of the sequences defining a biallelic marker are selected from the group consisting of P1 to P125, or a fragment or variant thereof or a complementary sequence thereto, said fragment comprising the polymorphic base.

More particularly, the invention concerns a set of purified and/or isolated nucleotide sequences, each sequence comprising a sequence defining a different biallelic marker located in the sequence of the PCTA-1 gene, said biallelic marker being either included in one of the nucleotide sequences of P1 to P125 or a complementary sequence thereto, or a biallelic marker preferably located in the sequence of the PCTA-1 gene, more preferably biallelic markers A1 to A125 and the complements thereof, and/or in linkage disequilibrium with one of the markers A1 to A125.

The invention also relates to a set of at least two, preferably four, five, six, seven, eight or more nucleotide sequences selected from the group consisting of P1 to P125, or a fragment or variant thereof or a complementary sequence thereto, said fragment comprising the polymorphic base.

The invention further concerns a nucleotide sequence selected from the group consisting of P1 to P125 or a fragment or a variant thereof or a complementary sequence thereto, said fragment comprising the polymorphic base.

The invention also encompasses the use of any polynucleotide for, or any polynucleotide for use in, determining the identity of one or more nucleotides at a PCTA-1-related biallelic marker. In addition, the polynucleotides of the invention for use in determining the identity of one or more nucleotides at a PCTA-1-related biallelic marker encompass polynucleotides with any further limitation described in this disclosure, or those following, specified alone or in any combination. Optionally, wherein said PCTA-1-related biallelic marker is selected from the group consisting of A1 to A125, and the complements thereof, or optionally the biallelic markers in linkage disequilibrium therewith; optionally, wherein said PCTA-1-related biallelic marker is selected from the group consisting of A1 to A44, A46 to A53, A57, A58, A62 to A76, A81, A82, A86 to A91, A107, A118, and A123 to A125, and the complements thereof, or optionally the biallelic markers in linkage disequilibrium therewith; optionally, wherein said PCTA-1-related biallelic marker is selected from the group consisting of A45, A54, A60, A61, A77 to A80, A83 to A85, A93, A102 to A106, A109, A110, A114, and A122, and the complements thereof, or optionally the biallelic markers in linkage disequilibrium therewith; optionally, wherein said PCTA-1-related biallelic marker is selected from the group consisting of A55, A56, A59, A92, A94 to A101, A108, A111 to A113, A115 to A117, and A119 to A121, and the complements thereof, or optionally the biallelic markers in linkage disequilibrium therewith; Optionally, said polynucleotide may comprise a sequence disclosed in the present specification; Optionally, said polynucleotide may consist of, or consist essentially of any polynucleotide described in the present specification; Optionally, said determining may be performed in a hybridization assay, a sequencing assay, a microsequencing assay, or an enzyme-based mismatch detection assay; A preferred polynucleotide may be used in a hybridization assay for determining the identity of the nucleotide at a PCTA-1-related biallelic marker. Another preferred polynucleotide may be used in a sequencing or microsequencing assay for determining the identity of the nucleotide at a PCTA-1-related biallelic marker. A third preferred polynucleotide may be used in an enzyme-based mismatch detection assay for determining the identity of the nucleotide at a PCTA-1-related biallelic marker. A fourth preferred polynucleotide may be used in amplifying a segment of polynucleotides comprising a PCTA-1-related biallelic marker. Optionally, any of the polynucleotides described above may be attached to a solid support, array, or addressable array; Optionally, said polynucleotide may be labeled.

Additionally, the invention encompasses the use of any polynucleotide for, or any polynucleotide for use in, amplifying a segment of nucleotides comprising a PCTA-1-related biallelic marker. In addition, the polynucleotides of the invention for use in amplifying a segment of nucleotides comprising a PCTA-1-related biallelic marker encompass polynucleotides with any further limitation described in this disclosure, or those following, specified alone or in any combination: Optionally, wherein said PCTA-1-related biallelic marker is selected from the group consisting of A1 to A125, and the complements thereof, or optionally the biallelic markers in linkage disequilibrium therewith; optionally, wherein said PCTA-1-related biallelic marker is selected from the group consisting of A1 to A44, A46 to A53, A57, A58, A62 to A76, A81, A82, A86 to A91, A107, A118, and A123 to A125, and the complements thereof, or optionally the biallelic markers in linkage disequilibrium therewith; optionally, wherein said PCTA-1-related biallelic marker is selected from the group consisting of A45, A54, A60, A61, A77 to A80, A83 to A85, A93, A102 to A106, A109, A110, A114, and A122, and the complements thereof, or optionally the biallelic markers in linkage disequilibrium therewith; optionally, wherein said PCTA-1-related biallelic marker is selected from the group consisting of A55, A56, A59, A92, A94 to A101, A108, A111 to A113, A115 to A117, and A119 to A121, and the complements thereof, or optionally the biallelic markers in linkage disequilibrium therewith; Optionally, said polynucleotide may comprise a sequence disclosed in the present specification; Optionally, said polynucleotide may consist of, or consist essentially of any polynucleotide described in the present specification; Optionally, said amplifying may be performed by a PCR or LCR. Optionally, said polynucleotide may be attached to a solid support, array, or addressable array. Optionally, said polynucleotide may be labeled.

The primers for amplification or sequencing reaction of a polynucleotide comprising a biallelic marker of the invention may be designed from the disclosed sequences for any method known in the art. A preferred set of primers are fashioned such that the 3' end of the contiguous span of identity with a sequence selected from the group consisting of SEQ ID Nos 1, 2, 3, 4 or a sequence complementary thereto or a variant thereof is present at the 3' end of the primer. Such a configuration allows the 3' end of the primer to hybridize to a selected nucleic acid sequence and dramatically increases the efficiency of the primer for amplification or sequencing reactions. Allele specific primers may be designed such that a polymorphic base of a biallelic marker is at the 3' end of the contiguous span and the contiguous span is present at the 3' end of the primer. Such allele specific primers tend to selectively prime an amplification or sequencing reaction so long as they are used with a nucleic acid sample that contains one of the two alleles present at a biallelic marker. The 3' end of the primer of the invention may be located within or at least 2, 4, 6, 8, 10, 12, 15, 18, 20, 25, 50, 100, 250, 500, or 1000 nucleotides upstream of a PCTA-1-related biallelic marker in said sequence or at any other location which is appropriate for their intended use in sequencing, amplification or the location of novel sequences or markers. Thus, another set of preferred amplification primers comprise an isolated polynucleotide consisting essentially of a contiguous span of 8 to 50 nucleotides in a sequence selected from the group consisting of SEQ ID Nos 1, 2, 3, 4 or a sequence complementary thereto or a variant thereof, wherein the 3' end of said contiguous span is located at the 3'end of said polynucleotide, and wherein the 3'end of said polynucleotide is located upstream of a PCTA-1-related biallelic marker in said sequence. Preferably, those amplification primers comprise a sequence selected from the group consisting of the sequences B1 to B47 and C1 to C47. Primers with their 3' ends located 1 nucleotide upstream of a biallelic marker of PCTA-1 have a special utility as microsequencing assays. Preferred microsequencing primers are described in Table 4. Optionally, wherein said PCTA-1-related biallelic marker is selected from the group consisting of A1 to A1125, and the complements thereof, or optionally the biallelic markers in linkage disequilibrium therewith; optionally, wherein said PCTA-1-related biallelic marker is selected from the group consisting of A1 to A44, A46 to A53, A57, A58, A62 to A76, A81, A82, A86 to A91, A107, A118, and A123 to A125, and the complements thereof, or optionally the biallelic markers in linkage disequilibrium therewith; optionally, wherein said PCTA-1-related biallelic marker is selected from the group consisting of A45, A54, A60, A61, A77 to A80, A83 to A85, A93, A102 to A106, A109, A110, A114, and A122, and the complements thereof, or optionally the biallelic markers in linkage disequilibrium therewith; optionally, wherein said PCTA-1-related biallelic marker is selected from the group consisting of A55, A56, A59, A92, A94 to A101, A108, A111 to A113, A115 to A117, and A119 to A121, and the complements thereof, or optionally the biallelic markers in linkage disequilibrium therewith; Optionally, microsequencing primers are selected from the group consisting of the nucleotide sequences D1 to D125 and E1 to E125. More preferred microsequencing primers are selected from the group consisting of the nucleotides sequences D15, D24, D30, D34, D36, D38, D41, D44, D50, D53, D54, D56, D57, D59, D76, D85, D93, D108, D111, D115, D124, E11, E14, E22, E25, E26, E35, E42, E52, E53, E55, E56, E60, E61, E64, E73, E75, E93, E96.

The probes of the present invention may be designed from the disclosed sequences for any method known in the art, particularly methods which allow for testing if a marker disclosed herein is present. A preferred set of probes may be designed for use in the hybridization assays of the invention in any manner known in the art such that they selectively bind to one allele of a biallelic marker, but not the other under any particular set of assay conditions. Preferred hybridization probes comprise the polymorphic base of either allele 1 or allele 2 of the considered biallelic marker. Optionally, said biallelic marker may be within 6, 5, 4, 3, 2, or 1 nucleotides of the center of the hybridization probe or at the center of said probe. In a preferred embodiment, the probes are selected from the group consisting of the sequences P1 to P125 and the complementary sequence thereto.

It should be noted that the polynucleotides of the present invention are not limited to having the exact flanking sequences surrounding the polymorphic bases which are enumerated in Sequence Listing. Rather, it will be appreciated that the flanking sequences surrounding the biallelic markers may be lengthened or shortened to any extent compatible with their intended use and the present invention specifically contemplates such sequences. The flanking regions outside of the contiguous span need not be homologous to native flanking sequences which actually occur in human subjects. The addition of any nucleotide sequence which is compatible with the nucleotides intended use is specifically contemplated.

Primers and probes may be labeled or immobilized on a solid support as described in "Oligonucleotide probes and primers".

The polynucleotides of the invention which are attached to a solid support encompass polynucleotides with any further limitation described in this disclosure, or those following, specified alone or in any combination: Optionally, said polynucleotides may be specified as attached individually or in groups of at least 2, 5, 8, 10, 12, 15, 20, or 25 distinct polynucleotides of the invention to a single solid support. Optionally, polynucleotides other than those of the invention may attached to the same solid support as polynucleotides of the invention. Optionally, when multiple polynucleotides are attached to a solid support they may be attached at random locations, or in an ordered array. Optionally, said ordered array may be addressable.

The present invention also encompasses diagnostic kits comprising one or more polynucleotides of the invention with a portion or all of the necessary reagents and instructions for genotyping a test subject by determining the identity of a nucleotide at a PCTA-1-related biallelic marker. The polynucleotides of a kit may optionally be attached to a solid support, or be part of an array or addressable array of polynucleotides. The kit may provide for the determination of the identity of the nucleotide at a marker position by any method known in the art including, but not limited to, a sequencing assay method, a microsequencing assay method, a hybridization assay method, or an enzyme-based mismatch detection assay method.

Methods for De Novo Identification of Biallelic Markers

Any of a variety of methods can be used to screen a genomic fragment for single nucleotide polymorphisms such as differential hybridization with oligonucleotide probes, detection of changes in the mobility measured by gel electrophoresis or direct sequencing of the amplified nucleic acid. A preferred method for identifying biallelic markers involves comparative sequencing of genomic DNA fragments from an appropriate number of unrelated individuals.

In a first embodiment, DNA samples from unrelated individuals are pooled together, following which the genomic DNA of interest is amplified and sequenced. The nucleotide sequences thus obtained are then analyzed to identify significant polymorphisms. One of the major advantages of this method resides in the fact that the pooling of the DNA samples substantially reduces the number of DNA amplification reactions and sequencing reactions, which must be carried out. Moreover, this method is sufficiently sensitive so that a biallelic marker obtained thereby usually demonstrates a sufficient frequency of its less common allele to be useful in conducting association studies.

In a second embodiment, the DNA samples are not pooled and are therefore amplified and sequenced individually. This method is usually preferred when biallelic markers need to be identified in order to perform association studies within candidate genes. Preferably, highly relevant gene regions such as promoter regions or exon regions may be screened for biallelic markers. A biallelic marker obtained using this method may show a lower degree of informativeness for conducting association studies, e.g. if the frequency of its less frequent allele may be less than about 10%. Such a biallelic marker will, however, be sufficiently informative to conduct association studies and it will further be appreciated that including less informative biallelic markers in the genetic analysis studies of the present invention, may allow in some cases the direct identification of causal mutations, which may, depending on their penetrance, be rare mutations.

The following is a description of the various parameters of a preferred method used by the inventors for the identification of the biallelic markers of the present invention.

Genomic DNA Samples

The genomic DNA samples from which the biallelic markers of the present invention are generated are preferably obtained from unrelated individuals corresponding to a heterogeneous population of known ethnic background. The number of individuals from whom DNA samples are obtained can vary substantially, preferably from about 10 to about 1000, preferably from about 50 to about 200 individuals. It is usually preferred to collect DNA samples from at least about 100 individuals in order to have sufficient polymorphic diversity in a given population to identify as many markers as possible and to generate statistically significant results.

As for the source of the genomic DNA to be subjected to analysis, any test sample can be foreseen without any particular limitation. These test samples include biological samples, which can be tested by the methods of the present invention described herein, and include human and animal body fluids such as whole blood, serum, plasma, cerebrospinal fluid, urine, lymph fluids, and various external secretions of the respiratory, intestinal and genitourinary tracts, tears, saliva, milk, white blood cells, myelomas and the like; biological fluids such as cell culture supernatants; fixed tissue specimens including tumor and non-tumor tissue and lymph node tissues; bone marrow aspirates and fixed cell specimens. The preferred source of genomic DNA used in the present invention is from peripheral venous blood of each donor. Techniques to prepare genomic DNA from biological samples are well known to the skilled technician. Details of a preferred embodiment are provided in Example 1. The person skilled in the art can choose to amplify pooled or unpooled DNA samples.

DNA Amplification

The identification of biallelic markers in a sample of genomic DNA may be facilitated through the use of DNA amplification methods. DNA samples can be pooled or unpooled for the amplification step. DNA amplification techniques are well known to those skilled in the art.

Amplification techniques that can be used in the context of the present invention include, but are not limited to, the ligase chain reaction (LCR) described in EP-A-320 308, WO 9320227 and EP-A-439 182, the disclosures of which are incorporated herein by reference in their entireties, the polymerase chain reaction (PCR, RT-PCR) and techniques such as the nucleic acid sequence based amplification (NASBA) described in Guatelli J. C., et al.(1990) and in Compton J.(1991), Q-beta amplification as described in European Patent Application No 4544610, the disclosures of which are incorporated herein by reference in their entireties, strand displacement amplification as described in Walker et al. (1996) and EP A684 315, the disclosures of which are incorporated herein by reference in their entireties, and, target mediated amplification as described in PCT Publication WO 9322461.

LCR and Gap LCR are exponential amplification techniques, both depend on DNA ligase to join adjacent primers annealed to a DNA molecule. In Ligase Chain Reaction (LCR), probe pairs are used which include two primary (first and second) and two secondary (third and fourth) probes, all of which are employed in molar excess to target. The first probe hybridizes to a first segment of the target strand and the second probe hybridizes to a second segment of the target strand, the first and second segments being contiguous so that the primary probes abut one another in 5' phosphate-3'hydroxyl relationship, and so that a ligase can covalently fuse or ligate the two probes into a fused product. In addition, a third (secondary) probe can hybridize to a portion of the first probe and a fourth (secondary) probe can hybridize to a portion of the second probe in a similar abutting fashion. Of course, if the target is initially double stranded, the secondary probes also will hybridize to the target complement in the first instance. Once the ligated strand of primary probes is separated from the target strand, it will hybridize with the third and fourth probes, which can be ligated to form a complementary, secondary ligated product. It is important to realize that the ligated products are functionally equivalent to either the target or its complement. By repeated cycles of hybridization and ligation, amplification of the target sequence is achieved. A method for multiplex LCR has also been described (WO 9320227, the disclosure of which is incorporated herein by reference in its entirety). Gap LCR (GLCR) is a version of LCR where the probes are not adjacent but are separated by 2 to 3 bases.

For amplification of mRNAs, it is within the scope of the present invention to reverse transcribe mRNA into cDNA followed by polymerase chain reaction (RT-PCR); or, to use a single enzyme for both steps as described in U.S. Pat. No. 5,322,770, the disclosure of which is incorporated herein by reference in its entirety, or, to use Asymmetric Gap LCR (RT-AGLCR) as described by Marshall et al.(1994). AGLCR is a modification of GLCR that allows the amplification of RNA.

The PCR technology is the preferred amplification technique used in the present invention. A variety of PCR techniques are familiar to those skilled in the art. For a review of PCR technology, see White (1997) and the publication entitled "PCR Methods and Applications" (1991, Cold Spring Harbor Laboratory Press). In each of these PCR procedures, PCR primers on either side of the nucleic acid sequences to be amplified are added to a suitably prepared nucleic acid sample along with dNTPs and a thermostable polymerase such as Taq polymerase, Pfu polymerase, or Vent polymerase. The nucleic acid in the sample is denatured and the PCR primers are specifically hybridized to complementary nucleic acid sequences in the sample. The hybridized primers are extended. Thereafter, another cycle of denaturation, hybridization, and extension is initiated. The cycles are repeated multiple times to produce an amplified fragment containing the nucleic acid sequence between the primer sites. PCR has further been described in several patents including U.S. Pat. Nos. 4,683,195; 4,683,202; and 4,965,188, the disclosures of which are incorporated herein by reference in their entireties.

The PCR technology is the preferred amplification technique used to identify new biallelic markers. A typical example of a PCR reaction suitable for the purposes of the present invention is provided in Example 2.

One of the aspects of the present invention is a method for the amplification of the human PCTA-1 gene, particularly of a fragment of the genomic sequence of SEQ ID No 1 or of the cDNA sequences of SEQ ID Nos 2, 3, 4, 8, or a fragment or a variant thereof in a test sample, preferably using the PCR technology. This method comprises the steps of:

a) contacting a test sample with amplification reaction reagents comprising a pair of amplification primers as described above and located on either side of the polynucleotide region to be amplified, and b) optionally, detecting the amplification products.

The invention also concerns a kit for the amplification of a PCTA-1 gene sequence, particularly of a portion of the genomic sequence of SEQ ID No 1 or of the cDNA sequences of SEQ ID Nos 2, 3 4, 9, or a variant thereof in a test sample, wherein said kit comprises:

a) a pair of oligonucleotide primers located on either side of the PCTA-1 region to be amplified;

b) optionally, the reagents necessary for performing the amplification reaction.

In one embodiment of the above amplification method and kit, the amplification product is detected by hybridization with a labeled probe having a sequence which is complementary to the amplified region. In another embodiment of the above amplification method and kit, primers comprise a sequence which is selected from the group consisting of the nucleotide sequences of B1 to B47, C1 to C47, D1 to D125, and E1 to E125.

In a first embodiment of the present invention, biallelic markers are identified using genomic sequence information generated by the inventors. Sequenced genomic DNA fragments are used to design primers for the amplification of 500 bp fragments. These 500 bp fragments are amplified from genomic DNA and are scanned for biallelic markers. Primers may be designed using the OSP software (Hillier L. and Green P., 1991). All primers may contain, upstream of the specific target bases, a common oligonucleotide tail that serves as a sequencing primer. Those skilled in the art are familiar with primer extensions, which can be used for these purposes.

Preferred primers, useful for the amplification of genomic sequences encoding the candidate genes, focus on promoters, exons and splice sites of the genes. A biallelic marker presents a higher probability to be an eventual causal mutation if it is located in these functional regions of the gene. Preferred amplification primers of the invention include the nucleotide sequences B1 to B47 and C1 to C47, detailed further in Example 2, Table 1.

Sequencing of Amplified Genomic DNA and Identification of Single Nucleotide Polymorphisms The amplification products generated as described above, are then sequenced using any method known and available to the skilled technician. Methods for sequencing DNA using either the dideoxy-mediated method (Sanger method) or the Maxam-Gilbert method are widely known to those of ordinary skill in the art. Such methods are for example disclosed in Sambrook et al.(1989). Alternative approaches include hybridization to high-density DNA probe arrays as described in Chee et al.(1996).

Preferably, the amplified DNA is subjected to automated dideoxy terminator sequencing reactions using a dye-primer cycle sequencing protocol. The products of the sequencing reactions are run on sequencing gels and the sequences are determined using gel image analysis. The polymorphism search is based on the presence of superimposed peaks in the electrophoresis pattern resulting from different bases occurring at the same position. Because each dideoxy terminator is labeled with a different fluorescent molecule, the two peaks corresponding to a biallelic site present distinct colors corresponding to two different nucleotides at the same position on the sequence. However, the presence of two peaks can be an artifact due to background noise. To exclude such an artifact, the two DNA strands are sequenced and a comparison between the peaks is carried out. In order to be registered as a polymorphic sequence, the polymorphism has to be detected on both strands.

The above procedure permits those amplification products, which contain biallelic markers to be identified. The detection limit for the frequency of biallelic polymorphisms detected by sequencing pools of 100 individuals is approximately 0.1 for the minor allele, as verified by sequencing pools of known allelic frequencies. However, more than 90% of the biallelic polymorphisms detected by the pooling method have a frequency for the minor allele higher than 0.25. Therefore, the biallelic markers selected by this method have a frequency of at least 0.1 for the minor allele and less than 0.9 for the major allele. Preferably at least 0.2 for the minor allele and less than 0.8 for the major allele, more preferably at least 0.3 for the minor allele and less than 0.7 for the major allele, thus a heterozygosity rate higher than 0.18, preferably higher than 0.32, more preferably higher than 0.42.

In another embodiment, biallelic markers are detected by sequencing individual DNA samples, the frequency of the minor allele of such a biallelic marker may be less than 0.1.

Validation of the Biallelic Markers of the Present Invention

The polymorphisms are evaluated for their usefulness as genetic markers by validating that both alleles are present in a population. Validation of the biallelic markers is accomplished by genotyping a group of individuals by a method of the invention and demonstrating that both alleles are present. Microsequencing is a preferred method of genotyping alleles. The validation by genotyping step may be performed on individual samples derived from each individual in the group or by genotyping a pooled sample derived from more than one individual. The group can be as small as one individual if that individual is heterozygous for the allele in question. Preferably the group contains at least three individuals, more preferably the group contains five or six individuals, so that a single validation test will be more likely to result in the validation of more of the biallelic markers that are being tested. It should be noted, however, that when the validation test is performed on a small group it may result in a false negative result if as a result of sampling error none of the individuals tested carries one of the two alleles. Thus, the validation process is less useful in demonstrating that a particular initial result is an artifact, than it is at demonstrating that there is a bonafide biallelic marker at a particular position in a sequence. All of the genotyping, haplotyping, association, and interaction study methods of the invention may optionally be performed solely with validated biallelic markers.

Evaluation of the Frequency of the Biallelic Markers of the Present Invention

The validated biallelic markers are further evaluated for their usefulness as genetic markers by determining the frequency of the least common allele at the biallelic marker site. The higher the frequency of the less common allele the greater the usefulness of the biallelic marker is association and interaction studies. The determination of the least common allele is accomplished by genotyping a group of individuals by a method of the invention and demonstrating that both alleles are present. This determination of frequency by genotyping step may be performed on individual samples derived from each individual in the group or by genotyping a pooled sample derived from more than one individual. The group must be large enough to be representative of the population as a whole. Preferably the group contains at least 20 individuals, more preferably the group contains at least 50 individuals, most preferably the group contains at least 100 individuals. Of course the larger the group the greater the accuracy of the frequency determination because of reduced sampling error. For an indication of the frequency for the less common allele of a particular biallelic marker of the invention see Table 2. A biallelic marker wherein the frequency of the less common allele is 30% or more is termed a "high quality biallelic marker." All of the genotyping, haplotyping, association, and interaction study methods of the invention may optionally be performed solely with high quality biallelic markers.

Methods for Genotyping an Individual for Biallelic Markers

Methods are provided to genotype a biological sample for one or more biallelic markers of the present invention, all of which may be performed in vitro. Such methods of genotyping comprise determining the identity of a nucleotide at a PCTA-1 biallelic marker site by any method known in the art. These methods find use in genotyping case-control populations in association studies as well as individuals in the context of detection of alleles of biallelic markers which are known to be associated with a given trait, in which case both copies of the biallelic marker present in individual's genome are determined so that an individual may be classified as homozygous or heterozygous for a particular allele.

These genotyping methods can be performed on nucleic acid samples derived from a single individual or pooled DNA samples.

Genotyping can be performed using similar methods as those described above for the identification of the biallelic markers, or using other genotyping methods such as those further described below. In preferred embodiments, the comparison of sequences of amplified genomic fragments from different individuals is used to identify new biallelic markers whereas microsequencing is used for genotyping known biallelic markers in diagnostic and association study applications.

In one embodiment the invention encompasses methods of genotyping comprising determining the identity of a nucleotide at a PCTA-1-related biallelic marker or the complement thereof in a biological sample; optionally, wherein said PCTA-1-related biallelic marker is selected from the group consisting of A1 to A125, and the complements thereof, or optionally the biallelic markers in linkage disequilibrium therewith; optionally, wherein said PCTA-1-related biallelic marker is selected from the group consisting of A1 to A44, A46 to A53, A57, A58, A62 to A76, A81, A82, A86 to A91, A107, A118, and A123 to A125, and the complements thereof, or optionally the biallelic markers in linkage disequilibrium therewith; optionally, wherein said PCTA-1-related biallelic marker is selected from the group consisting of A45, A54, A60, A61, A77 to A80, A83 to A85, A93, A102 to A106, A109, A110, A114, and A122, and the complements thereof, or optionally the biallelic markers in linkage disequilibrium therewith; optionally, wherein said PCTA-1-related biallelic marker is selected from the group consisting of A55, A56, A59, A92, A94 to A101, A108, A111 to A113, A115 to A117, and A19 to A121, and the complements thereof, or optionally the biallelic markers in linkage disequilibrium therewith; optionally, wherein said biological sample is derived from a single subject; optionally, wherein the identity of the nucleotides at said biallelic marker is determined for both copies of said biallelic marker present in said individual's genome; optionally, wherein said biological sample is derived from multiple subjects; Optionally, the genotyping methods of the invention encompass methods with any further limitation described in this disclosure, or those following, specified alone or in any combination; Optionally, said method is performed in vitro; optionally, further comprising amplifying a portion of said sequence comprising the biallelic marker prior to said determining step; Optionally, wherein said amplifying is performed by PCR, LCR, or replication of a recombinant vector comprising an origin of replication and said fragment in a host cell; optionally, wherein said determining is performed by a hybridization assay, a sequencing assay, a microsequencing assay, or an enzyme-based mismatch detection assay.

Source of Nucleic Acids for Genotyping

Any source of nucleic acids, in purified or non-purified form, can be utilized as the starting nucleic acid, provided it contains or is suspected of containing the specific nucleic acid sequence desired. DNA or RNA may be extracted from cells, tissues, body fluids and the like as described above. While nucleic acids for use in the genotyping methods of the invention can be derived from any mammalian source, the test subjects and individuals from which nucleic acid samples are taken are generally understood to be human.

Amplification of DNA Fragments Comprising Biallelic Markers

Methods and polynucleotides are provided to amplify a segment of nucleotides comprising one or more biallelic marker of the present invention. It will be appreciated that amplification of DNA fragments comprising biallelic markers may be used in various methods and for various purposes and is not restricted to genotyping. Nevertheless, many genotyping methods, although not all, require the previous amplification of the DNA region carrying the biallelic marker of interest. Such methods specifically increase the concentration or total number of sequences that span the biallelic marker or include that site and sequences located either distal or proximal to it. Diagnostic assays may also rely on amplification of DNA segments carrying a biallelic marker of the present invention. Amplification of DNA may be achieved by any method known in the art. Amplification techniques are described above in the section entitled, "DNA amplification."

The invention also concerns a method for the amplification of a PCTA-1 gene region, preferably containing at least one of the polymorphic bases identified in the context of the present invention, or a fragment or variant thereof, in a test sample. The method comprises the step of contacting a test sample suspected of containing the targeted PCTA-1 gene sequence or a fragment thereof with amplification reaction reagents comprising a pair of amplification primers, preferably located on either side of the polymorphic base. Preferred amplification primers consist of B1 to B47 and C1 to C47. The method may further comprise the step of detecting the amplification product. For example, the amplification product may be detected using a detection probe that can hybridize with an internal region of the amplicon sequences. In some embodiments, the polymorphic base is included in one of the sequences of P1 to P125, and the complementary sequences thereof.

Some of these amplification methods are particularly suited for the detection of single nucleotide polymorphisms and allow the simultaneous amplification of a target sequence and the identification of the polymorphic nucleotide as it is further described below.

The identification of biallelic markers as described above allows the design of appropriate oligonucleotides, which can be used as primers to amplify DNA fragments comprising the biallelic markers of the present invention. Amplification can be performed using the primers initially used to discover new biallelic markers which are described herein or any set of primers allowing the amplification of a DNA fragment comprising a biallelic marker of the present invention.

In some embodiments the present invention provides primers for amplifying a DNA fragment containing one or more biallelic markers of the present invention. Preferred amplification primers are listed in Example 2. It will be appreciated that the primers listed are merely exemplary and that any other set of primers which produce amplification products containing one or more biallelic markers of the present invention are also of use.

The spacing of the primers determines the length of the segment to be amplified. In the context of the present invention, amplified segments carrying biallelic markers can range in size from at least about 25 bp to 35 kbp. Amplification fragments from 25-3000 bp are typical, fragments from 50-1000 bp are preferred and fragments from 100-600 bp are highly preferred. It will be appreciated that amplification primers for the biallelic markers may be any sequence which allow the specific amplification of any DNA fragment carrying the markers. Amplification primers may be labeled or immobilized on a solid support as described in "Oligonucleotide probes and primers".

Methods of Genotyping DNA samples for Biallelic Markers

Any method known in the art can be used to identify the nucleotide present at a biallelic marker site. Since the biallelic marker allele to be detected has been identified and specified in the present invention, detection will prove simple for one of ordinary skill in the art by employing any of a number of techniques. Many genotyping methods require the previous amplification of the DNA region carrying the biallelic marker of interest. While the amplification of target or signal is often preferred at present, ultrasensitive detection methods which do not require amplification are also encompassed by the present genotyping methods. Methods well-known to those skilled in the art that can be used to detect biallelic polymorphisms include methods such as, conventional dot blot analyzes, single strand conformational polymorphism analysis (SSCP) described by Orita et al.(1989), denaturing gradient gel electrophoresis (DGGE), heteroduplex analysis, mismatch cleavage detection, and other conventional techniques as described in Sheffield et al.(1991), White et al.(1992), Grompe et al.(1989 and 1993). Another method for determining the identity of the nucleotide present at a particular polymorphic site employs a specialized exonuclease-resistant nucleotide derivative as described in U.S. Pat. No. 4,656,127.

Preferred methods involve directly determining the identity of the nucleotide present at a biallelic marker site by sequencing assay, enzyme-based mismatch detection assay, or hybridization assay. The following is a description of some preferred methods. A highly preferred method is the microsequencing technique. The term "sequencing" is generally used herein to refer to polymerase extension of duplex primer/ template complexes and includes both traditional sequencing and microsequencing.

1) Sequencing Assays

The nucleotide present at a polymorphic site can be determined by sequencing methods. In a preferred embodiment, DNA samples are subjected to PCR amplification before sequencing as described above. DNA sequencing methods are described in "Sequencing Of Amplified Genomic DNA And Identification Of Single Nucleotide Polymorphisms".

Preferably, the amplified DNA is subjected to automated dideoxy terminator sequencing reactions using a dye-primer cycle sequencing protocol. Sequence analysis allows the identification of the base present at the biallelic marker site.

2) Microsequencing Assays

In microsequencing methods, the nucleotide at a polymorphic site in a target DNA is detected by a single nucleotide primer extension reaction. This method involves appropriate microsequencing primers which, hybridize just upstream of the polymorphic base of interest in the target nucleic acid. A polymerase is used to specifically extend the 3' end of the primer with one single ddNTP (chain terminator) complementary to the nucleotide at the polymorphic site. Next the identity of the incorporated nucleotide is determined in any suitable way.

Typically, microsequencing reactions are carried out using fluorescent ddNTPs and the extended microsequencing primers are analyzed by electrophoresis on ABI 377 sequencing machines to determine the identity of the incorporated nucleotide as described in EP 412 883, the disclosure of which is incorporated herein by reference in its entirety. Alternatively capillary electrophoresis can be used in order to process a higher number of assays simultaneously. An example of a typical microsequencing procedure that can be used in the context of the present invention is provided in Example 4.

Different approaches can be used for the labeling and detection of ddNTPs. A homogeneous phase detection method based on fluorescence resonance energy transfer has been described by Chen and Kwok (1997) and Chen et al. (1997). In this method, amplified genomic DNA fragments containing polymorphic sites are incubated with a 5'-fluorescein-labeled primer in the presence of allelic dye-labeled dideoxyribonucleoside triphosphates and a modified Taq polymerase. The dye-labeled primer is extended one base by the dye-terminator specific for the allele present on the template. At the end of the genotyping reaction, the fluorescence intensities of the two dyes in the reaction mixture are analyzed directly without separation or purification. All these steps can be performed in the same tube and the fluorescence changes can be monitored in real time. Alternatively, the extended primer may be analyzed by MALDI-TOF Mass Spectrometry. The base at the polymorphic site is identified by the mass added onto the microsequencing primer (see Haff and Smirnov, 1997).

Microsequencing may be achieved by the established microsequencing method or by developments or derivatives thereof. Alternative methods include several solid-phase microsequencing techniques. The basic microsequencing protocol is the same as described previously, except that the method is conducted as a heterogeneous phase assay, in which the primer or the target molecule is immobilized or captured onto a solid support. To simplify the primer separation and the terminal nucleotide addition analysis, oligonucleotides are attached to solid supports or are modified in such ways that permit affinity separation as well as polymerase extension. The 5' ends and internal nucleotides of synthetic oligonucleotides can be modified in a number of different ways to permit different affinity separation approaches, e.g., biotinylation. If a single affinity group is used on the oligonucleotides, the oligonucleotides can be separated from the incorporated terminator regent. This eliminates the need of physical or size separation. More than one oligonucleotide can be separated from the terminator reagent and analyzed simultaneously if more than one affinity group is used. This permits the analysis of several nucleic acid species or more nucleic acid sequence information per extension reaction. The affinity group need not be on the priming oligonucleotide but could alternatively be present on the template. For example, immobilization can be carried out via an interaction between biotinylated DNA and streptavidin-coated microtitration wells or avidin-coated polystyrene particles. In the same manner, oligonucleotides or templates may be attached to a solid support in a high-density format. In such solid phase microsequencing reactions, incorporated ddNTPs can be radiolabeled (Syvanen, 1994) or linked to fluorescein (Livak and Hainer, 1994). The detection of radiolabeled ddNTPs can be achieved through scintillation-based techniques. The detection of fluorescein-linked ddNTPs can be based on the binding of antifluorescein antibody conjugated with alkaline phosphatase, followed by incubation with a chromogenic substrate (such as p-nitrophenyl phosphate). Other possible reporter-detection pairs include: ddNTP linked to dinitrophenyl (DNP) and anti-DNP alkaline phosphatase conjugate (Hariju et al., 1993) or biotinylated ddNTP and horseradish peroxidase-conjugated streptavidin with o-phenylenediamine as a substrate (WO 92/15712, the disclosure of which is incorporated herein by reference in its entirety). As yet another alternative solid-phase microsequencing procedure, Nyren et al.(1993) described a method relying on the detection of DNA polymerase activity by an enzymatic luminometric inorganic pyrophosphate detection assay (ELIDA).

Pastinen et al.(1997) describe a method for multiplex detection of single nucleotide polymorphism in which the solid phase minisequencing principle is applied to an oligonucleotide array format. High-density arrays of DNA probes attached to a solid support (DNA chips) are further described below.

In one aspect the present invention provides polynucleotides and methods to genotype one or more biallelic markers of the present invention by performing a microsequencing assay. Preferred microsequencing primers include the nucleotide sequences D1 to D125 and E1 to E125. More preferred microsequencing primers are selected from the group consisting of the nucleotide sequences D15, D24, D30, D34, D36, D38, D41, D44, D50, D53, D54, D56, D57, D59, D76, D85, D93, D108, D1, D115, D124, E11, E14, E22, E25, E26, E35, E42, E52, E53, E55, E56, E60, E61, E64, E73, E75, E93, E96. It will be appreciated that the microsequencing primers listed in Example 4 are merely exemplary and that, any primer having a 3' end immediately adjacent to the polymorphic nucleotide may be used. Similarly, it will be appreciated that microsequencing analysis may be performed for any biallelic marker or any combination of biallelic markers of the present invention. One aspect of the present invention is a solid support which includes one or more microsequencing primers listed in Example 4, or fragments comprising at least 8, 12, 15, 20, 25, 30, 40, or 50 consecutive nucleotides thereof, to the extent that such lengths are consistent with the primer described, and having a 3' terminus immediately upstream of the corresponding biallelic marker, for determining the identity of a nucleotide at a biallelic marker site.

3) Mismatch Detection Assays Based on Polymerases and Ligases

In one aspect the present invention provides polynucleotides and methods to determine the allele of one or more biallelic markers of the present invention in a biological sample, by mismatch detection assays based on polymerases and/or ligases. These assays are based on the specificity of polymerases and ligases. Polymerization reactions places particularly stringent requirements on correct base pairing of the 3' end of the amplification primer and the joining of two oligonucleotides hybridized to a target DNA sequence is quite sensitive to mismatches close to the ligation site, especially at the 3' end. Methods, primers and various parameters to amplify DNA fragments comprising biallelic markers of the present invention are further described above in "Amplification Of DNA Fragments Comprising Biallelic Markers".

Allele Specific Amplification Primers

Discrimination between the two alleles of a biallelic marker can also be achieved by allele specific amplification, a selective strategy, whereby one of the alleles is amplified without amplification of the other allele. For allele specific amplification, at least one member of the pair of primers is sufficiently complementary with a region of a PCTA-1 gene comprising the polymorphic base of a biallelic marker of the present invention to hybridize therewith and to initiate the amplification. Such primers are able to discriminate between the two alleles of a biallelic marker.

This is accomplished by placing the polymorphic base at the 3' end of one of the amplification primers. Because the extension forms from the 3'end of the primer, a mismatch at or near this position has an inhibitory effect on amplification. Therefore, under appropriate amplification conditions, these primers only direct amplification on their complementary allele. Determining the precise location of the mismatch and the corresponding assay conditions are well within the ordinary skill in the art.

Ligation/Amplification Based Methods

The "Oligonucleotide Ligation Assay" (OLA) uses two oligonucleotides which are designed to be capable of hybridizing to abutting sequences of a single strand of a target molecules. One of the oligonucleotides is biotinylated, and the other is detectably labeled. If the precise complementary sequence is found in a target molecule, the oligonucleotides will hybridize such that their termini abut, and create a ligation substrate that can be captured and detected. OLA is capable of detecting single nucleotide polymorphisms and may be advantageously combined with PCR as described by Nickerson et al.(1990). In this method, PCR is used to achieve the exponential amplification of target DNA, which is then detected using OLA.

Other amplification methods which are particularly suited for the detection of single nucleotide polymorphism include LCR (ligase chain reaction), Gap LCR (GLCR) which are described above in "DNA Amplification". LCR uses two pairs of probes to exponentially amplify a specific target. The sequences of each pair of oligonucleotides, is selected to permit the pair to hybridize to abutting sequences of the same strand of the target. Such hybridization forms a substrate for a template-dependant ligase. In accordance with the present invention, LCR can be performed with oligonucleotides having the proximal and distal sequences of the same strand of a biallelic marker site. In one embodiment, either oligonucleotide will be designed to include the biallelic marker site. In such an embodiment, the reaction conditions are selected such that the oligonucleotides can be ligated together only if the target molecule either contains or lacks the specific nucleotide that is complementary to the biallelic marker on the oligonucleotide. In an alternative embodiment, the oligonucleotides will not include the biallelic marker, such that when they hybridize to the target molecule, a "gap" is created as described in WO 90/01069, the disclosure of which is incorporated herein by reference in its entirety. This gap is then "filled" with complementary dNTPs (as mediated by DNA polymerase), or by an additional pair of oligonucleotides. Thus at the end of each cycle, each single strand has a complement capable of serving as a target during the next cycle and exponential allele-specific amplification of the desired sequence is obtained.

Ligase/Polymerase-mediated Genetic Bit Analysis™ is another method for determining the identity of a nucleotide at a preselected site in a nucleic acid molecule (WO 95/21271, the disclosure of which is incorporated herein by reference in its entirety). This method involves the incorporation of a nucleoside triphosphate that is complementary to the nucleotide present at the preselected site onto the terminus of a primer molecule, and their subsequent ligation to a second oligonucleotide. The reaction is monitored by detecting a specific label attached to the reaction's solid phase or by detection in solution.

4) Hybridization Assay Methods

A preferred method of determining the identity of the nucleotide present at a biallelic marker site involves nucleic acid hybridization. The hybridization probes, which can be conveniently used in such reactions, preferably include the probes defined herein. Any hybridization assay may be used including Southern hybridization, Northern hybridization, dot blot hybridization and solid-phase hybridization (see Sambrook et al., 1989).

Hybridization refers to the formation of a duplex structure by two single stranded nucleic acids due to complementary base pairing. Hybridization can occur between exactly complementary nucleic acid strands or between nucleic acid strands that contain minor regions of mismatch. Specific probes can be designed that hybridize to one form of a biallelic marker and not to the other and therefore are able to discriminate between different allelic forms. Allele-specific probes are often used in pairs, one member of a pair showing perfect match to a target sequence containing the original allele and the other showing a perfect match to the target sequence containing the alternative allele. Hybridization conditions should be sufficiently stringent that there is a significant difference in hybridization intensity between alleles, and preferably an essentially binary response, whereby a probe hybridizes to only one of the alleles. Stringent, sequence specific hybridization conditions, under which a probe will hybridize only to the exactly complementary target sequence are well known in the art (Sambrook et al., 1989). Stringent conditions are sequence dependent and will be different in different circumstances. Generally, stringent conditions are selected to be about 5° C. lower than the thermal melting point (Tm) for the specific sequence at a defined ionic strength and pH. Although such hybridization can be performed in solution, it is preferred to employ a solid-phase hybridization assay. The target DNA comprising a biallelic marker of the present invention may be amplified prior to the hybridization reaction. The presence of a specific allele in the sample is determined by detecting the presence or the absence of stable hybrid duplexes formed between the probe and the target DNA. The detection of hybrid duplexes can be carried out by a number of methods. Various detection assay formats are well known which utilize detectable labels bound to either the target or the probe to enable detection of the hybrid duplexes. Typically, hybridization duplexes are separated from unhybridized nucleic acids and the labels bound to the duplexes are then detected. Those skilled in the art will recognize that wash steps may be employed to wash away excess target DNA or probe as well as unbound conjugate. Further, standard heterogeneous assay formats are suitable for detecting the hybrids using the labels present on the primers and probes.

Two recently developed assays allow hybridization-based allele discrimination with no need for separations or washes (see Landegren U. et al., 1998). The TaqMan assay takes advantage of the 5' nuclease activity of Taq DNA polymerase to digest a DNA probe annealed specifically to the accumulating amplification product. TaqMan probes are labeled with a donor-acceptor dye pair that interacts via fluorescence energy transfer. Cleavage of the TaqMan probe by the advancing polymerase during amplification dissociates the donor dye from the quenching acceptor dye, greatly increasing the donor fluorescence. All reagents necessary to detect two allelic variants can be assembled at the beginning of the reaction and the results are monitored in real time (see Livak et al., 1995). In an alternative homogeneous hybridization based procedure, molecular beacons are used for allele discriminations. Molecular beacons are hairpin-shaped oligonucleotide probes that report the presence of specific nucleic acids in homogeneous solutions. When they bind to their targets they undergo a conformational reorganization that restores the fluorescence of an internally quenched fluorophore (Tyagi et al., 1998).

The polynucleotides provided herein can be used to produce probes which can be used in hybridization assays for the detection of biallelic marker alleles in biological samples. These probes are characterized in that they preferably comprise between 8 and 50 nucleotides, and in that they are sufficiently complementary to a sequence comprising a biallelic marker of the present invention to hybridize thereto and preferably sufficiently specific to be able to discriminate the targeted sequence for only one nucleotide variation. A particularly preferred probe is 25 nucleotides in length. Another particularly preferred probe is 47 nucleotides in length. Preferably the biallelic marker is within 4 nucleotides of the center of the polynucleotide probe. In particularly preferred probes, the biallelic marker is at the center of said polynucleotide. Preferred probes comprise a nucleotide sequence selected from the group consisting of amplicons listed in Table 1 and the sequences complementary thereto, or a fragment thereof, said fragment comprising at least about 8 consecutive nucleotides, preferably 10, 15, 20, more preferably 25, 30, 40, 47, or 50 consecutive nucleotides and containing a polymorphic base. Preferred probes comprise a nucleotide sequence selected from the group consisting of P1 to P125 and the sequences complementary thereto. In preferred embodiments the polymorphic base(s) are within 5, 4, 3, 2, 1, nucleotides of the center of the said polynucleotide, more preferably at the center of said polynucleotide.

Preferably the probes of the present invention are labeled or immobilized on a solid support. Labels and solid supports are further described in "Oligonucleotide Probes and Primers". The probes can be non-extendable as described in "Oligonucleotide Probes and Primers".

By assaying the hybridization to an allele specific probe, one can detect the presence or absence of a biallelic marker allele in a given sample. High-Throughput parallel hybridization in array format is specifically encompassed within "hybridization assays" and are described below.

5) Hybridization to Addressable Arrays of Oligonucleotides

Hybridization assays based on oligonucleotide arrays rely on the differences in hybridization stability of short oligonucleotides to perfectly matched and mismatched target sequence variants. Efficient access to polymorphism information is obtained through a basic structure comprising high-density arrays of oligonucleotide probes attached to a solid support (e.g., the chip) at selected positions. Each DNA chip can contain thousands to millions of individual synthetic DNA probes arranged in a grid-like pattern and miniaturized to the size of a dime.

The chip technology has already been applied with success in numerous cases. For example, the screening of mutations has been undertaken in the BRCA1 gene, in S. cerevisiae mutant strains, and in the protease gene of HIV-1 virus (Hacia et al., 1996; Shoemaker et al., 1996; Kozal et al., 1996). Chips of various formats for use in detecting biallelic polymorphisms can be produced on a customized basis by Affymetrix (GeneChip™), Hyseq (HyChip and HyGnostics), and Protogene Laboratories.

In general, these methods employ arrays of oligonucleotide probes that are complementary to target nucleic acid sequence segments from an individual which, target sequences include a polymorphic marker. EP 785280, the disclosure of which is incorporated herein by reference in its entirety, describes a tiling strategy for the detection of single nucleotide polymorphisms. Briefly, arrays may generally be "tiled" for a large number of specific polymorphisms. By "tiling" is generally meant the synthesis of a defined set of oligonucleotide probes which is made up of a sequence complementary to the target sequence of interest, as well as preselected variations of that sequence, e.g., substitution of one or more given positions with one or more members of the basis set of nucleotides. Tiling strategies are further described in PCT application No. WO 95/11995, the disclosure of which is incorporated herein by reference in its entirety. In a particular aspect, arrays are tiled for a number of specific, identified biallelic marker sequences. In particular, the array is tiled to include a number of detection blocks, each detection block being specific for a specific biallelic marker or a set of biallelic markers. For example, a detection block may be tiled to include a number of probes, which span the sequence segment that includes a specific polymorphism. To ensure probes that are complementary to each allele, the probes are synthesized in pairs differing at the biallelic marker. In addition to the probes differing at the polymorphic base, monosubstituted probes are also generally tiled within the detection block. These monosubstituted probes have bases at and up to a certain number of bases in either direction from the polymorphism, substituted with the remaining nucleotides (selected from A, T, G, C and U). Typically the probes in a tiled detection block will include substitutions of the sequence positions up to and including those that are 5 bases away from the biallelic marker. The monosubstituted probes provide internal controls for the tiled array, to distinguish actual hybridization from artefactual cross-hybridization. Upon completion of hybridization with the target sequence and washing of the array, the array is scanned to determine the position on the array to which the target sequence hybridizes. The hybridization data from the scanned array is then analyzed to identify which allele or alleles of the biallelic marker are present in the sample. Hybridization and scanning may be carried out as described in PCT application No. WO 92/10092 and WO 95/11995 and U.S. Pat. No. 5,424,186, the disclosures of which are incorporated herein by reference in their entireties.

Thus, in some embodiments, the chips may comprise an array of nucleic acid sequences of fragments of about 15 nucleotides in length. In further embodiments, the chip may comprise an array including at least one of the sequences selected from the group consisting of amplicons listed in table 1 and the sequences complementary thereto, or a fragment thereof, said fragment comprising at least about 8 consecutive nucleotides, preferably 10, 15, 20, more preferably 25, 30, 40, 47, or 50 consecutive nucleotides and containing a polymorphic base. In preferred embodiments the polymorphic base is within 5, 4, 3, 2, 1, nucleotides of the center of the said polynucleotide, more preferably at the center of said polynucleotide. In some embodiments, the chip may comprise an array of at least 2, 3, 4, 5, 6, 7, 8 or more of these polynucleotides of the invention. Solid supports and polynucleotides of the present invention attached to solid supports are further described in "Oligonucleotide Probes And Primers".

6) Integrated Systems

Another technique, which may be used to analyze polymorphisms, includes multicomponent integrated systems, which miniaturize and compartmentalize processes such as PCR and capillary electrophoresis reactions in a single functional device. An example of such technique is disclosed in U.S. Pat. No. 5,589,136, the disclosure of which is incorporated herein by reference in its entirety, which describes the integration of PCR amplification and capillary electrophoresis in chips.

Integrated systems can be envisaged mainly when microfluidic systems are used. These systems comprise a pattern of microchannels designed onto a glass, silicon, quartz, or plastic wafer included on a microchip. The movements of the samples are controlled by electric, electroosmotic or hydrostatic forces applied across different areas of the microchip to create functional microscopic valves and pumps with no moving parts.

For genotyping biallelic markers, the microfluidic system may integrate nucleic acid amplification, microsequencing, capillary electrophoresis and a detection method such as laser-induced fluorescence detection.

Methods of Genetic Analysis Using the Biallelic Markers of the Present Invention Different methods are available for the genetic analysis of complex traits (see Lander and Schork, 1994). The search for disease-susceptibility genes is conducted using two main methods: the linkage approach in which evidence is sought for cosegregation between a locus and a putative trait locus using family studies, and the association approach in which evidence is sought for a statistically significant association between an allele or a trait causing allele and a trait (Khoury et al., 1993). In general, the biallelic markers of the present invention find use in any method known in the art to demonstrate a statistically significant correlation between a genotype and a phenotype. The biallelic markers may be used in parametric and non-parametric linkage analysis methods. Preferably, the biallelic markers of the present invention are used to identify genes associated with detectable traits using association studies, an approach which does not require the use of affected families and which permits the identification of genes associated with complex and sporadic traits.

The genetic analysis using the biallelic markers of the present invention may be conducted on any scale. The whole set of biallelic markers of the present invention or any subset of biallelic markers of the present invention corresponding to the candidate gene may be used. Further, any set of genetic markers including a biallelic marker of the present invention may be used. A set of biallelic polymorphisms that could be used as genetic markers in combination with the biallelic markers of the present invention has been described in WO 98/20165, the disclosure of which is incorporated herein by reference in its entirety. As mentioned above, it should be noted that the biallelic markers of the present invention may be included in any complete or partial genetic map of the human genome. These different uses are specifically contemplated in the present invention and claims.

Linkage Analysis

Linkage analysis is based upon establishing a correlation between the transmission of genetic markers and that of a specific trait throughout generations within a family. Thus, the aim of linkage analysis is to detect marker loci that show cosegregation with a trait of interest in pedigrees.

Parametric Methods

When data are available from successive generations there is the opportunity to study the degree of linkage between pairs of loci. Estimates of the recombination fraction enable loci to be ordered and placed onto a genetic map. With loci that are genetic markers, a genetic map can be established, and then the strength of linkage between markers and traits can be calculated and used to indicate the relative positions of markers and genes affecting those traits (Weir, 1996). The classical method for linkage analysis is the logarithm of odds (lod) score method (see Morton, 1955; Ott, 1991). Calculation of lod scores requires specification of the mode of inheritance for the disease (parametric method). Generally, the length of the candidate region identified using linkage analysis is between 2 and 20 Mb. Once a candidate region is identified as described above, analysis of recombinant individuals using additional markers allows further delineation of the candidate region. Linkage analysis studies have generally relied on the use of a maximum of 5,000 microsatellite markers, thus limiting the maximum theoretical attainable resolution of linkage analysis to about 600 kb on average.

Linkage analysis has been successfully applied to map simple genetic traits that show clear Mendelian inheritance patterns and which have a high penetrance (i.e., the ratio between the number of trait positive carriers of allele a and the total number of a carriers in the population). However, parametric linkage analysis suffers from a variety of drawbacks. First, it is limited by its reliance on the choice of a genetic model suitable for each studied trait. Furthermore, as already mentioned, the resolution attainable using linkage analysis is limited, and complementary studies are required to refine the analysis of the typical 2 Mb to 20 Mb regions initially identified through linkage analysis. In addition, parametric linkage analysis approaches have proven difficult when applied to complex genetic traits, such as those due to the combined action of multiple genes and/or environmental factors. It is very difficult to model these factors adequately in a lod score analysis. In such cases, too large an effort and cost are needed to recruit the adequate number of affected families required for applying linkage analysis to these situations, as recently discussed by Risch, N. and Merikangas, K. (1996).

Non-Parametric Methods

The advantage of the so-called non-parametric methods for linkage analysis is that they do not require specification of the mode of inheritance for the disease, they tend to be more useful for the analysis of complex traits. In non-parametric methods, one tries to prove that the inheritance pattern of a chromosomal region is not consistent with random Mendelian segregation by showing that affected relatives inherit identical copies of the region more often than expected by chance. Affected relatives should show excess "allele sharing" even in the presence of incomplete penetrance and polygenic inheritance. In non-parametric linkage analysis the degree of agreement at a marker locus in two individuals can be measured either by the number of alleles identical by state (IBS) or by the number of alleles identical by descent (IBD). Affected sib pair analysis is a well-known special case and is the simplest form of these methods.

The biallelic markers of the present invention may be used in both parametric and non-parametric linkage analysis. Preferably biallelic markers may be used in non-parametric methods which allow the mapping of genes involved in complex traits. The biallelic markers of the present invention may be used in both IBD- and IBS-methods to map genes affecting a complex trait. In such studies, taking advantage of the high density of biallelic markers, several adjacent biallelic marker loci may be pooled to achieve the efficiency attained by multi-allelic markers (Zhao et al., 1998).

Population Association Studies

The present invention comprises methods for identifying if the PCTA-1 gene is associated with a detectable trait using the biallelic markers of the present invention. In one embodiment the present invention comprises methods to detect an association between a biallelic marker allele or a biallelic marker haplotype and a trait. Further, the invention comprises methods to identify a trait causing allele in linkage disequilibrium with any biallelic marker allele of the present invention.

Alternative approaches can be employed to perform association studies: genome-wide association studies, candidate region association studies and candidate gene association studies. In a preferred embodiment, the biallelic markers of the present invention are used to perform candidate gene association studies. The candidate gene analysis clearly provides a short-cut approach to the identification of genes and gene polymorphisms related to a particular trait when some information concerning the biology of the trait is available. Further, the biallelic markers of the present invention may be incorporated in any map of genetic markers of the human genome in order to perform genome-wide association studies. Methods to generate a high-density map of biallelic markers has been described in U.S. Provisional Patent application Ser. No. 60/082,614. The biallelic markers of the present invention may further be incorporated in any map of a specific candidate region of the genome (a specific chromosome or a specific chromosomal segment for example).

As mentioned above, association studies may be conducted within the general population and are not limited to studies performed on related individuals in affected families. Association studies are extremely valuable as they permit the analysis of sporadic or multifactor traits. Moreover, association studies represent a powerful method for fine-scale mapping enabling much finer mapping of trait causing alleles than linkage studies. Studies based on pedigrees often only narrow the location of the trait causing allele. Association studies using the biallelic markers of the present invention can therefore be used to refine the location of a trait causing allele in a candidate region identified by Linkage Analysis methods. Moreover, once a chromosome segment of interest has been identified, the presence of a candidate gene such as a candidate gene of the present invention, in the region of interest can provide a shortcut to the identification of the trait causing allele. Biallelic markers of the present invention can be used to demonstrate that a candidate gene is associated with a trait. Such uses are specifically contemplated in the present invention.

Determining the Frequency of a Biallelic Marker Allele or of a Biallelic Marker Haplotype in a Population Association studies explore the relationships among frequencies for sets of alleles between loci.

Determining the Frequency of an Allele in a Population

Allelic frequencies of the biallelic markers in a populations can be determined using one of the methods described above under the heading "Methods For Genotyping An Individual For Biallelic Markers", or any genotyping procedure suitable for this intended purpose. Genotyping pooled samples or individual samples can determine the frequency of a biallelic marker allele in a population. One way to reduce the number of genotypings required is to use pooled samples. A major obstacle in using pooled samples is in terms of accuracy and reproducibility for determining accurate DNA concentrations in setting up the pools. Genotyping individual samples provides higher sensitivity, reproducibility and accuracy and; is the preferred method used in the present invention. Preferably, each individual is genotyped separately and simple gene counting is applied to determine the frequency of an allele of a biallelic marker or of a genotype in a given population.

The invention also relates to methods of estimating the frequency of a PCTA-1-related biallelic marker allele in a population comprising: a) genotyping individuals from said population for said biallelic marker according to the method of the present invention; and b) determining the proportional representation of said biallelic marker in said population. In addition, the methods of estimating the frequency of an allele in a population of the invention encompass methods with any further limitation described in this disclosure, or those following, specified alone or in any combination; optionally, wherein said PCTA-1-related biallelic marker is selected from the group consisting of A1 to A125, and the complements thereof, or optionally the biallelic markers in linkage disequilibrium therewith; optionally, wherein said PCTA-1-related biallelic marker is selected from the group consisting of A1 to A44, A46 to A53, A57, A58, A62 to A76, A81, A82, A86 to A91, A107, A118, and A123 to A125, and the complements thereof, or optionally the biallelic markers in linkage disequilibrium therewith; optionally, wherein said PCTA-1-related biallelic marker is selected from the group consisting of A45, A54, A60, A61, A77 to A80, A83 to A85, A93, A102 to A106, A109, A110, A114, and A122, and the complements thereof, or optionally the biallelic markers in linkage disequilibrium therewith; optionally, wherein said PCTA-1-related biallelic marker is selected from the group consisting of A55, A56, A59, A92, A94 to A101, A108, A111 to A113, A115 to A117, and A119 to A121, and the complements thereof, or optionally the biallelic markers in linkage disequilibrium therewith; Optionally, determining the frequency of a biallelic marker allele in a population may be accomplished by determining the identity of the nucleotides for both copies of said biallelic marker present in the genome of each individual in said population and calculating the proportional representation of said nucleotide at said PCTA-1-related biallelic marker for the population; Optionally, determining the proportional representation may be accomplished by performing a genotyping method of the invention on a pooled biological sample derived from a representative number of individuals, or each individual, in said population, and calculating the proportional amount of said nucleotide compared with the total.

Determining the Frequency of a Haplotype in a Population

The gametic phase of haplotypes is unknown when diploid individuals are heterozygous at more than one locus. Using genealogical information in families gametic phase can sometimes be inferred (Perlin et al., 1994). When no genealogical information is available different strategies may be used. One possibility is that the multiple-site heterozygous diploids can be eliminated from the analysis, keeping only the homozygotes and the single-site heterozygote individuals, but this approach might lead to a possible bias in the sample composition and the underestimation of low-frequency haplotypes. Another possibility is that single chromosomes can be studied independently, for example, by asymmetric PCR amplification (see Newton et al, 1989; Wu et al., 1989) or by isolation of single chromosome by limit dilution followed by PCR amplification (see Ruano et al., 1990). Further, a sample may be haplotyped for sufficiently close biallelic markers by double PCR amplification of specific alleles (Sarkar, G. and Sommer S. S., 1991). These approaches are not entirely satisfying either because of their technical complexity, the additional cost they entail, their lack of generalization at a large scale, or the possible biases they introduce. To overcome these difficulties, an algorithm to infer the phase of PCR-amplified DNA genotypes introduced by Clark, A. G.(1990) may be used. Briefly, the principle is to start filling a preliminary list of haplotypes present in the sample by examining unambiguous individuals, that is, the complete homozygotes and the single-site heterozygotes. Then other individuals in the same sample are screened for the possible occurrence of previously recognized haplotypes. For each positive identification, the complementary haplotype is added to the list of recognized haplotypes, until the phase information for all individuals is either resolved or identified as unresolved. This method assigns a single haplotype to each multiheterozygous individual, whereas several haplotypes are possible when there are more than one heterozygous site. Alternatively, one can use methods estimating haplotype frequencies in a population without assigning haplotypes to each individual. Preferably, a method based on an expectation-maximization (EM) algorithm (Dempster et al., 1977) leading to maximum-likelihood estimates of haplotype frequencies under the assumption of Hardy-Weinberg proportions (random mating) is used (see Excoffier L. and Slatkin M., 1995). The EM algorithm is a generalized iterative maximum-likelihood approach to estimation that is useful when data are ambiguous and/or incomplete. The EM algorithm is used to resolve heterozygotes into haplotypes. Haplotype estimations are further described below under the heading "Statistical Methods." Any other method known in the art to determine or to estimate the frequency of a haplotype in a population may be used.

The invention also encompasses methods of estimating the frequency of a haplotype for a set of biallelic markers in a population, comprising the steps of: a) genotyping at least one PCTA-1-related biallelic marker according to a method of the invention for each individual in said population; b) genotyping a second biallelic marker by determining the identity of the nucleotides at said second biallelic marker for both copies of said second biallelic marker present in the genome of each individual in said population; and c) applying a haplotype determination method to the identities of the nucleotides determined in steps a) and b) to obtain an estimate of said frequency. In addition, the methods of estimating the frequency of a haplotype of the invention encompass methods with any further limitation described in this disclosure, or those following, specified alone or in any combination: optionally, wherein said PCTA-1-related biallelic marker is selected from the group consisting of A1 to A125, and the complements thereof, or optionally the biallelic markers in linkage disequilibrium therewith; optionally, wherein said PCTA-1-related biallelic marker is selected from the group consisting of A1 to A44, A46 to A53, A57, A58, A62 to A76, A81, A82, A86 to A91, A107, A118, and A123 to A125, and the complements thereof, or optionally the biallelic markers in linkage disequilibrium therewith; optionally, wherein said PCTA-1-related biallelic marker is selected from the group consisting of A45, A54, A60, A61, A77 to A80, A83 to A85, A93, A102 to A106, A109, A110, A114, and A122, and the complements thereof, or optionally the biallelic markers in linkage disequilibrium therewith; optionally, wherein said PCTA-1-related biallelic marker is selected from the group consisting of A55, A56, A59, A92, A94 to A101, A108, A111 to A113, A115 to A117, and A119 to A121, and the complements thereof, or optionally the biallelic markers in linkage disequilibrium therewith; Optionally, said haplotype determination method is performed by asymmetric PCR amplification, double PCR amplification of specific alleles, the Clark algorithm, or an expectation-maximization algorithm.

Linkage Disequilibrium Analysis

Linkage disequilibrium is the non-random association of alleles at two or more loci and represents a powerful tool for mapping genes involved in disease traits (see Ajioka R. S. et al., 1997). Biallelic markers, because they are densely spaced in the human genome and can be genotyped in greater numbers than other types of genetic markers (such as RFLP or VNTR markers), are particularly useful in genetic analysis based on linkage disequilibrium.

When a disease mutation is first introduced into a population (by a new mutation or the immigration of a mutation carrier), it necessarily resides on a single chromosome and thus on a single "background" or "ancestral" haplotype of linked markers. Consequently, there is complete disequilibrium between these markers and the disease mutation: one finds the disease mutation only in the presence of a specific set of marker alleles. Through subsequent generations recombination events occur between the disease mutation and these marker polymorphisms, and the disequilibrium gradually dissipates. The pace of this dissipation is a function of the recombination frequency, so the markers closest to the disease gene will manifest higher levels of disequilibrium than those that are further away. When not broken up by recombination, "ancestral" haplotypes and linkage disequilibrium between marker alleles at different loci can be tracked not only through pedigrees but also through populations. Linkage disequilibrium is usually seen as an association between one specific allele at one locus and another specific allele at a second locus.

The pattern or curve of disequilibrium between disease and marker loci is expected to exhibit a maximum that occurs at the disease locus. Consequently, the amount of linkage disequilibrium between a disease allele and closely linked genetic markers may yield valuable information regarding the location of the disease gene. For fine-scale mapping of a disease locus, it is useful to have some knowledge of the patterns of linkage disequilibrium that exist between markers in the studied region. As mentioned above the mapping resolution achieved through the analysis of linkage disequilibrium is much higher than that of linkage studies. The high density of biallelic markers combined with linkage disequilibrium analysis provides powerful tools for fine-scale mapping. Different methods to calculate linkage disequilibrium are described below under the heading "Statistical Methods".

Population-Based Case-Control Studies of Trait-Marker Associations

As mentioned above, the occurrence of pairs of specific alleles at different loci on the same chromosome is not random and the deviation from random is called linkage disequilibrium. Association studies focus on population frequencies and rely on the phenomenon of linkage disequilibrium. If a specific allele in a given gene is directly involved in causing a particular trait, its frequency will be statistically increased in an affected (trait positive) population, when compared to the frequency in a trait negative population or in a random control population. As a consequence of the existence of linkage disequilibrium, the frequency of all other alleles present in the haplotype carrying the trait-causing allele will also be increased in trait positive individuals compared to trait negative individuals or random controls. Therefore, association between the trait and any allele (specifically a biallelic marker allele) in linkage disequilibrium with the trait-causing allele will suffice to suggest the presence of a trait-related gene in that particular region. Case-control populations can be genotyped for biallelic markers to identify associations that narrowly locate a trait causing allele. As any marker in linkage disequilibrium with one given marker associated with a trait will be associated with the trait. Linkage disequilibrium allows the relative frequencies in case-control populations of a limited number of genetic polymorphisms (specifically biallelic markers) to be analyzed as an alternative to screening all possible functional polymorphisms in order to find trait-causing alleles. Association studies compare the frequency of marker alleles in unrelated case-control populations, and represent powerful tools for the dissection of complex traits.

Case-Control Populations (Inclusion Criteria)

Population-based association studies do not concern familial inheritance but compare the prevalence of a particular genetic marker, or a set of markers, in case-control populations. They are case-control studies based on comparison of unrelated case (affected or trait positive) individuals and unrelated control (unaffected, trait negative or random) individuals. Preferably the control group is composed of unaffected or trait negative individuals. Further, the control group is ethnically matched to the case population. Moreover, the control group is preferably matched to the case-population for the main known confusion factor for the trait under study (for example age-matched for an age-dependent trait). Ideally, individuals in the two samples are paired in such a way that they are expected to differ only in their disease status. The terms "trait positive population", "case population" and "affected population" are used interchangeably herein.

An important step in the dissection of complex traits using association studies is the choice of case-control populations (see Lander and Schork, 1994). A major step in the choice of case-control populations is the clinical definition of a given trait or phenotype. Any genetic trait may be analyzed by the association method proposed here by carefully selecting the individuals to be included in the trait positive and trait negative phenotypic groups. Four criteria are often useful: clinical phenotype, age at onset, family history and severity. The selection procedure for continuous or quantitative traits (such as blood pressure for example) involves selecting individuals at opposite ends of the phenotype distribution of the trait under study, so as to include in these trait positive and trait negative populations individuals with non-overlapping phenotypes. Preferably, case-control populations consist of phenotypically homogeneous populations. Trait positive and trait negative populations consist of phenotypically uniform populations of individuals representing each between 1 and 98%, preferably between 1 and 80%, more preferably between 1 and 50%, and more preferably between 1 and 30%, most preferably between 1 and 20% of the total population under study, and preferably selected among individuals exhibiting non-overlapping phenotypes. The clearer the difference between the two trait phenotypes, the greater the probability of detecting an association with biallelic markers. The selection of those drastically different but relatively uniform phenotypes enables efficient comparisons in association studies and the possible detection of marked differences at the genetic level, provided that the sample sizes of the populations under study are significant enough.

In preferred embodiments, a first group of between 50 and 300 trait positive individuals, preferably about 100 individuals, are recruited according to their phenotypes. A similar number of control individuals are included in such studies.

In the present invention, typical examples of inclusion criteria include, but are not restricted to, prostate cancer or aggressiveness of prostate cancer tumors. In one preferred embodiment of the present invention, association studies are carried out on the basis of a presence (trait positive) or absence (trait negative) of prostate cancer.

Associations studies can be carried out by the skilled technician using the biallelic markers of the invention defined above, with different trait positive and trait negative populations. Suitable further examples of association studies using biallelic markers of the PCTA-1 gene, including the biallelic markers A1 to A125, involve studies on the following populations:

- a trait positive population suffering from a cancer and a healthy unaffected population, or
- a trait positive population suffering from prostate cancer treated with agents acting against prostate cancer and suffering from side-effects resulting from this treatment and an trait negative population suffering from prostate cancer treated with same agents without any substantial side-effects, or
- a trait positive population suffering from prostate cancer treated with agents acting against prostate cancer showing a beneficial response and a trait negative population suffering from prostate cancer treated with same agents without any beneficial response, or
- a trait positive population suffering from prostate cancer presenting highly aggressive prostate cancer tumors and a trait negative population suffering from prostate cancer with prostate cancer tumors devoid of aggressiveness.

Association Analysis

The general strategy to perform association studies using biallelic markers derived from a region carrying a candidate gene is to scan two groups of individuals (case-control populations) in order to measure and statistically compare the allele frequencies of the biallelic markers of the present invention in both groups.

If a statistically significant association with a trait is identified for at least one or more of the analyzed biallelic markers, one can assume that: either the associated allele is directly responsible for causing the trait (i.e. the associated allele is the trait causing allele), or more likely the associated allele is in linkage disequilibrium with the trait causing allele. The specific characteristics of the associated allele with respect to the candidate gene function usually give further insight into the relationship between the associated allele and the trait (causal or in linkage disequilibrium). If the evidence indicates that the associated allele within the candidate gene is most probably not the trait causing allele but is in linkage disequilibrium with the real trait causing allele, then the trait causing allele can be found by sequencing the vicinity of the associated marker, and performing further association studies with the polymorphisms that are revealed in an iterative manner.

Association studies are usually run in two successive steps. In a first phase, the frequencies of a reduced number of biallelic markers from the candidate gene are determined in the trait positive and control populations. In a second phase of the analysis, the position of the genetic loci responsible for the given trait is further refined using a higher density of markers from the relevant region. However, if the candidate gene under study is relatively small in length, as is the case for PCTA-1, a single phase may be sufficient to establish significant associations.

It is another object of the present invention to provide a method for the identification and characterization of an association between an allele of one or more biallelic markers of a PCTA-1 gene and a trait. The method comprises the steps of:
genotyping a marker or a group of biallelic markers according to the invention in trait positive and control individuals; and
establishing a statistically significant association between one allele of at least one marker and the trait.

The control individuals can be random or trait negative populations. Preferably, the trait positive and trait negative individuals are selected from non-overlapping phenotypes relating trait under study. In some embodiments, the biallelic marker is comprised in one or more of the sequences of P1 to P125, and the complementary sequences thereof. The invention also comprises methods of detecting an association between a genotype and a phenotype, comprising the steps of a) determining the frequency of at least one PCTA-1-related biallelic marker in a trait positive population according to a genotyping method of the invention; b) determining the frequency of said PCTA-1-related biallelic marker in a control population according to a genotyping method of the invention; and c) determining whether a statistically significant association exists between said genotype and said phenotype. In addition, the methods of detecting an association between a genotype and a phenotype of the invention encompass methods with any further limitation described in this disclosure, or those following, specified alone or in any combination: Optionally, wherein said PCTA-1-related biallelic marker is selected from the group consisting of A1 to A125, and the complements thereof, or optionally the biallelic markers in linkage disequilibrium therewith; optionally, wherein said PCTA-1-related biallelic marker is selected from the group consisting of A1 to A44, A46 to A53, A57, A58, A62 to A76, A81, A82, A86 to A91, A107, A118, and A123 to A125, and the complements thereof, or optionally the biallelic markers in linkage disequilibrium therewith; optionally, wherein said PCTA-1-related biallelic marker is selected from the group consisting of A45, A54, A60, A61, A77 to A80, A83 to A85, A93, A102 to A106, A109, A110, A114, and A122, and the complements thereof, or optionally the biallelic markers in linkage disequilibrium therewith; optionally, wherein said PCTA-1-related biallelic marker is selected from the group consisting of A55, A56, A59, A92, A94 to A101, A108, A111 to A113, A115 to A117, and A119 to A121, and the complements thereof, or optionally the biallelic markers in linkage disequilibrium therewith; Optionally, said control population may be a trait negative population, or a random population; Optionally, each of said genotyping steps a) and b) may be performed on a pooled biological sample derived from each of said populations; Optionally, each of said genotyping of steps a) and b) is performed separately on biological samples derived from each individual in said population or a subsample thereof; Optionally, the identity of the nucleotides at the biallelic markers of the PCTA-1 gene is determined in steps a) and b). Optionally, said phenotype is symptoms of, or susceptibility to cancer, preferably prostate cancer, the level of aggressiveness of prostate cancer tumors, an early onset of prostate cancer, a beneficial response to or side effects related to treatment against prostate cancer.

If the trait is a beneficial response or inversely a side effect to a treatment of prostate cancer, the method of the invention referred to above further comprises some or all of the following steps:
selecting a population or cohort of subjects diagnosed as suffering from prostate cancer;
administering a specified treatment of prostate cancer to said cohort of subjects;
monitoring the outcome of drug administration and identifying those individuals that are trait positive or trait negative relative to the treatment;
taking from said cohort biological samples containing DNA and testing this DNA for the presence of a specific allele or of a set of alleles of biallelic markers of the PCTA-1 gene;
analyzing the distribution of alleles of biallelic markers between trait positive and trait negative individuals; and
performing a statistical analysis to determine a statistically significant association between the presence or absence of alleles of biallelic markers of the PCTA-1 gene and the treatment related trait.

Haplotype Analysis

As described above, when a chromosome carrying a disease allele first appears in a population as a result of either mutation or migration, the mutant allele necessarily resides on a chromosome having a set of linked markers: the ancestral haplotype. This haplotype can be tracked through populations and its statistical association with a given trait can be analyzed. Complementing single point (allelic) association studies with multi-point association studies also called haplotype studies increases the statistical power of association studies. Thus, a haplotype association study allows one to define the frequency and the type of the ancestral carrier haplotype. A haplotype analysis is important in that it increases the statistical power of an analysis involving individual markers.

In a first stage of a haplotype frequency analysis, the frequency of the possible haplotypes based on various combinations of the identified biallelic markers of the invention is determined. The haplotype frequency is then compared for distinct populations of trait positive and control individuals. The number of trait positive individuals, which should be, subjected to this analysis to obtain statistically significant results usually ranges between 30 and 300, with a preferred number of individuals ranging between 50 and 150. The same considerations apply to the number of unaffected individuals (or random control) used in the study. The results of this first analysis provide haplotype frequencies in case-control populations, for each evaluated haplotype frequency a p-value and an odd ratio are calculated. If a statistically significant association is found the relative risk for an individual carrying the given haplotype of being affected with the trait under study can be approximated.

The present invention also provides a method for the identification and characterization of an association between a haplotype comprising alleles of several biallelic markers of the genomic sequence of the PCTA-1 gene and a trait. The method comprises the steps of:
  genotyping a group of biallelic markers according to the invention in trait positive and control individuals; and
  establishing a statistically significant association between a haplotype and the trait.

Preferably, the control individuals can be random or trait negative populations. In some embodiments, the haplotype comprises two or more biallelic markers comprised in the sequences of P1 to P125, and the complementary sequences thereof.

An additional embodiment of the present invention encompasses methods of detecting an association between a haplotype and a phenotype, comprising the steps of: a) estimating the frequency of at least one haplotype in a trait positive population, according to a method of the invention for estimating the frequency of a haplotype; b) estimating the frequency of said haplotype in a control population, according to a method of the invention for estimating the frequency of a haplotype; and c) determining whether a statistically significant association exists between said haplotype and said phenotype. In addition, the methods of detecting an association between a haplotype and a phenotype of the invention encompass methods with any further limitation described in this disclosure, or those following: Optionally, wherein said PCTA-1-related biallelic marker is selected from the group consisting of A1 to A125, and the complements thereof, or optionally the biallelic markers in linkage disequilibrium therewith; optionally, wherein said PCTA-1-related biallelic marker is selected from the group consisting of A1 to A44, A46 to A53, A57, A58, A62 to A76, A81, A82, A86 to A91, A107, A118, and A123 to A125, and the complements thereof, or optionally the biallelic markers in linkage disequilibrium therewith; optionally, wherein said PCTA-1-related biallelic marker is selected from the group consisting of A45, A54, A60, A61, A77 to A80, A83 to A85, A93, A102 to A106, A109, A110, A114, and A122, and the complements thereof, or optionally the biallelic markers in linkage disequilibrium therewith; optionally, wherein said PCTA-1-related biallelic marker is selected from the group consisting of A55, A56, A59, A92, A94 to A101, A108, A111 to A113, A115 to A117, and A119 to A121, and the complements thereof, or optionally the biallelic markers in linkage disequilibrium therewith; Optionally, said control population is a trait negative population, or a random population. Optionally, said phenotype is symptoms of, or susceptibility to cancer, preferably prostate cancer, the level of aggressiveness of prostate cancer tumors, an early onset of prostate cancer, a beneficial response to or side effects related to treatment against prostate cancer; Optionally, said method comprises the additional steps of determining the phenotype in said trait positive and said control populations prior to step c).

Interaction Analysis

The biallelic markers of the present invention may also be used to identify patterns of biallelic markers associated with detectable traits resulting from polygenic interactions. The analysis of genetic interaction between alleles at unlinked loci requires individual genotyping using the techniques described herein. The analysis of allelic interaction among a selected set of biallelic markers with appropriate level of statistical significance can be considered as a haplotype analysis. Interaction analysis consists of stratifying the case-control populations with respect to a given haplotype for the first loci and performing a haplotype analysis with the second loci with each subpopulation.

Statistical methods used in association studies are further described below.

Testing for Linkage in the Presence Of Association

The biallelic markers of the present invention may further be used in TDT (transmission/disequilibrium test). TDT tests for both linkage and association and is not affected by population stratification. TDT requires data for affected individuals and their parents or data from unaffected sibs instead of from parents (see Spielmann S. et al., 1993; Schaid D. J. et al., 1996, Spielmann S. and Ewens W. J., 1998). Such combined tests generally reduce the false—positive errors produced by separate analyses.

Association of Biallelic Markers of the Invention with Prostate Cancer

Trait Positive and Control Populations

Two groups of independent individuals were used: the overall trait positive and the trait negative populations included 491 individuals suffering from prostate cancer and 313 individuals without any sign of prostate cancer. A specific protocol for the collection of DNA samples from trait positive and trait negative individuals is described in Example 5. The 491 individuals suffering from prostate cancer can be subdivided into a population of individuals who developed prostate cancer under 65 years-old and a population of individuals who developed prostate cancer after the age of 65. The population of individuals who are less than 65 years-old was used to determine an association with an early onset of prostate cancer. The affected individuals can also be subdivided in familial cases and sporadic cases.

In order to have as much certainty as possible on the absence of prostate cancer in trait negative individuals, it is preferred to conduct a PSA dosage analysis on this population. Several commercial assays can be used (WO 96/21042, the disclosure of which is incorporated herein by reference in its entirety). In one preferred embodiment, a Hybritech assay is used and trait negative individuals must have a level of PSA less than 2.8 ng/ml of serum in order to be selected as such. In a preferred embodiment, the Yang assay is used and trait negative individuals must have a level of PSA of less than 4 ng/ml of serum in order to be included in the population under study.

Association Analysis

In one preferred embodiment of the invention in which a correlation was found between biallelic markers of the PCTA-1 gene and prostate cancer, results of the association study, further details of which are provided in example 5, seem to indicate that prostate cancer, preferably familial prostate cancer, more preferably early onset familial prostate cancer, is associated most strongly with the biallelic markers A30 (99-1572/440) and A41 (5-171/204) which present a particular interest. These association results constitute new elements for studying the genetic susceptibility of individuals to prostate cancer, preferably to familial prostate cancer, more preferably familial early onset prostate cancer. Further details concerning this association study are provided below.

The biallelic markers most strongly associated with prostate cancer, namely A30 and A41, are located in the regulatory region of the PCTA-1 gene, more particularly in the promoter region. The consequences of the presence of these markers in these regions are discussed below.

Furthermore, the biallelic marker A2 (99-1601/402) was found to be also associated with prostate cancer, more particularly with sporadic prostate cancer. This biallelic marker is localized in the 5' regulatory region of the PCTA-1 gene.

Similar association studies can also be carried out with other biallelic markers within the scope of the invention, preferably with biallelic markers in linkage disequilibrium with the markers associated with prostate cancer as described above, including the biallelic markers A1 to A125.

Analysis of Biallelic Marker Associations

Even though polymorphisms associated with prostate cancer have been identified in the coding region of the PCTA-1 gene, these polymorphisms do not appear to be as significant as those found in the upstream regulatory region of the PCTA-1 gene. The results further suggest that a trait-causing mutation is likely to be located within the 5' regulatory region of the PCTA-1 gene. The extent to which the markers found within the coding region of PCTA-1 are significant in relation to cancer can be determined using haplotype analyses involving at least two of the biallelic markers of the present invention.

Six of the biallelic markers of the present invention result in a change in the amino acid sequence of a PCTA-1 protein. These are biallelic markers A54, A56, A60, A75, A76 and A85. These mutations may change the function and/or the stability of the PCTA-1 protein. An amino acid change in a PCTA-1 protein can lead to alterations in PCTA-1 biological activity. Either a modified function or an increased stability can be involved in prostate cancer appearance.

Furthermore, as the expression of the PCTA-1 gene has mainly been reported in prostate cancer cells, one can assume that its expression is closely linked to the development of cancer, particularly prostate cancer. Generally, a major control of gene expression proceeds at the level of the initiation of the transcription. This initiation involves the promoter which can be considered as a concentration of transcription factor binding sites. The initiation of the transcription also involves enhancers which modulate the efficiency of the initiation and consist of DNA binding sites which are located in regulatory regions of the considered gene which may be at a certain distance in 3' or 5' of the gene.

Most of the biallelic polymorphisms of the PCTA-1 gene associated with prostate cancer according to the present invention are located in the regulatory region upstream of the transcription start site of the PCTA-1 gene and particularly in the promoter. Biallelic marker A41, which is located about 120 bp upstream of the beginning of the first exon (exon 0), may be comprised in the proximal promoter of the PCTA-1 gene. This biallelic marker could be a trait causing mutation of prostate cancer. Biallelic marker A30, which is located about 1.5 kb upstream the beginning of the first exon (exon 0), may be comprised in the distal promoter of the PCTA-1 gene. Biallelic marker A2 is located in the 5' regulatory region of the PCTA-1 gene.

As the expression of the PCTA-1 gene has mainly been reported in prostate cancer cells, the expression of PCTA-1 gene is modified during the carcinogenesis. The exact mechanism through which PCTA expression is modified is not understood. However, it is possible that the polymorphisms A41, A30, and A2 modulate PCTA-1 expression by modulating PCTA-1 transcription through DNA binding proteins, which will be explained in further detail below.

The regulation of PCTA-1 expression is a key factor in the onset and for development of cancer and particularly prostate cancer. In this regard, the polymorphisms located in the 5' regulatory region of the PCTA-1 gene appear to play the most significant role in the association of PCTA-1 with cancer. It appears clear that the polymorphisms found in the promoter region adjacent to the transcription initiation site, and particularly those located in the proximal PCTA-1 promoter, are more strongly associated with prostate cancer than polymorphisms of the other promoter elements located further upstream of this site. Furthermore, some polymorphisms, such as the biallelic marker A41, are clearly associated with early onset prostate cancer. The polymorphisms found in the proximal 2000 to 3000 bp of the 5' regulatory region are associated with early onset prostate cancer. The inventors have also shown an association between some of the biallelic markers of the present invention located at the 3' end of the PCTA-1 genomic DNA and prostate cancer.

The involvement of the associated polymorphisms in the modification of the PCTA-1 expression in prostate cancer cells can be confirmed through the assays described below.

The expression levels of a PCTA-1 gene, preferably a gene comprising at least one biallelic marker according to the invention, in different tissues, can be determined by analyses of tissue samples from individuals typed for the presence or absence of a specific polymorphism. Any convenient method can be used such as Northern, or Dot blot or other hybridization analyses, and quantitative RT-PCR for mRNA quantitation, Western blot ELISA, RIA for protein quantitation. The tissue specific expression can then be correlated with the genotype. More details on some of these methods are provided below under the heading "Method For Screening".

The effects of modifications in the regulatory regions of the PCTA-1 gene, and particularly in the sequence of its promoter, can be studied through the determination of expression levels by expression assays for the particular promoter sequence. The assays are performed with the PCTA-1 coding sequence or with a detectable marker sequence using a reporter gene. To determine tissue specificity, the assay is performed in cells from different sources. Preferably the assay is performed on normal tissue cells and cancerous cells of the same tissue type (e.g. prostate cells and on prostate cancer cells). More preferably, the assay is performed on a large range of cell lines with an increasing level of malignancy. Some methods are discussed in more detail below under the heading "Method For Screening".

An assay to determine the effect of a sequence polymorphism on PCTA-1 expression may be performed in cell-free extracts, or in cell-culture assays, such as transient or stable transfection assays. This assay is also within the scope of the present invention. Alterations in expression may be correlated to decreases or increases in the basic amounts of PCTA-1 mRNA and/or protein that are expressed in one or more cell types. Expression levels of different alleles are compared using various methods known in the art. Methods for determining whether the level of expression triggered by promoter or enhancer sequences is increased or decreased depending on the studied allele of said sequence include the insertion into a vector of said sequence upstream a reporter gene such as β-galactosidase, luciferase, green fluorescent protein or chloramphenicol acetyltransferase. Expression levels are assessed by quantitation of expressed reporter proteins that provides for convenient quantitation.

The changes in PCTA-1 expression can be the result of modifications in the modulation of PCTA-1 transcription by DNA binding proteins, which are able to activate or inhibit the initiation of the transcription of the PCTA-1 gene. The term "DNA binding protein" is intended to encompass more particularly transcriptional factors. The binding of these proteins on the sites located in the promoter is critical for a correct binding of polymerases and consequently for the initiation of transcription. The binding of these proteins on the sites located in the 5' upstream regulatory regions modulates transcription.

The binding sites of DNA binding proteins, preferably transcription factors, are generally 6-20 nucleotides in length. A polymorphic site located in a transcription factor binding site may result in a difference of binding affinity of the said transcription factor between the two allele of the polymorphism. This difference of affinity could explain the changes of expression of the PCTA-1 gene.

When one or more alleles of the biallelic markers of the PCTA-1 gene associated with cancer are present in the genome of an individual since conception, there would be an event which provokes a drastic increase in the expression of PCTA-1. There are at least two possible hypotheses that can be formulated to explain this event. Firstly, as cancer is the result of a succession of mutations, one mutation could lead to either the expression of a new DNA binding activity, or the overexpression of a DNA binding factor which binds to the site containing the polymorphism and which is involved in the transcription of the PCTA-1 gene. Secondly the DNA binding factor readily binds to the site containing the polymorphism in normal cells where it is either unable to activate the transcription of PCTA-1 or repressor of the PCTA-1 transcription initiation. A mutation in the transcription factor can make the transcription factor either functional in the case of an activator or unfunctional in the case of a repressor. Likewise, a mutation in an additional protein can induce the binding of this protein which is needed by the DNA binding factor for activating the transcription of the PCTA-1 gene.

In order to confirm the capacity of transcription factors to bind sites containing the biallelic markers of the present invention, so as to assess the difference in affinity between the two alleles of the considered biallelic marker and to discriminate between these hypotheses, a gel retardation assay or DNA mobility shift assay can be carried out. This type of assay is well-known to those skilled in the art and is described in U.S. Pat. No. 5,698,389, U.S. Pat. No. 5,502,176, Fried and Crothers (1981), Garner and Revzin (1981) and Dent and Latchman (1993).

This type of method relies on the principle that a fragment of DNA to which a protein has bound will move more slowly in gel electrophoresis than the same DNA fragment without the bound protein. The DNA mobility shift assay is carried out, therefore, by first labeling the specific DNA segment whose protein-binding properties are being investigated. The labeled DNA is then incubated with a nuclear (Dignam et al., 1983; Schreiber et al., 1989; Muller et al., 1989; Mizokami et al., 1994) or whole cell (Manley et al., 1980) extract of cells prepared in such a way as to contain DNA-binding proteins. DNA-protein complexes are then allowed to form. The complexes are then electrophoresed on a non-denaturing polyacrylamide gel and the position of the labeled DNA is visualized by suitable techniques. Various types of suitable labels can be selected by the person skilled in the art. Notably, the radioactive labeling is appropriate. If no protein has bound to the DNA, all the label is free to migrate quickly, whereas labeled protein-DNA complexes migrate more slowly and hence give a different signal from that of the unbound DNA near the top of the gel. The interaction specificity can be estimated by carrying out a gel retardation assay with increasing amount of unlabeled DNA segment which can compete with the labeled one. A positive control can be realized with an oligonucleotide containing the androgene responsive element.

The investigated DNA segment preferably comprises the sequence of a potential binding site containing an allele of a polymorphism of the present invention, more preferably a sequence comprising a sequence selected from P1 to P125 and the complementary sequences thereto, still more preferably a sequence comprising a sequence selected from P1 to P43 and the complementary sequences thereto. In an embodiment, the polymorphism site is located in the middle of the DNA fragment. In an other embodiment, the polymorphism site can be located close to an end of the DNA fragment, for example at 6 nucleotides away from the end. The DNA fragment has a sufficient length to hybridize with the complementary strand and to form a stable double strand. For example, the DNA fragment comprises at least 8 nucleotides, preferably at least 20 nucleotides, more preferable 30 nucleotides. In a specific embodiment, the DNA fragment comprises the sequence of interest at the middle of the fragment and some poly G, poly C, or poly GC at its 5' and/or 3' ends.

In a preferred embodiment, the DNA segment consists of an oligonucleotide selected from the group consisting of Oligo1 to Oligo60 which are described in Table C and detailed as feature in SEQ ID No 1. For each polymorphic site, 4 oligonucleotides are generated and correspond to the two complementary strands of the DNA for each of the two alleles of the considered polymorphism. The DNA segments are designed such as the polymorphic base is surrounded with 14 nucleotides on each side.

TABLE C

| Biallelic marker | All | Oligonucleotide name | Position range of the oligonucleotide in SEQ ID No 1 | | Oligonucleotide name | Complementary position range of the oligonucleotide in SEQ ID No 1 | |
|---|---|---|---|---|---|---|---|
| | | | Beginning | End | | Beginning | End |
| 5-169-208 | A | Oligo 1 | 67820 | 67848 | Oligo31 | 67820 | 67850 |
| 5-169-208 | G | Oligo2 | 67820 | 67848 | Oligo32 | 67820 | 67850 |
| 5-169-331 | C | Oligo3 | 67940 | 67969 | Oligo33 | 67941 | 67969 |
| 5-169-331 | T | Oligo4 | 67940 | 67969 | Oligo34 | 67941 | 67969 |
| 5-169-97 | C | Oligo5 | 67707 | 67737 | Oligo35 | 67709 | 67738 |
| 5-169-97 | G | Oligo6 | 67707 | 67737 | Oligo36 | 67709 | 67738 |
| 5-170-238 | A | Oligo7 | 68198 | 68227 | Oligo37 | 68199 | 68228 |

TABLE C-continued

| Biallelic marker | All | Oligonucleotide name | Position range of the oligonucleotide in SEQ ID No 1 Beginning | End | Oligonucleotide name | Complementary position range of the oligonucleotide in SEQ ID No 1 Beginning | End |
|---|---|---|---|---|---|---|---|
| 5-170-238 | G | Oligo8 | 68198 | 68227 | Oligo38 | 68199 | 68228 |
| 5-170-288 | A | Oligo9 | 68247 | 68277 | Oligo39 | 68249 | 68277 |
| 5-170-288 | C | Oligo10 | 68247 | 68277 | Oligo40 | 68249 | 68277 |
| 5-171-156 | G | Oligo11 | 68463 | 68491 | Oligo41 | 68463 | 68492 |
| 5-171-156 | T | Oligo12 | 68463 | 68491 | Oligo42 | 68463 | 68492 |
| 5-171-204 | C | Oligo13 | 68511 | 68539 | Oligo43 | 68511 | 68539 |
| 5-171-204 | T | Oligo14 | 68511 | 68539 | Oligo44 | 68511 | 68539 |
| 5-171-273 | A | Oligo15 | 68580 | 68608 | Oligo45 | 68580 | 68608 |
| 5-171-273 | G | Oligo16 | 68580 | 68608 | Oligo46 | 68580 | 68608 |
| 5-171-289 | C | Oligo17 | 68596 | 68624 | Oligo47 | 68596 | 68626 |
| 5-171-289 | T | Oligo18 | 68596 | 68624 | Oligo48 | 68596 | 68626 |
| 5-171-54 | C | Oligo19 | 68360 | 68389 | Oligo49 | 68361 | 68389 |
| 5-171-54 | G | Oligo20 | 68360 | 68389 | Oligo50 | 68361 | 68389 |
| 99-1572-315 | C | Oligo21 | 66951 | 66981 | Oligo51 | 66953 | 66983 |
| 99-1572-315 | T | Oligo22 | 66951 | 66981 | Oligo52 | 66953 | 66983 |
| 99-1572-335 | A | Oligo23 | 66973 | 67001 | Oligo53 | 66973 | 67002 |
| 99-1572-335 | G | Oligo24 | 66973 | 67001 | Oligo54 | 66973 | 67002 |
| 99-1572-440 | C | Oligo25 | 67078 | 67106 | Oligo55 | 67078 | 67106 |
| 99-1572-440 | T | Oligo26 | 67078 | 67106 | Oligo56 | 67078 | 67106 |
| 99-1572-477 | A | Oligo27 | 67113 | 67143 | Oligo57 | 67115 | 67144 |
| 99-1572-477 | T | Oligo28 | 67113 | 67143 | Oligo58 | 67115 | 67144 |
| 99-1572-578 | C | Oligo29 | 67212 | 67243 | Oligo59 | 67215 | 67247 |
| 99-1572-578 | T | Oligo30 | 67212 | 67243 | Oligo60 | 67215 | 67247 |

Each oligonucleotide selected from Oligo1 to Oligo60 comprises 4 additional bases, namely GATC, at its 5' end.

In a preferred embodiment, either the nuclear or whole cell extracts are provided from normal and cancer cells, particularly from normal prostate cells and prostate cancer cells. For example, suitable cell extracts can be provided from PZ-HPV-7 (ATCC: CRL-2221), CA-HPV-10 (ATCC: CRL-2220), PC-3 (ATCC: CRL-1435), DU 145 (ATCC: HTB-81), LNCaP-FGC (ATCC: CRL-10995 and CRL-1740), or NCI-H660 (ATCC: CRL-5813) cells. In a more preferred embodiment, the cell extracts are provided form PNT1A, PNT2, LNCaP-JMV, DU145 (ATCC Nr: HTB-81) or PC3 (ATCC Nr: CRL-1435) cells.

In case a new transcription factor is specifically expressed in cancer cells, a gel retardation assay will show a retarded or shifted band only when the DNA was incubated with cell extracts from prostate cancer cells. If the DNA binding activity already exists in normal cells, the gel retardation assay will show a shifted band with cell extracts from normal prostate cells and prostate cancer cells. Gel retardation assays will also allow to show a significant difference in affinity between a DNA binding factor and binding sites containing the two alleles of the considered polymorphism.

The interaction of the DNA segment described above with transcription factors can also be studied with an optical biosensor such as BIACORE. This technology is well-known to those skilled in the art and is described in Szabo et al. (1995) and Edwards et al. (1997). The main advantage of this method is that it allows the determination of the association rate between the DNA fragment which is investigated and the DNA binding protein. Typically, a DNA segment such as those defined above is biotinylated at its 5' or 3' ends and is immobilized on a streptavidin-coated sensor chip. Then, a whole or a nuclear extract of cells is placed in contact with the DNA segment. The binding of DNA binding proteins to the DNA fragment causes a change in the refractive index and/or thickness. This change is detected by the Biosensor provided it occurs in the evanescent field. The affinity of the DNA binding protein to the DNA fragment can then be measured.

In order to precisely localize the binding site of the transcription factors, DNAse I footprinting or DMS protection footprinting assays can also be carried out with DNA fragments which contain the sequence of a potential binding site containing an allele of a polymorphism of the present invention, preferably a sequence comprising a sequence selected from P1 to P125 and the complementary sequences thereto, more preferably a sequence comprising a sequence selected from P1 to P43 and the complementary sequences thereto. This type of assay is well-known to those skilled in the art and is described in Galas and Schmitz (1978), and Dynan and Tjian (1983). Briefly, in the DNAse I footprinting assay, end-labeled DNA is incubated with protein extract and then partially digested with DNAse I. Specific binding of proteins to DNA will modify nuclease digestion at the site of interaction relative to free DNA, leaving an "imprint" which can be visualized after extraction of the labeled DNA and electrophoresis in a sequence gel.

The interaction with transcription factors can also be studied with the methylation interference assay which is well-known to those skilled in the art and is described in Siebenlist and Gilbert (1980) and Maxam and Gilbert (1980). Briefly, this method relies on the ability of DMS to methylate G residues, which can be cleaved with piperidine. The target DNA is partially methylated so that, on average, only one G residue per DNA molecule is methylated. These partially methylated molecules is used in a DNA mobility shift experiment with an appropriate cell extract containing transcription factors. After electrophoresis, the band produced by the DNA which has bound protein and that produced by the unbound DNA are excised from the gel and treated with piperidine to cleave the DNA at the methylated G residues and not at unmethylated G residues. If methylation of a particular G residue prevents transcription factors binding, then cleavage at this methylated G residue will be observed only in the DNA that failed to bind the protein.

In order to confirm the implication of a particular PCTA-1 derived sequence containing the biallelic marker as a binding site for a transcription regulator of PCTA-1 in cancer cells, a transient expression assay can be carried out in which a vector comprising the considered binding site upstream of the HSV1 thymidine kinase promoter operably linked to a reporter gene such as chloramphenicol acetyltransferase is transfected in appropriate cell lines. This assay is well-known to those skilled in the art and is described in Doucas et al. (1991). This assay can also be realized by cloning the considered binding site upstream the SV40 promoter into the pGL3-promoter luciferase vector (Promega) as described in Coles et al. (1998). Both normal and cancer cells, more particularly normal and cancer cells from prostate, are transfected with said vector. The effect of the binding site and more particularly of the alleles comprised in the binding site can be assessed through the expression level of the reporter gene.

The inventors believe that these polymorphisms, particularly the polymorphisms located on or close to polyadenylation sites have a direct although somewhat milder effect on prostate cancer development.

Haplotype Analysis

In the context of the present invention, a haplotype can be defined as a combination of biallelic markers found in a given individual and which may be associated more or less significantly, as a result of appropriate statistical analyses, with the expression of a given trait.

A two-marker haplotype including markers A30 and A41 (TT alleles respectively) was shown to be significantly associated with prostate cancer, preferably with a familial prostate cancer, more preferably with a familial early onset prostate cancer. As shown in Table 8, the "TT" haplotype present a p-value of $2.5 \times 10^{-6}$ for the familial early onset prostate cancer (see Example 5).

A three-marker haplotype including markers A2, A30, and A41 (ATT alleles respectively) was shown to be significantly associated with prostate cancer, preferably with a familial prostate cancer, more preferably with a familial early onset prostate cancer. As shown in table 8, the "ATT" haplotype present a p-value of $2.5 \times 10^{-7}$ for the familial early onset prostate cancer (see Example 5).

A first two-marker haplotype including markers A2 and A57 (99-1605/112) (TA alleles, respectively) was shown to be significantly associated with prostate cancer, preferably with a sporadic prostate cancer. As shown in table 8, the "TA" haplotype present a p-value of $3.4 \times 10^{-5}$ for the sporadic informative prostate cancer (see Example 5). A second two-marker haplotype including markers A2 and A55 (5-2/178) (TT alleles, respectively) was shown to be significantly associated with prostate cancer, preferably with a sporadic prostate cancer. As shown in table 8, the "TT" haplotype present a p-value of $1 \times 10^{-5}$ for the sporadic informative prostate cancer (see Example 5).

Therefore, one preferred haplotype of the present invention associated with a familial prostate cancer comprises a biallelic marker selected from the group consisting of A30 (allele T), A41 (allele T), A2 (allele A), A55 (allele C) and A57 (allele G). One more preferred haplotype of the present invention associated with a familial prostate cancer comprises a biallelic marker selected from the group consisting of A30 (allele T), A41 (allele T), and A2 (allele A). One still more haplotype of the present invention associated with a familial prostate cancer comprises a biallelic marker selected from the group consisting of A30 (allele T), and A41 (allele T).

Furthermore, one preferred haplotype of the present invention associated with a sporadic prostate cancer comprises a biallelic marker selected from the group consisting of A2 (allele T), A55 (allele T), A57 (allele A), A30 (allele T) and A41 (allele T). One more preferred haplotype of the present invention associated with a sporadic prostate cancer comprises a biallelic marker selected from the group consisting of A2 (allele T), A41 (allele T), A55 (allele T), A57 (allele A).

The permutation tests clearly validated the statistical significance of the association between these haplotypes and the prostate cancer (see Example 5). All these haplotypes can be used in diagnostic of prostate cancer, more particularly either familial prostate cancer or sporadic prostate cancer.

One can observe that the haplotypes associated to familial cases of prostate cancer are not associated with the sporadic cases of prostate cancer and that the haplotypes associated to the sporadic cases are not associated with the familial cases (see Table 7 of Example 5). Moreover, except the biallelic markers A2, the familial and sporadic cases haplotypes do not present any common biallelic marker. Therefore, the ancestral haplotypes would be different and the causing trait allele would not be the same.

This information is extremely valuable. The knowledge of a potential genetic predisposition to prostate cancer, even if this predisposition is not absolute, might contribute in a very significant manner to treatment efficacy of prostate cancer and to the development of new therapeutic and diagnostic tools.

Statistical Methods

In general, any method known in the art to test whether a trait and a genotype show a statistically significant correlation may be used.

1) Methods in Linkage Analysis

Statistical methods and computer programs useful for linkage analysis are well-known to those skilled in the art (see Terwilliger J. D. and Ott J., 1994; Ott J., 1991).

2) Methods to Estimate Haplotype Frequencies in a Population

As described above, when genotypes are scored, it is often not possible to distinguish heterozygotes so that haplotype frequencies cannot be easily inferred. When the gametic phase is not known, haplotype frequencies can be estimated from the multilocus genotypic data. Any method known to person skilled in the art can be used to estimate haplotype frequencies (see Lange K., 1997; Weir, B. S., 1996) Preferably, maximum-likelihood haplotype frequencies are computed using an Expectation—Maximization (EM) algorithm (see Dempster et al., 1977; Excoffier L. and Slatkin M., 1995). This procedure is an iterative process aiming at obtaining maximum-likelihood estimates of haplotype frequencies from multi-locus genotype data when the gametic phase is unknown. Haplotype estimations are usually performed by applying the EM algorithm using for example the EM-HAPLO program (Hawley M. E. et al., 1994) or the Arlequin program (Schneider et al., 1997). The EM algorithm is a generalized iterative maximum likelihood approach to estimation and is briefly described below.

Please note that in the present section, "Methods To Estimate Haplotype Frequencies In A Population," of this text, phenotypes will refer to multi-locus genotypes with unknown phase. Genotypes will refer to known-phase multi-locus genotypes.

A sample of N unrelated individuals is typed for K markers. The data observed are the unknown-phase K-locus phenotypes that can categorized in F different phenotypes. Suppose that we have H underlying possible haplotypes (in case of K biallelic markers, $H=2^K$).

For phenotype j, suppose that $c_j$ genotypes are possible. We thus have the following equation $$P_j = \sum_{i=1}^{c_j} pr(genotype_i) = \sum_{i=1}^{c_j} pr(h_k, h_l) \qquad \text{Equation 1}$$

where Pj is the probability of the phenotype j, $h_k$ and $h_l$ are the two haplotypes constituent the genotype i. Under the Hardy-Weinberg equilibrium, $pr(h_k, h_l)$ becomes:

$$pr(h_k, h_l) = pr(h_k)^2 \text{ if } h_k = h_l, pr(h_k, h_l) = 2pr(h_k) \cdot pr(h_l) \text{ if } h^k \neq h_l. \qquad \text{Equation 2}$$

The successive steps of the E-M algorithm can be described as follows:

Starting with initial values of the of haplotypes frequencies, noted $p_1^{(0)}, p_2^{(0)}, \ldots p_H^{(0)}$, these initial values serve to estimate the genotype frequencies (Expectation step) and then estimate another set of haplotype frequencies (Maximization step), noted $p_1^{(1)}, p_2^{(1)}, \ldots p_H^{(1)}$, these two steps are iterated until changes in the sets of haplotypes frequency are very small.

A stop criterion can be that the maximum difference between haplotype frequencies between two iterations is less than $10^{-7}$. These values can be adjusted according to the desired precision of estimations.

At a given iteration s, the Expectation step consists of calculating the genotypes frequencies by the following equation:

$$pr(genotype_i)^{(s)} = pr(phenotype_j) \cdot \qquad \text{Equation 3}$$
$$pr(genotype_i \mid phenotype_j)^{(s)}$$
$$= \frac{n_j}{N} \cdot \frac{pr(h_k, h_l)^{(s)}}{P_j^{(s)}}$$

where genotype i occurs in phenotype j, and where $h_k$ and $h_l$ constitute genotype i. Each probability is derived according to eq. 1, and eq. 2 described above.

Then the Maximization step simply estimates another set of haplotype frequencies given the genotypes frequencies. This approach is also known as the gene-counting method (Smith, 1957).

$$p_t^{(s+1)} = \frac{1}{2} \sum_{j=1}^{F} \sum_{i=1}^{c_j} \delta_{it} \cdot pr(genotype_i)^{(s)} \qquad \text{Equation 4}$$

Where $\delta_{it}$ is an indicator variable which count the number of time haplotype t in genotype i. It takes the values of 0, 1 or 2.

To ensure that the estimation finally obtained is the maximum-likelihood estimation several values of departures are required. The estimations obtained are compared and if they are different the estimations leading to the best likelihood are kept.

3) Methods to Calculate Linkage Disequilibrium Between Markers

A number of methods can be used to calculate linkage disequilibrium between any two genetic positions, in practice linkage disequilibrium is measured by applying a statistical association test to haplotype data taken from a population.

Linkage disequilibrium between any pair of biallelic markers comprising at least one of the biallelic markers of the present invention ($M_i$, $M_j$) having alleles ($a_i/b_i$) at marker $M_i$ and alleles ($a_j/b_j$) at marker $M_j$ can be calculated for every allele combination ($a_i,a_j$; $a_i,b_j$; $b_i,a_j$ and $b_i,b_j$), according to the Piazza formula:

$$\Delta_{aiaj} = \sqrt{\theta 4} - \sqrt{(\theta 4 + \theta 3)(\theta 4 + \theta 2)}, \text{ where:}$$

$\theta 4 = --=$ frequency of genotypes not having allele $a_i$ at $M_i$ and not having allele $a_j$ at $M_j$ $\theta 3 = -+=$ frequency of genotypes not having allele $a_i$ at $M_i$ and having allele $a_j$ at $M_j$ $\theta 2 = +-=$ frequency of genotypes having allele $a_i$ at $M_i$ and not having allele $a_j$ at $M_j$ Linkage disequilibrium (LD) between pairs of biallelic markers ($M_i$, $M_j$) can also be calculated for every allele combination ($a_i,a_j$; $a_i,b_j$; $b_i,a_j$ and $b_i,b_j$), according to the maximum-likelihood estimate (MLE) for delta (the composite genotypic disequilibrium coefficient), as described by Weir (Weir B. S., 1996). The MLE for the composite linkage disequilibrium is:

$$D_{aiaj} = (2n_1 + n_2 + n_3 + n_4/2)/N - 2(pr(a_i) \cdot pr(a_j))$$

Where $n_1 = \Sigma$ phenotype ($a_i/a_i$, $a_j/a_j$), $n_2 = \Sigma$ phenotype ($a_i/a_i$, $a_j/b_j$), $n_3 = \Sigma$ phenotype ($a_i/b_i$, $a_j/a_j$), $n4 = \Sigma$ phenotype ($a_i/b_i$, $a_j/b_j$) and N is the number of individuals in the sample.

This formula allows linkage disequilibrium between alleles to be estimated when only genotype, and not haplotype, data are available.

Another means of calculating the linkage disequilibrium between markers is as follows. For a couple of biallelic markers, $M_i$ ($a_i/b_i$) and $M_j$ ($a_j/b_j$), fitting the Hardy-Weinberg equilibrium, one can estimate the four possible haplotype frequencies in a given population according to the approach described above.

The estimation of gametic disequilibrium between ai and aj is simply:

$$D_{aiaj} = pr(\text{haplotype}(a_i, a_j)) - pr(a_i) \cdot pr(a_j).$$

Where $pr(a_i)$ is the probability of allele $a_i$ and $pr(a_j)$ is the probability of allele $a_j$ and where pr(haplotype ($a_i$, $a_j$)) is estimated as in Equation 3 above.

For a couple of biallelic marker only one measure of disequilibrium is necessary to describe the association between $M_i$ and $M_j$.

Then a normalized value of the above is calculated as follows:

$$D'_{aiaj} = D_{aiaj} / \max(-pr(a_i) \cdot pr(a_j), -pr(b_i) \cdot pr(b_j)) \text{ with } D_{aiaj} < 0$$

$$D'_{aiaj} = D_{aiaj} / \max(pr(b_i) \cdot pr(a_j), pr(a_i) \cdot pr(b_j)) \text{ with } D_{aiaj} > 0$$

The skilled person will readily appreciate that other linkage disequilibrium calculation methods can be used.

Linkage disequilibrium among a set of biallelic markers having an adequate heterozygosity rate can be determined by genotyping between 50 and 1000 unrelated individuals, preferably between 75 and 200, more preferably around 100.

4) Testing for Association

Methods for determining the statistical significance of a correlation between a phenotype and a genotype, in this case an allele at a biallelic marker or a haplotype made up of such alleles, may be determined by any statistical test known in the art and with any accepted threshold of statistical significance being required. The application of particular methods and thresholds of significance are well with in the skill of the ordinary practitioner of the art.

Testing for association is performed by determining the frequency of a biallelic marker allele in case and control populations and comparing these frequencies with a statistical test to determine if their is a statistically significant difference in frequency which would indicate a correlation between the trait and the biallelic marker allele under study. Similarly, a haplotype analysis is performed by estimating the frequencies of all possible haplotypes for a given set of biallelic markers in case and control populations, and comparing these frequencies with a statistical test to determine if their is a statistically significant correlation between the haplotype and the phenotype (trait) under study. Any statistical tool useful to test for a statistically significant association between a genotype and a phenotype may be used. Preferably the statistical test employed is a chi-square test with one degree of freedom. A P-value is calculated (the P-value is the probability that a statistic as large or larger than the observed one would occur by chance).

Statistical Significance

In preferred embodiments, significance for diagnosis purposes, either as a positive basis for further diagnostic tests or as a preliminary starting point for early preventive therapy, the p value related to a biallelic marker association is preferably about $1 \times 10^{-2}$ or less, more preferably about $1 \times 10^{-4}$ or less, for a single biallelic marker analysis and about $1 \times 10^{-3}$ or less, still more preferably $1 \times 10^{-6}$ or less and most preferably of about $1 \times 10^{-8}$ or less, for a haplotype analysis involving two or more markers. These values are believed to be applicable to any association studies involving single or multiple marker combinations.

The skilled person can use the range of values set forth above as a starting point in order to carry out association studies with biallelic markers of the present invention. In doing so, significant associations between the biallelic markers of the present invention and prostate cancer, the level of aggressiveness of prostate cancer tumors, an early onset of prostate cancer, or a beneficial response to or side effects related to treatment against prostate cancer can be revealed and used for diagnosis and drug screening purposes.

Phenotypic Permutation

In order to confirm the statistical significance of the first stage haplotype analysis described above, it might be suitable to perform further analyses in which genotyping data from case-control individuals are pooled and randomized with respect to the trait phenotype. Each individual genotyping data is randomly allocated to two groups, which contain the same number of individuals as the case-control populations used to compile the data obtained in the first stage. A second stage haplotype analysis is preferably run on these artificial groups, preferably for the markers included in the haplotype of the first stage analysis showing the highest relative risk coefficient. This experiment is reiterated preferably at least between 100 and 10000 times. The repeated iterations allow the determination of the probability to obtain by chance the tested haplotype.

Assessment of Statistical Association

To address the problem of false positives similar analysis may be performed with the same case-control populations in random genomic regions. Results in random regions and the candidate region are compared as described in a co-pending US Provisional Patent Application entitled "Methods, Software And Apparati For Identifying Genomic Regions Harboring A Gene Associated With A Detectable Trait," U.S. Ser. No. 60/107,986, filed Nov. 10, 1998.

5) Evaluation of Risk Factors

The association between a risk factor (in genetic epidemiology the risk factor is the presence or the absence of a certain allele or haplotype at marker loci) and a disease is measured by the odds ratio (OR) and by the relative risk (RR). If $P(R^+)$ is the probability of developing the disease for individuals with R and $P(R^-)$ is the probability for individuals without the risk factor, then the relative risk is simply the ratio of the two probabilities, that is:

$$RR = P(R^+)/P(R^-)$$

In case-control studies, direct measures of the relative risk cannot be obtained because of the sampling design. However, the odds ratio allows a good approximation of the relative risk for low-incidence diseases and can be calculated:

$$OR = (F^+/(1-F^+))/(F^-/(1-F^-))$$

$F^+$ is the frequency of the exposure to the risk factor in cases and $F^-$ is the frequency of the exposure to the risk factor in controls. $F^+$ and $F^-$ are calculated using the allelic or haplotype frequencies of the study and further depend on the underlying genetic model (dominant, recessive, additive . . . ).

One can further estimate the attributable risk (AR) which describes the proportion of individuals in a population exhibiting a trait due to a given risk factor. This measure is important in quantifying the role of a specific factor in disease etiology and in terms of the public health impact of a risk factor. The public health relevance of this measure lies in estimating the proportion of cases of disease in the population that could be prevented if the exposure of interest were absent. AR is determined as follows:

$$AR = P_E(RR-1)/(P_E(RR-1)+1)$$

AR is the risk attributable to a biallelic marker allele or a biallelic marker haplotype. $P_E$ is the frequency of exposure to an allele or a haplotype within the population at large; and RR is the relative risk which, is approximated with the odds ratio when the trait under study has a relatively low incidence in the general population.

Identification of Biallelic Markers in Linkage Disequilibrium with the PCTA-1-Related Biallelic Markers Once an association has been demonstrated between a given biallelic marker and a trait, the discovery of additional biallelic markers associated to trait and in linkage disequilibrium with one of the biallelic markers disclosed herein can easily be carried out by the skilled person.

The present invention then also concerns biallelic markers in linkage disequilibrium with the specific biallelic markers described above, more particularly with biallelic markers A1 to A125, and which are expected to present similar characteristics in terms of their respective association with a given trait.

Hence, once linkage disequilibrium has been demonstrated between a trait and a given biallelic marker, all the biallelic markers shown to be in linkage disequilibrium with the given biallelic marker are expected to present similar characteristics in terms of their respective association with a given trait. The discovery of additional biallelic markers associated with this trait is of great interest in order to increase the density of biallelic markers in this particular region because the causal mutation will be found in the vicinity of the marker or set of markers showing the highest correlation with the trait. These additional markers which can be identified and sequenced by the skilled person using the teachings of the present application also fall within the scope of the present invention.

The invention also concerns a method for the identification and characterization of a biallelic marker in linkage disequilibrium with a biallelic marker of the PCTA-1 gene, preferably a biallelic marker of the PCTA-1 gene of which one allele is associated with a trait. In one embodiment, the biallelic marker of the PCTA-1 gene is outside of the PCTA-1 gene itself. In another embodiment, the biallelic marker in linkage disequilibrium with a biallelic marker of the PCTA-1 gene is itself located within the PCTA-1 gene. The method comprises the following steps: (a) amplifying a genomic fragment, preferably comprising a first biallelic marker, from a plurality of individuals; (b) identifying second biallelic markers in said amplified portion; (c) conducting a linkage disequilibrium analysis between said first biallelic marker and second biallelic markers; and, (d) identifying second biallelic markers in linkage disequilibrium with said first marker. Subcombinations comprising steps (b) and (c) are also contemplated. Optionally, the first biallelic marker is selected from the group consisting of A1 to A125 and the complements thereof. Preferably, the first biallelic marker is selected from the group consisting of A2, A30, A41, A55, A57 and the complements thereof.

Methods to identify biallelic markers and to conduct linkage disequilibrium analysis are described herein and can be carried out by the skilled person without undue experimentation.

Once identified, the sequences in linkage disequilibrium with a biallelic marker of the PCTA-1 gene may be used in any of the methods described herein, including methods for determining an association between a biallelic marker and a trait, methods for identifying individuals having a predisposition for a trait, methods of administration of prophylactic or therapeutic agents disease treatment, methods of identifying individuals likely to respond positively or negatively to said agents, and methods of using drugs and vaccines.

An example of identification of additional biallelic markers associated to a trait based on the previous knowledge of the localization of a first marker associated to a given trait is given below.

Biallelic Markers in Linkage Disequilibrium with a Particular Marker: Apo E4

The following example relating to the identification of markers in linkage disequilibrium with the apoE4 allele is representative of the procedures of the present invention in which markers in LD with a target gene are identified. 3 major isoforms of human apolipoprotein E (apoE2, -E3, and -E4) have been identified by isoelectric focusing and are coded for by 3 alleles ($\epsilon$ 2, 3, and 4) of the Apo E gene. As originally reported by Strittmatter et al. and by Saunders et al. in 1993, the Apo E $\epsilon$4 allele is strongly associated with both late-onset familial and sporadic Alzheimer's Disease (AD).

Biallelic markers in linkage disequilibrium with the Apo E $\epsilon$4 allele were identified. This example is illustrative of the general principle that the generation of biallelic markers associated with a trait leads to markers in linkage disequilibrium with any biallelic marker already known to be associated with the trait.

An Apo E marker was used to screen the human genomic BAC library. A BAC, which gave a unique hybridization signal on chromosomal region 19q13.2.3 by FISH, was selected for finding biallelic markers.

This BAC contained an insert of 205 kb that was subcloned. Fifty BAC subclones were randomly selected and sequenced. Twenty-five subclone sequences were selected and used to design twenty-five couples of PCR primers that allowed amplicons of approximately 500 bp to be generated. These PCR primers were then used to amplify the corresponding genomic sequences in a pool of DNA from 100 individuals (French origin, blood donors) as already described. Amplification products from pooled DNA were sequenced and analyzed for the presence of biallelic polymorphisms using the software described herein. Five amplicons were shown to contain a polymorphic base in the pool of 100 individuals, and therefore these polymorphisms (99-366/274; 99-344/439; 99-365/344; 99-359/308; 99-355/219) were selected as the random biallelic markers in the vicinity of the Apo E gene.

An additional couple of primers was designed that allowed amplification of the genomic fragment carrying the already known polymorphism of Apo E, (99-2452/54 C/T).

An association study was then performed. As expected, there was a clear association between Alzheimer disease (AD) and the known Apo E4 polymorphism (biallelic marker 99-2452/54), the C allele frequency being increased in 26% in the AD case population studied compared to the AD control population analyzed (pvalue of this difference=$2\times10^{-21}$).

In addition, the association study with the random markers generated in the vicinity of the Apo E gene showed that the biallelic marker 99-365/344 C/T is also associated to AD, the T allele frequency being increased of 17% in the AD case population respect to the AD control population under study (pvalue of this allele frequency difference=$7\times10^{-10}$). Thus individuals who possess a T allele at the biallelic marker 99-365/344 are at risk of developing AD.

Among the biallelic markers generated in the Apo E region, 99-365/344 is in LD with the previously known Apo E4 marker 99-2452/54. The linkage disequilibrium is detected in a control population (LD value=0.08) and is clearly increased in the AD case population (LD=0.21). Hence the generated biallelic marker which are associated with Alzheimer's disease, namely the biallelic marker 99-365, is in linkage disequilibrium with the biallelic marker 99-2452 already known to be associated with this disease.

Identification of a Trait Causing Mutation in the PCTA-1 Gene

If a statistically significant association with a trait is identified for at least one or more of the analyzed PCTA-1-related biallelic markers, one can assume that: either the associated allele is directly responsible for causing the trait, or more likely the associated allele is in linkage disequilibrium with the trait causing allele. More probably, the trait causing mutation would be found near to the associated biallelic markers.

Mutations in the PCTA-1 gene which are responsible for a detectable phenotype may be identified by comparing the sequences of the PCTA-1 gene from trait positive and trait negative individuals. Preferably, trait positive individuals to be sequenced carry a single marker allele or a haplotype shown to be associated to the trait and trait negative individuals to be sequenced do not carry such allele or haplotype associated to the trait. The detectable phenotype may comprise cancer, preferably prostate cancer, a response to or side effects related to a prophylactic or curative agent acting against prostate cancer, the aggressiveness of prostate cancer tumors, expression of the PCTA-1 gene, a modified or forthcoming production of the PCTA-1 protein, or the production of a modified PCTA-1 protein. The mutations may comprise point mutations, deletions, or insertions in the PCTA-1 gene. These mutations are called trait causing mutations and are at least partly responsible for a particular detectable phenotype in an individual. The mutations may lie within the coding sequence for the PCTA-1 protein or within intronic and/or within regulatory regions in the PCTA-1 gene, including splice sites, 5' UTRs, 3' UTRs and promoter sequences, including one or more transcription factor binding sites.

A further embodiment of the invention is a method to identify a trait causing mutation in the PCTA-1 gene pursuant to the detection of an association between alleles of one or several of the biallelic markers of the present invention and a particular trait.

This method comprises the following steps:
amplifying a region of the PCTA-1 gene comprising a biallelic marker or a group of biallelic markers associated to the considered trait from DNA samples of trait positive and trait negative individuals;
sequencing the amplified region;
comparing DNA sequences from trait positive and trait negative individuals; and
determining mutations specific to trait positive patients.

In some embodiments, the amplified region is a region located close to a biallelic marker of PCTA-1 gene. In further embodiments, the amplified region is located close to one or more of the biallelic markers A1 to A125 and the complements thereof. In a preferred embodiment, the amplified region is located close to one or more of the biallelic markers A2, A30, A41, A55, A57 and the complements thereof.

Oligonucleotide primers are constructed as described previously to amplify the sequences of each of the exons, introns, the promoter region and the regulatory regions of the PCTA-1 gene. Amplification is carried out on genomic DNA samples from trait positive patients and trait negative controls, preferably using the PCR conditions described in the examples. Amplification products from the genomic PCRs are then subjected to sequencing, preferably through automated dideoxy terminator sequencing reactions and electrophoresed, preferably on ABI 377 sequencers. Following gel image analysis and DNA sequence extraction, ABI sequence data are automatically analyzed to detect the presence of sequence variations among trait positive and trait negative individuals. Sequences are verified by determining the sequences of both DNA strands for each individual.

Candidate polymorphisms suspected of being responsible for the detectable phenotype, are then verified by screening a larger population of trait positive and trait negative individuals using polymorphism analysis techniques such as the techniques described above. Polymorphisms which exhibit a statistically significant correlation with the detectable phenotype are deemed responsible for the detectable phenotype.

The invention also concerns a mutated PCTA-1 gene comprising a trait causing mutation, and particularly the mutated genes obtained by the process described above.

A mutated PCTA-1 gene can be defined as a gene encoding either a modified or native PCTA-1 protein through a nucleotide sequence which is different from the nucleotide sequence of the PCTA-1 gene found in a majority of trait negative individuals.

The region of the PCTA-1 gene containing the mutation responsible for the detectable phenotype may be used in diagnostic techniques such as those described below. For example, microsequencing oligonucleotides, or oligonucleotides containing the mutation responsible for the detectable phenotype for amplification, or hybridization based diagnostics, such as those described herein, may be used for detecting individuals suffering from the detectable phenotype or individuals at risk of developing the detectable phenotype at a subsequent time. In addition, the PCTA-1 allele responsible for the detectable phenotype may be used in gene therapy. The PCTA-1 allele responsible for the detectable phenotype may also be cloned into an expression vector to express the mutant PCTA-1 protein as described herein.

Biallelic Markers of the Invention in Methods of Genetic Diagnostics

The biallelic markers of the present invention can also be used to develop diagnostics tests capable of identifying individuals who express a detectable trait as the result of a specific genotype or individuals whose genotype places them at risk of developing a detectable trait at a subsequent time. The trait analyzed using the present diagnostics may be any detectable trait, including susceptibility to cancer, preferably prostate cancer, the level of aggressiveness of prostate cancer tumors, an early onset of prostate cancer, a beneficial response to or side effects related to treatment against prostate cancer.

Information resulting from single marker association and for haplotype analyses is extremely valuable as it can, in certain circumstances, be used to initiate preventive treatments or to allow an individual carrying a significant haplotype to foresee warning signs such as minor symptoms. In diseases such as prostate cancer, in which metastasis can be fatal if not stopped in time, the knowledge of a potential predisposition, might contribute in a very significant manner to treatment efficacy. Similarly, a diagnosed predisposition to a potential side-effect could immediately direct the physician toward a treatment for which such side-effects have not been observed during clinical trials.

The invention concerns a method for the detection in an individual of alleles of PCTA-1-related biallelic markers associated with a trait preferably selected from prostate cancer, an early onset of prostate cancer, a susceptibility to prostate cancer, the level of aggressiveness of prostate cancer tumors, or the level of expression of the PCTA-1 gene. The information obtained using this method is useful in the diagnosis, staging, monitoring, prognosis and/or prophylactic or curative therapy of prostate cancer. The method also concerns the detection of specific alleles present within the PCTA-1 gene expressing a modified level of PCTA-1 mRNA or an altered PCTA-1 mRNA, coding for an altered PCTA-1 protein. The identities of the polymorphic bases may be determined using any of the genotyping procedures described above in "Method For Genotyping An Individual For Biallelic Markers". More particularly, the invention concerns the detection of a PCTA-1 nucleic acid comprising at least one of the nucleotide sequences of P1 to P125 and the complementary sequence thereof. This method comprises the following steps:

obtaining a nucleic acid sample from the individual to be tested; and
determining the presence in the sample of an allele of a biallelic marker or of a group of biallelic markers of the PCTA-1 gene which, when taken alone or in combination with another/other biallelic marker/s of the PCTA-1 gene, is indicative of prostate cancer, of an early onset of prostate cancer, of the level of aggressiveness of prostate cancer tumors, of a modified or forthcoming expression of the PCTA-1 gene, of a modified or forthcoming production of the PCTA-1 protein, or of the production of a modified PCTA-1 protein.

In some embodiments, the biallelic marker comprises at least one of the biallelic markers defined by the sequences P1 to P125, and the complementary sequences thereto, more preferably at least one biallelic marker selected from the group consisting of A1 to A125, and the complements thereof, or optionally the biallelic markers in linkage disequilibrium therewith. In a preferred embodiment, the biallelic marker comprises at least one of the biallelic markers defined by the sequences of P2, P30, P41, P55, P57, and the complementary sequence thereto, more particularly at least one biallelic marker selected from the group consisting of A2, A30, A41, A55, A57 and the complement thereof. In a preferred embodiment, the detection method comprises an additional step of amplifying a nucleotide sequence of the PCTA-1 gene comprising biallelic markers. Optionally, the amplification primers can be selected from the group consisting of B1 to B47 and C1 to C47.

In preferred embodiments of the detection method described above, the presence of alleles of one or more biallelic markers of the PCTA-1 gene is determined through microsequencing reactions. Optionally, the microsequencing primers are selected from the group consisting of D1 to D125 and E1 to E125. Optionally, the microsequencing primers can be bound to a solid support, preferably in the form of arrays of primers attached to appropriate chips or be used in microfluidic devices. Such arrays are described in further detail in the "Oligonucleotide arrays" section. Optionally, the microsequencing primers can be labeled.

In additional preferred embodiments of the detection method, the presence of alleles of one or more biallelic markers of the PCTA-1 gene is determined through an allele specific amplification assay or an enzyme based mismatch detection assay. Optionally, the allele specific amplification assay comprises a step of detecting the presence of the amplification product.

In further preferred embodiments of the detection method, the presence of alleles of one or more biallelic markers of the PCTA-1 gene is determined through a hybridization assay. The probes used in the hybridization assay may include a probe selected from the group consisting of P1 to P125, a complementary sequence thereto or a fragment thereof, said fragment comprising the polymorphic base. Preferably, the probe is labeled.

A diagnostic method according to the present invention can also consist on the detection of an allele of the PCTA-1 gene comprising a trait causing mutation.

The invention also specifically relates to a method of determining whether an individual suffering from prostate cancer or susceptible of developing prostate cancer is likely to respond positively to treatment with a selected medicament acting against prostate cancer.

The method comprises the following steps:
 obtaining a DNA sample from the individual to be tested; and
 analyzing said DNA sample to determine whether it comprises alleles of one or more biallelic markers associated with a positive response to treatment with the medicament and/or alleles of one or more biallelic markers associated with a negative response to treatment with the medicament.

In a preferred embodiment, the biallelic marker is selected from the group consisting of A1 to A125, and the complements thereof, or optionally the biallelic markers in linkage disequilibrium therewith.

The detection methods of the present invention can be applied to, for example, the preliminary screening of patient populations suffering from prostate cancer. This preliminary screening is useful to initiate adequate treatment when needed or to determine and select appropriate patient populations for clinical trials on new compounds in order to avoid the potential occurrence of specific side effects or to enhance the probability of beneficial patient response. By establishing in advance a homogeneous genotype selection for the population to be tested, the assessment of drug efficacy and/or toxicity can be more readily achieved and less hampered by divergences in population response. This approach can yield better therapeutic approaches based on patient population targeting resulting from pharmacogenomics studies.

The invention also relates to diagnostic kits useful for determining the presence in a DNA sample of alleles associated with the trait, preferably with prostate cancer, with an early onset of prostate cancer, with the level of aggressiveness of prostate cancer tumors, with a modified or forthcoming expression of the PCTA-1 gene, with a modified or forthcoming production of the PCTA-1 protein, or with the production of a modified PCTA-1 protein. Diagnostic kits can comprise any of the polynucleotides of the present invention.

In a first embodiment, the kit comprises primers such as those described above, preferably forward and reverse primers which are used to amplify the PCTA-1 gene or a fragment thereof. In some embodiments, at least one of the primers is complementary to a nucleotide sequence of the PCTA-1 gene comprising a biallelic marker associated with prostate cancer, with an early onset of prostate cancer, with the level of aggressiveness of prostate cancer tumors, with a modified or forthcoming expression of the PCTA-1 gene, with a modified or forthcoming production of the PCTA-1 protein, or with the production of a modified PCTA-1 protein. In one embodiment, the biallelic marker is comprised in one of the sequences P1 to P125 and the complementary sequences thereto. Optionally, the kit comprises an amplification primer which includes a polymorphic base of at least one biallelic marker selected from the group consisting of A1 to A125 and the complements thereof. In a preferred embodiment, the kit comprises one or more of the sequences B1 to B47 and C1 to C47. In a more preferred embodiment, the kit comprises one or more of the sequences B1, B16, B20, B23, B24 and C1, C16, C20, C23, C24.

In a second embodiment, the kit comprises microsequencing primers, wherein at least one of said primers is an oligonucleotide capable of hybridizing, either with the coding or with the non-coding strand, immediately upstream of the polymorphic base of a biallelic marker selected from the group consisting of A1 to A125 and the complements thereof, preferably those of D1 to D125 and E1 to E125, more preferably those of D2, D30, D41, D55, D57 and E2, E30, E41, E55, E57.

In a third embodiment, the kit comprises a hybridization DNA probe, that is or eventually becomes immobilized on a solid support, which is capable of hybridizing with the PCTA-1 gene or fragment thereof, preferably which is capable of hybridizing with a region of the PCTA-1 gene which comprises an allele of a biallelic marker of the present invention, more preferably an allele associated with prostate cancer, with an early onset of prostate cancer, with a susceptibility to prostate cancer, with the level of aggressiveness of prostate cancer tumors, with a modified or forthcoming expression of the PCTA-1 gene, with a modified or forthcoming production of the PCTA-1 protein, or with the production of a modified PCTA-1 protein. In a preferred embodiment, the probe is selected from the group consisting of P1 to P125 and the complementary sequences thereto, or a fragment thereof, said fragment comprising the polymorphic base. In a more preferred embodiment, the probe is selected from the group consisting of P2, P30, P41, P55, P57 and the complementary sequences thereto, or a fragment thereof, said fragment comprising the polymorphic base.

The kits of the present invention can also comprise optional elements including appropriate amplification reagents such as DNA polymerases when the kit comprises primers, reagents useful in hybridization reactions and reagents useful to reveal the presence of a hybridization reaction between a labeled hybridization probe and the PCTA-1 gene containing at least one biallelic marker.

Treatment of Cancer or Prostate Cancer

The invention also concerns methods for the treatment of prostate cancer using an allele of a biallelic marker or of a group of biallelic markers, preferably markers of the PCTA-1 gene, associated with a susceptibility to prostate cancer, with an aggressive form of prostate cancer or with a positive or negative response to treatment with an effective amount of a medicament acting against prostate cancer.

As the metastasis of prostate cancer can be fatal, it is important to detect prostate cancer susceptibility of individuals. Consequently, the invention also concerns a method for the treatment of prostate cancer comprising the following steps:
  selecting an individual whose DNA comprises alleles of a biallelic marker or of a group of biallelic markers, preferably markers of the PCTA-1 gene, associated with prostate cancer;
  following up said individual for the appearance (and optionally the development) of tumors in prostate; and
  administering an effective amount of a medicament acting against prostate cancer to said individual at an appropriate stage of the prostate cancer.

In some embodiments, the biallelic marker is comprised in one of the sequences P1 to P125 and the complementary sequences thereto. Preferably the biallelic marker is at least one biallelic marker selected from the group consisting of A1 to A125, and the complements thereof, or optionally the biallelic markers in linkage disequilibrium therewith. In particular embodiments, the individual is selected by genotyping one or more biallelic markers of the present invention.

The prophylactic administration of a treatment serves to prevent, attenuate or inhibit the growth of cancer cells.

Therefore, another embodiment of the present invention consists of a method for the treatment of prostate cancer comprising the following steps:
  selecting an individual whose DNA comprises alleles of a biallelic marker or of a group of biallelic markers, preferably markers of the PCTA-1 gene, associated with prostate cancer; and
  administering to said individual, preferably as a preventive treatment of prostate cancer, an effective amount of a medicament acting against prostate cancer such as 4HPR or of a vaccine composition capable of conferring immunity against PCTA-1 related prostate cancer.

In some embodiments, the biallelic marker is comprised in one of the sequences P1 to P125 and the complementary sequences thereto. Preferably the biallelic marker is at least one biallelic marker selected from the group consisting of A1 to A125, and the complements thereof, or optionally the biallelic markers in linkage disequilibrium therewith. More preferably the biallelic marker is at least one biallelic marker selected from the group consisting of A2, A30, A41, A55, A57, and the complements thereof, or optionally the biallelic markers in linkage disequilibrium therewith. In particular embodiments, the individual is selected by genotyping one or more biallelic markers of the present invention.

In a further embodiment, the present invention concerns a method for the treatment of prostate cancer comprising the following steps:
  selecting an individual whose DNA comprises alleles of a biallelic marker or of a group of biallelic markers, preferably markers of the PCTA-1 gene, associated with a susceptibility prostate cancer;
  administering to said individual, as a preventive treatment of prostate cancer, an effective amount of a medicament acting against prostate cancer such as 4HPR or of a vaccine composition capable of conferring immunity against PCTA-1-related prostate cancer;
  following up said individual for the appearance and the development of tumors in prostate; and optionally
  administering an effective amount of a medicament acting against prostate cancer to said individual at the appropriate stage of the prostate cancer.

In some embodiments, the biallelic marker is comprised in one of the sequences P1 to P125 and the complementary sequences thereto. Preferably the biallelic marker is at least one biallelic marker selected from the group consisting of A1 to A125, and the complements thereof, or optionally the biallelic markers in linkage disequilibrium therewith. More preferably the biallelic marker is at least one biallelic marker selected from the group consisting of A2, A30, A41, A55, A57, and the complements thereof, or optionally the biallelic markers in linkage disequilibrium therewith. In particular embodiments, the individual is selected by genotyping one or more biallelic markers of the present invention.

To enlighten the choice of the appropriate beginning of the treatment of prostate cancer, the present invention also concerns a method for the treatment of prostate cancer comprising the following steps:
  selecting an individual suffering from a prostate cancer whose DNA comprises alleles of a biallelic marker or of a group of biallelic markers, preferably markers of the PCTA-1 gene, associated with the aggressiveness of prostate cancer tumors; and
  administering an effective amount of a medicament acting against prostate cancer to said individual.

In some embodiments, the biallelic marker is comprised in one of the sequences P1 to P125 and the complementary sequences thereto. Preferably the biallelic marker is at least one biallelic marker selected from the group consisting of A1 to A125, and the complements thereof, or optionally the biallelic markers in linkage disequilibrium therewith. More preferably the biallelic marker is at least one biallelic marker selected from the group consisting of A2, A30, A41, A55, A57, and the complements thereof, or optionally the biallelic markers in linkage disequilibrium therewith. In particular embodiments, the individual is selected by genotyping one or more biallelic markers of the present invention.

The invention concerns a method of determining whether a subject is likely to respond positively to treatment with a selected medicament acting against prostate cancer.

The invention also concerns a method for the treatment of prostate cancer in a selected population of individuals. The method comprises:
  selecting an individual suffering from prostate cancer and whose DNA comprises alleles of a biallelic marker or of a group of biallelic markers, preferably markers of the PCTA-1 gene, associated with a positive response to treatment with an effective amount of a medicament acting against prostate cancer, and/or whose DNA does not comprise alleles of a biallelic marker or of a group of biallelic markers, preferably markers of the PCTA-1 gene, associated with a negative response to treatment with said medicament; and administering at suitable intervals an effective amount of said medicament to said selected individual.

In some embodiments, the biallelic marker is comprised in one of the sequences P1 to P125 and the complementary sequences thereto. Preferably the biallelic marker is at least one biallelic marker selected from the group consisting of A1 to A125, and the complements thereof, or optionally the biallelic markers in linkage disequilibrium therewith. In particular embodiments, the individual is selected by genotyping one or more biallelic markers of the present invention.

Another aspect of the invention is a method of using a medicament acting against prostate cancer. The method comprises obtaining a DNA sample from a subject, determining whether the DNA sample contains one or more biallelic markers associated with a positive response to the medicament and/or whether the DNA sample contains one or more biallelic markers associated with a negative response to the medicament, and administering the medicament to the subject if the DNA sample contains one or more biallelic markers associated with a positive response to the medicament and/or if the DNA sample lacks one or more biallelic markers associated with a negative response to the medicament.

The invention also concerns a method for the clinical testing of a medicament, preferably a medicament acting against prostate cancer.

In some embodiments, the medicament may be administered to the subject in a clinical trial if the DNA sample contains alleles of one or more biallelic markers associated with a positive response to treatment with the medicament and/or if the DNA sample lacks alleles of one or more biallelic markers associated with a negative response to treatment with the medicament. In preferred embodiments, the medicament is a drug acting against prostate cancer. In other embodiments, the biallelic marker is selected from the group consisting of A1 to A125 and the complements thereof or optionally the biallelic markers in linkage disequilibrium therewith.

Using the method of the present invention, the evaluation of drug efficacy may be conducted in a population of individuals likely to respond favorably to the medicament.

The invention also concerns a method for the clinical testing of a medicament, preferably a medicament acting against prostate cancer. The method comprises the following steps:

administering a medicament, preferably a medicament susceptible of acting against prostate cancer to a heterogeneous population of individuals;

identifying a first population of individuals who respond positively to said medicament and a second population of individuals who respond negatively to said medicament;

identifying biallelic markers in said first population which are associated with a positive response to said medicament;

selecting individuals whose DNA comprises biallelic markers associated with a positive response to said medicament; and administering said medicament to said individuals.

Such methods are deemed to be extremely useful to increase the benefit/risk ratio resulting from the administration of medicaments which may cause undesirable side effects and/or be inefficacious to a portion of the patient population to which it is normally administered.

Once an individual has been diagnosed as suffering from a prostate cancer, selection tests are carried out to determine whether the DNA of this individual comprises alleles of a biallelic marker or of a group of biallelic markers associated with a positive response to treatment or with a negative response to treatment which may include either side effects or unresponsiveness.

The selection of the patient to be treated using the method of the present invention can be carried out through the detection methods described above. The individuals which are to be selected are preferably those whose DNA does not comprise alleles of a biallelic marker or of a group of biallelic markers associated with a negative response to treatment. The knowledge of an individual's genetic predisposition to unresponsiveness or side effects to particular medicaments allows the clinician to direct treatment toward appropriate drugs against prostate cancer.

Once the patient's genetic predispositions have been determined, the clinician can select appropriate treatment for which negative response, particularly side effects, has not been reported or has been reported only marginally for the patient.

Recombinant Vectors

The term "vector" is used herein to designate either a circular or a linear DNA or RNA molecule, which is either double-stranded or single-stranded, and which comprise at least one polynucleotide of interest that is sought to be transferred in a cell host or in a unicellular or multicellular host organism.

Another embodiment of the present invention is a recombinant vector. This recombinant vector comprises a nucleotide sequence encoding a regulatory region of the PCTA-1 gene, the promoter region of the PCTA-1 gene, an intron of the PCTA-1 gene, exon 0 and/or exon 1 of the PCTA-1 gene, exon 6bis of the PCTA-1 gene, exon 9bis of the PCTA-1 gene, the genomic sequence of the PCTA-1 gene, a cDNA sequence of the PCTA-1 gene, or combinations of such sequences, or complementary sequences thereto or fragments or variants thereof. Preferred nucleotide sequences included in such an expression vector include at least one nucleotide sequence selected from the group consisting of SEQ ID Nos 1, 2, 3, 4, 8 or fragments or variants thereof or a complementary sequence thereto.

Generally, a recombinant vector of the invention may comprise any of the polynucleotides described herein, including regulatory sequences and coding sequences, as well as any PCTA-1 primer or probe as defined above. More particularly, the recombinant vectors of the present invention can comprise any of the polynucleotides described in the "PCTA-1 cDNA Sequences" section, the "Coding Regions" section, and the "Oligonucleotide Probes And Primers" section.

In another embodiment, the vector includes a PCTA-1 gene or cDNA or a fragment thereof comprising at least one of the biallelic markers described herein, and more preferably a mutated PCTA-1 gene or cDNA comprising a trait causing mutation, particularly a mutation determined using the method described above. Preferably, the biallelic marker is selected from the group consisting of A1 to A125 and the complements thereof, or optionally the biallelic markers in linkage disequilibrium therewith.

One embodiment of the invention is the production of a PCTA-1 protein under the control of its own promoter or of an exogenous promoter. The present invention also relates to expression vectors which include nucleic acids encoding a native or mutated PCTA-1 protein under the control of either a native PCTA-1 regulatory region, preferably a native PCTA-1 promoter which comprises at least one of the biallelic markers of the present invention, more particularly at least one among the A1 to A43 and the complements thereof, or an exogenous promoter.

More particularly, the present invention relates to expression vectors which include nucleic acids encoding a PCTA-1 protein, preferably a PCTA-1 protein comprising a amino acid sequence selected from the group consisting of SEQ ID Nos 5, 6, 7, 9 or variants or fragments thereof, under the control of a regulatory sequence selected among the PCTA-1 regulatory polynucleotides, or alternatively under the control of an exogenous regulatory sequence.

The present invention also concerns an expression vector comprising a PCTA-1 regulatory region or any sequence thereof of 10 to 3000 nucleotides capable of regulating the expression of a nucleotide sequence encoding a protein and operably linked to the regulatory region. A further preferred regulatory region is the promoter sequence. In this regard, it is to be noted that a portion of the promoter can be used in the expression vector as long as it can influence the transcription of the coding sequence operably linked thereto.

Any nucleotide sequence encoding a polypeptide of interest can be included in an expression vector comprising a PCTA-1 regulatory region and operably linked thereto. Preferred polypeptides are therapeutic proteins which are described in further detail later on.

In some embodiments, expression vectors are employed to express a PCTA-1 polypeptide which can be then purified and, for example be used in ligand screening assays or as an immunogen in order to raise specific antibodies directed against a PCTA-1 protein. In other embodiments, the expression vectors are used for constructing transgenic animals and also for gene therapy.

Some of the elements which can be found in the vectors of the present invention are described in further detail in the following sections.

1. General Features of the Expression Vectors of the Invention

A recombinant vector according to the invention comprises, but is not limited to, a YAC (Yeast Artificial Chromosome), a BAC (Bacterial Artificial Chromosome), a phage, a phagemid, a cosmid, a plasmid or even a linear DNA molecule which may consist of a chromosomal, non-chromosomal, semi-synthetic or synthetic DNA. Such a recombinant vector can comprise a transcriptional unit comprising an assembly of:

(1) a genetic element or elements having a regulatory role in gene expression, for example promoters or enhancers. Enhancers are cis-acting elements of DNA, usually from about 10 to 300 bp in length that act on the promoter to increase the transcription.

(2) a structural or coding sequence which is transcribed into mRNA and eventually translated into a polypeptide, said structural or coding sequence being operably linked to the regulatory elements described in (1); and (3) appropriate transcription initiation and termination sequences. Structural units intended for use in yeast or eukaryotic expression systems preferably include a leader sequence enabling extracellular secretion of translated protein by a host cell. Alternatively, when a recombinant protein is expressed without a leader or transport sequence, it may include a N-terminal residue. This residue may or may not be subsequently cleaved from the expressed recombinant protein to provide a final product.

Generally, recombinant expression vectors will include origins of replication, selectable markers permitting transformation of the host cell, and a promoter derived from a highly expressed gene to direct transcription of a downstream structural sequence. The heterologous structural sequence is assembled in appropriate phase with translation initiation and termination sequences, and preferably a leader sequence capable of directing secretion of the translated protein into the periplasmic space or the extracellular medium. In a specific embodiment wherein the vector is adapted for transfecting and expressing desired sequences in mammalian host cells, preferred vectors will comprise an origin of replication in the desired host, a suitable promoter and enhancer, and also any necessary ribosome binding sites, polyadenylation site, splice donor and acceptor sites, transcriptional termination sequences, and 5'-flanking non-transcribed sequences. DNA sequences derived from the SV40 viral genome, for example SV40 origin, early promoter, enhancer, splice and polyadenylation sites may be used to provide the required non-transcribed genetic elements.

The in vivo expression of a PCTA-1 polypeptide may be useful in order to correct a genetic defect related to the expression of the native gene in a host organism or to the production of a biologically inactive PCTA-1 protein.

Consequently, the present invention also deals with recombinant expression vectors mainly designed for the in vivo production of a PCTA-1 polypeptide of SEQ ID Nos 5, 6, 7, 9 or fragments or variants thereof by the introduction of the appropriate genetic material in the organism of the patient to be treated. This genetic material may be introduced in vitro in a cell that has been previously extracted from the organism, the modified cell being subsequently reintroduced in the said organism, directly in vivo into the appropriate tissue.

2. Regulatory Elements

Promoters

The suitable promoter regions used in the expression vectors according to the present invention are chosen taking into account the cell host in which the heterologous gene has to be expressed. The particular promoter employed to control the expression of a nucleic acid sequence of interest is not believed to be important, so long as it is capable of directing the expression of the nucleic acid in the targeted cell. Thus, where a human cell is targeted, it is preferable to position the nucleic acid coding region adjacent to and under the control of a promoter that is capable of being expressed in a human cell, such as, for example, a human or a viral promoter.

A suitable promoter may be heterologous with respect to the nucleic acid for which it controls the expression or alternatively can be endogenous to the native polynucleotide containing the coding sequence to be expressed. Additionally, the promoter is generally heterologous with respect to the recombinant vector sequences within which the construct promoter/coding sequence has been inserted.

Promoter regions can be selected from any desired gene using, for example, CAT (chloramphenicol transferase) vectors and more preferably pKK232-8 and pCM7 vectors.

Preferred bacterial promoters are the LacI, LacZ, the T3 or T7 bacteriophage RNA polymerase promoters, the gpt, lambda PR, PL and trp promoters (EP 0036776, the disclosure of which is incorporated herein by reference in its entirety), the polyhedrin promoter, or the p10 protein promoter from baculovirus (Kit Novagen) (Smith et al., 1983; O'Reilly et al., 1992), the lambda PR promoter or also the trc promoter.

Eukaryotic promoters include CMV immediate early, HSV thymidine kinase, early and late SV40, LTRs from retrovirus, and mouse metallothionine-L. Selection of a convenient vector and promoter is well within the level of ordinary skill in the art.

The choice of a promoter is well within the ability of a person skilled in the field of genetic engineering. For example, one may refer to the book of Sambrook et al.(1989) or also to the procedures described by Fuller et al.(1996).

Other Regulatory Elements

Where a cDNA insert is employed, one will typically desire to include a polyadenylation signal to effect proper polyadenylation of the gene transcript. The nature of the polyadenylation signal is not believed to be crucial to the successful practice of the invention, and any such sequence may be employed such as human growth hormone and SV40 polyadenylation signals. Also contemplated as an element of the expression cassette is a terminator. These elements can serve to enhance message levels and to minimize read through from the cassette into other sequences.

The vector containing the appropriate DNA sequence as described above, more preferably PCTA-1 gene regulatory polynucleotide, a polynucleotide encoding a PCTA-1 polypeptide selected from the group consisting of SEQ ID No 1 or a fragment or a variant thereof and SEQ ID Nos 2, 3, 4, 8, or both of them, can be utilized to transform an appropriate host to allow the expression of the desired polypeptide or polynucleotide.

3. Selectable Markers

Such markers would confer an identifiable change to the cell permitting easy identification of cells containing the expression construct. The selectable marker genes for selection of transformed host cells are preferably dihydrofolate reductase or neomycin resistance for eukaryotic cell culture, TRP1 for *S. cerevisiae* or tetracycline, rifampicin or ampicillin resistance in *E. coli*, or levan saccharase for mycobacteria, this latter marker being a negative selection marker.

4. Preferred Vectors.

Bacterial Vectors

As a representative but non-limiting example, useful expression vectors for bacterial use can comprise a selectable marker and a bacterial origin of replication derived from commercially available plasmids comprising genetic elements of pBR322 (ATCC 37017). Such commercial vectors include, for example, pKK223-3 (Pharmacia, Uppsala, Sweden), and GEM1 (Promega Biotec, Madison, Wis., USA).

Large numbers of other suitable vectors are known to those of skill in the art, and commercially available, such as the following bacterial vectors: pQE70, pQE60, pQE-9 (Qiagen), pbs, pD10, phagescript, psiX174, pbluescript SK, pbsks, pNH8A, pNH16A, pNH18A, pNH46A (Stratagene); ptrc99a, pKK223-3, pKK233-3, pDR540, pRIT5 (Pharmacia); pWLNEO, pSV2CAT, pOG44, pXT1, pSG (Stratagene); pSVK3, pBPV, pMSG, pSVL (Pharmacia); pQE-30 (QIAexpress).

Bacteriophage Vectors

The P1 bacteriophage vector may contain large inserts ranging from about 80 to about 100 kb.

The construction of P1 bacteriophage vectors such as p158 or p158/neo8 are notably described by Stemberg (1994). Recombinant P1 clones comprising PCTA-1 nucleotide sequences may be designed for inserting large polynucleotides of more than 40 kb (Linton et al., 1993). To generate P1 DNA for transgenic experiments, a preferred protocol is the protocol described by McCormick et al.(1994). Briefly, *E. coli* (preferably strain NS3529) harboring the P1 plasmid are grown overnight in a suitable broth medium containing 25 µg/ml of kanamycin. The P1 DNA is prepared from the *E. coli* by alkaline lysis using the Qiagen Plasmid Maxi kit (Qiagen, Chatsworth, Calif., USA), according to the manufacturer's instructions. The P1 DNA is purified from the bacterial lysate on two Qiagen-tip 500 columns, using the washing and elution buffers contained in the kit. A phenol/chloroform extraction is then performed before precipitating the DNA with 70% ethanol. After solubilizing the DNA in TE (10 mM Tris-HCl, pH 7.4, 1 mM EDTA), the concentration of the DNA is assessed by spectrophotometry.

When the goal is to express a P1 clone comprising PCTA-1 nucleotide sequences in a transgenic animal, typically in transgenic mice, it is desirable to remove vector sequences from the P1 DNA fragment, for example by cleaving the P1 DNA at rare-cutting sites within the P1 polylinker (SfiI, NotI or SalI). The P1 insert is then purified from vector sequences on a pulsed-field agarose gel, using methods similar using methods similar to those originally reported for the isolation of DNA from YACs (Schedl et al., 1993a; Peterson et al., 1993). At this stage, the resulting purified insert DNA can be concentrated, if necessary, on a Millipore Ultrafree-MC Filter Unit (Millipore, Bedford, Mass., USA—30,000 molecular weight limit) and then dialyzed against microinjection buffer (10 mM Tris-HCl, pH 7.4; 250 µM EDTA) containing 100 mM NaCl, 30 µM spermine, 70 µM spermidine on a microdyalisis membrane (type VS, 0.025 µM from Millipore). The intactness of the purified P1 DNA insert is assessed by electrophoresis on 1% agarose (Sea Kem GTG; FMC Bio-products) pulse-field gel and staining with ethidium bromide.

Baculovirus Vectors

A suitable vector for the expression of a PCTA-1 polypeptide of SEQ ID Nos 5, 6, 7, 9 or fragments or variants thereof is a baculovirus vector that can be propagated in insect cells and in insect cell lines. A specific suitable host vector system is the pVL1392/1393 baculovirus transfer vector (Pharmingen) that is used to transfect the SF9 cell line (ATCC NoCRL 1711) which is derived from *Spodoptera frugiperda*.

Other suitable vectors for the expression of a PCTA-1 polypeptide of SEQ ID Nos 5, 6, 7, 9 or fragments or variants thereof in a baculovirus expression system include those described by Chai et al.(1993), Vlasak et al.(1983) and Lenhard et al.(1996).

Viral Vectors

In one specific embodiment, the vector is derived from an adenovirus. Preferred adenovirus vectors according to the invention are those described by Feldman and Steg (1996) or Ohno et al.(1994). Another preferred recombinant adenovirus according to this specific embodiment of the present invention is the human adenovirus type 2 or 5 (Ad 2 or Ad 5) or an adenovirus of animal origin (French patent application No FR-93.05954).

Retrovirus vectors and adeno-associated virus vectors are generally understood to be the recombinant gene delivery systems of choice for the transfer of exogenous polynucleotides in vivo, particularly to mammals, including humans. These vectors provide efficient delivery of genes into cells, and the transferred nucleic acids are stably integrated into the chromosomal DNA of the host.

Particularly preferred retroviruses for the preparation or construction of retroviral in vitro or in vitro gene delivery vehicles of the present invention include retroviruses selected from the group consisting of Mink-Cell Focus Inducing Virus, Murine Sarcoma Virus, Reticuloendotheliosis virus and Rous Sarcoma virus. Particularly preferred Murine Leukemia Viruses include the 4070A and the 1504A viruses, Abelson (ATCC No VR-999), Friend (ATCC No VR-245), Gross (ATCC No VR-590), Rauscher (ATCC No VR-998) and Moloney Murine Leukemia Virus (ATCC No VR-190; PCT Application No WO 94/24298). Particularly preferred Rous Sarcoma Viruses include Bryan high titer (ATCC Nos VR-334, VR-657, VR-726, VR-659 and VR-728). Other preferred retroviral vectors are those described in Roth et al. (1996), PCT Application No WO 93/25234 (the disclosure of which is incorporated herein by reference in its entirety), PCT Application No WO 94/06920 (the disclosure of which is incorporated herein by reference in its entirety), Roux et al., 1989, Julan et al., 1992 and Neda et al., 1991.

Yet another viral vector system that is contemplated by the invention consists of the adeno-associated virus (AAV). The adeno-associated virus is a naturally occurring defective virus that requires another virus, such as an adenovirus or a herpes virus, as a helper virus for efficient replication and a productive life cycle (Muzyczka et al., 1992). It is also one of the few viruses that may integrate its DNA into non-dividing cells, and exhibits a high frequency of stable integration (Flotte et al., 1992; Samulski et al., 1989; McLaughlin et al., 1989). One advantageous feature of AAV derives from its reduced efficacy for transducing primary cells relative to transformed cells.

BAC Vectors

The bacterial artificial chromosome (BAC) cloning system (Shizuya et al., 1992) has been developed to stably maintain large fragments of genomic DNA (100-300 kb) in $E.\ coli$. A preferred BAC vector consists of pBeloBAC11 vector that has been described by Kim et al.(1996). BAC libraries are prepared with this vector using size-selected genomic DNA that has been partially digested using enzymes that permit ligation into either the Bam HI or HindIII sites in the vector. Flanking these cloning sites are T7 and SP6 RNA polymerase transcription initiation sites that can be used to generate end probes by either RNA transcription or PCR methods. After the construction of a BAC library in $E.\ coli$, BAC DNA is purified from the host cell as a supercoiled circle. Converting these circular molecules into a linear form precedes both size determination and introduction of the BACs into recipient cells. The cloning site is flanked by two Not I sites, permitting cloned segments to be excised from the vector by Not I digestion. Alternatively, the DNA insert contained in the pBeloBAC11 vector may be linearized by treatment of the BAC vector with the commercially available enzyme lambda terminase that leads to the cleavage at the unique cosN site, but this cleavage method results in a full length BAC clone containing both the insert DNA and the BAC sequences.

5. Delivery of the Recombinant Vectors

In order to effect expression of the polynucleotides and polynucleotide constructs of the invention, these constructs must be delivered into a cell. This delivery may be accomplished in vitro, as in laboratory procedures for transforming cell lines, or in vivo or ex vivo, as in the treatment of certain diseases states.

One mechanism is viral infection where the expression construct is encapsulated in an infectious viral particle.

Several non-viral methods for the transfer of polynucleotides into cultured mammalian cells are also contemplated by the present invention, and include, without being limited to, calcium phosphate precipitation (Graham et al., 1973; Chen et al., 1987;), DEAE-dextran (Gopal, 1985), electroporation (Tur-Kaspa et al., 1986; Potter et al., 1984), direct microinjection (Harland et al., 1985), DNA-loaded liposomes (Nicolau et al., 1982; Fraley et al., 1979), and receptor-mediate transfection (Wu and Wu, 1987; 1988). Some of these techniques may be successfully adapted for in vivo or ex vivo use.

Once the expression polynucleotide has been delivered into the cell, it may be stably integrated into the genome of the recipient cell. This integration may be in the cognate location and orientation via homologous recombination (gene replacement) or it may be integrated in a random, non specific location (gene augmentation). In yet further embodiments, the nucleic acid may be stably maintained in the cell as a separate, episomal segment of DNA. Such nucleic acid segments or "episomes" encode sequences sufficient to permit maintenance and replication independent of or in synchronization with the host cell cycle.

One specific embodiment for a method for delivering a protein or peptide to the interior of a cell of a vertebrate in vivo comprises the step of introducing a preparation comprising a physiologically acceptable carrier and a naked polynucleotide operatively coding for the polypeptide of interest into the interstitial space of a tissue comprising the cell, whereby the naked polynucleotide is taken up into the interior of the cell and has a physiological effect. This is particularly applicable for transfer in vitro but it may be applied to in vivo as well.

Compositions for use in vitro and in vivo comprising a "naked" polynucleotide are described in PCT application No. WO 90/11092 (Vical Inc.) and also in PCT application No. WO 95/11307 (Institut Pasteur, INSERM, Universite d'Ottawa) as well as in the articles of Tacson et al.(1996) and of Huygen et al.(1996).

In still another embodiment of the invention, the transfer of a naked polynucleotide of the invention, including a polynucleotide construct of the invention, into cells may be proceeded with a particle bombardment (biolistic), said particles being DNA-coated microprojectiles accelerated to a high velocity allowing them to pierce cell membranes and enter cells without killing them, such as described by Klein et al.(1987).

In a further embodiment, the polynucleotide of the invention may be entrapped in a liposome (Ghosh and Bacchawat, 1991; Wong et al., 1980; Nicolau et al., 1987)

In a specific embodiment, the invention provides a composition for the in vivo production of a PCTA-1 protein or polypeptide described herein. It comprises a naked polynucleotide operatively coding for this polypeptide, in solution in a physiologically acceptable carrier, and suitable for introduction into a tissue to cause cells of the tissue to express the said protein or polypeptide.

The amount of vector to be injected to the desired host organism varies according to the site of injection. As an indicative dose, it will be injected between 0,1 and 100 µg of the vector in an animal body, preferably a mammal body, for example a mouse body.

In another embodiment of the vector according to the invention, it may be introduced in vitro in a host cell, preferably in a host cell previously harvested from the animal to be treated and more preferably a somatic cell such as a muscle cell. In a subsequent step, the cell that has been transformed with the vector coding for the desired PCTA-1 polypeptide or the desired fragment thereof is reintroduced into the animal body in order to deliver the recombinant protein within the body either locally or systemically.

Cell Hosts

The invention also concerns host cells transformed by one of the vectors described above that produce either a heterologous protein, a PCTA-1 protein or fragments thereof encoded by the PCTA-1 gene, preferably comprising at least one of the biallelic polymorphisms described herein, and more preferably a mutated PCTA-1 gene comprising the trait causing mutation determined using the above-noted method.

Another object of the invention consists of a host cell that has been transformed or transfected with one of the polynucleotides described herein, and in particular a polynucleotide either comprising a PCTA-1 regulatory polynucleotide or the coding sequence of a PCTA-1 polypeptide selected from the group consisting of SEQ ID No 1 2, 3, 4, 8 or a fragment or a variant thereof. Also included are host cells that are transformed (prokaryotic cells) or that are transfected (eukaryotic cells) with a recombinant vector such as one of those described above. More particularly, the cell hosts of the present invention can comprise any of the polynucleotides described in the "PCTA-1 cDNA Sequences" section, the "Coding Regions" section, and the "Oligonucleotide Probes And Primers" section.

A further recombinant cell host according to the invention comprises a polynucleotide containing a biallelic marker selected from the group consisting of A1 to A125, and the complements thereof.

Generally, a recombinant host cell of the invention comprises any one of the polynucleotides or the recombinant vectors described herein.

Preferred host cells used as recipients for the expression vectors of the invention are the following:

a) Prokaryotic host cells: *Escherichia coli* strains (I.E.DH5-αstrain), *Bacillus subtilis*, *Salmonella typhimurium*, and strains from species like *Pseudomonas, Streptomyces* and *Staphylococcus*.

b) Eukaryotic host cells: HeLa cells (ATCC NoCCL2; NoCCL2.1; NoCCL2.2), Cv 1 cells (ATCC NoCCL70), COS cells (ATCC NoCRL1650; NoCRL1651), Sf-9 cells (ATCC NoCRL1711), C127 cells (ATCC No CRL-1804), 3T3 (ATCC No CRL-6361), CHO (ATCC No CCL-61), human kidney 293. (ATCC No 45504; No CRL-1573) and BHK (ECACC No 84100501; No 84111301).

c) Other mammalian host cells.

The PCTA-1 gene expression in mammalian, and typically human, cells may be rendered defective, or alternatively it may be proceeded with the insertion of a PCTA-1 genomic or cDNA sequence with the replacement of the PCTA-1 gene counterpart in the genome of an animal cell by a PCTA-1 polynucleotide according to the invention. These genetic alterations may be generated by homologous recombination events using specific DNA constructs that have been previously described.

One kind of cell hosts that may be used are mammal zygotes, such as murine zygotes. For example, murine zygotes may undergo microinjection with a purified DNA molecule of interest, for example a purified DNA molecule that has previously been adjusted to a concentration range from 1 ng/ml—for BAC inserts—3 ng/μl—for P1 bacteriophage inserts—in 10 mM Tris-HCl, pH 7.4, 250 μM EDTA containing 100 mM NaCl, 30 μM spermine, and 70 μM spermidine. When the DNA to be microinjected has a large size, polyamines and high salt concentrations can be used in order to avoid mechanical breakage of this DNA, as described by Schedl et al (1993b).

Anyone of the polynucleotides of the invention, including the DNA constructs described herein, may be introduced in an embryonic stem (ES) cell line, preferably a mouse ES cell line. ES cell lines are derived from pluripotent, uncommitted cells of the inner cell mass of pre-implantation blastocysts. Preferred ES cell lines are the following: ES-E14TG2a (ATCC no CRL-1821), ES-D3 (ATCC no CRL1934 and no CRL-11632), YS001 (ATCC no CRL-11776), 36.5 (ATCC no CRL-11116). To maintain ES cells in an uncommitted state, they are cultured in the presence of growth inhibited feeder cells which provide the appropriate signals to preserve this embryonic phenotype and serve as a matrix for ES cell adherence. Preferred feeder cells consist of primary embryonic fibroblasts that are established from tissue of day 13-day 14 embryos of virtually any mouse strain, that are maintained in culture, such as described by Abbondanzo et al.(1993) and are inhibited in growth by irradiation, such as described by Robertson (1987), or by the presence of an inhibitory concentration of LIF, such as described by Pease and Williams (1990).

The constructs in the host cells can be used in a conventional manner to produce the gene product encoded by the recombinant sequence.

Following transformation of a suitable host and growth of the host to an appropriate cell density, the selected promoter is induced by appropriate means, such as temperature shift or chemical induction, and cells are cultivated for an additional period.

Cells are typically harvested by centrifugation, disrupted by physical or chemical means, and the resulting crude extract retained for further purification.

Microbial cells employed in the expression of proteins can be disrupted by any convenient method, including freeze-thaw cycling, sonication, mechanical disruption, or use of cell lysing agents. Such methods are well known by the skill artisan.

Transgenic Animals

The invention also relates to transgenic animals having an exogenous PCTA-1 regulatory region or a PCTA-1 gene, preferably comprising at least one of the biallelic polymorphisms described herein, and more preferably to a mutated PCTA-1 gene comprising the trait causing mutation determined using the above-noted method. Preferably, the biallelic marker is selected from the group consisting of A1 to A125 and the complements thereof, or optionally the biallelic markers in linkage disequilibrium therewith. In another embodiment, the invention concerns animals, preferably a mouse, having the mouse PCTA-1 gene which is modified or knocked out. These animals could be used to screen compounds of interest.

The terms "transgenic animals" or "host animals" are used herein to designate animals that have their genome genetically and artificially manipulated so as to include one of the nucleic acids according to the invention. Preferred animals are non-human mammals and include those belonging to a genus selected from *Mus* (e.g. mice), *Rattus* (e.g. rats) and *Oryctogalus* (e.g. rabbits) which have their genome artificially and genetically altered by the insertion of a nucleic acid according to the invention.

In one embodiment, the invention encompasses non-human host mammals and animals comprising a recombinant vector of the invention, a polynucleotide construct according to the invention, or a PCTA-1 gene disrupted by homologous recombination with a knock out vector. Generally, a transgenic animal according the present invention comprises any one of the polynucleotides, the recombinant vectors and the cell hosts described in the present invention. More particularly, the transgenic animals according to the present invention can comprise any of the polynucleotides described in the "PCTA-1 cDNA Sequences" section, the "Coding Regions" section, and the "Oligonucleotide Probes And Primers" section.

The transgenic animals of the invention all include within a plurality of their cells a cloned recombinant or synthetic DNA sequence, more specifically one of the purified or isolated nucleic acids comprising a PCTA-1 coding sequence, a PCTA-1 regulatory polynucleotide or a DNA sequence encoding an antisense polynucleotide such as described in the present specification, and still more preferably a nucleotide comprising an allele of at least one biallelic marker of the PCTA-1 gene.

In a first preferred embodiment, these transgenic animals may be good experimental models in order to study cancer, preferably prostate cancer, in particular concerning the transgenic animals within the genome of which has been inserted one or several copies of a polynucleotide encoding a native PCTA-1 protein, or alternatively a mutant PCTA-1 protein.

In a second preferred embodiment, these transgenic animals may express a desired polypeptide of interest under the control of the regulatory polynucleotides of the PCTA-1 gene, leading to good yields in the synthesis of this protein of interest, and eventually a tissue specific expression of this protein of interest.

The design of the transgenic animals of the invention may be made according to the conventional techniques well known from the one skilled in the art. For more details regarding the production of transgenic animals, and specifically transgenic mice, it may be referred to U.S. Pat. Nos. 4,873,191, issued Oct. 10, 1989; 5,464,764 issued Nov. 7, 1995; and 5,789,215, issued Aug. 4, 1998, the disclosures of which are incorporated herein by reference in their entireties.

Transgenic animals of the present invention are produced by the application of procedures which result in an animal with a genome that incorporates exogenous genetic material which is integrated into the genome. The procedure involves obtaining the genetic material, or a portion thereof, which encodes either a PCTA-1 coding sequence, a PCTA-1 regulatory polynucleotide or a DNA sequence encoding an antisense polynucleotide such as described in the present specification.

A recombinant polynucleotide of the invention is inserted into an embryonic or ES stem cell line. The insertion is made using electroporation. The cells subjected to electroporation are screened (e.g. Southern blot analysis) to find positive cells which have integrated the exogenous recombinant polynucleotide into their genome. An illustrative positive-negative selection procedure that may be used according to the invention is described by Mansour et al. (1988).

Then, the positive cells are isolated, cloned and injected into 3.5 days old blastocysts from mice. The blastocysts are then inserted into a female host animal and allowed to grow to term.

Alternatively, the positive ES cells are brought into contact with embryos at the 2.5 days old 8-16 cell stage (morulae) such as described by Wood et al.(1993) or by Nagy et al. (1993), the ES cells being internalized to colonize extensively the blastocyst including the cells which will give rise to the germ line.

The offsprings of the female host are tested to determine which animals are transgenic e.g. include the inserted exogenous DNA sequence and which are wild-type.

Thus, the present invention also concerns a transgenic animal containing a nucleic acid, a recombinant expression vector or a recombinant host cell according to the invention.

Recombinant Cell Lines Derived from the Transgenic Animals of the Invention.

A further object of the invention consists of recombinant host cells obtained from a transgenic animal described herein.

In one embodiment the invention encompasses cells derived from non-human host mammals and animals comprising a recombinant vector of the invention or a PCTA-1 gene disrupted by homologous recombination with a knock out vector.

Recombinant cell lines may be established in vitro from cells obtained from any tissue of a transgenic animal according to the invention, for example by transfection of primary cell cultures with vectors expressing onc-genes such as SV40 large T antigen, as described by Chou (1989) and Shay et al.(1991).

Screening of Agents Acting Against Prostate Cancer

In a further embodiment, the present invention also concerns a method for the screening of new agents, or candidate substances, acting against cancer, preferably against prostate cancer and which may be suitable for the treatment of a patient whose DNA comprises an allele of the PCTA-1 gene associated with cancer, preferably with prostate cancer, with an early onset of prostate cancer, or with the aggressiveness of prostate cancer tumors, or more generally with a modified or forthcoming expression of the PCTA-1 gene, with a modified or forthcoming production of the PCTA-1 protein, or with the production of a modified PCTA-1 protein.

In a preferred embodiment, the invention relates to a method for the screening of candidate substances for cancer treatment, preferably prostate cancer treatment. The method comprises the following steps:

providing a cell line, an organ, or a mammal expressing a PCTA-1 gene or a fragment thereof, preferably the regulatory region or the promoter region of the PCTA-1 gene;

obtaining a candidate substance, preferably a candidate substance capable of inhibiting the binding of a transcription factor to the PCTA-1 regulatory region; and testing the ability of the candidate substance to decrease the symptoms of cancer, preferably of prostate cancer and/or to modulate the expression levels of PCTA-1.

In some embodiments, the cell line, organ or mammal expresses a heterologous protein, the coding sequence of which is operably linked to the PCTA-1 regulatory or promoter sequence. In other embodiments, they express a PCTA-1 gene comprising alleles of one or more biallelic markers associated with cancer, preferably with prostate cancer, an early onset of prostate cancer, or the aggressiveness of prostate cancer tumors, or a mutated PCTA-1 gene comprising a trait causing mutation determined using the above-noted method. Optionally, the biallelic marker is selected from the group consisting of A1 to A125 and the complements thereof. Preferably, the biallelic marker is selected from the group consisting of A2, A30, A41, A55, A57 and the complements thereof. In a further embodiment, a mice expressing a PCTA-1 protein, preferably a mouse PCTA-1 protein encoded by a nucleic acid sequence of SEQ ID No 9 or a variant or a fragment thereof can be used to screen agents acting against cancer, preferably prostate cancer.

A candidate substance is a substance which can interact with or modulate, by binding or other intermolecular interactions, expression, stability, and function of PCTA-1. Such substances may be potentially interesting for patients who are not responsive to existing drugs or develop side effects to them. Screening may be effected using either in vitro methods or in vivo methods.

Such methods can be carried out in numerous ways such as on transformed cells which express the considered alleles of the PCTA-1 gene, on tumors induced by said transformed cells, for example in mice, or on PCTA-1 protein encoded by the considered allelic variant of PCTA-1. This method preferably includes preparing transformed cells with different forms of PCTA-1 sequences containing particular alleles of one or more biallelic markers and/or trait causing mutations described above. Optionally, the biallelic marker is selected from the group consisting of A1 to A125 and the complements thereof.

Screening assays of the present invention generally involve determining the ability of a candidate substance to present a cytotoxic effect, to change the characteristics of transformed cells such as proliferative and invasive capacity, to affect the tumor growth, or to modify the expression level of PTCA-1.

Typical examples of such drug screening assays are provided below. It is to be understood that the parameters set forth in these examples can be modified by the skilled person without undue experimentation.

Screening Substances Interacting with the Regulatory Sequences of the PCTA-1 Gene.

The present invention also concerns a method for screening substances or molecules that are able to interact with the regulatory sequences of the PCTA-1 gene, such as for example promoter or enhancer sequences.

Nucleic acids encoding proteins which are able to interact with the regulatory sequences of the PCTA-1 gene, more particularly a nucleotide sequence selected from the group consisting of the polynucleotides of the 5' and 3' regulatory region or a fragment or variant thereof, and preferably a variant comprising one of the biallelic markers of the invention, may be identified by using a one-hybrid system, such as that described in the booklet enclosed in the Matchmaker One-Hybrid System kit from Clontech (Catalog Ref. no K1603-1). Briefly, the target nucleotide sequence is cloned upstream of a selectable reporter sequence and the resulting DNA construct is integrated in the yeast genome (*Saccharomyces cerevisiae*). The yeast cells containing the reporter sequence in their genome are then transformed with a library consisting of fusion molecules between cDNAs encoding candidate proteins for binding onto the regulatory sequences of the PCTA-1 gene and sequences encoding the activator domain of a yeast transcription factor such as GAL4. The recombinant yeast cells are plated in a culture broth for selecting cells expressing the reporter sequence. The recombinant yeast cells thus selected contain a fusion protein that is able to bind onto the target regulatory sequence of the PCTA-1 gene. Then, the cDNAs encoding the fusion proteins are sequenced and may be cloned into expression or transcription vectors in vitro. The binding of the encoded polypeptides to the target regulatory sequences of the PCTA-1 gene may be confirmed by techniques familiar to the one skilled in the art, such as gel retardation assays or DNAse protection assays. Such assays are detailed in the section "Analysis Of Biallelic Markers Of The Invention With Prostate Cancer".

Screening for Expression Modifiers

The PCTA-1 gene appears to be involved in a series of events which most likely include a modification of at least one step of its transcription process. In fact, and as mentioned previously, there is a strong possibility that this modification is directly related to the binding efficiency of DNA binding factors to sites of the PCTA-1 regulatory region.

Screening programs can be used to test potentially therapeutic compounds, either by competitively binding to the sites of the PCTA-1 promoter which would normally bind the DNA transcription factor, or directly binding to the DNA binding factor itself. These compounds could reduce the speed at which the cascade of events leading to the development of PCTA-1 related cancers takes place. In fact, even though it seems clear that a combination of several DNA binding sites may be involved in the development of a PCTA-1 related prostate cancer, binding inhibition of only a few such sites is likely to be sufficient to significantly impact on PCTA-1 production and hence the proliferation of cancer.

The screening of expression modifiers is important as it can be used for detecting modifiers specific to one allele or a group of alleles of the PCTA-1 gene. The alteration of PCTA-1 expression in response to a modifier can be determined by administering or combining the candidate modifier with an expression system such as animals, cells, and in vitro transcription assay.

The term "expression modifier" is intended to encompass but is not limited to chemical agents and polypeptides that modulate the action of PCTA-1 through modulation of the PCTA-1 gene expression.

The effect of the modifier on PCTA-1 transcription and/or steady state mRNA levels can be also determined. As with the basic expression levels, tissue specific interactions are of interest. Correlations are made between the ability of an expression modifier to affect PCTA-1 activity, and the presence of the targeted polymorphisms. A panel of different modifiers may be screened in order to determine the effect under a number of different conditions.

Another subject of the present invention is a method for screening molecules that modulate the expression of the PCTA-1 protein. Such a screening method comprises the steps of:

a) cultivating a prokaryotic or an eukaryotic cell that has been transfected with a nucleotide sequence encoding the PCTA-1 protein or a variant or a fragment thereof, placed under the control of its own promoter;

b) bringing into contact the cultivated cell with a molecule to be tested; and c) quantifying the expression of the PCTA-1 protein or a variant or a fragment thereof.

In an embodiment, the nucleotide sequence encoding the PCTA-1 protein or a variant or a fragment thereof comprises an allele of at least one of the biallelic markers A1 to A125, preferably A2, A30, A41, A55, A57, and the complements thereof.

Using DNA recombination techniques well known by the one skilled in the art, the PCTA-1 protein encoding DNA sequence is inserted into an expression vector, downstream from its promoter sequence.

The quantification of the expression of the PCTA-1 protein may be realized either at the mRNA level or at the protein level. In the latter case, polyclonal or monoclonal antibodies may be used to quantify the amounts of the PCTA-1 protein that have been produced, for example in an ELISA or a RIA assay.

In a preferred embodiment, the quantification of the PCTA-1 mRNA is realized by a quantitative PCR amplification of the cDNA obtained by a reverse transcription of the total mRNA of the cultivated PCTA-1-transfected host cell, using a pair of primers specific for PCTA-1.

Thus, is also part of the present invention a method for screening of a candidate substance or molecule that modulated the expression of the PCTA-1 gene, this method comprises the following steps:

providing a recombinant cell host containing a nucleic acid, wherein said nucleic acid comprises a nucleotide sequence of the 5' regulatory region or a biologically active fragment or variant thereof located upstream a polynucleotide encoding a detectable protein;

obtaining a candidate substance; and
determining the ability of the candidate substance to modulate the expression levels of the polynucleotide encoding the detectable protein.

In a further embodiment, the nucleic acid comprising the nucleotide sequence of the 5' regulatory region or a biologically active fragment or variant thereof also includes a 5'UTR region of the PCTA-1 cDNAs, or one of its biologically active fragments or variants thereof.

Among the preferred polynucleotides encoding a detectable protein, there may be cited polynucleotides encoding luciferase, beta galactosidase, green fluorescent protein (GFP) and chloramphenicol acetyl transferase (CAT).

In another embodiment of a method for the screening of a candidate substance or molecule that modulates the expression of the PCTA-1 gene, wherein said method comprises the following steps:
a) providing a recombinant host cell containing a nucleic acid, wherein said nucleic acid comprises the 5'UTR sequence of a PCTA-1 cDNA, or one of its biologically active fragments or variants, the 5'UTR sequence or its biologically active fragment or variant being operably linked to a polynucleotide encoding a detectable protein;
b) obtaining a candidate substance; and
c) determining the ability of the candidate substance to modulate the expression levels of the polynucleotide encoding the detectable protein.

In one particular embodiment of the above screening method, the nucleic acid that comprises a nucleotide sequence selected from the group consisting of the 5'UTR sequence of a PCTA-1 cDNA or one of its biologically active fragments or variants, includes a promoter sequence which is exogenous with respect to the PCTA-1 5'UTR sequence defined therein. In a further preferred embodiment, the nucleic acid comprising the 5'-UTR sequence of a PCTA-1 cDNA or the biologically active fragments thereof includes a biallelic marker selected from the group consisting of A1 to A125, preferably A2, A30, A41, A55, A57, or the complements thereof.

The invention also pertains to kits useful for performing the herein described screening method. Preferably, such kits comprise a recombinant vector that allows the expression of a nucleotide sequence of the 5' regulatory region or a biologically active fragment or variant thereof located upstream and operably linked to a polynucleotide encoding a detectable protein or a PCTA-1 protein or a fragment or a variant thereof. Moreover, the kit can comprise a recombinant vector that comprises a nucleic acid including a 5'UTR sequence of a PCTA-1 cDNA, or one of their biologically active fragments or variants, said nucleic acid being operably linked to a polynucleotide encoding a detectable protein or a PCTA-1 protein or a fragment or a variant thereof.

For the design of suitable recombinant vectors useful for performing the screening methods described above, it will be referred to the section of the present specification wherein the preferred recombinant vectors of the invention are detailed.

Expression levels and patterns of PCTA-1 may be analyzed by solution hybridization with long probes as described in International Patent Application No. WO 97/05277. Briefly, a PCTA-1 cDNA or the PCTA-1 genomic DNA described above, or fragments thereof, is inserted at a cloning site immediately downstream of a bacteriophage (T3, T7 or SP6) RNA polymerase promoter to produce antisense RNA. Preferably, the PCTA-1 insert comprises at least 100 or more consecutive nucleotides of the genomic DNA sequence or a cDNA sequence, particularly those comprising at least one of biallelic markers according the present invention, preferably at least one of the biallelic markers A1 to A125 and the complements thereof or those comprising the trait causing mutation. The plasmid is linearized and transcribed in the presence of ribonucleotides comprising modified ribonucleotides (i.e. biotin-UTP and DIG-UTP). An excess of this doubly labeled RNA is hybridized in solution with mRNA isolated from cells or tissues of interest. The hybridizations are performed under standard stringent conditions (40-50° C. for 16 hours in an 80% formamide, 0.4 M NaCl buffer, pH 7-8). The unhybridized probe is removed by digestion with ribonucleases specific for single-stranded RNA (i.e. RNases CL3, T1, Phy M, U2 or A). The presence of the biotin-UTP modification enables capture of the hybrid on a microtitration plate coated with streptavidin. The presence of the DIG modification enables the hybrid to be detected and quantified by ELISA using an anti-DIG antibody coupled to alkaline phosphatase.

Quantitative analysis of the PCTA-1 gene expression may also be performed using arrays. As used herein, the term array means a one dimensional, two dimensional, or multidimensional arrangement of a plurality of nucleic acids of sufficient length to permit specific detection of expression of mRNAs capable of hybridizing thereto. For example, the arrays may contain a plurality of nucleic acids derived from genes whose expression levels are to be assessed. The arrays may include the PCTA-1 genomic DNA, a PCTA-1 cDNA sequence or the sequences complementary thereto or fragments thereof, particularly those comprising at least one of the biallelic markers according the present invention, preferably at least one of the biallelic markers A1 to A125 and the complements thereof or those comprising a trait causing mutation. Preferably, the fragments are at least 15 nucleotides in length. In other embodiments, the fragments are at least 25 nucleotides in length. In some embodiments, the fragments are at least 50 nucleotides in length. More preferably, the fragments are at least 100 nucleotides in length. In another preferred embodiment, the fragments are more than 100 nucleotides in length. In some embodiments the fragments may be more than 500 nucleotides in length.

For example, quantitative analysis of PCTA-1 gene expression may be performed with a complementary DNA microarray as described by Schena et al. (1995 and 1996). Full length PCTA-1 cDNAs or fragments thereof are amplified by PCR and arrayed from a 96-well microtiter plate onto silylated microscope slides using high-speed robotics. Printed arrays are incubated in a humid chamber to allow rehydration of the array elements and rinsed, once in 0.2% SDS for 1 min, twice in water for 1 min and once for 5 min in sodium borohydride solution. The arrays are submerged in water for 2 min at 95° C., transferred into 0.2% SDS for 1 min, rinsed twice with water, air dried and stored in the dark at 25° C.

Cell or tissue mRNA is isolated or commercially obtained and probes are prepared by a single round of reverse transcription. Probes are hybridized to 1 cm$^2$ microarrays under a 14×14 mm glass coverslip for 6-12 hours at 60° C. Arrays are washed for 5 min at 25° C. in low stringency wash buffer (1×SSC/0.2% SDS), then for 10 min at room temperature in high stringency wash buffer (0.1×SSC/0.2% SDS). Arrays are scanned in 0.1×SSC using a fluorescence laser scanning device fitted with a custom filter set. Accurate differential expression measurements are obtained by taking the average of the ratios of two independent hybridizations.

Quantitative analysis of PCTA-1 gene expression may also be performed with full length PCTA-1 cDNAs or fragments thereof in complementary DNA arrays as described by Pietu et al. (1996). The full length PCTA-1 cDNA or fragments thereof is PCR amplified and spotted on membranes. Then, mRNAs originating from various tissues or cells are labeled with radioactive nucleotides. After hybridization and washing in controlled conditions, the hybridized mRNAs are detected by phospho-imaging or autoradiography. Duplicate experiments are performed and a quantitative analysis of differentially expressed mRNAs is then performed.

Alternatively, expression analysis using the PCTA-1 genomic DNA, a PCTA-1 cDNA, or fragments thereof can be done through high density nucleotide arrays as described by Lockhart et al. (1996) and Sosnowsky et al. (1997). Oligonucleotides of 15-50 nucleotides from the sequence of the PCTA-1 genomic DNA, a PCTA-1 cDNA sequence, particularly a sequence comprising at least one of biallelic markers according the present invention, preferably at least one of the biallelic markers A1 to A125 and the complements thereof or comprising the trait causing mutation, or a sequence complementary thereto, are synthesized directly on the chip (Lockhart et al., supra) or synthesized and then addressed to the chip (Sosnowski et al., supra). Preferably, the oligonucleotides are about 20 nucleotides in length.

PCTA-1 cDNA probes labeled with an appropriate compound, such as biotin, digoxigenin or fluorescent dye, are synthesized from the appropriate mRNA population and then randomly fragmented to an average size of 50 to 100 nucleotides. The said probes are then hybridized to the chip. After washing as described in Lockhart et al., supra and application of different electric fields (Sosnowsky et al:, 1997)., the dyes or labeling compounds are detected and quantified. Duplicate hybridizations are performed. Comparative analysis of the intensity of the signal originating from cDNA probes on the same target oligonucleotide in different cDNA samples indicates a differential expression of PCTA-1 mRNA.

Screening for Molecules Interacting with a PCTA-1 Protein

The PCTA-1 proteins or fragments thereof described above may be used in drug screening procedures to identify molecules which are agonists, antagonists, or inhibitors of PCTA-1 activity. In a preferred embodiment, the PCTA-1 proteins or fragments thereof comprise at least one mutation provided either by biallelic markers of the present invention, preferably at least one mutation encoding by the biallelic markers A54, A56, A60, A75, A76, A85, or by a trait causing mutation according to the present invention. The PCTA-1 proteins or fragments thereof used in such analyses may be free in solution or linked to a solid support. Alternatively, the PCTA-1 proteins or fragments thereof can be expressed on a cell surface. The cell may naturally express a PCTA-1 protein or a fragment thereof or, alternatively, the cell may express a PCTA-1 protein or a fragment thereof from an expression vector such as those described above.

In one method of drug screening, eucaryotic or procaryotic host cells which are stably transformed with recombinant polynucleotides in order to express a PCTA-1 protein or a fragment thereof are used in conventional competitive binding assays or standard direct binding assays.

To study the interaction of a PCTA-1 protein or a fragment thereof with drugs or small molecules, such as molecules generated through combinatorial chemistry approaches, the microdialysis coupled to HPLC method described by Wang et al. (1997) or the affinity capillary electrophoresis method described by Bush et al. (1997) can be used.

In further methods, molecules which interact with a PCTA-1 protein or a fragment thereof may be identified using assays such as the following. The molecule to be tested for binding is labeled with a detectable label, such as a fluorescent, radioactive, or enzymatic tag and placed in contact with an immobilized PCTA-1 protein or a fragment thereof under conditions which permit specific binding to occur. After removal of non-specifically bound molecules, bound molecules are detected using appropriate means.

Another object of the present invention consists of methods and kits for the screening of candidate substances that interact with a PCTA-1 polypeptide.

A method for the screening of a candidate substance comprises the following steps: a) providing a polypeptide consisting of a PCTA-1 protein or a fragment thereof; b) obtaining a candidate substance; c) bringing into contact said polypeptide with said candidate substance; and d) detecting the complexes formed between said polypeptide and said candidate substance. Optionally, said PCTA-1 protein or fragment thereof is selected from the group consisting of polypeptides of SEQ ID Nos 5, 6, 7, 9 and fragments thereof.

The invention also pertains to kits useful for performing the hereinbefore described screening method. Preferably, such kits comprise a PCTA-1 polypeptide or a fragment thereof, and optionally means useful to detect the complex formed between a PCTA-1 polypeptide or a fragment thereof and the candidate substance. In a preferred embodiment the detection means consist in monoclonal or polyclonal antibodies directed against the corresponding PCTA-1 polypeptide or a fragment thereof.

Various candidate substances or molecules can be assayed for interaction with a PCTA-1 protein or a fragment thereof. These substances or molecules include, without being limited to, natural or synthetic organic compounds or molecules of biological origin such as polypeptides, antibodies, fatty acids and lipoproteins. When the candidate substance or molecule consists of a polypeptide, this polypeptide may be the resulting expression product of a phage clone belonging to a phage-based random peptide library, or alternatively the polypeptide may be the resulting expression product of a cDNA library cloned in a vector suitable for performing a two-hybrid screening assay.

For the purpose of the present invention, a ligand means a molecule, such as a protein, a peptide, an antibody, a fatty acid, a lipoprotein, or any synthetic chemical compound capable of binding to a PCTA-1 protein or a fragment thereof.

A. Candidate Ligands Obtained from Random Peptide Libraries

In a particular embodiment of the screening method, the putative ligand is the expression product of a DNA insert contained in a phage vector (Parmley and Smith, 1988). Specifically, random peptide phages libraries are used. The random DNA inserts encode for peptides of 8 to 20 amino acids in length (Oldenburg K. R. et al., 1992; Valadon P., et al., 1996; Lucas A. H., 1994; Westerink M. A. J., 1995; Felici F. et al., 1991). According to this particular embodiment, the recombinant phages expressing a protein that binds to the immobilized PCTA-1 protein or a fragment thereof is retained and the complex formed between the PCTA-1 polypeptide and the recombinant phage may be subsequently immunoprecipitated by a polyclonal or a monoclonal antibody directed against the PCTA-1 polypeptide.

Once the ligand library in recombinant phages has been constructed, the phage population is brought into contact with the immobilized PCTA-1 protein or a fragment thereof. Then the preparation of complexes is washed in order to remove the non-specifically bound recombinant phages. The phages that bind specifically to the PCTA-1 protein or a fragment thereof are then eluted by a buffer (acid pH) or immunoprecipitated by the monoclonal antibody produced by the hybridoma anti-PCTA-1, and this phage population is subsequently amplified by an over-infection of bacteria (for example *E. coli*). The selection step may be repeated several times, preferably 2-4 times, in order to select the more specific recombinant phage clones. The last step consists of characterizing the peptide produced by the selected recombinant phage clones either by expression in infected bacteria and isolation, expressing the phage insert in another host-vector system, or sequencing the insert contained in the selected recombinant phages.

B. Candidate Ligands Obtained by Competition Experiments.

Alternatively, peptides, drugs or small molecules which bind to the PCTA-1 protein, or a fragment thereof may be identified in competition experiments. In such assays, the PCTA-1 protein or a fragment thereof is immobilized to a surface, such as a plastic plate. Increasing amounts of the peptides, drugs or small molecules are placed in contact with the immobilized PCTA-1 protein or a fragment thereof in the presence of a detectable labeled known PCTA-1 protein ligand. For example, the PCTA-1 ligand may be detectably labeled with a fluorescent, radioactive, or enzymatic tag. The ability of the test molecule to bind the PCTA-1 protein or a fragment thereof is determined by measuring the amount of detectably labeled known ligand bound in the presence of the test molecule. A decrease in the amount of known ligand bound to the PCTA-1 protein or a fragment thereof when the test molecule is present indicated that the test molecule is able to bind to the PCTA-1 protein or a fragment thereof.

C. Candidate Ligands Obtained by Affinity Chromatography.

Proteins or other molecules interacting with the PCTA-1 protein or a fragment thereof can also be found using affinity columns which contain the PCTA-1 protein or a fragment thereof. The PCTA-1 protein or a fragment thereof may be attached to the column using conventional techniques including chemical coupling to a suitable column matrix such as agarose, Affi Gel®, or other matrices familiar to those of skill in art. In some embodiments of this method, the affinity column contains chimeric proteins in which the PCTA-1 protein or a fragment thereof is fused to glutathion S transferase (GST). A mixture of cellular proteins or pool of expressed proteins as described above is applied to the affinity column. Proteins or other molecules interacting with the PCTA-1 protein or a fragment thereof attached to the column can then be isolated and analyzed on 2-D electrophoresis gel as described in Ramunsen et al. (1997). Alternatively, the proteins retained on the affinity column can be purified by electrophoresis based methods and sequenced. The same method can be used to isolate antibodies, to screen phage display products, or to screen phage display human antibodies.

D. Candidate Ligands Obtained by Optical Biosensor Methods

Proteins interacting with the PCTA-1 protein or a fragment thereof can also be screened by using an Optical Biosensor as described in Edwards and Leatherbarrow (1997) and also in Szabo et al. (1995). This technique permits the detection of interactions between molecules in real time, without the need of labeled molecules. This technique is based on the surface plasmon resonance (SPR) phenomenon. Briefly, the candidate ligand molecule to be tested is attached to a surface (such as a carboxymethyl dextran matrix). A light beam is directed towards the side of the surface that does not contain the sample to be tested and is reflected by said surface. The SPR phenomenon causes a decrease in the intensity of the reflected light with a specific association of angle and wavelength. The binding of candidate ligand molecules cause a change in the refraction index on the surface, which change is detected as a change in the SPR signal. For screening of candidate ligand molecules or substances that are able to interact with the PCTA-1 protein or a fragment thereof, the PCTA-1 polypeptide is immobilized onto a surface. This surface consists of one side of a cell through which flows the candidate molecule to be assayed. The binding of the candidate molecule on the PCTA-1 protein or a fragment thereof is detected as a change of the SPR signal. The candidate molecules tested may be proteins, peptides, carbohydrates, lipids, or small molecules generated by combinatorial chemistry. This technique may also be performed by immobilizing eukaryotic or prokaryotic cells or lipid vesicles exhibiting an endogenous or a recombinantly expressed PCTA-1 protein at their surface.

The main advantage of the method is that it allows the determination of the association rate between the PCTA-1 protein and molecules interacting with the PCTA-1 protein. It is thus possible to select specifically ligand molecules interacting with the PCTA-1 protein, or a fragment thereof, through strong or conversely weak association constants.

E. Candidate Ligands Obtained Through a Two-Hybrid Screening Assay.

The yeast two-hybrid system is designed to study protein-protein interactions in vivo (Fields and Song, 1989), and relies upon the fusion of a bait protein to the DNA binding domain of the yeast Gal4 protein. This technique is also described in the U.S. Pat. No. 5,667,973 and the U.S. Pat. No. 5,283,173 (Fields et al.), the disclosures of which are incorporated herein by reference in their entireties.

The general procedure of library screening by the two-hybrid assay may be performed as described by Harper et al. (1993) or as described by Cho et al. (1998) or also Fromont-Racine et al. (1997).

The bait protein or polypeptide consists of a PCTA-1 polypeptide or a fragment thereof.

More precisely, the nucleotide sequence encoding the PCTA-1 polypeptide or a fragment thereof is fused to a polynucleotide encoding the DNA binding domain of the GAL4 protein, the fused nucleotide sequence being inserted in a suitable expression vector, for example pAS2 or pM3.

Then, a human cDNA library is constructed in a specially designed vector, such that the human cDNA insert is fused to a nucleotide sequence in the vector that encodes the transcriptional domain of the GAL4 protein. Preferably, the vector used is the pACT vector. The polypeptides encoded by the nucleotide inserts of the human cDNA library are termed "pray" polypeptides.

A third vector contains a detectable marker gene, such as beta galactosidase gene or CAT gene that is placed under the control of a regulation sequence that is responsive to the binding of a complete Gal4 protein containing both the transcriptional activation domain and the DNA binding domain. For example, the vector pG5EC may be used.

Two different yeast strains are also used. As an illustrative but non limiting example the two different yeast strains may be the followings:

Y190, the phenotype of which is (MATa, Leu2-3, 112 ura3-12, trp1-901, his3-D200, ade2-101, gal4Dgal180D URA3 GAL-LacZ, LYS GAL-HIS3, cyh$^r$);

Y187, the phenotype of which is (MATa gal4 gal80 his3 trp1-901 ade2-101 ura3-52 leu2-3, -112 URA3 GAL-lac-Zmet$^-$), which is the opposite mating type of Y190.

Briefly, 20 µg of pAS2/PCTA-1 and 20 µg of pACT-cDNA library are co-transformed into yeast strain Y190. The transformants are selected for growth on minimal media lacking histidine, leucine and tryptophan, but containing the histidine synthesis inhibitor 3-AT (50 mM). Positive colonies are screened for beta galactosidase by filter lift assay. The double positive colonies (His⁺, beta-gal⁺) are then grown on plates lacking histidine, leucine, but containing tryptophan and cycloheximide (10 mg/ml) to select for loss of pAS21PCTA-1 plasmids bu retention of pACT-cDNA library plasmids. The resulting Y190 strains are mated with Y187 strains expressing PCTA-1 or non-related control proteins; such as cyclophilin B, lamin, or SNF1, as Gal4 fusions as described by Harper et al. (1993) and by Bram et al. (1993), and screened for beta galactosidase by filter lift assay. Yeast clones that are beta gal– after mating with the control Gal4 fusions are considered false positives.

In another embodiment of the two-hybrid method according to the invention, interaction between the PCTA-1 or a fragment thereof with cellular proteins may be assessed using the Matchmaker Two Hybrid System 2 (Catalog No. K1604-1, Clontech). As described in the manual accompanying the Matchmaker Two Hybrid System 2 (Catalog No. K1604-1, Clontech), nucleic acids encoding the PCTA-1 protein or a fragment thereof, are inserted into an expression vector such that they are in frame with DNA encoding the DNA binding domain of the yeast transcriptional activator GAL4. A desired cDNA, preferably human cDNA, is inserted into a second expression vector such that they are in frame with DNA encoding the activation domain of GAL4. The two expression plasmids are transformed into yeast and the yeast are plated on selection medium which selects for expression of selectable markers on each of the expression vectors as well as GAL4 dependent expression of the HIS3 gene. Transformants capable of growing on medium lacking histidine are screened for GAL4 dependent lacZ expression. Those cells which are positive in both the histidine selection and the lacZ assay contain interaction between PCTA-1 and the protein or peptide encoded by the initially selected cDNA insert.

Screening Through Spontaneous Metastatic Assay

Screening of new compounds can be carried out through a spontaneous metastatic assay as described in Nihei et al. (1995). Hence, it can be possible to assess the decrease of metastatic potential of transformed cells related to treatment of said compounds. Indeed, according to the present invention, the metastatic potential of cells constitutes the major criteria of the aggressiveness of prostate cancer tumors.

To evaluate the metastatic ability, about $5 \times 10^5$ cells expressing a PCTA-1 gene comprising alleles for one or more biallelic markers associated with cancer, preferably with prostate cancer, or with the aggressiveness of prostate cancer tumors, are injected subcutaneously in the flank of male athymic nude mice. The mice are treated with the screened compounds. Tumor volume and tumor volume doubling time are used as the index of the tumor growth rate and are determined as described in Isaacs & Hukku, 1988). The tumor-bearing animals are scored for lung metastases at spontaneous death or when killed at day 35 post-inoculation.

Gene Therapy

Gene therapy involves the alteration of the phenotypic expression of a targeted cell, usually a cancer cell through the alteration of the cell's genotypic content. The desired effect of gene therapy is a reduction or interruption of tumor growth or, ideally, the destruction of the cell itself. An appropriate gene for gene therapy must be capable of altering the biological behavior of the cancer cell in order to slow growth, reduce local invasive potential, or induce apoptosis. The PCTA-1 gene, or certain portions thereof, is a good candidate for gene therapy.

The present invention also comprises the use of the genomic PCTA-1 DNA described above or a fragment thereof, in gene therapy strategies, such as antisense and triple helix strategies, and in the introduction of a therapeutic gene. Preferred nucleotide sequences useful in gene therapy include the sequences of SEQ ID Nos 1, 2, 3, 4, 8, complementary sequences thereto, and fragments thereof. More particularly, preferred nucleotide sequences comprise any of the polynucleotides described in the "PCTA-1 cDNA Sequences" section, the "Coding Regions" section, and the "Oligonucleotide Probes And Primers" section. Preferred PCTA-1 DNA fragments used in such approaches are those comprising a nucleotide sequence comprising a PCTA-1 regulatory region or a fragment thereof. More particularly, the regulatory regions comprise at least one of the biallelic markers according to the invention, more particularly those comprising a biallelic marker selected from the group consisting of A1 to A125, preferably A2, A30, A41, A55, A57, or a trait causing mutation, or complementary sequences thereof or variants or fragments thereof.

In a first embodiment, the invention therefore concerns a method for the treatment of prostate cancer. The method comprises: (a) selecting an individual whose DNA comprises an allele of biallelic marker or of a group of biallelic markers, preferably markers of the PCTA-1 gene, associated with a susceptibility to prostate cancer; and (b) administering to the individual an effective amount of a molecule capable of modifying the expression of the PCTA-1 gene.

In one embodiment, the molecule is an antisense nucleotide sequence, capable of competitively binding to the mRNA sequence resulting from the transcription of the PCTA-1 genomic DNA so as to prevent the translation of said mRNA. In preferred embodiments of this method, the antisense nucleotide sequence is characterized in that it hybridizes with exons of the PCTA-1 gene, preferably with a region of such exons comprising a least an allele of one of the biallelic markers of the present invention. Optionally, the antisense nucleotide sequence hybridizes with exons 0, 1, 6bis, 9 or 9ter of the PCTA-1 gene.

In an other embodiment, the molecule is a nucleotide sequence comprising a homopurine or homopyridine, preferably a 10-mer to 20-mer homopurine or homopyridine, which is complementary to a homopurine or homopyridine sequence of the PCTA-1 genomic DNA so as to prevent transcription of said genomic DNA into mRNA.

In a further embodiment, the molecule is a nucleotide sequence comprising a DNA sequence encoding a protein capable, when expressed, of exerting a therapeutic effect on prostate cancer cells, operably linked to the promoter of PCTA-1 gene, so as to kill or disable said prostate cancer cells.

The invention also concerns a method for the treatment of prostate cancer comprising:

administering to an individual an effective amount of a nucleotide sequence comprising a DNA sequence encoding a protein capable, when expressed, of exerting a therapeutic effect on prostate cancer cells, operably linked to the promoter of PCTA-1 gene.

The gene encoding a protein capable of exerting a therapeutic effect on prostate cancer cells is called the therapeutic gene in the present application. In some embodiments, the therapeutic gene is a toxin gene encoding a cytotoxic or cytostatic gene product. In another embodiment, the therapeutic gene is a gene encoding an immunogenic antigen which is highly visible to the immune system. In further embodiment, the therapeutic gene is a gene encoding a lymphokine which activates an anti-tumor immune response. In additional embodiments, the therapeutic gene encodes an antisense sequence having as a target the coding region of an essential gene for the proliferation or viability of the cell.

Antisense Approach

In antisense approaches, nucleic acid sequences complementary to a targeted mRNA are hybridized to the mRNA intracellularly, thereby blocking the expression of the protein encoded by the mRNA. The antisense sequences can prevent gene expression through a variety of mechanisms. For example, the antisense sequences may inhibit the ability of ribosomes to translate the mRNA. Alternatively, the antisense sequences may block transport of the mRNA from the nucleus to the cytoplasm, thereby limiting the amount of mRNA available for translation. Another mechanism through which antisense sequences may inhibit gene expression is by interfering with mRNA splicing. In yet another strategy, the antisense nucleic acid may be incorporated in a ribozyme capable of specifically cleaving the target mRNA.

The antisense nucleic acid molecules to be used in gene therapy may be either DNA or RNA sequences. They comprise a nucleotide sequence complementary to the targeted sequence of the PCTA-1 genomic DNA or a PCTA-1 cDNA. The targeted DNA or RNA sequence preferably comprises at least one of the biallelic markers according to the present invention, particularly a biallelic marker selected from the group consisting of A1 to A125 and the complements thereof, or comprises a trait causing mutation. In a preferred embodiment, the antisense oligonucleotide are able to hybridize with at least one of the splicing sites of the targeted PCTA-1 gene, with the 3'UTR or the 5'UTR, with exon 0, 1, 6bis, 9 or 9ter, or with an exonic region comprising at least one of the biallelic markers of the present invention or comprising a trait causing mutation.

Preferred methods using antisense polynucleotide according to the present invention are the procedures described by Sczakiel et al.(1995).

Preferably, the antisense tools are chosen among the polynucleotides (15-200 bp long) that are complementary to the 5'end of the PCTA-1 mRNA. In another embodiment, a combination of different antisense polynucleotides complementary to different parts of the desired targeted gene are used.

Preferred antisense polynucleotides according to the present invention are complementary to a sequence of the mRNAs of PCTA-1 that contains either the translation initiation codon ATG or a splicing donor or acceptor site.

The antisense nucleic acids should have a length and melting temperature sufficient to permit formation of an intracellular duplex having sufficient stability to inhibit the expression of the PCTA-1 mRNA in the duplex. Strategies for designing antisense nucleic acids suitable for use in gene therapy are disclosed in Green et al., (1986) and Izant and Weintraub, (1984).

In some strategies, antisense molecules are obtained by reversing the orientation of the PCTA-1 coding region with respect to a promoter so as to transcribe the opposite strand from that which is normally transcribed in the cell. The antisense molecules may be transcribed using in vitro transcription systems such as those which employ T7 or SP6 polymerase to generate the transcript. Another approach involves transcription of PCTA-1 antisense nucleic acids in vivo by operably linking DNA containing the antisense sequence to a promoter in a suitable expression vector.

Alternatively, suitable antisense strategies are those described by Rossi et al.(1991), in the International Applications Nos. WO 94/23026, WO 95/04141, WO 92/18522, WO 96/31523 and in the European Patent Application No. EP 0 572 287 A2, the disclosures of which are incorporated herein by reference in their entireties.

An alternative to the antisense technology that is used according to the present invention consists of using ribozymes that will bind to a target sequence via their complementary polynucleotide tail and that will cleave the corresponding RNA by hydrolyzing its target site (namely "hammerhead ribozymes"). Briefly, the simplified cycle of a hammerhead ribozyme consists of (1) sequence specific binding to the target RNA via complementary antisense sequences; (2) site-specific hydrolysis of the cleavable motif of the target strand; and (3) release of cleavage products, which gives rise to another catalytic cycle. Indeed, the use of long-chain antisense polynucleotide (at least 30 bases long) or ribozymes with long antisense arms are advantageous. A preferred delivery system for antisense ribozyme is achieved by covalently linking these antisense ribozymes to lipophilic groups or to use liposomes as a convenient vector. Preferred antisense ribozymes according to the present invention are prepared as described by Sczakiel et al.(1995).

Triple Helix Approach

The PCTA-1 genomic DNA, preferably comprising at least one of the biallelic markers according to the invention, more preferably at least one biallelic marker selected from the group consisting of A1 to A125, or comprising a trait causing mutation, or complementary sequences, variants or fragments thereof, may also be used in gene therapy approaches based on intracellular triple helix formation.

Triple helix oligonucleotides are used to inhibit transcription from a genome. They are particularly useful for studying alterations in cell activity when it is associated with a particular gene. Fragments of the PCTA-1 genomic DNA can be used to inhibit gene expression in individuals suffering from prostate cancer or from another detectable phenotype, or in individuals at risk of developing prostate cancer or another detectable phenotype at a later date as a result of their PCTA-1 genotype.

Similarly, a portion of the PCTA-1 genomic DNA can be used to study the effect of inhibiting PCTA-1 transcription within a cell. Traditionally, homopurine sequences were considered the most useful for triple helix strategies. However, homopyrimidine sequences can also inhibit gene expression. Such homopyrimidine oligonucleotides bind to the major groove at homopurine: homopyrimidine sequences. Thus, both types of sequences from the PCTA-1 genomic DNA, preferably comprising at least one of the biallelic markers according to the invention, more preferably at least one of the biallelic markers A1 to A125, or comprising the trait causing mutation, or complementary sequences thereof, variants thereof, are contemplated within the scope of this invention.

To carry out gene therapy strategies using the triple helix approach, the sequences of the PCTA-1 genomic DNA, preferably comprising at least one of the biallelic markers according to the invention, or comprising the trait causing mutation, or complementary sequences thereof, or variants thereof, are first scanned to identify 10-mer to 20-mer homopyrimidine or homopurine stretches which could be used in triple-helix based strategies for inhibiting PCTA-1 expression. Following identification of candidate homopyrimidine or homopurine stretches, their efficiency in inhibiting PCTA-1 expression is assessed by introducing varying amounts of oligonucleotides containing the candidate sequences into tissue culture cells which express the PCTA-1 gene.

The oligonucleotides can be introduced into the cells using a variety of methods known to those skilled in the art, including but not limited to calcium phosphate precipitation, DEAE-Dextran, electroporation, liposome-mediated transfection or native uptake.

Treated cells are monitored for altered cell function or reduced PCTA-1 expression using techniques such as Northern blotting, RNase protection assays, or PCR based strategies to monitor the transcription levels of the PCTA-1 gene in cells which have been treated with the oligonucleotide.

The oligonucleotides which are effective in inhibiting gene expression in tissue culture cells may then be introduced in vivo using the techniques described above in the antisense approach at a dosage calculated based on the in vitro results, as described in antisense approach.

In some embodiments, the natural (beta) anomers of the oligonucleotide units can be replaced with alpha anomers to render the oligonucleotide more resistant to nucleases. Further, an intercalating agent such as ethidium bromide, or the like, can be attached to the 3' end of the alpha oligonucleotide to stabilize the triple helix. For information on the generation of oligonucleotides suitable for triple helix formation see Griffin et al. (1989).

Introduction of a Therapeutic Gene

One important aspect of the present invention concerns a promoter specifically expressed in prostate cancer cells. More particularly, the present invention relates to the regulatory sequences, and particularly the promoter of the PCTA-1 gene. The expression of PCTA-1 appears to be specific to prostate cancer cells.

The term "specific", when used herein with reference to a promoter, is intended to designate a promoter which is specifically expressed in prostate cancer cells, at a level which is sufficient to have a significant impact on the metabolism of such cells. In other words, the promoter is specific in activity, effect or function. However, the term does not necessarily designate a promoter which is expressed solely in prostate cancer cells. Indeed, it is possible that the PCTA-1 gene is expressed, under the control of its promoter, in other cells at levels which are sufficiently low to be undetectable by current detection techniques such as those involving antibodies, hybridization with a probe or even PCR. The promoter of the PCTA-1 gene can be advantageously used to introduce a therapeutic gene which will be expressed specifically in prostate cancer cells.

The invention therefore also concerns an expression vector comprising a DNA sequence encoding a functional protein, particularly a functional protein capable of exerting a therapeutic effect on prostate cancer cells, operably linked to the promoter of the PCTA-1 gene which is specifically expressed in prostate cancer cells.

Furthermore, the PCTA-1 promoter preferably comprises biallelic markers according to the invention, more particularly those described previously. Some alleles of the biallelic markers of the invention show an association with prostate cancer and may be involved in a modified or forthcoming expression of the PCTA-1 gene in prostate cancer cells. It may therefore advantageous to use the PCTA-1 promoter comprising such an allele to introduce a therapeutic gene for enhancing its expression in prostate cancer cells.

The term "therapeutic gene" is intended to designate DNA encoding an amino acid sequence corresponding to a functional peptide or protein capable of exerting a therapeutic effect on prostate cancer cells preferably by killing or disabling such cells, or having a regulatory effect on the expression of an important function in prostate cells.

In one embodiment, a single enhancer element or multiple enhancer elements which amplify the expression of the therapeutic gene without compromising tissue specificity can also be combined with the promoter of the PCTA-1 gene. In a preferred embodiment, the enhancer element may be a portion of the cytomegalovirus LTR, SV40 enhancer sequences, or MMTV LTR. Preferably, the enhancer element is positioned upstream of the PCTA-1 promoter.

The term "enhancer element" is intended to designate a nucleotide sequence that increases the rate of transcription of therapeutic genes or genes of interest but does not have promoter activity. An enhancer can be moved upstream, downstream, and to the other side of the PCTA-1 promoter without significant loss of activity.

In a preferred embodiment, a vector is constructed by inserting the therapeutic gene downstream of the PCTA-1 promoter. The therapeutic gene is inserted so as to be operably linked to the promoter.

Examples of therapeutic genes include suicide genes. These are gene sequences, the expression of which produces a protein or agent that inhibits prostate tumor cell growth or induces prostate tumor cell death. Genes of interest include genes encoding enzymes, oncogenes, tumor suppressor genes, genes encoding toxins, genes encoding cytokines, or a gene encoding oncostatin. The purpose of the therapeutic genes is to inhibit the growth of or kill prostate cancer cells or to produce cytokines or other cytotoxic agents which directly or indirectly inhibit the growth of or kill prostate cancer cell.

Suitable enzymes include thymidine kinase, xanthine-guanine phosphoribosyltransferase, cytosine deaminase, and hypoxanthine phosphoribosyl transferase. Suitable oncogenes and tumor suppressor genes include neu, EGF, ras, p53, retinoblastoma tumor suppressor gene (Rb), Wilm's tumor gene product, phosphotyrosine phosphatase, and nm23. Suitable toxins include *Pseudomonas* exotoxin A and S, diphteria toxin, *E. coli* LT toxins, Shiga toxin, Shiga-like toxins, ricin, abrin, supporin, and gelonin. Suitable cytokines include interferons, GM-CSF interleukins, tumor necrosis factor.

Other gene therapy strategies include antisense sequences as mentioned above of at least about 30 bp, preferably 50 pb, having as target the coding sequence of an essential gene for the proliferation or viability of the cell. Numerous proteins associated with transcription, translation, metabolic pathways, cytostructural genes can be used as target, preferably those which are essential, present at relatively low levels, and particularly associated with cancer cells.

The three presently available methodologies for DNA delivery are well-known by the skilled artisan: transfection with a viral vector; fusion with a lipid; and cationic supported DNA introduction. A suitable DNA delivery method should meet the following criteria: 1) capable of directing the therapeutic polynucleotides into specific target cell types, 2) highly efficient in mediating uptake of the therapeutic polynucleotide into the target cells, and 3) suited for use in vivo for therapeutic application.

The preferred method relies on replication-defective viral vectors harboring the therapeutic polynucleotide sequence as part of retroviral genome. Preferred vectors for use in the present invention are viral including adenoviruses, retroviral vectors, and adeno-associated viral vectors. Retroviral vectors and adenoviruses offer an efficient, useful, and presently the best-characterized means of introducing and expressing foreign genes efficiently in mammalian cells. These vectors have very broad host and cell type range and express genes stably and efficiently.

Other virus vectors that may be used for gene transfer into cells include retroviruses such as Moloney murine lekemia virus, papovaviruses such as JC, SV40, polyoma, and adenoviruses, Epstein-Barr virus, papilloma viruses such as bovine papilloma virus type I, vaccinia, and poliovirus.

Another gene transfer method is physical transfer of plasmid DNA comprising the therapeutic polynucleotide in liposomes directly into prostate, preferably into tumors cells in situ. Immunoliposomes may improve cell type specificity as compared to liposomes by virtue of the inclusion of specific antibodies which presumably bind to surface antigens specific of prostate cells. In one embodiment, antibodies are directed against PCTA-1 protein which is specific to prostate cancer cells.

Direct physical application of naked DNA comprising the therapeutic polynucleotide to the target cells is believed to be preferred in many cases.

Vaccine Composition

The invention concerns a vaccine composition comprising a vaccination agent including one of the following polypeptide:

a) a polypeptide comprising a contiguous span of at least 6 amino acids, preferably at least 8 to 10 amino acids, more preferably at least 12, 15, 20, 25, 30, 40, 50, or 100 amino acids of SEQ ID No 5, wherein said contiguous span comprises:
   i) a serine residue at amino acid position 170 and/or a lysine residue at amino acid position 203 in SEQ ID No 5; and/or
   ii) at least one residue selected from the group consisting of a tyrosine residue at amino acid position 18, a cysteine residue at amino acid position 35, a methionine residue at amino acid position 55 and an arginine residue at amino acid position 183 in SEQ ID No 5;

b) a polypeptide comprising a contiguous span of at least 6 amino acids, preferably at least 8 to 10 amino acids, more preferably at least 12, 15, 20, 25, 30, 40, 50, or 100 amino acids of SEQ ID No 6, wherein said contiguous span comprises:
   i) a serine residue at amino acid position 170 and/or a lysine residue at amino acid position 245 in SEQ ID No 6; and/or
   ii) at least one residue selected from the group consisting of a tyrosine residue at amino acid position 18, a cysteine residue at amino acid position 35, a methionine residue at amino acid position 55 and an arginine residue at amino acid position 225 in SEQ ID No 6; and/or
   iii) at least 1, 2, 3, 5 or 10 of the amino acid encoded by the exon 6bis, more particularly at least 1, 2, 3, 5 or 10 of the amino acid positions 183-224 of the SEQ ID No 6;

c) a polypeptide comprising a contiguous span of at least 6 amino acids, preferably at least 8 to 10 amino acids, more preferably at least 12, 15, 20, 25, 30, 40, 50, or 100 amino acids of SEQ ID No 7, wherein said contiguous span comprises:
   i) a serine residue at amino acid position 170 and/or a lysine residue at amino acid position 203 in SEQ ID No 7; and/or
   ii) at least one residue selected from the group consisting of a tyrosine residue at amino acid position 18, a cysteine residue at amino acid position 35, a methionine residue at amino acid position 55 and an arginine residue at amino acid position 183 in SEQ ID No 7; and/or
   iii) at least 1, 2, 3, 5 or 10 of the amino acid encoded by the exons 9bis and 9ter, more particularly at least 1, 2, 3, 5 or 10 of the amino acid positions 313-368 of the SEQ ID No 7; and d) a polypeptide comprising a contiguous span of at least 6 amino acids, preferably at least 8 to 10 amino acids, more preferably at least 12, 15, 20, 25, 30, 40, 50, or 100 amino acids of SEQ ID No 9.

"Vaccine agent or vaccination agent" is intended to designate a substance which has the ability, when administered to a patient in suitable amounts, to generate an immunogenic reaction which can confer either immunity to the patent against prostate cancer or kill or disable prostate cancer cells bearing on their surface the PCTA-1 protein or a fragment thereof.

The vaccine compositions of the present invention are intended to be administered to patients in an amount sufficient to inhibit the growth of cancer cells expressing the PCTA-1 protein. More particularly the vaccine composition is intended to decrease the growth rate, rate of division, or viability of the prostate cancer cells.

The administration of a vaccine composition of the invention may be for either a "prophylactic" or "therapeutic" purposes. When provided prophylactically, the vaccine agent are provided in advance of symptoms indicative of prostate cancer. The prophylactic administration of vaccine agent serves to prevent, attenuate, or inhibit of the growth of prostate cancer cells. The therapeutic administration of the vaccine agent serves to attenuate the pathological symptoms of prostate cancer, to decrease the size or growth of cancer tumors and or metastasis or to remove them.

The term "inhibition of growth" refers in the present application to the decrease of the rate of growth, rate of division, or viability of the cells in question.

Indeed, as the PCTA-1 gene is specifically expressed in prostate cancer cells, these vaccine agents can initiate the production of PCTA-1 specific cytotoxic T lymphocytes which lyse cells bearing, preferably on their surface, PCTA-1, a fragment of PCTA-1, or one or more PCTA-1 epitope peptides thereof and which lead to an inhibition of the growth of cancer also bearing the PCTA-1 protein.

Vaccine preparations which contain protein or peptide sequences as active substances are generally well known in the art, as exemplified by U.S. Pat. Nos. 4,608,251; 4,601,903; 4,599,231; 4,599,230; 4,596,792; and 4,578,770, the disclosures of which are incorporated herein by reference in their entireties.

A vaccine according to the present invention may further contain auxiliary vaccine constituents, such as carriers, buffers, stabilizers, solubilizers, adjuvants and preservatives.

In order to enhance the immunogenic character of the polypeptides taken from the mutated PCTA-1 protein, the polypeptides may be prepared as homopolymers (a multitude of identical polypeptides coupled to one another) or heteropolymers (a multitude of at least two different polypeptides coupled to one another).

The vaccine agents of the present invention can be used in native form or can be modified to form a chemical derivative. As used herein, a molecule is said to be a "chemical derivative" of another molecule when it contains additional chemical moieties not normally a part of the molecule. Such moieties may improve the molecule's solubility, absorption, biological half life, etc. . . . . The moieties may alternatively decrease the toxicity of the molecule, eliminate or attenuate any undesirable side effect of the molecule, et. Moieties capable of mediating such effects are disclosed in Remington's Pharmaceutical Sciences (1980).

The vaccine agents of the present invention may be administered in a convenient manner such as by oral, topical, intravenous, intraperitoneal, intramuscular, subcutaneous, intranasal, or intradermal routes. The vaccine agents of the present invention are administered in an amount which is effective for treatment and/or prophylaxis of the specific indication. In general, they are administered in an amount of at least about 10 µg/kg body weight per day and in most cases they are administered in an amount not in excess of about 8 mg/kg body weight per day. In most cases, the dosage is from about 10 µg/kg to about 1 mg/kg body weight daily, taking into account the routes of administration, symptoms, etc.

When administering the vaccine agent of the present invention to a patient, the dosage of the administered vaccine agent varies depending upon such factors as the patient's age, weight, sex, general medical condition, previous medical history. In general, it is desirable to provide the recipient with a dosage of vaccine agent which is in the range of from about 1 µg/kg to 10 mg/kg body weight, although a lower or higher dosage may be administered. The therapeutically effective dose can be lowered by using combinations of the vaccine agents of the present invention or other agents.

It is normally necessary to have multiple administrations of the vaccine agents, usually not exceeding six vaccinations, more usually not exceeding four vaccinations, preferably one or more vaccinations, more preferably about three vaccinations. The vaccinations will be normally be at from two to twelve week intervals, more usually from three to five week intervals. Periodic boosters at intervals of 1-5 years will be desirable to maintain levels of protective immunity.

The vaccine agents of the present invention are intended to be provided to recipient subjects in an amount sufficient to inhibit the growth (as defined above) of cancer cells bearing PCTA-1 protein.

The effect of the vaccine agents of the present invention can be assessed through the measurement of released IFN-γ from memory T-lymphocytes. The stronger of the immune response, the more IFN-γ will be released. Accordingly, a vaccine according to the invention comprises a polypeptide capable of releasing from the memory T-lymphocytes at least 1500 µg/ml, preferably 200 µg/ml, and more preferably 300 µg/ml of IFN-γ. Practically, the levels of IFN-γ from the primed lymphocytes are measured with in vitro proliferation assays of peripheral blood lymphocytes co-cultured with a vaccine agents to be tested. These techniques are well known and may be found in a wide variety of patents, such as U.S. Pat. No. 3,791,932; 4,174,384; and 3,949,064, the disclosures of which are incorporated herein by reference in their entireties, as illustrative of these types of assays.

The administration of the vaccine agent of the invention may be for either a "prophylactic" or "therapeutic" purposes. When provided prophylactically, the vaccine agent are administered in advance of any symptoms indicative of prostate cancer. The prophylactic administration of the vaccine agent serves to prevent, attenuate, or inhibit of the growth of prostate cancer cells. The therapeutic administration of the vaccine agent serves to attenuate the pathological symptoms of prostate cancer and to decrease the size of prostate cancer tumors or to remove them.

Typically, such vaccine agents are prepared as injectable either as liquid solutions or suspensions. Solid forms suitable for solution in, or suspension in, liquid prior to injection may also be prepared. The preparation may be emulsified. The active immunogenic ingredient is often mixed with excipients which are pharmaceutically acceptable and compatible with the vaccine agent. Suitable excipients are, for example, water, saline, dextrose, ethanol, or the like, and combinations thereof. In addition, if desired, the vaccine may contain minor amounts of auxiliary substances such as wetting or emulsifying agents, pH buffering agents, or adjuvants which enhance the effectiveness of the vaccines.

PCTA-1 protein and peptides, preferably mutated, may be formulated into the vaccine as neutral or salt forms. Pharmaceutically acceptable salts include acid addition salts which are formed between the free amino groups of the peptide, and inorganic acids, such as hydrochloric or phosphoric acids, or organic acids, such as acetic oxalic, tartaric, mandelic, and the like. Salts formed with the free carboxyl groups may also be derived from inorganic bases such as sodium, potassium, ammonium, calcium, or ferric hydroxydes, or from organic bases such as isopropylamine, trimethylamine, 2-ethylaminoethanol, histidine, procaine, and the like.

Some of the polypeptides of the vaccine agents of the invention are sufficiently immunogenic in a vaccine, but the immune response can be enhanced if the vaccine further comprises an adjuvant substance.

Various methods of achieving adjuvant effects for vaccines include the use of agents such as aluminim hydroxide or phosphate, commonly used as 0.05 to 0.1 percent solution in phosphate buffered saline, admixture with synthetic polymers of sugars (Carbopol) used as 0.25 percent solution, aggregation of the protein in the vaccine by heat treatment with temperature ranging between 70° C. and 101° C. for 30 second to 2 minute periods, respectively. Aggregation by reacting with pepsin treated antibodies (Fab) to albumin, mixture with bacterial cells such as *C. parvum* or endotoxins or lipopolysaccharide components of gram-negative bacteria, emulsion in physiologically acceptable oil vehicles such as mannide monoleate (Aracel A) or emulsion with 20 percent solution of a perfluorocarbon (Fluosol-DA) used as a block substitute may also be employed. According to the invention, dimethyldioctadecylammonium bromide is an interesting candidate for an adjuvant, but also Freund's complete and incomplete adjuvants as well as QuilA and RIBI are interesting possibilities. Other possibilities involve the use of immune modulating substances such as lymphokines (e.g. IFN-γ, IL-2 and IL-12) or synthetic IFN-γ inducers such as poly I:C in combination with the above-mentioned adjuvants.

The vaccine agent of the present invention can be formulated according to known methods to prepare pharmaceutically useful compositions, whereby immunogenic peptides, or their functional derivatives, are combined in admixture with a pharmaceutically acceptable carrier vehicle. Suitable vehicles and their formulation, inclusive of other human proteins, such as human serum albumin, are described Remington's Pharmaceutical Sciences (1980). In order to form a pharmaceutically acceptable composition suitable for effective administration, such compositions will contain an effective amount of one or more of the vaccine agents of the present invention, together with a suitable amount of a carrier vehicle.

Additional pharmaceutical methods may be employed to control the duration of action. Control release preparations may be achieved through the use of polymers to complex or absorb one or more of the vaccine agents of the present invention. The controlled delivery may be exercised by selecting appropriate macromolecule (for example polyesters, polyamino acids, polyvinyl, pyrrolidone, ethylenevinylacetate, methylcellulose, carboxymethylcellulose, protamine, or sulfate) and the concentration of macromolecules as well as the methods of incorporation in order to control release. Another possible method to control the duration of action by controlled release preparations is to incorporate vaccine agents of the present invention into particles of a polymeric material such as polyesters, polyamino acids, hydrogels, poly(lactic acid) or ethylene vinylacetate copolymers. Alternatively, instead of incorporating these vaccine agents into polymeric particles, it is possible to entrap these materials in microcapsules prepared, for example, bu coacervation techniques or by interfacial polymerization, for example, hydroxymethylcellulose or gelatine-microcapsules and poly(methylmethacylate) microcapsules, respectively, or in colloidal drug delivery systems, for example, liposomes, albumin microspheres, microemulsions, nanoparticles, and nanocapsules or in macroemulsions. Such techniques are disclosed in Remington's Pharmaceutical Sciences (1980).

The invention further provides a pharmaceutical pack or kit comprising one or more containers filled with one or more of the ingredients of the vaccine compositions of the invention.

Computer-Related Embodiments

As used herein the term "nucleic acid codes of the invention" encompass the nucleotide sequences comprising, consisting essentially of, or consisting of any one of the following: a) a contiguous span of at least 12, 15, 18, 20, 25, 30, 35, 40, 50, 60, 70, 80, 90, 100, 150, 200, 500, or 1000 nucleotides of SEQ ID No 1, wherein said contiguous span comprises at least 1, 2, 3, 5, or 10 of the following nucleotide positions of SEQ ID No 1: 1-70715, 70795-82207, 82297-83612, 83824-85297, 85418-86388, 86446-87495, 87523-88294, 88384-89483, 89650-92748, 97156-98309, 98476-99329, 99491-100026, 100212-100281, 100396-100538, 100682-100833, 100995-101920, 102087-102970, 103264-103724, and 103753-106746; b) a contiguous span of at least 12, 15, 18, 20, 25, 30, 35, 40, 50, 60, 70, 80, 90, 100, 150, 200, 500, or 1000 nucleotides of SEQ ID No 1 or the complements thereof, wherein said contiguous span comprises at least one nucleotide selected from the group consisting of a nucleotide G at positions 70728, 87860, 88297, 94432, and 95340 of SEQ ID No 1; a nucleotide A at positions 82218, 83644, 83808, 87787, 87806, 94218, and 97144 of SEQ ID No 1; a nucleotide C at positions 87902, 88215, 88283, 92760, 93726, and 94422 of SEQ ID No 1; and a nucleotide T at positions 93903, and 94170 of SEQ ID No 1; c) a contiguous span of at least 12, 15, 18, 20, 25, 30, 35, 40, 50, 60, 70, 80, 90, 100, 150, 200, 500, or 1000 nucleotides of SEQ ID No 1 or the complements thereof, wherein said contiguous span comprises at least one nucleotide selected from the group consisting of a nucleotide G at positions 86435, 93592, 93680, 93681, 93682, 93728, 93761, and 95445 of SEQ ID No 1; a nucleotide A at positions 86434, 88355, 93240, 93471, and 93747 of SEQ ID No 1; a nucleotide C at positions 93683, 95126, and 95444 of SEQ ID No 1; and a nucleotide T at positions 94154, and 94430 of SEQ ID No 1; d) a contiguous span of at least 12, 15, 18, 20, 25, 30, 35, 40, 50, 60, 70, 80, 90, 100, 150, 200, 500, or 1000 nucleotides of SEQ ID No 1 or the complements thereof, wherein said contiguous span comprises nucleotide positions selected from the group consisting of the nucleotide positions of SEQ ID No 1: 92975-92977, 93711-93715, 94151-94153, 94240-94243, 94770-94773, 94804-94808, 95121-95122, 95129-95135, 95148-95153, 95154-95159, 95173-95178, 95367-95374, 95410-95413, 95418-95420, 95430-95436, 95533-95535, and 95677-95677; e) a contiguous span of at least 12, 15, 18, 20, 25, 30, 35, 40, 50, 60, 70, 80, 90, 100, 150, 200, 500, or 1000 nucleotides of SEQ ID No 2 or the complements thereof, wherein said contiguous span comprises at least 1, 2, 3, 5, or 10 of the nucleotide positions 1-162 of SEQ ID No 2; f) a contiguous span of at least 12, 15, 18, 20, 25, 30, 35, 40, 50, 60, 70, 80, 90, 100, 150, 200, 500, or 1000 nucleotides of SEQ ID No 2 or the complements thereof, wherein said contiguous span comprises at least one nucleotide selected from the group consisting of a nucleotide A at positions 253, 363, 527, 2471, and 5397 of SEQ ID No 2; a nucleotide C at positions 1013, 1979, and 2675 of SEQ ID No 2; a nucleotide G at positions 176, 749, 2685, 3593 of SEQ ID No 2; and a nucleotide T at positions 2156, and 2423 of SEQ ID No 2; g) a contiguous span of at least 12, 15, 18, 20, 25, 30, 35, 40, 50, 60, 70, 80, 90, 100, 150, 200, 500, or 1000 nucleotides of SEQ ID No 2 or the complements thereof, wherein said contiguous span comprises at least one nucleotide selected from the group consisting of a nucleotide A at positions 708, 807, 1493, 1724, and 2000; a nucleotide C at positions 1936, 3379, and 3697; a nucleotide G at positions 709, 1845, 1933, 1934, 1935, 1981, 2014, and 3698; and a nucleotide T at positions 2407, and 2683 of SEQ ID No 2; h) a contiguous span of at least 12, 15, 18, 20, 25, 30, 35, 40, 50, 60, 70, 80, 90, 100, 150, 200, 500, or 1000 nucleotides of SEQ ID No 2 or the complements thereof, wherein said contiguous span comprises nucleotide positions selected from the group consisting of the nucleotide positions of SEQ ID No 2: 1229-1231, 1964-1968, 2404-2406, 2493-2496, 3023-3026, 3057-3061, 3374-3375, 3382-3388, 3401-3406, 3407-3412, 3426-3431, 3620-3627, 3663-3666, 3671-3673, 3683-3689, 3786-3788 and 3930-3932; i) a contiguous span of at least 12, 15, 18, 20, 25, 30, 35, 40, 50, 60, 70, 80, 90, 100, 150, 200, 500, or 1000 nucleotides of SEQ ID No 3 or the complements thereof, wherein said contiguous span comprises at least 1, 2, 3, 5, or 10 of the following nucleotide positions of SEQ ID No 3: 1-162 and 747-872; j) a contiguous span of at least 12, 15, 18, 20, 25, 30, 35, 40, 50, 60, 70, 80, 90, 100, 150, 200, 500, or 1000 nucleotides of SEQ ID No 3 or the complements thereof, wherein said contiguous span comprises at least one nucleotide selected from the group consisting of a nucleotide A at positions 253, 363, 527, 2597, and 5523 of SEQ ID No 3; a nucleotide C at positions 1139, 2105, and 2801 of SEQ ID No 3; a nucleotide G at positions 176, 875, 2811, 3719 of SEQ ID No 3; and a nucleotide T at positions 2282, and 2549 of SEQ ID No 3; k) a contiguous span of at least 12, 15, 18, 20, 25, 30, 35, 40, 50, 60, 70, 80, 90, 100, 150, 200, 500, or 1000 nucleotides of SEQ ID No 3 or the complements thereof, wherein said contiguous span comprises at least one nucleotide selected from the group consisting of a nucleotide A at positions 708, 807, 1619, 1850, and 2126; a nucleotide C at positions 2062, 3505, and 3823; a nucleotide G at positions 709, 1971, 2059, 2060, 2061, 2107, 2140, and 3824; and a nucleotide T at positions 2533, and 2809 of SEQ ID No 3; l) a contiguous span of at least 12, 15, 18, 20, 25, 30, 35, 40, 50, 60, 70, 80, 90, 100, 150, 200, 500, or 1000 nucleotides of SEQ ID No 3 or the complements thereof, wherein said contiguous span comprises nucleotide positions selected from the group consisting of the nucleotide positions of SEQ ID No 3: 1355-1357, 1892-1894, 2090-2094, 2530-2532, 2619-2622, 3149-3152, 3183-3187, 3500-3501, 3508-3514, 3527-3532, 3533-3538, 3552-3557, 3746-3749, 3789-3792, 3797-3799, 3809-3815, 3912-3914 and 40564058; m) a contiguous span of at least 12, 15, 18, 20, 25, 30, 35, 40, 50, 60, 70, 80, 90, 100, 150, 200, 500, or 1000 nucleotides of SEQ ID No 4 or the complements thereof, wherein said contiguous span comprises at least 1, 2, 3, 5, or 10 of the nucleotide positions 1-162 of SEQ ID No 4; n) a contiguous span of at least 12, 15, 18, 20, 25, 30, 35, 40, 50, 60, 70, 80, 90, 100, 150, 200, 500, or 1000 nucleotides of SEQ ID No 4 or the complements thereof, wherein said contiguous span comprises at least one nucleotide selected from the group consisting of a nucleotide A at positions 253, 363, 527 and 2460 of SEQ ID No 4; a nucleotide C at position 1013 of SEQ ID No 4 and a nucleotide G at positions 176, and 749 of SEQ ID No 4; o) a contiguous span of at least 12, 15, 18, 20, 25, 30, 35, 40, 50, 60, 70, 80, 90, 100, 150, 200, 500, or 1000 nucleotides of SEQ ID No 4 or the complements thereof, wherein said contiguous span comprises at least one nucleotide selected from the group consisting of a nucleotide A at positions 708 and 807 and a nucleotide G at position 709 of SEQ ID No 4; p) a contiguous span of at least 12, 15, 18, 20, 25, 30, 35, 40, 50, 60, 70, 80, 90, 100, 150, 200, 500, or 1000 nucleotides of SEQ ID No 4 or the complements thereof, wherein said contiguous span comprises the pairs of nucleotide positions 1136-1137 of SEQ ID No 4; q) a contiguous span of at least 12, 15, 18, 20, 25, 30, 35, 40, 50, 60, 70, 80, 90, 100, 150, 200, 500, or 1000 nucleotides of SEQ ID No 8 or the complements thereof, wherein said contiguous span comprises at least 1, 2, 3, 5, or 10 of the following nucleotide positions of SEQ ID No 8:1-500, 501-1000, 1001-1500, and 1501-1738; and, r) a nucleotide sequence complementary to any one of the preceding nucleotide sequences.

The "nucleic acid codes of the invention" further encompass nucleotide sequences homologous to: a) a contiguous span comprises at least 1, 2, 3, 5, or 10 of the following nucleotide positions of SEQ ID No 1: 1-70715, 70795-82207, 82297-83612, 83824-85297, 85418-86388, 86446-87495, 87523-88294, 88384-89483, 89650-92748, 97156-98309, 98476-99329, 99491-100026, 100212-100281, 100396-100538, 100682-100833, 100995-101920, 102087-102970, 103264-103724, and 103753-106746; b) a contiguous span of at least 12, 15, 18, 20, 25, 30, 35, 40, 50, 60, 70, 80, 90, 100, 150, 200, 500, or 1000 nucleotides of SEQ ID No 2 or the complements thereof, wherein said contiguous span comprises at least 1, 2, 3, 5, or 10 of the nucleotide positions 1-162 of SEQ ID No 2; c) a contiguous span of at least 12, 15, 18, 20, 25, 30, 35, 40, 50, 60, 70, 80, 90, 100, 150, 200, 500, or 1000 nucleotides of SEQ ID No 3 or the complements thereof, wherein said contiguous span comprises at least 1, 2, 3, 5, or 10 of the following nucleotide positions of SEQ ID No 3: 1-162 and 747-872; d) a contiguous span of at least 12, 15, 18, 20, 25, 30, 35, 40, 50, 60, 70, 80, 90, 100, 150, 200, 500, or 1000 nucleotides of SEQ ID No 4 or the complements thereof, wherein said contiguous span comprises at least 1, 2, 3, 5, or 10 of the nucleotide positions 1-162 of SEQ ID No 4; e) a contiguous span of at least 12, 15, 18, 20, 25, 30, 35, 40, 50, 60, 70, 80, 90, 100, 150, 200, 500, or 1000 nucleotides of SEQ ID No 8 or the complements thereof, wherein said contiguous span comprises at least 1, 2, 3, 5, or 10 of the following nucleotide positions of SEQ ID No 8: 1-500, 501-1000, 1001-1500, and 1501-1738; and f) sequences complementary to all of the preceding sequences. Homologous sequences refer to a sequence having at least 99%, 98%, 97%, 96%, 95%, 90%, 85%, 80%, or 75% homology to these contiguous spans. Homology may be determined using any method described herein, including BLAST2N with the default parameters or with any modified parameters. Homologous sequences also may include RNA sequences in which uridines replace the thymines in the nucleic acid codes of the invention. It will be appreciated that the nucleic acid codes of the invention can be represented in the traditional single character format (See the inside back cover of Stryer, Lubert. *Biochemistry*, $3^{rd}$ edition. W. H Freeman & Co., New York.) or in any other format or code which records the identity of the nucleotides in a sequence.

As used herein the term "polypeptide codes of the invention" encompass the polypeptide sequences comprising:

a) a contiguous span of at least 6 amino acids, preferably at least 8 to 10 amino acids, more preferably at least 12, 15, 20, 25, 30, 40, 50, or 100 amino acids of SEQ ID No 5, wherein said contiguous span includes:

i) a serine residue at amino acid position 170 and/or a lysine residue at amino acid position 203 in SEQ ID No 5; and/or ii) at least one residue selected from the group consisting of a tyrosine residue at amino acid position 18, a cysteine residue at amino acid position 35, a methionine residue at amino acid position 55 and an arginine residue at amino acid position 183 in SEQ ID No 5;

b) a contiguous span of at least 6 amino acids, preferably at least 8 to 10 amino acids, more preferably at least 12, 15, 20, 25, 30, 40, 50, or 100 amino acids of SEQ ID No 6, wherein said contiguous span includes:

i) a serine residue at amino acid position 170 and/or a lysine residue at amino acid position 245 in SEQ ID No 6; and/or ii) at least one residue selected from the group consisting of a tyrosine residue at amino acid position 18, a cysteine residue at amino acid position 35, a methionine residue at amino acid position 55 and an arginine residue at amino acid position 225 in SEQ ID No 6; and/or iii) at least 1, 2, 3, 5 or 10 of the amino acid encoded by the exon 6bis, more particularly at least 1, 2, 3, 5 or 10 of the amino acid positions 183-224 of the SEQ ID No 6;

c) a contiguous span of at least 6 amino acids, preferably at least 8 to 10 amino acids, more preferably at least 12, 15, 20, 25, 30, 40, 50, or 100 amino acids of SEQ ID No 7, wherein said contiguous span includes:

i) a serine residue at amino acid position 170 and/or a lysine residue at amino acid position 203 in SEQ ID No 7; and/or ii) at least one residue selected from the group consisting of a tyrosine residue at amino acid position 18, a cysteine residue at amino acid position 35, a methionine residue at amino acid position 55 and an arginine residue at amino acid position 183 in SEQ ID No 7; and/or iii) at least 1, 2, 3, 5 or 10 of the amino acid encoded by the exons 9bis and 9ter, more particularly at least 1, 2, 3, 5 or 10 of the amino acid positions 313-368 of the SEQ ID No 7; and, d) a contiguous span of at least 6 amino acids, preferably at least 8 to 10 amino acids, more preferably at least 12, 15, 20, 25, 30, 40, 50, or 100 amino acids of SEQ ID No 9.

It will be appreciated that the polypeptide codes of the invention can be represented in the traditional single character format or three letter format (See the inside back cover of Stryer, Lubert. Biochemistry, $3^{rd}$ edition. W. H Freeman & Co., New York.) or in any other format or code which records the identity of the polypeptides in a sequence.

It will be appreciated by those skilled in the art that the nucleic acid codes of the invention and polypeptide codes of the invention can be stored, recorded, and manipulated on any medium which can be read and accessed by a computer. As used herein, the words "recorded" and "stored" refer to a process for storing information on a computer medium. A skilled artisan can readily adopt any of the presently known methods for recording information on a computer readable medium to generate manufactures comprising one or more of the nucleic acid codes of the invention, or one or more of the polypeptide codes of the invention. Another aspect of the present invention is a computer readable medium having recorded thereon at least 2, 5, 10, 15, 20, 25, 30, or 50 nucleic acid codes of the invention. Another aspect of the present invention is a computer readable medium having recorded thereon at least 2, 5, 10, 15, 20, 25, 30, or 50 polypeptide codes of the invention.

Computer readable media include magnetically readable media, optically readable media, electronically readable media and magnetic/optical media. For example, the computer readable media may be a hard disk, a floppy disk, a magnetic tape, CD-ROM, Digital Versatile Disk (DVD), Random Access Memory (RAM), or Read Only Memory (ROM) as well as other types of other media known to those skilled in the art.

Figure 3:
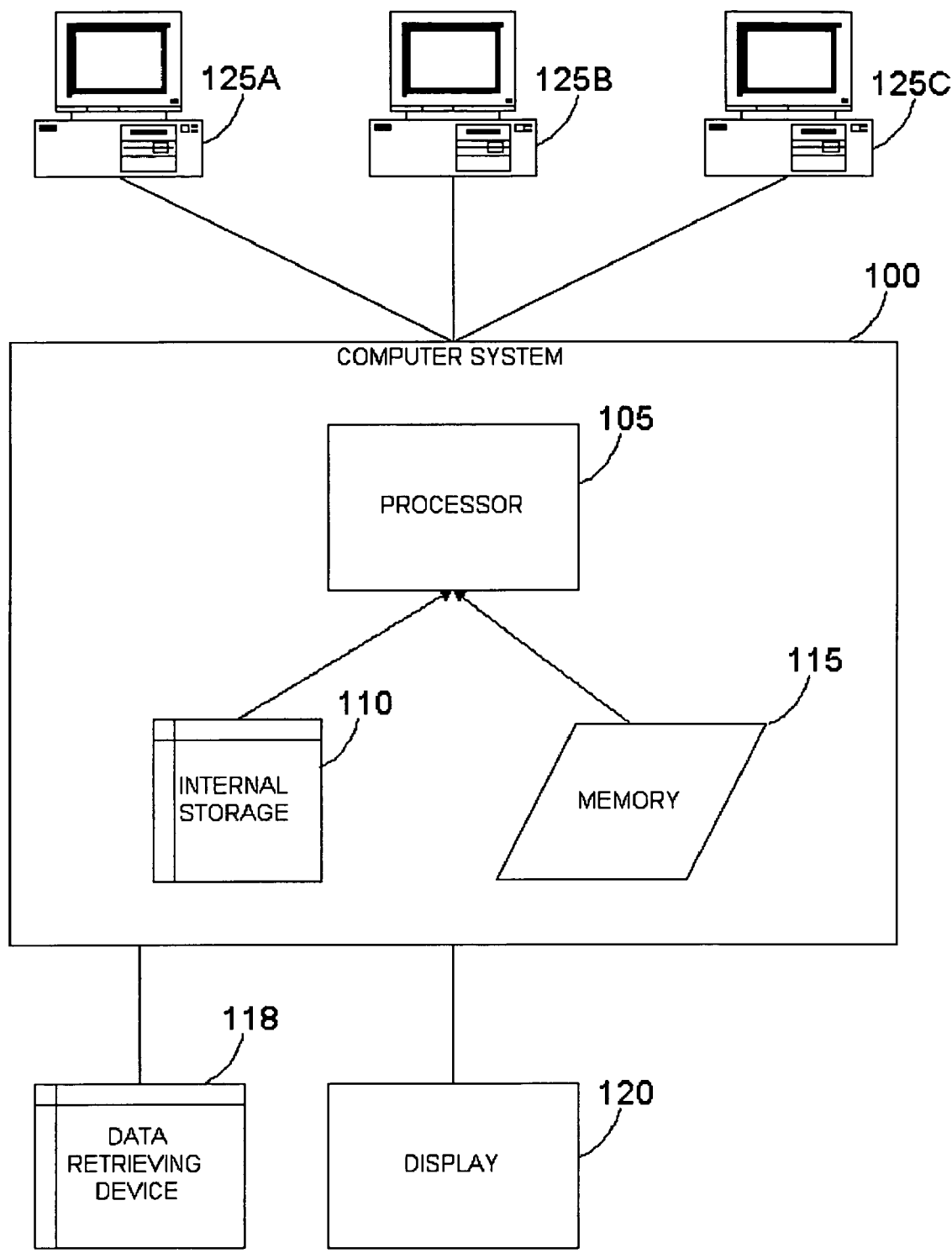
FIG. 3 is a block diagram of an exemplary computer system.

Embodiments of the present invention include systems, particularly computer systems which store and manipulate the sequence information described herein. One example of a computer system 100 is illustrated in block diagram form in FIG. 3. As used herein, "a computer system" refers to the hardware components, software components, and data storage components used to analyze the nucleotide sequences of the nucleic acid codes of the invention or the amino acid sequences of the polypeptide codes of the invention. In one embodiment, the computer system 100 is a Sun Enterprise 1000 server (Sun Microsystems, Palo Alto, Calif.). The computer system 100 preferably includes a processor for processing, accessing and manipulating the sequence data. The processor 105 can be any well-known type of central processing unit, such as the Pentium III from Intel Corporation, or similar processor from Sun, Motorola, Compaq or International Business Machines.

Preferably, the computer system 100 is a general purpose system that comprises the processor 105 and one or more internal data storage components 110 for storing data, and one or more data retrieving devices for retrieving the data stored on the data storage components. A skilled artisan can readily appreciate that any one of the currently available computer systems are suitable.

In one particular embodiment, the computer system 100 includes a processor 105 connected to a bus which is connected to a main memory 115 (preferably implemented as RAM) and one or more internal data storage devices 110, such as a hard drive and/or other computer readable media having data recorded thereon. In some embodiments, the computer system 100 further includes one or more data retrieving device 118 for reading the data stored on the internal data storage devices 110.

The data retrieving device 118 may represent, for example, a floppy disk drive, a compact disk drive, a magnetic tape drive, etc. In some embodiments, the internal data storage device 110 is a removable computer readable medium such as a floppy disk, a compact disk, a magnetic tape, etc. containing control logic and/or data recorded thereon. The computer system 100 may advantageously include or be programmed by appropriate software for reading the control logic and/or the data from the data storage component once inserted in the data retrieving device.

The computer system 100 includes a display 120 which is used to display output to a computer user. It should also be noted that the computer system 100 can be linked to other computer systems 125a-c in a network or wide area network to provide centralized access to the computer system 100.

Software for accessing and processing the nucleotide sequences of the nucleic acid codes of the invention or the amino acid sequences of the polypeptide codes of the invention (such as search tools, compare tools, and modeling tools etc.) may reside in main memory 115 during execution.

In some embodiments, the computer system 100 may further comprise a sequence comparer for comparing the above-described nucleic acid codes of the invention or the polypeptide codes of the invention stored on a computer readable medium to reference nucleotide or polypeptide sequences stored on a computer readable medium. A "sequence comparer" refers to one or more programs which are implemented on the computer system 100 to compare a nucleotide or polypeptide sequence with other nucleotide or polypeptide sequences and/or compounds including but not limited to peptides, peptidomimetics, and chemicals stored within the data storage means. For example, the sequence comparer may compare the nucleotide sequences of nucleic acid codes of the invention or the amino acid sequences of the polypeptide codes of the invention stored on a computer readable medium to reference sequences stored on a computer readable medium to identify homologies, motifs implicated in biological function, or structural motifs. The various sequence comparer programs identified elsewhere in this patent specification are particularly contemplated for use in this aspect of the invention.

Figure 4:
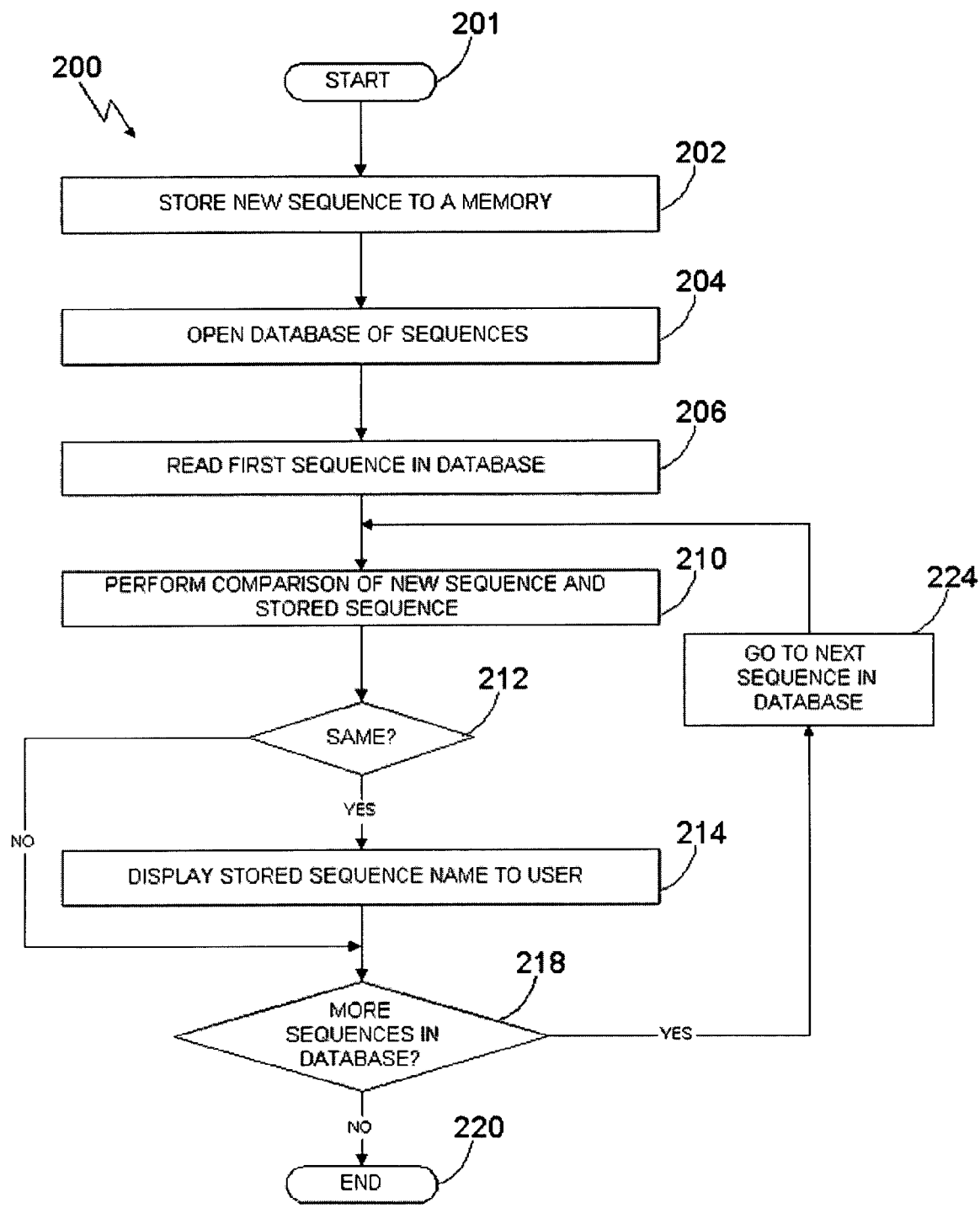
FIG. 4 is a flow diagram illustrating one embodiment of a process 200 for comparing a new nucleotide or protein sequence with a database of sequences in order to determine the homology levels between the new sequence and the sequences in the database.

FIG. 4 is a flow diagram illustrating one embodiment of a process 200 for comparing a new nucleotide or protein sequence with a database of sequences in order to determine the homology levels between the new sequence and the sequences in the database. The database of sequences can be a private database stored within the computer system 100, or a public database such as GENBANK, PIR OR SWISSPROT that is available through the Internet.

The process 200 begins at a start state 201 and then moves to a state 202 wherein the new sequence to be compared is stored to a memory in a computer system 100. As discussed above, the memory could be any type of memory, including RAM or an internal storage device.

The process 200 then moves to a state 204 wherein a database of sequences is opened for analysis and comparison. The process 200 then moves to a state 206 wherein the first sequence stored in the database is read into a memory on the computer. A comparison is then performed at a state 210 to determine if the first sequence is the same as the second sequence. It is important to note that this step is not limited to performing an exact comparison between the new sequence and the first sequence in the database. Well-known methods are known to those of skill in the art for comparing two nucleotide or protein sequences, even if they are not identical. For example, gaps can be introduced into one sequence in order to raise the homology level between the two tested sequences. The parameters that control whether gaps or other features are introduced into a sequence during comparison are normally entered by the user of the computer system.

Once a comparison of the two sequences has been performed at the state 210, a determination is made at a decision state 210 whether the two sequences are the same. Of course, the term "same" is not limited to sequences that are absolutely identical. Sequences that are within the homology parameters entered by the user will be marked as "same" in the process 200.

If a determination is made that the two sequences are the same, the process 200 moves to a state 214 wherein the name of the sequence from the database is displayed to the user. This state notifies the user that the sequence with the displayed name fulfills the homology constraints that were entered. Once the name of the stored sequence is displayed to the user, the process 200 moves to a decision state 218 wherein a determination is made whether more sequences exist in the database. If no more sequences exist in the database, then the process 200 terminates at an end state 220. However, if more sequences do exist in the database, then the process 200 moves to a state 224 wherein a pointer is moved to the next sequence in the database so that it can be compared to the new sequence. In this manner, the new sequence is aligned and compared with every sequence in the database.

It should be noted that if a determination had been made at the decision state 212 that the sequences were not homologous, then the process 200 would move immediately to the decision state 218 in order to determine if any other sequences were available in the database for comparison.

Accordingly, one aspect of the present invention is a computer system comprising a processor, a data storage device having stored thereon a nucleic acid code of the invention or a polypeptide code of the invention, a data storage device having retrievably stored thereon reference nucleotide sequences or polypeptide sequences to be compared to the nucleic acid code of the invention or polypeptide code of the invention and a sequence comparer for conducting the comparison. The sequence comparer may indicate a homology level between the sequences compared or identify structural motifs in the nucleic acid code of the invention and polypeptide codes of the invention or it may identify structural motifs in sequences which are compared to these nucleic acid codes and polypeptide codes. In some embodiments, the data storage device may have stored thereon the sequences of at least 2, 5, 10, 15, 20, 25, 30, or 50 of the nucleic acid codes of the invention or polypeptide codes of the invention.

Another aspect of the present invention is a method for determining the level of homology between a nucleic acid code of the invention and a reference nucleotide sequence, comprising the steps of reading the nucleic acid code and the reference nucleotide sequence through the use of a computer program which determines homology levels and determining homology between the nucleic acid code and the reference nucleotide sequence with the computer program. The computer program may be any of a number of computer programs for determining homology levels, including those specifically enumerated herein, including BLAST2N with the default parameters or with any modified parameters. The method may be implemented using the computer systems described above. The method may also be performed by reading 2, 5, 10, 15, 20, 25, 30, or 50 of the above described nucleic acid codes of the invention through the use of the computer program and determining homology between the nucleic acid codes and reference nucleotide sequences.

Figure 5:
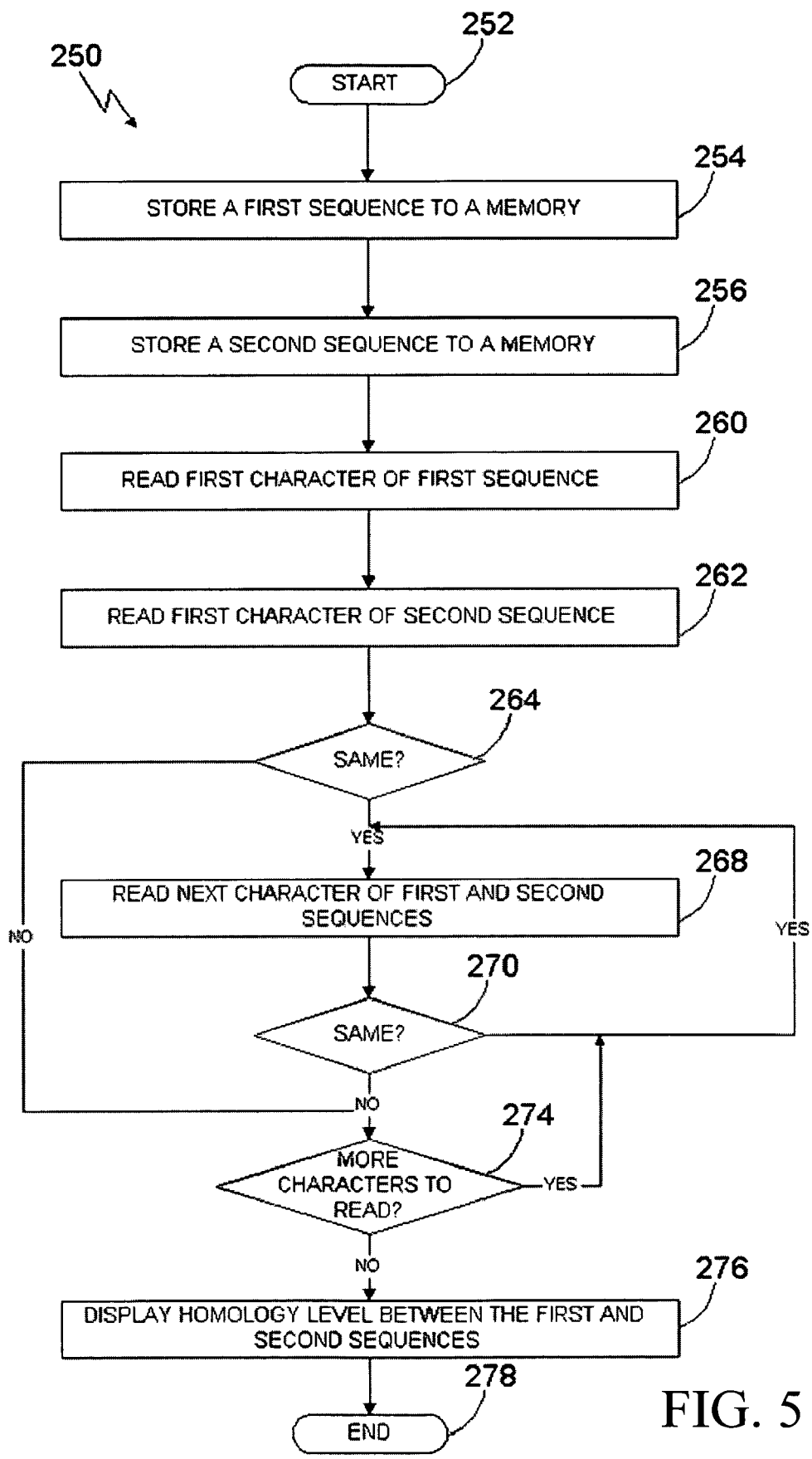
FIG. 5 is a flow diagram illustrating one embodiment of a process 250 in a computer for determining whether two sequences are homologous.

FIG. 5 is a flow diagram illustrating one embodiment of a process 250 in a computer for determining whether two sequences are homologous. The process 250 begins at a start state 252 and then moves to a state 254 wherein a first sequence to be compared is stored to a memory. The second sequence to be compared is then stored to a memory at a state 256. The process 250 then moves to a state 260 wherein the first character in the first sequence is read and then to a state 262 wherein the first character of the second sequence is read. It should be understood that if the sequence is a nucleotide sequence, then the character would normally be either A, T, C, G or U. If the sequence is a protein sequence, then it should be in the single letter amino acid code so that the first and sequence sequences can be easily compared.

A determination is then made at a decision state 264 whether the two characters are the same. If they are the same, then the process 250 moves to a state 268 wherein the next characters in the first and second sequences are read. A determination is then made whether the next characters are the same. If they are, then the process 250 continues this loop until two characters are not the same. If a determination is made that the next two characters are not the same, the process 250 moves to a decision state 274 to determine whether there are any more characters either sequence to read.

If there aren't any more characters to read, then the process 250 moves to a state 276 wherein the level of homology between the first and second sequences is displayed to the user. The level of homology is determined by calculating the proportion of characters between the sequences that were the same out of the total number of sequences in the first sequence. Thus, if every character in a first 100 nucleotide sequence aligned with a every character in a second sequence, the homology level would be 100%.

Alternatively, the computer program may be a computer program which compares the nucleotide sequences of the nucleic acid codes of the present invention, to reference nucleotide sequences in order to determine whether the nucleic acid code of the invention differs from a reference nucleic acid sequence at one or more positions. Optionally such a program records the length and identity of inserted, deleted or substituted nucleotides with respect to the sequence of either the reference polynucleotide or the nucleic acid code of the invention. In one embodiment, the computer program may be a program which determines whether the nucleotide sequences of the nucleic acid codes of the invention contain one or more single nucleotide polymorphisms (SNP) with respect to a reference nucleotide sequence. These single nucleotide polymorphisms may each comprise a single base substitution, insertion, or deletion.

Another aspect of the present invention is a method for determining the level of homology between a polypeptide code of the invention and a reference polypeptide sequence, comprising the steps of reading the polypeptide code of the invention and the reference polypeptide sequence through use of a computer program which determines homology levels and determining homology between the polypeptide code and the reference polypeptide sequence using the computer program.

Accordingly, another aspect of the present invention is a method for determining whether a nucleic acid code of the invention differs at one or more nucleotides from a reference nucleotide sequence comprising the steps of reading the nucleic acid code and the reference nucleotide sequence through use of a computer program which identifies differences between nucleic acid sequences and identifying differences between the nucleic acid code and the reference nucleotide sequence with the computer program. In some embodiments, the computer program is a program which identifies single nucleotide polymorphisms The method may be implemented by the computer systems described above and the method illustrated in FIG. 5. The method may also be performed by reading at least 2, 5, 10, 15, 20, 25, 30, or 50 of the nucleic acid codes of the invention and the reference nucleotide sequences through the use of the computer program and identifying differences between the nucleic acid codes and the reference nucleotide sequences with the computer program.

In other embodiments the computer based system may further comprise an identifier for identifying features within the nucleotide sequences of the nucleic acid codes of the invention or the amino acid sequences of the polypeptide codes of the invention.

An "identifier" refers to one or more programs which identifies certain features within the above-described nucleotide sequences of the nucleic acid codes of the invention or the amino acid sequences of the polypeptide codes of the invention. In one embodiment, the identifier may comprise a program which identifies an open reading frame in the cDNAs codes of the invention.

Figure 6:
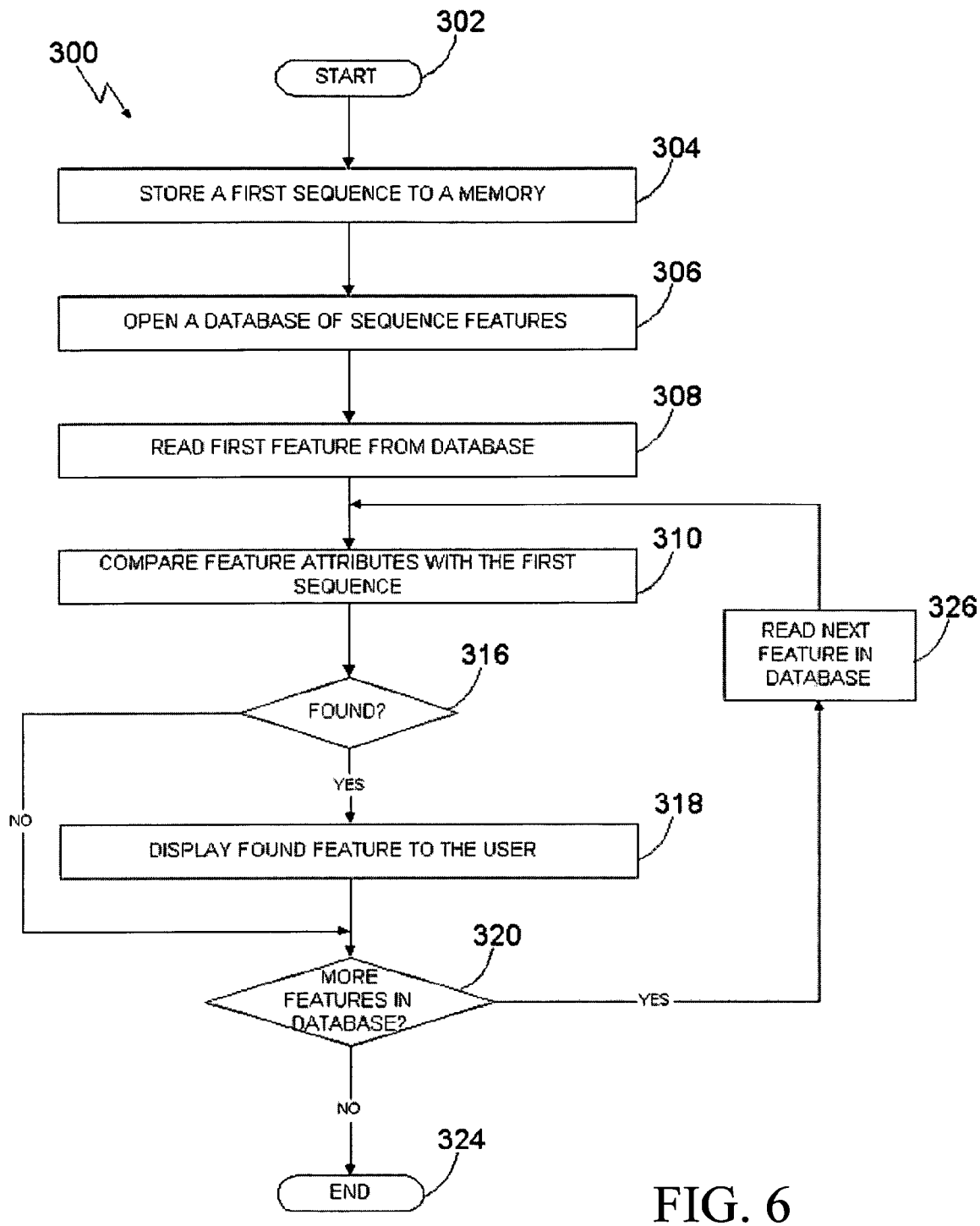
FIG. 6 is a flow diagram illustrating one embodiment of an identifier process 300 for detecting the presence of a feature in a sequence.

FIG. 6 is a flow diagram illustrating one embodiment of an identifier process 300 for detecting the presence of a feature in a sequence. The process 300 begins at a start state 302 and then moves to a state 304 wherein a first sequence that is to be checked for features is stored to a memory 115 in the computer system 100. The process 300 then moves to a state 306 wherein a database of sequence features is opened. Such a database would include a list of each feature's attributes along with the name of the feature. For example, a feature name could be "Initiation Codon" and the attribute would be "ATG". Another example would be the feature name "TAATAA Box" and the feature attribute would be "TAATAA". An example of such a database is produced by the University of Wisconsin Genetics Computer Group (Worldwide web address: gcg.com).

Once the database of features is opened at the state 306, the process 300 moves to a state 308 wherein the first feature is read from the database. A comparison of the attribute of the first feature with the first sequence is then made at a state 310. A determination is then made at a decision state 316 whether the attribute of the feature was found in the first sequence. If the attribute was found, then the process 300 moves to a state 318 wherein the name of the found feature is displayed to the user.

The process 300 then moves to a decision state 320 wherein a determination is made whether move features exist in the database. If no more features do exist, then the process 300 terminates at an end state 324. However, if more features do exist in the database, then the process 300 reads the next sequence feature at a state 326 and loops back to the state 310 wherein the attribute of the next feature is compared against the first sequence.

It should be noted, that if the feature attribute is not found in the first sequence at the decision state 316, the process 300 moves directly to the decision state 320 in order to determine if any more features exist in the database.

In another embodiment, the identifier may comprise a molecular modeling program which determines the 3-dimensional structure of the polypeptides codes of the invention. In some embodiments, the molecular modeling program identifies target sequences that are most compatible with profiles representing the structural environments of the residues in known three-dimensional protein structures. (See, e.g., Eisenberg et al., U.S. Pat. No. 5,436,850 issued Jul. 25, 1995, the disclosure of which is incorporated herein by reference in its entirety). In another technique, the known three-dimensional structures of proteins in a given family are superimposed to define the structurally conserved regions in that family. This protein modeling technique also uses the known three-dimensional structure of a homologous protein to approximate the structure of the polypeptide codes of the invention. (See e.g., Srinivasan, et al., U.S. Pat. No. 5,557,535 issued Sep. 17, 1996, the disclosure of which is incorporated herein by reference in its entirety). Conventional homology modeling techniques have been used routinely to build models of proteases and antibodies. (Sowdhamini et al., 1997). Comparative approaches can also be used to develop three-dimensional protein models when the protein of interest has poor sequence identity to template proteins. In some cases, proteins fold into similar three-dimensional structures despite having very weak sequence identities. For example, the three-dimensional structures of a number of helical cytokines fold in similar three-dimensional topology in spite of weak sequence homology.

The recent development of threading methods now enables the identification of likely folding patterns in a number of situations where the structural relatedness between target and template(s) is not detectable at the sequence level. Hybrid methods, in which fold recognition is performed using Multiple Sequence Threading (MST), structural equivalencies are deduced from the threading output using a distance geometry program DRAGON to construct a low resolution model, and a full-atom representation is constructed using a molecular modeling package such as QUANTA.

According to this 3-step approach, candidate templates are first identified by using the novel fold recognition algorithm MST, which is capable of performing simultaneous threading of multiple aligned sequences onto one or more 3-D structures. In a second step, the structural equivalencies obtained from the MST output are converted into interresidue distance restraints and fed into the distance geometry program DRAGON, together with auxiliary information obtained from secondary structure predictions. The program combines the restraints in an unbiased manner and rapidly generates a large number of low resolution model confirmations. In a third step, these low resolution model confirmations are converted into full-atom models and subjected to energy minimization using the molecular modeling package QUANTA. (See e.g., Aszódi et al., 1997).

The results of the molecular modeling analysis may then be used in rational drug design techniques to identify agents which modulate the activity of the polypeptide codes of the invention.

Accordingly, another aspect of the present invention is a method of identifying a feature within the nucleic acid codes of the invention or the polypeptide codes of the invention comprising reading the nucleic acid code(s) or the polypeptide code(s) through the use of a computer program which identifies features therein and identifying features within the nucleic acid code(s) or polypeptide code(s) with the computer program. In one embodiment, computer program comprises a computer program which identifies open reading frames. In a further embodiment, the computer program identifies structural motifs in a polypeptide sequence. In another embodiment, the computer program comprises a molecular modeling program. The method may be performed by reading a single sequence or at least 2, 5, 10, 15, 20, 25, 30, or 50 of the nucleic acid codes of the invention or the polypeptide codes of the invention through the use of the computer program and identifying features within the nucleic acid codes or polypeptide codes with the computer program.

The nucleic acid codes of the invention or the polypeptide codes of the invention may be stored and manipulated in a variety of data processor programs in a variety of formats. For example, they may be stored as text in a word processing file, such as MicrosoftWORD or WORDPERFECT or as an ASCII file in a variety of database programs familiar to those of skill in the art, such as DB2, SYBASE, or ORACLE. In addition, many computer programs and databases may be used as sequence comparers, identifiers, or sources of reference nucleotide or polypeptide sequences to be compared to the nucleic acid codes of the invention or the polypeptide codes of the invention. The following list is intended not to limit the invention but to provide guidance to programs and databases which are useful with the nucleic acid codes of the invention or the polypeptide codes of the invention. The programs and databases which may be used include, but are not limited to: MacPattern (EMBL), DiscoveryBase (Molecular Applications Group), GeneMine (Molecular Applications Group), Look (Molecular Applications Group), MacLook (Molecular Applications Group), BLAST and BLAST2 (NCBI), BLASTN and BLASTX (Altschul et al, 1990), FASTA (Pearson and Lipman, 1988), FASTDB (Brutlag et al., 1990), Catalyst (Molecular Simulations Inc.), Catalyst/SHAPE (Molecular Simulations Inc.), Cerius$^2$.DBAccess (Molecular Simulations Inc.), HypoGen (Molecular Simulations Inc.), Insight II, (Molecular Simulations Inc.), Discover (Molecular Simulations Inc.), CHARMm (Molecular Simulations Inc.), Felix (Molecular Simulations Inc.), DelPhi, (Molecular Simulations Inc.), QuanteMM, (Molecular Simulations Inc.), Homology (Molecular Simulations Inc.), Modeler (Molecular Simulations Inc.), ISIS (Molecular Simulations Inc.), Quanta/Protein Design (Molecular Simulations Inc.), WebLab (Molecular Simulations Inc.), WebLab Diversity Explorer (Molecular Simulations Inc.), Gene Explorer (Molecular Simulations Inc.), SeqFold (Molecular Simulations Inc.), the EMBL/Swissprotein database, the MDL Available Chemicals Directory database, the MDL Drug Data Report data base, the Comprehensive Medicinal Chemistry database, Derwents's World Drug Index database, the BioByteMasterFile database, the Genbank database, and the Genseqn database. Many other programs and data bases would be apparent to one of skill in the art given the present disclosure.

Motifs which may be detected using the above programs include sequences encoding leucine zippers, helix-turn-helix motifs, glycosylation sites, ubiquitination sites, alpha helices, and beta sheets, signal sequences encoding signal peptides which direct the secretion of the encoded proteins, sequences implicated in transcription regulation such as homeoboxes, acidic stretches, enzymatic active sites, substrate binding sites, and enzymatic cleavage sites.

Throughout this application, various publications, patents and published patent applications are cited. The disclosures of these publications, patents and published patent specification referenced in this application are hereby incorporated by reference into the present disclosure to more fully describe the sate of the art to which this invention pertains.

EXAMPLES

Example 1

Detection of PCTA-1 Biallelic Markers: DNA Extraction

Blood donors were from French Caucasian origin. They presented a sufficient diversity for being representative of a French heterogeneous population. The DNA from 100 unrelated and healthy individuals was extracted, pooled and tested for the detection of biallelic markers. The pool was constituted by mixing equivalent quantities of DNA from each individual.

30 ml of peripheral venous blood were taken from each donor in the presence of EDTA. Cells (pellet) were collected after centrifugation for 10 minutes at 2000 rpm. Red cells were lysed by a lysis solution (50 ml final volume: 10 mM Tris pH7.6; 5 mM $MgCl_2$; 10 mM NaCl). The solution was centrifuged (10 minutes, 2000 rpm) as many times as necessary to eliminate the residual red cells present in the supernatant, after resuspension of the pellet in the lysis solution.

The pellet of white cells was lysed overnight at 42° C. with 3.7 ml of lysis solution composed of:
  3 ml TE 10-2 (Tris-HCl 10 mM, EDTA 2 mM)/NaCl 0.4 M
  200 µl SDS 10%
  500 µl K-proteinase (2 mg K-proteinase in TE 10-2/NaCl 0.4 M).

For the extraction of proteins, 1 ml saturated NaCl (6M) (1/3.5 v/v) was added. After vigorous agitation, the solution was centrifuged for 20 minutes at 10000 rpm.

For the precipitation of DNA, 2 to 3 volumes of 100% ethanol were added to the previous supernatant, and the solution was centrifuged for 30 minutes at 2000 rpm. The DNA solution was rinsed three times with 70% ethanol to eliminate salts, and centrifuged for 20 minutes at 2000 rpm. The pellet was dried at 37° C., and resuspended in 1 ml TE 10-1 or 1 ml water. The DNA concentration was evaluated by measuring the OD at 260 nm (1 unit OD=50 µg/ml DNA).

To determine the presence of proteins in the DNA solution, the OD 260/OD 280 ratio was determined. Only DNA preparations having a OD 260/OD 280 ratio between 1.8 and 2 were used in the subsequent examples described below.

Example 2

Detection of the Biallelic Markers: Amplification of Genomic DNA by PCR

The amplification of specific genomic sequences of the DNA samples of example 1 was carried out on the pool of DNA obtained previously. In addition, 10 individual samples were similarly amplified.

PCR assays were performed using the following protocol:

| Final volume | 25 µl |
|---|---|
| DNA | 2 ng/µl |
| $MgCl_2$ | 2 mM |
| dNTP (each) | 200 µM |
| primer (each) | 2.9 ng/µl |
| Ampli Taq Gold DNA polymerase | 0.05 unit/µl |

PCR buffer (10×=0.1 M Tris HCl pH8.3 0.5M KCl 1×

Each pair of primers was designed using the sequence information of our total genomic sequence (SEQ ID No 1) and the OSP software (Hillier & Green, 1991). These primers had about 20 nucleotides in length and their respective sequences are disclosed in Table 1 and had the sequences disclosed in Table 1 in the columns labeled "Position range of amplification primer in SEQ ID No 1" and "Complementary position range of amplification primer in SEQ ID No 1".

The primers contained a common oligonucleotide tail upstream of the specific bases targeted for amplification which was useful for sequencing.

Primers from the columns labeled "Position range of amplification primer in SEQ ID No 1," contain the following additional PU 5' sequence: TGTAAAACGACGGCCAGT; and primers from the columns labeled "Complementary position range of amplification primer in SEQ ID No 1," contain the following RP 5' sequence: CAGGAAACAGCTATGACC. The primer containing the additional PU 5' sequence is listed in SEQ ID No 10. The primer containing the additional RP 5' sequence is listed in SEQ ID No 11.

The synthesis of these primers was performed following the phosphoramidite method, on a GENSET UFPS 24.1 synthesizer.

DNA amplification was performed on a Genius II thermocycler. After heating at 94° C. for 10 min, 40 cycles were performed. Each cycle comprised: 30 sec at 94° C., 55° C. for 1 min, and 30 sec at 72° C. For final elongation, 7 min at 72° C. end the amplification. The quantities of the amplification products obtained were determined on 96-well microtiter plates, using a fluorometer and Picogreen as intercalant agent (Molecular Probes).

TABLE 1

| Amplicon | Position range of the amplicon in SEQ ID 1 | | Primer name | Position range of amplification primer in SEQ ID No 1 | | primer name | Complementary position range of amplification primer in SEQ ID No 1 | |
|---|---|---|---|---|---|---|---|---|
| 99-1601 | 1 | 506 | B1 | 1 | 18 | C1 | 486 | 506 |
| 99-13801 | 2607 | 3054 | B2 | 2607 | 2627 | C2 | 3035 | 3054 |
| 99-13806 | 11883 | 12331 | B3 | 11883 | 11902 | C3 | 12313 | 12331 |
| 99-13799 | 12379 | 12909 | B4 | 12379 | 12399 | C4 | 12889 | 12909 |
| 99-13798 | 17442 | 17887 | B5 | 17442 | 17462 | C5 | 17868 | 17887 |
| 99-1602 | 21881 | 22506 | B6 | 21881 | 21899 | C6 | 22487 | 22506 |
| 99-13794 | 28669 | 29149 | B7 | 28669 | 28689 | C7 | 29131 | 29149 |
| 99-13812 | 30941 | 31457 | B8 | 30941 | 30961 | C8 | 31437 | 31457 |
| 99-13805 | 31560 | 32075 | B9 | 31560 | 31579 | C9 | 32057 | 32075 |
| 99-1587 | 34515 | 34909 | B10 | 34515 | 34535 | C10 | 34890 | 34909 |
| 99-1582 | 45325 | 46018 | B11 | 45325 | 45343 | C11 | 46000 | 46018 |
| 99-1585 | 49765 | 50310 | B12 | 49765 | 49784 | C12 | 50291 | 50310 |
| 99-1607 | 54726 | 55325 | B13 | 54726 | 54746 | C13 | 55307 | 55325 |
| 99-1577 | 64135 | 64536 | B14 | 64135 | 64153 | C14 | 64518 | 64536 |
| 99-1591 | 65202 | 65834 | B15 | 65202 | 65219 | C15 | 65815 | 65834 |
| 99-1572 | 66653 | 67295 | B16 | 66653 | 66671 | C16 | 67275 | 67295 |
| 5-169 | 67627 | 68043 | B17 | 67627 | 67646 | C17 | 68024 | 68043 |
| 5-264 | 67246 | 67696 | B18 | 67246 | 67263 | C18 | 67678 | 67696 |
| 5-170 | 67977 | 68424 | B19 | 67977 | 67994 | C19 | 68406 | 68424 |
| 5-171 | 68322 | 68742 | B20 | 68322 | 68340 | C20 | 68725 | 68742 |
| 5-1 | 70507 | 70928 | B21 | 70507 | 70524 | C21 | 70909 | 70928 |
| 99-1578 | 79940 | 80575 | B22 | 79940 | 79957 | C22 | 80557 | 80575 |
| 99-1605 | 82057 | 82504 | B23 | 82057 | 82077 | C23 | 82484 | 82504 |
| 5-2 | 82058 | 82492 | B24 | 82058 | 82077 | C24 | 82473 | 82492 |
| 5-3 | 83561 | 83982 | B25 | 83561 | 83578 | C25 | 83965 | 83982 |
| 5-4 | 83597 | 84017 | B26 | 83597 | 83616 | C26 | 83999 | 84017 |
| 5-260 | 83793 | 84167 | B27 | 83793 | 83812 | C27 | 84148 | 84167 |
| 5-9 | 85153 | 85576 | B28 | 85153 | 85170 | C28 | 85559 | 85576 |
| 5-5 | 86239 | 86539 | B29 | 86239 | 86257 | C29 | 86519 | 86539 |
| 5-202 | 87619 | 88050 | B30 | 87619 | 87638 | C30 | 88033 | 88050 |
| 5-7 | 88104 | 88536 | B31 | 88104 | 88122 | C31 | 88519 | 88536 |
| 5-181 | 89338 | 89758 | B32 | 89338 | 89357 | C32 | 89739 | 89758 |
| 5-10 | 92722 | 93142 | B33 | 92722 | 92741 | C33 | 93124 | 93142 |
| 5-11 | 93090 | 93509 | B34 | 93090 | 93108 | C34 | 93490 | 93509 |
| 5-12 | 93460 | 93881 | B35 | 93460 | 93478 | C35 | 93862 | 93881 |
| 5-13 | 93759 | 94192 | B36 | 93759 | 93776 | C36 | 94175 | 94192 |
| 5-14 | 94127 | 94554 | B37 | 94127 | 94144 | C37 | 94535 | 94554 |
| 5-15 | 94504 | 94921 | B38 | 94504 | 94521 | C38 | 94904 | 94921 |
| 5-16 | 94833 | 95251 | B39 | 94833 | 94850 | C39 | 95232 | 95251 |
| 5-17 | 95124 | 95561 | B40 | 95124 | 95142 | C40 | 95542 | 95561 |
| 5-18 | 95290 | 95708 | B41 | 95290 | 95308 | C41 | 95689 | 95708 |
| 5-300 | 95533 | 95952 | B42 | 95533 | 95551 | C42 | 95934 | 95952 |
| 5-262 | 96097 | 96591 | B43 | 96097 | 96115 | C43 | 96574 | 96591 |
| 5-263 | 96548 | 97001 | B44 | 96548 | 96565 | C44 | 96982 | 97001 |
| 5-265 | 96901 | 97309 | B45 | 96901 | 96918 | C45 | 97292 | 97309 |
| 99-7183 | 102156 | 102604 | B46 | 102156 | 102176 | C46 | 102584 | 102604 |
| 99-7207 | 105570 | 106074 | B47 | 105570 | 105588 | C47 | 106056 | 106074 |

Example 3

Detection of the Biallelic Markers: Sequencing of Amplified Genomic DNA and Identification of Polymorphisms The sequencing of the amplified DNA obtained in example 2 was carried out on ABI 377 sequencers. The sequences of the amplification products were determined using automated dideoxy terminator sequencing reactions with a dye terminator cycle sequencing protocol. The products of the sequencing reactions were run on sequencing gels and the sequences were determined using gel image analysis (ABI Prism DNA Sequencing Analysis software (2.1.2 version)).

The sequence data were further evaluated using the above mentioned polymorphism analysis software designed to detect the presence of biallelic markers among the pooled amplified fragments. The polymorphism search was based on the presence of superimposed peaks in the electrophoresis pattern resulting from different bases occurring at the same position as described previously.

47 fragments of amplification were analyzed. In these segments, 125 markers were detected. The localization of the biallelic markers was as shown in Table 2. Table 3 comprises the polynucleotides defining the PCTA-1-related biallelic markers. They could be used as probes and their sequence are disclosed in Table 3 in "Position range of probes in SEQ ID No 1".

TABLE 2

| Amplicon | Marker BM | Marker Name | Localization in PCTA-1 gene | Polymorphism (frequency %) all1 | all2 | BM position in SEQ ID No 1 | No 2 | No 3 | No 4 |
|---|---|---|---|---|---|---|---|---|---|
| 99-1601 | A1 | 99-1601-278 | 5'regulatory | A | C | 278 | | | |
| 99-1601 | A2 | 99-1601-402 | 5'regulatory | A (66) | T | 402 | | | |
| 99-1601 | A3 | 99-1601-472 | 5'regulatory | A | T | 472 | | | |
| 99-13801 | A4 | 99-13801-100 | 5'regulatory | T | C | 2955 | | | |
| 99-13806 | A5 | 99-13806-166 | 5'regulatory | G | A | 12167 | | | |
| 99-13799 | A6 | 99-13799-376 | 5'regulatory | T | G | 12536 | | | |
| 99-13798 | A7 | 99-13798-297 | 5'regulatory | T | C | 17593 | | | |
| 99-13798 | A8 | 99-13798-284 | 5'regulatory | T | C | 17606 | | | |
| 99-1602 | A9 | 99-1602-200 | 5'regulatory | C | G | 22079 | | | |
| 99-13794 | A10 | 99-13794-186 | 5'regulatory | T | C | 28964 | | | |
| 99-13794 | A11 | 99-13794-147 | 5'regulatory | C | G | 29003 | | | |
| 99-13812 | A12 | 99-13812-384 | 5'regulatory | T | C | 31077 | | | |
| 99-13805 | A13 | 99-13805-313 | 5'regulatory | T | C | 31766 | | | |
| 99-1587 | A14 | 99-1587-281 | 5'regulatory | A | G | 34791 | | | |
| 99-1582 | A15 | 99-1582-430 | 5'regulatory | C | T | 45751 | | | |
| 99-1585 | A16 | 99-1585-465 | 5'regulatory | T | C | 49847 | | | |
| 99-1585 | A17 | 99-1585-457 | 5'regulatory | T | C | 49855 | | | |
| 99-1585 | A18 | 99-1585-426 | 5'regulatory | G | A | 49886 | | | |
| 99-1585 | A19 | 99-1585-412 | 5'regulatory | G | A | 49900 | | | |
| 99-1585 | A20 | 99-1585-406 | 5'regulatory | C | A | 49906 | | | |
| 99-1585 | A21 | 99-1585-391 | 5'regulatory | C | A | 49921 | | | |
| 99-1585 | A22 | 99-1585-373 | 5'regulatory | G | A | 49939 | | | |
| 99-1585 | A23 | 99-1585-55 | 5'regulatory | C | A | 50256 | | | |
| 99-1607 | A24 | 99-1607-373 | 5'regulatory | T | C | 54955 | | | |
| 99-1577 | A25 | 99-1577-105 | 5'regulatory | A (54) | G | 64239 | | | |
| 99-1591 | A26 | 99-1591-235 | 5'regulatory | A | G | 65436 | | | |
| 99-1591 | A27 | 99-1591-295 | 5'regulatory | G | T | 65496 | | | |
| 99-1572 | A28 | 99-1572-315 | Promoter | C | T | 66967 | | | |
| 99-1572 | A29 | 99-1572-335 | Promoter | A | G | 66987 | | | |
| 99-1572 | A30 | 99-1572-440 | Promoter | C (32) | T | 67092 | | | |
| 99-1572 | A31 | 99-1572-477 | Promoter | A | T | 67129 | | | |
| 99-1572 | A32 | 99-1572-578 | Promoter | C | T | 67229 | | | |
| 5-264 | A33 | 5-264-188 | Promoter | A | G | 67433 | | | |
| 5-169 | A34 | 5-169-97 | Promoter | G (18) | C | 67723 | | | |
| 5-169 | A35 | 5-169-208 | Promoter | A (<1) | G | 67834 | | | |
| 5-169 | A36 | 5-169-331 | Promoter | C (99) | T | 67955 | | | |
| 5-170 | A37 | 5-170-238 | Promoter | A | G | 68213 | | | |
| 5-170 | A38 | 5-170-288 | Promoter | A (1) | C | 68263 | | | |
| 5-170 | A39 | 5-170-400 | Promoter | G | C | 68375 | | | |
| 5-171 | A40 | 5-171-156 | Promoter | G | T | 68477 | | | |
| 5-171 | A41 | 5-171-204 | Promoter | C (30) | T | 68525 | | | |
| 5-171 | A42 | 5-171-273 | Promoter | A | G | 68594 | | | |
| 5-171 | A43 | 5-171-289 | Promoter | C | T | 68610 | | | |
| 5-1 | A44 | 5-1-60 | Intron 0 | C (1) | T | 70566 | | | |
| 5-1 | A45 | 5-1-222 | Exon 1 | A | G | 70728 | 176 | 176 | 176 |
| 99-1578 | A46 | 99-1578-99 | Intron 1 | G | T | 80038 | | | |
| 99-1578 | A47 | 99-1578-179 | Intron 1 | A | T | 80118 | | | |
| 99-1578 | A48 | 99-1578-231 | Intron 1 | Ins AC | | 80170 | | | |
| 99-1578 | A49 | 99-1578-245 | Intron 1 | del AT | | 80183 | | | |
| 99-1578 | A50 | 99-1578-496 | Intron 1 | C | T | 80435 | | | |
| 5-2 | A51 | 5-2-30 | Intron 1 | Ins CAG | | 82090 | | | |
| 5-2 | A52 | 5-2-109 | Intron 1 | G | T | 82165 | | | |
| 5-2 | A53 | 5-2-113 | Intron 1 | Del GTTT | | 82169 | | | |
| 5-2 | A54 | 5-2-162 | Exon 2 | A (67) | T | 82218 | 253 | 253 | 253 |
| 5-2 | A55 | 5-2-178 | Exon 2 | C (67) | T | 82234 | 269 | 269 | 269 |
| 5-2 | A56 | 5-2-213 | Exon 2 | C (33) | T | 82268 | 303 | 303 | 303 |
| 99-1605 | A57 | 99-1605-112 | Intron 2 | T (67) | C | 82393 | | | |

TABLE 2-continued

| Amplicon | BM | Marker Name | Localization in PCTA-1 gene | Polymorphism (frequency %) all1 | all2 | BM position in SEQ ID No 1 | No 2 | No 3 | No 4 |
|---|---|---|---|---|---|---|---|---|---|
| 5-3 | A58 | 5-3-27 | Intron 2 | A | G | 83587 | | | |
| 5-3 | A59 | 5-3-83 | Exon 3 | C (39) | T | 83643 | 362 | 362 | 362 |
| 5-3 | A60 | 5-3-84 | Exon 3 | A (29) | G | 83644 | 363 | 363 | 363 |
| 5-3 | A61 | 5-3-248 | Exon 3 | A | G | 83808 | 527 | 527 | 527 |
| 5-3 | A62 | 5-3-321 | Intron 3 | G | T | 83881 | | | |
| 5-3 | A63 | 5-3-324 | Intron 3 | C | T | 83884 | | | |
| 5-4 | A64 | 5-4-313 | Intron 3 | A | G | 83909 | | | |
| 5-3 | A65 | 5-3-377 | Intron 3 | ins TTTG | | 83937 | | | |
| 5-4 | A66 | 5-4-351 | Intron 3 | C | T | 83947 | | | |
| 5-4 | A67 | 5-4-386 | Intron 3 | A | G | 83982 | | | |
| 5-4 | A68 | 5-4-392 | Intron 3 | GGG | TA | 83988 | | | |
| 5-260 | A69 | 5-260-255 | Intron 3 | C | T | 84047 | | | |
| 5-260 | A70 | 5-260-300 | Intron 3 | C | T | 84092 | | | |
| 5-260 | A71 | 5-260-353 | Intron 3 | C | T | 84145 | | | |
| 5-9 | A72 | 5-9-50 | Intron 3 | C | T | 85202 | | | |
| 5-5 | A73 | 5-5-21 | Intron 4 | A | G | 86259 | | | |
| 5-5 | A74 | 5-5-85 | Intron 4 | TATA AAAT ATT | ACAG GTTA TATA | 86323 | | | |
| 5-202 | A75 | 5-202-95 | Exon 6bis | G | T (<1) | 87713 | | 810 | |
| 5-202 | A76 | 5-202-117 | Exon 6bis | A (<1) | T | 87735 | | 832 | |
| 5-202 | A77 | 5-202-169 | Intron 6bis | A | C | 87787 | | | |
| 5-202 | A78 | 5-202-188 | Intron 6bis | A | G | 87806 | | | |
| 5-202 | A79 | 5-202-242 | Intron 6bis | A | G | 87860 | | | |
| 5-202 | A80 | 5-202-284 | Intron 6bis | C | T | 87902 | | | |
| 5-202 | A81 | 5-202-362 | Intron 6bis | del CC | | 87980 | | | |
| 5-202 | A82 | 5-202-394 | Intron 6bis | C | T | 88012 | | | |
| 5-7 | A83 | 5-7-113 | Intron 6bis | C | T | 88215 | | | |
| 5-7 | A84 | 5-7-181 | Intron 6bis | G | C | 88283 | | | |
| 5-7 | A85 | 5-7-195 | Exon 7 | G (25) | C | 88297 | 749 | 875 | 749 |
| 5-7 | A86 | 5-7-340 | Intron 7 | C | T | 88442 | | | |
| 5-7 | A87 | 5-7-369 | Intron 7 | A | T | 88471 | | | |
| 5-7 | A88 | 5-7-378 | Intron 7 | C | T | 88480 | | | |
| 5-181 | A89 | 5-181-57 | Intron 7 | A | G | 89394 | | | |
| 5-181 | A90 | 5-181-127 | Intron 7 | C | T | 89464 | | | |
| 5-181 | A91 | 5-181-134 | Intron 7 | C | T | 89471 | | | |
| 5-181 | A92 | 5-181-321 | Intron 8 | A | C | 89658 | | | |
| 5-10 | A93 | 5-10-39 | Exon 9 exon 9bis | C | T | 92760 | 1013 | 1139 | 1013 |
| 5-10 | A94 | 5-10-302 | Exon 9 Intron 9bis | A | G | 93023 | 1276 | 1402 | |
| 5-10 | A95 | 5-10-334 | Exon 9 Intron 9bis | A | C | 93055 | 1308 | 1434 | |
| 5-11 | A96 | 5-11-158 | Exon 9 Intron 9bis | A (22) | G | 93247 | 1500 | 1626 | |
| 5-11 | A97 | 5-11-230 | Exon 9 Intron 9bis | G | T | 93319 | 1572 | 1698 | |
| 5-11 | A98 | 5-11-234 | Exon 9 Intron 9bis | C | T | 93323 | 1576 | 1702 | |
| 5-11 | A99 | 5-11-299 | Exon 9 Intron 9bis | A | T | 93388 | 1641 | 1767 | |
| 5-11 | A100 | 5-11-304 | Exon 9 Intron 9bis | A | C | 93393 | 1646 | 1772 | |
| 5-11 | A101 | 5-11-329 | Exon 9 Intron 9bis | C | T | 93418 | 1671 | 1797 | |
| 5-12 | A102 | 5-12-56 | Exon 9 Intron 9bis | ins CTTT | | 93515 | 1768 | 1894 | |
| 5-12 | A103 | 5-12-267 | Exon 9 Intron 9bis | A | C | 93726 | 1979 | 2105 | |
| 5-13 | A104 | 5-13-145 | Exon 9 Intron 9bis | C | T | 93903 | 2156 | 2282 | |
| 5-14 | A105 | 5-14-44 | Exon 9 Intron 9bis | C | T | 94170 | 2423 | 2549 | |
| 5-14 | A106 | 5-14-93 | Exon 9 Intron 9bis | A | T | 94218 | 2471 | 2597 | |
| 5-14 | A107 | 5-14-144 | Exon 9 Intron 9bis | ins T | | 94269 | 2522 | 2648 | |

TABLE 2-continued

| Amplicon | BM | Marker Name | Localization in PCTA-1 gene | Polymorphism (frequency %) all1 | all2 | BM position in SEQ ID No 1 | No 2 | No 3 | No 4 |
|---|---|---|---|---|---|---|---|---|---|
| 5-14 | A108 | 5-14-165 | Exon 9 Intron 9bis | C | T | 94290 | 2543 | 2669 | |
| 5-14 | A109 | 5-14-297 | Exon 9 Intron 9bis | A | C | 94422 | 2675 | 2801 | |
| 5-14 | A110 | 5-14-307 | Exon 9 Intron 9bis | G | T | 94432 | 2685 | 2811 | |
| 5-15 | A111 | 5-15-219 | Exon 9 Intron 9bis | A | T | 94720 | 2973 | 3099 | |
| 5-16 | A112 | 5-16-157 | Exon 9 Intron 9bis | A | G | 94989 | 3242 | 3368 | |
| 5-17 | A113 | 5-17-140 | Exon 9 Intron 9bis | A | G | 95261 | 3514 | 3640 | |
| 5-18 | A114 | 5-18-51 | Exon 9 Intron 9bis | G | T | 95340 | 3593 | 3719 | |
| 5-18 | A115 | 5-18-208 | Exon 9 Intron 9bis | A | C | 95497 | 3750 | 3876 | |
| 5-300 | A116 | 5-300-238 | Exon 9 Intron 9bis | C | T | 95770 | 4023 | 4149 | |
| 5-300 | A117 | 5-300-287 | Exon 9 Intron 9bis | A | G | 95819 | 4072 | 4198 | |
| 5-262 | A118 | 5-262-49 | Exon 9 Exon 9ter | ins C | | 96145 | 4398 | 4524 | 1461 |
| 5-262 | A119 | 5-262-85 | Exon 9 Exon 9ter | C | T | 96181 | 4434 | 4560 | 1497 |
| 5-262 | A120 | 5-262-254 | Exon 9 Exon 9ter | C | T | 96350 | 4603 | 4729 | 1666 |
| 5-263 | A121 | 5-263-404 | Exon 9 Exon 9ter | C | T | 96951 | 5204 | 5330 | 2267 |
| 5-265 | A122 | 5-265-244 | Exon 9 Exon 9ter | A | G | 97144 | 5397 | 5523 | 2460 |
| 5-265 | A123 | 5-265-376 | 3'regualtory | A | G | 97276 | | | |
| 99-7183 | A124 | 99-7183-338 | 3'regualtory | C | T | 102267 | | | |
| 99-7207 | A125 | 99-7207-138 | 3'regualtory | A | G | 105937 | | | |

BM refers to "biallelic marker". All1 and all2 refer respectively to allele 1 and allele 2 of the biallelic marker. "Frequency %" refers to the frequency of the allele in percentage in control population. Frequencies corresponded to a population of random blood donors of French Caucasian origin.

TABLE 3

| BM | Marker Name | Position range of probes in SEQ ID No 1 | | Probes |
|---|---|---|---|---|
| A1 | 99-1601-278 | 255 | 301 | P1 |
| A2 | 99-1601-402 | 379 | 425 | P2 |
| A3 | 99-1601-472 | 449 | 495 | P3 |
| A4 | 99-13801-100 | 2932 | 2978 | P4 |
| A5 | 99-13806-166 | 12144 | 12190 | P5 |
| A6 | 99-13799-376 | 12513 | 12559 | P6 |
| A7 | 99-13798-297 | 17570 | 17616 | P7 |
| A8 | 99-13798-284 | 17583 | 17629 | P8 |
| A9 | 99-1602-200 | 22056 | 22102 | P9 |
| A10 | 99-13794-186 | 28941 | 28987 | P10 |
| A11 | 99-13794-147 | 28980 | 29026 | P11 |
| A12 | 99-13812-384 | 31054 | 31100 | P12 |
| A13 | 99-13805-313 | 31743 | 31789 | P13 |
| A14 | 99-1587-281 | 34768 | 34814 | P14 |
| A15 | 99-1582-430 | 45728 | 45774 | P15 |
| A16 | 99-1585-465 | 49824 | 49870 | P16 |
| A17 | 99-1585-457 | 49832 | 49878 | P17 |
| A18 | 99-1585-426 | 49863 | 49909 | P18 |
| A19 | 99-1585-412 | 49877 | 49923 | P19 |
| A20 | 99-1585-406 | 49883 | 49929 | P20 |
| A21 | 99-1585-391 | 49898 | 49944 | P21 |
| A22 | 99-1585-373 | 49916 | 49962 | P22 |
| A23 | 99-1585-55 | 50233 | 50279 | P23 |
| A24 | 99-1607-373 | 54932 | 54978 | P24 |
| A25 | 99-1577-105 | 64216 | 64262 | P25 |
| A26 | 99-1591-235 | 65413 | 65459 | P26 |
| A27 | 99-1591-295 | 65473 | 65519 | P27 |
| A28 | 99-1572-315 | 66944 | 66990 | P28 |
| A29 | 99-1572-335 | 66964 | 67010 | P29 |
| A30 | 99-1572-440 | 67069 | 67115 | P30 |
| A31 | 99-1572-477 | 67106 | 67152 | P31 |
| A32 | 99-1572-578 | 67206 | 67252 | P32 |
| A33 | 5-264-188 | 67410 | 67456 | P33 |
| A34 | 5-169-97 | 67700 | 67746 | P34 |
| A35 | 5-169-208 | 67811 | 67857 | P35 |
| A36 | 5-169-331 | 67932 | 67978 | P36 |
| A37 | 5-170-238 | 68190 | 68236 | P37 |
| A38 | 5-170-288 | 68240 | 68286 | P38 |
| A39 | 5-170-400 | 68352 | 68398 | P39 |
| A40 | 5-171-156 | 68454 | 68500 | P40 |
| A41 | 5-171-204 | 68502 | 68548 | P41 |
| A42 | 5-171-273 | 68571 | 68617 | P42 |
| A43 | 5-171-289 | 68587 | 68633 | P43 |
| A44 | 5-1-60 | 70543 | 70589 | P44 |
| A45 | 5-1-222 | 70705 | 70751 | P45 |
| A46 | 99-1578-99 | 80015 | 80061 | P46 |
| A47 | 99-1578-179 | 80095 | 80141 | P47 |
| A48 | 99-1578-231 | 80147 | 80193 | P48 |
| A49 | 99-1578-245 | 80160 | 80206 | P49 |
| A50 | 99-1578-496 | 80412 | 80458 | P50 |
| A51 | 5-2-30 | 82067 | 82113 | P51 |
| A52 | 5-2-109 | 82142 | 82188 | P52 |
| A53 | 5-2-113 | 82146 | 82192 | P53 |
| A54 | 5-2-162 | 82195 | 82241 | P54 |

TABLE 3-continued

| BM | Marker Name | Position range of probes in SEQ ID No 1 | | Probes |
|---|---|---|---|---|
| A55 | 5-2-178 | 82211 | 82257 | P55 |
| A56 | 5-2-213 | 82245 | 82291 | P56 |
| A57 | 99-1605-112 | 82370 | 82416 | P57 |
| A58 | 5-3-27 | 83564 | 83610 | P58 |
| A59 | 5-3-83 | 83620 | 83666 | P59 |
| A60 | 5-3-84 | 83621 | 83667 | P60 |
| A61 | 5-3-248 | 83785 | 83831 | P61 |
| A62 | 5-3-321 | 83858 | 83904 | P62 |
| A63 | 5-3-324 | 83861 | 83907 | P63 |
| A64 | 5-4-313 | 83886 | 83932 | P64 |
| A65 | 5-3-377 | 83914 | 83960 | P65 |
| A66 | 5-4-351 | 83924 | 83970 | P66 |
| A67 | 5-4-386 | 83959 | 84005 | P67 |
| A68 | 5-4-392 | 83965 | 84011 | P68 |
| A69 | 5-260-255 | 84024 | 84070 | P69 |
| A70 | 5-260-300 | 84069 | 84115 | P70 |
| A71 | 5-260-353 | 84122 | 84168 | P71 |
| A72 | 5-9-50 | 85179 | 85225 | P72 |
| A73 | 5-5-21 | 86236 | 86282 | P73 |
| A74 | 5-5-85 | 86300 | 86346 | P74 |
| A75 | 5-202-95 | 87690 | 87736 | P75 |
| A76 | 5-202-117 | 87712 | 87758 | P76 |
| A77 | 5-202-169 | 87764 | 87810 | P77 |
| A78 | 5-202-188 | 87783 | 87829 | P78 |
| A79 | 5-202-242 | 87837 | 87883 | P79 |
| A80 | 5-202-284 | 87879 | 87925 | P80 |
| A81 | 5-202-362 | 87957 | 88003 | P81 |
| A82 | 5-202-394 | 87989 | 88035 | P82 |
| A83 | 5-7-113 | 88192 | 88238 | P83 |
| A84 | 5-7-181 | 88260 | 88306 | P84 |
| A85 | 5-7-195 | 88274 | 88320 | P85 |
| A86 | 5-7-340 | 88419 | 88465 | P86 |
| A87 | 5-7-369 | 88448 | 88494 | P87 |
| A88 | 5-7-378 | 88457 | 88503 | P88 |
| A89 | 5-181-57 | 89371 | 89417 | P89 |
| A90 | 5-181-127 | 89441 | 89487 | P90 |
| A91 | 5-181-134 | 89448 | 89494 | P91 |
| A92 | 5-181-321 | 89635 | 89681 | P92 |
| A93 | 5-10-39 | 92737 | 92783 | P93 |
| A94 | 5-10-302 | 93000 | 93046 | P94 |
| A95 | 5-10-334 | 93032 | 93078 | P95 |
| A96 | 5-11-158 | 93224 | 93270 | P96 |
| A97 | 5-11-230 | 93296 | 93342 | P97 |
| A98 | 5-11-234 | 93300 | 93346 | P98 |
| A99 | 5-11-299 | 93365 | 93411 | P99 |
| A100 | 5-11-304 | 93370 | 93416 | P100 |
| A101 | 5-11-329 | 93395 | 93441 | P101 |
| A102 | 5-12-56 | 93492 | 93538 | P102 |
| A103 | 5-12-267 | 93703 | 93749 | P103 |
| A104 | 5-13-145 | 93880 | 93926 | P104 |
| A105 | 5-14-44 | 94147 | 94193 | P105 |
| A106 | 5-14-93 | 94195 | 94241 | P106 |
| A107 | 5-14-144 | 94246 | 94292 | P107 |
| A108 | 5-14-165 | 94267 | 94313 | P108 |
| A109 | 5-14-297 | 94399 | 94445 | P109 |
| A110 | 5-14-307 | 94409 | 94455 | P110 |
| A111 | 5-15-219 | 94697 | 94743 | P111 |
| A112 | 5-16-157 | 94966 | 95012 | P112 |
| A113 | 5-17-140 | 95238 | 95284 | P113 |
| A114 | 5-18-51 | 95317 | 95363 | P114 |
| A115 | 5-18-208 | 95474 | 95520 | P115 |
| A116 | 5-300-238 | 95747 | 95793 | P116 |
| A117 | 5-300-287 | 95796 | 95842 | P117 |
| A118 | 5-262-49 | 96122 | 96168 | P118 |
| A119 | 5-262-85 | 96158 | 96204 | P119 |
| A120 | 5-262-254 | 96327 | 96373 | P120 |
| A121 | 5-263-404 | 96928 | 96974 | P121 |
| A122 | 5-265-244 | 97121 | 97167 | P122 |
| A123 | 5-265-376 | 97253 | 97299 | P123 |
| A124 | 99-7183-338 | 102244 | 102290 | P124 |
| A125 | 99-7207-138 | 105914 | 105960 | P125 |

Example 4

Validation of the Polymorphisms through Microsequencing

The biallelic markers identified in example 3 were further confirmed and their respective frequencies were determined through microsequencing. Microsequencing was carried out for each individual DNA sample described in Example 1.

Amplification from genomic DNA of individuals was performed by PCR as described above for the detection of the biallelic markers with the same set of PCR primers (Table 1).

The preferred primers used in microsequencing had about 19 nucleotides in length and hybridized just upstream of the considered polymorphic base. Their sequences are disclosed in Table 4 in columns labeled "Position range of microsequencing primer mis. 1 in SEQ ID No 1" and "Complementary position range of microsequencing primer mis. 2 in SEQ ID No 1".

Mis 1 and Mis 2 respectively refer to microsequencing primers which hybridized with the non-coding strand of the PCTA-1 gene or with the coding strand of the PCTA-1 gene.

The microsequencing reaction was performed as follows:

10 μl of PCR products were added to 20 μl of microsequencing reaction mixture containing: 10 pmol microsequencing oligonucleotide (crude synthesis, 50D), 1 U Thermosequenase (Amersham E79000G), 1.25 μl Thermosequenase buffer (260 mM Tris HCl pH 9.5, 65 mM $MgCl_2$), and the appropriate fluorescent ddNTPs complementary to the nucleotides at the polymorphic site corresponding to the polymorphic bases (11.25 nM TAMRA-ddTTP; 16.25 nM ROX-ddCTP; 1.675 nM REG-ddATP; 1.25 nM RHO-ddGTP; Perkin Elmer, Dye Terminator Set 401095). After 4 minutes at 94° C., 20 PCR cycles of 15 sec at 55° C., 5 sec at 72° C., and 10 sec at 94° C. were carried out in a thermocycler. After amplification, the unincorporated dye terminators were removed by ethanol precipitation. After discarding the supernatants, the microplate was evaporated to dryness under reduced pressure (Speed Vac); samples were resuspended in 2.5 μl formamide EDTA loading buffer and heated for 2 min at 95° C. 0.8 μl microsequencing reaction were loaded on a 10% (19:1) polyacrylamide sequencing gel. The data were collected by an ABI PRISM 377 DNA sequencer and processed using the GENESCAN software (Perkin Elmer).

Following gel analysis, data were automatically processed with software that allows the determination of the alleles of biallelic markers present in each amplified fragment.

The software evaluates such factors as whether the intensities of the signals resulting from the above microsequencing procedures are weak, normal, or saturated, or whether the signals are ambiguous. In addition, the software identifies significant peaks (according to shape and height criteria). Among the significant peaks, peaks corresponding to the targeted site are identified based on their position. When two significant peaks are detected for the same position, each sample is categorized classification as homozygous or heterozygous type based on the height ratio.

TABLE 4

| Marker Name | BM | Mis. 1 | Position range of microsequencing primer mis. 1 in SEQ ID No 1 | | Mis. 2 | Complementary position range of microsequencing primer mis. 2 in SEQ ID No 1 | |
|---|---|---|---|---|---|---|---|
| 99-1601-278 | A1 | D1 | 258 | 277 | E1 | 279 | 298 |
| 99-1601-402 | A2 | D2 | 382 | 401 | E2 | 403 | 422 |
| 99-1601-472 | A3 | D3 | 452 | 471 | E3 | 473 | 492 |
| 99-13801-100 | A4 | D4 | 2935 | 2954 | E4 | 2956 | 2975 |
| 99-13806-166 | A5 | D5 | 12147 | 12166 | E5 | 12168 | 12187 |
| 99-13799-376 | A6 | D6 | 12516 | 12535 | E6 | 12537 | 12556 |
| 99-13798-297 | A7 | D7 | 17573 | 17592 | E7 | 17594 | 17613 |
| 99-13798-284 | A8 | D8 | 17586 | 17605 | E8 | 17607 | 17626 |
| 99-1602-200 | A9 | D9 | 22059 | 22078 | E9 | 22080 | 22099 |
| 99-13794-186 | A10 | D10 | 28944 | 28963 | E10 | 28965 | 28984 |
| 99-13794-147 | A11 | D11 | 28983 | 29002 | E11 | 29004 | 29023 |
| 99-13812-384 | A12 | D12 | 31057 | 31076 | E12 | 31078 | 31097 |
| 99-13805-313 | A13 | D13 | 31746 | 31765 | E13 | 31767 | 31786 |
| 99-1587-281 | A14 | D14 | 34771 | 34790 | E14 | 34792 | 34811 |
| 99-1582-430 | A15 | D15 | 45731 | 45750 | E15 | 45752 | 45771 |
| 99-1585-465 | A16 | D16 | 49827 | 49846 | E16 | 49848 | 49867 |
| 99-1585-457 | A17 | D17 | 49835 | 49854 | E17 | 49856 | 49875 |
| 99-1585-426 | A18 | D18 | 49866 | 49885 | E18 | 49887 | 49906 |
| 99-1585-412 | A19 | D19 | 49880 | 49899 | E19 | 49901 | 49920 |
| 99-1585-406 | A20 | D20 | 49886 | 49905 | E20 | 49907 | 49926 |
| 99-1585-391 | A21 | D21 | 49901 | 49920 | E21 | 49922 | 49941 |
| 99-1585-373 | A22 | D22 | 49919 | 49938 | E22 | 49940 | 49959 |
| 99-1585-55 | A23 | D23 | 50236 | 50255 | E23 | 50257 | 50276 |
| 99-1607-373 | A24 | D24 | 54935 | 54954 | E24 | 54956 | 54975 |
| 99-1577-105 | A25 | D25 | 64219 | 64238 | E25 | 64240 | 64259 |
| 99-1591-235 | A26 | D26 | 65416 | 65435 | E26 | 65437 | 65456 |
| 99-1591-295 | A27 | D27 | 65476 | 65495 | E27 | 65497 | 65516 |
| 99-1572-315 | A28 | D28 | 66947 | 66966 | E28 | 66968 | 66987 |
| 99-1572-335 | A29 | D29 | 66967 | 66986 | E29 | 66988 | 67007 |
| 99-1572-440 | A30 | D30 | 67072 | 67091 | E30 | 67093 | 67112 |
| 99-1572-477 | A31 | D31 | 67109 | 67128 | E31 | 67130 | 67149 |
| 99-1572-578 | A32 | D32 | 67209 | 67228 | E32 | 67230 | 67249 |
| 5-264-188 | A33 | D33 | 67413 | 67432 | E33 | 67434 | 67453 |
| 5-169-97 | A34 | D34 | 67703 | 67722 | E34 | 67724 | 67743 |
| 5-169-208 | A35 | D35 | 67814 | 67833 | E35 | 67835 | 67854 |
| 5-169-331 | A36 | D36 | 67935 | 67954 | E36 | 67956 | 67975 |
| 5-170-238 | A37 | D37 | 68193 | 68212 | E37 | 68214 | 68233 |
| 5-170-288 | A38 | D38 | 68243 | 68262 | E38 | 68264 | 68283 |
| 5-170-400 | A39 | D39 | 68355 | 68374 | E39 | 68376 | 68395 |
| 5-171-156 | A40 | D40 | 68457 | 68476 | E40 | 68478 | 68497 |
| 5-171-204 | A41 | D41 | 68505 | 68524 | E41 | 68526 | 68545 |
| 5-171-273 | A42 | D42 | 68574 | 68593 | E42 | 68595 | 68614 |
| 5-171-289 | A43 | D43 | 68590 | 68609 | E43 | 68611 | 68630 |
| 5-1-60 | A44 | D44 | 70546 | 70565 | E44 | 70567 | 70586 |
| 5-1-222 | A45 | D45 | 70708 | 70727 | E45 | 70729 | 70748 |
| 99-1578-99 | A46 | D46 | 80018 | 80037 | E46 | 80039 | 80058 |
| 99-1578-179 | A47 | D47 | 80098 | 80117 | E47 | 80119 | 80138 |
| 99-1578-231 | A48 | D48 | 80150 | 80169 | E48 | 80171 | 80190 |
| 99-1578-245 | A49 | D49 | 80163 | 80182 | E49 | 80184 | 80203 |
| 99-1578-496 | A50 | D50 | 80415 | 80434 | E50 | 80436 | 80455 |
| 5-2-30 | A51 | D51 | 82070 | 82089 | E51 | 82091 | 82110 |
| 5-2-109 | A52 | D52 | 82145 | 82164 | E52 | 82166 | 82185 |
| 5-2-113 | A53 | D53 | 82149 | 82168 | E53 | 82170 | 82189 |
| 5-2-162 | A54 | D54 | 82198 | 82217 | E54 | 82219 | 82238 |
| 5-2-178 | A55 | D55 | 82214 | 82233 | E55 | 82235 | 82254 |
| 5-2-213 | A56 | D56 | 82248 | 82267 | E56 | 82269 | 82288 |
| 99-1605-112 | A57 | D57 | 82373 | 82392 | E57 | 82394 | 82413 |
| 5-3-27 | A58 | D58 | 83567 | 83586 | E58 | 83588 | 83607 |
| 5-3-83 | A59 | D59 | 83623 | 83642 | E59 | 83644 | 83663 |
| 5-3-84 | A60 | D60 | 83624 | 83643 | E60 | 83645 | 83664 |
| 5-3-248 | A61 | D61 | 83788 | 83807 | E61 | 83809 | 83828 |
| 5-3-321 | A62 | D62 | 83861 | 83880 | E62 | 83882 | 83901 |
| 5-3-324 | A63 | D63 | 83864 | 83883 | E63 | 83885 | 83904 |
| 5-4-313 | A64 | D64 | 83889 | 83908 | E64 | 83910 | 83929 |
| 5-3-377 | A65 | D65 | 83917 | 83936 | E65 | 83938 | 83957 |
| 5-4-351 | A66 | D66 | 83927 | 83946 | E66 | 83948 | 83967 |
| 5-4-386 | A67 | D67 | 83962 | 83981 | E67 | 83983 | 84002 |
| 5-4-392 | A68 | D68 | 83968 | 83987 | E68 | 83989 | 84008 |
| 5-260-255 | A69 | D69 | 84027 | 84046 | E69 | 84048 | 84067 |
| 5-260-300 | A70 | D70 | 84072 | 84091 | E70 | 84093 | 84112 |
| 5-260-353 | A71 | D71 | 84125 | 84144 | E71 | 84146 | 84165 |
| 5-9-50 | A72 | D72 | 85182 | 85201 | E72 | 85203 | 85222 |
| 5-5-21 | A73 | D73 | 86239 | 86258 | E73 | 86260 | 86279 |

TABLE 4-continued

| Marker Name | BM | Mis. 1 | Position range of microsequencing primer mis. 1 in SEQ ID No 1 | | Mis. 2 | Complementary position range of microsequencing primer mis. 2 in SEQ ID No 1 | |
|---|---|---|---|---|---|---|---|
| 5-5-85 | A74 | D74 | 86303 | 86322 | E74 | 86324 | 86343 |
| 5-202-95 | A75 | D75 | 87693 | 87712 | E75 | 87714 | 87733 |
| 5-202-117 | A76 | D76 | 87715 | 87734 | E76 | 87736 | 87755 |
| 5-202-169 | A77 | D77 | 87767 | 87786 | E77 | 87788 | 87807 |
| 5-202-188 | A78 | D78 | 87786 | 87805 | E78 | 87807 | 87826 |
| 5-202-242 | A79 | D79 | 87840 | 87859 | E79 | 87861 | 87880 |
| 5-202-284 | A80 | D80 | 87882 | 87901 | E80 | 87903 | 87922 |
| 5-202-362 | A81 | D81 | 87960 | 87979 | E81 | 87981 | 88000 |
| 5-202-394 | A82 | D82 | 87992 | 88011 | E82 | 88013 | 88032 |
| 5-7-113 | A83 | D83 | 88195 | 88214 | E83 | 88216 | 88235 |
| 5-7-181 | A84 | D84 | 88263 | 88282 | E84 | 88284 | 88303 |
| 5-7-195 | A85 | D85 | 88277 | 88296 | E85 | 88298 | 88317 |
| 5-7-340 | A86 | D86 | 88422 | 88441 | E86 | 88443 | 88462 |
| 5-7-369 | A87 | D87 | 88451 | 88470 | E87 | 88472 | 88491 |
| 5-7-378 | A88 | D88 | 88460 | 88479 | E88 | 88481 | 88500 |
| 5-181-57 | A89 | D89 | 89374 | 89393 | E89 | 89395 | 89414 |
| 5-181-127 | A90 | D90 | 89444 | 89463 | E90 | 89465 | 89484 |
| 5-181-134 | A91 | D91 | 89451 | 89470 | E91 | 89472 | 89491 |
| 5-181-321 | A92 | D92 | 89638 | 89657 | E92 | 89659 | 89678 |
| 5-10-39 | A93 | D93 | 92740 | 92759 | E93 | 92761 | 92780 |
| 5-10-302 | A94 | D94 | 93003 | 93022 | E94 | 93024 | 93043 |
| 5-10-334 | A95 | D95 | 93035 | 93054 | E95 | 93056 | 93075 |
| 5-11-158 | A96 | D96 | 93227 | 93246 | E96 | 93248 | 93267 |
| 5-11-230 | A97 | D97 | 93299 | 93318 | E97 | 93320 | 93339 |
| 5-11-234 | A98 | D98 | 93303 | 93322 | E98 | 93324 | 93343 |
| 5-11-299 | A99 | D99 | 93368 | 93387 | E99 | 93389 | 93408 |
| 5-11-304 | A100 | D100 | 93373 | 93392 | E100 | 93394 | 93413 |
| 5-11-329 | A101 | D101 | 93398 | 93417 | E101 | 93419 | 93438 |
| 5-12-56 | A102 | D102 | 93495 | 93514 | E102 | 93516 | 93535 |
| 5-12-267 | A103 | D103 | 93706 | 93725 | E103 | 93727 | 93746 |
| 5-13-145 | A104 | D104 | 93883 | 93902 | E104 | 93904 | 93923 |
| 5-14-44 | A105 | D105 | 94150 | 94169 | E105 | 94171 | 94190 |
| 5-14-93 | A106 | D106 | 94198 | 94217 | E106 | 94219 | 94238 |
| 5-14-144 | A107 | D107 | 94249 | 94268 | E107 | 94270 | 94289 |
| 5-14-165 | A108 | D108 | 94270 | 94289 | E108 | 94291 | 94310 |
| 5-14-297 | A109 | D109 | 94402 | 94421 | E109 | 94423 | 94442 |
| 5-14-307 | A110 | D110 | 94412 | 94431 | E110 | 94433 | 94452 |
| 5-15-219 | A111 | D111 | 94700 | 94719 | E111 | 94721 | 94740 |
| 5-16-157 | A112 | D112 | 94969 | 94988 | E112 | 94990 | 95009 |
| 5-17-140 | A113 | D113 | 95241 | 95260 | E113 | 95262 | 95281 |
| 5-18-51 | A114 | D114 | 95320 | 95339 | E114 | 95341 | 95360 |
| 5-18-208 | A115 | D115 | 95477 | 95496 | E115 | 95498 | 95517 |
| 5-300-238 | A116 | D116 | 95750 | 95769 | E116 | 95771 | 95790 |
| 5-300-287 | A117 | D117 | 95799 | 95818 | E117 | 95820 | 95839 |
| 5-262-49 | A118 | D118 | 96125 | 96144 | E118 | 96146 | 96165 |
| 5-262-85 | A119 | D119 | 96161 | 96180 | E119 | 96182 | 96201 |
| 5-262-254 | A120 | D120 | 96330 | 96349 | E120 | 96351 | 96370 |
| 5-263-404 | A121 | D121 | 96931 | 96950 | E121 | 96952 | 96971 |
| 5-265-244 | A122 | D122 | 97124 | 97143 | E122 | 97145 | 97164 |
| 5-265-376 | A123 | D123 | 97256 | 97275 | E123 | 97277 | 97296 |
| 99-7183-338 | A124 | D124 | 102247 | 102266 | E124 | 102268 | 102287 |
| 99-7207-138 | A125 | D125 | 105917 | 105936 | E125 | 105938 | 105957 |

Example 5

Association Study Between Prostate Cancer and the Biallelic Markers of the PCTA-1 Gene Collection of DNA Samples from Affected and Non-Affected Individuals Affected Population:

The positive trait followed in this association study was prostate cancer. Prostate cancer patients were recruited according to a combination of clinical, histological and biological inclusion criteria. Clinical criteria can include rectal examination and prostate biopsies. Biological criteria can include PSA assays. The affected individuals were recorded as familial forms when at least two persons affected by prostate cancer have been diagnosed in the family. Remaining cases were classified as non-familial informative cases (at least two sibs of the case both aged over 50 years old are unaffected), or non-familial uniformative cases (no information about sibs over 50 years old is available). All affected individuals included in the statistical analysis of this patent were unrelated. Cases were also separated following the criteria of diagnosis age: early onset prostate cancer (under 65 years old) and late onset prostate cancer (65 years old or more).

Unaffected Population:

Control individuals included in this study were checked for both the absence of all clinical and biological criteria defining the presence or the risk of prostate cancer (PSA<4) (WO 96/21042), and for their age (aged 65 years old or more). All unaffected individuals included in the statistical analysis of this patent were unrelated.

The affected group was composed by 491 unrelated individuals, comprising:
197 familial cases among which 91 individuals were under 65 years old and 106 individuals were 65 years old or more; and
294 sporadic cases.

The unaffected group contained 313 individuals which were 65 years or older.

As used herein, the term "early onset cancer" refers to a cancer in which the individuals are under 65 years old.

Genotyping of Affected and Control Individuals

The general strategy to perform the association studies was to individually scan the DNA samples from all individuals in each of the populations described above in order to establish the allele frequencies of the above described biallelic markers in each of these populations. More particularly, the biallelic markers used in the present association study are A2, A9, A15, A22, A24, A25, A26, A30, A34, A35, A36, A38, A41, A42, A44, A51, A52, A54, A55, A56, A57, A59, A60, A64, A73, A75, A76, A85, A93, A96, A108, A111, A115.

Allelic frequencies of the above-described biallelic markers in each population were determined by performing microsequencing reactions on amplified fragments obtained by genomic PCR performed on the DNA samples from each individual. Genomic PCR and microsequencing were performed as detailed above in examples 2 and 4 using the described PCR and microsequencing primers.

Association Study Between Prostate Cancer and the Biallelic Markers of the PCTA-1 Gene The alleles of two biallelic markers, namely (T) A30 and (T) A41, have been shown to be significantly associated to familial prostate cancer, more particularly early onset familial prostate cancer. Indeed, the allele T of the biallelic marker A30 showed a p-value of $1.08 \times 10^{-2}$ for the early onset familial prostate cancer and of $3.39 \times 10^{-2}$ for the familial prostate cancer. The allele T of the biallelic marker A41 presented a p-value of $4.04 \times 10^{-2}$ for the early onset familial prostate cancer. These two markers could be then used in diagnostics.

Some other biallelic markers, namely A54, A55, A56, A57, A59, A60, A61, A85, A96, A108, A115, showed a moderate association. These biallelic markers are localized in the exons and introns of the PCTA-1 gene.

The inventors observed that all the PCTA-1-related biallelic markers were in linkage disequilibrium with each other in the controls individuals. In the familial cases of prostate cancer, the biallelic markers localized in the promoter did not show a linkage disequilibrium with those localized in exonic and intronic region of the PCTA-1 gene and were not in linkage disequilibrium with each other. This lack of linkage disequilibrium for the promoter biallelic markers suggests that this region comprises a trait causing mutation and could explain the cases haplotypes.

A strong association has been observed between the allele A of the biallelic marker and sporadic cases of prostate cancer. This association is highly significant with a pvalue of $7.71 \times 10^{-3}$. The marker A2 can be then used in diagnostics.

Haplotype Frequency Analysis

One way of increasing the statistical power of individual markers, is by performing haplotype association analysis.

Haplotype analysis for association of PCTA-1 markers and prostate cancer was performed by estimating the frequencies of all possible haplotypes comprising biallelic markers selected from the group consisting of A2, A9, A15, A22, A24, A25, A26, A30, A34, A35, A36, A38, A41, A42, A44, A51, A52, A54, A55, A56, A57, A59, A60, A64, A73, A75, A76, A85, A93, A96, A108, A111, A115 in the cases and control populations described in Example 5, and comparing these frequencies by means of a chi square statistical test (one degree of freedom). Haplotype estimations were performed by applying the Expectation-Maximization (EM) algorithm (Excoffier L & Slatkin M, 1995), using the EM-HAPLO program (Hawley M E, Pakstis A J & Kidd K K, 1994).

Haplotype Frequency Analysis for Familial Cases of Prostate Cancer

The most significant haplotypes obtained with the familial cases of prostate cancer are shown in Table 5. These haplotypes comprise the biallelic markers A2, A30, A41, A55, A57, and 5-202/95.

The preferred two-markers haplotypes are described in Table 5 as H1 to H7 of PT2. The more preferred haplotype is the haplotype H1/PT2 and comprises the biallelic markers A30 (99-1572/440 allele T) and A41 (allele T). This haplotype presented a p-value of $1.1 \times 10^{-4}$ and an odd-ratio of 1.67. Estimated haplotype frequencies were 57.2% in the cases and 44.4% in the controls.

The preferred three-markers haplotypes are described in Table 5 as H1, H2, H3, H7, H8, H9, H10, H11, and H12 of PT3. The more preferred haplotype is the haplotype H1/PT3 and comprises the biallelic markers A2 (allele A), A30 (99-1572/440 allele T) and A41 (allele T). This haplotype presented a p-value of $1.1 \times 10^{-5}$ and an odd-ratio of 1.84. Estimated haplotype frequencies were 42.9% in the cases and 29% in the controls.

The preferred four-markers haplotypes are described in Table 5 as H1, H2, H4, H5, H7, H9, H16, H17, H18 and H19 of PT4.

In conclusion, most preferred haplotypes for the familial cases of prostate cancer comprise the biallelic markers A30 (99-1572/440 allele T) and/or A41 (allele T). Some other preferred haplotypes for the familial cases of prostate cancer comprise the biallelic marker A2 (allele A). Optionally, preferred haplotypes for the familial cases of prostate cancer comprise the biallelic markers A55 (allele C) and/or A57 (allele G). These haplotypes can be used in diagnostic of prostate cancer susceptibility.

Haplotype Frequency Analysis for Sporadic Cases of Prostate Cancer

The most significant haplotypes obtained with the sporadic cases of prostate cancer are shown in Table 6. These haplotypes comprise the biallelic markers A2, A30, A41, A55, A57, and 5-202/95.

The preferred two-markers haplotypes are described in Table 6 as H1 to H4, H6, and H7 of PT2. The first more preferred haplotype is the haplotype H1/PT2 and comprises the biallelic markers A2 (allele T) and A55 (allele T). This haplotype presented a p-value of $2.4 \times 10^{-4}$ and an odd-ratio of 1.94. Estimated haplotype frequencies were 16.2% in the cases and 9% in the controls. The second more preferred haplotype is the haplotype H2/PT2 and comprises the biallelic markers A2 (allele T) and A57 (allele A). This haplotype presented a p-value of $5.3 \times 10^{-4}$ and an odd-ratio of 1.84. Estimated haplotype frequencies were 16.3% in the cases and 9.5% in the controls.

The preferred three-markers haplotypes are described in Table 6 as H1, H2, H3, H4, H6, H7, and H8 of PT3. The more preferred haplotype is the haplotype H2/PT3 and comprises the biallelic markers A2 (allele T), A55 (allele T), and A57 (allele A). This haplotype presented a p-value of $2.3 \times 10^{-3}$ and an odd-ratio of 1.75. Estimated haplotype frequencies were 15% in the cases and 9.2% in the controls.

The preferred four-markers haplotypes are described in Table 6 as H1, H2, H3, H4, and H6 of PT4.

In conclusion, most preferred haplotypes for the sporadic cases of prostate cancer comprise a biallelic marker selected from the group consisting of A2 (allele T), A55 (allele T), and A57 (allele A). Optionally, preferred haplotypes for the familial cases of prostate cancer comprise the biallelic markers A30 (allele T) and/or A41 (allele T). These haplotypes can be used in diagnostic of prostate cancer.

Summary of Haplotype Frequency Analysis

The most preferred two- and three-biallelic markers haplotypes for the familial and sporadic prostate cancer are summarized in Table 7. These haplotypes can be used in diagnostic of prostate cancer susceptibility.

The statistical significance of the results obtained for the haplotype analysis was evaluated by a phenotypic permutation test reiterated 1000 or 10,000 times on a computer. For this computer simulation, data from the cases and control individuals were pooled and randomly-allocated to two groups which contained the same number of individuals as the case-control populations used to produce the haplotype frequency analysis data. A haplotype analysis was then run on these artificial groups for the five haplotypes of the Table 7 which presented a strong association with prostate cancer. This experiment was reiterated 1000 times and the results are shown in Table 8.

The haplotypes 1 and 2 of the Table 7 are clearly associated with familial prostate cancer and more particularly with familial cases which were under 65 years and with >3caP familial cases. The permutation test clearly validate the statistical significance of the association between these haplotypes and familial prostate cancer since, among 1000 iterations, none of the obtained haplotypes had a p-value comparable to the one obtained for the haplotypes 1 and 2 of Table 7 for the familial cases, the familial cases under 65 years and the >3caP familial cases.

The haplotypes 3, 4, and 5 of the Table 7 are clearly associated with the sporadic prostate cancer. The permutation test clearly validate the statistical significance of the association between these haplotypes and sporadic prostate cancer since, among 1000 iterations, less than 6 of the obtained haplotypes had a p-value comparable to the one obtained for the haplotypes 3, 4 and 5 of Table 7 for the sporadic cases. Moreover, among 1000 iterations, none of the obtained haplotypes had a p-value comparable to the one obtained for the haplotypes 3, 4 and 5 of Table 7 for the informative sporadic cases.

Attributable Risk

The attributable risk has been calculated as described in the "Evaluation of risk factors" of the part entitled "Statistic method". The results are disclosed in Table 9.

These results show that the preferred haplotypes disclosed in the present invention are highly significant for the prostate cancer. Indeed, 16.92% of the sporadic prostate cancer cases carried the haplotype 4 of the Table 7 considering a dominant model which is the more relevant model for prostate cancer. Moreover, 60.77% of the familial early onset prostate cancer cases carried the haplotype 1 of the Table 7 considering a dominant model.

TABLE 5

Haplotype frequency analysis for the familial cases of prostate cancer

| | | | A2 | A30 | A41 | A55 | A57 | A75 | haplotype frequencies | | | |
|---|---|---|---|---|---|---|---|---|---|---|---|---|
| | frequency % | | 67/67 (A) | 72/66 (T) | 75/71 (T) | 72/68 (C) | 72/69 (G) | 95/95 (G) | cases | Controls | Odds ratio | Pvalue (ldf) |
| | abs diff freq. all. | | 0,1 | 6,4 | 4,2 | 3,8 | 3,4 | 0 | | | | |
| | pvalue | | 7,5e-01 | 3,3e-02 | 1,4e-01 | 2,0e-01 | 2,5e-01 | 7,5e-01 | | | | |
| Cases/controls ↓ | | | | | | | | | | | | |
| H1 | PT2 | 183/298 | | T | T | | | | 0.572 | 0.444 | 1.67 | 1.1e-04 |
| H2 | | 188/298 | | T | | | G | | 0.540 | 0.431 | 1.55 | 8.6e-04 |
| H3 | | 183/296 | | T | | C | | | 0.536 | 0.428 | 1.54 | 1.1e-03 |
| H4 | | 183/299 | A | | T | | | | 0.543 | 0.460 | 1.40 | 1.1e-02 |
| H5 | | 192/299 | A | T | | | | | 0.517 | 0.440 | 1.36 | 1.8e-02 |
| H6 | | 184/300 | | T | | | | T | 0.046 | 0.022 | 2.15 | 3.4e-02 |
| H7 | | 183/298 | A | | | C | | | 0.518 | 0.451 | 1.31 | 4.3e-02 |
| H1 | PT3 | 181/294 | A | T | T | | | | 0.429 | 0.290 | 1.84 | 1.1e-05 |
| H2 | | 186/295 | A | T | | | G | | 0.406 | 0.274 | 1.82 | 1.8e-05 |
| H3 | | 181/292 | A | T | | C | | | 0.405 | 0.274 | 1.80 | 3.2e-05 |
| H7 | | 180/294 | | T | T | C | | | 0.506 | 0.396 | 1.56 | 9.1e-04 |
| H8 | | 179/295 | | T | | | G | G | 0.547 | 0.436 | 1.56 | 9.1e-04 |
| H9 | | 181/293 | | T | | C | | G | 0.542 | 0.432 | 1.55 | 1.0e-03 |
| H10 | | 181/295 | | T | T | | | G | 0.534 | 0.426 | 1.54 | 1.2e-03 |
| H11 | | 179/291 | | T | | C | G | | 0.540 | 0.433 | 1.54 | 1.4e-03 |
| H12 | | 178/293 | | T | T | | G | | 0.510 | 0.404 | 1.54 | 1.5e-03 |

TABLE 5-continued

Haplotype frequency analysis for the familial cases of prostate cancer

| H1 | PT4 | 177/288 | A | T |   | C | G |   | 0.413 | 0.276 | 1.85 | 1.5e-05 |
|---|---|---|---|---|---|---|---|---|---|---|---|---|
| H2 |   | 177/292 | A | T |   |   | G | G | 0.415 | 0.278 | 1.84 | 1.5e-05 |
| H4 |   | 179/289 | A | T |   | C |   | G | 0.409 | 0.279 | 1.79 | 3.4e-05 |
| H5 |   | 176/290 | A | T | T |   | G |   | 0.389 | 0.260 | 1.81 | 3.7e-05 |
| H7 |   | 178/290 | A | T | T | C |   |   | 0.383 | 0.260 | 1.77 | 6.7e-05 |
| H9 |   | 179/291 | A | T | T |   |   | G | 0.395 | 0.280 | 1.67 | 2.7e-04 |
| H16 |   | 177/288 |   | T |   | C | G | G | 0.545 | 0.438 | 1.54 | 1.5e-03 |
| H17 |   | 178/291 |   | T | T | C |   | G | 0.506 | 0.400 | 1.53 | 1.5e-03 |
| H18 |   | 176/289 |   | T | T | C | G |   | 0.508 | 0.405 | 1.52 | 2.1e-03 |
| H19 |   | 176/290 |   | T | T |   | G | G | 0.510 | 0.408 | 1.51 | 2.2e-03 |

1df refers to one degree of freedom.

TABLE 6

Haplotype frequency analysis for the sporadic cases of prostate cancer

|   |   |   | A2 | A30 | A41 | A55 | A57 | A75 | haplotype frequencies | | | |
|---|---|---|---|---|---|---|---|---|---|---|---|---|
|   | frequency % |   | 60/67 (A) | 64/66 (T) | 73/71 (T) | 64/68 (C) | 65/69 (G) | 94/95 (G) | cases | Controls | Odds ratio | Pvalue (1df) |
|   | abs diff freq. all. |   | -7,4 | -2,0 | 2,7 | -3,7 | -3,9 | -1 |   |   |   |   |
|   | pvalue |   | 7,7e-03 | 4,3e-01 | 2,9e-01 | 1,6e-01 | 1,4e-01 | 3,4e-01 |   |   |   |   |
|   | Cases/controls ↓ |   |   |   |   |   |   |   |   |   |   |   |
| H1 | PT2 | 281/298 | T |   |   | T |   |   | 0.162 | 0.090 | 1.94 | 2.4e-04 |
| H2 |   | 282/301 | T |   |   |   | A |   | 0.163 | 0.095 | 1.85 | 5.3e-04 |
| H3 |   | 282/301 |   |   | T | T |   |   | 0.140 | 0.083 | 1.79 | 2.1e-03 |
| H4 |   | 283/298 |   |   | T |   | A |   | 0.136 | 0.083 | 1.74 | 3.6e-03 |
| H6 |   | 283/299 | T |   |   | T |   |   | 0317 | 0.246 | 1.42 | 7.3e-03 |
| H7 |   | 279/300 |   | T |   |   |   | T | 0.045 | 0.022 | 2.08 | 3.0e-02 |
| H1 | PT3 | 278/295 | T |   | T | T |   |   | 0.083 | 0.037 | 2.33 | 1.1e-03 |
| H2 |   | 277/294 | T |   |   | T | A |   | 0.150 | 0.092 | 1.75 | 2.3e-03 |
| H3 |   | 279/295 | T |   | T |   | A |   | 0.081 | 0.040 | 2.12 | 3.4e-03 |
| H4 |   | 278/294 |   |   | T | T | A |   | 0134 | 0.082 | 1.75 | 3.8e-03 |
| H6 |   | 277/295 | T |   |   | T |   | G | 0.126 | 0.076 | 1.76 | 4.7e-03 |
| H7 |   | 277/293 |   | T | T |   | A |   | 0.091 | 0.048 | 1.96 | 4.7e-03 |
| H8 |   | 275/294 |   | T | T | T |   |   | 0.093 | 0.051 | 1.91 | 5.5e-03 |
| H1 | PT4 | 273/290 | T | T | T |   | A |   | 0.046 | 0.010 | 4.76 | 2.0e-04 |
| H2 |   | 271/290 | T | T | T | T |   |   | 0.044 | 0.010 | 4.54 | 3.9e-04 |
| H3 |   | 274/291 | T |   | T | T | A |   | 0.078 | 0.038 | 2.15 | 3.6e-03 |
| H4 |   | 274/292 | T |   | T | T |   | G | 0.053 | 0.021 | 2.57 | 4.4e-03 |
| H6 |   | 272/289 |   | T | T | T | A |   | 0.090 | 0.048 | 1.95 | 5.5e-03 |

TABLE 7

Haplotype frequency analysis of the preferred haplotypes

| | | | HAPLOTYPE | | | | | Pvalue haplo. Frequency % (cases vs controls) | |
|---|---|---|---|---|---|---|---|---|---|
| | | | | | | | | familial cases vs controls | sporadic cases vs controls |
| | | MARKERS | A2 | A30 | A41 | A55 | A57 | | |
| FAMILIAL CASES HAPLOTYPES | PT2 | haplotype 1 | | T | T | | | 1e−04 (57/44) | 6e−01 (45/44) |
| | PT3 | haplotype 2 | A | T | T | | | 1e−05 (43/29) | 2e−01 (26/29) |
| SPORADICS CASES HAPLOTYPES | PT2 | haplotype 3 | T | | | | A | 4e−01 (11/10) | 5e−04 (16/10) |
| | | haplotype 4 | T | | | T | | 3e−01 (11/9) | 2e−04 (16/9) |
| | PT3 | haplotype 5 | T | | | T | A | 3e−01 (11/9) | 2e−03 (15/9) |

TABLE 8

Haplotype frequency analysis with permutation test results

| SAMPLES | number cases/ controls | haplotype frequency | | Odds ratio | Pvalue (1df) | PERMUTATIONS TEST Iter/nb of Iter. |
|---|---|---|---|---|---|---|
| | | cases | controls | | | |
| HAPLOTYPE 1 of Table 7 | | | | | | |
| cases vs controls | 463/298 | 0.501 | 0.444 | 1.26 | 2.8e−02 | 30/1000 |
| cases (<=65 years) vs controls | 176/298 | 0.546 | 0.444 | 1.51 | 2.3e−03 | 3/1000 |
| cases (>65 years) vs controls | 283/298 | 0.467 | 0.444 | 1.10 | 4.0e−01 | 273/1000 |
| sporadic cases vs controls | 280/298 | 0.455 | 0.444 | 1.04 | 6.5e−01 | 572/1000 |
| sporadic cases (<=65 years) vs controls | 89/298 | 0.454 | 0.444 | 1.04 | 7.5e−01 | 696/1000 |
| sporadic cases (>65 years) vs controls | 187/298 | 0.450 | 0.444 | 1.02 | 7.5e−01 | 771/1000 |
| sporadic informatif vs controls | 67/298 | 0.434 | 0.444 | 0.96 | 7.5e−01 | 699/1000 |
| familial cases vs controls | 183/298 | 0.572 | 0.444 | 1.67 | 1.1e−04 | 0/1000 |
| familial cases (<=65 years) vs controls | 87/298 | 0.646 | 0.444 | 2.28 | 2.7e−06 | 0/1000 |
| familial cases (>65 years) vs controls | 96/298 | 0.501 | 0.444 | 1.25 | 1.7e−01 | 103/1000 |
| familial cases (>=3caP) vs controls | 82/298 | 0.588 | 0.444 | 1.79 | 1.1e−03 | 0/1000 |
| HAPLOTYPE 2 of Table 7 | | | | | | |
| cases vs controls | 457/294 | 0.325 | 0.290 | 1.18 | 1.4e−01 | 127/1000 |
| cases (<=65 years) vs controls | 174/294 | 0.362 | 0.290 | 1.39 | 2.1e−02 | 24/1000 |
| cases (>65 years) vs controls | 279/294 | 0.297 | 0.290 | 1.03 | 7.5e−01 | 770/1000 |
| sporadic cases vs controls | 276/294 | 0.257 | 0.290 | 0.85 | 2.1e−01 | 176/1000 |
| sporadic cases (<=65 years) vs controls | 88/294 | 0.229 | 0.290 | 0.73 | 1.1e−01 | 99/1000 |

TABLE 8-continued

Haplotype frequency analysis with permutation test results

| SAMPLES | number cases/ controls | haplotype frequency | | Odds ratio | Pvalue (1df) | PERMUTATIONS TEST Iter/nb of Iter. |
|---|---|---|---|---|---|---|
| | | cases | controls | | | |
| sporadic cases (>65 years) vs controls | 184/294 | 0.265 | 0.290 | 0.88 | 4.0e−01 | 351/1000 |
| sporadic informatif vs controls | 67/294 | 0.176 | 0.290 | 0.52 | 6.9e−03 | 9/1000 |
| familial cases vs controls | 181/294 | 0.429 | 0.290 | 1.84 | 1.1e−05 | 0/1000 |
| familial cases (<=65 years) vs controls | 86/294 | 0.501 | 0.290 | 2.46 | 2.5e−07 | 0/1000 |
| familial cases (>65 years) vs controls | 95/294 | 0.365 | 0.290 | 1.41 | 4.8e−02 | 48/1000 |
| familial cases (>=3caP) vs controls | 82/294 | 0.467 | 0.290 | 2.14 | 2.0e−05 | 0/1000 |
| HAPLOTYPE 3 of Table 7 | | | | | | |
| cases vs controls | 470/301 | 0.143 | 0.095 | 1.58 | 5.8e−03 | 15/1000 |
| cases (<=65 years) vs controls | 175/301 | 0.132 | 0.095 | 1.44 | 7.8e−02 | 96/1000 |
| cases (>65 years) vs controls | 292/301 | 0.145 | 0.095 | 1.61 | 8.2e−03 | 14/1000 |
| sporadic cases vs controls | 282/301 | 0.163 | 0.095 | 1.85 | 5.3e−04 | 4/1000 |
| sporadic cases (<=65 years) vs controls | 90/301 | 0.163 | 0.095 | 1.85 | 1.1e−02 | 11/1000 |
| sporadic cases (>65 years) vs controls | 189/301 | 0.158 | 0.095 | 1.77 | 3.4e−03 | 10/1000 |
| sporadic informatif vs controls | 70/301 | 0.221 | 0.095 | 2.69 | 3.4e−05 | 0/1000 |
| familial cases vs controls | 188/301 | 0.110 | 0.095 | 1.17 | 4.4e−01 | 487/1000 |
| familial cases (<=65 years) vs controls | 85/301 | 0.096 | 0.095 | 1.00 | 7.5e−01 | 991/1000 |
| familial cases (>65 years) vs controls | 103/301 | 0.121 | 0.095 | 1.31 | 2.7e−01 | 317/1000 |
| familial cases (>=3caP) vs controls | 83/301 | 0.074 | 0.095 | 0.76 | 3.7e−01 | 462/1000 |
| HAPLOTYPE 4 of Table 7 | | | | | | |
| cases vs controls | 464/298 | 0.143 | 0.090 | 1.68 | 2.2e−03 | 7/1000 |
| cases (<=65 years) vs controls | 174/298 | 0.135 | 0.090 | 1.57 | 3.0e−02 | 47/1000 |
| cases (>65 years) vs controls | 286/298 | 0.145 | 0.090 | 1.70 | 3.8e−03 | 9/1000 |
| sporadic cases vs controls | 281/298 | 0.162 | 0.090 | 1.94 | 2.4e−04 | 2/1000 |
| sporadic cases (<=65 years) vs controls | 88/298 | 0.165 | 0.090 | 2.00 | 4.7e−03 | 17/1000 |
| sporadic cases (>65 years) vs controls | 189/298 | 0.156 | 0.090 | 1.87 | 1.7e−03 | 4/1000 |
| sporadic informatif vs controls | 69/298 | 0.223 | 0.090 | 2.89 | 1.1e−05 | 0/1000 |
| familial cases vs controls | 183/298 | 0.110 | 0.090 | 1.25 | 2.9e−01 | 318/1000 |
| familial cases (<=65 years) vs controls | 86/298 | 0.100 | 0.090 | 1.12 | 6.5e−01 | 726/1000 |

TABLE 8-continued

Haplotype frequency analysis with permutation test results

| SAMPLES | number cases/ controls | haplotype frequency cases | haplotype frequency controls | Odds ratio | Pvalue (1df) | PERMUTATIONS TEST Iter/nb of Iter. |
|---|---|---|---|---|---|---|
| familial cases (>65 years) vs controls | 97/298 | 0.120 | 0.090 | 1.37 | 2.2e−01 | 271/1000 |
| familial cases (>=3caP) vs controls | 81/298 | 0.084 | 0.090 | 0.93 | 7.5e−01 | 839/1000 |
| HAPLOTYPE 5 of Table 7 | | | | | | |
| cases vs controls | 456/294 | 0.136 | 0.092 | 1.56 | 9.1e−03 | 14/1000 |
| cases (<=65 years) vs controls | 171/294 | 0.131 | 0.092 | 1.48 | 6.5e−02 | 80/1000 |
| cases (>65 years) vs controls | 282/294 | 0.136 | 0.092 | 1.55 | 1.8e−02 | 30/1000 |
| sporadic cases vs controls | 277/294 | 0.150 | 0.092 | 1.75 | 2.3e−03 | 6/1000 |
| sporadic cases (<=65 years) vs controls | 88/294 | 0.155 | 0.092 | 1.81 | 1.7e−02 | 27/1000 |
| sporadic cases (>65 years) vs controls | 186/294 | 0.142 | 0.092 | 1.64 | 1.5e−02 | 34/1000 |
| sporadic informatif vs controls | 69/294 | 0.226 | 0.092 | 2.89 | 1.0e−05 | 0/1000 |
| familial cases vs controls | 179/294 | 0.112 | 0.092 | 1.24 | 3.2e−01 | 354/1000 |
| familial cases (<=65 years) vs controls | 83/294 | 0.102 | 0.092 | 1.12 | 6.5e−01 | 733/1000 |
| familial cases (>65 years) vs controls | 96/294 | 0.121 | 0.092 | 1.36 | 2.4e−01 | 262/1000 |
| familial cases (>=3caP) vs controls | 79/294 | 0.082 | 0.092 | 0.88 | 6.5e−01 | 749/1000 |

Familial forms in which at least three persons are affected by prostate cancer in the family are described in the present application as >3CaP. Sporadic cases were classified as informative sporadic cases when at least two sibs of the case both aged over 50 years old are unaffected.

CARRIER: Individual carrying the haplotype
ODD RATIO of Carrier (OR): Carrier of cases*(1-Carrier of controls)/Carrier of controls*(1-Carrier of cases)
ATTRIBUTABLE RISK (RR): Carrier of Randoms controls* (OR−1)/(Carrier of Randoms controls*(OR−1)+1)

TABLE 9

Attributable risk for prostate cancer

| | Sample sizes cases vs controls | Estimating of haplotype frequency cases | Estimating of haplotype frequency Controls (unaffected) | Random controls (French) | Dominant Model Carriers frequency (cases vs controls) | Dominant Model Attributable Risk % | Recessif Model Carriers frequency (cases vs controls) | Recessif Model Attributable Risk % |
|---|---|---|---|---|---|---|---|---|
| Haplotype 4 of Table 7 | 281 vs 298 | 16.2% | 9% | 10.3% | 30% vs 17% | 16.92 | 3% vs 1% | 2.38 |
| Haplotype 1 of Table 7 | 87 vs 298 | 64.6% | 44% | 48% | 88% vs 69% | 60.77 | 42% vs 20% | 30.63 |

Example 6

Mouse PCTA-1 Protein

The inventors have cloned a cDNA molecule encoding a mouse homologue of the PCTA-1 protein (SEQ ID No 8). The deduce amino acid sequence is provided in SEQ ID No 9. FIGS. 7A-D show alignments between the human and mouse PCTA-1 protein sequences of the inventions, as well as that of GenBank L78132. It shows an 80% homology between the human and mouse homologues.

Further comparisons between these mouse and human cDNA and protein sequences, taking into consideration the position of significant polymorphisms in relation with potentially conserved motifs, should allow the person skilled in the art to identify regions of specific physiological interest, in the design of suitable vaccine or therapeutic candidates. Two galactoside binding sites shown in FIGS. 7A-D are of special interest. These sites are conserved among the PCTA-1 proteins and the galectins, and seem to be involved in the cell-cell and cell-matrix interactions which are of high relevance to cancer. Two other sites, HFNPRF and VVCN, are also highly conserved among all these proteins.

Example 7

Preparation of Antibody Compositions to a PCTA-1 Protein

Substantially pure protein or polypeptide is isolated from transfected or transformed cells containing an expression vector encoding a PCTA-1 protein or a portion thereof. The concentration of protein in the final preparation is adjusted, for example, by concentration on an Amicon filter device, to the level of a few micrograms/ml. Monoclonal or polyclonal antibody to the protein can then be prepared as follows:

A. Monoclonal Antibody Production by Hybridoma Fusion

Monoclonal antibody to epitopes in a PCTA-1 protein or a portion thereof can be prepared from murine hybridomas according to the classical method of Kohler et al. (1975) or derivative methods thereof. Also see Harlow et al. 1988.

Briefly, a mouse is repetitively inoculated with a few micrograms of a PCTA-1 protein or a portion thereof over a period of a few weeks. The mouse is then sacrificed, and the antibody producing cells of the spleen isolated. The spleen cells are fused by means of polyethylene glycol with mouse myeloma cells, and the excess unfused cells destroyed by growth of the system on selective media comprising aminopterin (HAT media). The successfully fused cells are diluted and aliquots of the dilution placed in wells of a microtiter plate where growth of the culture is continued. Antibody-producing clones are identified by detection of antibody in the supernatant fluid of the wells by immunoassay procedures, such as ELISA, as originally described by Engvall, (1980), and derivative methods thereof. Selected positive clones can be expanded and their monoclonal antibody product harvested for use. Detailed procedures for monoclonal antibody production are described in Davis et al.

B. Polyclonal Antibody Production by Immunization

Polyclonal antiserum containing antibodies to heterogeneous epitopes in a PCTA-protein or a portion thereof can be prepared by immunizing suitable non-human animal with this PCTA-1 protein or a portion thereof, which can be unmodified or modified to enhance immunogenicity. A suitable non-human animal is preferably a non-human mammal is selected, usually a mouse, rat, rabbit, goat, or horse. Alternatively, a crude preparation which has been enriched for the PCTA-1 concentration can be used to generate antibodies. Such proteins, fragments or preparations are introduced into the non-human mammal in the presence of an appropriate adjuvant (e.g. aluminum hydroxide, RIBI, etc.) which is known in the art. In addition the protein, fragment or preparation can be pretreated with an agent which will increase antigenicity, such agents are known in the art and include, for example, methylated bovine serum albumin (mBSA), bovine serum albumin (BSA), Hepatitis B surface antigen, and keyhole limpet hemocyanin (KLH). Serum from the immunized animal is collected, treated and tested according to known procedures. If the serum contains polyclonal antibodies to undesired epitopes, the polyclonal antibodies can be purified by immunoaffinity chromatography.

Effective polyclonal antibody production is affected by many factors related both to the antigen and the host species. Also, host animals vary in response to site of inoculations and dose, with both inadequate or excessive doses of antigen resulting in low titer antisera. Small doses (ng level) of antigen administered at multiple intradermal sites appears to be most reliable. Techniques for producing and processing polyclonal antisera are known in the art, see for example, Mayer and Walker (1987). An effective immunization protocol for rabbits can be found in Vaitukaitis, et al. (1971).

Booster injections can be given at regular intervals, and antiserum harvested when antibody titer thereof, as determined semi-quantitatively, for example, by double immunodiffusion in agar against known concentrations of the antigen, begins to fall. See, for example, Ouchterlony, O. et al., (1973). Plateau concentration of antibody is usually in the range of 0.1 to 0.2 mg/ml of serum (about 12 µM). Affinity of the antisera for the antigen is determined by preparing competitive binding curves, as described, for example, by Fisher, (1980).

Antibody preparations prepared according to either the monoclonal or the polyclonal protocol are useful in quantitative immunoassays which determine concentrations of antigen-bearing substances in biological samples; they are also used semi-quantitatively or qualitatively to identify the presence of antigen in a biological sample. The antibodies may also be used in therapeutic compositions for killing cells expressing the protein or reducing the levels of the protein in the body.

While the preferred embodiment of the invention has been illustrated and described, it will be appreciated that various changes can be made therein by the one skilled in the art without departing from the spirit and scope of the invention. Accordingly, the scope of this invention is intended to be defined only by reference to the appended claims.

REFERENCES

The following references are cited herein and are incorporated herein by reference in their entireties:

Abbondanzo S J et al., 1993, Methods in Enzymology, Academic Press, New York, pp 803-823
Ajioka R. S. et al., *Am. J. Hum. Genet.*, 60:1439-1447, 1997
Altschul et al., 1990, J. Mol. Biol. 215(3):403-410
Altschul et al., 1993, Nature Genetics 3:266-272
Altschul et al., 1997, Nuc. Acids Res. 25:3389-3402
Anton M. et al., 1995, J. Virol., 69: 4600-4606
Araki K et al. (1995) *Proc. Natl. Acad. Sci. USA.* 92(1):160-4.

Aszódi et al., Proteins:Structure, Function, and Genetics, Supplement 1:3842 (1997)
Ausubel et al. (1989)Current Protocols in Molecular Biology, Green Publishing Associates and Wiley Interscience, N.Y.
Baubonis W. (1993) *Nucleic Acids Res.* 21(9):2025-9.
Beaucage et al., *Tetrahedron Lett* 1981, 22: 1859-1862
Bram R J et al., 1993, Mol. Cell Biol., 13: 4760-4769
Brown E L, Belagaje R, Ryan M J, Khorana H G, *Methods Enzymol* 1979;68:109-151
Brutlag et al. Comp. App. Biosci. 6:237-245, 1990
Bush et al., 1997, J. Chromatogr., 777: 311-328.
Chai H. et al. (1993) *Biotechnol. Appl. Biochem.* 18:259-273.
Chee et al. (1996) *Science.* 274:610-614.
Chen and Kwok *Nucleic Acids Research* 25:347-353 1997
Chen et al. (1987) *Mol. Cell. Biol.* 7:2745-2752.
Chen et al. *Proc. Natl. Acad. Sci. USA* 94/20 10756-10761, 1997
Cho R J et al., 1998, Proc. Natl. Acad. Sci. USA, 95(7): 3752-3757.
Chou J. Y., 1989, Mol. Endocrinol., 3: 1511-1514.
Clark A. G. (1990) *Mol. Biol. Evol.* 7:111-122.
Coles R, Caswell R, Rubinsztein D C, *Hum Mol Genet* 1998; 7:791-800
Compton J. (1991) *Nature.* 350(6313):91-92.
Davis L. G., M. D. Dibner, and J. F. Battey, Basic Methods in Molecular Biology, ed., Elsevier Press, NY, 1986
Dempster et al., (1977) *J. R. Stat. Soc.,* 39B:1-38.
Dent D S & Latchman D S (1993) The DNA mobility shift assay. In: *Transcription Factors: A Practical Approach* (Latchman D S, ed.) pp1-26. Oxford: IRL Press
Dignam J D, et al, *Nucleic Acids Res.* 1983 Mar 11; 11(5): 1475-1489.
Doucas V, et al, *EMBO J.* 1991 August; 10(8): 2237-2245
Dynan W S, Tjian R, *Cell* 1983;35:79-87
Edwards et Leatherbarrow, *Analytical Biochemistry,* 246, 1-6 (1997)
Engvall, E., Meth. Enzymol. 70:419 (1980)
Excoffier L. and Slatkin M. (1995) *Mol. Biol. Evol.,* 12(5): 921-927.
Feldman and Steg, 1996, Medecine/Sciences, synthese, 12:47-55
Felici F., 1991, J. Mol. Biol., Vol. 222:301-310
Fields and Song, 1989, Nature, 340:245-246
Fisher, D., Chap. 42 in: Manual of Clinical Immunology, 2d Ed. (Rose and Friedman, Eds.) Amer. Soc. For Microbiol., Washington, D.C. (1980)
Flotte et al. (1992) *Am. J. Respir. Cell Mol. Biol.* 7:349-356.
Fodor et al. (1991) *Science* 251:767-777.
Fraley et al. (1979) *Proc. Natl. Acad. Sci. USA.* 76:3348-3352.
Fried M, Crothers D M, *Nucleic Acids Res* 1981;9:6505-6525
Fromont-Racine M. et al., 1997, Nature Genetics, 16(3): 277-282.
Fuller S. A. et al. (1996) *Immunology in Current Protocols in Molecular Biology,* Ausubel et al. Eds, John Wiley & Sons, Inc., USA.
Furth P. A. et al. (1994) *Proc. Natl. Acad. Sci USA.* 91:9302-9306.
Galas D J, Schmitz A, *Nucleic Acids Res* 1978;5:3157-3170
Garner M M, Revzin A, *Nucleic Acids Res* 1981;9:3047-3060
Geysen H. Mario et al. 1984. Proc. Natl. Acad. Sci. U.S.A. 81:3998-4002
Ghosh and Bacchawat, 1991, *Targeting of liposomes to hepatocytes,* IN: *Liver Diseases, Targeted diagnosis and therapy using specific receptors and ligands.* Wu et al. Eds., Marcel Dekeker, New York, pp. 87-104.
Gonnet et al., 1992, Science 256:1443-1445
Gopal (1985) *Mol. Cell. Biol.,* 5:1188-1190.
Gossen M. et al. (1992) *Proc. Natl. Acad. Sci. USA.* 89:5547-5551.
Gossen M. et al. (1995) *Science.* 268:1766-1769.
Graham et al. (1973) *Virology* 52:456-457.
Green et al., *Ann. Rev. Biochem.* 55:569-597 (1986)
Griffin et al. *Science* 245:967-971 (1989)
Grompe, M. (1993) *Nature Genetics.* 5:111-117.
Grompe, M. et al. (1989) *Proc. Natl. Acad. Sci. U.S.A.* 86:5855-5892.
Gu H. et al. (1993) *Cell* 73:1155-1164.
Gu H. et al. (1994) *Science* 265:103-106.
Guatelli J C et al. *Proc. Natl. Acad. Sci. USA.* 35:273-286.
Hacia J G, Brody L C, Chee M S, Fodor S P, Collins F S, *Nat Genet* 1996;14(4):441-447
Haff L. A. and Smirnov I. P. (1997) *Genome Research,* 7:378-388.
Hames B. D. and Higgins S. J. (1985) *Nucleic Acid Hybridization: A Practical Approach.* Hames and Higgins Ed., IRL Press, Oxford.
Harju L, Weber T, Alexandrova L, Lukin M, Ranki M, Jalanko A, *Clin Chem* 1993;39(11Pt 1):2282-2287
Harland et al. (1985) *J. Cell. Biol.* 101:1094-1095.
Harlow, E., and D. Lane. 1988. Antibodies A Laboratory Manual. Cold Spring Harbor Laboratory. pp. 53-242
Harper J W et al., 1993, Cell, 75:805-816
Hawley M. E. et al. (1994) *Am. J. Phys. Anthropol.* 18:104.
Henikoff and Henikoff, 1993, Proteins 17:49-61
Higgins et al., 1996, Methods Enzymol. 266:383-402
Hillier L. and Green P. *Methods Appl.,* 1991, 1: 124-8.
Hoess et al. (1986) *Nucleic Acids Res.* 14:2287-2300.
Huang L. et al. (1996) *Cancer Res* 56(5):1137-1141.
Huygen et al. (1996) *Nature Medicine.* 2(8):893-898.
Izant J G, Weintraub H, *Cell* 1984 April;36(4):1007-15
Julan et al. (1992) *J. Gen. Virol.* 73:3251-3255.
Kanegae Y. et al., *Nucl. Acids Res.* 23:3816-3821.
Karlin and Altschul, 1990, Proc. Natl. Acad. Sci. USA 87:2267-2268
Khoury J. et al., *Fundamentals of Genetic Epidemiology,* Oxford University Press, NY, 1993
Kim U-J. et al. (1996) *Genomics* 34:213-218.
Klein et al. (1987) *Nature.* 327:70-73.
Kohler, G. and Milstein, C., Nature 256:495 (1975)
Koller et al. (1992) *Annu. Rev. Immunol.* 10:705-730.
Kozal M J, Shah N, Shen N, Yang R, Fucini R, Merigan T C, Richman D D, Morris D, Hubbell E, Chee M, Lander and Schork, *Science,* 265, 2037-2048, 1994
Landegren U. et al. (1998) *Genome Research,* 8:769-776.
Lange K. (1997) *Mathematical and Statistical Methods for Genetic Analysis.* Springer, New York.
Lenhard T. et al. (1996) *Gene.* 169:187-190.
Linton M. F. et al. (1993) *J. Clin. Invest.* 92:3029-3037.
Livak et al., *Nature Genetics,* 9:341-342, 1995
Livak K J, Hainer J W, *Hum Mutat* 1994;3(4):379-385
Lockhart et al. *Nature Biotechnology* 14: 1675-1680, 1996
Lucas A. H., 1994, In: Development and Clinical Uses of Haempophilus b Conjugate;
Manley J L, et al, *Proc Natl Acad Sci USA.* 1980 July; 77(7): 3855-3859
Mansour S. L. et al. (1988) *Nature.* 336:348-352.
Marshall R. L. et al. (1994) *PCR Methods and Applications.* 4:80-84.
Maxam A M, Gilbert W, *Methods Enzymol* 1980;65:499-560
McCormick et al. (1994) *Genet. Anal. Tech. Appl.* 11:158-164.
McLaughlin B. A. et al. (1996) *Am. J. Hum. Genet.* 59:561-569.

Mizokami A, Yeh S Y, Chang C, *Mol Endocrinol* 1994;8:77-88

Morton N. E., *Am. J. Hum. Genet.*, 7:277-318, 1955

Muller M M, Schreiber E, Schaffner W, Matthias P, *Nucleic Acids Res* 1989;17:6420

Muzyczka et al. (1992) *Curr. Topics in Micro. and Immunol.* 158:97-129.

Nada S. et al. (1993) *Cell* 73:1125-1135.

Nagy A. et al., 1993, Proc. Natl. Acad. Sci. USA, 90: 8424-8428.

Narang S A, Hsiung H M, Brousseau R, *Methods Enzymol* 1979;68:90-98

Neda et al. (1991) *J. Biol. Chem.* 266:14143-14146.

Newton et al. (1989) *Nucleic Acids Res.* 17:2503-2516.

Nickerson D. A. et al. (1990) *Proc. Natl. Acad. Sci. USA.* 87:8923-8927.

Nicolau C. et al., 1987, Methods Enzymol., 149:157-76.

Nicolau et al. (1982) *Biochim. Biophys. Acta.* 721:185-190.

Nihei et al, *Genes Chromosomes Cancer* 1995;14: 112-119

Nyren P, Pettersson B, Uhlen M, *Anal Biochem* 1993;208(1): 171-175

O'Reilly et al. (1992) *Baculovirus Expression Vectors: A Laboratory Manual.* W. H. Freeman and Co., New York.

Ohno et al. (1994) *Science.* 265:781-784.

Oldenburg K. R. et al., 1992, Proc. Natl. Acad. Sci., 89:5393-5397.

Orita et al. (1989) *Proc. Natl. Acad. Sci. U.S.A.*86: 2776-2770.

Ott J., *Analysis of Human Genetic Linkage*, John Hopkins University Press, Baltimore, 1991

Ouchterlony, O. et al., Chap. 19 in: Handbook of Experimental Immunology D. Wier (ed) Blackwell (1973)

Parmley and Smith, Gene, 1988, 73:305-318

Pastinen et al., *Genome Research* 1997; 7:606-614

Pearson and Lipman, 1988, Proc. Natl. Acad. Sci. USA 85(8): 2444-2448

Pease S. ans William R. S., 1990, Exp. Cell. Res., 190: 209-211.

Perlin et al. (1994) *Am. J. Hum. Genet.* 55:777-787.

Peterson et al., 1993, Proc. Natl. Acad. Sci. USA, 90: 7593-7597.

Pietu et al. *Genome Research* 6:492-503, 1996

Potter et al. (1984) *Proc. Natl. Acad. Sci. U.S.A.* 81(22):7161-7165.

Ramunsen et al., 1997, Electrophoresis, 18: 588-598.

Reid L. H. et al. (1990) *Proc. Natl. Acad. Sci. U.S.A.* 87:4299-4303.

Risch, N. and Merikangas, K. (*Science,* 273:1516-1517, 1996

Robertson E., 1987, Embryo-derived stem cell lines. In: E. J. Robertson Ed. *Teratocarcinomas and embrionic stem cells: a practical approach*. IRL Press, Oxford, pp. 71.

Rossi et al., *Pharmacol. Ther.* 50:245-254, (1991)

Roth J. A. et al. (1996) *Nature Medicine.* 2(9):985-991.

Roux et al. (1989) *Proc. Natl. Acad. Sci. U.S.A.* 86:9079-9083.

Ruano et al. (1990) *Proc. Natl. Acad. Sci. U.S.A.* 87:6296-6300.

Sambrook, J., Fritsch, E. F., and T. Maniatis. (1989) *Molecular Cloning: A Laboratory Manual.* 2ed. Cold Spring Harbor Laboratory, Cold Spring Harbor, N.Y.

Samson M, et al. (1996) *Nature*, 382(6593):722-725.

Samulski et al. (1989) *J. Virol.* 63:3822-3828.

Sanchez-Pescador R. (1988) *J. Clin. Microbiol.* 26(10):1934-1938.

Sarkar, G. and Sommer S. S. (1991) *Biotechniques.*

Sauer B. et al. (1988) *Proc. Natl. Acad. Sci. U.S.A.* 85:5166-5170.

Saunders A M, et al, *Neurology* 1993;43;1467-1472

Schaid D. J. et al., *Genet. Epidemiol.*,13:423-450, 1996

Schedl A. et al., 1993a, Nature, 362: 258-261.

Schedl et al., 1993b, Nucleic Acids Res., 21: 4783-4787.

Schena et al. *Science* 270:467-470, 1995

Schena et al., 1996, Proc Natl Acad Sci USA, 93(20):10614-10619.

Schneider et al.(1997) *Arlequin: A Software For Population Genetics Data Analysis*. University of Geneva.

Schreiber E, Matthias P, Muller M M, Schaffner W, *Nucleic Acids Res* 1989;17:6419

Schwartz and Dayhoff, eds., 1978, Matrices for Detecting Distance Relationships: Atlas of Protein Sequence and Structure, Washington: National Biomedical Research Foundation Sczakiel G. et al. (1995) *Trends Microbiol.* 3(6):213-217.

Shay J. W. et al., 1991, Biochem. Biophys. Acta, 1072: 1-7.

Sheffield, V. C. et al. (1991) *Proc. Natl. Acad. Sci. U.S.A.* 49:699-706.

Shizuya et al. (1992) *Proc. Natl. Acad. Sci. U.S.A.* 89:8794-8797.

Shoemaker D D, et al., *Nat Genet* 1996;14(4):450-456

Siebenlist U, Gilbert W, *Proc Natl Acad Sci USA* 1980;77: 122-126

Smith (1957) *Ann. Hum. Genet.* 21:254-276.

Smith et al. (1983) *Mol. Cell. Biol.* 3:2156-2165.

Sosnowski R G, et al., *Proc Natl Acad Sci USA* 1997;94:1119-1123

Sowdhamini et al., Protein Engineering 10:207, 215 (1997)

Spielmann S. and Ewens W. J., *Am. J. Hum. Genet.*, 62:450-458, 1998

Spielmann S. et al., *Am. J. Hum. Genet.*, 52:506-516, 1993

Sternberg N. L. (1994) *Mamm. Genome.* 5:397-404.

Strittmatter W J, et al., *Proc Natl Acad Sci USA* 1993;90: 1977-1981

Stryer, L., *Biochemistry*, 4th edition, 1995

Syvanen A C, *Clin Chim Acta* 1994;226(2):225-236

Szabo A. et al. *Curr Opin Struct Biol* 5, 699-705 (1995)

Szabo et al., 1995, Curr Opin Struct Biol., 5(5):699-705

Tacson et al. (1996) *Nature Medicine.* 2(8):888-892.

Te Riele et al. (1990) Nature. 348:649-651.

Terwilliger J. D. and Ott J., *Handbook of Human Genetic Linkage*, John Hopkins University Press, London, 1994

Thomas K. R. et al. (1986) *Cell.* 44:419-428.

Thomas K. R. et al. (1987) *Cell.* 51:503-512.

Thompson et al., 1994, Nucleic Acids Res. 22(2):4673-4680

Tur-Kaspa et al. (1986) *Mol. Cell. Biol.* 6:716-718.

Tyagi et al. (1998) *Nature Biotechnology.* 16:49-53.

Urdea M. S. (1988) *Nucleic Acids Research.* 11:4937-4957.

Urdea M. S. et al.(1991) *Nucleic Acids Symp. Ser.* 24:197-200.

Vaitukaitis, J. et al. J. Clin. Endocrinol. Metab. 33:988-991 (1971)

Valadon P., et al., 1996, J. Mol. Biol., 261:11-22.

Van der Lugt et al. (1991) *Gene.* 105:263-267.

Vlasak R. et al. (1983) *Eur. J. Biochem.* 135:123-126.

Wabiko et al. (1986) *DNA.* 5(4):305-314.

Walker et al. (1996) *Clin. Chem.* 42:9-13.

Wang et al., 1997, Chromatographia, 44: 205-208.

Weir, B. S. (1996) *Genetic data Analysis II Methods for Discrete population genetic Data, Sinauer Assoc., Inc., Sunderland, Mass., U.S.A.*

Westerink M. A. J., 1995, Proc. Natl. Acad. Sci., 92:4021-4025

White, M. B. et al. (1992) *Genomics.* 12:301-306.

White, M. B. et al. (1997) *Genomics.* 12:301-306.

Wong et al. (1980) *Gene.* 10:87-94.

Wood S. A. et al., 1993, Proc. Natl. Acad. Sci. USA, 90: 4582-4585.
Wu and Wu (1987) *J. Biol. Chem.* 262:4429-4432.
Wu and Wu (1988) *Biochemistry.* 27:887-892.
Wu et al. (1989) *Proc. Natl. Acad. Sci. U.S.A.* 86:2757.
Yagi T. et al. (1990) *Proc. Natl. Acad. Sci. U.S.A.* 87:9918-9922.
Zhao et al., *Am. J. Hum. Genet.,* 63:225-240, 1998
Zou Y. R. et al. (1994) *Curr. Biol.* 4:1099-1103.

What is claimed is:

1. An isolated, purified or recombinant polynucleotide comprising SEQ ID NO: 12 or the complement thereof.

2. An isolated or purified human polynucleotide consisting of a contiguous span of SEQ ID NO: 12 or the complement thereof, wherein said contiguous span includes the biallelic marker at position 67092 of SEQ ID NO: 12 and said contiguous span is:
   a) nucleotides 1-70715;
   b) 12, 15, 18, 20, 25, 30, 35, 40, 50, 60, 70, 80, 90, 100, 150, 200, 500 or 1000 contiguous nucleotides of SEQ ID NO: 12;
   c) nucleotides 1-70715 attached to a label or solid support; or
   d) 12, 15, 18, 20, 25, 30, 35, 40. 50, 60, 70, 80, 90, 100, 150, 200, 500 or 1000 contiguous nucleotides of SEQ ID NO: 12 attached to a label or solid support.

3. The isolated or purified human polynucleotide according to claim 2, wherein said contiguous span consists of nucleotides 1-70715.

4. The isolated or purified human polynucleotide according to claim 2, wherein said contiguous span consists of nucleotides 1-70715 attached to a label.

5. The isolated or purified human polynucleotide according to claim 2, wherein said contiguous span consists of nucleotides 1-70715 attached to a solid support.

6. The isolated or purified human polynucleotide according to claim 2, wherein said contiguous span consists of 12 contiguous nucleotides of SEQ ID NO: 12 and includes the biallelic marker at position 67092 of SEQ ID NO: 12.

7. The isolated or purified human polynucleotide according to claim 2, wherein said contiguous span consists of 15 contiguous nucleotides of SEQ ID NO: 12 and includes the biallelic marker at position 67092 of SEQ ID NO: 12.

8. The isolated or purified human polynucleotide according to claim 2, wherein said contiguous span consists of 18 contiguous nucleotides of SEQ ID NO: 12 and includes the biallelic marker at position 67092 of SEQ ID NO: 12.

9. The isolated or purified human polynucleotide according to claim 2, wherein said contiguous span consists of 20 contiguous nucleotides of SEQ ID NO: 12 and includes the biallelic marker at position 67092 of SEQ ID NO: 12.

10. The isolated or purified human polynucleotide according to claim 2, wherein said contiguous span consists of 25 contiguous nucleotides of SEQ ID NO: 12 and includes the biallelic marker at position 67092 of SEQ ID NO: 12.

11. The isolated or purified human polynucleotide according to claim 2, wherein said contiguous span consists of 30 contiguous nucleotides of SEQ ID NO: 12 and includes the biallelic marker at position 67092 of SEQ ID NO: 12.

12. The isolated or purified human polynucleotide according to claim 2, wherein said contiguous span consists of 35 contiguous nucleotides of SEQ ID NO: 12 and includes the biallelic marker at position 67092 of SEQ ID NO: 12.

13. The isolated or purified human polynucleotide according to claim 2, wherein said contiguous span consists of 40 contiguous nucleotides of SEQ ID NO: 12 and includes the biallelic marker at position 67092 of SEQ ID NO: 12.

14. The isolated or purified human polynucleotide according to claim 2, wherein said contiguous span consists of 50 contiguous nucleotides of SEQ ID NO: 12 and includes the biallelic marker at position 67092 of SEQ ID NO: 12.

15. The isolated or purified human polynucleotide according to claim 2, wherein said contiguous span consists of 60 contiguous nucleotides of SEQ ID NO: 12 and includes the biallelic marker at position 67092 of SEQ ID NO: 12.

16. The isolated or purified human polynucleotide according to claim 2, wherein said contiguous span consists of 70 contiguous nucleotides of SEQ ID NO: 12 and includes the biallelic marker at position 67092 of SEQ ID NO: 12.

17. The isolated or purified human polynucleotide according to claim 2, wherein said contiguous span consists of 80 contiguous nucleotides of SEQ ID NO: 12 and includes the biallelic marker at position 67092 of SEQ ID NO: 12.

18. The isolated or purified human polynucleotide according to claim 2, wherein said contiguous span consists of 90 contiguous nucleotides of SEQ ID NO: 12 and includes the biallelic marker at position 67092 of SEQ ID NO: 12.

19. The isolated or purified human polynucleotide according to claim 2, wherein said contiguous span consists of 100 contiguous nucleotides of SEQ ID NO: 12 and includes the biallelic marker at position 67092 of SEQ ID NO: 12.

20. The isolated or purified human polynucleotide according to claim 2, wherein said contiguous span consists of 150 contiguous nucleotides of SEQ ID NO: 12 and includes the biallelic marker at position 67092 of SEQ ID NO: 12.

21. The isolated or purified human polynucleotide according to claim 2, wherein said contiguous span consists of 200 contiguous nucleotides of SEQ ID NO: 12 and includes the biallelic marker at position 67092 of SEQ ID NO: 12.

22. The isolated or purified human polynucleotide according to claim 2, wherein said contiguous span consists of 500 contiguous nucleotides of SEQ ID NO: 12 and includes the biallelic marker at position 67092 of SEQ ID NO: 12.

23. The isolated or purified human polynucleotide according to claim 2, wherein said contiguous span consists of 1000 contiguous nucleotides of SEQ ID NO: 12 and includes the biallelic marker at position 67092 of SEQ ID NO: 12.

24. The isolated or purified human polynucleotide according to claim 2, wherein said contiguous span is attached to a label or solid support and consists of 12 contiguous nucleotides of SEQ ID NO: 12 and includes the biallelic marker at position 67092 of SEQ ID NO: 12.

25. The isolated or purified human polynucleotide according to claim 2, wherein said contiguous span is attached to a label or solid support and consists of 15 contiguous nucleotides of SEQ ID NO: 12 and includes the biallelic marker at position 67092 of SEQ ID NO: 12.

26. The isolated or purified human polynucleotide according to claim 2, wherein said contiguous span is attached to a label or solid support and consists of 18 contiguous nucleotides of SEQ ID NO: 12 and includes the biallelic marker at position 67092 of SEQ ID NO: 12.

27. The isolated or purified human polynucleotide according to claim 2, wherein said contiguous span is attached to a label or solid support and consists of 20 contiguous nucleotides of SEQ ID NO: 12 and includes the biallelic marker at position 67092 of SEQ ID NO: 12.

28. The isolated or purified human polynucleotide according to claim 2, wherein said contiguous span is attached to a label or solid support and consists of 25 contiguous nucleotides of SEQ ID NO: 12 and includes the biallelic marker at position 67092 of SEQ ID NO: 12.

29. The isolated or purified human polynucleotide according to claim 2, wherein said contiguous span is attached to a label or solid support and consists of 30 contiguous nucleotides of SEQ ID NO: 12 and includes the biallelic marker at position 67092 of SEQ ID NO: 12.

30. The isolated or purified human polynucleotide according to claim 2, wherein said contiguous span is attached to a label or solid support and consists of 35 contiguous nucleotides of SEQ ID NO: 12 and includes the biallelic marker at position 67092 of SEQ ID NO: 12.

31. The isolated or purified human polynucleotide according to claim 2, wherein said contiguous span is attached to a label or solid support and consists of 40 contiguous nucleotides of SEQ ID NO: 12 and includes the biallelic marker at position 67092 of SEQ ID NO: 12.

32. The isolated or purified human polynucleotide according to claim 2, wherein said contiguous span is attached to a label or solid support and consists of 50 contiguous nucleotides of SEQ ID NO: 12 and includes the biallelic marker at position 67092 of SEQ ID NO: 12.

33. The isolated or purified human polynucleotide according to claim 2, wherein said contiguous span is attached to a label or solid support and consists of 60 contiguous nucleotides of SEQ ID NO: 12 and includes the biallelic marker at position 67092 of SEQ ID NO: 12.

34. The isolated or purified ha polynucleotide according to claim 2, wherein said contiguous span is attached to a label or solid support and consists of 70 contiguous nucleotides of SEQ ID NO: 12 and includes the biallelic marker at position 67092 of SEQ ID NO: 12.

35. The isolated or purified human polynucleotide according to claim 2, wherein said contiguous span is attached to a label or solid support and consists of SO contiguous nucleotides of SEQ ID NO: 12 and includes the biallelic marker at position 67092 of SEQ ID NO: 12.

36. The isolated or purified ha polynucleotide according to claim 2, wherein said contiguous span is attached to a label or solid support and consists of 90 contiguous nucleotides of SEQ ID NO: 12 and includes the biallelic marker at position 67092 of SEQ ID NO: 12.

37. The isolated or purified human polynucleotide according to claim 2, wherein said contiguous span is attached to a label or solid support and consists of 100 contiguous nucleotides of SEQ ID NO: 12 and includes the biallelic marker at position 67092 of SEQ ID NO: 12.

38. The isolated or purified human polynucleotide according to claim 2,wherein said contiguous span is attached to a label or solid support and consists of 150 contiguous nucleotides of SEQ ID NO: 12 and includes the biallelic marker at position 67092 of SEQ ID NO: 12.

39. The isolated or purified human polynucleotide according to claim 2, wherein said contiguous span is attached to a label or solid support and consists of 200 contiguous nucleotides of SEQ ID NO: 12 and includes the biallelic marker at position 67092 of SEQ ID NO: 12.

40. The isolated or purified human polynucleotide according to claim 2, wherein said contiguous span is attached to a label or solid support and consists of 500 contiguous nucleotides of SEQ ID NO: 12 and includes the biallelic marker at position 67092 of SEQ ID NO: 12.

41. The isolated or purified human polynucleotide according to claim 2, wherein said contiguous span is attached to a label or solid support and consists of 1000 contiguous nucleotides of SEQ ID NO: 12 and includes the biallelic marker at position 67092 of SEQ ID NO: 12.

* * * * *

UNITED STATES PATENT AND TRADEMARK OFFICE
CERTIFICATE OF CORRECTION

PATENT NO. : 7,547,771 B2
APPLICATION NO. : 10/856888
DATED : June 16, 2009
INVENTOR(S) : Marta Blumenfeld, Lydie Bougueleret and Ilya Chumakov It is certified that error appears in the above-identified patent and that said Letters Patent is hereby corrected as shown below:

Column 4,
Line 33, "SEQ ID NO: 19 (gal), 20 (leg7)" should read
--SEQ ID NO: 19 (gal), SEQ ID NO: 20 (leg7)--.

Column 9,
Line 17, "biallelic polymoriphism" should read --biallelic polymorphism--.

Column 27,
Line 28, "PCTA-I" should read --PCTA-1--.

Column 31,
Line 23, "40564058" should read --4056-4058--.

Column 42,
Line 21, "COS I" should read --COS 1--.

Column 50,
Line 51, "A1 to A1125" should read --A1 to A125--.

Column 57,
Line 30, "A19 to A121" should read --A119 to A121--.

Column 60,
Line 53, "(Hariju et al., 1993)" should read --(Harju et al., 1993)--.

Column 61,
Line 9, "D108, D1, D115" should read --D108, D111, D115--.

Column 85,
Line 18, "$pr(h_k, h_l) = pr(h_k)^2$ if $h_k = h_l$, $pr(h_k, h_l) = 2pr(h_k).pr(h_l)$ if $h^k \neq h_l$. Equation 2"
should read --$pr(h_k, h_l) = pr(h_k)^2$ if $h_k = h_l$, $pr(h_k, h_l) = 2pr(h_k).pr(h_l)$ if $h_k \neq h_l$. Equation 2--.

Column 101,
Line 61, "Stemberg" should read --Sternberg--.

Column 117,
Line 4, "pAS21PCTA-1" should read --pAS2/PCTA-1--.

UNITED STATES PATENT AND TRADEMARK OFFICE
CERTIFICATE OF CORRECTION

PATENT NO. : 7,547,771 B2
APPLICATION NO. : 10/856888
DATED : June 16, 2009
INVENTOR(S) : Marta Blumenfeld, Lydie Bougueleret and Ilya Chumakov It is certified that error appears in the above-identified patent and that said Letters Patent is hereby corrected as shown below:

Column 125,
Lines 14-15, "1 µg/kg" should read --1 pg/kg--.
Lines 37-38, "1500 µg/ml, preferably 200 µg/ml, and more preferably 300 µg/ml" should read --1500 pg/ml, preferably 200 pg/ml, and more preferably 300 pg/ml--.

Column 141,
Table 2, Row 99-13794, "All" should read --A11--.

Column 148,
Line 32, "50D" should read --5 OD--.

Column 156,
Table 5, Row H1, Column Pvalue (ldf), "1.1c-04" should read --1.1e-04--.

Column 572,
Line 43, "of SO contiguous" should read --of 80 contiguous--.
Line 46, "purified ha polynucleotide" should read --purified human polynucleotide--.

Signed and Sealed this

First Day of September, 2009

David J. Kappos
*Director of the United States Patent and Trademark Office*